(12) United States Patent
Cox et al.

(10) Patent No.: US 6,897,207 B2
(45) Date of Patent: May 24, 2005

(54) AZAINDOLES

(75) Inventors: Paul J. Cox, Millington, NJ (US);
Tahir N. Majid, Hoboken, NJ (US);
Justine Yeun Quai Lai, Epping (GB);
Andrew D. Morley, Macclesfield (GB);
Shelley Amendola, Bedminster, NJ
(US); Stephanie D. Deprets,
Morristown, NJ (US); Christopher
Edlin, Newark (GB); Charles J.
Gardner, Royersford, PA (US);
Dorothea Kominos, Millington, NJ
(US); Brian L. Pedgrift, Morristown,
NJ (US); Frank Halley, Cedex (FR);
Timothy A. Gillespy, Hillsboro, NJ
(US); Michael Edwards, Morristown,
NJ (US); Francois F. Clerc, Antony
(FR); Conception Nemecek, Cedex
(FR); Olivier Houille, Magstatt-le-Bas
(FR); Dominique Damour, Orly (FR);
Herve Bouchard, Thiais (FR); Daniel
N. A. Bezard, Bagnolet (FR); Chantal
Carrez, Thiais (FR)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 10/177,804

(22) Filed: Jun. 21, 2002

(65) Prior Publication Data

US 2004/0053931 A1 Mar. 18, 2004

Related U.S. Application Data

(60) Provisional application No. 60/300,257, filed on Jun. 22, 2001.

(30) Foreign Application Priority Data

Jun. 21, 2001 (GB) ................................ 0115109

(51) Int. Cl.$^7$ .................. A61K 31/33; A61K 31/66; C07D 417/02
(52) U.S. Cl. .................. 514/183; 514/299; 514/300; 514/410; 546/113; 546/126
(58) Field of Search ............................... 514/183, 299, 514/300, 410; 546/113, 126

(56) References Cited

U.S. PATENT DOCUMENTS

| | | |
|---|---|---|
| 5,338,849 A | 8/1994 | Didier |
| 5,521,213 A | 5/1996 | Prasit |
| 5,681,959 A | 10/1997 | Bishop |
| 5,714,495 A | 2/1998 | Viaud |
| 6,025,366 A | 2/2000 | Walsh |
| 6,169,091 B1 | 1/2001 | Cockerill |
| 6,207,699 B1 | 3/2001 | Cockerill |
| 6,232,320 B1 | 5/2001 | Stewart |
| 6,348,487 B1 | 2/2002 | Connor |
| 6,384,235 B1 | 5/2002 | Henkelmann |
| 6,387,900 B1 | 5/2002 | Pevarello |
| 6,407,259 B1 | 6/2002 | Harris |

FOREIGN PATENT DOCUMENTS

| | | |
|---|---|---|
| EP | 0405602 | 1/1991 |
| EP | 509974 | * 10/1992 |
| EP | 0509974 | 10/1992 |
| EP | 0557171 | 7/1995 |
| EP | 0716855 | 6/1996 |
| EP | 0737685 | 10/1996 |
| EP | 1086950 | 3/2001 |
| GB | 966.264 | 8/1964 |
| GB | 2298199 | 8/1996 |
| JP | 06-247966 | 9/1994 |

(Continued)

OTHER PUBLICATIONS

Chemical Abstract DN 71:49810, also cited as J. Chem Soc. 11, 1505–14(1969).*
Chemical Abstract DN 116:174021, also cited as Tetrahedron, 48/5,939062(1992).*
Chemical Abstract DN 129:352830, also cited as WO 9822457 dated May 1998.*
Chemical Abstract DN 125:167834, also cited as Synthesis, 7,877–82(1996).*
Chemical Abstract DN118:101981, also cited as EP509974.*
Chemical Abstract DN 116:174021, also cited as Tetrahydron,48/5,939–52(1992).*
Chemical Abstract DN 125:167834, also cited as Synthesis, 7,877–882(1996).*
Chemical Abstract DN 133:252337, also cited as Angewandte Chemie, International Edition, 39/14, 2488–2490(2000).*

(Continued)

Primary Examiner—Richard L. Raymond
Assistant Examiner—Sudhaker B. Patel
(74) Attorney, Agent, or Firm—Paul Darkes; George Wang; Raymond Parker

(57) ABSTRACT

The invention is directed to physiologically active compounds of general formula (I):

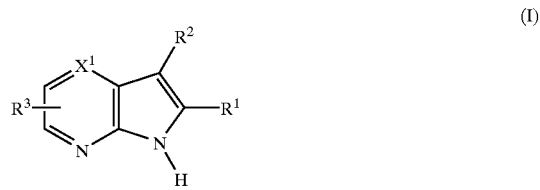

(I)

and compositions containing such compounds; and their prodrugs, and pharmaceutically acceptable salts and solvates of such compounds and their prodrugs, as well as to novel compounds within the scope of formula (I). Such compounds and compositions have valuable pharmaceutical properties, in particular the ability to inhibit kinases.

50 Claims, No Drawings

FOREIGN PATENT DOCUMENTS

| WO | WO95/10513 | 4/1995 |
|---|---|---|
| WO | WO96/06840 | 3/1996 |
| WO | WO98/06703 | 2/1998 |
| WO | WO98/22457 | 5/1998 |
| WO | 9822457 | * 5/1998 |
| WO | WO98/47899 | 10/1998 |
| WO | WO99/20624 | 4/1999 |
| WO | WO01/30774 | 10/1999 |
| WO | WO99/51231 | 10/1999 |
| WO | WO99/51232 | 10/1999 |
| WO | WO99/51234 | 10/1999 |
| WO | WO99/51595 | 10/1999 |
| WO | WO99/58518 | 11/1999 |
| WO | WO00/17202 | 3/2000 |
| WO | WO00/40547 | 7/2000 |
| WO | WO00/75117 | 12/2000 |
| WO | WO01/02369 | 1/2001 |
| WO | WO01/30774 | 5/2001 |
| WO | WO01/47922 | 7/2001 |
| WO | WO01/53268 | 7/2001 |
| WO | WO01/60816 | 8/2001 |
| WO | WO01/62252 | 8/2001 |
| WO | WO01/30774 | 10/2001 |
| WO | WO01/72720 | 10/2001 |
| WO | WO01/96336 | 12/2001 |
| WO | WO02/10137 | 2/2002 |
| WO | WO01/30774 | 3/2002 |
| WO | WO02/22601 | 3/2002 |
| WO | WO02/22602 | 3/2002 |
| WO | WO02/22603 | 3/2002 |
| WO | WO02/22604 | 3/2002 |
| WO | WO02/22605 | 3/2002 |
| WO | WO02/22606 | 3/2002 |
| WO | WO02/22607 | 3/2002 |
| WO | WO03/000688 | 1/2003 |

OTHER PUBLICATIONS

Chemical ASbstract DN 132:317221, also cited as J. Am. Chem. Soc., 122/15,3671–3678(2000).*

Chemical Abstract DN 132:303464, also cited as J. Receptor & Signal Transduction Research, 20/1,105–118(2000).*

Cecil TextBook of Medicine, 20$^{th}$ edition, vol. 2, pp. 19921996(1996).*

PubMed Abstract 12467573, also cited as Structure(Camb), 1 '0/12,1659–67(2002).*

PubMed Abstract 14522925, also cited as Cancer res., 63/18,5978–91(2003).*

U.S. Appl. No. 09/847,962, filed May 2, 2001, Li.

Busev et al.. Extraction–Photometric Determination of Molybdenum by Means of 6.7–Dihydroxy–2,4–Diphenylbenzopyrillum Chloride, Zhum. Analit. Khimii, vol. 16, pp. 571–577, 1961.

Chumakov, Yu I. et al., 3–Formyl–7–Azaindoles, Byulleten Izobretnii Tovamykh Znakor, V. 10, p. 22, 1964, Su 162534.

Clark, B. A. J. et al., Mass Spectrometry of Pyrrolo[2,3–b] pyrazines and Pyraziono[2,3–b]indole, Org. Mass Spectrom, vol. 12(7), pp. 421–423, 1977.

Clark, Bernard A. J. et al., Preparation of pyrrolo[2,3–b] pyrazines and pyrazino[2,3–b]indole. Chemistry and Industry (London), 1975, pp. 215–216.

Clark, B. A. J. et al., Formation of Certain Substituted 5H–Pyrrolo[2,3–b]pyrazines by Thermal Cyclisaton of Pyrazinlhydrazones and a Route to 5H–Pyrazino[2,3–b] indole: a Synthesis of 5H–Pyrrolo[2,3–b] pyrazine and Some of its Properties, Journal of Chemical Society, Perkin Transactions 1, vol. 1(13), pp. 1361–1363, 1976.

Davis, Michael L. et al., Reactions of beta–Lihiomethyl)azines with Nitriles as a Route to Pyrrolo–pyridines, –quinolines, –pyrazines, –quinoxalines and –pyrimidines, Tetrahedron, vol. 48, No. 5, pp. 939–952, 1992.

Hands, David et al., A Convenient Method of the Preparation for 5–, 6–and 7–Azaindoles and Their Derivatives, Synthesis, Jul. 1996, (Jul. 1996), pp. 877–882.

Hardy, O. R. et al., Ring Opening or Rearrangement vs. N–Oxidation in the Action of Peracids upon Pyrrolo[2,3b] pyridines, Pyrrolo[2,3b]pyrazines, & Triazolo[1,5–a]–& Triazolo[4,3–a]–pyrazine. Some Chemical and Spectroscopic Properties of the Triazolopyrazines & Their N–Oxides, J.C.S., Perkin Trans.1. 506–511, 1980.

Henry, James R. et al., 6–amino–2(4–flurophnyl)–4–methoxy–3–(4–pyridyl)–1H–pyrrolo[2,3b]pyrdine (RWY 68354): A Potent and Selective p38 Kinase Inhibitor, J. Med. Chem., vol. 41, No. 22, 4196–4198, 1998.

Herbert, R. et al., 1H–Pyrrolo[2,3–b]pyridines. Part II. Fragmentation of Some 1H–Pyrrolo[2,3–b]pyridines induced by Electron Impact, Journal of the Chemical Society Sect. B. Physical Organic, 1970, vol. 3, pp. 459–463.

Herbert, R. et al., Syntheses and Properties of 1H–Pyrrolo [2,3–b]pyridines, J. Chem. Soc., 1969, pp. 1505–1514.

Kruse, C. G. et al., Furo– and Thieno[2,3–b]pyrazines, Part 2. Chemical Properties of 2–Substituted Derivatives, Recueil des Travaux Chimiques des Pays–Bas, Journal of the Royal Netherlands Chemical Society, vol. 97(6), pp. 151–155, 1978.

Marot, Christophe et al., Pharmacophoric Search and 3D–QSAR Comparative Molecular Field Analysis Studies on Agonist of Melatonin Sheep Receptors, J. Med. Chem., vol. 41, No. 23, pp. 4453–4465, 1998.

Martin, par Christian et al., Reactions Selectives de L'O.Chlorobenzonitrile : SNAr, Tetrahedron Letters, vol. 30, No. 8, pp. 935–936, 1989.

Park, Sang Sun et al., A Facile Synthesis of 2,3–Disubstituted Pyrrolo[2,3–b]pyridines via Palladium–Catalyzed Heteroannulaton with Internal Alkynes, Tetrahedron Letters, NL, Elsevier Science Publishers, vol. 39, No. 7, pp. 627–630, 1998.

Protiva, Miroslav et al., Anthistaminove latky XXVI. Nekolik novych heterocyklickych derivatu ethylendiaminu, Chem. Listy, vol. 46, pp. 551–554, 1952.

Rubtsov, M.V. et al., Preparaton of Vinylpyridines, Byulleten Izobretnii i Tovarnykh Znakor, V. 10, p. 22, 1964, Su 162535.

Vierfond, par Jean–Michel et al., Cyclisation par Amination Intramoleculaire Dane la Serie de la Pyrazine, Tetrahedron Letters, vol. 22, No. 13, pp. 1219–1222, 1981.

* cited by examiner

AZAINDOLES

This application is entitled to the benefit of earlier filed applications GB 0115109.1, filed Jun. 21, 2001, and U.S. No. 60/300,257 filed Jun. 22, 2001.

This invention is directed to substituted azaindoles, their preparation, pharmaceutical compositions containing these compounds, and their pharmaceutical use in the treatment of disease states capable of being modulated by the inhibition of the protein kinases.

Protein kinases participate in the signalling events which control the activation, growth and differentiation of cells in response to extracellular mediators and to changes in the environment. In general, these kinases fall into several groups; those which preferentially phosphorylate serine and/or threonine residues and those which preferentially phosphorylate tyrosine residues [S. K. Hanks and T. Hunter, FASEB. J., 1995, 9, pages 576–596]. The serine/threonine kinases include for example, protein kinase C isoforms [A. C. Newton, J. Biol. Chem., 1995, 270, pages 28495–28498] and a group of cyclin-dependent kinases such as cdc2 [J. Pines, Trends in Biochemical Sciences, 1995, 18, pages 195–197]. The tyrosine kinases include membrane-spanning growth factor receptors such as the epidermal growth factor receptor [S. Iwashita and M. Kobayashi, Cellular Signalling, 1992, 4, pages 123–132], and cytosolic non-receptor kinases such as p56tck, p59fYn, ZAP-70 and csk kinases [C. Chan et. al., Ann. Rev. Immunol., 1994,12, pages 555–592]. Inappropriately high protein kinase activity has been implicated in many diseases resulting from abnormal cellular function. This might arise either directly or indirectly, for example by failure of the proper control mechanisms for the kinase, related for example to mutation, over-expression or inappropriate activation of the enzyme; or by over- or underproduction of cytokines or growth factors also participating in the transduction of signals upstream or downstream of the kinase. In all of these instances, selective inhibition of the action of the kinase might be expected to have a beneficial effect. Spleen tyrosine kinase (Syk) is a 72-kDa cytoplasmic protein tyrosine kinase that is expressed in a variety of hematopoietic cells and is an essential element in several cascades that couple antigen receptors to cellular responses. Thus, Syk plays a pivotal role in signalling of the high affinity IgE receptor, FcεR1, in mast cells and in receptor antigen signalling in T and B lymphocytes. The signal transduction pathways present in mast, T and B cells have common features. The ligand binding domain of the receptor lacks intrinsic tyrosine kinase activity. However, they interact with transducing subunits that contain immunoreceptor tyrosine based activation motifs (ITAMs) [M. Reth, Nature, 1989, 338, pages 383–384]. These motifs are present in both the β and γ subunits of the FcεR1, in the ξ-subunit the of T cell receptor (TCR) and in the IgGα and IgGβ subunits of the B cell receptor (BCR). [N. S. van Oers and A. Weiss, Seminars in Immunology, 1995, 7, pages 227–236] Upon binding of antigen and multimerization, the ITAM residues are phosphorylated by protein tyrosine kinases of the Src family. Syk belongs to a unique class of tyrosine kinases that have two tandem Src homology 2 (SH2) domains and a C terminal catalytic domain. These SH2 domains bind with high affinity to ITAMs and this SH2-mediated association of Syk with an activated receptor stimulates Syk kinase activity and localises Syk to the plasma membrane.

In Syk deficient mice, mast cell degranulation is inhibited, suggesting that this is an important target for the development of mast cell stabilising agents [P. S. Costello, Oncogene, 1996, 13, pages 2595–2605]. Similar studies have demonstrated a critical role for Syk in BCR and TCR signalling [A. M. Cheng, Nature, 1995, 378, pages 303–306, (1995) and D. H. Chu et al., Immunological Reviews, 1998, 165, pages 167–180]. Syk also appears to be involved in eosinophil survival in response to IL-5 and GM-CSF [S. Yousefi et al., J. Exp. Med., 1996, 183, pages 1407–1414]. Despite the key role of Syk in mast cell, BCR and T cell signalling, little is known about the mechanism by which Syk transmits downstream effectors. Two adaptor proteins, BLNK (B cell Linker protein, SLP-65) and SLP-76 have been shown to be substrates of Syk in B cells and mast cells respectively and have been postulated to interface Syk with downstream effectors [M. Ishiai et al., Immunity, 1999, 10, pages 117–125 and L. R. Hendricks-Taylor et al., J. Biol. Chem, 1997, 272, pages 1363–1367]. In addition Syk appears to play an important role in the CD40 signalling pathway, which plays an important role in B cell proliferation [M. Faris et al., J. Exp. Med., 1994, 179, pages 1923–1931].

Syk is further involved in the activation of platelets stimulated via the low-affinity IgG receptor (Fc gamma-RIIA) or stimulated by collagen [F. Yanaga et al., Biochem. J., 1995, 311, (Pt. 2) pages 471–478].

Focal adhesion kinase (FAK) is a non-receptor tyrosine kinase involved in integrin-mediated signal transduction pathways. FAK colocalizes with integrins in focal contact sites and FAK activation and its tyrosine phosphorylation have been shown in many cell types to be dependent on integrins binding to their extracellular ligands. Results from several studies support the hypothesis that FAK inhibitors could be useful in cancer treatment. For example, FAK-deficient cells migrate poorly in response to chemotactic signals and overexpression of C-terminal domain of FAK blocks cell spreading as well as chemotactic migration (Sieg et al, J. Cell Science, 1999, 112, 2677–2691; Richardson A. and Parsons T., Cell, 1997, 97, 221–231); in addition, tumor cells treated with FAK antisense oligonucleotides lost their attachment and underwent apoptosis (Xu et al, Cell Growth Differ. 1996, 4, 413–418). FAK has been reported to be overexpressed in prostate, breast, thyroid, colon and lung cancers. The level of expression of FAK is directly correlated with tumors demonstrating the most aggressive phenotype.

Angiogenesis or the formation of new blood vessels by sprouting from the preexisting vasculature is of central importance for embryonic development and organogenesis. Abnormal enhanced neovascularization is observed in rheumatoid arthritis, diabetic retinopathy and during tumor development (Folkman, Nat. Med., 1995, 1, 27–31.). Angiogenesis is a complex multistage process which includes activation, migration, proliferation and survival of endothelial cells. Extensive studies in the field of tumor angiogenesis in the past two decades have identified a number of therapeutic targets including kinases, proteases and integrins resulting in the discovery of many new anti-angiogenic agents, including kinase insert domain-containing receptor (KDR, also known as VEGFR-2, vascular endothelial growth factor receptor-2) inhibitors some of which are currently under clinical evaluation (Jekunen, et al Cancer Treatment Rev. 1997, 23, 263–286.). Angiogenesis inhibitors may be used in frontline, adjuvant and even preventive settings for the emergence or regrowth of malignancies.

Several proteins involved in chromosome segregation and spindle assembly have been identified in yeast and drosophila. Disruption of these proteins results in chromosome missegregation and monopolar or disrupted spindles.

Among these kinases are the Ipl1 and aurora kinases from *S. cerevisiae* and drosophila respectively, which are required for centrosome separation and chromosome segregation. One human homologue of yeast Ipl1 was recently cloned and characterized by different laboratories. This kinase termed Aurora2, STK15 or BTAK belongs to the serine/threonine kinase family. Bischoff et al showed that Aurora2 is oncogenic and is amplified in human colorectal cancers (EMBO J, 1998, 17, 3052–3065). It has also been exemplified in cancers involving epithelial tumors such as breast cancer.

The type 1 insulin-like growth factor receptor (IGF1R) is a transmembrane receptor tyrosine kinase that binds primarily to IGF1 but also to IGF2 and insulin with lower affinity. Binding of IGF1 to its receptor results in receptor oligomerization, activation of tyrosine kinase, intermolecular receptor autophosphorylation and phosphorylation of cellular substrates (its two major substrates are IRS1 and Shc). The ligand-activated IGF1R induces mitogenic activity in normal cells. Several clinical reports underline the important role of the IGF-I pathway in human tumor development: (i) IGF-I-R over-expression is frequently found in various tumors (for example breast, colon, lung, skin, sarcoma) and is often associated with an aggressive phenotype; (ii) high circulating IGF1 concentrations are strongly correlated with prostate, lung and breast cancer risk; (iii) epidemiological studies implicate the IGF1 axis as a predisposing factor in the pathogenesis of breast and prostate cancer [Baserga R. The IGF-I receptor in cancer research, Exp Cell Res. (1999) 253:1–6; Baserga R. The contradictions of the IGF1-Receptor, Oncogene (2000) 19: 5574–81; Khandwala H M. et al. The effects of IGFs on tumorigenesis and neoplastic growth, Endocrine Reviews (2000) 21: 215–44; Adams T E et al. Structure and function of the IGF1R, CMLS (2000) 57: 1050–93.]

International Application Number PCT/US/00/15181, filed Jun. 2, 2000, dicloses a series of 2-substituted benzimidazoles, indoles, benzoxazoles, and benzothiazoles which are reported to be useful for inhibiting cell death.

We have now found a novel group of substituted azaindoles, which have valuable pharmaceutical properties, in particular, the ability to inhibit protein kinases, more particularly, the ability to inhibit Syk kinase, Aurora2, KDR, FAK and IGF1R.

Thus, in one aspect, the present invention is directed to pharmaceutical compositions comprising compounds of general formula (I):

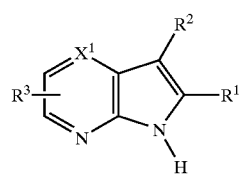

(I)

wherein:

$R^1$ represents aryl or heteroaryl each optionally substituted by one or more groups selected from alkylenedioxy, alkenyl, alkenyloxy, alkynyl, aryl, cyano, halo, hydroxy, heteroaryl, heterocycloalkyl, nitro, $R^4$, —C(=O)—R, —C(=O)—OR$^5$, —C(=O)—NY$^1$Y$^2$, —NY$^1$Y$^2$, —N(R$^6$)—C(=O)—R$^7$, —N(R$^6$)—C(=O)—NY$^3$Y$^4$, —N(R$^6$)—C(=O)—OR$^7$, —N(R$^6$)—SO$_2$—R$^7$, —N(R$^6$)—SO$_2$—NY$^3$Y$^4$, —SO$_2$—NY$^1$Y$^2$ and —Z$^2$R;

$R^2$ represents hydrogen, acyl, cyano, halo, lower alkenyl, —Z$^2$R$^4$, —SO$_2$NY$^3$Y$^4$, —NY$^1$Y$^2$ or lower alkyl optionally substituted by a substituent selected from aryl, cyano, heteroaryl, heterocycloalkyl, hydroxy, —Z$^2$R$^4$, —C(=O)—NY$^1$Y$^2$, —C(=O)—R, —CO$_2$R$^8$, —NY$^3$Y$^4$, —N(R$^6$)—C(=O)—R, —N(R$^6$)—C(=O)—NY$^1$Y$^2$, —N(R$^6$)—C(=O)—OR$^7$, —N(R$^6$)—SO$_2$—R$^7$, —N(R$^6$)—SO$_2$—NY$^3$Y$^4$, —SO$_2$NY$^1$Y$^2$ and one or more halogen atoms;

$R^3$ represents hydrogen, aryl, cyano, halo, heteroaryl, lower alkyl, —Z$^2$R$^4$, —C(=O)—OR$^5$ or —C(=O)—NY$^3$Y$^4$;

$R^4$ represents alkyl, cycloalkyl, cycloalkylalkyl, heterocycloalkyl or heterocycloalkylalkyl each optionally substituted by a substituent selected from aryl, cycloalkyl, cyano, halo, heteroaryl, heterocycloalkyl, —CHO (or a 5-, 6- or 7-membered cyclic acetal derivative thereof), —C(=O)—NY$^1$Y$^2$, —C(=O)—OR$^5$, —NY$^1$Y$^2$, —N(R$^6$)—C(=O)—R$^7$, —N(R$^6$)—C(=O)—NY$^3$Y$^4$, —N(R$^6$)—SO$_2$—R$^7$, —N(R$^6$)—SO$_2$—NY$^3$Y$^4$, —Z$^3$R$^7$ and one or more groups selected from hydroxy, alkoxy and carboxy;

$R^5$ represents hydrogen, alkyl, alkenyl, aryl, arylalkyl, heteroaryl or heteroarylalkyl;

$R^6$ represents hydrogen or lower alkyl;

$R^7$ represents alkyl, aryl, arylalkyl, cycloalkyl, cycloalkylalkyl, heteroaryl, heteroarylalkyl, heterocycloalkyl or heterocycloalkylalkyl;

$R^8$ represents hydrogen or lower alkyl;

R represents aryl or heteroaryl; alkenyl; or alkyl, cycloalkyl, cycloalkylalkyl, heterocycloalkyl or heterocycloalkylalkyl each optionally substituted by a substituent selected from aryl, cycloalkyl, cyano, halo, heteroaryl, heterocycloalkyl, —CHO (or a 5-, 6- or 7-membered cyclic acetal derivative thereof), —C(=O)—NY$^1$Y$^2$, —C(=O)—OR$^5$, —NY$^1$Y$^2$, —N(R$^6$)—C(=O)—R$^7$, —N(R$^6$)—C(=O)—NY$^3$Y$^4$, —N(R$^6$)—SO$_2$—R$^7$, —N(R$^6$)—SO$_2$—NY$^3$Y$^4$, —Z$^3$R$^7$ and one or more groups selected from hydroxy, alkoxy and carboxy;

$X^1$ represents N, CH, C-aryl, C-heteroaryl, C-heterocycloalkyl, C-heterocycloalkenyl, C-halo, C—CN, C—R$^4$, C—NY$^1$Y$^2$, C—OH, C—Z$^2$R, C—C(=O)—R, C—C(=O)—OR$^5$, C—C(=O)—NY$^1$Y$^2$, C—N(R$^8$)—C(=O)—R, C—N(R$^6$)—C(=O)—OR$^7$, C—N(R$^6$)—C(=O)—NY$^3$Y$^4$, C—N(R$^6$)—SO$_2$—NY$^3$Y$^4$, C—N(R$^6$)—SO$_2$—R, C—SO$_2$—NY$^3$Y$^4$, C—NO$_2$, or C-alkenyl or C-alkynyl optionally substituted by aryl, cyano, halo, hydroxy, heteroaryl, heterocycloalkyl, nitro, —C(=O)—NY$^1$Y$^2$, —C(=O)—OR$^5$, —NY$^1$Y$^2$, —N(R$^6$)—C(=O)—R$^7$, —N(R$^6$)—C(=O)—NY$^3$Y$^4$, —N(R$^6$)—C(=O)—OR$^7$, —N(R$^6$)—SO$_2$—R$^7$, —N(R$^6$)—SO$_2$—NY$^3$Y$^4$, —SO$_2$—NY$^1$Y$^2$ and —Z$^2$R$^4$;

$Y^1$ and $Y^2$ are independently hydrogen, alkenyl, aryl, cycloalkyl, heteroaryl or alkyl optionally substituted by one or more groups selected from aryl, halo, heteroaryl, heterocycloalkyl, hydroxy, —C(=O)—NY$^3$Y$^4$, —C(=O)—OR$^5$, —NY$^3$Y$^4$, —N(R$^6$)—C(=O)—R$^7$, —N(R$^6$)—C(=O)—NY$^3$Y$^4$, —N(R$^6$)—SO$_2$—R$^7$, —N(R$^6$)—SO$_2$—NY$^3$Y$^4$ and —OR$^7$; or the group —NY$^1$Y$^2$ may form a cyclic amine;

$Y^3$ and $Y^4$ are independently hydrogen, alkenyl, alkyl, aryl, arylalkyl, cycloalkyl, heteroaryl or heteroarylalkyl; or the group —NY$^3$Y$^4$ may form a cyclic amine;

$Z^1$ represents O or S;

$Z^2$ represents O or S(O)$_n$;

$Z^3$ represents O, S(O)$_n$, NR$^6$;

n is zero or an integer 1 or 2;

and their corresponding N-oxides, and their prodrugs, and their acid bioisosteres; and pharmaceutically acceptable salts and solvates (e.g. hydrates) of such compounds and their N-oxides and their prodrugs, and their acid bioisosteres; together with one or more pharmaceutically acceptable carriers or excipients.

In another aspect, the invention concerns the compounds of formula (I) as defined above, but excluding the compounds 2-phenyl-1H-pyrrolo[2,3-b]pyridine, 2-(4-bromophenyl)-3-methyl-1H-pyrrolo[2,3-b]pyridine, 4-(3-methyl-1H-pyrrolo[2,3-b]pyridin-2-yl)-benzoic acid methyl ester, 2-(4-chloro-phenyl)-1H-pyrrolo[2,3-b]pyridine, 2-(4-methoxy-phenyl)-1H-pyrrolo[2,3-b]pyridine, 5-methyl-2-phenyl-1H-pyrrolo[2,3-b]pyridine, 4-methyl-2-phenyl-1H-pyrrolo[2,3-b]pyridine, 2-pyridin-3-yl-1H-pyrrolo[2,3-b]pyridine, 4-(3-methyl-1H-pyrrolo[2,3-b]pyridin-2-yl)-benzoic acid, 2-(4-methoxy-phenyl)-3-methyl-1H-pyrrolo[2,3-b]pyridine, 2-(4-methyl-phenyl)-3-methyl-1H-pyrrolo[2,3-b]pyridine, 4-(3-methyl-1H-pyrrolo[2,3-b]pyridin-2-yl)-benzoic acid isopropyl ester, 2-phenyl-3-methyl-1H-pyrrolo[2,3-b]pyridine, 5-bromo-2-phenyl-3-methyl-1H-pyrrolo[2,3-b]pyridine, 6-chloro-2-phenyl-1H-pyrrolo[2,3-b]pyridine, 6-chloro-4-methyl-2-phenyl-1H-pyrrolo[2,3-b]pyridine, 4-methyl-2-phenyl-1H-pyrrolo[2,3-b]pyridin-3-yl-carboxaldehyde, 2-phenyl-1H-pyrrolo[2,3-b]pyridin-3-yl-acetonitrile, 2-phenyl-3-prop-1-enyl-1H-pyrrolo[2,3-b]pyridine, 4-methyl-2-phenyl-1H-pyrrolo[2,3-b]pyridin-3-yl-carboxaldehyde, dimethyl-(2-phenyl-1H-pyrrolo[2,3-b]pyridin-3-ylmethyl)-amine, 2,2'-diphenyl-1H,1'H-[3,3']bi[pyrrolo[2,3-b]pyridinyl], 2-(2-phenyl-1H-pyrrolo[2,3-b]pyridin-3-yl)-acetamide, 3-allyl-2-phenyl-1H-pyrrolo[2,3-b]pyridine, (2-phenyl-1H-pyrrolo[2,3-b]pyridin-3-yl)-acetonitrile, 2-phenyl-1H-pyrrolo[2,3-b]pyridine-3-carbaldehyde, 3-morpholin-4-ylmethyl-2-phenyl-1H-pyrrolo[2,3-b]pyridine, N-[2-(2-phenyl-1H-pyrrolo[2,3-b]pyridin-3-yl)-ethyl]-acetamide, 6-phenyl-5H-pyrrolo[2,3-b]pyrazine, 6-(4-methoxy-phenyl)-5H-pyrrolo[2,3-b]pyrazine, 6-(4-chloro-phenyl)-5H-pyrrolo[2,3-b]pyrazine, 6-(2-chloro-phenyl)-5H-pyrrolo[2,3-b]pyrazine, 3-methyl-6-phenyl-5H-pyrrolo[2,3-b]pyrazine, 2-methyl-6-phenyl-5H-pyrrolo[2,3-b]pyrazine and 7-methyl-6-phenyl-5H-pyrrolo[2,3-b]pyrazine.

In the present specification, the term "compounds of the invention", and equivalent expressions, are meant to embrace compounds of general formula (I) as hereinbefore described, which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

As used above, and throughout the description of the invention, the following terms, unless otherwise indicated, shall be understood to have the following meanings:

"Patient" includes both human and other mammals.

"Acid bioisostere" means a group which has chemical and physical similarities producing broadly similar biological properties to a carboxy group (see Lipinski, Annual Reports in Medicinal Chemistry, 1986,21,p283 "Bioisosterism In Drug Design"; Yun, Hwahak Sekye, 1993, 33, pages 576–579 "Application Of Bioisosterism To New Drug Design"; Zhao, Huaxue Tongbao, 1995, pages 34–38 "Bioisosteric Replacement And Development Of Lead Compounds In Drug Design"; Graham, Theochem, 1995, 343, pages 105–109 "Theoretical Studies Applied To Drug Design:ab initio Electronic Distributions In Bioisosteres"). Examples of suitable acid bioisosteres include: —C(=O)—NHOH, —C(=O)—CH$_2$OH, —C(=O)—CH$_2$SH, —C(=O)—NH—CN, sulfo, phosphono, alkylsulfonylcarbamoyl, tetrazolyl, arylsulfonylcarbamoyl, heteroarylsulfonylcarbamoyl, N-methoxycarbamoyl, 3-hydroxy-3-cyclobutene-1,2-dione, 3,5-dioxo-1,2,4-oxadiazolidinyl or heterocyclic phenols such as 3-hydroxyisoxazolyl and 3-hydoxy-1-methylpyrazolyl.

"Acyl" means an H—CO— or alkyl-CO— group in which the alkyl group is as described herein.

"Acylamino" is an acyl-NH— group wherein acyl is as defined herein.

"Alkenyl" means an aliphatic hydrocarbon group containing a carbon-carbon double bond and which may be straight or branched having about 2 to about 15 carbon atoms in the chain. Preferred alkenyl groups have 2 to about 12 carbon atoms in the chain; and more preferably 2 to about 6 carbon atoms (e.g. 2 to 4 carbon atoms) in the chain. "Branched," as used herein and throughout the text, means that one or more lower alkyl groups such as methyl, ethyl or propyl are attached to a linear chain; here a linear alkenyl chain. "Lower alkenyl" means about 2 to about 4 carbon atoms in the chain, which may be straight or branched. Exemplary alkenyl groups include ethenyl, propenyl, n-butenyl, i-butenyl, 3-methylbut-2-enyl, n-pentenyl, heptenyl, octenyl, cyclohexylbutenyl and decenyl.

"Alkenyloxy" is an alkenyl-O— group wherein alkenyl is as defined above. Exemplary alkenyloxy groups include allyloxy.

"Alkoxy" means an alkyl-O— group in which the alkyl group is as described herein. Exemplary alkoxy groups include difluoromethoxy, methoxy, trifluoromethoxy, ethoxy, n-propoxy, i-propoxy, n-butoxy and heptoxy.

"Alkoxycarbonyl" means an alkyl-O—CO— group in which the alkyl group is as described herein. Exemplary alkoxycarbonyl groups include methoxy- and ethoxycarbonyl.

"Alkyl" means, unless otherwise specified, an aliphatic hydrocarbon group which may be straight or branched chain having about 1 to about 15 carbon atoms in the chain, optionally substituted by one or more halogen atoms. Particular alkyl groups have from 1 to about 6 carbon atoms. "Lower alkyl" as a group or part of a lower alkoxy, lower alkylthio, lower alkylsulfinyl or lower alkylsulfonyl group means unless otherwise specified, an aliphatic hydrocarbon group which may be a straight or branched chain having 1 to about 4 carbon atoms in the chain. Exemplary alkyl groups include methyl, ethyl, n-propyl, i-propyl, n-butyl, s-butyl, t-butyl, n-pentyl, 3-pentyl, heptyl, octyl, nonyl, decyl and dodecyl. Exemplary alkyl groups substituted by one or more halogen atoms include trifluoromethyl.

"Alkylene" means an aliphatic bivalent radical derived from a straight or branched alkyl group, in which the alkyl group is as described herein. Exemplary alkylene radicals include methylene, ethylene and trimethylene.

"Alkylenedioxy" means an —O-alkylene-O— group in which alkylene is as defined above. Exemplary alkylenedioxy groups include methylenedioxy and ethylenedioxy.

"Alkylsulfinyl" means an alkyl-SO— group in which the alkyl group is as previously described. Preferred alkylsulfinyl groups are those in which the alkyl group is $C_{1-4}$alkyl.

"Alkylsulfonyl" means an alkyl-SO$_2$— group in which the alkyl group is as previously described. Preferred alkylsulfonyl groups are those in which the alkyl group is $C_{1-4}$alkyl.

"Alkylsulfonylcarbamoyl" means an alkyl-SO$_2$—NH—C(=O)— group in which the alkyl group is as previously described. Preferred alkylsulfonylcarbamoyl groups are those in which the alkyl group is $C_{1-4}$alkyl.

"Alkylthio" means an alkyl-S— group in which the alkyl group is as previously described. Exemplary alkylthio groups include methylthio, ethylthio, isopropylthio and heptylthio.

"Alkynyl" means an aliphatic hydrocarbon group containing a carbon-carbon triple bond and which group may be a straight or branched chain having about 2 to about 15 carbon atoms in the chain. Preferred alkynyl groups have 2 to about 12 carbon atoms in the chain; and more preferably 2 to about 6 carbon atoms (e.g. 2 to 4 carbon atoms) in the chain. Exemplary alkynyl groups include ethynyl, propynyl, n-butynyl, i-butynyl, 3-methylbut-2-ynyl, and n-pentynyl.

"Aroyl" means an aryl-CO— group in which the aryl group is as described herein. Exemplary aroyl groups include benzoyl and 1- and 2-naphthoyl.

"Aroylamino" is an aroyl-NH— group wherein aroyl is as previously defined.

"Aryl" as a group or part of a group denotes: (i) an optionally substituted monocyclic or multicyclic aromatic carbocyclic moiety of about 6 to about 14 carbon atoms, such as phenyl or naphthyl; or (ii) an optionally substituted partially saturated multicyclic aromatic carbocyclic moiety in which an aryl and a cycloalkyl or cycloalkenyl group are fused together to form a cyclic structure, such as a tetrahydronaphthyl, indenyl or indanyl ring. Except where otherwise defined, aryl groups may be substituted with one or more aryl group substituents, which may be the same or different, where "aryl group substituent" includes, for example, acyl, acylamino, alkoxy, alkoxycarbonyl, alkylenedioxy, alkylsulfinyl, alkylsulfonyl, alkylthio, aroyl, aroylamino, aryl, arylalkyloxy, arylalkyloxycarbonyl, arylalkylthio, aryloxy, aryloxycarbonyl, arylsulfinyl, arylsulfonyl, arylthio, carboxy (or an acid bioisostere), cyano, halo, heteroaroyl, heteroaryl, heteroarylalkyloxy, heteroaroylamino, heteroaryloxy, hydroxy, nitro, trifluoromethyl, —NY$^3$Y$^4$, —CONY$^3$Y$^4$, —SO$_2$NY$^3$Y$^4$, —NY$^3$—C(=O)alkyl, —NY$^3$SO$_2$alkyl or alkyl optionally substituted with aryl, heteroaryl, hydroxy, or —NY$^3$Y$^4$.

"Arylalkyl" means an aryl-alkyl-group in which the aryl and alkyl moieties are as previously described. Preferred arylalkyl groups contain a $C_{1-4}$alkyl moiety. Exemplary arylalkyl groups include benzyl, 2-phenethyl and naphthlenemethyl.

"Arylalkyloxy" means an arylalkyl-O— group in which the arylalkyl group is as previously described. Exemplary arylalkyloxy groups include benzyloxy and 1- or 2-naphthalenemethoxy.

"Arylalkyloxycarbonyl" means an arylalkyl-O—CO— group in which arylalkyl is as previously described. An exemplary arylalkyloxycarbonyl group is benzyloxycarbonyl.

"Arylalkylthio" means an arylalkyl-S— group in which the arylalkyl group is as previously described. An exemplary arylalkylthio group is benzylthio.

"Aryloxy" means an aryl-O— group in which the aryl group is as previously described. Exemplary aryloxy groups include phenoxy and naphthoxy, each optionally substituted.

"Aryloxycarbonyl" means an aryl-O—C(=O)— group in which the aryl group is as previously described. Exemplary aryloxycarbonyl groups include phenoxycarbonyl and naphthoxycarbonyl.

"Arylsulfinyl" means an aryl-SO— group in which the aryl group is as previously described.

"Arylsulfonyl" means an aryl-SO$_2$— group in which the aryl group is as previously described.

"Arylsulfonylcarbamoyl" means an aryl-SO$_2$—NH—C(=O)— group in which the aryl group is as previously described.

"Arylthio" means an aryl-S— group in which the aryl group is as previously described. Exemplary arylthio groups include phenylthio and naphthylthio.

"Azaheteroaryl" means an aromatic carbocyclic moiety of about 5 to about 10 ring members in which one of the ring members is nitrogen and the other ring members are selected from carbon, oxygen, sulfur, and nitrogen. Examples of azaheteroaryl groups include benzimidazolyl, imidazolyl, indazolinyl, indolyl, isoquinolinyl, pyridyl, pyrimidinyl, pyrrolyl, quinolinyl, quinazolinyl and tetrahydroindolizinyl.

"Cyclic amine" means a 3 to 8 membered monocyclic cycloalkyl ring system wherein one of the ring carbon atoms is replaced by nitrogen and which (i) may also contain a further heteroatom-containing group selected from O, S, SO$_2$, or NY$^7$ (where Y$^7$ is hydrogen, alkyl, aryl, arylalkyl, —C(=O)—R$^7$, —C(=O)—OR$^7$ or —SO$_2$R$^7$); and (ii) may be fused to additional aryl (e.g. phenyl), heteroaryl (e.g. pyridyl), heterocycloalkyl or cycloalkyl rings to form a bicyclic or tricyclic ring system. Exemplary cyclic amines include pyrrolidine, piperidine, morpholine, piperazine, indoline, pyrindoline, tetrahydroquinoline and the like groups.

"Cycloalkenyl" means a non-aromatic monocyclic or multicyclic ring system containing at least one carbon-carbon double bond and having about 3 to about 10 carbon atoms. Exemplary monocyclic cycloalkenyl rings include cyclopentenyl, cyclohexenyl and cycloheptenyl.

"Cycloalkyl" means a saturated monocyclic or bicyclic ring system of about 3 to about 10 carbon atoms, optionally substituted by oxo. Exemplary monocyclic cycloalkyl rings include $C_{3-8}$cycloalkyl rings such as cyclopropyl, cyclopentyl, cyclohexyl and cycloheptyl.

"Cycloalkylalkyl" means a cycloalkyl-alkyl-group in which the cycloalkyl and alkyl moieties are as previously described. Exemplary monocyclic cycloalkylalkyl groups include cyclopropylmethyl, cyclopentylmethyl, cyclohexylmethyl and cycloheptylmethyl.

"Halo" or "halogen" means fluoro, chloro, bromo, or iodo. Preferred are fluoro and chloro.

"Heteroaroyl" means a heteroaryl-C(=O)— group in which the heteroaryl group is as described herein. Exemplary heteroaryl groups include pyridylcarbonyl.

"Heteroaroylamino" means a heteroaroyl-NH— group in which the heteroaryl moiety is as previously described.

"Heteroaryl" as a group or part of a group denotes: (i) an optionally substituted aromatic monocyclic or multicyclic organic moiety of about 5 to about 10 ring members in which one or more of the ring members is/are element(s) other than carbon, for example nitrogen, oxygen or sulfur (examples of such groups include benzimidazolyl, benzthiazolyl, furyl, imidazolyl, indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl and triazolyl groups, optionally substituted by one or more aryl group substituents as defined above except where otherwise defined); (ii) an optionally substituted partially saturated multicyclic heterocarbocyclic moiety in which a heteroaryl and a cycloalkyl or cycloalkenyl group are fused together to form a cyclic structure (examples of such groups include pyrindanyl groups, optionally substituted by one or more "aryl group substituents" as defined above, except where otherwise defined). Optional substituents include one or more "aryl group substituents" as defined above, except where otherwise defined.

"Heteroarylalkyl" means a heteroaryl-alkyl-group in which the heteroaryl and alkyl moieties are as previously described. Preferred heteroarylalkyl groups contain a $C_{1-4}$alkyl moiety. Exemplary heteroarylalkyl groups include pyridylmethyl.

"Heteroarylalkyloxy" means a heteroarylalkyl-O— group in which the heteroarylalkyl group is as previously described. Exemplary heteroaryloxy groups include optionally substituted pyridylmethoxy.

"Heteroaryloxy" means a heteroaryl-O— group in which the heteroaryl group is as previously described. Exemplary heteroaryloxy groups include optionally substituted pyridyloxy.

"Heteroarylsulfonylcarbamoyl" means a heteroaryl-$SO_2$—NH—C(=O)— group in which the heteroaryl group is as previously described.

"Heterocycloalkenyl" means a cycloalkenyl group which contains one or more heteroatoms or heteroatom-containing groups selected from O, S and $NY^7$.

"Heterocycloalkyl" means: (i) a cycloalkyl group of about 3 to 7 ring members which contains one or more heteroatoms or heteroatom-containing groups selected from O, S and $NY^7$ and may be optionally substituted by oxo; (ii) a partially saturated multicyclic heterocarbocyclic moiety in which an aryl (or heteroaryl) ring, each optionally substituted by one or more "aryl group substituents," and a heterocycloalkyl group are fused together to form a cyclic structure. (Examples of such groups include chromanyl, dihydrobenzofuranyl, indolinyl and pyrindolinyl groups).

"Heterocycloalkylalkyl" means a heterocycloalkyl-alkyl-group in which the heterocycloalkyl and alkyl moieties are as previously described.

"Prodrug" means a compound which is convertible in vivo by metabolic means (e.g. by hydrolysis) to a compound of formula (I), including N-oxides thereof. For example an ester of a compound of formula (I) containing a hydroxy group may be convertible by hydrolysis in vivo to the parent molecule. Alternatively, an ester of a compound of formula (I) containing a carboxy group may be convertible by hydrolysis in vivo to the parent molecule.

Suitable esters of compounds of formula (I) containing a hydroxy group are, for example acetates, citrates, lactates, tartrates, malonates, oxalates, salicylates, propionates, succinates, fumarates, maleates, methylene-bis-β-hydroxynaphthoates, gentisates, isethionates, di-p-toluoyltartrates, methanesulfonates, ethanesulfonates, benzenesulfonates, p-toluenesulfonates, cyclohexylsulfamates and quinates.

Suitable esters of compounds of formula (I) containing a carboxy group are, for example, those described by F. J. Leinweber, Drug Metab. Res., 1987, 18, page 379.

Suitable esters of compounds of formula (I) containing both a carboxy group and a hydroxy group within the moiety -$L^1$-Y include lactones formed by loss of water between said carboxy and hydroxy groups. Examples of such lactones include caprolactones and butyrolactones.

An especially useful class of esters of compounds of formula (I) containing a hydroxy group, may be formed from acid moieties selected from those described by Bundgaard et. al., J. Med. Chem., 1989, 32, page 2503–2507, and include substituted (aminomethyl)-benzoates, for example dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl)benzoates, e.g. 3- or 4-(morpholinomethyl)-benzoates, and (4-alkylpiperazin-1-yl)benzoates, e.g. 3- or 4-(4-alkylpiperazin-1-yl)benzoates.

Where the compound of the invention contains a carboxy group, or a sufficiently acidic bioisostere, base addition salts may be formed and are simply a more convenient form for use; in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the patient in pharmaceutical doses of the salts, so that the beneficial inhibitory effects inherent in the free base are not vitiated by side effects ascribable to the cations. Pharmaceutically acceptable salts, including those derived from alkali and alkaline earth metal salts, within the scope of the invention include those derived from the following bases: sodium hydride, sodium hydroxide, potassium hydroxide, calcium hydroxide, aluminium hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris (hydroxymethyl)aminomethane, tetramethylammonium hydroxide, and the like.

Some of the compounds of the present invention are basic, and such compounds are useful in the form of the free base or in the form of a pharmaceutically acceptable acid addition salt thereof.

Acid addition salts are a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention include those derived from mineral acids and organic acids, and include hydrohalides, e.g. hydrochlorides and hydrobromides, sulfates, phosphates, nitrates, sulfamates, acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methane-sulfonates, ethanesulfonates, benzenesulfonates, p-toluenesulfonates, cyclohexylsulfamates and quinates.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

With reference to formula (I) above, the following are particular and preferred groupings:

$R^1$ may particularly represent optionally substituted heteroaryl, especially optionally substituted azaheteroaryl. Exemplary optionally substituted azaheteroaryls include indolyl, pyridyl, pyrrolyl, pyrazolyl, quinolinyl, isoquinolinyl, imidazolyl, indazolyl, indolizinyl, tetrahydroindolizinyl and indazolinyl. Optional substituents include one or more groups selected from alkylenedioxy, alkenyl, alkenyloxy, aryl, cyano, halo, hydroxy, heteroaryl, heterocycloalkyl, $R^4$, —C(=O)—R, —C(=O)—$OR^5$, —C(=O)—$NY^1Y^2$, —$NY^1Y^2$ and —OR. $R^1$ more preferably represents optionally substituted indolyl, optionally substituted indolizinyl or optionally substituted pyrrolyl. $R^1$ still more preferably represents optionally substituted indol-3-yl, indolizin-1-yl, optionally substituted pyrrol-3-yl, optionally substituted indol-2-yl or optionally substituted pyrrol-2-yl.

$R^1$ may also particularly represent optionally substituted aryl, especially optionally substituted phenyl. Optional substituents include one or more groups selected from alkylenedioxy, halo, heteroaryl, hydroxy, $R^4$, —$NY^1Y^2$ and —OR. $R^1$ still more preferably represents 4-substituted phenyl, more especially 4-tertiarybutylphenyl.

$R^2$ may particularly represent hydrogen.
$R^2$ may also particularly represent acyl.
$R^2$ may also particularly represent halo.
$R^2$ may also particularly represent lower alkyl optionally substituted by cyano, halo, hydroxy, heteroaryl, —C(=O)—$NY^1Y^2$, tetrazolyl, —C(=O)—R, —$CO_2R^8$, —$NY^3Y^4$, —N($R^6$)—C(=O)—R, —N($R^6$)—C(=O)—$NY^1Y^2$, —N($R^6$)—$SO_2$—$R^7$, or —N($R^6$)—$SO_2$—$NY^3Y^4$.

$R^2$ may also particularly represent lower alkenyl.
$R^3$ may particularly represent hydrogen.
$R^3$ may also particularly represent optionally substituted aryl, especially optionally substituted phenyl.
$R^3$ may also particularly represent —C(=O)—$OR^5$ (e.g. —C(=O)—OH)
$R^3$ may also particularly represent lower alkyl (e.g. methyl).
$X^1$ may particularly represent N.
$X^1$ may also particularly represent CH.
$X^1$ may also particularly represent C-halo, especially C—Cl.
$X^1$ may also particularly represent C—CN.
$X^1$ may also particularly represent C—OH.
$X^1$ may also particularly represent C-aryl (e.g. C-phenyl).
$X^1$ may also particularly represent C-heteroaryl, especially C-azaheteroaryl (e.g. C-pyridyl,

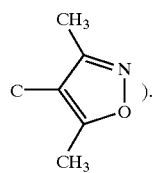

).

$X^1$ may also particularly represent C—$Z^2$R, especially C-lower alkoxy, more especially C—$OCH_3$.
$X^1$ may also particularly represent C—C(=O)—$OR^5$, especially C—C(=O)—OH or C—C(=O)—O'Bu.
$X^1$ may also particularly represent C—C(=O)—$NY^1Y^2$, especially C—C(=O)—$NH_2$, C—C(=O)—NH—$CH_3$, C—C(=O)—NH—$CH_2$—$CH_2$—$CH_2$—$CH_3$,

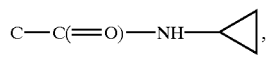

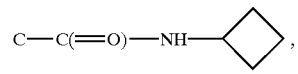

C—C(=O)—NH—$CH_2$—$CH_2$OH, C—C(=O)—NH—$CH_2$—CH($CH_3$)OH, C—C(=O)—NH—$CH_2$—C($CH_3$)$_2$—OH, C—C(=O)—NH—C($CH_3$)$_2$—$CH_2$OH, C—C(=O)—NH—$CH_2CH_2OCH_3$,

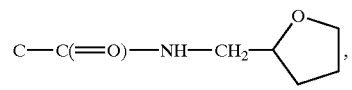

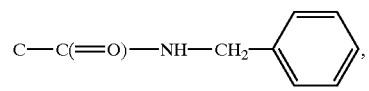

C—C(=O)—N($CH_3$)$_2$,

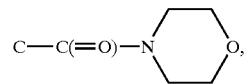

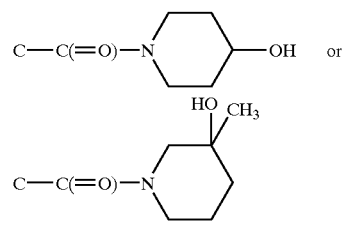

more especially C—C(=O)—NH—C($CH_3$)$_2$—$CH_2$OH.
$X^1$ may also particularly represent

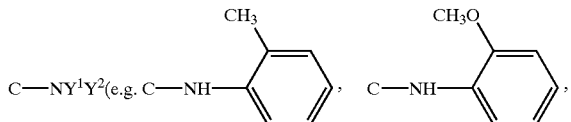

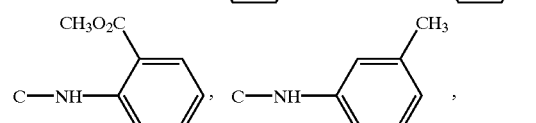

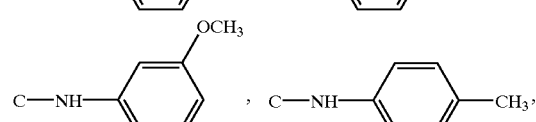

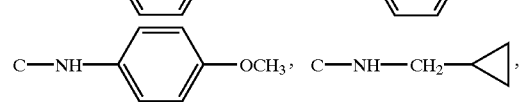

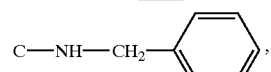

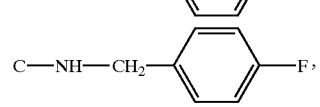

-continued

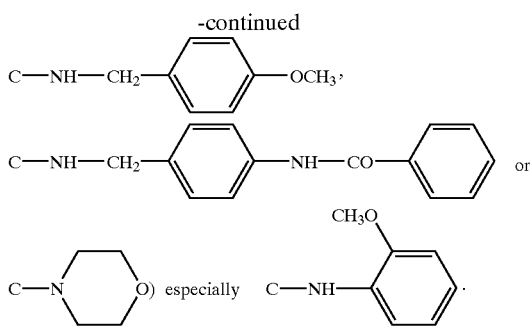

$X^1$ may also particularly represent C-heterocycloalkenyl (e.g.

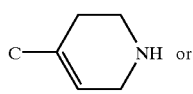

or

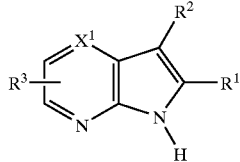

It is to be understood that this invention covers all appropriate combinations of the particular and preferred groupings referred to herein.

A particular embodiment of the invention is a compound of formula (I)

(I)

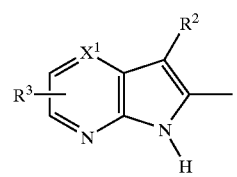

wherein:

$R^1$ represents aryl or heteroaryl each optionally substituted by one or more groups selected from alkylenedioxy, alkenyl, alkenyloxy, alkynyl, aryl, hydroxy, heteroaryl, heterocycloalkyl, —C(=O)—R, —C(=O)—NY$^1$Y$^2$, —N(R$^6$)—C(=O)—R$^7$, —N(R$^6$)—C(=O)—NY$^3$Y$^4$, —N(R$^6$)—C(=O)—OR$^7$, —N(R$^6$)—SO$_2$—R$^7$, —N(R$^6$)—SO$_2$—NY$^3$Y$^4$, and —SO$_2$—NY$^1$Y$^2$;

or an N-oxide, prodrug, acid bioisostere, pharmaceutically acceptable salt or solvate of such compound; or an N-oxide, prodrug, or acid bioisostere of such salt or solvate.

A particular preferred group of compounds of the invention are compounds of formula (Ia):

(Ia)

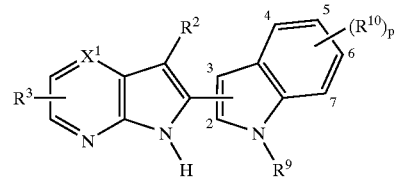

in which $R^2$, $R^3$ and $X^1$ are as hereinbefore defined; $R^9$ is hydrogen, alkenyl or $R^4$; $R^{10}$ is alkenyloxy, carboxy (or an acid bioisostere), cyano, halo, hydroxy, heteroaryl, $R^4$, —C(=O)—R, —C(=O)—NY$^1$Y$^2$, —OR$^4$, —N(R$^6$)—C(=O)—R$^7$, —N(R$^6$)—SO$_2$—R$^7$ or —NY$^1$Y$^2$; p is zero, or an integer 1 or 2; and the residue

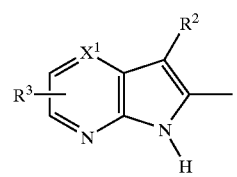

is attached to position 2 or 3 of the indole ring; and their corresponding N-oxides, and their prodrugs; and pharmaceutically acceptable salts and solvates (e.g. hydrates) of such compounds and their N-oxides and their prodrugs.

Compounds of formula (Ia) in which $R^2$ represents hydrogen are preferred.

Compounds of formula (Ia) in which $R^3$ represents hydrogen are preferred.

Compounds of formula (Ia) in which $X^1$ represents:

(i) N;
(ii) CH;
(iii) C-aryl (e.g. C-phenyl);
(iv) C-heteroaryl, especially C-azaheteroaryl (e.g. C-pyridyl or

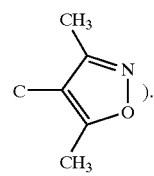

).

(v) C-halo (e.g. C—Cl);
(vi) C—CN;
(vii) C—Z$^2$R, particularly C-lower alkoxy (e.g.C—OCH$_3$);
(viii) C—C(=O)—OR$^5$, particularly C—C(=O)—O$^t$Bu;
(ix) C—C(=O)—NY$^1$Y$^2$ (e.g. C—C(=O)—NH—CH$_3$, C—C(=O)—NH—CH$_2$—CH$_2$OH, C—C(=O)—NH—CH$_2$—CH(CH$_3$)OH, C—C(=O)—NH—CH$_2$—C(CH$_3$)$_2$—OH, C—C(=O)—NH—C(CH$_3$)$_2$—CH$_2$OH, or C—C(=O)—NH—CH$_2$CH$_2$OCH$_3$) more especially C—C(=O)—NH—C(CH$_3$)$_2$—CH$_2$OH; or (x) C—NY¹Y² (e.g. C—NH

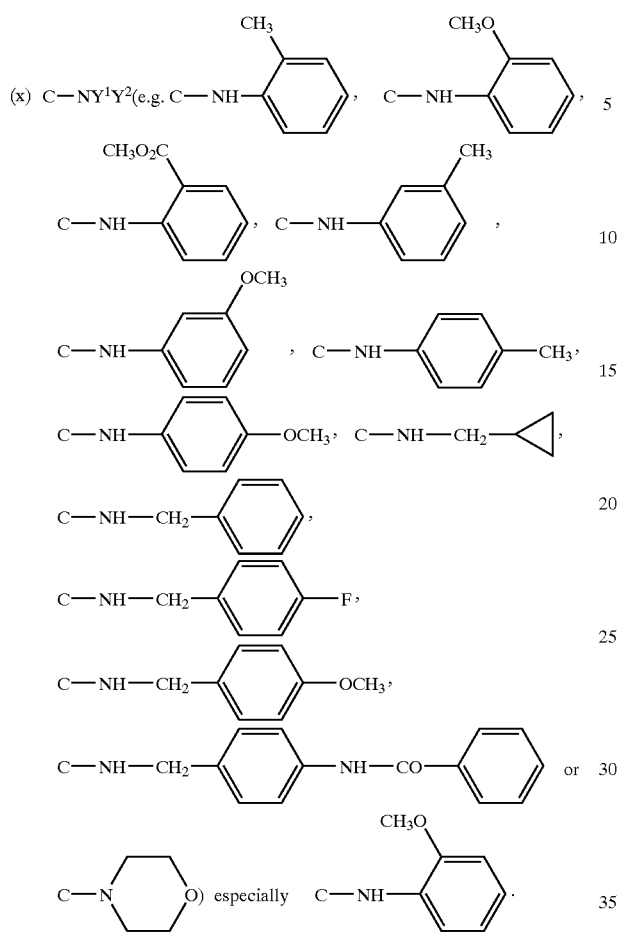

are preferred. Compounds of formula (Ia) in which X¹ represents N, C—H, C—CN,

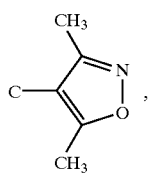

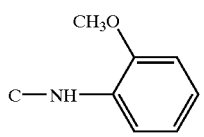

or C—C(=O)—NH—C(CH₃)₂—CH₂OH are especially preferred.

Compounds of formula (Ia) in which R⁹ represents:
(i) hydrogen;
(ii) $C_{1-4}$alkyl [e.g. —CH₃ or —CH₂CH₃];
(iii) $C_{1-4}$alkyl substituted by hydroxy [e.g. —CH₂OH, —CH₂CH₂OH or —CH₂CH₂CH₂OH];
(iv) $C_{1-4}$alkyl substituted by —N(R⁶)C(=O)—R⁷ [e.g. —CH₂CH₂CH₂NHC(=O)CH₃];
(v) $C_{1-4}$alkyl substituted by —C(=O)—NY¹Y² [e.g.

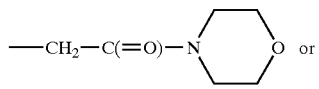

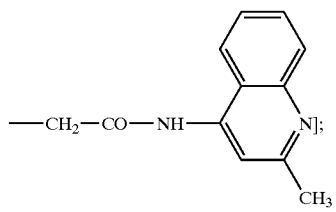

or
(vi) cycloalkylalkyl substituted by hydroxy [e.g.

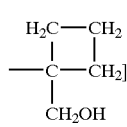

are preferred. Compounds of formula (Ia) in which R⁹ represents hydrogen, —CH₃ or —CH₂CH₃ are especially preferred.

Compounds of formula (Ia) in which R¹⁰ represents:
(i) carboxy or an acid bioisostere (e.g.

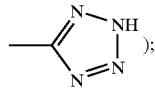

(ii) hydroxy;
(iii) alkyl substituted by carboxy [e.g. —CH₂CH₂CO₂H];
(iv) alkyl substituted by —N(R⁶)—SO₂—R⁷ [e.g.

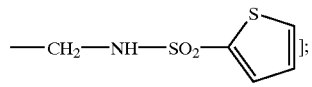

(v) alkyl substituted by —N(R⁶)—CO—NY³Y⁴ [e.g.

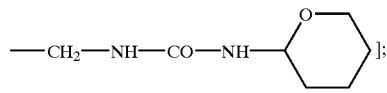

(vi) heteroaryl [e.g.

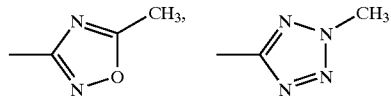

or pyridyl];
(vii) —OR⁴ in which R⁴ is alkyl [e.g. —OCH₃];
(viii) —OR⁴ in which R⁴ is alkyl or cycloalkylalkyl substituted by one or more hydroxy groups [e.g. —OCH₂CH₂OH, —OCH₂CH₂CH₂OH, —OCH(CH₃)CH₂OH, —OCH₂CH(OH)CH₃,

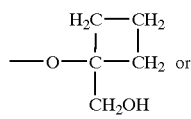 or —OCH$_2$CH(OH)CH$_2$OH];

(ix) —OR$^4$ in which R$^4$ is alkyl substituted by one or more alkoxy groups [e.g. —OCH(CH$_3$)CH$_2$OCH$_3$];

(x) —OR$^4$ in which R$^4$ is alkyl or cycloalkyl substituted by one or more carboxy groups [e.g. —OCH$_2$CO$_2$H, —OCH(CH$_3$)CO$_2$H,

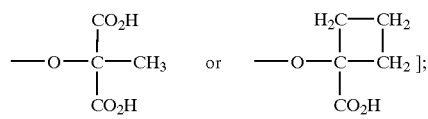];

(xi) —OR$^4$ in which R$^4$ is cycloalkyl substituted by —C(=O)—NY$^1$Y$^2$ [e.g.

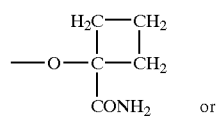 or

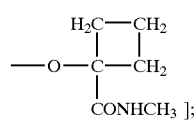];

(xii) —C(=O)—R in which R is alkyl [e.g. —C(=O)—CH$_3$];

(xiii) —C(=O)—NY$^1$Y$^2$ [e.g. —CONH$_2$, —CONHCH$_3$, —CONHCH(CH$_2$OH)$_2$, —CONHCH$_2$CH$_2$OH, —CONHC(CH$_3$)$_2$CH$_2$OH, —C(=O)—NH—CH$_2$—C(CH$_3$)$_2$—OH, —C(=O)—NH—CH$_2$—CH$_2$—CO$_2$H, —CONHCH$_2$CH$_2$OCH$_3$, —CONHCH$_2$CH$_2$CONH$_2$ or

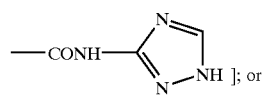]; or (xiv) —N(R$^6$)—C(=O)—R$^7$ [e.g. —NHC(=O)CH$_3$];

are preferred. Compounds of formula (Ia) in which R$^{10}$ represents carboxy, pyridyl,

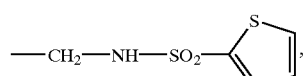

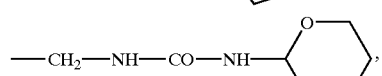

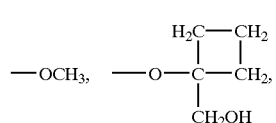, 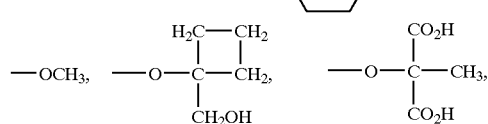

—CONHC(CH$_3$)$_2$CH$_2$OH, —C(=O)—NH—CH$_2$—C(CH$_3$)$_2$—OH or —CONHCH$_2$CH$_2$OCH$_3$ are especially preferred.

When p is 1, R$^{10}$ is preferably attached to position 5, or position 6, of the indolyl ring.

When p is 2, the R$^{10}$ groups are preferably attached to positions 5 and 6 of the indolyl ring.

A preferred group of compounds of the invention are compounds of formula (Ia) in which: R$^2$ is hydrogen; R$^3$ is hydrogen; X$^1$ is CH, C-aryl [e.g. C-phenyl], C-heteroaryl, [e.g. C-pyridyl or

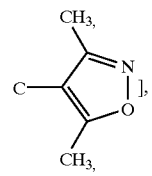],

C-halo [e.g. C—Cl], C—CN, C-lower alkoxy [e.g. C—OCH$_3$], C—C(=O)—OR$^5$ [e.g. C—C(=O)—O$^t$Bu], C—C(=O)—NY$^1$Y$^2$ [especially C—C(=O)—NH—CH$_3$, C—C(=O)—NH—CH$_2$—CH$_2$OH, C—C(=O)—NH—CH$_2$—CH(CH$_3$)OH, C—C(=O)—NH—CH$_2$—C(CH$_3$)$_2$—OH, C—C(=O)—NH—C(CH$_3$)$_2$—CH$_2$OH or C—C(=O)—NH—CH$_2$CH$_2$OCH$_3$, more especially C—C(=O)—NH—C(CH$_3$)$_2$—CH$_2$OH], or C—NY$^1$Y$^2$ [especially

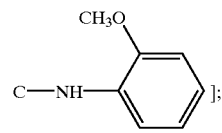];

R$^9$ is (i) hydrogen, (ii) C$_{1-4}$alkyl [e.g. e.g. —CH$_3$ or —CH$_2$CH$_3$], (iii) C$_{1-4}$alkyl substituted by hydroxy [e.g. —CH$_2$OH, —CH$_2$CH$_2$OH or —CH$_2$CH$_2$CH$_2$OH], (iv) C$_{1-4}$alkyl substituted by —N(R$^6$)C(=O)—R$^7$ [e.g. —CH$_2$CH$_2$CH$_2$NHC(=O)CH$_3$], (v) C$_{1-4}$alkyl substituted by —C(=O)—NY$^1$Y$^2$ [e.g.

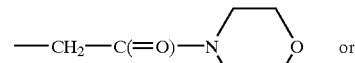 or

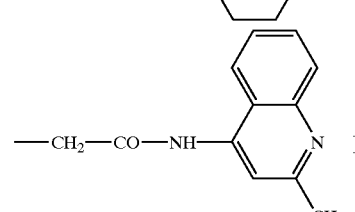]

or (vi) cycloalkylalkyl substituted by hydroxy [e.g.]; R$^{10}$ is (i) carboxy or an acid bioisostere [e.g.

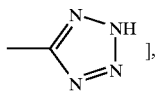, (ii) hydroxy, (iii) alkyl substituted by carboxy [e.g. —CH$_2$CH$_2$CO$_2$H], (iv) alkyl substituted by —N(R$^6$)—SO$_2$—R$^7$ [e.g.

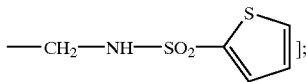];

(v) alkyl substituted by —N(R$^6$)—CO—NY$^3$Y$^4$ [e.g.

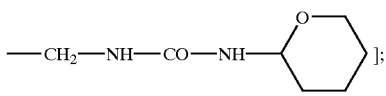];

(vi) heteroaryl [e.g.

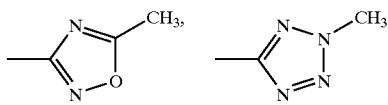

or pyridyl], (vii) —OR$^4$ in which R$^4$ is alkyl [e.g. —OCH$_3$], (viii) —OR$^4$ in which R$^4$ is alkyl or cycloalkylalkyl substituted by one or more hydroxy groups [e.g. —OCH$_2$CH$_2$OH, —OCH$_2$CH$_2$CH$_2$OH, —OCH(CH$_3$)CH$_2$OH, —OCH$_2$CH(OH)CH$_3$,

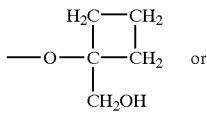

—OCH$_2$CH(OH)CH$_2$OH], (ix) —OR$^4$ in which R$^4$ is alkyl substituted by one or more alkoxy groups [e.g. —OCH(CH$_3$)CH$_2$OCH$_3$], (x) —OR$^4$ in which R$^4$ is alkyl or cycloalkyl substituted by one or more carboxy groups [e.g. —OCH$_2$CO$_2$H, —OCH(CH$_3$) CO$_2$H or

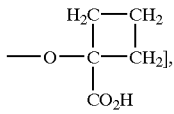], (xi) —OR$^4$ in which R$^4$ is cycloalkyl substituted by —C(=O)—NY$^1$Y$^2$ [e.g.

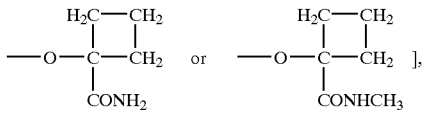

(xii) —C(=O)—R in which R is alkyl [e.g. —C(=O)—CH$_3$], (xiii) —C(=O)—NY$^1$Y$^2$ [e.g. —CONH$_2$, —CONHCH$_3$, —CONHCH(CH$_2$OH)$_2$, —CONHCH$_2$CH$_2$OH, —CONHC(CH$_3$)$_2$CH$_2$OH, —C(=O)—NH—CH$_2$—C(CH$_3$)$_2$—OH, —C(=O)—NH—CH$_2$—CH$_2$—CO$_2$H, —CONHCH$_2$CH$_2$OCH$_3$, —CONHCH$_2$CH$_2$CONH$_2$ or

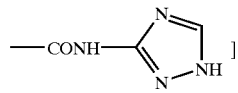]

or (xiv) —N(R$^6$)—C(=O)—R$^7$ [e.g. —NHC(=O)CH$_3$]; the R$^{10}$ group is attached to position 5, or position 6, of the indolyl ring when p is 1 and the R$^{10}$ groups are attached to position 5 and 6 of the indolyl ring when p is 2; and the corresponding N-oxides, and their prodrugs; and pharmaceutically acceptable salts and solvates (e.g. hydrates) of such compounds and their N-oxides and prodrugs.

A further preferred group of compounds of the invention are compounds of formula (Ia) in which: R$^2$ is hydrogen; R$^3$ is hydrogen; X$^1$ is N; R$^9$ is (i) hydrogen, (ii) C$_{1-4}$alkyl [e.g. e.g. —CH$_3$ or —CH$_2$CH$_3$], (iii) C$_{1-4}$alkyl substituted by hydroxy [e.g. —CH$_2$OH, —CH$_2$CH$_2$OH or —CH$_2$CH$_2$CH$_2$OH], (iv) C$_{1-4}$alkyl substituted by —N(R$^6$) C(=O)—R$^7$ [e.g. —CH$_2$CH$_2$CH$_2$NHC(=O)CH$_3$], (v) C$_{1-4}$alkyl substituted by —C(=O)—NY$^1$Y$^2$ [e.g.

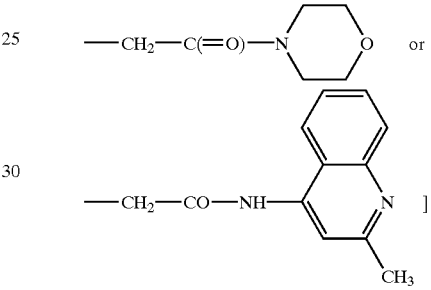

or (vi) cycloalkylalkyl substituted by hydroxy [e.g.

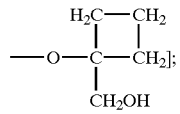];

R$^{10}$ is (i) carboxy or an acid bioisostere [e.g.

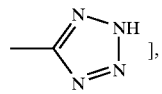], (ii) hydroxy, (iii) alkyl substituted by carboxy [e.g. —CH$_2$CH$_2$CO$_2$H], (iv) alkyl substituted by —N(R$^6$)—SO$_2$—R$^7$ [e.g.

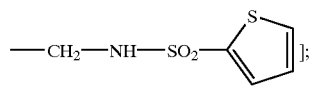];

(v) alkyl substituted by —N(R$^6$)—CO-NY$^3$Y$^4$ [e.g.

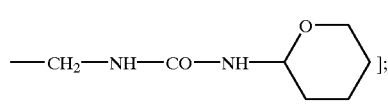];

(vi) heteroaryl [e.g.

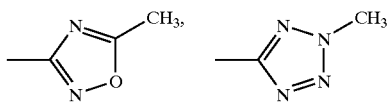

or pyridyl], (vii) —OR⁴ in which R⁴ is alkyl [e.g. —OCH₃], (viii) —OR⁴ in which R⁴ is alkyl or cycloalkylalkyl substituted by one or more hydroxy groups [e.g. —OCH₂CH₂OH, —OCH₂CH₂CH₂OH, —OCH(CH₃)CH₂OH, —OCH₂CH(OH)CH₃,

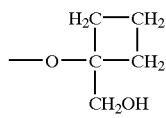

or —OCH₂CH(OH)CH₂OH], (ix) —OR⁴ in which R⁴ is alkyl substituted by one or more alkoxy groups [e.g. —OCH(CH₃)CH₂OCH₃], (x) —OR⁴ in which R⁴ is alkyl or cycloalkyl substituted by one or more carboxy groups [e.g. —OCH₂CO₂H, —OCH(CH₃)CO₂H or

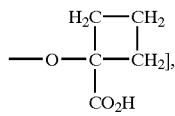

(xi) —OR⁴ in which R⁴ is cycloalkyl substituted by —C(=O)—NY¹Y² [e.g.

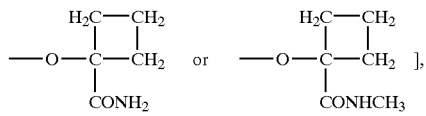

(xii) —C(=O)—R in which R is alkyl [e.g. —C(=O)—CH₃, (xiii) —C(=O)—NY¹Y² [e.g. —CONH₂, —CONHCH₃, —CONHCH(CH₂OH)₂, —CONHCH₂CH₂OH, —CONHC(CH₃)₂CH₂OH, —C(=O)—NH—CH₂—C(CH₃)₂—OH, —C(=O)—NH—CH₂—CH₂—CO₂H, —CONHCH₂CH₂OCH₃, —CONHCH₂CH₂CONH₂ or

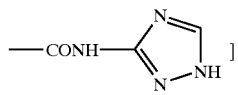

or (xiv) —N(R⁶)—C(=O)—R⁷ [e.g. —NHC(=O)CH₃]; the R¹⁰ group is attached to position 5, or position 6, of the indolyl ring when p is 1 and the R¹⁰ groups are attached to position 5 and 6 of the indolyl ring when p is 2; and the corresponding N-oxides, and their prodrugs; and pharmaceutically acceptable salts and solvates (e.g. hydrates) of such compounds and their N-oxides and prodrugs.

Another particular group of compounds of the invention are compounds of formula (Ib):

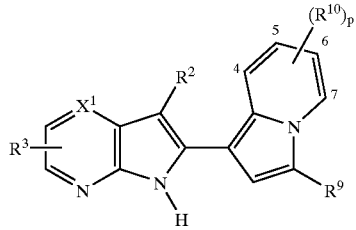

in which R², R³, R⁹, R¹⁰, X¹ and p are as hereinbefore defined, and the corresponding N-oxides, and their prodrugs; and pharmaceutically acceptable salts and solvates (e.g. hydrates) of compounds of formula (Ib) and their N-oxides and prodrugs.

Compounds of formula (Ib) in which R² represents hydrogen are preferred.

Compounds of formula (Ib) in which R³ is hydrogen are preferred.

Compounds of formula (Ib) in which X¹ represents:

(i) N;
(ii) CH;
(iii) C-aryl (e.g. C-phenyl);
(iv) C-heteroaryl, especially C-azaheteroaryl (e.g. C-pyridyl or

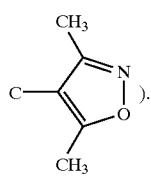

(v) C-halo (e.g. C—Cl);
(vi) C—CN;
(vii) C—Z²R, particularly C-lower alkoxy (e.g. C—OCH₃);
(viii) C—C(=O)—OR⁵, particularly C—C(=O)—OᵗBu;
(ix) C—C(=O)—NY¹Y² (e.g. C—C(=O)—NH—CH₃, C—C(=O)—NH—CH₂—CH₂OH, C—C(=O)—NH—CH₂—CH(CH₃)OH, C—C(=O)—NH—CH₂—C(CH₃)₂—OH, C—C(=O)—NH—C(CH₃)₂—CH₂OH, or C—C(=O)—NH—CH₂CH₂OCH₃) more especially C—C(=O)—NH—C(CH₃)₂—CH₂OH; or (x) C—NY¹Y²(e.g.

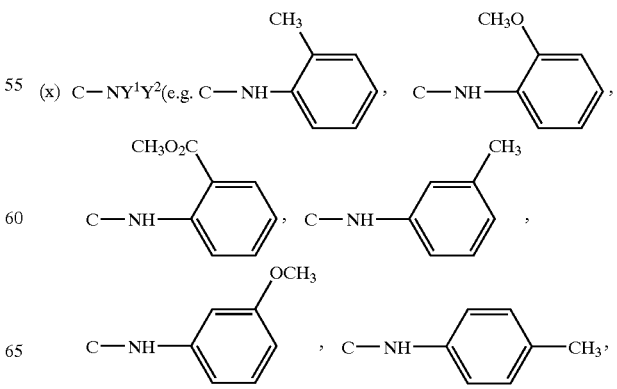

-continued

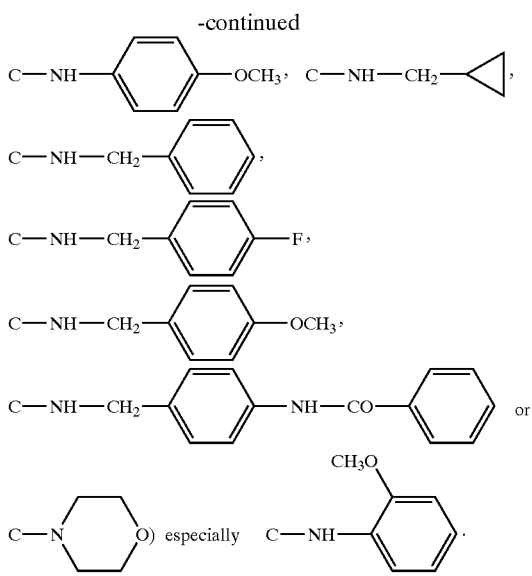

are preferred. Compounds of formula (Ib) in which $X^1$ represents N, C—H, C—CN, or C—C(=O)—NH—C(CH$_3$)$_2$—CH$_2$OH are especially preferred.

Compounds of formula (Ib) in which $R^9$ represents hydrogen are preferred.

Compounds of formula (Ib) in which $R^9$ represents $C_{1-4}$alkyl [e.g. —CH$_3$] are also preferred.

Compounds of formula (Ib) in which p is zero are preferred.

A preferred group of compounds of the invention are compounds of formula (Ib) in which: $R^2$ is hydrogen; $R^3$ is hydrogen; $X^1$ is CH, C-aryl [e.g. C-phenyl], C-heteroaryl, [e.g. C-pyridyl or C-halo [e.g. C—Cl], C—CN, C-lower alkoxy [e.g. C—OCH$_3$], C—C(=O)—OR$^5$ [e.g. C—C(=O)—O$^t$Bu], C—C(=O)—NY$^1$Y$^2$ [especially C—C(=O)—NH—CH$_3$, C—C(=O)—NH—CH$_2$—CH$_2$OH, C—C(=O)—NH—CH$_2$—CH(CH$_3$)OH, C—C(=O)—NH—CH$_2$—C(CH$_3$)$_2$—OH, C—C(=O)—NH—C(CH$_3$)$_2$—CH$_2$OH or C—C(=O)—NH—CH$_2$CH$_2$OCH$_3$, more especially C—C(=O)—NH—C(CH$_3$)$_2$—CH$_2$OH] or C—NY$^1$Y$^2$ [especially $R^9$ is hydrogen or $C_{1-4}$alkyl [e.g. —CH$_3$]; p is zero; and the corresponding N-oxides, and their prodrugs; and pharmaceutically acceptable salts and solvates (e.g. hydrates) of such compounds and their N-oxides and prodrugs.

A further preferred group of compounds of the invention are compounds of formula (Ib) in which: $R^2$ is hydrogen; $R^3$ is hydrogen; $X^1$ is N; $R^9$ is hydrogen or $C_{1-4}$alkyl [e.g. —CH$_3$]; p is zero; and the corresponding N-oxides, and their prodrugs; and pharmaceutically acceptable salts and solvates (e.g. hydrates) of such compounds and their N-oxides and prodrugs.

Another particular group of compounds of the invention are compounds of formula (Ic):

(Ic)

in which $R^2$, $R^3$, $R^9$, $R^{10}$, $X^1$ and p are as hereinbefore defined, and the residue is preferably attached to position 2 or 3 of the pyrrole ring and the group —(R$^{10}$)$_p$ is preferably attached to position 4 or 5 of the pyrrole ring, and the corresponding N-oxides, and their prodrugs; and pharmaceutically acceptable salts and solvates (e.g. hydrates) of compounds of formula (Ic) and their N-oxides and prodrugs.

Compounds of formula (Ic) in which $R^2$ represents hydrogen are preferred.

Compounds of formula (Ic) in which $R^3$ is hydrogen are preferred.

Compounds of formula (Ic) in which $X^1$ represents:

(i) N;
(ii) CH;
(iii) C-aryl (e.g. C-phenyl);
(iv) C-heteroaryl, especially C-azaheteroaryl (e.g. C-pyridyl or

).

(v) C-halo (e.g. C—Cl);
(vi) C—CN;
(vii) C—$Z^2$R, particularly C-lower alkoxy (e.g. C—$OCH_3$);
(viii) C—C(=O)—$OR^5$, particularly C—C(=O)—$O^tBu$; or
(ix) C—C(=O)—$NY^1Y^2$ (e.g. C—C(=O)—NH—$CH_3$, C—C(=O)—NH—$CH_2$—$CH_2$OH, C—C(=O)—NH—$CH_2$—CH($CH_3$)OH, C—C(=O)—NH—$CH_2$—C($CH_3$)$_2$—OH, C—C(=O)—NH—C($CH_3$)$_2$—$CH_2$OH, or C—C(=O)—NH—$CH_2CH_2OCH_3$) more especially C—C(=O)—NH—C($CH_3$)$_2$—$CH_2$OH; or (x) C—$NY^1Y^2$ (e.g.

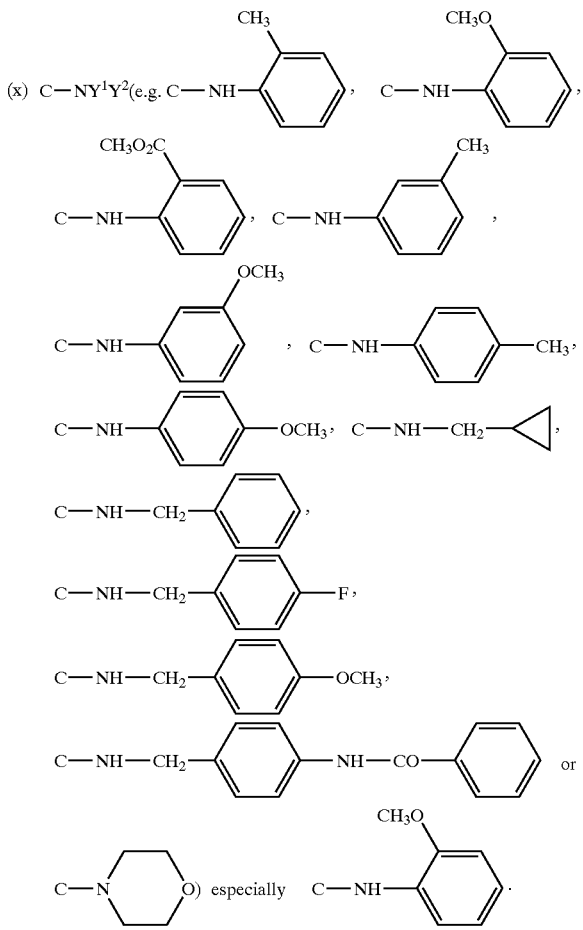

are preferred. Compounds of formula (Ic) in which $X^1$ represents N, C—H, C—CN,

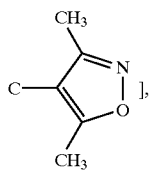

or C—C(=O)—NH—C($CH_3$)$_2$—$CH_2$OH are especially preferred.

Compounds of formula (Ic) in which $R^9$ represents $C_{1-4}$alkyl [e.g. —$CH_3$] are preferred.

A particular embodiment of of the invention is given by compounds of formula (Ic) in which $R^9$ represents optionally substituted $C_{1-4}$ alkyl.

Compounds of formula (Ic) in which p is 1 are preferred.
Compounds of formula (Ic) in which $R^{10}$ represents aryl [e.g. phenyl] are preferred.

A particular embodiment of of the invention is given by compounds of formula (Ic) in which $R^{10}$ represents optionally substituted aryl or optionally substituted heteroaryl.

A preferred group of compounds of the invention are compounds of formula (Ic) in which: $R^2$ is hydrogen; $R^3$ is hydrogen; $X^1$ is CH, C-aryl [e.g. C-phenyl], C-heteroaryl, [e.g. C-pyridyl or

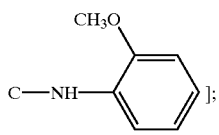

C-halo [e.g. C—Cl], C—CN, C-lower alkoxy [e.g. C—$OCH_3$], C—C(=O)—$OR^5$ [e.g. C—C(=O)—$O^tBu$], C—C(=O)—$NY^1Y^2$ [especially C—C(=O)—NH—$CH_3$, C—C(=O)—NH—$CH_2$—$CH_2$OH, C—C(=O)—NH—$CH_2$—CH($CH_3$)OH, C—C(=O)—NH—$CH_2$—C($CH_3$)$_2$—OH, C—C(=O)—NH—C($CH_3$)$_2$—$CH_2$OH or C—C(=O)—NH—$CH_2CH_2OCH_3$] more especially C—C(=O)—NH—C($CH_3$)$_2$—$CH_2$OH or C—$NY^1Y^2$ [especially

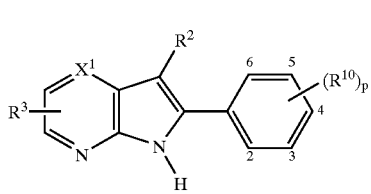

$R^9$ is $C_{1-4}$alkyl [e.g. —$CH_3$]; p is 1; $R^{10}$ is aryl [e.g. phenyl]; and the corresponding N-oxides, and their prodrugs; and pharmaceutically acceptable salts and solvates (e.g. hydrates) of such compounds and their N-oxides and prodrugs.

A further preferred group of compounds of the invention are compounds of formula (Ic) in which: $R^2$ is hydrogen; $R^3$ is hydrogen; $X^1$ is N; $R^9$ is $C_{1-4}$alkyl [e.g. —$CH_3$]; p is 1; $R^{10}$ is aryl [e.g. phenyl]; and the corresponding N-oxides, and their prodrugs; and pharmaceutically acceptable salts and solvates (e.g. hydrates) of such compounds and their N-oxides and prodrugs.

A particular embodiment of the invention are compounds of formula (Ic) wherein $R^9$ is $C_{1-4}$ alkyl substituted by alkoxy or $C_{1-4}$alkyl substituted by —$NY^1Y^2$; and $R^{10}$ is optionally substituted heteroaryl or optionally substituted aryl.

Another particular group of compounds of the invention are compounds of formula (Id):

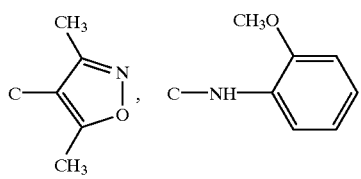

(Id)

in which $R^2$, $R^3$, $R^{10}$, $X^1$ and p are as hereinbefore defined, and the corresponding N-oxides, and their prodrugs; and pharmaceutically acceptable salts and solvates (e.g. hydrates) of compounds of formula (Id) and their N-oxides and prodrugs.

Compounds of formula (Id) in which $R^2$ represents:
(i) hydrogen;
(ii) lower alkyl (e.g. methyl);
(iii) lower alkyl substituted by —$CONY^1Y^2$ (e.g. —$CH_2CH_2CONH_2$ or —$CH_2CH_2CONHCH_3$);
(iv) lower alkyl substituted by carboxy (e.g. —$CH_2CH_2CO_2H$);
(v) lower alkyl substituted by tetrazolyl (e.g.

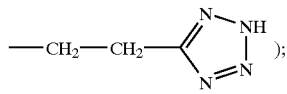

);

(vi) lower alkyl substituted by hydroxy (e.g. —$CH_2CH_2CH_2OH$ or —$CH_2CH_2C(CH_3)_2OH$);
(vii) lower alkyl substituted by —$N(R^6)$—$SO_2$—$R^7$ (e.g. —$CH_2CH_2CH_2NHSO_2CH_3$);
(viii) lower alkyl substituted by —$N(R^6)$—$C(=O)$—R (e.g. —$CH_2CH_2CH_2NHC(=O)CH_3$); or
(ix) lower alkyl substituted by —$C(=O)$—R (e.g. —$CH_2CH_2C(=O)CH_3$);
are preferred.

Compounds of formula (Id) in which $R^3$ is hydrogen are preferred.

Compounds of formula (Id) in which $X^1$ is N are preferred.

Compounds of formula (Id) in which p is 1 are preferred.

Compounds of formula (Id) in which $R^{10}$ represents alkyl [e.g. tertiarybutyl] are preferred.

$R^{10}$ is preferably attached at position 4.

A preferred group of compounds of the invention are compounds of formula (Id) in which: $R^2$ is (i) hydrogen, (ii) lower alkyl (e.g. methyl), (iii) lower alkyl substituted by —$CONY^1Y^2$ (e.g. —$CH_2CH_2CONH_2$ or —$CH_2CH_2CONHCH_3$), (iv) lower alkyl substituted by carboxy (e.g. —$CH_2CH_2CO_2H$), (v) lower alkyl substituted by tetrazolyl (e.g.

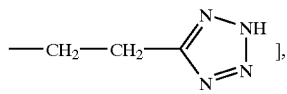

], (vi) lower alkyl substituted by hydroxy [e.g. —$CH_2CH_2CH_2OH$ or —$CH_2CH_2C(CH_3)_2OH$]; (vii) lower alkyl substituted by —$N(R^6)$—$SO_2$—$R^7$ (e.g. —$CH_2CH_2CH_2NHSO_2CH_3$); (viii) lower alkyl substituted by —$N(R^6)$—$C(=O)$—R (e.g. —$CH_2CH_2CH_2NHC(=O)CH_3$); or (ix) lower alkyl substituted by —$C(=O)$—R (e.g. —$CH_2CH_2C(=O)CH_3$); $R^3$ is hydrogen; $X^1$ is N; p is 1; $R^{10}$ is alkyl [e.g. tertiary-butyl] and $R^{10}$ is attached at position 4; and the corresponding N-oxides, and their prodrugs; and pharmaceutically acceptable salts and solvates (e.g. hydrates) of such compounds and their N-oxides and prodrugs.

Particular compounds of the invention of formula (I) are selected from the compounds formed by joining the carbon atom (C*) of one of the azaindoles fragments (A1 to A87) shown in Table 1 to the carbon atom (*C) in the heteroaromatic ring of one of the fragments (B103 to B116) shown in Table 2.

Particular compounds of the invention of formula (Ia) are selected from the compounds formed by joining the carbon atom (C*) of one of the azaindoles fragments (A1 to A87) shown in Table 1 to the carbon atom (*C) in the five membered ring of one of the fragments (B1 to B39 or B117 to B123) shown in Table 2, and joining the carbon atom (C*) of the phenyl ring in one of the fragments (B1 to B39 or B117 to B123) shown in Table 2 to the oxygen atom (*O) of one of the fragments (C1 to C19 or C79 to C96) depicted in Table 3.

Particular compounds of the invention of formula (Ia) are also selected from the compounds formed by joining the carbon atom (C*) of one of the azaindoles fragments (A1 to A87) shown in Table 1 to the carbon atom (*C) in the five membered ring of one of the fragments (B1 to B39 or B117 to B123) shown in Table 2, and joining the carbon atom (C*) of the phenyl ring in one of the fragments (B1 to B39 or B117 to B123) shown in Table 2 to the carbon atom (*C) of one of the fragments (C20 to C44, C47 to C61, C65 to C78 or C97) depicted in Table 3.

Particular compounds of the invention of formula (Ia) are also selected from the compounds formed by joining the carbon atom (C*) of one of the azaindoles fragments (A1 to A87) shown in Table 1 to the carbon atom (*C) in the five membered ring of one of the fragments (B1 to B39) shown in Table 2, and joining the carbon atom (C*) of the phenyl ring in one of the fragments (B1 to B39) shown in Table 2 to one of the nitrogen atom (*N) of the fragments (C45, C62 or C63), or to a hydrogen atom (*H, fragment (C46) or to a fluorine atom (*F, fragment C64) depicted in Table 3.

Particular compounds of the invention of formula (Ib) are selected from the compounds formed by joining the carbon atom (C*) of one of the azaindoles fragments (A1 to A87) shown in Table 1 to the carbon atom (*C) in the five membered ring of one of the indolizine fragments (B40 or B41) shown in Table 2, and joining the carbon atom (C*) in the six membered ring of one of the indolizine fragments (B40 or B41) shown in Table 2 to (i) the oxygen atom (*O) of one of the fragments (C1 to C19 or C79 to C96), (ii) the carbon atom (*C) of one of the fragments (C20 to C44, C47 to C61, C65 to C78 or C97), (iii) the nitrogen atom (*N) of one of the fragments (C45, C62 or C63), (iv) a hydrogen atom (*H, fragment (C46)) or (v) a fluorine atom (*F, fragment C64) depicted in Table 3.

Particular compounds of the invention of formula (Ib) are also selected from the compounds formed by joining the carbon atom (C*) of one of the azaindoles fragments (A1 to A87) shown in Table 1 to the carbon atom (*C) in the indolizine fragment (B42) shown in Table 2.

Particular compounds of the invention of formula (Ic) are selected from the compounds formed by joining the carbon atom (C*) of one of the azaindoles fragments (A1 to A87) shown in Table 1 to the carbon atom (*C) in one of the pyrrole fragments (B43 to B54) shown in Table 2.

Particular compounds of the invention of formula (Id) are selected from the compounds formed by joining the carbon atom (C*) of one of the azaindoles fragments (A1 or A29, A61 or A64 to A66) shown in Table 1 to the carbon atom (*C) in one of the fragments (B55 to B100) shown in Table 2.

TABLE 1
| | | | |
|---|---|---|---|
| A1 | 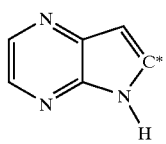 | A2 | 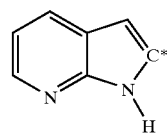 |
| A3 | 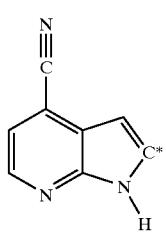 | A4 | 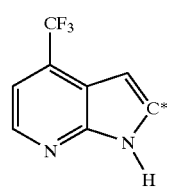 |
| A5 | 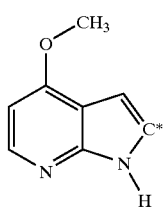 | A6 | 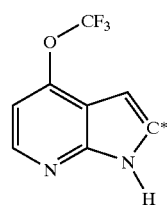 |
| A7 | 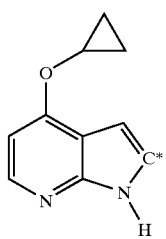 | A8 | 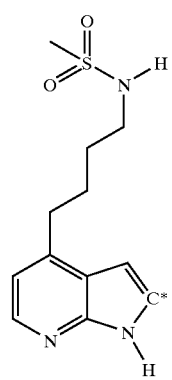 |
| A9 |  | A10 | 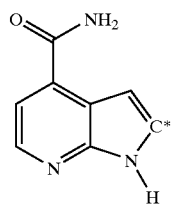 |
| A11 | 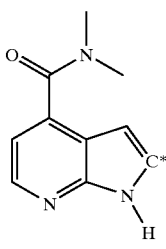 | A12 | 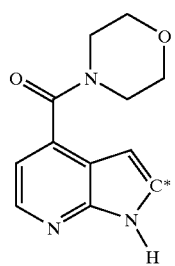 |

TABLE 1-continued
A13 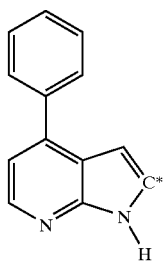
A14 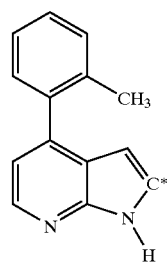
A15 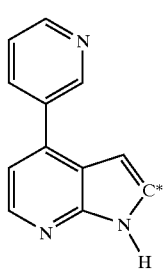
A16 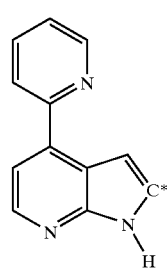
A17 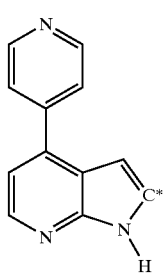
A18 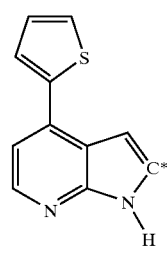
A19 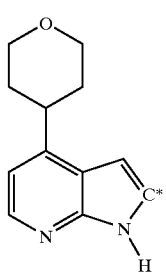
A20 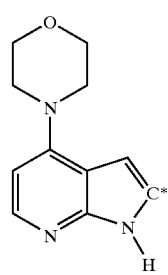
A21 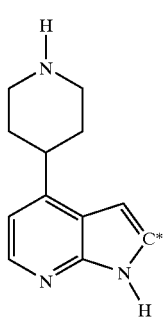
A22 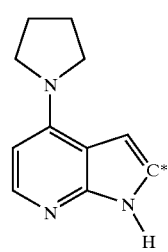

TABLE 1-continued
A23 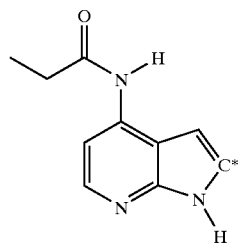
A24 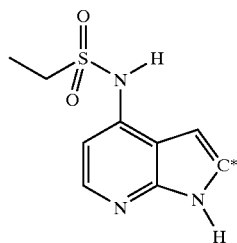
A25 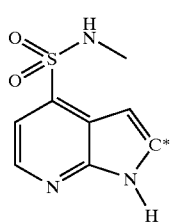
A26 
A27 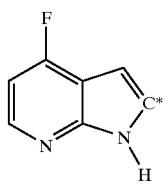
A28 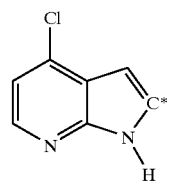
A29 
A30 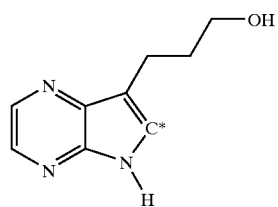
A31 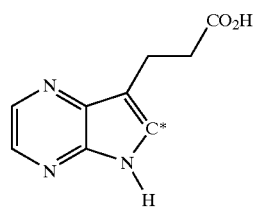
A32 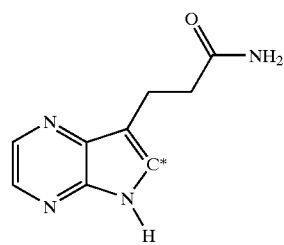
A33 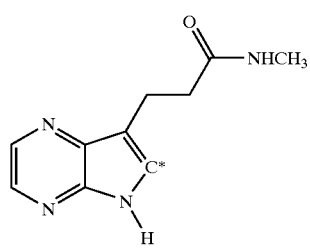
A34 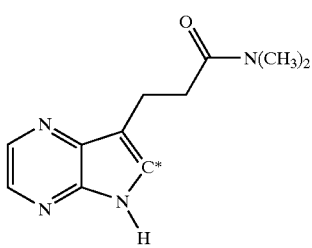

TABLE 1-continued
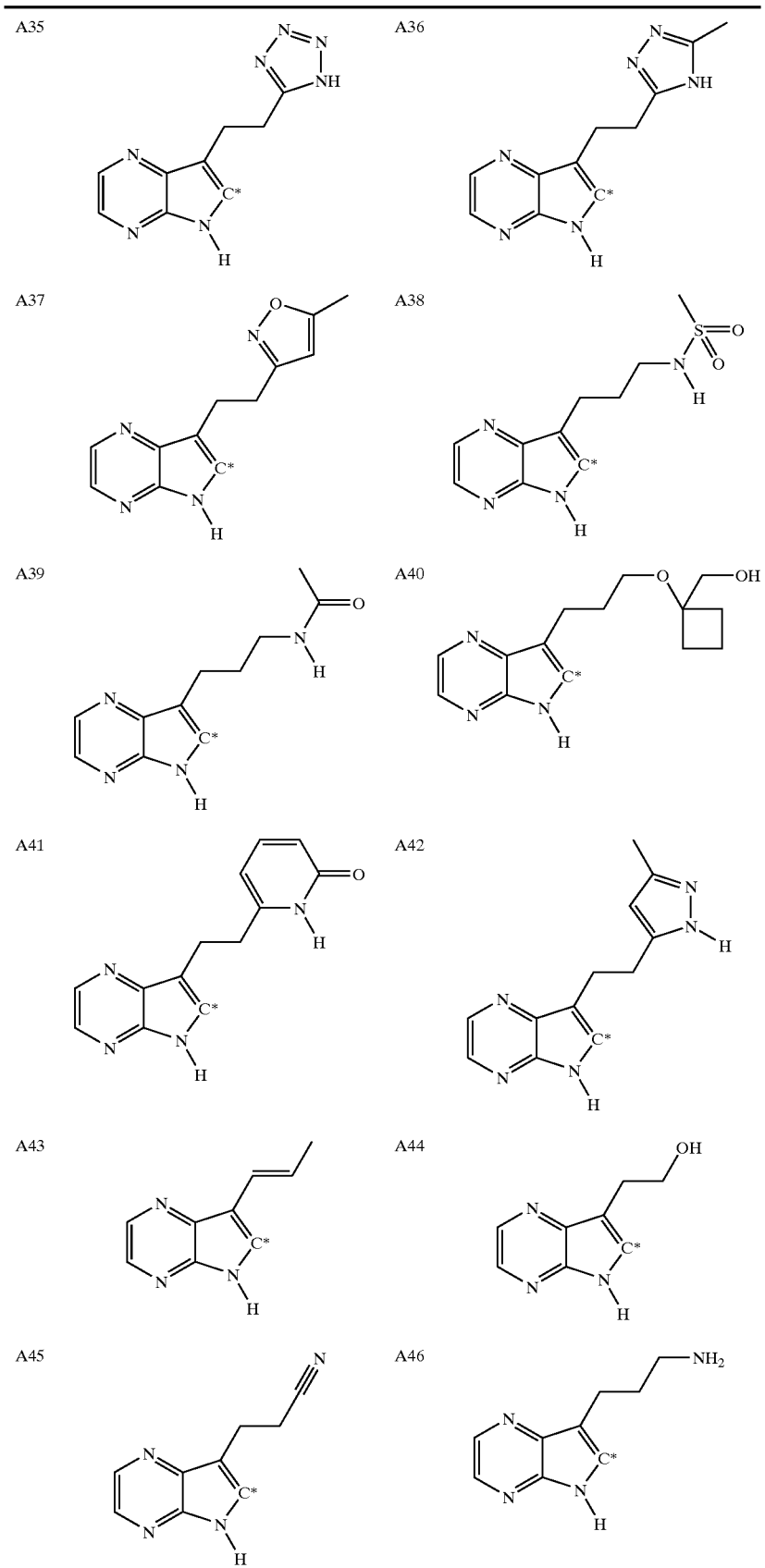

TABLE 1-continued
A47 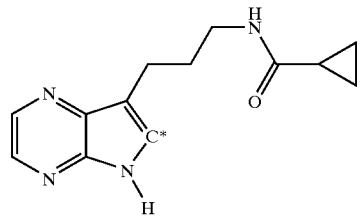 A48 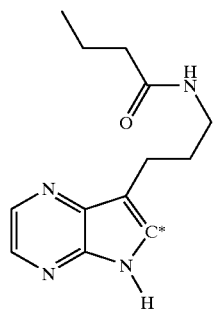
A49 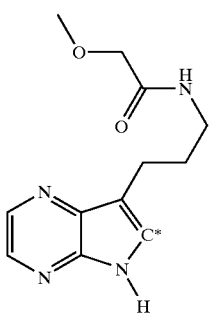 A50 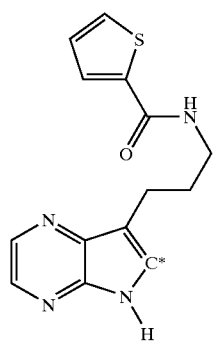
A51 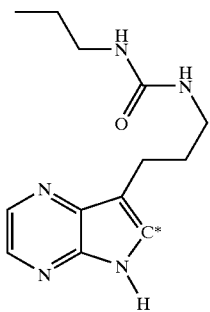 A52 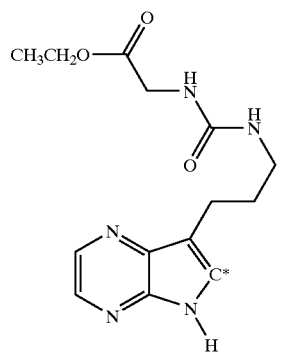
A53 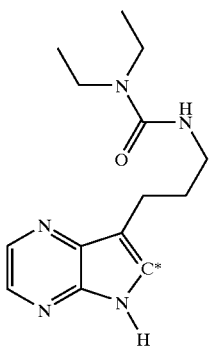 A54 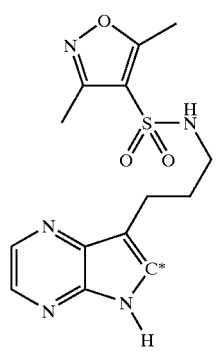

TABLE 1-continued
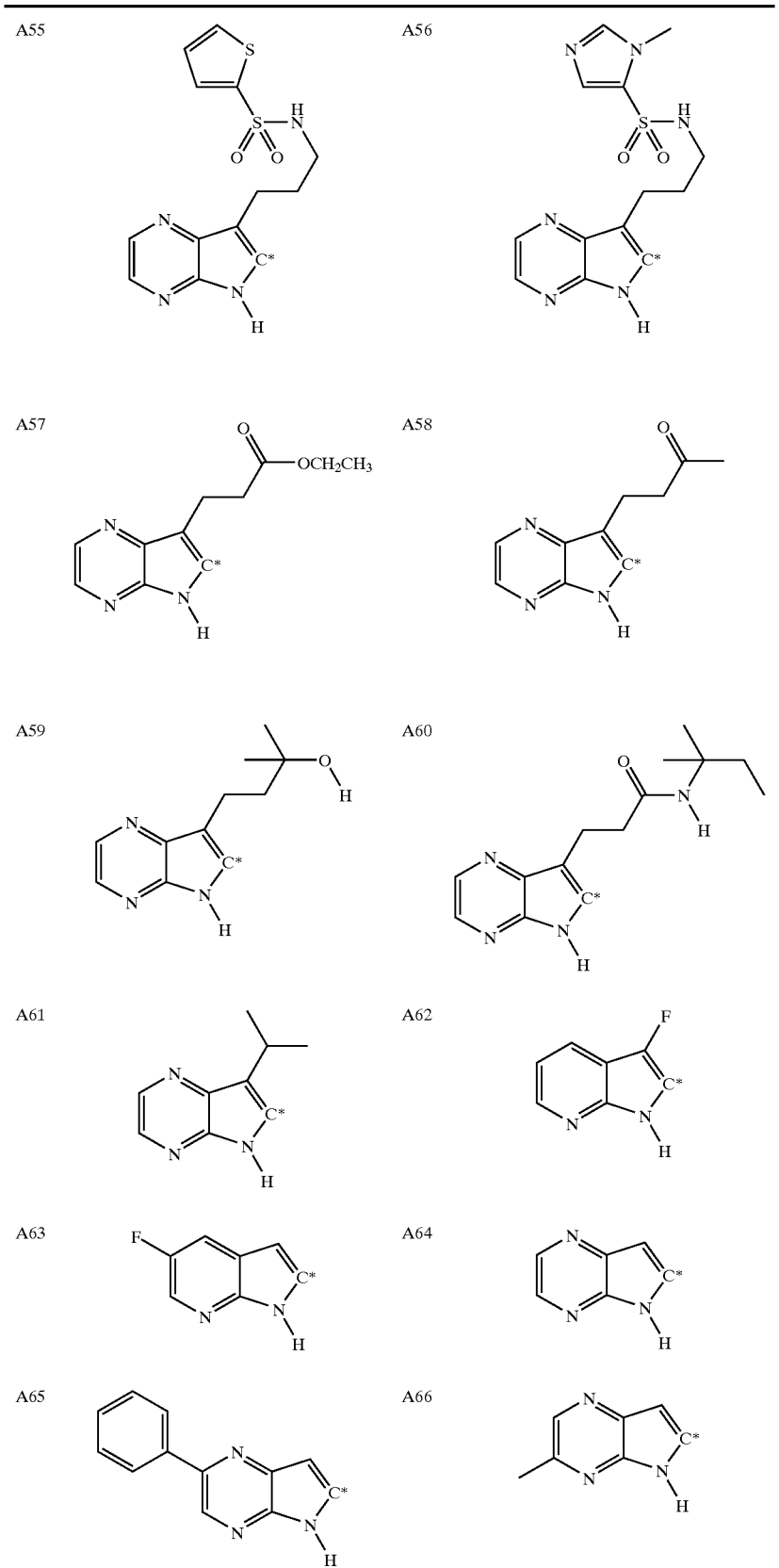

TABLE 1-continued
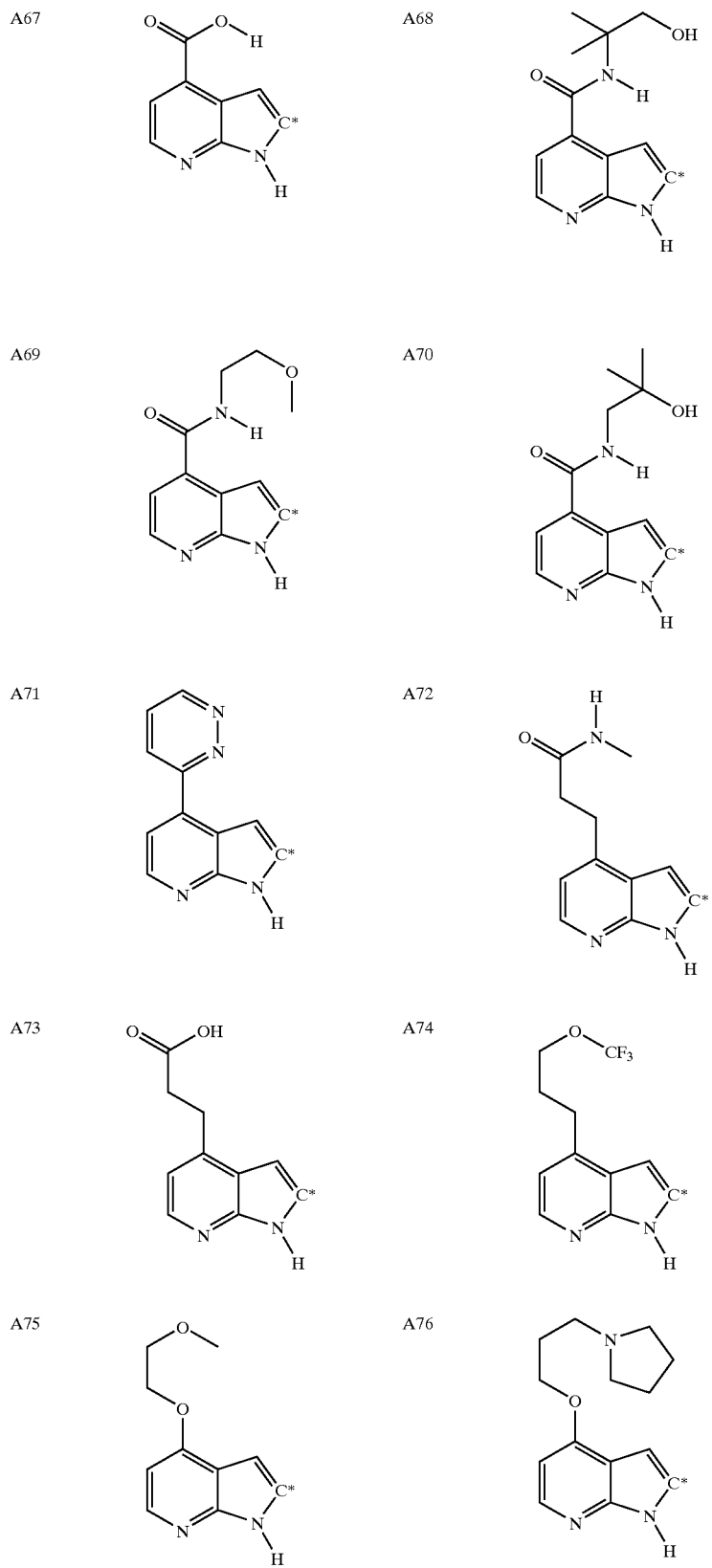

TABLE 1-continued
| A77 | 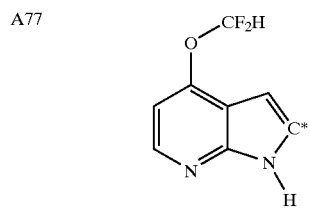 | A78 | 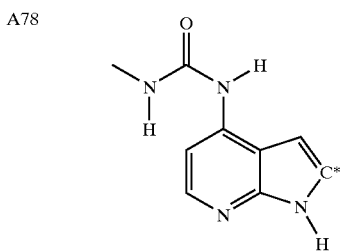 |
| A79 | 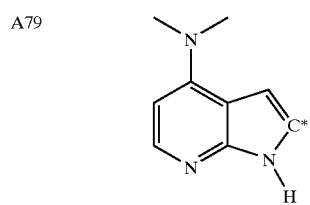 | A80 | 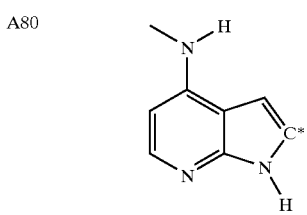 |
| A81 | 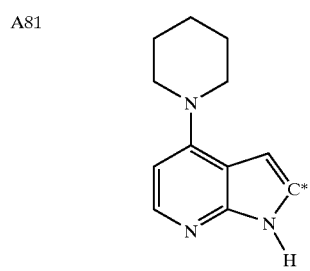 | A82 | 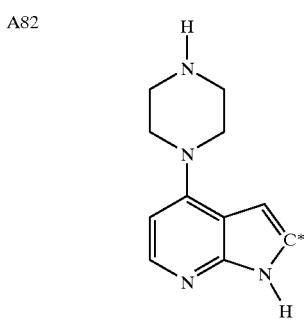 |
| A83 | 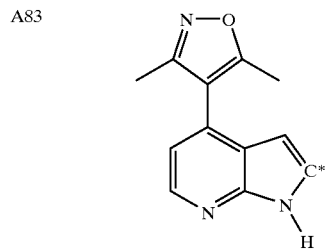 | A84 | 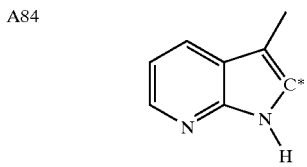 |
| A85 | 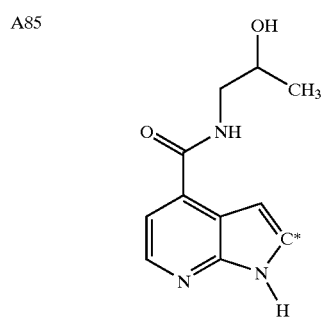 | A86 | 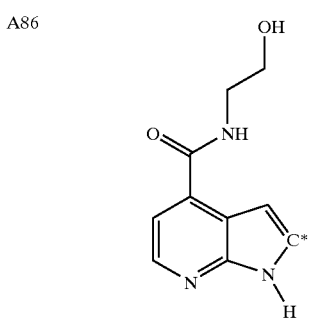 |

TABLE 1-continued
A87 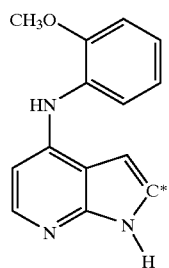
TABLE 2
| | | | |
|---|---|---|---|
| B1 | 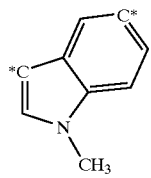 | B2 | 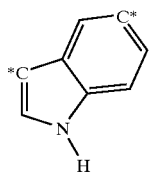 |
| B3 | 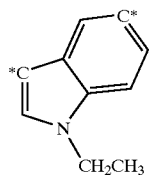 | B4 | 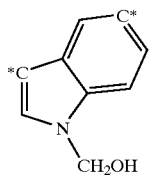 |
| B5 | 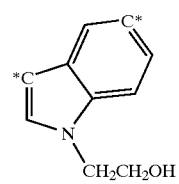 | B6 | 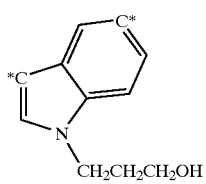 |
| B7 | 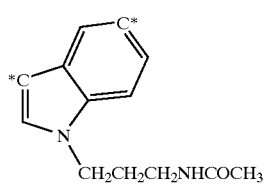 | B8 | 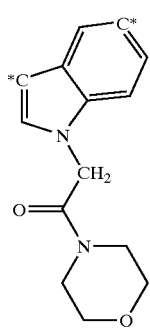 |
| B9 | 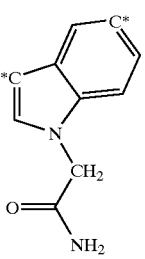 | B10 | 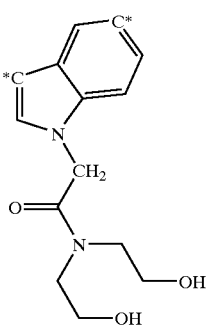 |

TABLE 2-continued
| | | | |
|---|---|---|---|
| B11 | 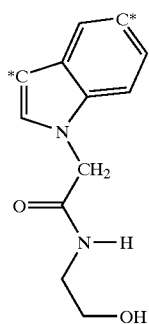 | B12 | 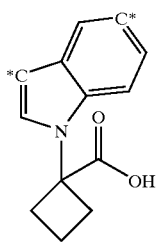 |
| B13 | 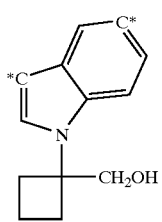 | B14 | 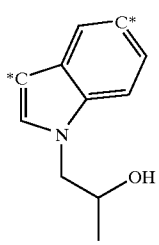 |
| B15 | 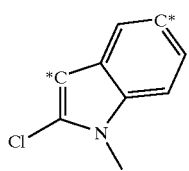 | B16 | 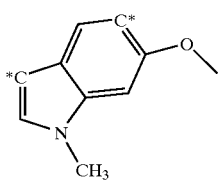 |
| B17 | 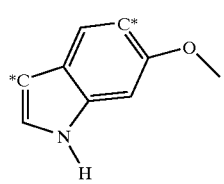 | B18 | 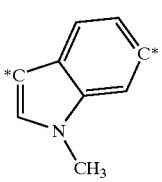 |
| B19 | 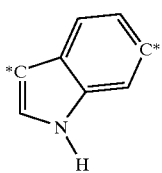 | B20 | 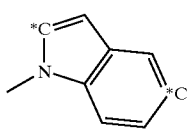 |
| B21 | 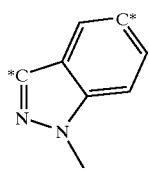 | B22 | 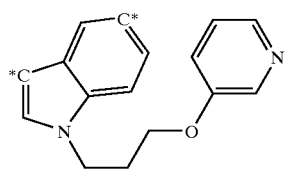 |
| B23 | 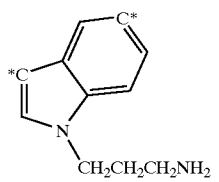 | B24 | 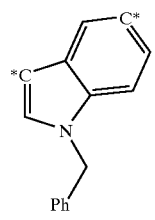 |

TABLE 2-continued
| B25 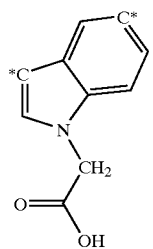 | B26 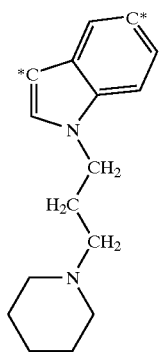 |
| --- | --- |
| B27 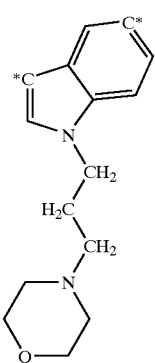 | B28 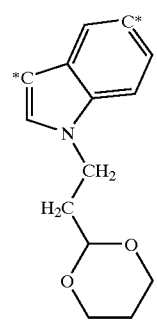 |
| B29 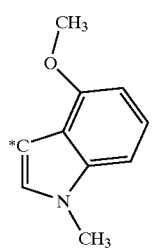 | B30 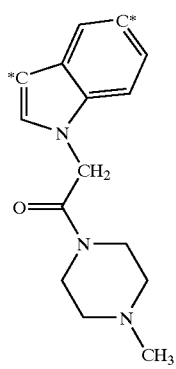 |
| B31 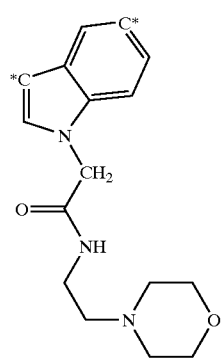 | B32 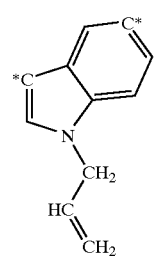 |

TABLE 2-continued
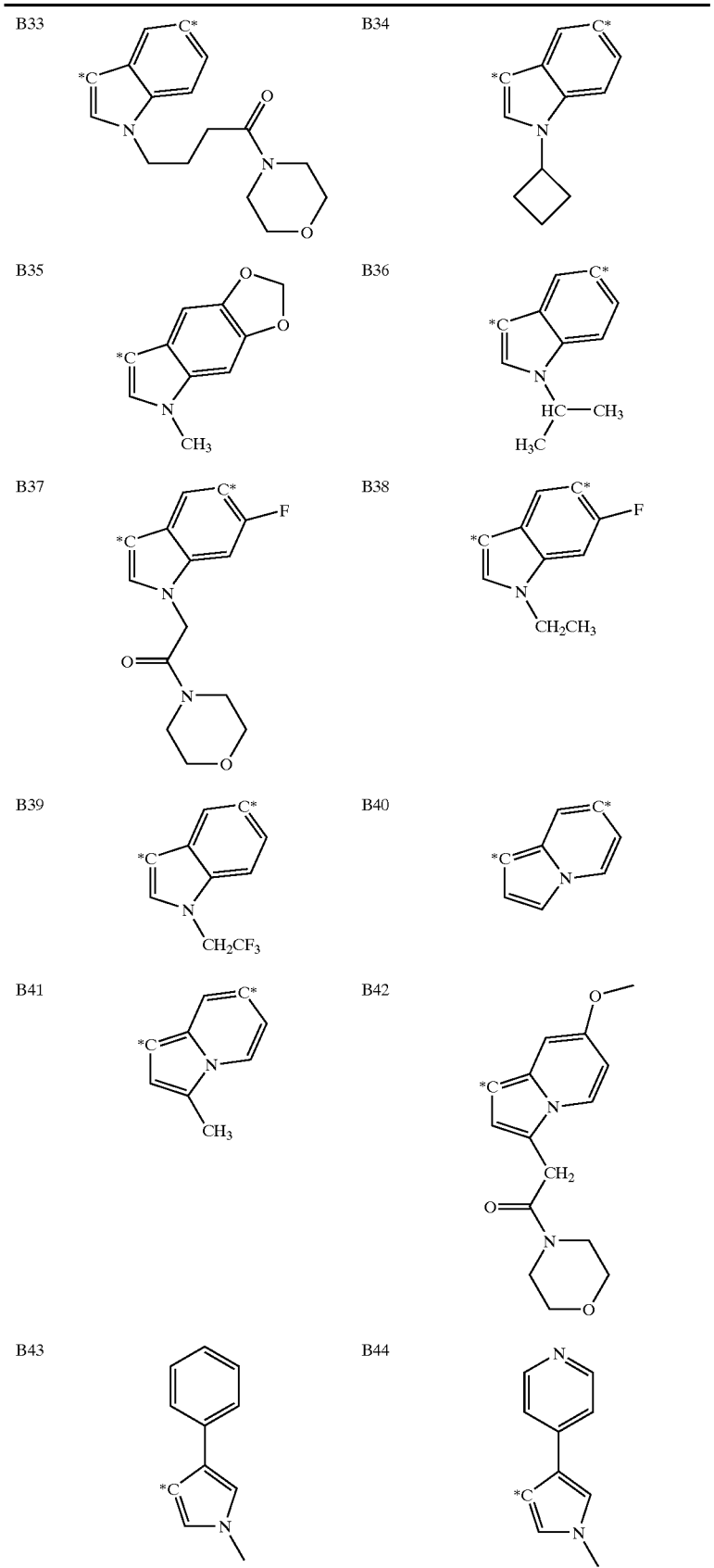

TABLE 2-continued
| | | | |
|---|---|---|---|
| B45 | 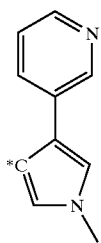 | B46 | 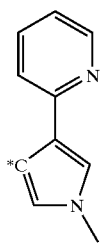 |
| B47 | 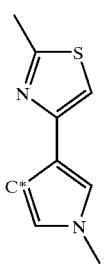 | B48 | 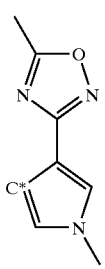 |
| B49 | 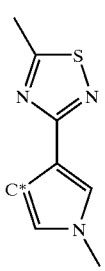 | B50 | 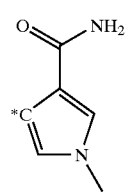 |
| B51 | 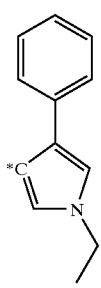 | B52 | 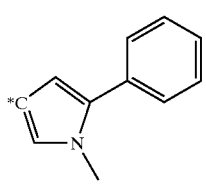 |
| B53 | 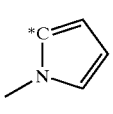 | B54 | 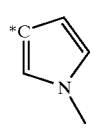 |
| B55 | 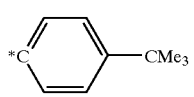 | B56 | 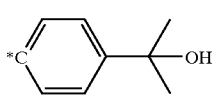 |
| B57 | 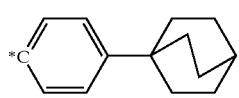 | B58 | 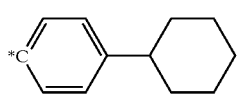 |
| B59 | 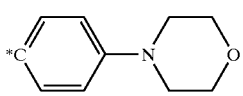 | B60 | 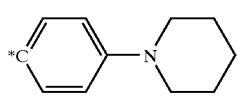 |

TABLE 2-continued
| | | | |
|---|---|---|---|
| B61 | 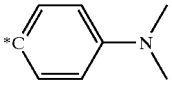 | B62 | 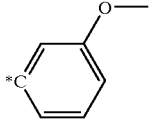 |
| B63 | 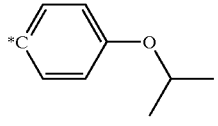 | B64 | 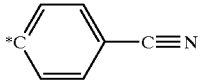 |
| B65 | 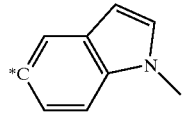 | B66 | 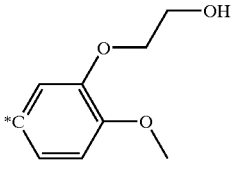 |
| B67 | 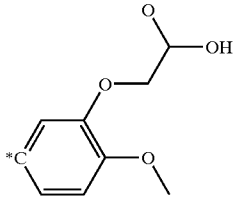 | B68 | 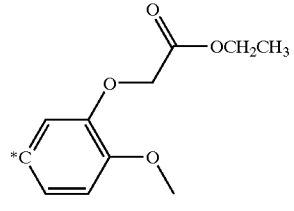 |
| B69 | 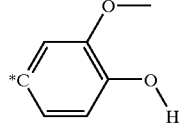 | B70 | 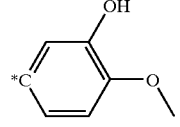 |
| B71 | 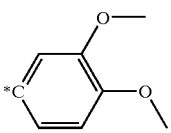 | B72 | 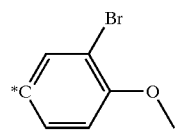 |
| B73 | 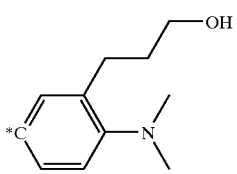 | B74 | 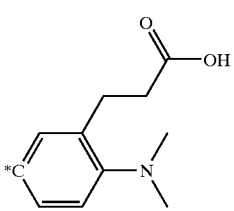 |
| B75 | 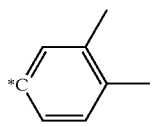 | B76 | 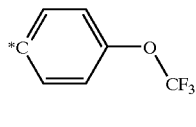 |
| B77 | 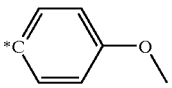 | B78 | 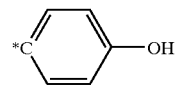 |
| B79 | 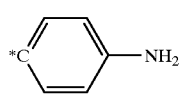 | B80 | 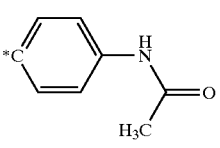 |

TABLE 2-continued
| | | | |
|---|---|---|---|
| B81 | 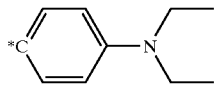 | B82 | 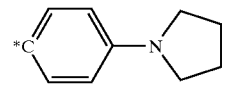 |
| B83 | 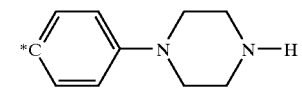 | B86 | 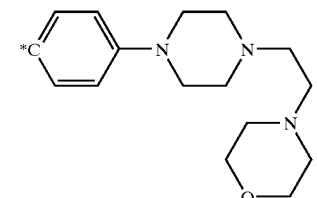 |
| B85 | 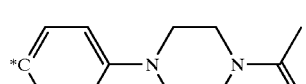 | B86 | 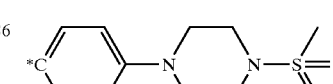 |
| B87 | 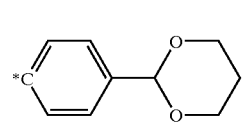 | B88 | 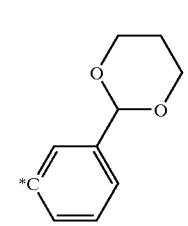 |
| B89 | 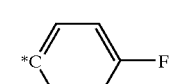 | B90 | 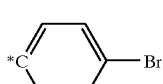 |
| B91 | 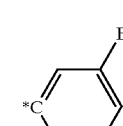 | B92 | 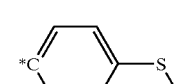 |
| B93 | 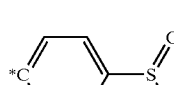 | B94 | 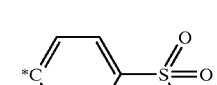 |
| B95 | 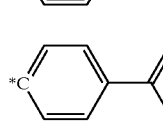 | B96 | 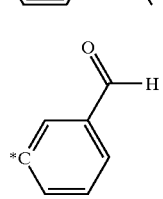 |
| B97 | 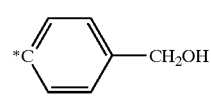 | B98 | 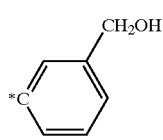 |
| B99 | 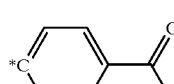 | B100 | 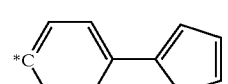 |
| B99 | 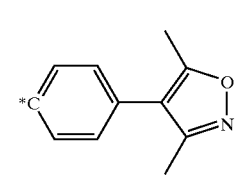 | B100 | 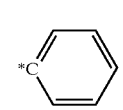 |

TABLE 2-continued
| | | | |
|---|---|---|---|
| B101 | 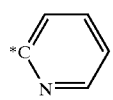 | B102 | 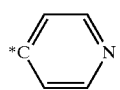 |
| B103 | 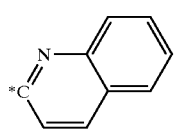 | B104 | 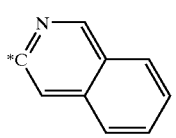 |
| B107 |  | B108 | 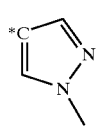 |
| B109 | 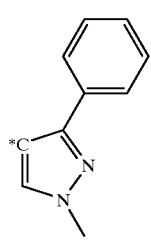 | B110 | 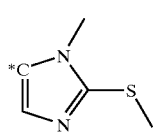 |
| B111 | 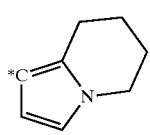 | B112 | 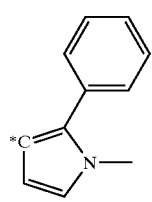 |
| B113 | 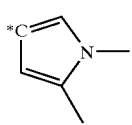 | B114 | 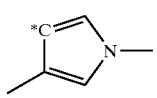 |
| B115 | 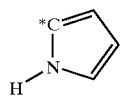 | B116 | 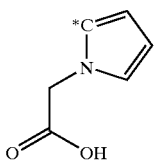 |
| B117 | 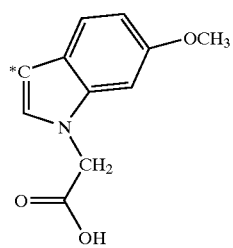 | B118 | 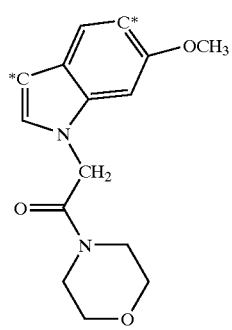 |

TABLE 2-continued
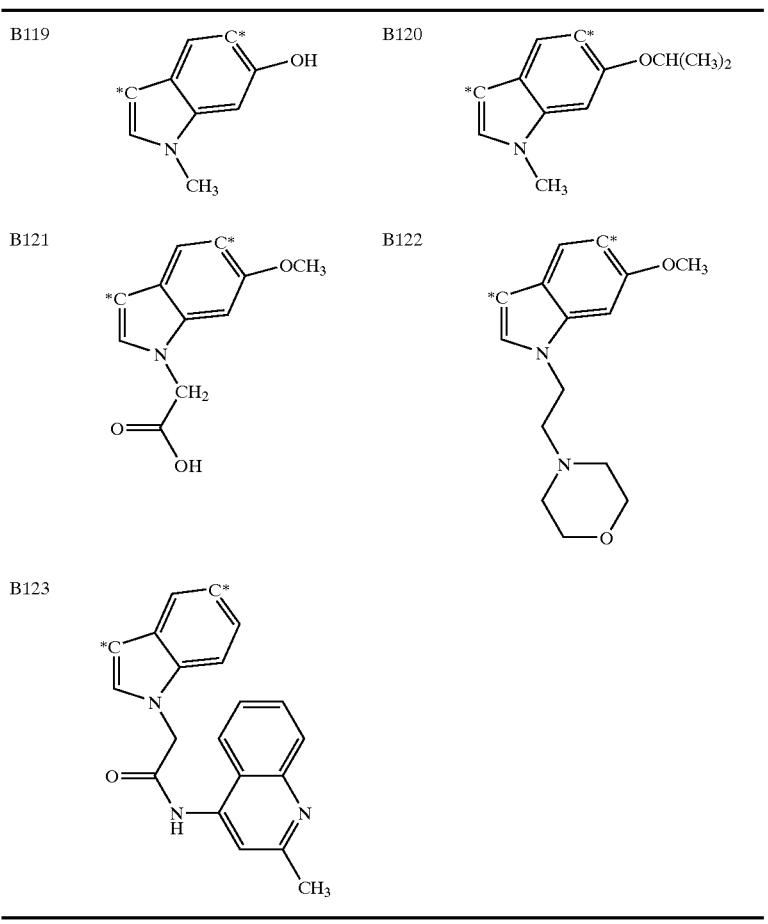
TABLE 3
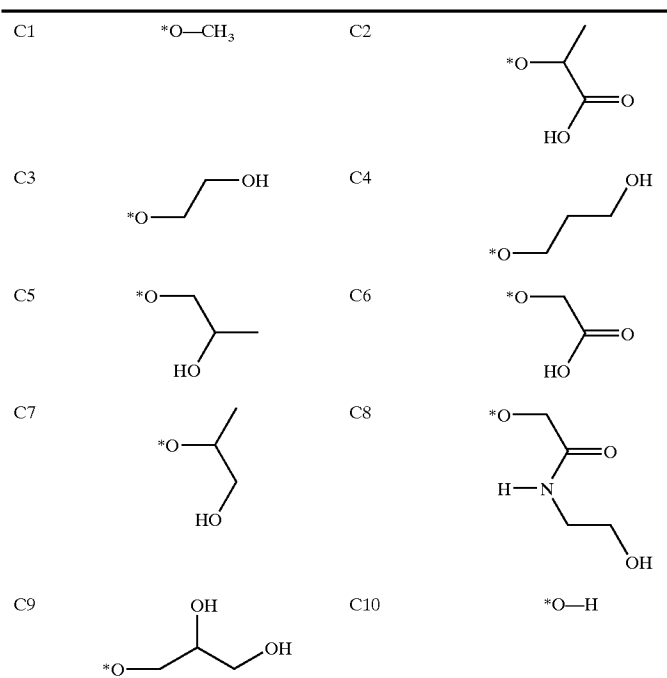

TABLE 3-continued

| | | | |
|---|---|---|---|
| C11 | *O–[cyclobutane]–COOH | C12 | *O–[cyclobutane]–CH2OH |
| C13 | *O–[cyclobutane]–CH2OMe | C14 | *O–[cyclobutane]–C(O)NH–CH2CH2OH |
| C15 | *O–[cyclobutane]–CONH2 | C16 | *O–[cyclobutane]–CONHCH3 |
| C17 | *O–CH(CH3)–CH2–OCH3 | C18 | *O–CH2CH2–NH–C(O)CH3 |
| C19 | *O–CH2–C(CH3)(CH2OH)–CH2OH | C20 | *C(O)–CH3 |
| C21 | *CH2—CH2—CO2H | C22 | *CH2—CH2CONH2 |
| C23 | *C(O)—NH—CH3 | C24 | *C(O)—NH—CH2—CH2—CONH2 |
| C25 | *C(O)—NH—CH2—CH2—OCH3 | C26 | *C(O)—NH—CH2—CH2—CON(H)CH3 |
| C27 | *C(O)—NH—CH2CH2—(2-thienyl) | C28 | *C(O)—OH |
| C29 | *C(O)—NH2 | C30 | *C(O)—NH—C(CH3)(CH2OH)(CH2OH) |
| C31 | *C(O)—NH—C(CH3)2—CH2OH | C32 | *C(O)—NH—CH(CH2OH)2 (with OH, OH) |
| C33 | *C(O)—NH—CH(CH2OH)2 | C34 | *C(O)—NH—CH2—CH2—OH |

TABLE 3-continued
| | | | |
|---|---|---|---|
| C35 | 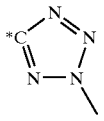 | C36 | 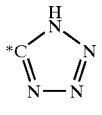 |
| C37 | 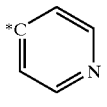 | C38 | 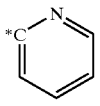 |
| C39 | 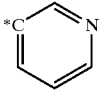 | C40 | 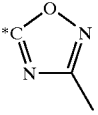 |
| C41 | *CH₂NH—SO₂—CH₃ | C42 | 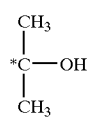 |
| C43 | 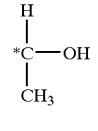 | C44 | *CH₂—NH—CO—NHCH₂CH₃ |
| C45 |  | C46 | *H |
| C47 | 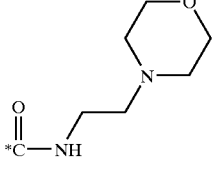 | C48 | 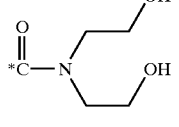 |
| C49 | 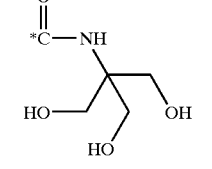 | C50 | 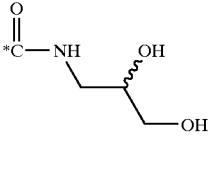 |
| C51 | 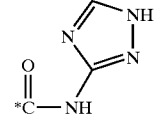 | C52 | 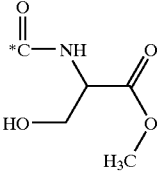 |
| C53 | *C(O)—NH—CH₂—CH₂—F | C54 | *C(O)—NH—CH₂—CH₂—C(O)OCH₂CH₃ |
| C55 |  | C56 | 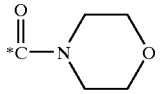 |
| C57 | 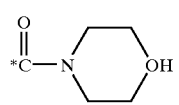 | C58 | *C(O)—NH—CH₂—CH₂—COOH |

TABLE 3-continued
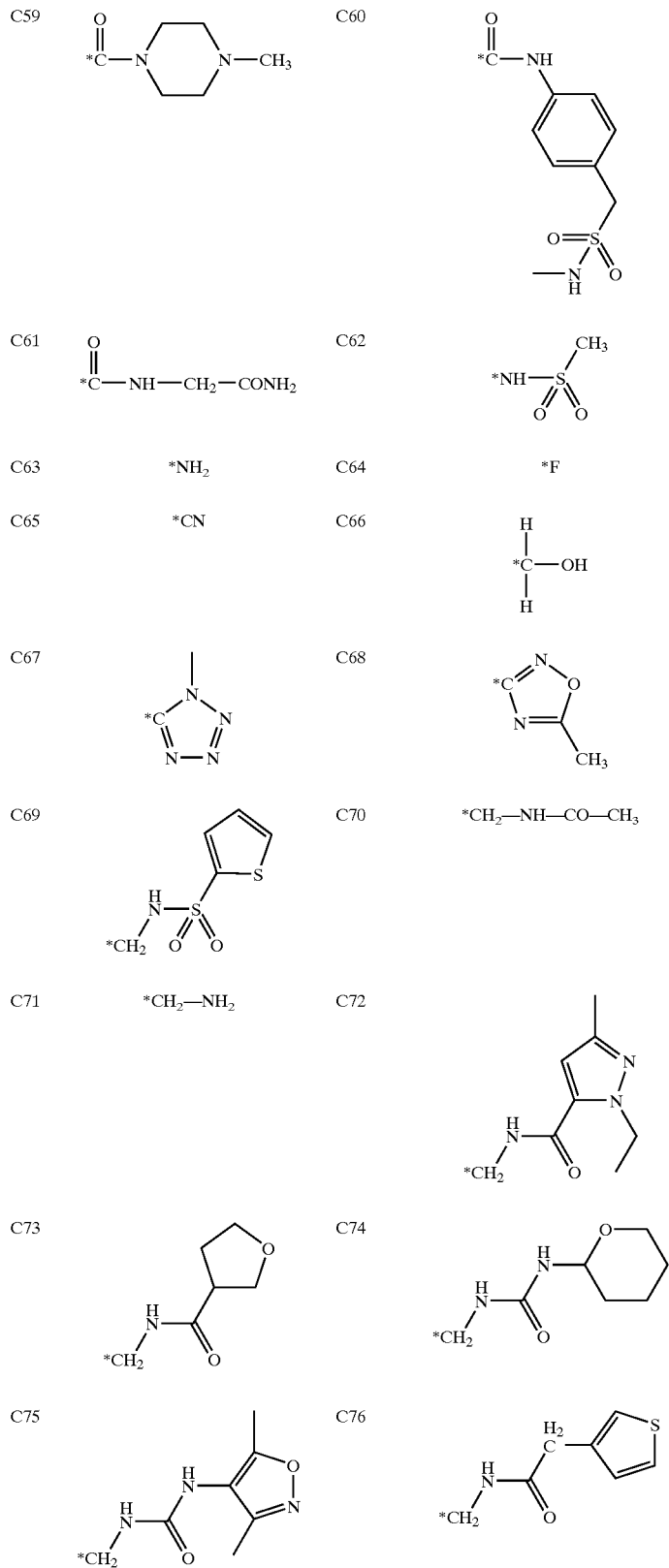

TABLE 3-continued
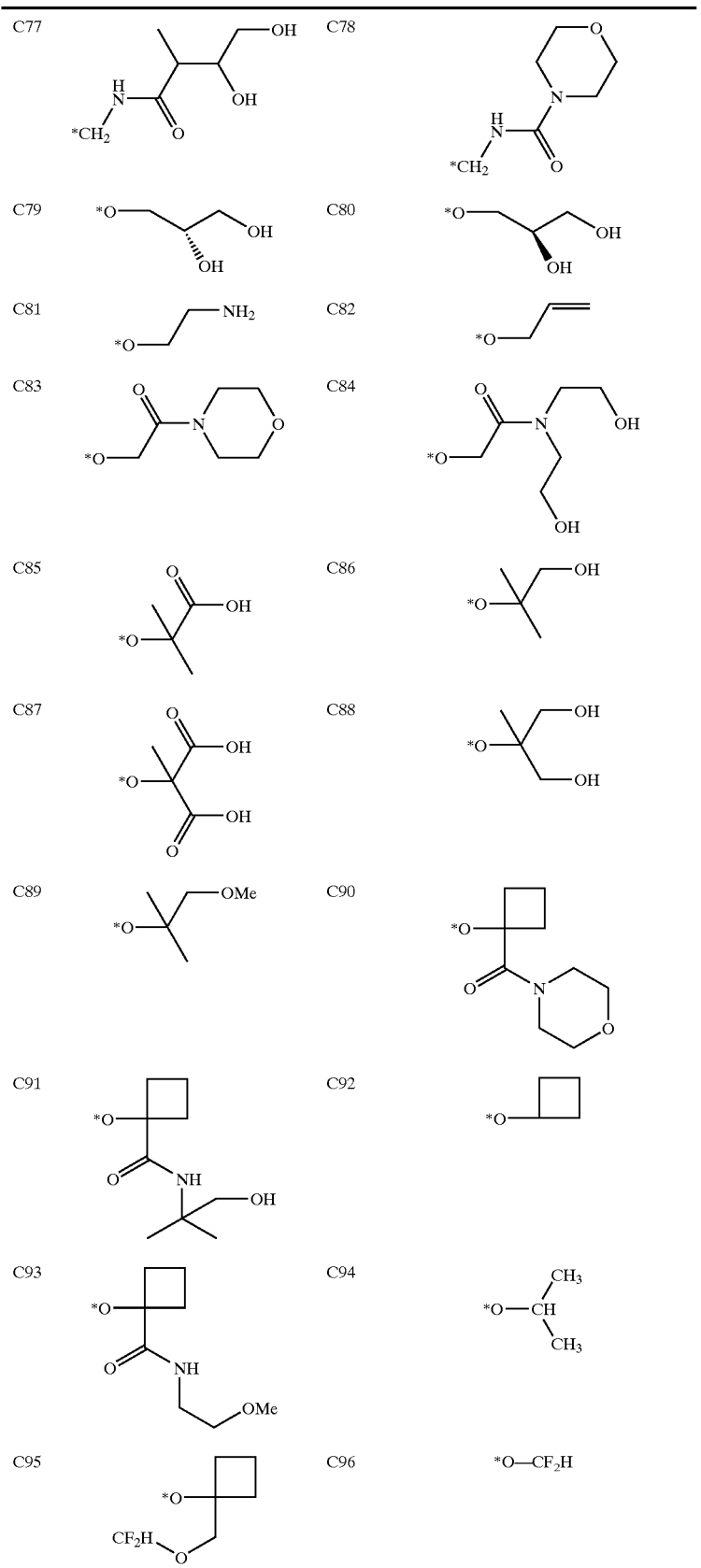

TABLE 3-continued

C97 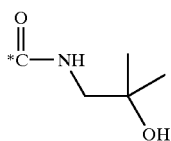

Particular compounds of the invention of formula (I) may be denoted as the product of all combinations of each of groups A1 to A87 in Table 1 and each of groups B1 to B123 in Table 2 and each of groups C1 to C97 in Table 3. Further particular compounds of the invention of formula (I) may be denoted also as the product of all combinations of each of groups A1 to A87 in Table 1 and each of groups B1 to B123 in Table 2.

Thus, for example, the combination which may be denoted as A1-B1-C1 is the product of the combination of group A1 in Table 1 and B1 in Table 2 and C1 in Table 3, namely

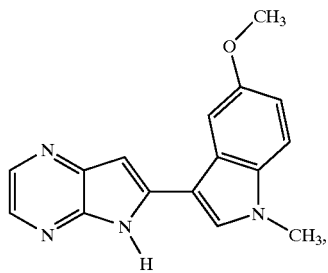

Example 1(a) hereinafter described.

Particular compounds contemplated by the present invention, then, include all of the compounds made up of each of the combinations A1 to A87-B1 to B123-C1 to C97, and each of the combinations A1 to A87-B1 to B123.

Particular compounds of the invention are:

6-(5-methoxy-1-methyl-1H-indol-3-yl)-5H-pyrrolo[2,3-b]pyrazine;
6-(1-methyl-1H-indol-3-yl)-5H-pyrrolo[2,3-b]pyrazine;
6-(3-bromophenyl)-5H-pyrrolo[2,3-b]pyrazine;
7-iso-propyl-6-phenyl-5H-pyrrolo[2,3-b]pyrazine;
6-(4-bromophenyl)-5H-pyrrolo[2,3-b]pyrazine;
2-(4-bromophenyl)-1H-pyrrolo[2,3-b]pyrazine;
6-(4-[1,3]dioxan-2-yl-phenyl)-5H-pyrrolo[2,3-b]pyrazine;
6-(3-[1,3]dioxan-2-yl-phenyl)-5H-pyrrolo[2,3-b]pyrazine;
2-(5H-pyrrolo[2,3-b]pyrazin-6-yl)-quinoline;
3-(5H-pyrrolo[2,3-b]pyrazin-6-yl)-isoquinoline;
6-[1-methyl-1H-indol-5-yl]-5H-pyrrolo[2,3-b]pyrazine;
6-(5-methoxy-1-methyl-1H-indol-3-yl)-2-methyl-5H-pyrrolo[2,3-b]pyrazine;
3-methyl-6-(1-methyl-1H-indol-3-yl)-5H-pyrrolo[2,3-b]pyrazine;
6-(1-benzyl-5-methoxy-1H-indol-3-yl)-5H-pyrrolo[2,3-b]pyrazine;
6-(1-methyl-1H-pyrrol-3-yl)-5H-pyrrolo[2,3-b]pyrazine;
6-(1-methyl-1H-pyrrol-2-yl)-5H-pyrrolo[2,3-b]pyrazine;
6-indolizin-1-yl-5H-pyrrolo[2,3-b]pyrazine;
6-(3-methyl-indolizin-1-yl)-5H-pyrrolo[2,3-b]pyrazine;
6-(1-methyl-2-phenyl-1H-pyrrol-4-yl)-5H-pyrrolo[2,3-b]pyrazine;
6-(5,6,7,8-tetrahydro-indolizin-1-yl)-5H-pyrrolo[2,3-b]pyrazine;
6-furan-3-yl-5H-pyrrolo[2,3-b]pyrazine;
dimethyl-[4-(5H-pyrrolo[2,3-b]pyrazin-6-yl)-phenyl]-amine;
6-(5-methoxy-1-methyl-1H-indol-3-yl)-7-methyl-5H-pyrrolo[2,3-b]pyrazine;
6-(4-tert-butylphenyl)-5H-pyrrolo[2,3-b]pyrazine;
6-(4-tert-butylphenyl)-7-methyl-5H-pyrrolo[2,3-b]pyrazine;
6-(3,4-dimethoxyphenyl)-5H-pyrrolo[2,3-b]pyrazine;
6-(4-aminophenyl)-7-methyl-5H-pyrrolo[2,3-b]pyrazine;
6-[4-(1-methyl)ethoxyphenyl]-5H-pyrrolo[2,3-b]pyrazine;
6-(1H-1-methyl-2-(methylthio)imidazol-5-yl)-5H-pyrrolo[2,3-b]pyrazine;
6-(1-methyl-1H-indazol-3-yl)-5H-pyrrolo[2,3-b]pyrazine;
6-(1-methyl-4-phenyl-1H-pyrrol-3-yl)-5H-pyrrolo[2,3-b]pyrazine;
6-(4-fluorophenyl)-5H-pyrrolo[2,3-b]pyrazine;
6-(4-methoxyphenyl)-5H-pyrrolo[2,3-b]pyrazine;
6-[4-(tert-butyl)phenyl]-7-(prop-1-enyl)-5H-pyrrolo[2,3-b]pyrazine;
6-(4-methylthiophenyl)-5H-pyrrolo[2,3-b]pyrazine;
6-(3-methoxyphenyl)-5H-pyrrolo[2,3-b]pyrazine;
6-(1-methyl-1H-pyrazol-4-yl)-5H-pyrrolo[2,3-b]pyrazine;
6-(1-methyl-5-phenyl-1H-pyrazol-3-yl)-5H-pyrrolo[2,3-b]pyrazine;
6-(pyridin-2-yl)-5H-pyrrolo[2,3-b]pyrazine;
6-(pyridin-4-yl)-5H-pyrrolo[2,3-b]pyrazine;
6-(3,4-dimethylphenyl)-5H-pyrrolo[2,3-b]pyrazine;
6-(4-hydroxyphenyl)-5H-pyrrolo[2,3-b]pyrazine;
6-(4-trifluoromethoxyphenyl)-5H-pyrrolo[2,3-b]pyrazine;
6-(4-aminophenyl)-5H-pyrrolo[2,3-b]pyrazine;
6-(1-methyl-2-phenyl-1H-pyrrol-3-yl)-5H-pyrrolo[2,3-b]pyrazine;
6-(1,5-dimethyl-1H-pyrrol-3-yl)-5H-pyrrolo[2,3-b]pyrazine;
6-(1,4-dimethyl-1H-pyrrol-3-yl)-5H-pyrrolo[2,3-b]pyrazine;
2-(1-methyl-4-phenyl-1H-pyrrol-3-yl)-1H-pyrrolo[2,3-b]pyridine;
3-[3-(5H-pyrrolo[2,3-b]pyrazin-6-yl)-indol-1-yl]-propan-1-ol;
3-[5-methoxy-3-(5H-pyrrolo[2,3-b]pyrazin-6-yl)-indol-1-yl]-propan-1-ol;
2-[3-(5H-pyrrolo[2,3-b]pyrazin-6-yl)-indol-1-yl]-ethanol;
6-(1H-indol-3-yl)-5H-pyrrolo[2,3-b]pyrazine;
2-[5-methoxy-3-(5H-pyrrolo[2,3-b]pyrazin-6-yl)-indol-1-yl]-ethanol;
3-[3-(5H-pyrrolo[2,3-b]pyrazin-6-yl)-indol-1-yl]-propylamine;
3-[5-methoxy-3-(5H-pyrrolo[2,3-b]pyrazin-6-yl)-indol-1-yl]-propylamine;
N-{3-[3-(5H-pyrrolo[2,3-b]pyrazin-6-yl)-indol-1-yl]-propyl}-acetamide;
N-[4-(5H-pyrrolo[2,3-b]pyrazin-6-yl)-phenyl]-acetamide;
6-[1-(3-morpholin-4-yl-propyl)-1H-indol-3-yl]-5H-pyrrolo[2,3-b]pyrazine;
6-[1-(3-piperidin-1-yl-propyl)-1H-indol-3-yl]-5H-pyrrolo[2,3-b]pyrazine;

6-{1-[3-(pyridin-3-yloxy)-propyl]-1H-indol-3-yl}-5H-pyrrolo[2,3-b]pyrazine;
1-methyl-3-(5H-pyrrolo[2,3-b]pyrazin-6-yl)-1H-indol-5-ol;
6-(2-chloro-5-methoxy-1-methyl-1H-indol-3-yl)-5H-pyrrolo[2,3-b]pyrazine;
3-(5H-pyrrolo[2,3-b]pyrazin-6-yl)-benzaldehyde;
4-(5H-pyrrolo[2,3-b]pyrazin-6-yl)-benzaldehyde;
[3-(5H-pyrrolo[2,3-b]pyrazin-6-yl)-indol-1-yl]-methanol;
[3-(5H-pyrrolo[2,3-b]pyrazin-6-yl)-phenyl]-methanol;
[4-(5H-pyrrolo[2,3-b]pyrazin-6-yl)-phenyl]-methanol;
6-(5-methoxy-1H-indol-3-yl)-5H-pyrrolo[2,3-b]pyrazine;
2-[5-methoxy-3-(5H-pyrrolo[2,3-b]pyrazin-6-yl)-indol-1-yl]-1-morpholin-4-yl-ethanone;
2-[5-methoxy-1-(2-morpholin-4-yl-2-oxo-ethyl)-1H-indol-3-yl]-1H-pyrrolo[2,3-b]pyridine-4-carbonitrile;
[5-methoxy-3-(1H-pyrrolo[2,3-b]pyridin-2-yl)-indol-1-yl]-acetic acid;
4-methoxy-2-(5-methoxy-1-methyl-1H-indol-3-yl)-1H-pyrrolo[2,3-b]pyridine;
4-methoxy-2-(5-methoxy-1H-indol-3-yl)-1H-pyrrolo[2,3-b]pyridine;
4-chloro-2-(4-tert-butylphenyl)-1H-pyrrolo[2,3-b]pyridine;
2-(5-methoxy-1-methyl-1H-indol-3-yl)-5-phenyl-1H-pyrrolo[2,3-b]pyridine;
1-[1-methyl-3-(1H-pyrrolo[2,3-b]pyridin-2-yl)-1H-indol-5-yloxy]-propan-2-ol;
[5,6-dimethoxy-3-(1H-pyrrolo[2,3-b]pyridin-2-yl)-indol-1-yl]-acetic acid;
2-[5-methoxy-3-(1H-pyrrolo[2,3-b]pyridin-2-yl)-indol-1-yl]-1-morpholin-4-yl-ethanone;
1-[1-methyl-3-(1H-pyrrolo[2,3-b]pyridin-2-yl)-1H-indol-5-yloxy]-cyclobutanecarboxylic acid amide;
1-[1-methyl-3-(1H-pyrrolo[2,3-b] pyridin-2-yl)-1H-indol-5-yloxy]-cyclobutanecarboxylic acid methylamide;
1-methyl-3-(1H-pyrrolo[2,3-b]pyridin-2-yl)-1H-indole-5-carboxylic acid methylamide;
1-methyl-3-(1H-pyrrolo[2,3-b]pyridin-2-yl)-1H-indole-5-carboxylic acid (2-hydroxy-ethyl)-amide;
1-methyl-3-(1H-pyrrolo[2,3-b]pyridin-2-yl)-1H-indole-5-carboxylic acid (2-morpholin-4-yl-ethyl)-amide;
1-methyl-3-(1H-pyrrolo[2,3-b]pyridin-2-yl)-1H-indole-5-carboxylic acid (2-carbamoyl-ethyl)-amide;
1-methyl-3-(1H-pyrrolo[2,3-b]pyridin-2-yl)-1H-indole-5-carboxylic acid bis-(2-hydroxy-ethyl)-amide;
1-methyl-3-(1H-pyrrolo[2,3-b]pyridin-2-yl)-1H-indole-5-carboxylic acid amide;
1-methyl-3-(1H-pyrrolo[2,3-b]pyridin-2-yl)-1H-indole-5-carboxylic acid (2-hydroxy-1,1-bis-hydroxymethyl-ethyl)-amide;
1-methyl-3-(1H-pyrrolo[2,3-b]pyridin-2-yl)-1H-indole-5-carboxylic acid (2-hydroxy-1-hydroxymethyl-1-methyl-ethyl)-amide;
1-methyl-3-(1H-pyrrolo[2,3-b]pyridin-2-yl)-1H-indole-5-carboxylic acid (2,3-dihydroxy-propyl)-amide;
1-methyl-3-(1H-pyrrolo[2,3-b]pyridin-2-yl)-1H-indole-5-carboxylic acid (2-hydroxy-1,1-dimethyl-ethyl)-amide;
1-methyl-3-(1H-pyrrolo[2,3-b]pyridin-2-yl)-1H-indole-5-carboxylic acid (2-hydroxy-1-hydroxymethyl-ethyl)-amide;
1-methyl-3-(1H-pyrrolo[2,3-b]pyridin-2-yl)-1H-indole-6-carboxylic acid (2-carbamoyl-ethyl)-amide;
1-methyl-3-(1H-pyrrolo[2,3-b]pyridin-2-yl)-1H-indole-6-carboxylic acid (2-hydroxy-ethyl)-amide;
1-methyl-3-(1H-pyrrolo[2,3-b]pyridin-2-yl)-1H-indole-6-carboxylic acid (1H-[1,2,4]triazol-3-yl)-amide;
1-methyl-3-(1H-pyrrolo[2,3-b]pyridin-2-yl)-1H-indole-6-carboxylic acid (2-hydroxy-1-hydroxymethyl-ethyl)-amide;
1-methyl-3-(5H-pyrrolo[2,3-b]pyrazin-6-yl)-1H-indole-5-carboxylic acid (2-hydroxy-1,1-dimethyl-ethyl)-amide;
3-[6-(4-tert-butylphenyl)-5H-pyrrolo[2,3-b]pyrazin-7-yl]-N-methylpropionamide;
3-[6-(4-tert-butylphenyl)-5H-pyrrolo[2,3-b]pyrazin-7-yl]-N,N-dimethylpropionamide;
1-methyl-3-(5H-pyrrolo[2,3-b]pyrazin-6-yl)-1H-indole-5-carboxylic acid 2-methoxyethylamide;
1-methyl-3-(5H-pyrrolo[2,3-b]pyrazin-6-yl)-1H-indole-5-carboxylic acid 2-thien-2-ylethylamide;
1-methyl-3-(5H-pyrrolo[2,3-b]pyrazin-6-yl)-1H-indole-5-carboxylic acid 2-fluoroethylamide;
1-methyl-3-(5H-pyrrolo[2,3-b]pyrazin-6-yl)-1H-indole-5-carboxylic acid 2-carboethoxyethylamide;
1-methyl-3-(5H-pyrrolo[2,3-b]pyrazin-6-yl)-1H-indole-5-carboxylic acid (hydroxymethyl)-carbomethoxy-methylamide;
1-methyl-3-(5H-pyrrolo[2,3-b]pyrazin-6-yl)-1H-indole-5-carboxylic acid 2-hydroxyethylamide;
1-methyl-3-(5H-pyrrolo[2,3-b]pyrazin-6-yl)-1H-indole-5-carboxylic acid methylamide;
1-methyl-3-(5H-pyrrolo[2,3-b]pyrazin-6-yl)-1H-indole-5-carboxylic acid dimethylamide;
[1-methyl-3-(5H-pyrrolo[2,3-b]pyrazin-6-yl)-1H-indol-5-yl]morpholin-4-yl ketone;
4-hydroxy-[1-[1-methyl-3-(5H-pyrrolo[2,3-b]pyrazin-6-yl)-1H-indol-5-yl]carbonylpiperidine
3-[1-methyl-3-(5H-pyrrolo[2,3-b]pyrazin-6-yl)-1H-indol-5-yl]carbonylaminopropionic acid methylamide;
1-methyl-3-(5H-pyrrolo[2,3-b]pyrazin-6-yl)-1H-indole-5-carboxylic acid 3-hydroxypropylamide;
3-{6-[4-(1-methyl)ethoxyphenyl]-5H-pyrrolo[2,3-b]pyrazin-7-yl}propionic acid methylamide;
3-[6-(4-methoxyphenyl)-5H-pyrrolo[2,3-b]pyrazin-7-yl]propionic acid methylamide;
3-{6-[4-(1-methyl)ethoxyphenyl]-5H-pyrrolo[2,3-b]pyrazin-7-yl}propionamide;
3-{6-(4-hydroxyphenyl)-5H-pyrrolo[2,3-b]pyrazin-7-yl}propionamide;
3-[6-(4-fluorophenyl)-5H-pyrrolo[2,3-b]pyrazin-7-yl]propionic acid methylamide;
3-[4-(3,5-dimethyl-isoxazolyl-4-yl)-1H-pyrrolo[2,3-b]pyridin-2-yl]-1-methyl-1H-indole-5-carboxylic acid (2-methoxy-ethyl)-amide;
3-[4-(3,5-dimethyl-isoxazolyl-4-yl)-1H-pyrrolo[2,3-b]pyridin-2-yl]-1H-indole-5-carboxylic acid (2-methoxy-ethyl)-amide;
3-(4-cyano-1H-pyrrolo[2,3-b]pyridin-2-yl)-1-methyl-1H-indole-5-carboxylic acid (2-hydroxy-1,1-dimethyl-ethyl)-amide;
3-(4-cyano-1H-pyrrolo[2,3-b]pyridin-2-yl)-1-methyl-1H-indole-5-carboxylic acid (2-hydroxy-2-methyl-propyl)-amide;
2-[5,6-dimethoxy-3-(1H-pyrrolo[2,3-b]pyridin-2-yl)-indol-1-yl]-1-morpholin-4-yl-ethanone;
[1-methyl-3-(1H-pyrrolo[2,3-b]pyridin-2-yl)-1H-indol-5-yloxy]-acetic acid;
2-[1-methyl-3-(1H-pyrrolo[2,3-b]pyridin-2-yl)-1H-indol-5-yloxy]-propionic acid;
1-[1-methyl-3-(1H-pyrrolo[2,3-b]pyridin-2-yl)-1H-indol-5-yloxy]-cyclobutanecarboxylic acid;
1-methyl-3-(1H-pyrrolo[2,3-b]pyridin-2-yl)-1H-indole-5-carboxylic acid;
1-methyl-3-(1H-pyrrolo[2,3-b]pyridin-2-yl)-1H-indol-5-ol;
1-{1-(cyclobutanecarboxylic acid)-3-1H-pyrrolo[2,3-b]pyridin-2-yl]-1H-indol-5-yloxy}-cyclobutanecarboxylic acid;

1-methyl-3-(1H-pyrrolo[2,3-b]pyridin-2-yl)-1H-indole-6-carboxylic acid;
3-[1-methyl-3-(1H-pyrrolo[2,3-b]pyridin-2-yl)-1H-indol-5-yl]-propionic acid;
1-methyl-3-(5H-pyrrolo[2,3-b]pyrazin-6-yl)-1H-indole-5-carboxylic acid;
[2-methoxy-5-(5H-pyrrolo[2,3-b]pyrazin-6-yl)-phenoxy]acetic acid;
3-[2-dimethylamio-5-(5H-pyrrolo[2,3-b]pyrazin-6-yl)-phenyl]propionic acid;
3-[1-methyl-3-(5H-pyrrolo[2,3-b]pyrazin-6-yl)-1H-indol-5-yl]carbonylaminopropionic acid;
3-[4-(3,5-dimethyl-isoxazole-4-yl)-1H-pyrrolo[2,3-b]pyridine-2-yl]-1-methyl-1H-indole-5-carboxylic acid;
3-[4-(3,5-methyl-isoxazole-4-yl)-1H-pyrrolo[2,3-b]pyridine-2-yl]-1H-indole-5-carboxylic acid;
4-(3,5-dimethyl-isoxazole-4-yl)-2-(5-methoxy-1-methyl-1H-indol-3-yl)-1H-pyrrolo[2,3-b]pyridine;
4-(3,5-dimethyl-isoxazole-4-yl)-2-(5-methoxy-1H-indol-3-yl)-1H-pyrrolo[2,3-b]pyridine;
3-(4-methoxy-1H-pyrrolo[2,3-b]pyridine-2-yl)-1-methyl-1H-indole-5-carboxylic acid;
3-(4-cyano-1H-pyrrolo[2,3-b]pyridine-2-yl)-1-methyl-1H-indole-5-carboxylic acid;
3-(1H-pyrrolo[2,3-b]pyridine-2-yl)-1H-indole-5-carboxylic acid;
2-(5-methoxy-1H-indol-3-yl)-1H-pyrrolo[2,3-b]pyridine-4-carboxylic acid;
potassium 2-(5-methoxy-1H-indol-3-yl)-1H-pyrrolo[2,3-b]pyridine-4-carboxylate;
2-[1-methyl-3-(1H-pyrrolo[2,3-b]pyridin-2-yl)-1H-indol-5-yloxy]-ethanol;
2-[1-methyl-3-(1H-pyrrolo[2,3-b]pyridin-2-yl)-1H-indol-5-yloxy]-propan-1-ol;
{1-[1-methyl-3-(1H-pyrrolo[2,3-b]pyridin-2-yl)-1H-indol-5-yloxy]-cyclobutyl}-methanol;
2-(6-phenyl-5H-pyrrolo[2,3-b]pyrazin-7-yl)-ethanol;
3-[1-methyl-3-(5H-pyrrolo[2,3-b]pyrazin-6-yl)-1H-indol-5-yl]carbonylaminopropionic acid;
2-[2-methoxy-5-(5H-pyrrolo[2,3-b]pyrazin-6-yl)-phenoxy]-ethanol;
3-[2-dimethylamino-5-(5H-pyrrolo[2,3-b]pyrazin-6-yl)-phenyl]-propan-1-ol;
3-{6-[4-(1-methyl)ethoxyphenyl]-5H-pyrrolo[2,3-b]pyrazin-7-yl}propanol;
2-(5-methoxy-1-methyl-1H-indol-3-yl)-1H-pyrrolo[2,3-b]pyridine;
3-[1-methyl-3-(1H-pyrrolo[2,3-b]pyridin-2-yl)-1H-indol-5-yloxy]-propane-1,2-diol;
3-[1-methyl-3-(1H-pyrrolo[2,3-b]pyridin-2-yl)-1H-indol-5-yloxy]-propan-1-ol;
3-[1-methyl-3-(1H-pyrrolo[2,3-b]pyridin-2-yl)-1H-indol-5-yloxy]-propan-2-ol;
2-[1-methyl-5-(2H-tetrazol-5-yl)-1H-indol-3-yl]-1H-pyrrolo[2,3-b]pyridine;
2-[1-methyl-5-(2-methyl-2H-tetrazol-5-yl)-1H-indol-3-yl]-1H-pyrrolo[2,3-b]pyridine;
2-[1-methyl-5-(1-methyl-1H-tetrazol-5-yl)-1H-indol-3-yl]-1H-pyrrolo[2,3-b]pyridine;
1-[1-methyl-3-(1H-pyrrolo[2,3-b]pyridin-2-yl)-1H-indol-5-yl]-ethanone;
2-(5,6-dimethoxy-1-methyl-1H-indol-3-yl)-1H-pyrrolo[2,3-b]pyridine;
(S)-3-[1-methyl-3-(1H-pyrrolo[2,3-b]pyridin-2-yl)-1H-indol-5-yloxy]-propane-1,2-diol;
(R)-3-[1-methyl-3-(1H-pyrrolo[2,3-b]pyridin-2-yl)-1H-indol-5-yloxy]-propane-1,2-diol;
2-[5-(2-methoxy-1-methyl-ethoxy)-1-methyl-1H-indol-3-yl]-1H-pyrrolo[2,3-b]pyridine;
2-[1-methyl-5-(5-methyl-[1,2,4]oxadiazol-3-yl)-1H-indol-3-yl]-1H-pyrrolo[2,3-b]pyridine;
(R)-3-[6-methoxy-1-methyl-3-(1H-pyrrolo[2,3-b]pyridin-2-yl)-1H-indol-5-yloxy]-propane-1,2-diol;
6-methoxy-1-methyl-3-(1H-pyrrolo[2,3-b]pyridin-2-yl)-1H-indol-5-ol;
2-(5-methoxy-1-methyl-1H-indol-3-yl)-4-phenyl-1H-pyrrolo[2,3-b]pyridine;
2-[5-(pyridin-4-yl)-1-methyl-1H-indol-3-yl]-1H-pyrrolo[2,3-b]pyridine;
2-(5-methoxy-1-methyl-1H-indol-3-yl)-1H-pyrrolo[2,3-b]pyridine-4-carbonitrile;
4-chloro-2-(5-methoxy-1-methyl-1H-indol-3-yl)-1H-pyrrolo[2,3-b]pyridine;
2-(5-methoxy-1-methyl-1H-indol-3-yl)-4-(pyridin-3-yl)-1H-pyrrolo[2,3-b]pyridine;
2-(5-methoxy-1-methyl-1H-indol-2-yl)-1H-pyrrolo[2,3-b]pyridine;
2-(5-methoxy-1-methyl-1H-indol-3-yl)-3-methyl-1H-pyrrolo[2,3-b]pyridine;
2-(1H-pyrrol-2-yl)-1H-pyrrolo[2,3-b]pyridine;
2-(1-methyl-1H-pyrrol-2-yl)-1H-pyrrolo[2,3-b]pyridine;
4-chloro-2-(5-methoxy-1H-indol-3-yl)-1H-pyrrolo[2,3-b]pyridine;
5-methoxy-1-methyl-3-(1H-pyrrolo[2,3-b]pyridin-2-yl)-1H-indol-6-ol;
2-(6-isopropoxy-5-methoxy-1-methyl-1H-indol-3-yl)-1H-pyrrolo[2,3-b]pyridine;
2-[5,6-dimethoxy-1-(2-morpholin-4-yl-ethyl)-1H-indol-3-yl]-1H-pyrrolo[2,3-b]pyridine;
1-methyl-3-(1H-pyrrolo[2,3-b]pyridin-2-yl)-1H-indol-5-ylamine;
N-[1-methyl-3-(1H-pyrrolo[2,3-b]pyridin-2-yl)-1H-indol-5-yl]-methanesulfonamide;
N-[1-methyl-3-(1H-pyrrolo[2,3-b]pyridin-2-yl)-1H-indol-5-yl]-acetamide;
N-{1-methyl-3-(1H-pyrrolo[2,3-b]pyridin-2-yl)-1H-indol-5-yl]methyl}thien-2-yl-sulfonamide; {1-[5-(1-hydroxymethyl-cyclobutoxy)-3-(1H-pyrrolo[2,3-b]pyridin-2-yl)-indol-1-yl]-cyclobutyl}-ethanol;
{1-[1-methyl-3-(5H-pyrrolo[2,3-b]pyrazin-6-yl)-1H-indol-5-yloxy]-cyclobutyl}-methanol;
5-[6-(4-tert-butylphenyl)-5H-pyrrolo[2,3-b]pyrazin-7-yl]ethyl-2H-tetrazole;
3-[6-(4-tert-butylphenyl)-5H-pyrrolo[2,3-b]pyrazin-7-yl]-propionitrile;
3-[6-(4-tert-butylphenyl-5H-pyrrolo[2,3-b]pyrazin-7-yl]-propionamide;
3-[6-(4-tert-butylphenyl)-5H-pyrrolo[2,3-b]pyrazin-7-yl]-propionic acid;
3-{6-[4-(1-methyl)ethoxyphenyl]-5H-pyrrolo[2,3-b]pyrazin-7-yl}propionic acid;
3-[6-(4-fluorophenyl)-5H-pyrrolo[2,3-b]pyrazin-7-yl]propionic acid;
3-[6-(4-methoxyphenyl)-5H-pyrrolo[2,3-b]pyrazin-7-yl]propionic acid;
3-[6-(4-tert-butyl-phenyl)-5H-pyrrolo[2,3-b]pyrazin-7-yl]-propan-1-ol;
[2-methoxy-5-(5H-pyrrolo[2,3-b]pyrazin-6-yl)-phenoxy]acetic acid ethyl ester;
2-methoxy-5-(5H-pyrrolo[2,3-b]pyrazin-6-yl)phenol;
3-fluoro-2-(5-methoxy-1-methyl-1H-indol-3-yl)-1H-pyrrolo[2,3-b]pyridine;
3-{6-(4-hydroxyphenyl)-5H-pyrrolo[2,3-b]pyrazin-7-yl}propionic acid;

ethyl 3-{6-(4-hydroxyphenyl)-5H-pyrrolo[2,3-b]pyrazin-7-yl}propionate;
2-(5-methoxy-1H-indol-3-yl)-1H-pyrrolo[2,3-b]pyridine-4-carbonitrile;
6-(4-methylsulfinylphenyl)-5H-pyrrolo[2,3-b]pyrazine;
6-(4-methylsulfonylphenyl)-5H-pyrrolo[2,3-b]pyrazine;
3-(6-(4-tert-butylphenyl)-5H-pyrrolo[2,3-b]pyrazin-7-yl)propylamine;
N-{3-(6-(4-tert-butylphenyl)-5H-pyrrolo[2,3-b]pyrazin-7-yl)propyl}acetamide;
N-{3-(6-(4-tert-butylphenyl)-5H-pyrrolo[2,3-b]pyrazin-7-yl)propyl}cyclopropylcarboxylic acid amide;
N-{3-(6-(4-tert-butylphenyl)-5H-pyrrolo[2,3-b]pyrazin-7-yl)propyl}butyramide;
N-{3-(6-(4-tert-butylphenyl)-5H-pyrrolo[2,3-b]pyrazin-7-yl)propyl}methoxyacetamide;
N-{3-(6-(4-tert-butylphenyl)-5H-pyrrolo[2,3-b]pyrazin-7-yl)propyl}thien-2-ylcarboxylic acid amide;
N-{3-(6-(4-tert-butylphenyl)-5H-pyrrolo[2,3-b]pyrazin-7-yl)propyl}-N'-propyl urea;
N-{3-(6-(4-tert-butylphenyl)-5H-pyrrolo[2,3-b]pyrazin-7-yl)propyl}-N'-carboethoxymethyl urea;
N-{1-methyl-3-(1H-pyrrolo[2,3-b]pyridin-2-yl)-1H-indol-5-yl]methyl}-N'-tetrahydropyran-2-ylurea;
N-{3-(6-(4-tert-butylphenyl)-5H-pyrrolo[2,3-b]pyrazin-7-yl)propyl}-N',N'-diethyl urea;
N-{3-(6-(4-tert-butylphenyl)-5H-pyrrolo[2,3-b]pyrazin-7-yl)propyl}methanesulfonamide;
N-{3-(6-(4-tert-butylphenyl)-5H-pyrrolo[2,3-b]pyrazin-7-yl)propyl}thien-2-ylsulfonamide
N-{3-(6-(4-tert-butylphenyl)-5H-pyrrolo[2,3-b]pyrazin-7-yl)propyl}dimethylisoxazol-4-ylsulfonamide;
N-{3-(6-(4-tert-butylphenyl)-5H-pyrrolo[2,3-b]pyrazin-7-yl)propyl}1-methylimidazol-4-ylsulfonamide;
2-(5-methoxy-1-methyl-1H-indol-3-yl)-1H-pyrrolo[2,3-b]pyridine-4 carboxylic acid (2-hydroxy-1,1-dimethyl-ethyl)-amide;
3-(4-chloro-1H-pyrrolo[2,3-b]pyridin-2-yl)-1-methyl-1H-indole-5-carboxylic acid (2-hydroxy-1,1-dimethyl-ethyl)-amide;
[2-(5-methoxy-1-methyl-1H-indol-3-yl)-1H-pyrrolo[2,3-b]pyridin-4-yl]-morpholin-4-yl-methanone;
3-[6-(4-hydroxyphenyl)-5H-pyrrolo[2,3-b]pyrazin-7-yl]-N-methylpropionamide;
2-(1-ethyl-5-methoxy-1H-indol-3-yl)-1H-pyrrolo[2,3,-b]pyridine-4-carboxylic acid (2-hydroxy-1,1-dimethyl-ethyl)-amide;
2-(5-methoxy-1-methyl-1H-indol-3-yl)-1H-pyrrolo[2,3,-b]pyridine-4-carboxylic acid (2-methoxy-ethyl) amide;
2-(5-methoxy-1-methyl-1H-indol-3-yl)-1H-pyrrolo[2,3,-b]pyridine-4-carboxylic acid (2-hydroxy-2-methyl-propyl) amide;
2-(5-methoxy-1-methyl-1H-indol-3-yl)-1H-pyrrolo[2,3,-b]pyridine-4-carboxylic acid (2-hydroxy-propyl) amide;
2-(5-methoxy-1-methyl-1H-indol-3-yl)-1H-pyrrolo[2,3,-b]pyridine-4-carboxylic acid (2-hydroxy-ethyl) amide;
2-(5-methoxy-1H-indol-3-yl)-1H-pyrrolo[2,3,-b]pyridine-4-carboxylic acid (2-methoxy-ethyl) amide;
2-(5-methoxy-1-methyl-1H-indol-3-yl)-1H-pyrrolo[2,3-b]pyridine-4 carboxylic acid;
3-(4-chloro-1H-pyrrolo[2,3-b]pyridin-2-yl)-1-methyl-1H-indole-5-carboxylic acid;
2-(1-ethyl-5-methoxy-1H-indol-3-yl)-1H-pyrrolo[2,3,-b]pyridine-4-carboxylic acid;
2-(5-methoxy-1H-indol-3-yl)-1H-pyrrolo[2,3-b]pyridine-4 carboxamide;
3-[6-(4-morpholin-4-yl phenyl)-5H-pyrrolo[2,3-b]pyrazin-7-yl]-N-methylpropionamide;
6-(4-pyrrolidin-1-yl phenyl)-5H-pyrrolo[2,3-b]pyrazine;
6-(4-(furan-2-yl)phenyl)-5H-pyrrolo[2,3-b]pyrazine;
6-(4-(3,5-dimethylisoxazol-4-yl)phenyl)-5H-pyrrolo[2,3-b]pyrazine;
2-[4-(5H-pyrrolo[2,3,-b]pyrazin-6-yl)phenyl]-propan-2-ol;
1-[4-(5H-pyrrolo[2,3-b]pyrazin-6-yl)phenyl]ethanone;
6-[4-(4-{2-morpholin-4-ylethyl}-piperazin-1-yl)phenyl]-5H-pyrrolo[2,3-b]pyrazine;
6-(4-piperazin-1-ylphenyl)-5H-pyrrolo[2,3-b]pyrazine;
2-methyl-4-[6-(4-tert-butyl-phenyl)-5H-pyrrolo[2,3-b]pyrazin-7-yl]-butan-2-ol;
[3-(1H-pyrrolo[2,3-b]pyridin-2-yl)-1-methyl-1H-indol-5-yl]-methylamine;
2-{[5-methoxy-3-(1H-pyrrolo[2,3-b]pyridin-2-yl)-indol-1-yl]-1-(1-methylpiperazin)-4-yl}-ethanone;
N-cyclobutyl-2-[5-methoxy-3-(1H-pyrrolo[2,3-b]pyridin-2-yl)-indol-1-yl]-acetamide;
N-(3-imidazol-1-yl-propyl)-2-[5-methoxy-3-(1H-pyrrolo[2,3-b]pyridin-2-yl)-indol-1-yl]-acetamide;
1-(2,5-dihydro-pyrrol-1-yl)-2-[5-methoxy-3-(1H-pyrrolo[2,3-b]pyridin-2-yl)-indol-1-yl]-ethanone;
N-cyclohexyl-2-[5-methoxy-3-(1H-pyrrolo[2,3-b]pyridin-2-yl)-indol-1-yl]-acetamide;
N-cyclopentyl-2-[5-methoxy-3-(1H-pyrrolo[2,3-b]pyridin-2-yl)-indol-1-yl]-acetamide;
N-(3-dimethyl-amino-propyl)-2-[5-methoxy-3-(1H-pyrrolo[2,3-b]pyridin-2-yl)-indol-1-yl]-acetamide;
6-{2-[5-methoxy-3-(1H-pyrrolo[2,3-b]pyridin-2-yl)-indol-1-yl]-acetylamino}-hexanoic acid methyl ester;
1-[1,4']bipiperidinyl-1'-yl-2-[5-methoxy-3-(1H-pyrrolo[2,3-b]pyridin-2-yl)-indol-1-yl]-ethanone;
N-(3,3-dimethyl-butyl)-2-[5-methoxy-3-(1H-pyrrolo[2,3-b]pyridin-2-yl)-indol-1-yl]-acetamide;
N-(3-ethoxy-propyl)-2-[5-methoxy-3-(1H-pyrrolo[2,3-b]pyridin-2-yl)-indol-1-yl]-acetamide;
1-(3,3-dimethyl-piperidin-1-yl)-2-[5-methoxy-3-(1H-pyrrolo[2,3-b]pyridin-2-yl)-indol-1-yl]-ethanone;
2-[5-methoxy-3-(1H-pyrrolo[2,3-b]pyridin-2-yl)-indol-1-yl]-N-(3-oxo-isoxazolidin-4-yl)-acetamide;
1-[4-(4-chloro-phenyl)-piperazin-1-yl]-2-[5-methoxy-3-(1H-pyrrolo[2,3-b]pyridin-2-yl)-indol-1-yl]-ethanone;
1-(4-hydroxy-piperidin-1-yl)-2-[5-methoxy-3-(1H-pyrrolo[2,3-b]pyridin-2-yl)-indol-1-yl]-ethanone;
2-[5-methoxy-3-(1H-pyrrolo[2,3-b]pyridin-2-yl)-indol-1-yl]-1-thiazolidin-3-yl-ethanone;
2-[5-methoxy-3-(1H-pyrrolo[2,3-b]pyridin-2-yl)-indol-1-yl]-1-[4-(3-phenyl-allyl)-piperazin-1-yl]-ethanone;
N-furan-2-ylmethyl-2-[5-methoxy-3-(1H-pyrrolo[2,3-b]pyridin-2-yl)-indol-1-yl]-acetamide;
2-[5-methoxy-3-(1H-pyrrolo[2,3-b]pyridin-2-yl)-indol-1-yl]-N-(2-pyridin-4-yl-ethyl)-acetamide;
N-cyclopropylmethyl-2-[5-methoxy-3-(1H-pyrrolo[2,3-b]pyridin-2-yl)-indol-1-yl]-N-propyl-acetamide;
N-(1-cyclohexyl-ethyl)-2-[5-methoxy-3-(1H-pyrrolo[2,3-b]pyridin-2-yl)-indol-1-yl]-acetamide;
2-[5-methoxy-3-(1H-pyrrolo[2,3-b]pyridin-2-yl)-indol-1-yl]-N-methyl-N-pyridin-3-ylmethyl-acetamide;
2-[5-methoxy-3-(1H-pyrrolo[2,3-b]pyridin-2-yl)-indol-1-yl]-1-(4-m-tolyl-piperazin-1-yl)-ethanone;
2-[5-methoxy-3-(1H-pyrrolo[2,3-b]pyridin-2-yl)-indol-1-yl]-N-(2-phenylsulfanyl-ethyl)-acetamide;
2-[5-methoxy-3-(1H-pyrrolo[2,3-b]pyridin-2-yl)-indol-1-yl]-N-(4-morpholin-4-yl-phenyl)-acetamide;
N-cyclopropyl-2-[5-methoxy-3-(1H-pyrrolo[2,3-b]pyridin-2-yl)-indol-1-yl]-acetamide;
2-[5-methoxy-3-(1H-pyrrolo[2,3-b]pyridin-2-yl)-indol-1-yl]-1-(3-methyl-piperazin-1-yl)-ethanone;

N-(4-cyclohexyl-phenyl)-2-[5-methoxy-3-(1H-pyrrolo[2,3-b]pyridin-2-yl)-indol-1-yl]-acetamide;
2-[5-methoxy-3-(1H-pyrrolo[2,3-b]pyridin-2-yl)-indol-1-yl]-N-(2-methyl-cyclohexyl)-acetamide;
N-cyclohexylmethyl-2-[5-methoxy-3-(1H-pyrrolo[2,3-b]pyridin-2-yl)-indol-1-yl]-acetamide;
2-[5-methoxy-3-(1H-pyrrolo[2,3-b]pyridin-2-yl)-indol-1-yl]-1-pyrrolidin-1-yl-ethanone;
4-{2-[5-methoxy-3-(1H-pyrrolo[2,3-b]pyridin-2-yl)-indol-1-yl]-acetyl}-piperazin-2-one;
4-{2-[5-methoxy-3-(1H-pyrrolo[2,3-b]pyridin-2-yl)-indol-1-yl]-acetyl}-3,3-dimethyl-piperazin-2-one;
4-{2-[5-methoxy-3-(1H-pyrrolo[2,3-b]pyridin-2-yl)-indol-1-yl]-acetyl}-1-methyl-piperazin-2-one;
2-[5-methoxy-3-(1H-pyrrolo[2,3-b]pyridin-2-yl)-indol-1-yl]-1-thiomorpholin-4-yl-ethanone;
N-(2-hydroxy-2-phenyl-ethyl)-2-[5-methoxy-3-(1H-pyrrolo[2,3-b]pyridin-2-yl)-indol-1-yl]-acetamide;
1-(2,6-dimethyl-morpholin-4-yl)-2-[5-methoxy-3-(1H-pyrrolo[2,3-b]pyridin-2-yl)-indol-1-yl]-ethanone;
N-(4-diethylaminomethyl-phenyl)-2-[5-methoxy-3-(1H-pyrrolo[2,3-b]pyridin-2-yl)-indol-1-yl]-acetamide;
N-[2-(4-hydroxy-phenyl)-ethyl]-2-[5-methoxy-3-(1H-pyrrolo[2,3-b]pyridin-2-yl)-indol-1-yl]-acetamide;
2-[5-methoxy-3-(1H-pyrrolo[2,3-b]pyridin-2-yl)-indol-1-yl]-N-(tetrahydro-furan-2-ylmethyl)-acetamide;
2-[5-methoxy-3-(1H-pyrrolo[2,3-b]pyridin-2-yl)-indol-1-yl]-N-pyridin-2-ylmethyl-acetamide;
N-(1,2-dimethyl-propyl)-2-[5-methoxy-3-(1H-pyrrolo[2,3-b]pyridin-2-yl)-indol-1-yl]-acetamide;
N-(3-benzyloxy-pyridin-2-yl)-2-[5-methoxy-3-(1H-pyrrolo[2,3-b]pyridin-2-yl)-indol-1-yl]-acetamide;
2-[5-methoxy-3-(1H-pyrrolo[2,3-b]pyridin-2-yl)-indol-1-yl]-N-quinolin-3-yl-acetamide;
2-[5-methoxy-3-(1H-pyrrolo[2,3-b]pyridin-2-yl)-indol-1-yl]-N-quinolin-8-yl-acetamide;
N-isoquinolin-5-yl-2-[5-methoxy-3-(1H-pyrrolo[2,3-b]pyridin-2-yl)-indol-1-yl]-acetamide;
2-[5-methoxy-3-(1H-pyrrolo[2,3-b]pyridin-2-yl)-indol-1-yl]-N-(3-methyl-butyl)-acetamide;
N-isoquinolin-1-yl-2-[5-methoxy-3-(1H-pyrrolo[2,3-b]pyridin-2-yl)-indol-1-yl]-acetamide;
2-[5-methoxy-3-(1H-pyrrolo[2,3-b]pyridin-2-yl)-indol-1-yl]-N-quinolin-2-yl-acetamide;
1-(3,6-dihydro-2H-pyridin-1-yl)-2-[5-methoxy-3-(1H-pyrrolo[2,3-b]pyridin-2-yl)-indol-1-yl]-ethanone;
2-[5-methoxy-3-(1H-pyrrolo[2,3-b]pyridin-2-yl)-indol-1-yl]-N-[3-(4-methyl-piperazin-1-yl)-propyl]-acetamide;
N-(2-cyclohex-1-enyl-ethyl)-2-[5-methoxy-3-(1H-pyrrolo[2,3-b]pyridin-2-yl)-indol-1-yl]-acetamide;
N-[2-(1H-indol-3-yl)-ethyl]-2-[5-methoxy-3-(1H-pyrrolo[2,3-b]pyridin-2-yl)-indol-1-yl]-acetamide;
2-[5-methoxy-3-(1H-pyrrolo[2,3-b]pyridin-2-yl)-indol-1-yl]-1-[4-(tetrahydro-furan-2-carbonyl)-piperazin-1-yl]-ethanone;
N-adamantan-1-yl-2-[5-methoxy-3-(1H-pyrrolo[2,3-b]pyridin-2-yl)-indol-1-yl]-acetamide;
N-(2-dimethylamino-ethyl)-2-[5-methoxy-3-(1H-pyrrolo[2,3-b]pyridin-2-yl)-indol-1-yl]-N-methyl-acetamide;
1-(4-benzo[1,3]dioxol-5-ylmethyl-piperazin-1-yl)-2-[5-methoxy-3-(1H-pyrrolo[2,3-b]pyridin-2-yl)-indol-1-yl]-ethanone;
1-[4-(4-chloro-benzyl)-piperazin-1-yl]-2-[5-methoxy-3-(1H-pyrrolo[2,3-b]pyridin-2-yl)-indol-1-yl]-ethanone;
2-[5-methoxy-3-(1H-pyrrolo[2,3-b]pyridin-2-yl)-indol-1-yl]-1-[4-(1-phenyl-ethyl)-piperazin-1-yl]-ethanone;
2-[5-methoxy-3-(1H-pyrrolo[2,3-b]pyridin-2-yl)-indol-1-yl]-1-[4-(2-morpholin-4-yl-ethyl)-piperazin-1-yl]-ethanone;
1-[4-(4-methoxy-phenyl)-piperazin-1-yl]-2-[5-methoxy-3-(1H-pyrrolo[2,3-b]pyridin-2-yl)-indol-1-yl]-ethanone;
2-[5-methoxy-3-(1H-pyrrolo[2,3-b]pyridin-2-yl)-indol-1-yl]-N-[3-(2-oxo-pyrrolidin-1-yl)-propyl]-acetamide;
2-[5-methoxy-3-(1H-pyrrolo[2,3-b]pyridin-2-yl)-indol-1-yl]-1-piperidin-1-yl-ethanone;
2-[5-methoxy-3-(1H-pyrrolo[2,3-b]pyridin-2-yl)-indol-1-yl]-N-(2-piperidin-1-yl-ethyl)-acetamide;
2-[5-methoxy-3-(1H-pyrrolo[2,3-b]pyridin-2-yl)-indol-1-yl]-N-(2-pyrrolidin-1-yl-ethyl)-acetamide;
1-[4-(2-methoxy-ethyl)-piperazin-1-yl]-2-[5-methoxy-3-(1H-pyrrolo[2,3-b]pyridin-2-yl)-indol-1-yl]-ethanone;
1-[4-(2-dimethylamino-ethyl)-piperazin-1-yl]-2-[5-methoxy-3-(1H-pyrrolo[2,3-b]pyridin-2-yl)-indol-1-yl]-ethanone;
N-isobutyl-2-[5-methoxy-3-(1H-pyrrolo[2,3-b]pyridin-2-yl)-indol-1-yl]-acetamide;
1-[4-(4-tert-butyl-benzyl)-piperazin-1-yl]-2-[5-methoxy-3-(1H-pyrrolo[2,3-b]pyridin-2-yl)-indol-1-yl]-ethanone;
2-[5-methoxy-3-(1H-pyrrolo[2,3-b]pyridin-2-yl)-indol-1-yl]-N-(1-methyl-3-phenyl-propyl)-acetamide;
N-(4-diethylamino-1-methyl-butyl)-2-[5-methoxy-3-(1H-pyrrolo[2,3-b]pyridin-2-yl)-indol-1-yl]-acetamide;
N-benzyl-N-(2-hydroxy-ethyl)-2-[5-methoxy-3-(1H-pyrrolo[2,3-b]pyridin-2-yl)-indol-1-yl]-acetamide;
1-{4-[2-(2-hydroxy-ethoxy)-ethyl]-piperazin-1-yl}-2-[5-methoxy-3-(1H-pyrrolo[2,3-b]pyridin-2-yl)-indol-1-yl]-ethanone;
N-(1-hydroxymethyl-2-methyl-butyl)-2-[5-methoxy-3-(1H-pyrrolo[2,3-b]pyridin-2-yl)-indol-1-yl]-acetamide;
N-benzyl-2-[5-methoxy-3-(1H-pyrrolo[2,3-b]pyridin-2-yl)-indol-1-yl]-N-methyl-acetamide;
N-(2-methoxy-1-methyl-ethyl)-2-[5-methoxy-3-(1H-pyrrolo[2,3-b]pyridin-2-yl)-indol-1-yl]-acetamide;
N-(3-hydroxy-propyl)-2-[5-methoxy-3-(1H-pyrrolo[2,3-b]pyridin-2-yl)-indol-1-yl]-acetamide;
N-(3-methoxy-phenyl)-2-[5-methoxy-3-(1H-pyrrolo[2,3-b]pyridin-2-yl)-indol-1-yl]-acetamide;
1-(4-benzhydryl-piperazin-1-yl)-2-[5-methoxy-3-(1H-pyrrolo[2,3-b]pyridin-2-yl)-indol-1-yl]-ethanone;
1-(4-benzyl-piperazin-1-yl)-2-[5-methoxy-3-(1H-pyrrolo[2,3-b]pyridin-2-yl)-indol-1-yl]-ethanone;
2-[5-methoxy-3-(1H-pyrrolo[2,3-b]pyridin-2-yl)-indol-1-yl]-N-(3-pyrrolidin-1-yl-propyl)-acetamide;
N-(1-benzyl-piperidin-4-yl)-2-[5-methoxy-3-(1H-pyrrolo[2,3-b]pyridin-2-yl)-indol-1-yl]-acetamide;
1-[4-(4-chloro-phenyl)-4-hydroxy-piperidin-1-yl]-2-[5-methoxy-3-(1H-pyrrolo[2,3-b]pyridin-2-yl)-indol-1-yl]-ethanone;
2-{2-[5-methoxy-3-(1H-pyrrolo[2,3-b]pyridin-2-yl)-indol-1-yl]-acetylamino}-3-methyl-pentanoic acid methyl ester;
2-[5-methoxy-3-(1H-pyrrolo[2,3-b]pyridin-2-yl)-indol-1-yl]-N-(2-methyl-quinolin-4-yl)-acetamide;
N-(2-benzylsulfanyl-1-hydroxymethyl-ethyl)-2-[5-methoxy-3-(1H-pyrrolo[2,3-b]pyridin-2-yl)-indol-1-yl]-acetamide;
[2-(1H-pyrrolo[2,3-b]pyridin-2-yl)-pyrrol-1-yl]-acetic acid;
2-{[2-(1H-pyrrolo[2,3-b]pyridin-2-yl)-pyrrol-1-yl]-1-cyclopropylamino}-ethanone;
N-(3-ethoxy-propyl)-2-[2-(1H-pyrrolo[2,3-b]pyridin-2-yl)-pyrrol-1-yl]-acetamide;
1-pyrrolidin-1-yl-2-[2-(1H-pyrrolo[2,3-b]pyridin-2-yl)-pyrrol-1-yl]-ethanone;
1-(3,6-dihydro-2H-pyridin-1-yl)-2-[2-(1H-pyrrolo[2,3-b]pyridin-2-yl)-pyrrol-1-yl]-ethanone;
1-methyl-4-{2-[2-(1H-pyrrolo[2,3-b]pyridin-2-yl)-pyrrol-1-yl]-acetyl}-piperazin-2-one;

2-[2-(1H-pyrrolo[2,3-b]pyridin-2-yl)-pyrrol-1-yl]-N-(tetrahydro-furan-2-ylmethyl)-acetamide;
1-(2,6-dimethyl-morpholin-4-yl)-2-[2-(1H-pyrrolo[2,3-b]pyridin-2-yl)-pyrrol-1-yl]-ethanone;
2-[2-(1H-pyrrolo[2,3-b]pyridin-2-yl)-pyrrol-1-yl]-1-thiomorpholin-4-yl-ethanone;
1-(4-hydroxy-piperidin-1-yl)-2-[2-(1H-pyrrolo[2,3-b]pyridin-2-yl)-pyrrol-1-yl]-ethanone;
1-(3,3-dimethyl-piperidin-1-yl)-2-[2-(1H-pyrrolo[2,3-b]pyridin-2-yl)-pyrrol-1-yl]-ethanone;
4-{2-[2-(1H-pyrrolo[2,3-b]pyridin-2-yl)-pyrrol-1-yl]-acetyl}-piperazin-2-one;
N-(1-methyl-butyl)-2-[2-(1H-pyrrolo[2,3-b]pyridin-2-yl)-pyrrol-1-yl]-acetamide;
N-bicyclo[2.2.1]hept-2-yl-2-[2-(1H-pyrrolo[2,3-b]pyridin-2-yl)-pyrrol-1-yl]-acetamide;
N-[3-(4-methyl-piperazin-1-yl)-propyl]-2-[2-(1H-pyrrolo[2,3-b]pyridin-2-yl)-pyrrol-1-yl]-acetamide;
1-[4-(3-dimethylamino-propyl)-piperazin-1-yl]-2-[2-(1H-pyrrolo[2,3-b]pyridin-2-yl)-pyrrol-1-yl]-ethanone;
1-(4-methyl-piperazin-1-yl)-2-[2-(1H-pyrrolo[2,3-b]pyridin-2-yl)-pyrrol-1-yl]-ethanone;
1-[4-(4-chloro-phenyl)-4-hydroxy-piperidin-1-yl]-2-[2-(1H-pyrrolo[2,3-b]pyridin-2-yl)-pyrrol-1-yl]-ethanone;
1-[4-(3-hydroxy-phenyl)-piperazin-1-yl]-2-[2-(1H-pyrrolo[2,3-b]pyridin-2-yl)-pyrrol-1-yl]-ethanone;
3-[5-methoxy-2-(1H-pyrrolo[2,3-b]pyridin-2-yl)-indol-1-yl]-propionic acid;
3-[5-methoxy-2-(1H-pyrrolo[2,3-b]pyridin-2-yl)-indol-1-yl]-1-morpholin-4-yl-propan-1-one;
3-[5-methoxy-2-(1H-pyrrolo[2,3-b]pyridin-2-yl)-indol-1-yl]-N-phenyl-propionamide;
3-[5-methoxy-2-(1H-pyrrolo[2,3-b]pyridin-2-yl)-indol-1-yl]-1-thiomorpholin-4-yl-propan-1-one;
3-[5-methoxy-2-(1H-pyrrolo[2,3-b]pyridin-2-yl)-indol-1-yl]-1-(4-methyl-piperazin-1-yl)-propan-1-one;
3-[5-methoxy-2-(1H-pyrrolo[2,3-b]pyridin-2-yl)-indol-1-yl]-N-(tetrahydro-furan-2-ylmethyl)-propionamide;
N-(2-hydroxy-2-phenyl-ethyl)-3-[5-methoxy-2-(1H-pyrrolo[2,3-b]pyridin-2-yl)-indol-1-yl]-propionamide;
N-(2-hydroxy-ethyl)-3-[5-methoxy-2-(1H-pyrrolo[2,3-b]pyridin-2-yl)-indol-1-yl]-propionamide;
1-[4-(4-chloro-phenyl)-4-hydroxy-piperidin-1-yl]-2-[5-methoxy-2-(1H-pyrrolo[2,3-b]pyridin-2-yl)-indol-1-yl]-ethanone;
2-(5-methoxy-1-methyl-1H-indol-3-yl)-4-morpholin-4-yl-1H-pyrrolo[2,3-b]pyridine;
2-(5-methoxy-1-methyl-1H-indol-3-yl)-4-piperidin-1-yl-1H-pyrrolo[2,3-b]pyridine;
[2-(5-methoxy-1-methyl-1H-indol-3-yl)-1H-pyrrolo[2,3-b]pyridin-4-yl]-(2-methoxy-phenyl)-amine;
[2-(5-methoxy-1-methyl-1H-indol-3-yl)-1H-pyrrolo[2,3-b]pyridin-4-yl]-o-tolyl-amine;
[2-(5-methoxy-1-methyl-1H-indol-3-yl)-1H-pyrrolo[2,3-b]pyridin-4-yl]-(3-methoxy-phenyl)-amine;
[2-(5-methoxy-1-methyl-1H-indol-3-yl)-1H-pyrrolo[2,3-b]pyridin-4-yl]-m-tolyl-amine;
(4-fluoro-phenyl)-[2-(5-methoxy-1-methyl-1H-indol-3-yl)-1H-pyrrolo[2,3-b]pyridin-4-yl]-amine;
[2-(5-methoxy-1-methyl-1H-indol-3-yl)-1H-pyrrolo[2,3-b]pyridin-4-yl]-(4-methoxy-phenyl)-amine;
[2-(5-methoxy-1-methyl-1H-indol-3-yl)-1H-pyrrolo[2,3-b]pyridin-4-yl]-p-tolyl-amine;
benzyl-[2-(5-methoxy-1-methyl-1H-indol-3-yl)-1H-pyrrolo[2,3-b]pyridin-4-yl]-amine;
(4-fluoro-benzyl)-[2-(5-methoxy-1-methyl-1H-indol-3-yl)-1H-pyrrolo[2,3-b]pyridin-4-yl]-amine;
(4-methoxy-benzyl)-[2-(5-methoxy-1-methyl-1H-indol-3-yl)-1H-pyrrolo[2,3-b]pyridin-4-yl]-amine;
(2-methoxy-ethyl)-[2-(5-methoxy-1-methyl-1H-indol-3-yl)-1H-pyrrolo[2,3-b]pyridin-4-yl]-amine;
3-[2-(5-methoxy-1-methyl-1H-indol-3-yl)-1H-pyrrolo[2,3-b]pyridin-4-ylamino]-benzoic acid methyl ester;
cyclopropylmethyl-[2-(5-methoxy-1-methyl-1H-indol-3-yl)-1H-pyrrolo[2,3-b]pyridin-4-yl]-amine;
[2-(5-methoxy-1-methyl-1H-indol-3-yl)-1H-pyrrolo[2,3-b]pyridin-4-yl]-phenyl-amine;
butyl-[2-(5-methoxy-1-methyl-1H-indol-3-yl)-1H-pyrrolo[2,3-b]pyridin-4-yl]-amine;
2-(5-methoxy-1H-indol-3-yl)-1H-pyrrolo[2,3,-b]pyridine-4-carboxylic acid methylamide;
2-(5-methoxy-1H-indol-3-yl)-1H-pyrrolo[2,3,-b]pyridine-4-carboxylic acid, tert-butyl ester;

and the corresponding N-oxides, and their prodrugs; and pharmaceutically acceptable salts and solvates (e.g. hydrates) of such compounds and their N-oxides and prodrugs.

Preferred compounds of formula (Ia) of the invention for the inhibition of SYK are:

6-(5-methoxy-1-methyl-1H-indol-3-yl)-5H-pyrrolo[2,3-b]pyrazine, (compound denoted as A1-B1-C1), Example 1(a);
6-(1-methyl-1H-indol-3-yl)-5H-pyrrolo[2,3-b]pyrazine, (compound denoted as A1-B1-C46), Example 1(b);
3-[3-(5H-pyrrolo[2,3-b]pyrazin-6-yl)-indol-1-yl]-propan-1-ol, (compound denoted as A1-B6-C46), Example 2(a);
3-[5-methoxy-3-(5H-pyrrolo[2,3-b]pyrazin-6-yl)-indol-1-yl]-propan-1-ol, (compound denoted as A1-B6-C1), Example 2(b);
2-[5-methoxy-3-(5H-pyrrolo[2,3-b]pyrazin-6-yl)-indol-1-yl]-ethanol, (compound denoted as A1-B5-C1), Example 2(d);
6-(1H-indol-3-yl)-5H-pyrrolo[2,3-b]pyrazine, (compound denoted as A1-B2-C46), Example 2(e);
N-{3-[3-(5H-pyrrolo[2,3-b]pyrazin-6-yl)-indol-1-yl]-propyl}-acetamide, (compound denoted as A1-B7-C46), Example 4(a);
1-methyl-3-(5H-pyrrolo[2,3-b]pyrazin-6-yl)-1H-indol-5-ol, (compound denoted as A1-B1-C10), Example 7;
[3-(5H-pyrrolo[2,3-b]pyrazin-6-yl)-indol-1-yl]-methanol, (compound denoted as A2-B4-C46), Example 9(c);
6-(5-methoxy-1H-indol-3-yl)-5H-pyrrolo[2,3-b]pyrazine, (compound denoted as A1-B2-C1), Example 11;
2-[5-methoxy-3-(5H-pyrrolo[2,3-b]pyrazin-6-yl)-indol-1-yl]-1-morpholin-4-yl-ethanone, (compound denoted as A1-B8-C1), Example 12(a);
2-[5-methoxy-1-(2-morpholin-4-yl-2-oxo-ethyl)-1H-indol-3-yl]-1H-pyrrolo[2,3-b]pyridine-4-carbonitrile, (compound denoted as A3-B8-C1), Example 12(b)
4-methoxy-2-(5-methoxy-1-methyl-1H-indol-3-yl)-1H-pyrrolo[2,3-b]pyridine, (compound denoted as A5-B1-C1), Example 13(b);
4-methoxy-2-(5-methoxy-1H-indol-3-yl)-1H-pyrrolo[2,3-b]pyridine, (compound denoted as A5-B2-C1), Example 13(c);
1-[1-methyl-3-(1H-pyrrolo[2,3-b]pyridin-2-yl)-1H-indol-5-yloxy]-propan-2-ol, compound demoted as A2-B1-C5), Example 13(f);
1-[1-methyl-3-(1H-pyrrolo[2,3-b]pyridin-2-yl)-1H-indol-5-yloxy]-cyclobutanecarboxylic acid amide, (compound denoted as A2-B1-C15), Example 14(b);
1-[1-methyl-3-(1H-pyrrolo[2,3-b]pyridin-2-yl)-1H-indol-5-yloxy]-cyclobutanecarboxylic acid methylamide, (compound denoted as A21-B1-C16), Example 14(c);

1-methyl-3-(1H-pyrrolo[2,3-b]pyridin-2-yl)-1H-indole-5-carboxylic acid (2-hydroxy-ethyl)-amide, (compound denoted as A2-B1-C34), Example 14(e);

1-methyl-3-(1H-pyrrolo[2,3-b]pyridin-2-yl)-1H-indole-5-carboxylic acid (2-carbamoyl-ethyl)-amide, (compound denoted as A2-B1-C24), Example 14(g);

1-methyl-3-(1H-pyrrolo[2,3-b]pyridin-2-yl)-1H-indole-5-carboxylic acid amide, (compound denoted as A2-B1-C29), Example 14(i);

1-methyl-3-(1H-pyrrolo[2,3-b]pyridin-2-yl)-1H-indole-5-carboxylic acid (2-hydroxy-1,1-dimethyl-ethyl)-amide, (compound denoted as A2-B1-C31), Example 14(m);

1-methyl-3-(1H-pyrrolo[2,3-b]pyridin-2-yl)-1H-indole-5-carboxylic acid (2-hydroxy-1-hydroxymethyl-ethyl)-amide, (compound denoted as A2-B5-C33), Example 14(n);

1-methyl-3-(1H-pyrrolo[2,3-b]pyridin-2-yl)-1H-indole-6-carboxylic acid (2-carbamoyl-ethyl)-amide, (compound denoted as A2-B18-C24), Example 14(o);

1-methyl-3-(1H-pyrrolo[2,3-b]pyridin-2-yl)-1H-indole-6-carboxylic acid (1H-[1,2,4]triazol-3-yl)-amide, (compound denoted as A2-B1-C51), Example 14(q);

1-methyl-3-(5H-pyrrolo[2,3-b]pyrazin-6-yl)-1H-indole-5-carboxylic acid 2-methoxyethylamide, (compound denoted as A1-B1-C25), Example 14(v);

1-methyl-3-(5H-pyrrolo[2,3-b]pyrazin-6-yl)-1H-indole-5-carboxylic acid 2-hydroxyethylamide, (compound denoted as A1-B1-C34), Example 14(aa);

1-methyl-3-(5H-pyrrolo[2,3-b]pyrazin-6-yl)-1H-indole-5-carboxylic acid methylamide, (compound denoted as A1-B1-C23), Example 14(ab);

3-[4-(3,5-dimethyl-isoxazolyl-4-yl)-1H-pyrrolo[2,3-b]pyridin-2-yl]-1-methyl-1H-indole-5-carboxylic acid (2-methoxy-ethyl)-amide, compound denoted as A83-B1-C25), Example 14(am);

3-[4-(3,5-dimethyl-isoxazolyl-4-yl)-1H-pyrrolo[2,3-b]pyridin-2-yl]-1H-indole-5-carboxylic acid (2-methoxy-ethyl)-amide, (compound denoted as A83-B2-C25), Example 14(an);

3-(4-cyano-1H-pyrrolo[2,3-b]pyridin-2-yl]-1-methyl-1H-indole-5-carboxylic acid (2-hydroxy-1,1-dimethyl-ethyl)-amide, (compound denoted as A3-B1-C31), Example 14(ao);

3-(4-cyano-1H-pyrrolo[2,3-b]pyridin-2-yl]-1-methyl-1H-indole-5-carboxylic acid (2-hydroxy-2-methyl-propyl)-amide, (compound denoted as A3-B1-C97), Example 14(ap);

[1-methyl-3-(1H-pyrrolo[2,3-b]pyridin-2-yl)-1H-indol-5-yloxy]-acetic acid, (compound denoted as A2-B1-C6), Example 15(a);

2-[1-methyl-3-(1H-pyrrolo[2,3-b]pyridin-2-yl)-1H-indol-5-yloxy]-propionic acid, (compound denoted as A1-B1-C2), Example 15(b);

1-[1-methyl-3-(1H-pyrrolo[2,3-b]pyridin-2-yl)-1H-indol-5-yloxy]-cyclobutane-1-carboxylic acid, (compound denoted as A2-B1-C1), Example 15(c);

1-methyl-3-(1H-pyrrolo[2,3-b]pyridin-2-yl)-1H-indole-5-ol, (compound denoted as A2-B1-C 10), Example 15(e);

1-methyl-3-(1H-pyrrolo[2,3-b]pyridin-2-yl)-1H-indole-6-carboxylic acid, (compound denoted as A2-B18-C28), Example 15(g);

3-[1-methyl-3-(1H-pyrrolo[2,3-b]pyridin-2-yl)-1H-indol-5-yl]-propionic acid, (compound denoted as A2-B1-C21); Example 15(h);

1-methyl-3-(5H-pyrrolo[2,3-b]pyrazin-6-yl)-1H-indole-5-carboxylic acid, (compound denoted as A1-B1-C28), Example 15(i);

3-[4-(3,5-dimethyl-isoxazole-4-yl)-1H-pyrrolo[2,3-b]pyridine-2-yl]-1-methyl-1H-indole-5-carboxylic acid, (compound denoted as A83-B1-C28), Example 15(m);

3-[4-(3,5-methyl-isoxazole-4-yl)-1H-pyrrolo[2,3-b]pyridine-2-yl]-1H-indole-5-carboxylic acid, (compound denoted as A83-B2-C28), Example 15(n);

4-(3,5-dimethyl-isoxazole-4-yl)-2-(5-methoxy-1-methyl-1H-indol-3-yl)-1H-pyrrolo[2,3-b]pyridine, (compound denoted as A83-B1-C1), Example 15(o);

4-(3,5-dimethyl-isoxazole-4-yl)-2-(5-methoxy-1H-indol-3-yl)-1H-pyrrolo[2,3-b]pyridine, (compound denoted as A69-B2-C1), Example 15(p);

3-(4-methoxy-1H-pyrrolo[2,3-b]pyridine-2-yl)-1-methyl-1H-indole-5-carboxylic acid, (compound denoted as A5-B1-C28), Example 15(q);

3-(1H-pyrrolo[2,3-b]pyridine-2-yl)-1H-indole-5-carboxylic acid, (compound denoted as A2-B2-C28), Example 15(s);

2-[1-methyl-3-(1H-pyrrolo[2,3-b]pyridin-2-yl)-1H-indol-5-yloxy]-ethanol, (compound denoted as A2-B1-C3), Example 16(a);

2-[1-methyl-3-(1H-pyrrolo[2,3-b]pyridin-2-yl)-1H-indol-5-yloxy]-propan-1-ol, (compound denoted as A2-B1-C7), Example 16(b);

{1-[1-methyl-3-(1H-pyrrolo[2,3-b]pyridin-2-yl)-1H-indol-5-yloxy]-cyclobutyl}-methanol, (compound denoted as A2-B1-C12), Example 16(c);

2-(5-methoxy-1-methyl-1H-indol-3-yl)-1H-pyrrolo[2,3-b]pyridine, (compound denoted as A2-B1-C1), Example 17(a);

3-[1-methyl-3-(1H-pyrrolo[2,3-b]pyridin-2-yl)-1H-indol-5-yloxy]-propane-1,2-diol, (compound denoted as A2-B1-C9), Example 17(b);

3-[1-methyl-3-(1H-pyrrolo[2,3-b]pyridin-2-yl)-1H-indol-5-yloxy]-propan-1-ol, (compound denoted as A2-B1-C4), Example 17(c);

3-[1-methyl-3-(1H-pyrrolo[2,3-b]pyridin-2-yl)-1H-indol-5-yloxy]-propan-2-ol, (compound denoted as A2-B1-C5), Example 17(d);

2-[1-methyl-5-(2H-tetrazol-5-yl)-1H-indol-3-yl]-1H-pyrrolo[2,3-b]pyridine, (compound denoted as A2-B1-C36), Example 17(e);

2-[1-methyl-5-(2-methyl-2H-tetrazol-5-yl)-1H-indol-3-yl]-1H-pyrrolo[2,3-b]pyridine, (compound denoted as A2-B1-C35), Example 17(f);

1-[1-methyl-3-(1H-pyrrolo[2,3-b]pyridin-2-yl)-1H-indol-5-yl]-ethanone, (compound denoted as A2-B1-C20), Example 17(h);

2-(5,6-dimethoxy-1-methyl-1H-indol-3-yl)-1H-pyrrolo[2,3-b]pyridine, (compound denoted as A2-B17-C1), Example 17(i);

(R)-3-[1-methyl-3-(1H-pyrrolo[2,3-b]pyridin-2-yl)-1H-indol-5-yloxy]-propane-1,2-diol, (compound denoted as A2-B1-C80), Example 17(j);

(A)-3-[1-methyl-3-(1H-pyrrolo[2,3-b]pyridin-2-yl)-1H-indol-5-yloxy]-propane-1,2-diol, (compound denoted as A2-B1-C89), Example 17(k);

2-[5-(2-methoxy-1-methyl-ethoxy)-1-methyl-1H-indol-3-yl]-1H-pyrrolo[2,3-b]pyridine, (compound denoted as A2-B1-C17), Example 17(l);

2-[1-methyl-5-(5-methyl-[1,2,4]oxadiazol-3-yl)-1H-indol-3-yl]-1H-pyrrolo[2,3-b]pyridine, (compound denoted as A2-B1-C68), Example 17(m);

(R)-3-[6-methoxy-1-methyl-3-(1H-pyrrolo[2,3-b]pyridin-2-yl)-1H-indol-5-yloxy]-propane-1,2-diol, (compound denoted as A2-B17-C80), Example 17(n);

6-methoxy-1-methyl-3-(1H-pyrrolo[2,3-b]pyridin-2-yl)-1H-indol-5-ol, (compound denoted as A2-B17-C10), Example 17(o);

2-(5-methoxy-1-methyl-H-indol-3-yl)-4-phenyl-1H-pyrrolo[2,3-b]pyridine, (compound denoted as A13-B1-C1), Example 17(p);

2-(5-methoxy-1-methyl-1H-indol-3-yl)-1H-pyrrolo[2,3-b]pyridine-4-carbonitrile, (compound denoted as A3-B1-C1), Example 17(r);

4-chloro-2-(5-methoxy-1-methyl-1H-indol-3-yl)-1H-pyrrolo[2,3-b]pyridine, (compound denoted as A28-B1-C1), Example 17(s);

2-(5-methoxy-1-methyl-1H-indol-3-yl)$_4$-(pyridin-3-yl)-1H-pyrrolo[2,3-b]pyridine, (compound denoted as A15-B1-C1), Example 17(t);

4-chloro-2-(5-methoxy-1H-indol-3-yl)-1H-pyrrolo[2,3-b]pyridine, (compound denoted as A28-B2-C1), Example 17(y);

N-[1-methyl-3-(1H-pyrrolo[2,3-b]pyridin-2-yl)-1H-indol-5-yl]-acetamide, (compound denoted as A2-B1-C45), Example 19(b);

{1-[5-(1-hydroxymethyl-cyclobutoxy)-3-(1H-pyrrolo[2,3-b]pyridin-2-yl)-indol-1-yl]-cyclobutyl}-methanol, (compound denoted as A2-B13-C12), Example 20(a);

{1-[1-methyl-3-(5H-pyrrolo[2,3-b]pyrazin-6-yl)-1H-indol-5-yloxy]-cyclobutyl}-methanol, (compound denoted as A1-B1-C13), Example 20(b);

2-(5-methoxy-1H-indol-3-yl)-1H-pyrrolo[2,3-b]pyridine-4-carbonitrile, (compound denoted as A3-B2-C1), Example 32;

2-(5-methoxy-1-methyl-1H-indol-3-yl)-1H-pyrrolo[2,3-b]pyridine-4 carboxylic acid (2-hydroxy-1,1-dimethyl-ethyl)-amide, (compound denoted as A68-B1-C1), Example 40(a);

3-(4-chloro-1H-pyrrolo[2,3-b]pyridin-2-yl)-1-methyl-1H-indole-5-carboxylic acid (2-hydroxy-1,1-dimethyl-ethyl)-amide, (compound denoted as A28-B1-C31), Example 40(b);

2-(1-ethyl-5-methoxy-1H-indol-3-yl)-1H-pyrrolo[2,3,-b]pyridine-4-carboxylic acid (2-hydroxy-1,1-dimethyl-ethyl)-amide, (compound denoted as A68-B3-C1), Example 40(e);

2-(5-methoxy-1-methyl-1H-indol-3-yl)-1H-pyrrolo[2,3,-b]pyridine-4-carboxylic acid (2-hydroxy-2-methyl-propyl) amide, (compound denoted as A70-B1-C1), Example 40(g);

2-(5-methoxy-1-methyl-1H-indol-3-yl)-1H-pyrrolo[2,3,-b]pyridine-4-carboxylic acid (2-hydroxy-propyl)amide, (compound denpoted as A85-B1-C1), Example 40(h);

2-(5-methoxy-1-methyl-1H-indol-3-yl)-1H-pyrrolo[2,3,-b]pyridine-4-carboxylic acid (2-hydroxy-ethyl) amide, (compound enoted as A86-B1-C1), Example 40(i);

2-(5-methoxy-1H-indol-3-yl)-1H-pyrrolo[2,3,-b]pyridine-4-carboxylic acid (2-methoxy-ethyl)amide, (compound denoted as A69-B2-C1), Example 40(j);

2-(5-methoxy-1H-indol-3-yl)-1H-pyrrolo[2,3,-b]pyridine-4-carboxylic acid methylamide, (compound denoted as A9-B2-C1), Example 60;

2-(5-methoxy-1H-indol-3-yl)-1H-pyrrolo[2,3,-b]pyridine-4-carboxylic acid, tert-butyl ester, Example 61;

and the corresponding N-oxides, and their prodrugs; and pharmaceutically acceptable salts and solvates (e.g. hydrates) of such compounds and their N-oxides and prodrugs.

Especially preferred compounds of formula (Ia) of the invention for the inhibition of SYK are:

6-(5-methoxy-1-methyl-1 H-indol-3-yl)-5H-pyrrolo[2,3-b]pyrazine (compound denoted as A1-B1-C1), Example 1(a);

1-[1-methyl-3-(1H-pyrrolo[2,3-b]pyridin-2-yl)-1H-indol-5-yloxy]-cyclobutanecarboxylic acid amide, (compound denoted as A2-B1-C15), Example 14(b);

3-[4-(3,5-dimethyl-isoxazolyl-4-yl)-1H-pyrrolo[2,3-b]pyridin-2-yl]-1-methyl-1H-indole-5-carboxylic acid (2-methoxy-ethyl)-amide, (compound denoted as A83-B1-C25), Example 14(am);

3-(4-cyano-1H-pyrrolo[2,3-b]pyridin-2-yl]-1-methyl-1H-indole-5-carboxylic acid (2-hydroxy-2-methyl-propyl)-amide, (compound demoted as A3-B1-97), Example 14(ap);

3-[4-(3,5-dimethyl-isoxazole-4-yl)-1H-pyrrolo[2,3-b]pyridine-2-yl]-1-methyl-1H-indole-5-carboxylic acid, (compound denoted as A83-B1-C28), Example 15m;

3-[4-(3,5-methyl-isoxazole-4-yl)-1H-pyrrolo[2,3-b]pyridine-2-yl]-1H-indole-5-carboxylic acid, (compound denoted as A83-B2-C28), Example 15(n);

4-(3,5-dimethyl-isoxazole-4-yl)-2-(5-methoxy-1-methyl-1H-indol-3-yl)-1H-pyrrolo[2,3-b]pyridine, (compound denoted as A83-B1-C1), Example 15(o);

2-[1-methyl-5-(2H-tetrazol-5-yl)-1H-indol-3-yl]-1H-pyrrolo[2,3-b]pyridine, (compound denoted as A2-B1-C36), Example 17(e);

2-(5-methoxy-1-methyl-1H-indol-3-yl)-1H-pyrrolo[2,3-b]pyridine-4-carbonitrile, (compound denoted as A3-B1-C1), Example 17(r);

{1-[1-methyl-3-(5H-pyrrolo[2,3-b]pyrazin-6-yl)-1H-indol-5-yloxy]-cyclobutyl}-methanol, (compound denoted as A1-B1-C13), Example 20(b);

2-(5-methoxy-1-methyl-1H-indol-3-yl)-1H-pyrrolo[2,3-b]pyridine-4 carboxylic acid (2-hydroxy-1,1-dimethyl-ethyl)-amide, (compound denoted as A68-B1-C1), Example 40(a);

2-(1-ethyl-5-methoxy-1H-indol-3-yl)-1H-pyrrolo[2,3,-b]pyridine-4-carboxylic acid (2-hydroxy-1,1-dimethyl-ethyl)-amide, (compound denoted as A68-B3-C1), Example 40(e);

and the corresponding N-oxides, and their prodrugs; and pharmaceutically acceptable salts and solvates (e.g. hydrates) of such compounds and their N-oxides and prodrugs.

Preferred compounds of formula (Ib) of the invention for the inhibition of SYK are:

6-indolizin-1-yl-5H-pyrrolo[2,3-b]pyrazine, (compound denoted as A1-B40-C46), Example 1(p);

6-(3-methyl-indolizin-1-yl)-5H-pyrrolo[2,3-b]pyrazine, (compound denoted as A1-B41-C46), Example 1(q);

and the corresponding N-oxides, and their prodrugs; and pharmaceutically acceptable salts and solvates (e.g. hydrates) of such compounds and their N-oxides and prodrugs.

Preferred compounds of formula (Ic) of the invention for the inhibition of SYK are:

6-(1-methyl-4-phenyl-1H-pyrrol-3-yl)-5H-pyrrolo[2,3-b]pyrazine, (compound denoted as A1-B43), Example 1(ad);

and the corresponding N-oxides, and their prodrugs; and pharmaceutically acceptable salts and solvates (e.g. hydrates) of such compounds and their N-oxides and prodrugs.

Preferred compounds of formula (Id) of the invention for the inhibition of SYK are:

6-(4-tert-butylphenyl)-5H-pyrrolo[2,3-b]pyrazine, (compound denoted as A1-B55), Example 1(w);
6-(4-tert-butylphenyl)-7-methyl-5H-pyrrolo[2,3-b]pyrazine, (compound denoted as A29-B55), Example 1(x);
3-[6-(4-tert-butylphenyl-5H-pyrrolo[2,3-b]pyrazin-7-yl]-N-methylpropionamide, (compound denoted as A33-B33), Example 14(t);
5-[6-(4-tert-butylphenyl-5H-pyrrolo[2,3-b]pyrazin-7-yl] ethyl-2H-tetrazole, (compound denoted as A35-B55), Example 22;
3-[6-(4-tert-butylphenyl-5H-pyrrolo[2,3-b]pyrazin-7-yl]-propionamide, (compound denoted as A32-B55), Example 24;
3-[6-(4-tert-butylphenyl-51H-pyrrolo[2,3-b]pyrazin-7-yl]-propionic acid, (compound denoted as A31-B55), Example 25(a);
3-[6-(4-tert-butyl-phenyl)-5H-pyrrolo[2,3-b]pyrazin-7-yl]-propan-1-ol, (compound denoted as A30-B55), Example 26;
N-{3-(6-(4-tert-butylphenyl)-5H-pyrrolo[2,3-b]pyrazin-7-yl)propyl}acetamide, (compound denoted as A39-B55), Example 36(a);
N-{3-(6-(4-tert-butylphenyl)-5H-pyrrolo[2,3-b]pyrazin-7-yl)propyl}methanesulfonamide, A38-B55), Example 39(a);
2-methyl-4-[6-(4-tert-butyl-phenyl)-5H-pyrrolo[2,3-b]pyrazin-7-yl]-butan-2-ol, (compound denoted as A59-B55), Example 50;
4-[6-(4-tert-butyl-phenyl)-5H-pyrrolo[2,3-b]pyrazin-7-yl]-butan-2-one, (compound denoted as A58-B55), Example 51;

and the corresponding N-oxides, and their prodrugs; and pharmaceutically acceptable salts and solvates (e.g. hydrates) of such compounds and their N-oxides and prodrugs.

Preferred compounds of formula (Ia) of the invention for the inhibition of Aurora2 are:

1-methyl-3-(1H-pyrrolo[2,3-b]pyridin-2-yl)-1H-indole-6-carboxylic acid, (compound denoted as A2-B18-C28), Example 15(g);
2-[1-methyl-5-(pyridin-4-yl)-1H-indol-3-yl]-4-1H-pyrrolo[2,3-b]pyridine, (compound denoted as A2-B1-C37), Example 17(q);
N-{1-methyl-3-(1H-pyrrolo[2,3-b]pyridin-2-yl)-1H-indol-5-yl]methyl}thien-2-yl-sulfonamide, (compound denoted as A2-B1-C69), Example 19(c);
N-{1-methyl-3-(1H-pyrrolo[2,3-b]pyridin-2-yl)-1H-indol-5-yl]methyl}-N'-tetrahydropyran-2-ylurea, (compound denoted as A2-B1-C74), Example 37(c);
2-[5-methoxy-3-(1H-pyrrolo[2,3-b]pyridin-2-yl)-indol-1-yl]-N-(2-methyl-quinolin-4-yl)-acetamide, (compound denoted as A2-B123-C1), Example 53(cf);
[2-(5-methoxy-1-methyl-1H-indol-3-yl)-1H-pyrrolo[2,3-b]pyridin-4-yl]-(2-methoxy-phenyl)-amine, (compound denoted as A87-B1-C1), Example 59(b);

and the corresponding N-oxides, and their prodrugs; and pharmaceutically acceptable salts and solvates (e.g. hydrates) of such compounds and their N-oxides and prodrugs.

Preferred compounds of formula (Ic) of the invention for the inhibition of Aurora2 are:

6-(1-methyl-1H-pyrrol-2-yl)-5H-pyrrolo[2,3-b]pyrazine, (compound denoted as A1-B53), Example 1(o);

and the corresponding N-oxides, and their prodrugs; and pharmaceutically acceptable salts and solvates (e.g. hydrates) of such compounds and their N-oxides and prodrugs.

Compounds of formula (Ia) in which the

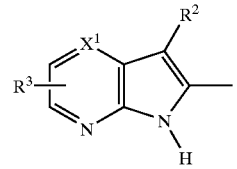

residue is attached to the 2 position of the indole ring and compounds of formula (Ic) in which the

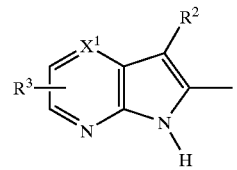

residue is attached to the 2 position of the pyrrole ring show selectivity for inhibition of Aurora2.

Compounds of formula (Ia) in which the

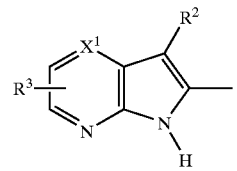

residue (wherein $R^2$ is hydrogen and $X^1$ is CH) is attached to the 3 position of the indole ring and compounds of formula (Ic) in which the

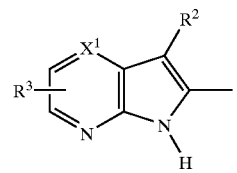

residue (wherein $R^2$ is hydrogen and $X^1$ is CH or N, especially N) is attached to the 3 position of the pyrrole ring are preferred for the inhibition of IGF1R.

Preferred compounds of formula (Ia) of the invention for the inhibition of IGF1R are:

2-[5,6-dimethoxy-3-(1H-pyrrolo[2,3-b]pyridin-2-yl)-indol-1-yl]-1-morpholin-4-yl-ethanone, A2-B118-C1, Example 14(aq);
2-[5,6-dimethoxy-1-(2-morpholin-4-yl-ethyl)-1H-indol-3-yl]-1H-pyrrolo[2,3-b]pyridine, A2-B122-C1, Example 17(ab);
2-(5,6-dimethoxy-1-methyl-1H-indol-3-yl)-1H-pyrrolo[2,3-b]pyridine methanesulfonate, Example 21(g);

and the corresponding N-oxides, and their prodrugs; and pharmaceutically acceptable salts and solvates (e.g. hydrates) of such compounds and their N-oxides and prodrugs.

The compounds of the invention exhibit useful pharmacological activity and accordingly are incorporated into pharmaceutical compositions and used in the treatment of patients suffering from certain medical disorders. The present invention thus provides, according to a further aspect, compounds of the invention and compositions containing compounds of the invention for use in therapy.

Compounds within the scope of the present invention block kinase catalytic activity according to tests described in the literature and in vitro procedures described hereinafter, and which tests results are believed to correlate to pharmacological activity in humans and other mammals. Thus, in a further embodiment, the present invention provides compounds of the invention and compositions containing compounds of the invention for use in the treatment of a patient suffering from, or subject to, conditions which can be ameliorated by the administration of protein kinase inhibitors (e.g. Syk, Aurora2, KDR, FAK and IGF1R). For example, compounds of the present invention are useful in the treatment of inflammatory diseases, for example asthma: inflammatory dermatoses (e.g. psoriasis, dematitis herpetiformis, eczema, necrotizing and cutaneous vasculitis, bullous disease); allergic rhinitis and allergic conjunctivitis; joint inflammation, including arthritis, rheumatoid arthritis and other arthritic conditions such as rheumatoid spondylitis, gouty arthritis, traumatic arthritis, rubella arthritis, psoriatic arthritis and osteoarthritis. The compounds are also useful in the treatment of Chronic Obstructive Pulmonary Disease (COPD), acute synovitis, autoimmune diabetes, autoimmune encephalomyelitis, collitis, atherosclerosis, peripheral vascular disease, cardiovascular disease, multiple sclerosis, restenosis, myocarditis, B cell lymphomas, systemic lupus erythematosus, graft v host disease and other transplant associated rejection events, cancers and tumours (such as colorectal, prostate, breast, thyroid, colon and lung cancers) and inflammatory bowel disease. Additionally, the compounds are useful as tumor anti-angiogenic agents.

A special embodiment of the therapeutic methods of the present invention is the treating of asthma.

Another special embodiment of the therapeutic methods of the present invention is the treating of psoriasis.

Another special embodiment of the therapeutic methods of the present invention is the treating of joint inflammation.

Another special embodiment of the therapeutic methods of the present invention is the treating of inflammatory bowel disease.

Another special embodiment of the therapeutic methods of the present invention is the treating of cancers and tumours.

According to a further feature of the invention there is provided a method for the treatment of a human or animal patient suffering from, or subject to, conditions which can be ameliorated by the administration of a protein kinase inhibitor (e.g. Syk, Aurora2, KDR, FAK and IGF1R) for example conditions as hereinbefore described, which comprises the administration to the patient of an effective amount of compound of the invention or a composition containing a compound of the invention. "Effective amount" is meant to describe an amount of compound of the present invention effective in inhibiting the catalytic activity a protein kinase, such as Syk, Aurora2, KDR, FAK and IGF1R, and thus producing the desired therapeutic effect.

References herein to treatment should be understood to include prophylactic therapy as well as treatment of established conditions.

The present invention also includes within its scope pharmaceutical compositions comprising at least one of the compounds of the invention in association with a pharmaceutically acceptable carrier or excipient.

Compounds of the invention may be administered by any suitable means. In practice compounds of the present invention may generally be administered parenterally, topically, rectally, orally or by inhalation, especially by the oral route.

Compositions according to the invention may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavourings, colourings, or stabilisers in order to obtain pharmaceutically acceptable preparations. The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilised by heating, irradiation or microfiltration.

For topical administration, gels (water or alcohol based), creams or ointments containing compounds of the invention may be used. Compounds of the invention may also be incorporated in a gel or matrix base for application in a patch, which would allow a controlled release of compound through the transdermal barrier.

For administration by inhalation compounds of the invention may be dissolved or suspended in a suitable carrier for use in a nebuliser or a suspension or solution aerosol, or may be absorbed or adsorbed onto a suitable solid carrier for use in a dry powder inhaler.

Solid compositions for rectal administration include suppositories formulated in accordance with known methods and containing at least one compound of the invention.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 1, mg/kg body weight per day by intravenous administration. In each particular case, the doses will be determined in accordance with the factors distinctive to the subject to be treated, such as age, weight, general state of health and other characteristics which can influence the efficacy of the medicinal product.

The compounds according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. Of course, for some patients, it will be necessary to prescribe not more than one or two doses per day.

Compounds of the invention may be prepared by the application or adaptation of known methods, by which is meant methods used heretofore or described in the literature, for example those described by R. C. Larock in Comprehensive Organic Transformations, VCH publishers, 1989.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Compounds of formula (I) wherein $R^1$, $R^2$ and $R^3$ are as hereinbefore defined, and $X^1$ is N or CH may be prepared by application or adaptation of the procedures described by Davis et al Tetrahedron, 1992, 48, page 939–952, for example:

(i) reaction of compounds of formula (III):

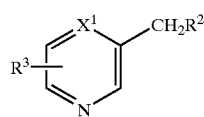

(III)

wherein $R^2$ and $R^3$ are as hereinbefore defined and $X^1$ is N or CH, with a suitable base, such as lithium diisopropylamide (or butyllithium), in an inert solvent, such as tetrahydrofuran, and at a temperature from about −26° C.;

(ii) treatment of the resulting anion with nitrites of formula (IV):

 (IV)

wherein $R^1$ is as defined hereinbefore at a temperature at about −15° C. to about room temperature.

This procedure is particularly suitable for the preparation of compounds of formula (I) where $R^1$ is optionally substituted N-methylindol-3-yl, $R^2$ and $R^3$ are hydrogen and $X^1$ is N or CH.

Compounds of formula (I) wherein $R^1$, $R^2$, $R^3$ and $X^1$ are as hereinbefore defined may also be prepared by application or adaptation of the procedure described by Chang and Bag, J. Org. Chem., 1995, 21, pages 7030–7032, for example reaction of compounds of formula (V):

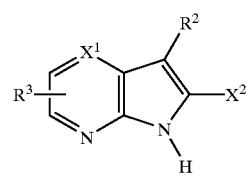

(V)

wherein $R^1$, $R^2$, $R^3$ and $X^1$ are as hereinbefore defined, and $X^2$ is a halogen, preferably iodine, atom or a triflate group, with a boronic acid of formula (VI):

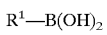 (VI)

wherein $R^1$ is as defined hereinbefore. The coupling reaction may conveniently be carried out for example in the presence of a complex metal catalyst such as tetrakis(triphenylphosphine)palladium(0) and sodium bicarbonate, in aqueous dimethylformamide at a temperature up to reflux temperature.

Compounds of formula (I) wherein $R^2$, $R^3$ and $X^1$ are as hereinbefore defined and $R^1$ is aryl or heteroaryl substituted by —$NY^1Y^2$ may be prepared by reaction of the corresponding compounds in which $R^1$ is aryl or heteroaryl substituted by —$OSO_2CF_3$ with amines of formula $HNY^1Y^2$. The reaction may conveniently be carried out at a temperature at about 200° C. in a microwave oven.

Compounds of formula (I) wherein $R^2$, $R^3$ and $X^1$ are as hereinbefore defined and $R^1$ is aryl or heteroaryl substituted by heteroaryl may be prepared by reaction of the corresponding compounds in which $R^1$ is aryl or heteroaryl substituted by —$OSO_2CF_3$ with an heteroaryl boronic acid. The reaction may conveniently be carried out in the presence of sodium carbonate solution and tetrakis(triphenylphosphine)palladium[0], in an inert solvent, such as dioxane, and at a temperature at about 180° C. in a microwave oven.

Compounds of the invention may also be prepared by interconversion of other compounds of the invention.

Thus, for example, compounds of formula (I) containing a carboxy group may be prepared by hydrolysis of the corresponding esters. The hydrolysis may conveniently be carried out by alkaline hydrolysis using a base, such as an alkali metal hydroxide, e.g. lithium hydroxide, or an alkali metal carbonate, e.g. potassium carbonate, in the presence of an aqueous/organic solvent mixture, using organic solvents such as dioxan, tetrahydrofuran or methanol, at a temperature from about ambient to about reflux. The hydrolysis of the esters may also be carried out by acid hydrolysis using an inorganic acid, such as hydrochloric acid, in the presence of an aqueous/inert organic solvent mixture, using organic solvents such as dioxan or tetrahydrofuran, at a temperature from about 50° C. to about 80° C.

As another example compounds of formula (I) containing a carboxy group may be prepared by acid catalysed removal of the tert-butyl group of the corresponding tert-butyl esters using standard reaction conditions, for example reaction with trifluoroacetic acid at a temperature at about room temperature.

As another example compounds of formula (I) containing a carboxy group may be prepared by hydrogenation of the corresponding benzyl esters. The reaction may be carried out in the presence of ammonium formate and a suitable metal catalyst, e.g. palladium, supported on an inert carrier such as carbon, preferably in a solvent such as methanol or ethanol and at a temperature at about reflux temperature. The reaction may alternatively be carried out in the presence of a suitable metal catalyst, e.g. platinum or palladium optionally supported on an inert carrier such as carbon, preferably in a solvent such as methanol or ethanol.

As another example of the interconversion process, compounds of formula (I) containing a —C(=O)—NY$^1$Y$^2$ group may be prepared by coupling compounds of formula (I) containing a carboxy group with an amine of formula HNY$^1$Y$^2$ to give an amide bond using standard peptide coupling procedures, for example coupling in the presence of O-(7-azabenzotriazol-1-yl)-1,1,3,3-tetramethyluronium hexafluorophosphate and triethylamine (or diisopropylethylamine) in tetrahydrofuran (or dimethylformamide) at room temperature. The coupling may also be brought about by reaction of compounds of formula (I) containing a carboxy group with N-{(dimethylamino)(1H-1,2,3-triazaolo[4,5-b]pyridin-1-yl)methylene}-N-methylmethanaminium hexafluorophosphate N-oxide in the presence of a suitable base, such as diisopropylethylamine, in an inert solvent, such as dimethylformamide, and at a temperature at about room temperature, followed by reaction with an amine of formula HNY$^1$Y$^2$ (ammonium chloride can be used for the preparation of compounds of formula (I) containing a —C(=O)—NH$_2$ group). The coupling may also be brought about by reaction of compounds of formula (I) containing a carboxy group with 2-(1H-benzotriazole-1-yl)1,1,3,3-tetramethyluronium hexafluorophosphate, in dry dimethylformamide, followed by reaction with an amine of formula HNY$^1$Y$^2$ in the presence of diisopropylethylamine.

As another example of the interconversion process, compounds of formula (I) containing a —CH$_2$OH group may be prepared by the reduction of corresponding compounds of formula (I) containing a —CHO or —CO$_2$R$^7$ (in which R$^7$ is lower alkyl) group. For example, the reduction may conveniently be carried out by means of reaction with lithium aluminium hydride, in an inert solvent, such as tetrahydrofuran, and at a temperature from about room temperature to about reflux temperature.

As another example of the interconversion process, compounds of formula (I) in which R$^1$ is aryl or heteroaryl substituted by —CO$_2$Me may be prepared by:

(i) treating compounds of formula (I) in which R$^1$ is aryl or heteroaryl substituted by hydroxy, with N-phenyltrifluoromethanesulfonimide in the presence of a suitable base, such as triethylamine, in an inert solvent, such as dichloromethane, and at a temperature at about −78° C.;

(ii) reaction of the resulting triflate with carbon monoxide in the presence of a suitable catalyst (e.g. palladium acetate), 1,3-bis(diphenylphosphino)propane, triethylamine and methanol, in an inert solvent, such as dimethylformamide at a pressure of about 1 atmosphere, and at a temperature at about room temperature.

This procedure is particularly suitable for the preparation of compounds of formula (I) in which R$^1$ is 5-carboxymethyl-N-methylindol-3-yl.

As another example of the interconversion process, compounds of formula (I) in which R$^1$ is aryl or heteroaryl substituted by —SO$_2$NY$^1$Y$^2$ may be prepared by:

(i) treating compounds of formula (I) in which R$^1$ is aryl or heteroaryl substituted by hydroxy, with N-phenyltrifluoromethanesulfonimide as described hereinabove;

(ii) treating the resulting triflate with tertiary-butylmercaptan in the presence of sodium tertiary-butoxide, palladium acetate, lithium chloride and R(+)-2,2'-bis(diphenylphosphino)-1,1'-binaphthyl in an inert solvent, such as toluene, and at a temperature at about 110–120° C.;

(iii) reaction of the resulting compounds of formula (I) in which R$^1$ is aryl or heteroaryl substituted by —S$^t$Bu, with trifluoroacetic acid and mercuric acetate, in an inert solvent, such as toluene, and at a temperature at about room temperature, followed by treatment with hydrogen sulfide;

(iv) reaction of the resulting compounds of formula (I) in which R$^1$ is aryl or heteroaryl substituted by —SH, with chlorine in aqueous acetic acid at a temperature at about room temperature;

(v) reaction of the resulting compounds of formula (I) in which R$^1$ is aryl or heteroaryl substituted by —SO$_2$Cl, with an amine of formula HNY$^1$Y$^2$.

As another example of the interconversion process, compounds of formula (I) in which R$^1$ is aryl or heteroaryl substituted by aryl (or heteroaryl) may be prepared by treating compounds of formula (1) in which R$^1$ is aryl or heteroaryl substituted by hydroxy with N-phenyltrifluoromethanesulfonimide as described hereinabove followed by reaction of the resulting triflate with an aryl (or heteroaryl) boronic acid ester in the presence of a suitable catalyst (e.g. palladium tetrakis(triphenylphosphine) and aqueous sodium bicarbonate, in an inert solvent, such as dimethylformamide, and at a temperature at about 120–150° C.

As another example of the interconversion process, compounds of formula (I) in which R$^1$ is aryl or heteroaryl substituted —C(=O)CH$_3$ may be prepared by treating compounds of formula (I) in which R$^1$ is aryl or heteroaryl substituted by hydroxy with N-phenyltrifluoromethanesulfonimide as described hereinabove followed by reaction of the resulting triflate with n-butyl vinyl ether in the presence of a suitable catalyst (e.g. palladium acetate), 1,3-bis(diphenylphosphino)butane and triethylamine, in an inert solvent, such as dimethylformamide, and at a temperature at about 80° C.

As another example of the interconversion process, compounds of formula (I) containing a —C(OH)CH$_3$R$^{12}$ (where R$^{12}$ is alkyl) group may be prepared by treating compounds of formula (T) containing a —C(=O)CH$_3$ group with a Grignard reagent, such as methyl magnesium iodide when R$^{12}$ is methyl, in an inert solvent, such as tetrahydrofuran, and at a temperature at about room temperature.

As another example of the interconversion process, compounds of formula (I) in which R$^1$ is aryl or heteroaryl substituted by hydroxy may be prepared by reaction of the corresponding compounds of formula (I) in which R$^1$ is aryl or heteroaryl substituted by methoxy with a Lewis acid, such as boron tribromide, in an inert solvent, such as dichloromethane and at a temperature from about 0° C. to about room temperature. Alternatively compounds of formula (I) in which R$^1$ is aryl or heteroaryl substituted by hydroxy may be prepared by reaction of the corresponding compounds of formula (I) in which R$^1$ is aryl or heteroaryl substituted by benzyloxy with iodotrimethylsilane, in an inert solvent, such as acetonitrile and at a temperature at about 50° C.

As another example of the interconversion process, compounds of formula (I) in which R$^1$ is aryl or heteroaryl substituted by —OR (in which R is optionally substituted alkyl, cycloalkyl, cycloalkylalkyl, heterocycloalkyl or heterocycloalkylalkyl) may be prepared by alkylation the corresponding compounds of formula (I) in which $R^1$ is aryl or heteroaryl substituted by hydroxy, with compounds of formula (VII):

R—$X^3$  (VII)

wherein R is as just hereinbefore defined and $X^3$ is a halogen, preferably bromo, atom, or a tosyl group, using standard alkylation conditions. The alkylation may for example be carried out in the presence of a base, such as an alkali metal carbonate (e.g. potassium carbonate or cesium carbonate), an alkali metal alkoxide (e.g. potassium tertiary butoxide) or alkali metal hydride (e.g. sodium hydride), in dimethylformamide, or dimethyl sulfoxide, at a temperature from about 0° C. to about 100° C.

Alternatively compounds of formula (I) in which $R^1$ is aryl or heteroaryl substituted by —OR (in which R is optionally substituted alkyl, cycloalkyl, cycloalkylalkyl, heterocycloalkyl or heterocycloalkylalkyl) may be prepared by reaction of the corresponding compounds of formula (I) in which $R^1$ is aryl or heteroaryl substituted by hydroxy with the appropriate alcohol of formula (VIII):

R—OH  (VIII)

wherein R is as just hereinbefore defined in the presence of a triarylphosphine, such a triphenylphosphine, and a dialkyl acetylenedicarboxylate, such as diisopropylacetylenedicarboxylate or dimethylacetylenedicarboxylate, in an inert solvent, such as toluene, and at a temperature at about room temperature. This procedure is particularly suitable for the preparation of compounds of formula (I) in which $R^1$ is heteroaryl substituted by —OR (in which R is optionally substituted alkyl, cycloalkyl, cycloalkylalkyl, heterocycloalkyl or heterocycloalkylalkyl).

As another example of the interconversion process, compounds of formula (I) in which $R^1$ is aryl or heteroaryl substituted by —OR (where R is propyl substituted by hydroxy), may be prepared by reaction of the corresponding compounds of formula (I) in which $R^1$ is aryl or heteroaryl substituted by —OR (where R is propenyl) with borane followed by reaction with hydrogen peroxide in the presence of sodium hydroxide. This procedure is particularly suitable for the preparation of compounds of formula (I) in which $R^1$ is indolyl substituted by —OCH$_2$CH(CH$_3$)OH and —OCH$_2$CH$_2$CH$_2$OH.

As another example of the interconversion process, compounds of formula (I) in which $R^1$ is aryl or heteroaryl substituted by —OR (where R is a 1,3-dihydroxyalkylene group) may be prepared by reaction of the corresponding compounds where R is alkenyl with osmium tetroxide in the presence of 4-methyl-morpholine N-oxide. The reaction may conveniently be carried out in an inert solvent, such as acetone, and at a temperature at about room temperature.

As another example of the interconversion process, compounds of formula (Ia) in which $R^9$ is alkyl, alkenyl, cycloalkyl, heterocycloalkyl, or alkyl substituted by —C(=O)NY$^1$Y$^2$, —OR$^7$, —C(=O)—OR$^7$, —NY$^1$Y$^2$ may be prepared by alkylation of the corresponding compounds of formula (Ia) in which $R^9$ is hydrogen, with the appropriate halide of formula (IX):

$R^9$—$X^4$  (IX)

wherein $R^9$ is alkyl, alkenyl, cycloalkyl, heterocycloalkyl, or alkyl substituted by —C(=O)NY$^1$Y$^2$, —OR$^7$, —C(=O)—OR$^7$, —NY$^1$Y$^2$ and $X^4$ is a halogen, preferably bromine, atom, using standard alkylation conditions for example those described hereinbefore.

As another example of the interconversion process, compounds of formula (I) containing a —N(R$^6$)—C(=O)—NY$^3$Y$^4$ group in which $R^6$ and $Y^3$ are both hydrogen and $Y^4$ is as hereinbefore defined may be prepared by reaction of the corresponding compounds of formula (I) containing an amino group with an isocyanate of formula O=C=NY$^4$ in an inert solvent, such as tetrahydrofuran, and at a temperature at about room temperature.

As another example of the interconversion process, compounds of formula (I) containing sulfoxide linkages may be prepared by the oxidation of corresponding compounds containing —S— linkages. For example, the oxidation may conveniently be carried out by means of reaction with a peroxyacid, e.g. 3-chloroperbenzoic acid, preferably in an inert solvent, e.g. dichloromethane, preferably at or near room temperature, or alternatively by means of potassium hydrogen peroxomonosulfate in a medium such as aqueous methanol, buffered to about pH 5, at temperatures between about 0° C. and room temperature. This latter method is preferred for compounds containing an acid-labile group.

As another example of the interconversion process, compounds of formula (1) containing sulfone linkages may be prepared by the oxidation of corresponding compounds containing —S— or sulfoxide linkages. For example, the oxidation may conveniently be carried out by means of reaction with a peroxyacid, e.g. 3-chloroperbenzoic acid; preferably in an inert solvent, e.g. dichloromethane, preferably at or near room temperature.

As another example of the interconversion process, compounds of formula (I) containing a cyano group may be prepared by reaction of the corresponding compounds of formula (I) containing a —C(=O)—NH$_2$ group with phosphorus pentachloride in the presence of triethylamine. The reaction may conveniently be carried out in an inert solvent, such as tetrahydrofuran, and at a temperature at about reflux temperature.

As another example of the interconversion process, compounds of formula (I) containing a —C(=O)—NH$_2$ group may be prepared by reaction of the corresponding compounds of formula (I) containing a cyano group with hydrogen peroxide in the presence of sodium hydroxide. The reaction may conveniently be carried out in methanol at a temperature at about room temperature.

As another example of the interconversion process, compounds of formula (I) containing a tetrazolyl group may be prepared by reaction of the corresponding compounds of formula (I) containing a cyano group with azidotributyltin. The reaction may conveniently be carried out in an inert solvent, such as toluene, and at a temperature at about reflux temperature.

As another example of the interconversion process, compounds of formula (I) in which $R^2$ is a fluoro may be prepared by reaction of the corresponding compounds of formula (I) in which $R^2$ is hydrogen with methyl magnesium bromide (in an inert solvent, such as tetrahydrofuran, and at a temperature at about 0° C.) followed by reaction with 1-chloromethyl-4-fluoro-1,4-diazoniabicyclo[2,2,2]octane bis(tetrafluoroborate) at a temperature from about 0° C. to about reflux temperature.

As another example of the interconversion process, compounds of formula (I) in which $X^1$ is C—NY$^1$Y$^2$ (wherein $Y^1$ and $Y^2$ are as hereinbefore defined and only one of $Y^1$ and $Y^2$ represents hydrogen), may be prepared by reaction of the corresponding compounds of formula (I) in which $X^1$ is halo (e.g. chloro) with an amine of formula HNY$^1$Y$^2$ (wherein Y$^1$ and Y$^2$ are as immediately hereinbefore defined) in the presence of cesium carbonate and tris-(dibenzylideneacetone)-dipalladium(0), in an inert solvent, such as 1,2-dimethoxyethane, and at a temperature at about 80° C.

As another example of the interconversion process, compounds of formula (I) in which X$^1$ is C—CN may be prepared by reaction of compounds of formula (I) in which X$^1$ is C-halo, preferably C—Cl, with zinc cyanide in the presence of zinc powder, [1'1-bis(diphenylphosphino) ferrocene] dichloropalladium(II) complex and dichloromethane (catalytic amount) and N,N-dimethylacetamide at a temperature at about 150° C.

As another example of the interconversion process, compounds of formula (I) containing a —C(=O)—OR$^5$ group (in which R$^5$ is as hereinbefore defined) may be prepared by reaction of the corresponding compounds of formula (I) containing a —C(=O)—OH group with alcohols of formula R$^5$—OH. For example when R$^5$ is tert-butyl the reaction may conveniently be carried out in the presence of 1-1'-carbonyldiimidazole and 1,8-diazabicyclo[5.4.0]undec-7-ene at a temperature at about room temperature.

It will be appreciated that compounds of the present invention may contain asymmetric centres. These asymmetric centres may independently be in either the R or S configuration. It will be apparent to those skilled in the art that certain compounds of the invention may also exhibit geometrical isomerism. It is to be understood that the present invention includes individual geometrical isomers and stereoisomers and mixtures thereof, including racemic mixtures, of compounds of formula (I) hereinabove. Such isomers can be separated from their mixtures, by the application or adaptation of known methods, for example chromatographic techniques and recrystallisation techniques, or they are separately prepared from the appropriate isomers of their intermediates.

According to a further feature of the invention, acid addition salts of the compounds of this invention may be prepared by reaction of the free base with the appropriate acid, by the application or adaptation of known methods. For example, the acid addition salts of the compounds of this invention may be prepared either by dissolving the free base in water or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The acid addition salts of the compounds of this invention can be regenerated from the salts by the application or adaptation of known methods. For example, parent compounds of the invention can be regenerated from their acid addition salts by treatment with an alkali, e.g. aqueous sodium bicarbonate solution or aqueous ammonia solution. Compounds of this invention can be regenerated from their base addition salts by the application or adaptation of known methods. For example, parent compounds of the invention can be regenerated from their base addition salts by treatment with an acid, e.g. hydrochloric acid.

Compounds of the present invention may be conveniently prepared, or formed during the process of the invention, as solvates (e.g. hydrates). Hydrates of compounds of the present invention may be conveniently prepared by recrystallisation from an aqueous/organic solvent mixture, using organic solvents such as dioxan, tetrahydrofuran or methanol.

According to a further feature of the invention, base addition salts of the compounds of this invention may be prepared by reaction of the free acid with the appropriate base, by the application or adaptation of known methods. For example, the base addition salts of the compounds of this invention may be prepared either by dissolving the free acid in water or aqueous alcohol solution or other suitable solvents containing the appropriate base and isolating the salt by evaporating the solution, or by reacting the free acid and base in an organic solvent, in which case the salt separates directly or can be obtained by concentration of the solution.

The starting materials and intermediates may be prepared by the application or adaptation of known methods, for example methods as described in the Reference Examples or their obvious chemical equivalents.

Compounds of formula (IV) wherein R$^1$ is as defined hereinbefore may be prepared by reaction of the corresponding compounds of formula (1):

$$R^1\text{—CHO} \qquad (1)$$

wherein R$^1$ is as hereinbefore defined, with hydroxylamine hydrochloride in an inert solvent, such as dimethylformamide, and at a temperature at about 150° C.

Compounds of formula (IV) wherein R$^1$ is represented by the formula (II):

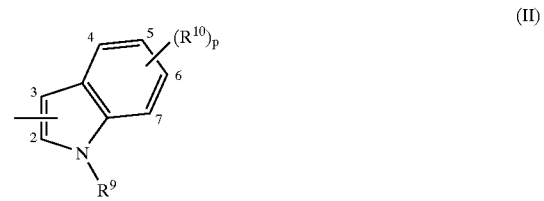

(II)

in which R$^{10}$ and p are as hereinbefore defined and R$^9$ is alkyl, alkenyl, cycloalkyl or alkyl substituted by —C(=O)NY$^1$Y$^2$, —OR$^7$, —C(=O)—OR$^7$, —NY$^1$Y$^2$, may be prepared by alkylation of the corresponding 1H-indoles of formula (IV) wherein R$^1$ is represented by the formula (II), in which R$^{10}$ and p are as hereinbefore defined and R$^9$ is hydrogen, with the appropriate (optionally substituted) alkyl-, alkenyl- or cycloalkyl-halide using standard alkylation conditions. The alkylation may for example be carried out in the presence of a base, such as an alkali metal carbonate, e.g. potassium carbonate, or alkali metal hydride, e.g. sodium hydride, in an inert solvent, such as dimethylformamide or dimethyl sulfoxide, at a temperature from about room temperature to about 100° C.

Compounds of formula (IV) wherein R$^1$ is 5,6,7,8-tetrahydroindolizin-1-yl may be prepared by:
(i) reaction of piperidine-2-carboxylic acid with formic acid and acetic anhydride at a temperature at about room temperature;
(ii) treatment of the resulting sodium-1-formyl-piperidine-2-carboxylate with 4-toluenesulfonyl chloride in an inert solvent, such as dichloromethane, and at a temperature at about room temperature;
(iii) reaction with acrylonitrile in the presence of triethylamine at a temperature at about room temperature.

Compounds of formula (1) wherein R$^1$ is as defined hereinbefore may be prepared by formylation of compounds of formula (2):

$$R^1\text{—H} \qquad (2)$$

wherein R$^1$ is as defined hereinbefore using standard reaction conditions, for example using a Vilsmeier-Haack formylation reaction with phosphorus oxychloride in dimethylformamide. This procedure is particularly suitable for the preparation of compounds of formula (1) where $R^1$ is optionally substituted N-methylindol-3-yl.

Compounds of formula (V) wherein $R^2$, $R^3$ and $X^1$ are as hereinbefore defined and $X^2$ is an iodine atom, may be prepared by iodination of compounds of formula (3):

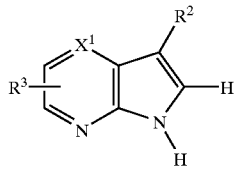
(3)

wherein $R^2$, $R^3$ and $X^1$ are as hereinbefore defined. The iodination reaction may conveniently be carried out by the application or adaptation of the procedure described by Saulnier and Gribble, J. Org. Chem., 1982, 47, 1982, for example by treatment of compounds of formula (3) with lithium diisopropylamide in an inert solvent, such as tetrahydrofuran, and at a temperature at about −78° C., followed by reaction of the resulting anion with iodine. This reaction is conveniently carried out with the indole NH protected with for example a tosyl group.

Compounds of formula (3) wherein $R^2$, $R^3$ and $X^1$ are as hereinbefore defined may be prepared by cyclisation of compounds of formula (4):

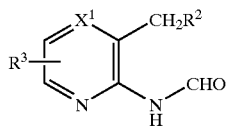
(4)

wherein $R^2$, $R^3$ and $X^1$ are as hereinbefore defined. The cyclisation reaction may conveniently be carried out in the presence of an alkali metal alkoxide, such as sodium ethoxide, in an inert solvent, such as ethanol, and at a temperature from about room temperature to about reflux temperature.

Compounds of formula (3) wherein $R^3$ and $X^1$ are as hereinbefore defined and $R^2$ is hydrogen may be prepared by cyclisation of compounds of formula (5):

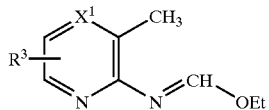
(5)

wherein $R^3$ and $X^1$ are as hereinbefore defined. The cyclisation reaction may conveniently be carried out in the presence of sodamide, in N-methylaniline and at a temperature from about 120° C. to about 200° C.

Compounds of formula (3) wherein $R^3$ and $X^1$ are as hereinbefore defined and $R^2$ is methyl (or $C_{1-4}$alkyl optionally substituted by —$Z^1R^4$, in which $Z^1$ and $R^4$ as hereinbefore defined) may be prepared by cyclisation of compounds of formula (6):

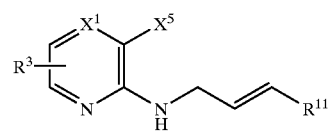
(6)

wherein $R^3$ and $X^1$ are as hereinbefore defined, $R^{11}$ is hydrogen (or $C_{1-3}$alkyl optionally substituted by —$Z^1R^4$, in which $Z^1$ and $R^4$ as hereinbefore defined) and $X^5$ represents a halogen, preferably a bromine, atom, or a triflate group. The cyclisation may conveniently be carried out in the presence of a complex metal catalyst such as tetrakis (triphenylphosphine)palladium(0), a tertiary amine, such as triethylamine, and a triarylphosphine, such as triphenylphosphine, in an inert solvent, such as dimethylformamide and at a temperature at about 60° C. to about 120° C. This procedure is particularly suitable for the preparation of compounds of formula (3) wherein $R^3$ and $X^1$ are as hereinbefore defined, $X^1$ is N and $R^2$ is C—$CH_3$.

Compounds of formula (3) wherein $R^3$, $R^2$ and $X^1$ are as hereinbefore defined may be prepared by:
(i) reaction of compounds of formula (7):

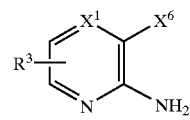
(7)

wherein $R^3$ and $X^1$ are as hereinbefore defined and $X^6$ is a halogen, preferably iodine, atom with acetylenes of formula (8):

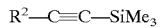
$$R^2—C≡C—SiMe_3 \quad (8)$$

wherein $R^2$ is as hereinbefore defined, in the presence of a complex metal catalyst such as [1,1'-bis(diphenylphosphino)-ferrocene]palladium (II) chloride, lithium chloride and sodium carbonate, in an inert solvent, such as dimethylformamide, and at a temperature up to about 100° C.
(ii) desilylation.

Compounds of formula (4) wherein $R^2$, $R^3$ and $X^1$ are as hereinbefore defined may be prepared by reaction of compounds of formula (9):

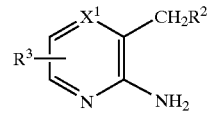
(9)

wherein $R^2$, $R^3$ and $X^1$ are as hereinbefore defined with a mixture of formic acid and acetic anhydride.

Compounds of formula (5) wherein $R^3$ and $X^1$ are as hereinbefore defined may be prepared by reaction of the corresponding compounds of formula (9) wherein $R^3$ and $X^1$ are as hereinbefore defined and $R^2$ is hydrogen with triethylorthoformate, in the presence of an acid catalyst, such as hydrogen chloride, in ethanol and at a temperature from about room temperature to about reflux temperature.

Compounds of formula (6) wherein $R^3$, $R^{11}$ and $X^1$ are as hereinbefore defined and $X^5$ is a halogen atom may be prepared by alkylation of compounds of formula (7) wherein $R^3$, $X^1$ and $X^6$ are as hereinbefore defined with the appropriate alkenyl halide of formula (10):

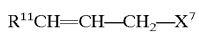 (10)

wherein $R^{11}$ is as hereinbefore defined and $X^7$ is a halogen, preferably bromine, atom. The alkylation may conveniently be carried out in the presence of an alkali metal hydride, such as sodium hydride, in an inert solvent, such as tetrahydrofuran, and at a temperature at about room temperature.

Compounds of formula (7) wherein $R^3$ and $X^1$ are as hereinbefore defined and $X^6$ is a bromine atom, may be prepared by bromination of compounds of formula (11):

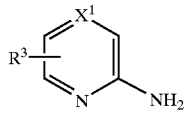 (11)

wherein $R^3$ and $X^1$ are as hereinbefore defined, in dimethylsulfoxide.

Compounds of formula (7) wherein $R^3$ and $X^1$ are as hereinbefore defined and $X^5$ is an iodine atom, may be prepared by iodination of compounds of formula (11) wherein $R^3$ and $X^1$ are as hereinbefore defined. The iodination may be carried out by the application or adaptation of the method of W—W. Sy, Synth.Comm., 1992, 22, pages 3215–3219.

Compounds of formula (V) wherein $R^1$, $R^2$, $R^3$ and $X^1$ are as hereinbefore defined and $X^5$ is a triflate group may be prepared by reaction of compounds of formula (12):

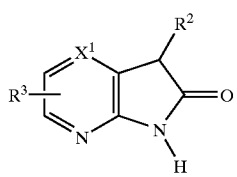 (12)

wherein $R^2$, $R^3$ and $X^1$ are as hereinbefore defined, with triflic anhydride in the presence of Hunigs base, in an inert solvent, such as dichloromethane, and at a temperature at about 0° C. This reaction is conveniently carried out with the indole NH protected with for example a tosyl group.

Compounds of formula (12) wherein $R^2$, $R^3$ and $X^1$ are as hereinbefore defined may be prepared by reaction of compounds of formula (13):

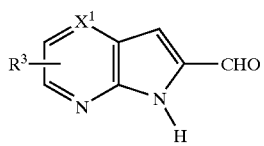 (13)

wherein $R^3$ and $X^1$ are as hereinbefore defined with meta-chloroperbenzoic acid, in an inert solvent, such as dichloromethane, and at a temperature at about 5° C. This reaction is conveniently carried out with the indole NH protected with for example a tosyl group.

Compounds of formula (13) wherein $R^3$ and $X^1$ are as hereinbefore defined may be prepared by reaction of compounds of formula (14):

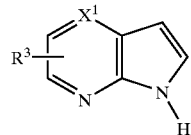 (14)

wherein $R^3$ and $X^1$ are as hereinbefore defined with lithium diisopropylamide, in an inert solvent, such as tetrahydrofuran, followed by reaction with dimethylformamide and at a temperature at about –78° C. This reaction is conveniently carried out with the indole NH protected with for example a tosyl group.

Compounds of formula (14) wherein $R^3$ and $X^1$ are as hereinbefore defined may be prepared by reaction of compounds of formula (7) wherein $R^3$ and $X^1$ are as hereinbefore defined and $X^6$ is iodo, with trimethylsilylacetylene in the presence of a complex metal catalyst such as [1,1'-bis(diphenylphosphino)-ferrocene]palladium (II) chloride, followed by desilylation.

Compounds of formula (14) wherein $R^3$ is as hereinbefore defined and $X^1$ is C—$Z^2$R (in which $Z^2$ is O and R is alkyl) may be prepared by reaction of compounds of formula (14) wherein $R^3$ is as hereinbefore defined and $X^1$ is C-halo, preferably C—Cl, with an alcohol of formula R—OH in the presence of an alkali metal hydroxide, such as sodium hydroxide. The reaction is conveniently carried out under pressure and at a temperature at about 170° C.

Compounds of formula (14) wherein $R^3$ is as hereinbefore defined and $X^1$ is C—OH may be prepared by reaction of compounds of formula (14) wherein $R^3$ is as hereinbefore defined and $X^1$ is C-halo, preferably C—Cl, with an aqueous alkali metal hydroxide solution, such as sodium hydroxide solution. The reaction is conveniently carried out under pressure and at a temperature at about 180° C.

Compounds of formula (14) wherein $R^3$ is as hereinbefore defined and $X^1$ is C—Cl may be prepared by oxidation of compounds of formula (14) wherein $R^3$ is as hereinbefore defined and $X^1$ is C—H with 3-chloroperbenzoic acid, in an inert solvent, such as dichloromethane, and at a temperature at about 0° C. followed by reaction of the resulting pyrrolo[2,3-b]pyridine N-oxide with phosphorus oxychloride at reflux.

Compounds of formula (14) wherein $R^3$ is as hereinbefore defined and $X^1$ is C—C(=O)—OR$^5$ group (in which $R^5$ is as hereinbefore defined) may be prepared by reaction of the corresponding compounds of formula (I) containing a —C(=O)—OH group with alcohols of formula $R^5$—OH. For example when $R^5$ is tert-butyl the reaction may conveniently be carried out in the presence of 1-1'-carbonyldiimidazole and 1,8-diazabicyclo[5.4.0]undec-7-ene at a temperature at about room temperature.

Compounds of formula (14) wherein $R^3$ is as hereinbefore defined and $X^1$ is C-heteroaryl (for example

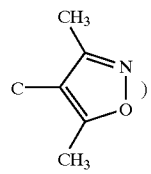

may be prepared by reaction of compounds of formula (16):

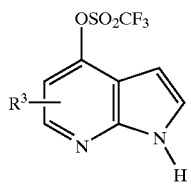

(16)

in which $R^3$ is as hereinbefore defined with the appropriate heteroaryl boronic acid (for example 3,5-dimethylisoxazole-4-boronic acid) in the presence of tetrakis(triphenylphosphine)palladium(0) and aqueous sodium bicarbonate. The reaction may conveniently be carried out in dimethylformamide at a temperature at about 110° C.

Compounds of formula (VI) wherein $R^1$ is as defined hereinbefore may be prepared by: reaction of compounds of formula (15):

$$R^1-X^8 \quad (15)$$

wherein $R^1$ is as defined hereinbefore and $X^8$ is a halogen, preferably bromine, atom, in the presence of tributylborate, with a suitable base, such as butyllithium, in an inert solvent, such as tetrahydrofuran, and at a temperature at about -100° C.

Compounds of formula (VI) wherein $R^1$ is as defined hereinbefore may also be prepared by treatment of compounds of formula (15), wherein $R^1$ is as defined hereinbefore and $X^8$ is a —HgOAc group, with borane, in an inert solvent, such as tetrahydrofuran, and at a temperature at about room temperature.

Compounds of formula (15) wherein $R^1$ is optionally substituted indol-3-yl and $X^8$ is a bromine atom may be prepared by reaction of optionally substituted indoles with bromine in an inert solvent, such as dimethylformamide, and at a temperature at about room temperature.

Compounds of formula (13) wherein $R^1$ is optionally substituted indol-3-yl and $X^8$ is a —HgOAc group may be prepared by reaction of optionally substituted indolines with mercuric acetate in glacial acetic acid at a temperature at about room temperature.

The present invention is further exemplified but not limited by the following illustrative Examples and Reference Examples.

400M Hz $^1$H nuclear magnetic resonance spectra (NMR) were recorded on a Varian Unity INOVA machine. In the nuclear magnetic resonance spectra (NMR) the chemical shifts (δ) are expressed in ppm relative to tetramethylsilane. Abbreviations have the following significances: s=singlet; d=doublet; t=triplet; m=multiplet; q=quartet; dd doublet of doublets; ddd=doublet of double doublets.

High Pressure Liquid Chromatography—Mass Spectrometry (LC-MS) conditions for determination of retention times ($R_T$) were as follows:

METHOD A: YMC ODS-A IPLC column (50 mm×4 mm) operated under gradient elution conditions with mixtures of water and acetonitrile, (A) 95:5 and (B) 5:95, containing 0.1% formic acid as the mobile phase gradient (0.00 minutes, 95%A:5%B; linear gradient to 100% B at 2 minutes; then hold until 3.4 minutes); flow rate 2 ml/minute with approximately 200 μl/minute split to the Mass Spectrometer; injection volume 10–40 μl; in line Diode Array (220–450 nm), in line Evaporative light scattering (ELS) detection ELS—temperature 50° C., Gain 8–1.8 ml/minute; Source temperature 150° C.;

METHOD B: 3 micron Luna C18 (2) IPLC column (30 mm×4.6 mm) operated under gradient elution conditions with mixtures of (A) water containing 0.1% trifluoroacetic acid and (B) acetonitrile containing 0.1% trifluoroacetic acid as the mobile phase gradient: 0.00 minutes, 95%A:5%B; 0.50 minutes, 95% A:5% B; 4.50 minutes, 5% A:95% B; 5.00 minutes, 5% A:95% B; 5.50 minutes, 95% A:5% B; flow rate 2 ml/minute with approximately 200 μl/minute split to the Mass Spectrometer; injection volume 10–40 μl; in line Diode Array (220–450 nm), in line Evaporative light scattering (ELS) detection ELS—temperature 50° C., Gain 8–1.8 ml/minute; Source temperature 150° C.

METHOD C: LC-MS analyses were conducted on a Micromass instrument model LCT linked to an HP 1100 model instrument. Compound abundance were detected using an HP model G1315A photodiode array detector in the 200–600 nm wavelength range and a Sedex model 65 evaporative light scattering detector. Mass spectra were acquired in the 180 to 800 range. Data were analysed using the Micromass MassLynx software. Separation were carried out on a Hypersil BDS C18, 3 μm particle size column (50×4.6 mm) eluted by a linear gradient of 5 to 90% acetonitrile containing 0.05% (v/v) trifluoroacetic acid in water containing 0.05% (v/v) trifluoroacetic acid in 3.5 minutes at a flow rate of 1 ml/minute. The total runtime including column reequilibration was 7 minutes.

METHOD D: Hypersil BDS C-18 column (4.6 mm×50 mm) reverse phase operated under gradient elution conditions with mixtures of (A) water containing 0.05% trifluoroacetic acid and (B) acetonitrile containing 0.05% trifluoroacetic acid as the mobile phase gradient: (0.00 minutes 100% A:0% B; linear gradient to 100% B at 2 minutes; then hold until 3.5 minutes); flow rate 1 mL/minute with approximately 0.25 mL/minute split to the Mass Spectrometer; injection volume 10 μL; Hewlett Packard Model HP1100 Series UV detector wavelength 200 nm; Evaporative light scattering (ELS) detection—temperature 46° C., nitrogen pressure 4 bar.

High Pressure Liquid Chromatography—Mass Spectrometry (LC-MS) triggered purification conditions were as follows:

Compounds were purified by LC/MS using a Waters FractionLynx system composed of a Waters model 600 gradient pump, a Waters model 515 regeneration pump, a Waters Reagent Manager make-up pump, a Waters model 2700 autoinjector, two Rheodyne model LabPro switches, a Waters model 996 photodiode $^1/_{1000}$ of the flow was mixed with methanol (0.5 ml/minute flow rate) and sent to the detectors, this flow was split again ¾ of the flow was sent to the photodiode array detector and ¼ to the mass spectrometer; the rest of the output of the column ($^{999}/_{1000}$) was sent to the fraction collector were flow was directed normally to waste unless expected mass signal was detected by the FractionLynx software. The FractionLynx software was supplied with molecular formulas of expected compounds and triggered the collection of compounds when mass signal corresponding to $[M+H]^+$ and $[M+Na]^+$ are detected. In certain cases (depending on analytical LC-MS result, when $[M+2H]^{++}$ was detected as an intense ion) the FractionLynx software was additionally supplied with calculated half molecular weight (MW/2), in these conditions collection was also triggered when mass signal corresponding to $[M+2H]^{++}$ and $[M+Na+H]^{++}$ are detected. Compounds were collected in tarred glass tubes. After collection, solvent was evaporated in a Jouan model RC 10.10 centrifuge evaporator or a Genevac model HT8 centrifuge evaporator and the amount of compound was determined by weighing of the tubes after solvent evaporation. Array detector, a Waters model ZMD mass spectrometer and a Gilson model 204 fraction collector. The Waters FractionLynx software controlled the instrument. Separation were conducted alternatively on two Waters Symmetry columns ($C_{18}$, 5 µM, 19×50 mm, catalogue number 186000210), one column was under regeneration by a 95/5 (v/v) water/acetonitrile mixture containing 0.07% trifluoroacetic acid (v/v) while the other one is separating. Columns were eluted by a linear gradient of acetonitrile containing 0.07% (v/v) trifluoroacetic acid in water containing 0.07% (v/v) trifluoroacetic acid, from 5 to 95% (v/v) in 8 minutes at a flow rate of 10 ml/minute. At the output of the separating column the flow was split to the 1/1000 ratio using a LC Packing AccuRate splitter.

The high pressure liquid chromatography retention times (HPLC: $R_T$ values) were determined by:—(i) Method A, C18 Phenomenex (150×4.6 mm) column using gradient elution with a mixture of acetonitrile and water with 0.1% trifluoroacetic acid as the mobile phase (0–1 minute 5% acetonitrile; 1–12 minutes ramp up to 95% acetonitrile; 12–14.95 minutes 95% acetonitrile; 14.95–15 minutes 0% acetonitrile); or Method B, YMC ODS-AQ (2×50 mm) column using gradient elution with a mixtures of acetonitrile and water with 0.1% formic acid as the mobile phase [95/5/0.1% (A) to 5/95/0.1% (B)] and a flow rate of 0.4 mL/minute); or Method C, 3 micron BDS C18 Hypersil (50×4.6 mm) using gradient elution with a mixture of acetonitrile and water with 0.1% formic acid as the mobile phase (95/5/0.1%, water/acetonitrile/formic acid for 0.1 minute linear gradient to 5/95/0.1%, water/acetonitrile/ formic acid at 2 minutes and hold until 3.5 minutes).

The thin layer chromatography (TLC) $R_F$ values were determined using Merck silica plates.

EXAMPLE 1

(a) 6-(5-Methoxy-1-methyl-1H-indol-3-yl)-5H-pyrrolo[2,3-b]pyrazine, A1-B1-C1, the product of the combination of group A1 in Table 1 and B1 in Table 2 and C41 in Table 3:

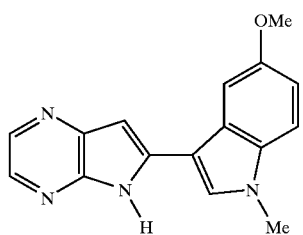

A stirred solution of diisopropylamine (59.9 mL) in tetrahydrofuran (1400 mL), at −15° C. and under nitrogen, was treated with a solution of n-butyllithium in hexanes (131 mL, 1.6M) over 25 minutes, whilst maintaining the temperature below −10° C. After stirring for 30 minutes the mixture was treated with methylpyrazine (26.8 g) over 15 minutes, then stirred for 1 hour and then treated with a solution of 5-methoxy-1-methyl-1H-indole-3-carbonitrile [53 g, Reference Example 1(a)] in tetrahydrofuran (600 mL) over 1 hour, keeping the temperature below −10° C. The reaction mixture was allowed to warm to room temperature over 2 hours, then stood overnight and then treated with water (100 mL). The tetrahydrofuran was removed in vacuo and the resultant mixture was partitioned between ethyl acetate (500 mL) and water (200 mL). The two layers were separated, and the aqueous layer was extracted with ethyl acetate (200 mL). The combined organics were washed with water (500 mL) then evaporated. The residue was subjected to flash chromatography on silica eluting with a mixture of dichloromethane and methanol (19:1, v/v) to give the title compound (19.4 g) as a grey solid, m.p. 270–272° C. MS: 279($MH^+$).

(b) 6-(1-methyl-1H-indol-3-yl)-5H-pyrrolo[2,3-b]pyrazine, A1-B1-C46, the product of the combination of group A1 in Table 1 and B1 in Table 2 and C46 in Table 3:

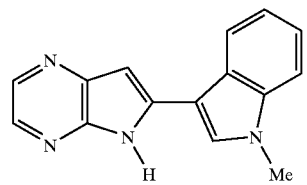

By proceeding in a manner similar to Example 1(a) above but using 1-methyl-indole-3-carbonitrile [Reference Example 2(b)], there was prepared 6-(1-methyl-1H-indol-3-yl)-5H-pyrrolo[2,3-b]pyrazine as a yellow solid, m.p. 264–266° C. [Elemental analysis:—C, 72.34; H, 4.68; N, 22.28%. Calculated for $C_{15}H_{12}N_4$:—C, 72.56; H, 4.87; N, 22.57%].

(c) 6-(3-bromophenyl)-5H-pyrrolo[2,3-b]pyrazine, A1-B91, the product of the combination of group A1 in Table 1 and B91 in Table 2:

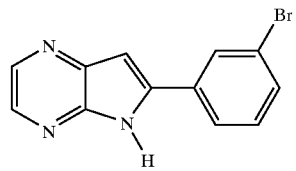

By proceeding in a manner similar to Example 1(a) above but using 3-bromobenzonitrile, there was prepared 6-(3-bromophenyl)-5H-pyrrolo[2,3-b]pyrazine as a colourless solid, m.p. 247–249° C. MS: 276($MH^+$).

(d) 7-iso-propyl-6-phenyl-5H-pyrrolo[2,3-b]pyrazine, A61-B100, the product of the combination of group A1 in Table 1 and B100 in Table 2:

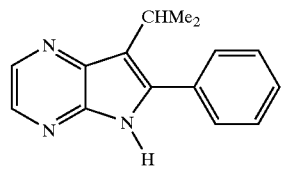

By proceeding in a manner similar to Example 1(a) above but using 2-isobutylpyrazine and benzonitrile, there was prepared 7-iso-propyl-6-phenyl-5H-pyrrolo[2,3-b]pyrazine as a colourless solid, m.p. 216–218° C. MS: 238($MH^+$).

(e) 6-(4-bromophenyl)-5H-pyrrolo[2,3-b]pyrazine, A1-B90, the product of the combination of group A1 in Table 1 and B90 in Table 2:

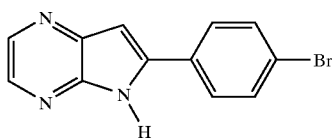

By proceeding in a manner similar to Example 1(a) above but using 4-bromobenzonitrile, there was prepared 6-(4-bromophenyl)-5H-pyrrolo[2,3-b]pyrazine as a colourless solid, m.p. 326–329° C. MS: 276(MH+).

(f) 6-(4-[1,3]dioxan-2-yl-phenyl)-5H-pyrrolo[2,3-b]pyrazine, A1-B87, the product of the combination of group A1 in Table 1 and B87 in Table 2:

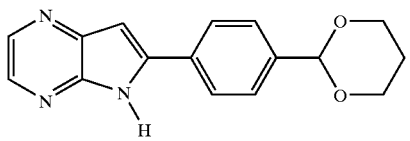

By proceeding in a manner similar to Example 1(a) above but using 2-(4-cyanophenyl)-1,3-dioxane (prepared according to the procedure described in U.S. Pat. No. 5,750,723 for example 3a), there was prepared 6-(4-[1,3]dioxan-2-yl-phenyl)-5H-pyrrolo[2,3-b]pyrazine as a yellow solid, m.p. 288–289° C. TLC: $R_F$=0.34 (ethyl acetate/pentane:1/1).

(g) 6-(3-[1,3]dioxan-2-yl-phenyl)-5H-pyrrolo[2,3-b]pyrazine, A1-B88, the product of the combination of group A1 in Table 1 and B88 in Table 2:

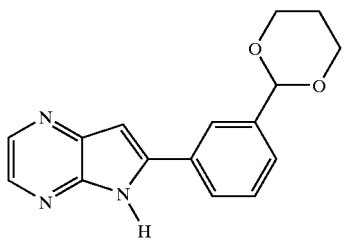

By proceeding in a manner similar to Example 1(a) above but using 2-(3-cyanophenyl)-1,3-dioxane (prepared according to the procedure described in U.S. Pat. No. 5,750,723 for example 3a), there was prepared 6-(3-[1,3]dioxan-2-yl-phenyl)-5H-pyrrolo[2,3-b]pyrazine as a yellow solid, m.p. 205–206° C. [Elemental analysis:—C, 68.28; H, 5.46; N,15.02%. Calculated for $C_{16}H_{15}N_3O_2$:—C, 68.31; H, 5.37; N, 14.94%].

(h) 2-(5H-pyrrolo[2,3-b]pyrazin-6-yl)-quinoline, A1-B103, the product of the combination of group A1 in Table 1 and B103 in Table 2:

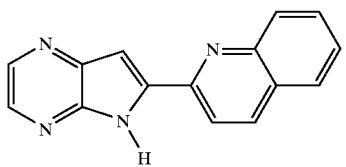

By proceeding in a manner similar to Example 1(a) above but using 2-quinolinecarbonitrile, there was prepared 2-(5H-pyrrolo[2,3-b]pyrazin-6-yl)-quinoline as a pale yellow solid, m.p. 293–295° C. MS: 247(MH+). [Elemental analysis:—C, 72.76; H, 3.82; N,22.56%. Calculated for $C_{16}H_{15}N_3O_2$:—C, 73.16; H, 4.09; N, 22.56%].

(i) 3-(5H-pyrrolo[2,3-b]pyrazin-6-yl)-isoquinoline, A1-B104, the product of the combination of group A1 in Table 1 and B104 in Table 2:

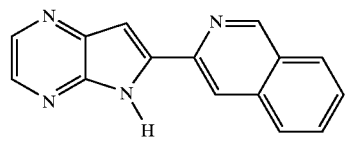

By proceeding in a manner similar to Example 1(a) above but using 3-isoquinolinecarbonitrile, there was prepared 3-(5H-pyrrolo[2,3-b]pyrazin-6-yl)-isoquinoline as a green solid, m.p. 281–285° C. MS: 247(MH+).

(j) 6-[1-methyl-1H-indol-5-yl]-5H-pyrrolo[2,3-b]pyrazine, A1-B65, the product of the combination of group A1 in Table 1 and B65 in Table 2:

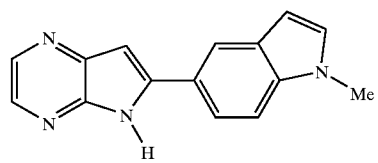

By proceeding in a manner similar to Example 1(a) above but using 1-methyl-1H-indole-5-carbonitrile [Reference Example 2(c)], there was prepared 6-[1-methyl-1H-indol-5-yl]-5H-pyrrolo[2,3-b]pyrazine as a yellow solid, m.p. 260–265° C. MS: 249(MH+).

(k) 6-(5-methoxy-1-methyl-1H-indol-3-yl)-2-methyl-5H-pyrrolo[2,3-b]pyrazine, A64-B1-C1, the product of the combination of group A64 in Table 1 and B1 in Table 2 and C1 in Table 3:

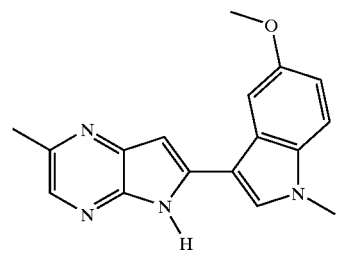

By proceeding in a manner similar to Example 1(a) above but using 2,6-dimethylpyrazine, there was prepared 6-(5-methoxy-1-methyl-1H-indol-3-yl)-2-methyl-5H-pyrrolo[2,3-b]pyrazine as a yellow solid, MS: 293(MH+). $^1$H NMR [$(CD_3)_2SO$]: δ 12.2–12.3 (1H, broad s); 8.54, 8.56 (each 1H, s); 7.50 (1H, d, J=8.9 Hz); 7.47 (1H, d, J=2.4 Hz); 6.96 (1H, dd, J=8.9 and 2.4 Hz); 6.91 (1H, s); 3.91, 3.87 and 2.57(each 3H, s).

(l) 3-methyl-6-(1-methyl-1H-indol-3-yl)-5H-pyrrolo[2,3-b]pyrazine, A66-B1-C1, the product of the combination of group A66 in Table 1 and B1 in Table 2 and C1 in Table 3:

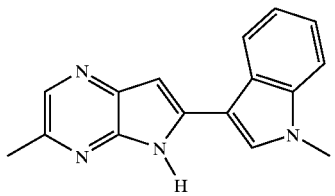

By proceeding in a manner similar to Example 1(a) above but using 2,5-dimethylpyrazine and 1-methyl-1H-indole-3-carbonitrile [Reference Example 2(c)], there was prepared 3-methyl-6-(1-methyl-1H-indol-3-yl)-5H-pyrrolo[2,3-b]pyrazine as a yellow solid, m.p. 170–175° C. MS: 263 (MH$^+$).

(m) 6-(1-benzyl-5-methoxy-1H-indol-3-yl)-5H-pyrrolo[2,3-b]pyrazine, A1-B24-C1, the product of the combination of group A1 in Table 1 and B24 in Table 2 and C1 in Table 3:

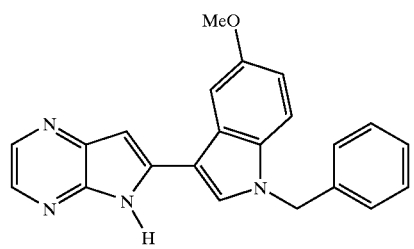

By proceeding in a manner similar to Example 1(a) above but using 1-benzyl-5-methoxy-1H-indole-3-carbonitrile [Reference Example 2(g)], there was prepared 6-(1-benzyl-5-methoxy-1H-indol-3-yl)-5H-pyrrolo[2,3-b]pyrazine as a yellow solid, m.p. 240–244° C. TLC: R$_F$=0.5 (dichloromethane/methanol: 19/1).

(n) 6-(1-methyl-1H-pyrrol-3-yl)-5H-pyrrolo[2,3-b]pyrazine, A1-B54, the product of the combination of group A1 in Table 1 and B54 in Table 2:

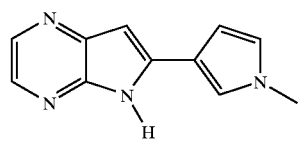

By proceeding in a manner similar to Example 1(a) above but using 1-methyl-1H-pyrrole-3-carbonitrile [Reference Example 2(i)], there was prepared 6-(1-methyl-1H-pyrrol-3-yl)-5H-pyrrolo[2,3-b]pyrazine as a yellow solid, m.p. 211–213° C. MS: 199(MH$^+$).

(o) 6-(1-methyl-1H-pyrrol-2-yl)-5H-pyrrolo[2,3-b]pyrazine, A1-B53, the product of the combination of group A1 in Table 1 and B53 in Table 2:

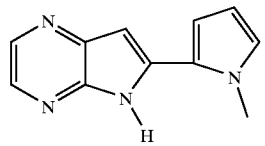

By proceeding in a manner similar to Example 1(a) above but using 1-methyl-1H-pyrrole-2-carbonitrile [Reference Example 2(j)], there was prepared 6-(1-methyl-1H-pyrrol-2-yl)-5H-pyrrolo[2,3-b]pyrazine as a yellow solid, m.p. 208–209° C. MS: 199(MH$^+$).

(p) 6-indolizin-1-yl-5H-pyrrolo[2,3-b]pyrazine, A1-B40-C46, the product of the combination of group A1 in Table 1 and B40 in Table 2 and C46 in Table 3:

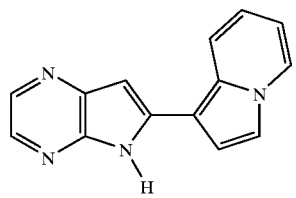

By proceeding in a manner similar to Example 1(a) above but using indolizine-1-carbonitrile [Reference Example 5], there was prepared 6-indolizin-1-yl-5H-pyrrolo[2,3-b]pyrazine as a yellow solid, m.p. 224–225° C. (with decomposition). MS: 235(MH$^+$).

(q) 6-(3-methyl-indolizin-1-yl)-5H-pyrrolo[2,3-b]pyrazine, A1-B41-C46, the product of the combination of group A1 in Table 1 and B41 in Table 2 and C46 in Table 3:

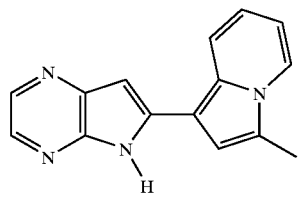

By proceeding in a manner similar to Example 1(a) above but using 3-methyl-indolizine-1-carbonitrile [Reference Example 6], there was prepared 6-(3-methyl-indolizin-1-yl)-5H-pyrrolo[2,3-b]pyrazine as a yellow solid, m.p. 233–235° C. (with decomposition). MS: 249(MH$^+$).

(r) 6-(1-methyl-2-phenyl-1H-pyrrol-4-yl)-5H-pyrrolo[2,3-b]pyrazine, A1-B52, the product of the combination of group A1 in Table 1 and B52 in Table 2:

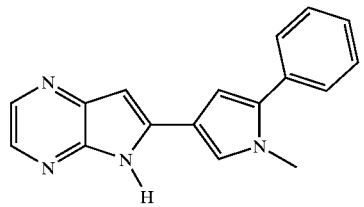

By proceeding in a manner similar to Example 1(a) above but using 1-methyl-5-phenyl-1H-pyrrole-3-carbonitrile [Reference Example 2(k)], there was prepared 6-(1-methyl- 2-phenyl-1H-pyrrol-4-yl)-5H-pyrrolo[2,3-b]pyrazine as a yellow solid, m.p. 221–222° C. (with decomposition). MS: 275(MH⁺).

(s) 6-(5,6,7,8-tetrahydro-indolizin-1-yl)-5H-pyrrolo[2,3-b]pyrazine, A1-B111, the product of the combination of group A1 in Table 1 and B111 in Table 2:

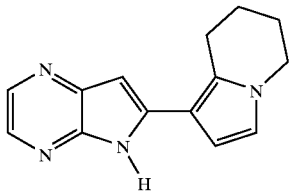

By proceeding in a manner similar to Example 1(a) above but using 5,6,7,8-tetrahydro-indolizine-1-carbonitrile [Reference Example 8], there was prepared 6-(5,6,7,8-tetrahydro-indolizin-1-yl)-5H-pyrrolo[2,3-b]pyrazine as a yellow solid, m.p. 236–238° C. (with decomposition). MS: 239(MH⁺).

(t) 6-furan-3-yl-5H-pyrrolo[2,3-b]pyrazine, A1-B107, the product of the combination of group A1 in Table 1 and B107 in Table 2:

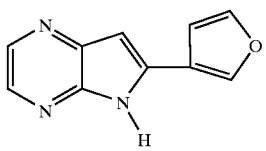

By proceeding in a manner similar to Example 1(a) above but using 3-furonitrile there was prepared 6-furan-3-yl-5H-pyrrolo[2,3-b]pyrazine as an orange solid. MS: 186.79 (MH⁺). TLC: $R_F$=0.45 (dichloromethane/methanol: 19/1).

(u) dimethyl-[4-(5H-pyrrolo[2,3-b]pyrazin-6-yl)-phenyl]-amine, A1-B61, the product of the combination of group A1 in Table 1 and B61 in Table 2:

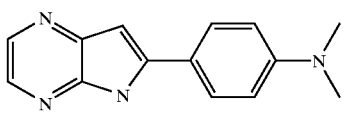

By proceeding in a manner similar to Example 1(a) above but using 4-N,N-dimethylaminobenzonitrile, there was prepared dimethyl-[4-(5H-pyrrolo[2,3-b]pyrazin-6-yl)-phenyl]-amine as a yellow solid, m.p. 297–298° C. MS: 239(MH⁺).

(v) 6-(5-methoxy-1-methyl-1H-indol-3-yl)-7-methyl-5H-pyrrolo[2,3-b]pyrazine, A29-B1-C1, the product of the combination of group A29 in Table 1 and B1 in Table 2 and C1 in Table 3:

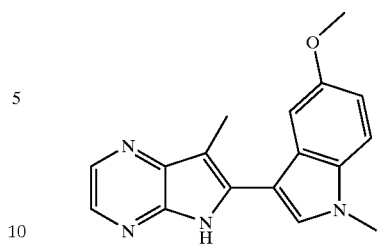

By proceeding in a similar manner to Example 1(a) but using ethylpyrazine there was prepared 6-(5-methoxy-1-methyl-1H-indol-3-yl)-7-methyl-5H-pyrrolo[2,3-b]pyrazine as a yellow solid, m.p. 243–244° C. HPLC (METHOD A): $R_T$=6.73 minutes.

(w) 6-(4-tert-butylphenyl)-5H-pyrrolo[2,3-b]pyrazine, A1-B55, the product of the combination of group A1 in Table 1 and B55 in Table 2:

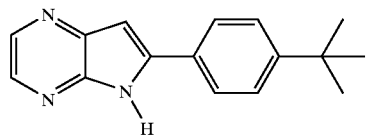

By proceeding in a manner similar to Example 1(a) above but using 4-tert-butylbenzonitrile, there was prepared 6-(4-tert-butylphenyl)-5H-pyrrolo[2,3-b]pyrazine as a yellow solid. LC-MS: Method B: $R_T$=3.29 minutes, 252(MH⁺).

(x) 6-(4-tert-butylphenyl)-7-methyl-5H-pyrrolo[2,3-b]pyrazine, A29-B55, the product of the combination of group A29 in Table 1 and B55 in Table 2:

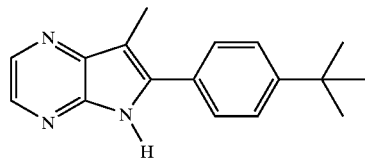

By proceeding in a manner similar to Example 1(a) above but using 2-ethylpyrazine and 4-tert-butylbenzonitrile, there was prepared 6-(4-tert-butylphenyl)-7-methyl-5H-pyrrolo[2,3-b]pyrazine as a yellow solid, m.p. 213–214° C. MS: 266(MH⁺).

(y) 6-(3,4-dimethoxyphenyl)-5H-pyrrolo[2,3-b]pyrazine, A1-B71, the product of the combination of group A1 in Table 1 and B71 in Table 2:

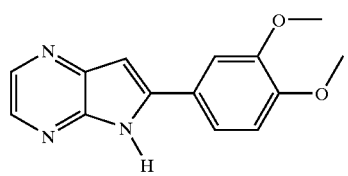

By proceeding in a manner similar to Example 1(a) above but using 3,4-dimethoxy-benzonitrile, there was prepared 6-(3,4-dimethoxyphenyl)-5H-pyrrolo[2,3-b]pyrazine as a yellow/orange solid, m.p. 212–214° C. MS: 256(MH⁺).

(z) 6-(4-aminophenyl)-7-methyl-5H-pyrrolo[2,3-b]pyrazine, A29-B79, the product of the combination of group A29 in Table 1 and B79 in Table 2:

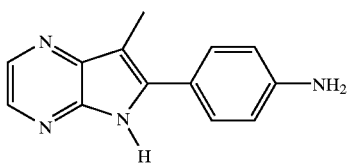

By proceeding in a manner similar to Example 1(a) above but using 2-ethylpyrazine and 4-aminobenzonitrile, there was prepared 6-(4-aminophenyl)-7-methyl-5H-pyrrolo[2,3-b]pyrazine as a brown solid, m.p. 330–332° C. MS: 225 (MH⁺).

(aa) 6-[4-(1-methyl)ethoxyphenyl]-5H-pyrrolo[2,3-b]pyrazine, A1-B63, the product of the combination of group A1 in Table 1 and B63 in Table 2:

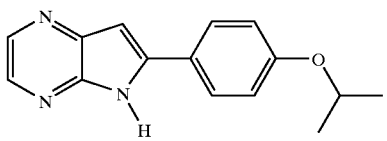

By proceeding in a manner similar to Example 1(a) above but using 4-(1-methyl)-ethoxybenzonitrile [Reference Example 51], there was prepared 6-[4-(1-methyl)ethoxyphenyl]-5H-pyrrolo[2,3-b]pyrazine as a yellow solid. MS: 254(MH⁺). HPLC (METHOD B): R$_T$=1.64 minutes.

(ab) 6-(1H-1-methyl-2-(methylthio)imidazol-5-yl)-5H-pyrrolo[2,3-b]pyrazine, A1-B110, the product of the combination of group A1 in Table 1 and B110 in Table 2:

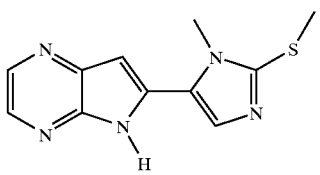

By proceeding in a manner similar to Example 1(a) above but using 1H-5-cyano-1-methyl-2-(methylthio)imidazole [Reference Example 52], there was prepared 6-(1H-1-methyl-2-(methylthio)imidazol-5-yl)-5H-pyrrolo[2,3-b]pyrazine as a yellow solid, m.p. 230° C. MS: 246(MH⁺).

(ac) 6-(1-methyl-1H-indazol-3-yl)-5H-pyrrolo[2,3-b]pyrazine, A1-B21, the product of the combination of group A1 in Table 1 and B21 in Table 2:

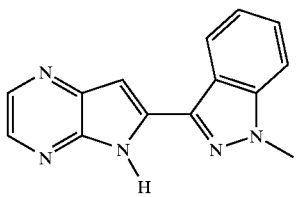

By proceeding in a manner similar to Example 1(a) above but using 3-cyano-1-methyl-1H-indazole [Reference Example 56(a)], there was prepared 6-(1-methyl-1H-indazol-3-yl)-5H-pyrrolo[2,3-b]pyrazine as a yellow solid. MS: 250(MH⁺), 248(MH⁻). ¹H NMR [(CD₃)₂SO]: δ 12.5–12.6 (1H, broad s); 8.38 (1H, d, J=2.4 Hz); 8.24 (d, 1H, J=7.9 Hz); 8.21 (s, 1H, J=2.4 Hz); 7.76 (d, 1H, J=8.1 Hz); 7.48 (t, 1H); 7.32 (t, 1H); 7.29 (s, 1H); 4.18 (s, 3H).

(ad) 6-(1-methyl-4-phenyl-1H-pyrrol-3-yl)-5H-pyrrolo[2,3-b]pyrazine, A1-B43, the product of the combination of group A1 in Table 1 and B43 in Table 2:

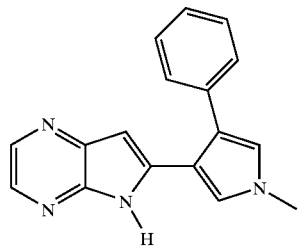

By proceeding in a manner similar to Example 1(a) above but using 3-cyano-1-methyl-4-phenyl-1H-pyrrole [Reference Example 56(b)], there was prepared 6-(1-methyl-4-phenyl-1H-pyrrol-3-yl)-5H-pyrrolo[2,3-b]pyrazine as a solid, m.p. 195° C. (with decomposition). MS: 275(MH⁺).

(ae) 6-(4-fluorophenyl)-5H-pyrrolo[2,3-b]pyrazine, A1-B89, the product of the combination of group A1 in Table 1 and B89 in Table 2:

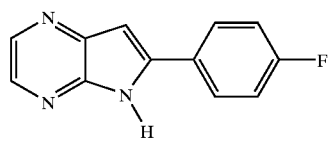

By proceeding in a manner similar to Example 1(a) above but using 4-fluorobenzonitrile, there was prepared 6-(4-fluorophenyl)-5H-pyrrolo[2,3-b]pyrazine as an off-white solid. ¹H NMR [(CD₃)₂SO]: δ 12.3 (s, 1H) 8.4 (d, 1H), 8.2 (d, 1H), 8.05 (d, 2H), 7.4 (d, 2H), 7.2 (s, 1H). MS: 213 (MH⁺).

(af) 6-(4-methoxyphenyl)-5H-pyrrolo[2,3-b]pyrazine, A1-B77, the product of the combination of group A1 in Table 1 and B77 in Table 2:

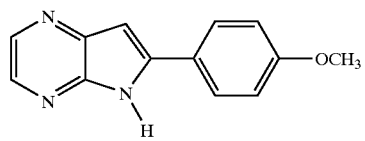

By proceeding in a manner similar to Example 1(a) above but using 4-methoxy-benzonitrile, there was prepared 6-(4-methoxyphenyl)-5H-pyrrolo[2,3-b]pyrazine as an off-white solid, m.p. 244–246° C. MS: 225(MH⁺).

(ag) 6-[4-(tert-butyl)phenyl]-7-(prop-1-enyl)-5H-pyrrolo[2,3-b]pyrazine, A43-B55, the product of the combination of group A43 in Table 1 and B55 in Table 2:

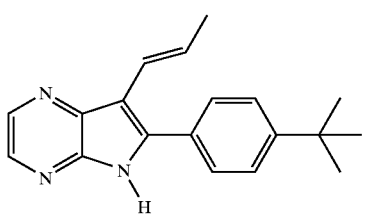

By proceeding in a manner similar to Example 1(a) above but using 4-(tertiary-butyl)benzonitrile and 4-(pyrazinyl)-1-butene [Reference Example 59] there was prepared 6-[4-(tert-butyl)phenyl]-7-(prop-1-enyl)-5H-pyrrolo[2,3-b]pyrazine as a yellow solid, m.p. 207–208° C. MS: 292 ($MH^+$).

(ah) 6-(4-methylthiophenyl)-5H-pyrrolo[2,3-b]pyrazine, A1-B92, the product of the combination of group A1 in Table 1 and B92 in Table 2:

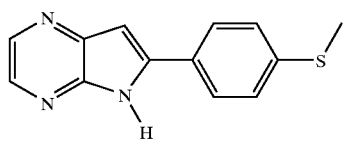

By proceeding in a manner similar to Example 1(a) above but using 4-(methylthio)benzonitrile there was prepared 6-(4-methylthiophenyl)-5H-pyrrolo[2,3-b]pyrazine as a yellow solid. MS: 242($MH^+$). $^1$H NMR [$(CD_3)_2SO$]: δ 12.48 (1H, s); 8.37 (1H, s); 8.18 (1H, s); 7.98 (2H, d, J=7.9 Hz); 7.19 (2H, d, J=7.9 Hz); 7.11 (1H, s); 2.52 (3H, s).

(ai) 6-(3-methoxylphenyl)-5H-pyrrolo[2,3-b]pyrazine, A1-B62, the product of the combination of group A1 in Table 1 and B62 in Table 2:

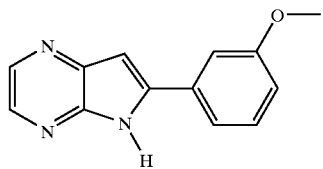

By proceeding in a manner similar to Example 1(a) above but using 3-methoxybenzonitrile there was prepared 6-(3-methoxylphenyl)-5H-pyrrolo[2,3-b]pyrazine as an orange solid, m.p. 194–196° C. MS: 226($MH^+$).

(aj) 6-(1-methyl-1H-pyrazol-4-yl)-5H-pyrrolo[2,3-b]pyrazine, A1-B108, the product of the combination of group A1 in Table 1 and B108 in Table 2:

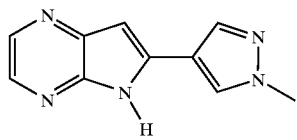

By proceeding in a manner similar to Example 1(a) above but using 1-methyl-4-cyanopyrazole (prepared according to the procedure described by Yoshida in J. Het. Chem., 1995, 32, page 701) there was prepared 6-(1-methyl-1H-pyrazol-4-yl)-5H-pyrrolo[2,3-b]pyrazine as an orange solid, m.p. 232–234° C. MS: 200($MH^+$).

(ak) 6-(1-methyl-5-phenyl-1H-pyrazol-3-yl)-5H-pyrrolo[2,3-b]pyrazine, A1-B109, the product of the combination of group A1 in Table 1 and B109 in Table 2:

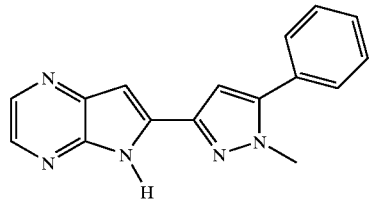

By proceeding in a manner similar to Example 1(a) above but using 1-methyl-3-cyano-5-phenylpyrazole [Reference Example 1(k)] there was prepared 6-(1-methyl-5-phenyl-1H-pyrazol-3-yl)-5H-pyrrolo[2,3-b]pyrazine as an orange solid, m.p. 222–223° C. HPLC $R_t$=7.36 minutes.

(al) 6-(pyridin-2-yl)-5H-pyrrolo[2,3-b]pyrazine, A1-B101, the product of the combination of group A1 in Table 1 and B101 in Table 2:

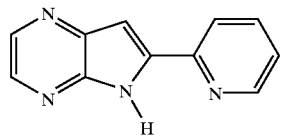

By proceeding in a manner similar to Example 1(a) above but using 2-cyano-pyridine there was prepared 6-(pyridin-2-yl)-5H-pyrrolo[2,3-b]pyrazine as a yellow solid, m.p. 234–235° C. $^1$H NMR [$(CD_3)_2SO$]: δ 8.71 (1H, d, J=4.1 Hz); 8.38 (1H, s); 8.24 (1H, s); 8.17 (1H, d, J=8.2 Hz); 7.93 (1H, t, J=8.2 Hz); 7.41 (1H, m); 7.36 (1H, s).

(am) 6-(pyridin-4-yl)-5H-pyrrolo[2,3-b]pyrazine, A1-B102, the product of the combination of group A1 in Table 1 and B102 in Table 2:

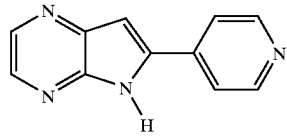

By proceeding in a manner similar to Example 1(a) above but using 4-cyano-pyridine there was prepared 6-(pyridin-4-yl)-5H-pyrrolo[2,3-b]pyrazine as a yellow solid, m.p. 324–326° C. $^1$H NMR [$(CD_3)_2SO$]: δ 8.69 (2H, d, J=7.1 Hz); 8.45 (1H, s); 8.33 (1H, s); 8.00 (2H, d, J=7.1 Hz); 7.47 (1H, s).

(an) 6-(3,4-dimethylphenyl)-5H-pyrrolo[2,3-b]pyrazine, A1-B75, the product of the combination of group A1 in Table 1 and B75 in Table 2:

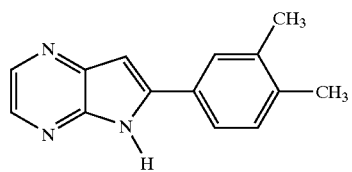

By proceeding in a manner similar to Example 1(a) above but using 3,4-dimethylbenzonitrile there was prepared 6-(3, 4-dimethylphenyl)-5H-pyrrolo[2,3-b]pyrazine as a yellow solid. MS: 224 (MH+). HPLC: $R_T$=2.4 minutes.

(ao) 6-(4-hydroxyphenyl)-5H-pyrrolo[2,3-b]pyrazine, A1-B78, the product of the combination of group A1 in Table 1 and B78 in Table 2:

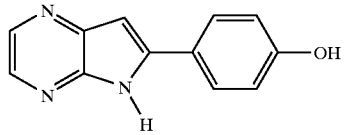

By proceeding in a manner similar to Example 1(a) above but using 4-hydroxybenzonitrile there was prepared 6-(4-hydroxyphenyl)-5H-pyrrolo[2,3-b]pyrazine as a pale yellow solid. MS: 212 (MH+).

(ap) 6-(4-trifluoromethoxyphenyl)-5H-pyrrolo[2,3-b]pyrazine, A1-B76, the product of the combination of group A1 in Table 1 and B76 in Table 2:

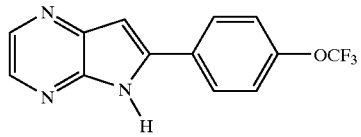

By proceeding in a manner similar to Example 1(a) above but using 4-trifluoromethoxybenzonitrile there was prepared 6-(4-trifluoromethoxyphenyl)-5H-pyrrolo[2,3-b]pyrazine as a pale orange solid. MS: 280 (MH+). $R_T$=2.64 minutes.

(aq) 6-(4-aminophenyl)-5H-pyrrolo[2,3-b]pyrazine, A1-B79, the product of the combination of group A1 in Table 1 and B79 in Table 2:

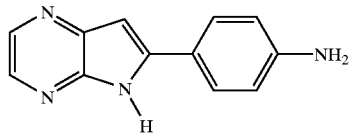

By proceeding in a manner similar to Example 1(a) above but using 4-aminobenzonitrile, and subjecting the reaction product to chromatography on silica eluting initially with a mixture of ethyl acetate and pentane and then with ethyl acetate, there was prepared 6-(4-aminophenyl)-5H-pyrrolo[2,3-b]pyrazine as a yellow solid. MS: 211.1(MH+). $R_T$=2.12 minutes.

(ar) 6-(1-methyl-2-phenyl-1H-pyrrol-3-yl)-5H-pyrrolo[2,3-b]pyrazine, A1-B112, the product of the combination of group A1 in table 1 and B112 in Table 2:

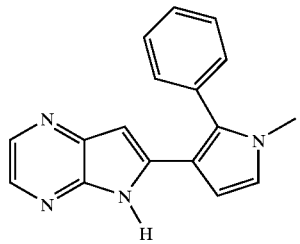

By proceeding in a manner similar to Example 1(a) above but using 1-methyl-2-phenyl-1H-pyrrole-3-carbonitrile [Reference Example 56(c)], there was prepared 6-(1-methyl-2-phenyl-1H-pyrrol-3-yl)-5H-pyrrolo[2,3-b]pyrazine as a yellow solid, m.p. 210° C. (with decomposition). MS: EI (70 eV); m/z=274 M+.(100%).

(as) 6-(1,2-dimethyl-1H-pyrrol-4-yl)-5H-pyrrolo[2,3-b]pyrazine, A1-B113, the product of the combination of group A1 in table 1 and B113 in table 2:

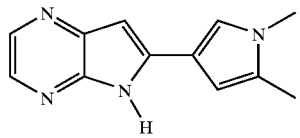

By proceeding in a manner similar to Example 1(a) above but using 1,5-dimethyl-1H-pyrrole-3-carbonitrile [Reference Example 56(d)], there was prepared 6-(1,2-dimethyl-1H-pyrrol-4-yl)-5H-pyrrolo[2,3-b]pyrazine as a yellow solid, m.p. 253° C. [Elemental analysis:—C, 67.60; H, 5.68; N, 26.22%. Calculated for $C_{12}H_{12}N_4$:—C, 67.91; H, 5.70; N, 26.40%].

(at) 6-(1,4-dimethyl-1H-pyrrol-3-yl)-5H-pyrrolo[2,3-b]pyrazine, A1-B114, the product of the combination of group A1 in table 1 and B114 in table 2:

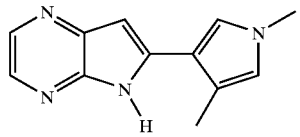

By proceeding in a manner similar to Example 1(a) but using 1,4-dimethyl-1H-pyrrole-3-carbonitrile [Reference Example 56(e)], there was prepared 6-(1,4-dimethyl-1H-pyrrol-3-yl)-5H-pyrrolo[2,3-b]pyrazine as a yellow solid, m.p. 210° C. MS: EI (70 eV); m/z=212 M+.(100%).

(au) 2-(1-methyl-4-phenyl-1H-pyrrol-3-yl)-1H-pyrrolo[2,3-b]pyridine, A2-B43, the product of the combination of group A2 in table 1 and B43 in table 2:

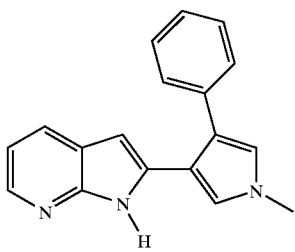

By proceeding in a manner similar to Example 1(a) but using 3-methylpyridine and 3-cyano-1-methyl-4-phenyl-1H-pyrrole [Reference Example 56(b)], there was prepared 2-(1-methyl-4-phenyl-1H-pyrrol-3-yl)-1H-pyrrolo[2,3-b]pyridine as a brown solid, m.p. 140° C. (with decomposition). MS: EI (70 eV); m/z=273 M+.(100%).

EXAMPLE 2

(a) 3-[3-(5H-Pyrrolo[2,3-b]pyrazin-6-yl)-indol-1-yl]-propan-1-ol, A1-B6-C46, the product of the combination of group A1 in Table 1 and B6 in Table 2 and C46 in Table 3:

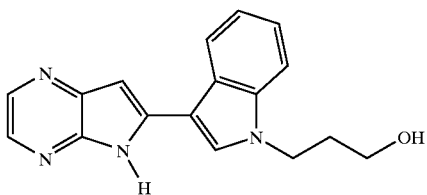

A solution of 6-{1-[3-(tert-butyl-dimethyl-silanyloxy)-propyl]-1H-indol-3-yl}-5H-pyrrolo[2,3-b]pyrazine [29 g, Reference Example 3(a)] in tetrahydrofuran (500 mL) under nitrogen was treated with a solution of tetrabutylammonium fluoride in tetrahydrofuran (144 mL, 11.0M). After stirring at ambient temperature for 4 hours the reaction mixture was concentrated in vacuo. The residue was treated with water to give a solid which was filtered then washed with water and then dried to give the title compound (17.5 g) as a yellow-brown solid, m.p. 220–221° C. MS: 293(MH+).

(b) 3-[5-methoxy-3-(5H-pyrrolo[2,3-b]pyrazin-6-yl)-indol-1-yl]-propan-1-ol, A1-B6-C1, the product of the combination of group A1 in Table 1 and B6 in Table 2 and C1 in Table 3:

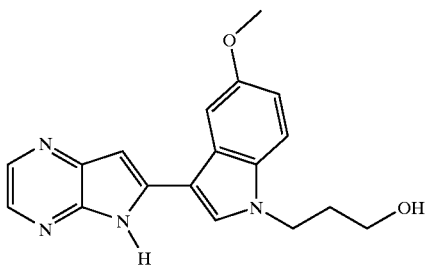

By proceeding in a manner similar to Example 2(a) above but using 6-{1-[3-(tert-butyl-dimethyl-silanyloxy)-propyl]-5-methoxy-1H-indol-3-yl}-5H-pyrrolo[2,3-b]pyrazine [Reference Example 3(b)], there was prepared 3-[5-methoxy-3-(5H-pyrrolo[2,3-b]pyrazin-6-yl)-indol-1-yl]-propan-1-ol as a yellow solid, m.p. 225–228° C. MS: 323(MH+).

TLC: $R_F$=0.16 (dichloromethane/methanol: 19/1, v/v).

(c) 2-[3-(5H-pyrrolo[2,3-b]pyrazin-6-yl)-indol-1-yl]-ethanol, A1-B5-C46, the product of the combination of group A1 in Table 1 and B5 in Table 2 and C46 in Table 3:

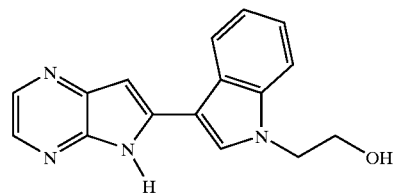

By proceeding in a manner similar to Example 2(a) above but using 6-{1-[2-(tert-butyl-dimethyl-silanyloxy)-ethyl]-1H-indol-3-yl}-5H-pyrrolo[2,3-b]pyrazine [Reference Example 3(c)], there was prepared 2-[3-(5H-pyrrolo[2,3-b]pyrazin-6-yl)-indol-1-yl]-ethanol as a yellow solid, m.p. 272–273° C. MS: 279(MH+).

(d) 2-[5-methoxy-3-(5H-pyrrolo[2,3-b]pyrazin-6-yl)-indol-1-yl]-ethanol, A1-B5-C1, the product of the combination of group A1 in Table 1 and B5 in Table 2 and C1 in Table 3:

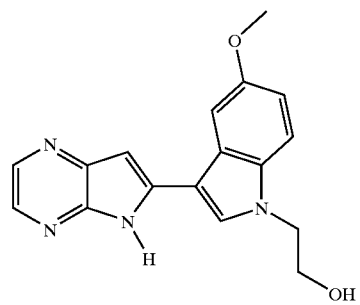

By proceeding in a manner similar to Example 2(a) above but using 6-{1-[2-(tert-butyl-dimethyl-silanyloxy)-ethyl]-5-methoxy-1H-indol-3-yl}-5H-pyrrolo[2,3-b]pyrazine [Reference Example 3(d)], there was prepared 2-[5-methoxy-3-(5H-pyrrolo[2,3-b]pyrazin-6-yl)-indol-1-yl]-ethanol as a grey solid, m.p. 270–273° C. MS: 309.43 (MH+).

(e) 6-(1H-Indol-3-yl)-5H-pyrrolo[2,3-b]pyrazine, A1-B2-C46, the product of the combination of group A1 in Table 1 and B2 in Table 2 and C46 in Table 3:

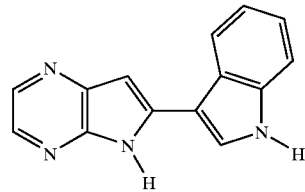

By proceeding in a manner similar to Example 2(a) above but using 6-[1-(2-trimethylsilanyl-ethoxymethyl)-1H-indol-3-yl]-5H-pyrrolo[2,3-b]pyrazine [Reference Example 3(f)], there was prepared 6-(1H-indol-3-yl)-5H-pyrrolo[2,3-b]pyrazine as an orange solid. $^1$H NMR [(CD$_3$)$_2$SO]: δ 12.54 (1H, br s); 8.32 (1H, d, J=2.8 Hz); 8.27 (1H, s); 8.19 (1H, d, J=2.8 Hz); 8.12 (1H, m); 7.71 (1H, m); 7.30 (2H, m); 7.03 (1H, d, J=2.01 Hz).

EXAMPLE 3

(a) 3-[3-(5H-Pyrrolo[2,3-b]pyrazin-6-yl)-indol-1-yl]-propylamine, A1-B23-C46, the product of the combination of group A1 in Table 1 and B23 in Table 2 and C46 in Table 3:

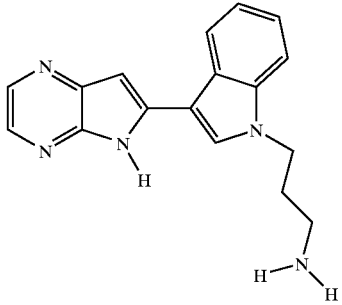

A solution of 3-[3-(5H-pyrrolo[2,3-b]pyrazin-6-yl)-indol-1-yl]-propan-1-ol [12 g, Example 2(a)] and carbon tetrabromide (19.1 g) in dichloromethane (300 mL) at ambient temperature was treated with a solution of triphenylphosphine (12.9 g) in dichloromethane (100 mL) over 5 minutes. After stirring at ambient temperature for 3 hour the reaction mixture was filtered and the solid was washed with sparing amounts of dichloromethane. The filtrate and washings were evaporated to yield a brown gum, which was mixed with liquid ammonia (ca 80 mL) in a sealed pressure vessel and allowed to stir at ambient temperature for 18 hours. The vessel was then cooled to −78° C. and then cautiously vented. The ammonia was allowed to evaporate and the residue was subjected to flash chromatography on silica eluting with a mixture of dichloromethane, methanol and concentrated ammonia (900:100:7, v/v/v) to give the title compound as a yellow solid (3 g), m.p. 170° C. $^{1}$H NMR [$(CD_3)_2SO$]: δ 8.28 (1H, d, J=2.7 Hz); 8.18 (1H, s); 8.10, 7.64 (each 1H, d, J=7.7 Hz); 8.09 (1H, d, J=2.7 Hz); 7.29, 7.23 (each 1H, td, J=7.1 and 1.0 Hz); 6.97 (1H, s); 4.32 (2H, t, J=7.0 Hz); 2.57 (2H, t, J=6.5 Hz); 1.89 (2H, quintet, J=6.4 Hz).

(b) 3-[5-methoxy-3-(5H-pyrrolo[2,3-b]pyrazin-6-yl)-indol-1-yl]-propylamine, A1-B23-C1, the product of the combination of group A1 in Table 1 and B23 in Table 2 and C1 in Table 3:

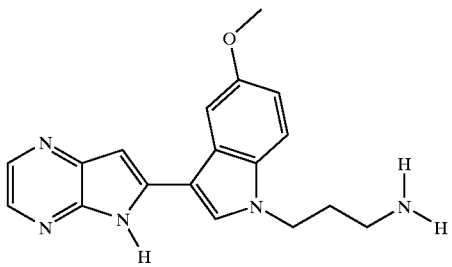

By proceeding in a manner similar to Example 3(a) above but using 3-[5-methoxy-3-(5H-pyrrolo[2,3-b]pyrazin-6-yl)-indol-1-yl]-propan-1-ol [Example 2(b)], there was prepared 3-[5-methoxy-3-(5H-pyrrolo[2,3-b]pyrazin-6-yl)-indol-1-yl]-propylamine as a yellow solid, m.p. 95–100° C. and 150–160° C. MS: 322(MH$^{+}$). TLC: $R_F$=0.2 (dichloromethane/methanol/concentrated ammonia: 900/100/7, v/v/v).

EXAMPLE 4

(a) N-{3-[3-(5H-Pyrrolo[2,3-b]pyrazin-6-yl)-indol-1-yl]-propyl}-acetamide, A1-B7-C46, the product of the combination of group A1 in Table 1 and B7 in Table 2 and C46 in Table 3:

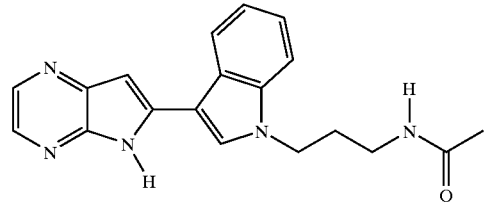

Acetyl chloride (31 μl) was added dropwise to a solution of 3-[3-(5H-pyrrolo[2,3-b]pyrazin-6-yl)-indol-1-yl]-propylamine [100 mg, Example 3(a)] and triethylamine (52.2 μl) and dichloromethane (20 mL) at ambient temperature under a nitrogen atmosphere. After stirring for 24 hours at ambient temperature the reaction mixture was evaporated. The residue was subjected to flash chromatography on silica eluting with a mixture of dichloromethane and methanol (9:1, v/v) to give the title compound (82 mg) as a yellow solid, m.p. 260° C. MS: 334(MH$^{+}$).

(b) N-[4-(5H-Pyrrolo[2,3-b]pyazin-6-yl)-phenyl]-acetamide, A1-B80, the product of the combination of group A1 in Table 1 and B80 in Table 2:

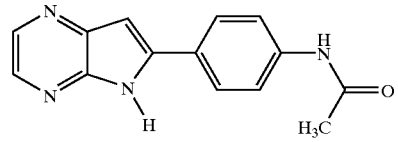

By proceeding in a manner similar to Example 4(a) above but using 6-(4-aminophenyl)-5H-pyrrolo[2,3-b]pyrazine [Example 1(aq) not Reference Example 1(aq)] there was prepared N-[4-(5H-pyrrolo[2,3-b]pyazin-6-yl)-phenyl]-acetamide as a yellow solid. MS: 253.1(MH$^{+}$). $R_T$=2.3 minutes.

EXAMPLE 5

(a) 6-[1-(3-Morpholin-4-yl-propyl)-1H-indol-3-yl]-5H-pyrrolo[2,3-b]pyrazine, A1-B27-C46, the product of the combination of group A1 in Table 1, B27 in Table 2 and C46 in Table 3:

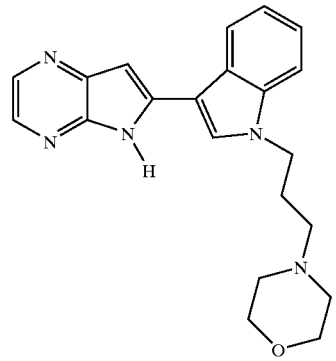

A mixture of 3-[3-(5H-pyrrolo[2,3-b]pyrazin-6-yl)-indol-1-yl]-propylbromide [250 mg, Reference Example 41, morpholine (0.5 mL), potassium carbonate (100 mg) and potassium iodide (2 crystals) in ethyl methyl ketone was heated at reflux for 2 hours. The mixture was then allowed to cool to ambient temperature over 16 hours then evaporated. The residue was subjected to flash chromatography on silica eluting with a mixture of dichloromethane and methanol (9:1, v/v) to give a yellow glass which was triturated with ethyl acetate and pentane to give the title compound (40 mg) as a yellow solid, m.p. 180–185° C. MS: 362(MH$^+$).

(b) 6-[1-(3-piperidin-1-yl-propyl)-1H-indol-3-yl]-5H-pyrrolo[2,3-b]pyrazine, A1-B26, the product of the combination of group A1 in Table 1 and B26 in Table 2:—

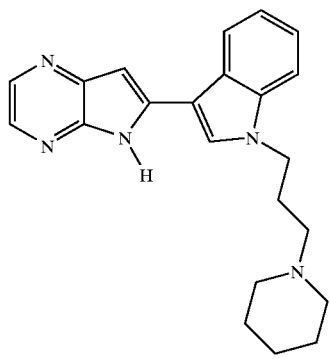

By proceeding in a manner similar to Example 5(a) above but using piperidine, there was prepared 6-[1-(3-piperidin-1-yl-propyl)-1H-indol-3-yl]-5H-pyrrolo[2,3-b]pyrazine as a yellow solid, m.p. 240° C. MS: 360(MH$^+$).

EXAMPLE 6

6-{1-[3-(Pyridin-3-yloxy)-propyl]-1H-indol-3-yl}-5H-pyrrolo[2,3-b]pyrazine, A1-B22-C46, the product of the combination of group A1 in Table 1 and B22 in Table 2 and C46 in Table 3:

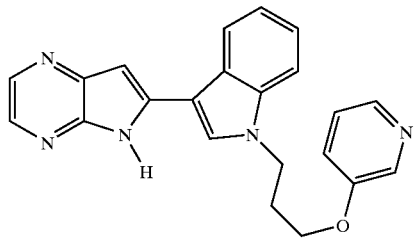

A solution of diisopropylazodicarboxylate (269 µM) in tetrahydrofuran (0.5 mL) was added dropwise, over 2 minutes, to a solution of triphenylphosphine (359 mg) in tetrahydrofuran (2.5 mL) at 0° C. under an atmosphere of nitrogen. After stirring at that temperature for 20 minutes the mixture was treated with a solution of 3-hydroxypyridine (65 mg) in tetrahydrofuran (1 mL) over 1 minute then with a suspension of 3-[3-(5H-pyrrolo[2,3-b]pyrazin-6-yl)-indol-1-yl]-propan-1-ol [200 mg, Example 2(a)] in tetrahydrofuran (2 mL). The mixture was allowed to warm to ambient temperature over 18 hours then evaporated. The residue was subjected to flash chromatography on silica eluting with a mixture of ethyl acetate and methanol (9:1, v/v) to give the title compound (110 mg) as a yellow solid, m.p. 208–209° C. MS: 370(MH$^+$).

EXAMPLE 7

1-Methyl-3-(5H-pyrrolo[2,3-b]pyrazin-6-yl)-1H-indol-5-ol, A1-B1-C10, the product of the combination of group A1 in Table 1 and B1 in Table 2 and C10 in Table 3:—

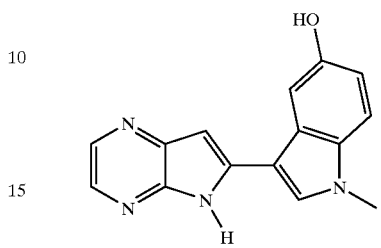

A mixture of 6-(5-methoxy-1-methyl-1H-indol-3-yl)-5H-pyrrolo[2,3-b]pyrazine [200 mg, Example 1(a)] hydrobromic acid (48%, 500 µl) and glacial acetic acid (3 mL) was heated under reflux for 14 hours. After cooling the mixture was neutralised by addition of saturated sodium bicarbonate solution. The resulting dark solid was filtered and then dried to give the title compound (180 mg) as a black solid, m.p. 289–290° C. MS: 264(MH$^+$).

EXAMPLE 8

6-(2-Chloro-5-methoxy-1-methyl-1H-indol-3-yl)-5H-pyrrolo[2,3-b]pyrazine, A1-B15-C1, the product of the combination of group A1 in Table 1 and B15 in Table 2 and C1 in Table 3:—

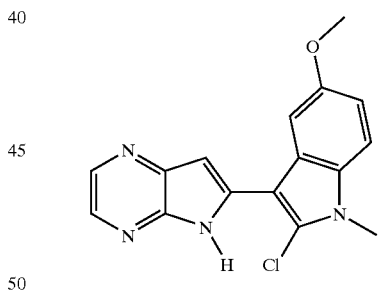

A solution of 6-(5-methoxy-1-methyl-1H-indol-3-yl)-5H-pyrrolo[2,3-b]pyrazine [100 mg, Example 1(a)] in dimethoxy ethanol (25 mL), cooled to −78° C., was treated with a solution of n-butyllithium in hexanes (172 µl, 2.5M). After stirring for 30 minutes the mixture was treated with 4-toluenesulfonyl chloride (82 mg) then allowed to warm slowly to ambient temperature and then evaporated. The residue was subjected to flash chromatography on silica eluting with a mixture of dichloromethane and methanol (19:1, v/v) to give the title compound (45 mg) as a black solid. MS: 313(MH$^+$). $^1$H NMR [(CD$_3$)$_2$SO]: δ 12.20 (1H, s); 8.39 (1H, d, J=3 Hz); 8.21 (1H, d, J=3 Hz); 7.54 (1H, d, J=9 Hz); 7.30 (1H, d, J=2 Hz); 6.96 (1H, dd, J=9 and 2 Hz); 6.84 (1H, d, J=2 Hz); 3.82 (3H, s); 3.81 (3H, s).

EXAMPLE 9

(a) 3-(5H-Pyfrolo[2,3-b]pyrazin-6-yl)-benzaldehyde, A1-B96, the product of the combination of group A1 in Table 1 and B96 in Table 2:

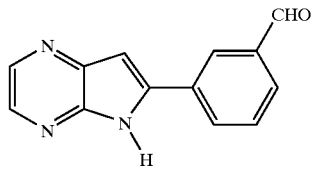

A solution of 6-(3-[1,3]dioxan-2-yl-phenyl)-5H-pyrrolo[2,3-b]pyrazine [1.6 g, Example 1(g)] in dichloromethane (50 mL) was treated with trifluoroacetic acid (5 mL). The resultant mixture was heated at reflux for 6 hours, then allowed to cool overnight and then evaporated. The residue was triturated with diethyl ether to give a yellow solid, which was recrystallised from ethyl acetate to give the title compound (0.6 g) as a yellow crystalline solid, m.p. 268–270° C. [Elemental analysis: C, 69.96; H, 3.92; N,18.69%. Calculated for $C_{13}H_9N_3O$:—C, 69.95; H, 4.06; N, 18.82%].

(b) 4-(5H-pyrrolo[2,3-b]pyrazin-6-yl)-benzaldehyde hydrate, A1-B95, the product of the combination of group A1 in Table 1 and B95 in Table 2:—

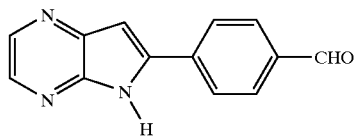

By proceeding in a manner similar to Example 9(a) above but using 6-(4-[1,3]dioxan-2-yl-phenyl)-5H-pyrrolo[2,3-b]pyrazine [Example 1(f)], there was prepared 4-(5H-pyrrolo[2,3-b]pyrazin-6-yl)-benzaldehyde hydrate as a yellow solid, m.p.>295° C. [Elemental analysis: C, 67.57; H, 4.33; N,18.04%. Calculated for $C_{13}H_9N_3O \cdot H_2O$: C, 67.23; H, 4.34; N, 18.09%].

(c) [3-(5H-pyrrolo[2,3-b]pyrazin-6-yl)-indol-1-yl]-methanol, A1-B4-C46, the product of the combination of group A1 in Table 1 and B4 in Table 2 and C46 in Table 3:

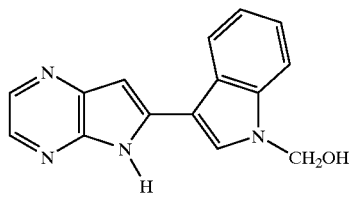

By proceeding in a manner similar to Example 9(a) above but using 6-[1-(2-trimethylsilanyl-ethoxymethyl)-1H-indol-3-yl]-5H-pyrrolo[2,3-b]pyrazine [Reference Example 3(f)], there was prepared [3-(5H-pyrrolo[2,3-b]pyrazin-6-yl)-indol-1-yl]-methanol as a brown solid, m.p. >320° C. $^1$H NMR [$(CD_3)_2SO$]: δ 8.13(1H, s); 7.90 (2H, s), 7.75 (1H, d); 7.50 (1H, d); 7.15–7.25 (2H, m), 6.85 (1H, s); 5.60 (2H, s).

EXAMPLE 10

(a) [3-(5H-Pyrrolo[2,3-b]pyrazin-6-yl)-phenyl]-methanol, A1-B98, the product of the combination of group A1 in Table 1 and B98 in Table 2:

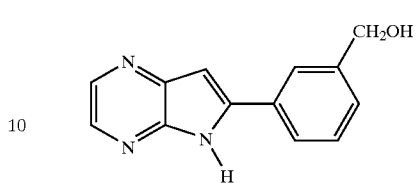

A suspension of 3-(5H-pyrrolo[2,3-b]pyrazin-6-yl)-benzaldehyde [0.4 g, Example 9(a)] in ethanol (50 mL) was treated with sodium borohydride (200 mg). The mixture was allowed to stir at ambient temperature for 1 hour then treated with water (10 mL) and then evaporated. The residual solid was triturated with water (50 mL) to give a pale yellow solid which was washed with water and then recrystallised from methanol to yield the title compound (0.35 g) as a yellow crystalline solid, m.p. 225–226° C. [Elemental analysis: C, 68.72; H, 4.73; N,18.44%. Calculated for $C_{13}H_{11}N_3O$:—C, 69.32; H, 4.92; N, 18.65%].

(b) [4-(5H-pyrrolo[2,3-b]pyrazin-6-yl)-phenyl]-methanol, A1-B97, the product of the combination of group A1 in Table 1 and B97 in Table 2:

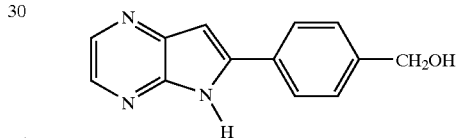

By proceeding in a manner similar to Example 10(a) above but using 4-(5H-pyrrolo[2,3-b]pyrazin-6-yl)-benzaldehyde [Example 9(b)], there was prepared [4-(5H-pyrrolo[2,3-b]pyrazin-6-yl)-phenyl]-methanol as a yellow solid, m.p. 284–285° C. [Elemental analysis: C, 68.61; H, 4.65; N,18.28. Calculated for $C_{13}H_{11}N_3O$: C, 69.32; H, 4.92; N, 18.65%].

EXAMPLE 11

6-(5-Methoxy-1H-indol-3-yl)-5H-pyrrolo[2,3-b]pyrazine, A1-B2-C1, the product of the combination of group A1 in Table 1 and B1 in Table 2 and C1 in Table 3:

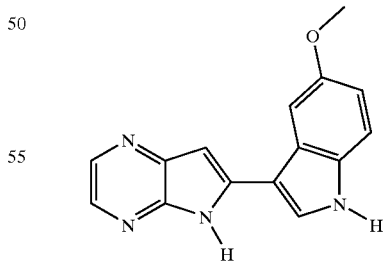

A cooled (−78° C.) solution of 6-(1-benzyl-5-methoxy-1H-indol-3-yl)-5H-pyrrolo[2,3-b]pyrazine [50 mg, Example 1(m)] in tetrahydrofuran (20 mL) was treated with liquid ammonia (20 mL) then with sodium (100 mg). After stirring at −78° C. for 30 minutes the reaction mixture was allowed to warm slowly to ambient temperature, then treated with water (50 mL) and then extracted three times with ethyl acetate (50 mL). The combined extracts were dried over sodium sulfate and then evaporated. The residue was triturated with diethyl ether to give the title compound (14 mg) as a brown solid, m.p. 268–271° C. MS: 265.24(MH$^+$).

EXAMPLE 12

(a) 2-[5-Methoxy-3-(5H-pyrrolo[2,3-b]pyrazin-6-yl)-indol-1-yl]-1-morpholin-4-yl-ethanone, A1-B8-C1, the product of the combination of group A1 in Table 1 and B8 in Table 2 and C1 in Table 3:

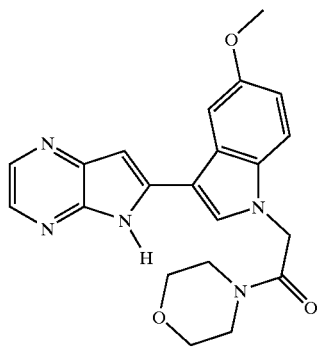

A stirred solution of 6-(5-methoxy-1H-indol-3-yl)-5H-pyrrolo[2,3-b]pyrazine [70 mg, Example 11] in dry dimethylformamide (10 mL) was treated with sodium hydride (21.6 mg, 60% dispersion in mineral oil). After stirring for 30 minutes this mixture was treated with a solution of 4-(2-chloroacetyl)morpholine (44.1 mg) in dimethylformamide (1 mL) and stirring was continued for a further 3 hours. The reaction mixture was poured into water (20 mL) and then extracted three times with ethyl acetate (30 mL). The combined extracts were dried over sodium sulfate and then evaporated. The residue was triturated with diethyl ether to give the title compound (55 mg) as a yellow solid, m.p. 263–267° C. MS: 392.21(MH$^+$).

(b) 2-[5-methoxy-1-(2-morpholin-4-yl-2-oxo-ethyl)-1H-indol-3-yl]-H-pyrrolo[2,3-b]pyridine-4-carbonitrile, A3-B8-C1, the product of the combination of group A3 in Table 1 and B8 in Table 2 and C1 in Table 3:

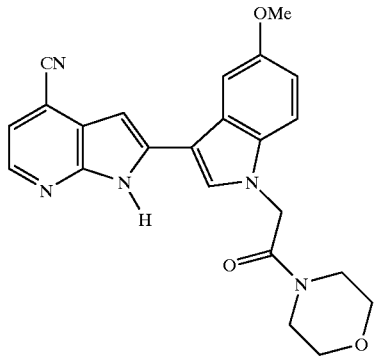

By proceeding in a manner similar to Example 12(a) above but using 2-(5-methoxy-1H-indol-3-yl)-1H-pyrrolo[2,3,-b]pyridine-4-carbonitrile [Example 32], there was prepared 2-[5-methoxy-1-(2-morpholin-4-yl-2-oxo-ethyl)-1H-indol-3-yl-1H-pyrrolo[2,3-b]pyridine-4-carbonitrile as a yellow solid. LC-MS: METHOD D: R$_T$=3.55 minutes, 416 (MH$^+$).

EXAMPLE 13

(a) [5-Methoxy-3-(1H-pyrrolo[2,3-b]pyridin-2-yl)-indol-1-yl]-acetic acid, A2-B25-C1, the product of the combination of group A2 in Table 1 and B25 in Table 2 and C1 in Table 3:

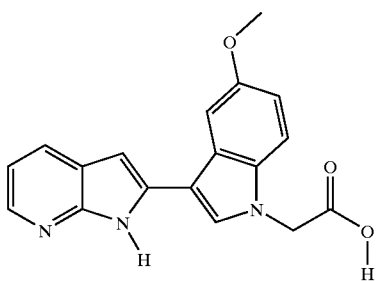

A mixture of {5-methoxy-3-[1-(toluene-4-sulfonyl)-1H-pyrrolo[2,3-b]pyridin-2-yl]-indol-1-yl}-acetic acid ethyl ester [4.67 g, Reference Example 13(a)], methanol (250 mL) and aqueous potassium hydroxide (5M, 25 mL) were heated under reflux for 7 hours. The methanol was removed under reduced pressure and the residue was treated with water (20 mL) and the pH of this solution was adjusted to 7 by addition of concentrated hydrochloric acid. The resulting yellow solid was filtered and subjected to flash chromatography on silica eluting with a mixture of ethyl acetate and methanol (7:3, v/v) to give the title compound (1.69 g) as a white solid. MS: 320(M−H$^+$). HPLC (METHOD A): R$_T$=6.67 minutes.

(b) 4-methoxy-2-(5-methoxy-1-methyl-1H-indol-3-yl)-1H-pyrrolo[2,3-b]pyridine, A5-B1-C1, the product of the combination of group A5 in Table 1 and B1 in Table 2 and C1 in Table 3:

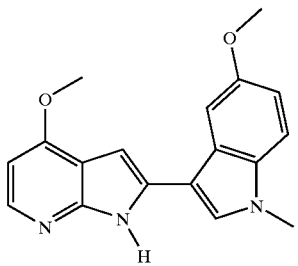

By proceeding in a similar manner to Example 13(a) but using 4-methoxy-2-(5-methoxy-1-methyl-1H-indol-3-yl)-1-(toluene-4-sulfonyl)-1H-pyrrolo[2,3-b]pyridine [Reference Example 2(1)] there was prepared 4-methoxy-2-(5-methoxy-1-methyl-1H-indol-3-yl)-1H-pyrrolo[2,3-b]pyridine as a tan solid, m.p. 288–289° C. MS: 307(MH$^+$).

(c) 4-methoxy-2-(5-methoxy-1H-indol-3-yl)-1H-pyrrolo[2,3-b]pyridine, A5-B2-C1, the product of the combination of group A5 in Table 1 and B2 in Table 2 and C1 in Table 3:

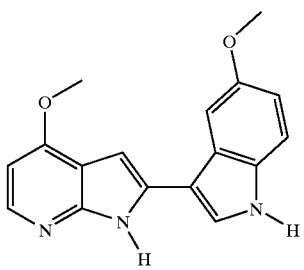

By proceeding in a similar manner to Example 13(a) but using 4-methoxy-2-(5-methoxy-1H-indol-3-yl)-1-(toluene-4-sulfonyl)-1H-pyrrolo[2,3-b]pyridine (Reference Example 39) there was prepared 4-methoxy-2-(5-methoxy-1H-indol-3-yl)-1H-pyrrolo[2,3-b]pyridine as a tan solid, m.p. 294–295° C. MS: 294(MH$^+$).

(d) 4-chloro-2-(4-tert-butylphenyl)-1H-pyrrolo[2,3-b]pyridine, A28-B55, the product of the combination of group A28 in Table 1 and B55 in Table 2:

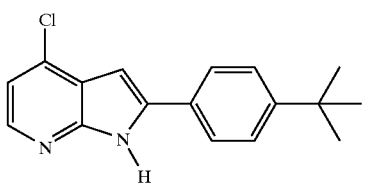

By proceeding in a similar manner to Example 13(a) but using 4-chloro-2-(4-tert-butylphenyl)-1-(toluene-4-sulfonyl)-1H-pyrrolo[2,3-b]pyridine [Reference Example 12(j)] there was prepared 4-chloro-2-(4-tert-butylphenyl)-1H-pyrrolo[2,3-b]pyridine as a cream coloured solid. TLC: $R_F$=0.71 (ethyl acetate/heptane 1:1). $^1$H NMR [(CD$_3$)$_2$SO]: δ 12.52 (1H, s); 8.16 (1H, d, J=6.1 Hz); 7.93 (2H, d, J=8.1 Hz); 7.50 (2H, d, J=8.1 Hz); 7.21 (1H, d, J=6.1 Hz); 6.96 (1H, s); 1.30 (9H, s).

(e) 2-(5-methoxy-1-methyl-1H-indol-3-yl)-5-phenyl-1H-pyrrolo[2,3-b]pyridine, A65-B1-C1, the product of the combination of group A65 in Table 1 and B1 in Table 2 and C1 in Table 3:

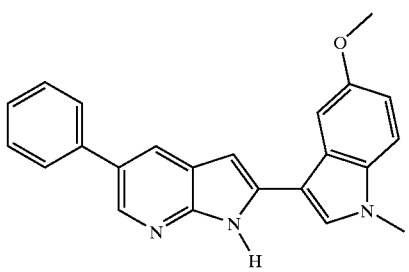

By proceeding in a similar manner to Example 13(a) but using 2-(5-methoxy-1-methyl-1H-indol-3-yl)-5-phenyl-1-(toluene-4-sulfonyl)1H-pyrrolo[2,3-b]pyridine [Reference Example 13(j)] there was prepared 2-(5-methoxy-1-methyl-1H-indol-3-yl)-5-phenyl-1H-pyrrolo[2,3-b]pyridine as a cream coloured solid, m.p. 240–242° C. MS: 354(MH$^+$).

(f) 1-[1-methyl-3-(1H-pyrrolo[2,3-b]pyridin-2-yl)-1H-indol-5-yloxy]-propan-2-ol, A2-B1-C5, the product of the combination of group A2 in Table 1 and B1 in Table 2 and C5 in Table 3:

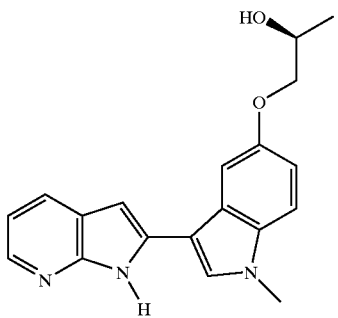

By proceeding in a manner similar to Example 13(a) above but using 1-{1-methyl-3-[1-toluene-4-sulfonyl)-1H-pyrrolo[2,3-b]pyridin-2-yl]-1H-indol-5-yloxy)-propan-2-ol [Reference Example 79], there was prepared 1-[1-methyl-3-(1H-pyrrolo[2,3-b]pyridin-2-yl)-1H-indol-5-yloxy]-propan-2-ol as a cream solid. m.p. 198–199° C. RPLC (Method A): RT=6.69 minutes.

(g) [5,6-Dimethoxy-3-(1H-pyrrolo[2,3-b]pyridin-2-yl)-indol-1-yl]-acetic acid, A2-B121-C1, the product of the combination of group A2 in Table 1 and B121 in Table 2 and C1 in Table 3:

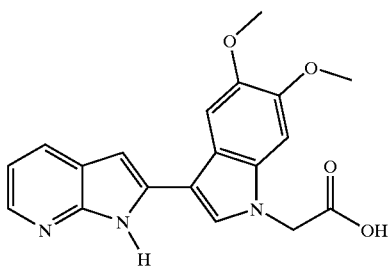

By proceeding in a manner similar to Example 13(a) but using {5,6-dimethoxy-3-[1-(toluene-4-sulfonyl)-1H-pyrrolo[2,3-b]pyridin-2-yl]-indol-1-yl}-acetic acid tert-butyl ester [Reference Example 13(q)] there was prepared [5,6-dimethoxy-3-(1H-pyrrolo[2,3-b]pyridin-2-yl)-indol-1-yl]-acetic acid as a khaki solid. [Elemental analysis:—C, 60.28; H, 5.16; N, 10.85%. Calculated for C$_{19}$H$_{17}$N$_3$O$_4$.1.5H$_2$O:— C, 60.31; H, 5.33; N, 11.11%]. MS: EI (70 eV); m/z=351 M$^+$.(100%).

EXAMPLE 14

(a) 2-{[5-Methoxy-3-(1H-pyrrolo[2,3-b]pyridin-2-yl)-indol-1-yl]-1-morpholin-4-yl}-ethanone, A2-B8-C1, the product of the combination of group A2 in Table 1 and B8 in Table 2 and C1 in Table 3:

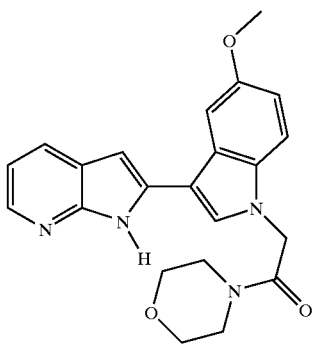

A suspension of [5-methoxy-3-(1H-pyrrolo[2,3-b]pyridin-2-yl)-indol-1-yl]-acetic acid [60 mg, Example 13(a)] in dry dimethylformamide (7 mL) was treated with N-{(dimethylamino)(1H-1,2,3,-triazolo [4,5,-b]pyridin-1-yl)methylene}-N-methylmethanaminium hexafluorophosphate N-oxide (71 mg) and diisopropylethylamine (45 μl). After stirring at room temperature for 30 minutes morpholine (18 μl) was added and the mixture stirred at ambient temperature for a further 12 hours. The solvent was removed in vacuo and the residue was suspended in saturated sodium bicarbonate solution. The precipitated solid was filtered then dried to give the title compound (10 mg) as a violet coloured solid, m.p. 243–247° C. MS: 391(MH$^+$).

(b) 1-[1-methyl-3-(1H-pyrrolo[2,3-b]pyridin-2-yl)-1H-indol-5-yloxy]-cyclobutanecarboxylic acid amide, A2-B1-C$_{15}$, the product of the combination of group A2 in Table 1 and B1 in Table 2 and C15 in Table 3:

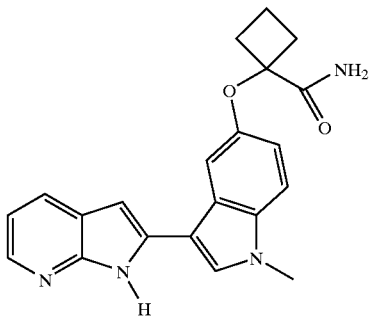

By proceeding in a manner similar to Example 14(a) above but using 1-[1-methyl-3-(1H-pyrrolo[2,3-b]pyridin-2-yl)-1H-indol-5-yloxy]-cyclobutanecarboxylic acid [Example 15(c)] and ammonium chloride, there was prepared 1-[1-methyl-3-(1H-pyrrolo[2,3-b]pyridin-2-yl)-1H-indol-5-yloxy]-cyclobutanecarboxylic acid amide as a pale lilac solid, m.p. 267–268° C. MS: 361(MH$^+$).

(c) 1-[1-methyl-3-(1H-pyrrolo[2,3-b]pyridin-2-yl)-1H-indol-5-yloxy]-cyclobutanecarboxylic acid methylamide, A2-B1-C16, the product of the combination of group A2 in Table 1 and B1 in Table 2 and C16 in Table 3:

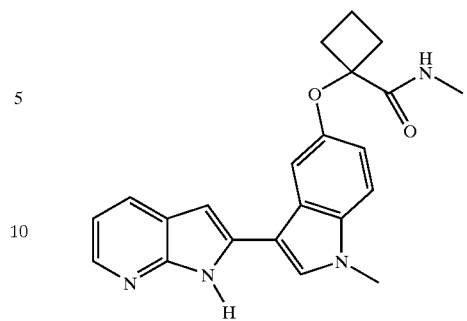

By proceeding in a manner similar to Example 14(a) above but using 1-[1-methyl-3-(1H-pyrrol[2,3-b]pyridin-2-yl)-1H-indol-5-yloxy]-cyclobutanecarboxylic acid [Example 15(c)] and methylamine, there was prepared 1-[1-methyl-3-(1H-pyrrolo[2,3-b]pyridin-2-yl)-1H-indol-5-yloxy]-cyclobutanecarboxylic acid methylamide as a pale lilac solid, m.p. 249–250° C. MS: 375(MH$^+$).

(d) 1-methyl-3-(1H-pyrrolo[2,3-b]pyridin-2-yl)-1H-indole-5-carboxylic acid methylamide, A2-B1-C23, the product of the combination of group A2 in Table 1 and B1 in Table 2 and C23 in Table 3:

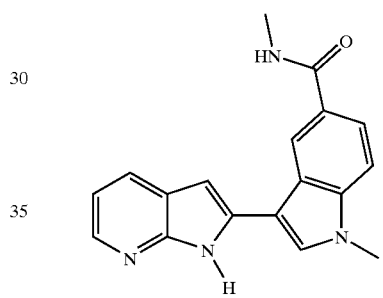

By proceeding in a manner similar to Example 14(a) above but using 1-methyl-3-(1H-pyrrolo[2,3-b]pyridin-2-yl)-1H-indole-5-carboxylic acid [Example 15(d)] and methylamine, there was prepared 1-methyl-3-(1H-pyrrolo[2,3-b]pyridin-2-yl)-1H-indole-5-carboxylic acid methylamide as a pale orange solid, m.p. 186° C. MS: 304(MH$^+$).

(e) 1-methyl-3-(1H-pyrrolo[2,3-b]pyridin-2-yl)-1H-indole-5-carboxylic acid (2-hydroxy-ethyl)-amide, A2-B1-C34, the product of the combination of group A2 in Table 1 and B1 in Table 2 and C34 in Table 3:

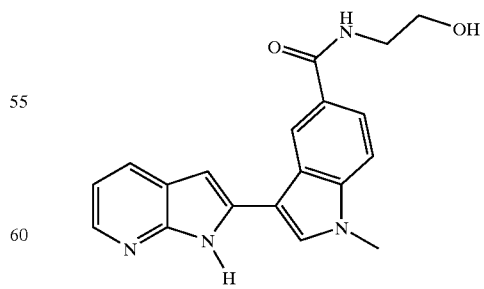

By proceeding in a manner similar to Example 14(a) above but using 1-methyl-3-(1H-pyrrolo[2,3-b]pyridin-2-yl)-1H-indole-5-carboxylic acid [Example 15(d)] and ethanolamine, there was prepared 1-methyl-3-(1H-pyrrolo

[2,3-b]pyridin-2-yl)-1H-indole-5-carboxylic acid (2-hydroxy-ethyl)-amide as a yellow solid, m.p. 256–257° C. MS: 335(MH⁺).

(f) 1-methyl-3-(1H-pyrrolo[2,3-b]pyridin-2-yl)-1H-indole-5-carboxylic acid (2-morpholin-4-yl-ethyl)-amide, A2-B1-C47, the product of the combination of group A2 in Table 1 and B1 in Table 2 and C47 in Table 3:

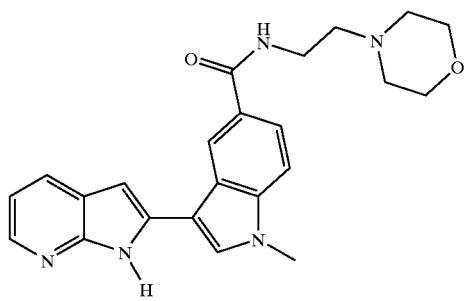

By proceeding in a manner similar to Example 14(a) above but using 1-methyl-3-(1H-pyrrolo[2,3-b]pyridin-2-yl)-1H-indole-5-carboxylic acid [Example 15(d)] and 2-aminoethyl morpholine, there was prepared 1-methyl-3-(1H-pyrrolo[2,3-b]pyridin-2-yl)-1H-indole-5-carboxylic acid (2-morpholin-4-yl-ethyl)-amide as a colourless solid, m.p. 268–270° C. MS: 404(MH⁺).

(g) 1-methyl-3-(1H-pyrrolo[2,3-b]pyridin-2-yl)-1H-indole-5-carboxylic acid (2-carbamoyl-ethyl)-amide, A2-B1-C24, the product of the combination of group A2 in Table 1 and B1 in Table 2 and C24 in Table 3:

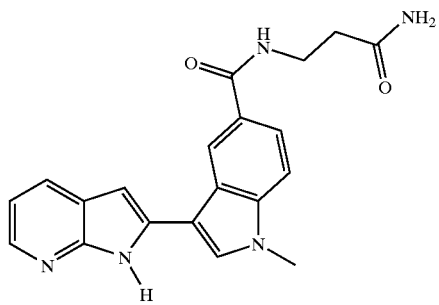

By proceeding in a manner similar to Example 14(a) above but using 1-methyl-3-(1H-pyrrolo[2,3-b]pyridin-2-yl)-1H-indole-5-carboxylic acid [Example 15(d)] and β-alanine-amide, there was prepared 1-methyl-3-(1H-pyrrolo[2,3-b]pyridin-2-yl)-1H-indole-5-carboxylic acid (2-carbamoyl-ethyl)-amide as a colourless solid, m.p. 286–288° C. MS: 362(MH⁺).

(h) 1-methyl-3-(1H-uyrrolo[2,3-b]pyridin-2-yl)-1H-indole-5-carboxylic acid bis-(2-hydroxy-ethyl)-amide, A2-B1-C48, the product of the combination of group A2 in Table 1 and B1 in Table 2 and C48 in Table 3:

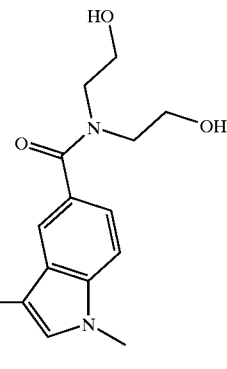

By proceeding in a manner similar to Example 14(a) above but using 1-methyl-3-(1H-pyrrolo[2,3-b]pyridin-2-yl)-1H-indole-5-carboxylic acid [Example 15(d)] and diethanolamine, there was prepared 1-methyl-3-(1H-pyrrolo[2,3-b]pyridin-2-yl)-1H-indole-5-carboxylic acid bis-(2-hydroxy-ethyl)-amide as a yellow solid, m.p. 230–232° C. MS: 379(MH⁺).

(i) 1-methyl-3-(1H-pyrrolo[2,3-b]pyridin-2-yl)-1H-indole-5-carboxylic acid amide, A2-B1-C29, the product of the combination of group A2 in Table 1 and B1 in Table 2 and C29 in Table 3:

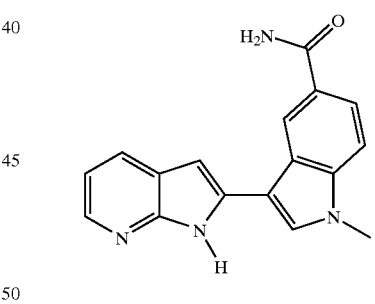

By proceeding in a manner similar to Example 14(a) above but using 1-methyl-3-(1H-pyrrolo[2,3-b]pyridin-2-yl)-1H-indole-5-carboxylic acid [Example 15(d)] and ammonium chloride, there was prepared 1-methyl-3-(1H-pyrrolo[2,3-b]pyridin-2-yl)-1H-indole-5-carboxylic acid amide as a yellow solid, m.p. 330–332° C. MS: 291(MH⁺).

(j) 1-methyl-3-(1H-pyrrolo[2,3-b]pyridin-2-yl)-1H-indole-5-carboxylic acid (2-hydroxy-1.1-bis-hydroxymethyl-ethyl)-amide, A2-B1-C49, the product of the combination of group A2 in Table 1 and B1 in Table 2 and C49 in Table 3:

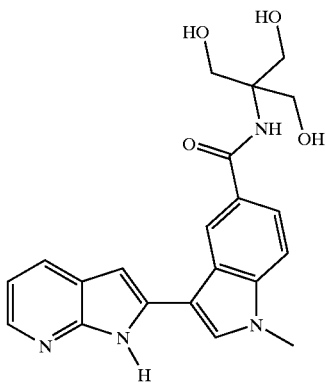

By proceeding in a manner similar to Example 14(a) above but using 1-methyl-3-(1H-pyrrolo[2,3-b]pyridin-2-yl)-1H-indole-5-carboxylic acid [Example 15(d)] and tris(hydroxymethyl) aminomethane, there was prepared 1-methyl-3-(1H-pyrrolo[2,3-b]pyridin-2-yl)-1H-indole-5-carboxylic acid (2-hydroxy-1,1-bis-hydroxymethyl-ethyl)-amide as a yellow solid, m.p. 205–206° C. MS: 395(MH$^+$).

(k) 1-methyl-3-(1H-pyrrolo[2,3-b]pyridin-2-yl)-1H-indole-5-carboxylic acid (2-hydroxy-1-hydroxymethyl-1-methyl-ethyl)-amide, A2-B1-C30, the product of the combination of group A2 in Table 1 and B1 in Table 2 and C30 in Table 3:

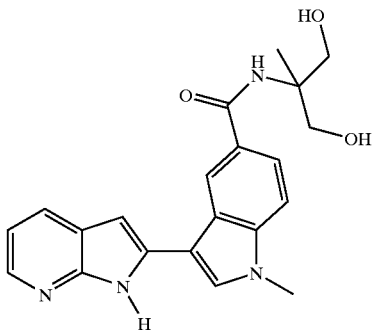

By proceeding in a manner similar to Example 14(a) above but using 1-methyl-3-(1H-pyrrolo[2,3-b]pyridin-2-yl)-1H-indole-5-carboxylic acid [Example 15(d)] and 2-amino-2-methyl-1,3-propanediol, there was prepared 1-methyl-3-(1H-pyrrolo[2,3-b]pyridin-2-yl)-1H-indole-5-carboxylic acid (2-hydroxy-1-hydroxymethyl-1-methyl-ethyl)-amide as a yellow solid, m.p. 180–182° C. MS: 379(MH$^+$).

(l) 1-methyl-3-(1H-pyrrolo[2,3-b]pyridin-2-yl)-1H-indole-5-carboxylic acid (2,3-dihydroxy-propyl)-amide, A2-B1-C50, the product of the combination of group A2 in Table 1 and B1 in Table 2 and C50 in Table 3:

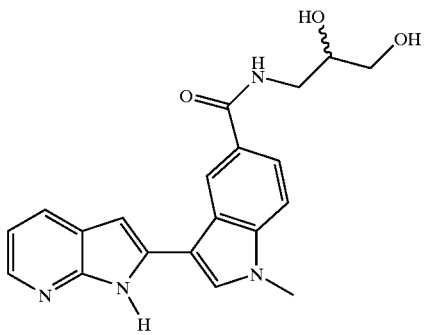

By proceeding in a manner similar to Example 14(a) above but using 1-methyl-3-(1H-pyrrolo[2,3-b]pyridin-2-yl)-1H-indole-5-carboxylic acid [Example 15(d)] and 3-amino-1,2-propanediol, there was prepared 1-methyl-3-(1H-pyrrolo[2,3-b]pyridin-2-yl)-1H-indole-5-carboxylic acid (2,3-dihydroxy-propyl)-amide as a yellow solid, m.p. 171–172° C. MS: 365(MH$^+$).

(m) 1-methyl-3-(1H-pyrrolo[2,3-b]pyridin-2-yl)-1H-indole-5-carboxylic acid (2-hydroxy-1,1-dimethyl-ethyl)-amide, A2-B1-C31, the product of the combination of group A2 in Table 1 and B15 in Table 2 and C31 in Table 3:

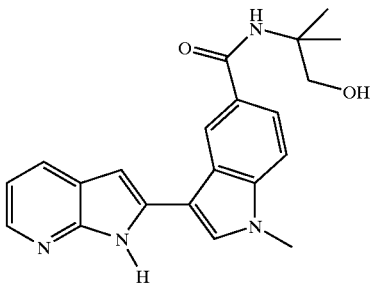

By proceeding in a manner similar to Example 14(a) above but using 1-methyl-3-(1H-pyrrolo[2,3-b]pyridin-2-yl)-1H-indole-5-carboxylic acid [Example 15(d)] and 2-amino-2-methyl-1-propanol, there was prepared 1-methyl-3-(1H-pyrrolo[2,3-b]pyridin-2-yl)-1H-indole-5-carboxylic acid (2-hydroxy-1,1-dimethyl-ethyl)-amide as a yellow solid, m.p. 161–162° C. MS: 365(MH$^+$).

(n) 1-methyl-3-(1H-pyrrolo[2,3-b]pyridin-2-yl)-1H-indole-5-carboxylic acid (2-hydroxy-1-hydroxymethyl-ethyl)-amide, A2-B1-C33, the product of the combination of group A2 in Table 1 and B1 in Table 2 and C33 in Table 3:

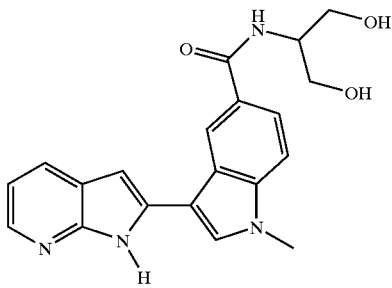

By proceeding in a manner similar to Example 14(a) above but using 1-methyl-3-(1H-pyrrolo[2,3-b]pyridin-2- yl)-1H-indole-5-carboxylic acid [Example 15(d)] and serinol, there was prepared 1-methyl-3-(1H-pyrrolo[2,3-b]pyridin-2-yl)-1H-indole-5-carboxylic acid (2-hydroxy-1-hydroxymethyl-ethyl)-amide as a yellow solid, m.p. 178–179° C. MS: 365.41(MH⁺).

(o) 1-methyl-3-(1H-pyrrolo[2,3-b]pyridin-2-yl)-1H-indole-6-carboxylic acid (2-carbamoyl-ethyl)-amide, A2-B18-C24, the product of the combination of group A2 in Table 1 and B18 in Table 2 and C24 in Table 3:

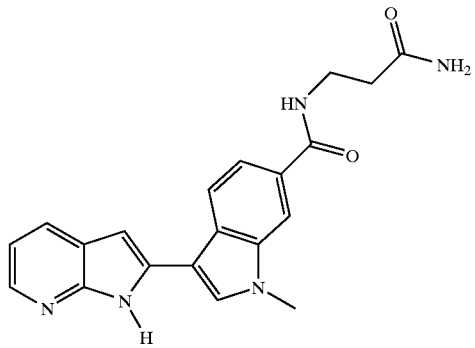

By proceeding in a manner similar to Example 14(a) above but using 1-methyl-3-(1H-pyrrolo[2,3-b]pyridin-2-yl)-1H-indole-6-carboxylic acid [Example 15(g)] and 3-amino-propionamide hydrochloride, there was prepared 1-methyl-3-(1H-pyrrolo[2,3-b]pyridin-2-yl)-1H-indole-6-carboxylic acid (2-carbamoyl-ethyl)-amide as a pale yellow solid, m.p. 277–280° C. MS: 362(MH⁺).

(p) 1-methyl-3-(1H-pyrrolo[2,3-b]pyridin-2-yl)-1H-indole-6-carboxylic acid (2-hydroxy-ethyl)-amide, A2-B18-C34, the product of the combination of group A2 in Table 1 and B18 in Table 2 and C34 in Table 3:

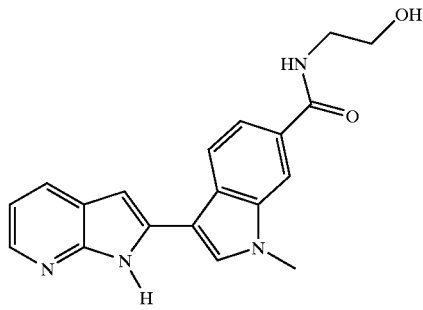

By proceeding in a manner similar to Example 14(a) above but using 1-methyl-3-(1H-pyrrolo[2,3-b]pyridin-2-yl)-1H-indole-6-carboxylic acid [Example 15(g)] and ethanolamine, there was prepared 1-methyl-3-(1H-pyrrolo[2,3-b]pyridin-2-yl)-1H-indole-6-carboxylic acid (2-hydroxy-ethyl)-amide as a brown solid, m.p. 264–267° C. MS: 335(MH⁺).

(q) 1-methyl-3-(1H-pyrrolo[2,3-b]pyridin-2-yl)-1H-indole-6-carboxylic acid (1H-[1,2,4]triazol-3-yl)-amide, A2-B18-C51, the product of the combination of group A2 in Table 1 and B18 in Table 2 and C51 in Table 3:

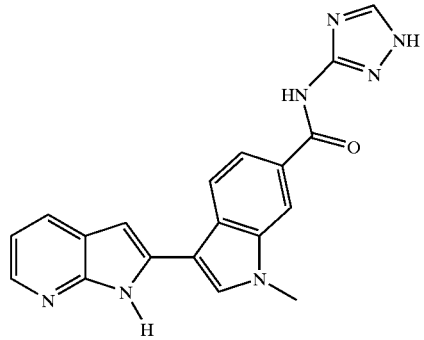

By proceeding in a manner similar to Example 14(a) above but using 1-methyl-3-(1H-pyrrolo[2,3-b]pyridin-2-yl)-1H-indole-6-carboxylic acid [Example 15(g)] and 1H-[1,2,4]triazol-3-ylamine, there was prepared 1-methyl-3-(1H-pyrrolo[2,3-b]pyridin-2-yl)-1H-indole-6-carboxylic acid (1H-[1,2,4]triazol-3-yl)-amide as a yellow solid, m.p. 343–345° C. MS: 358(MH⁺).

(r) 1-methyl-3-(1H-pyrrolo[2,3-b]pyridin-2-yl)-1H-indole-6-carboxylic acid (2-hydroxy-1-hydroxymethyl-ethyl)-amide, A2-B18-C33, the product of the combination of group A2 in Table 1 and B18 in Table 2 and C33 in Table 3:

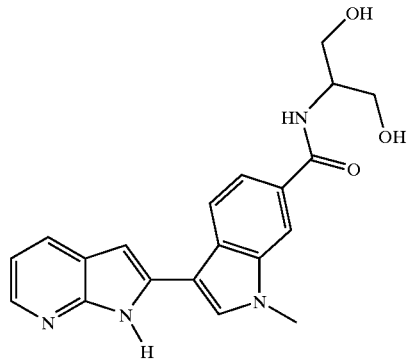

By proceeding in a manner similar to Example 14(a) above but using 1-methyl-3-(1H-pyrrolo[2,3-b]pyridin-2-yl)-1H-indole-6-carboxylic acid [Example 15(g)] and serinol, there was prepared 1-methyl-3-(1H-pyrrolo[2,3-b]pyridin-2-yl)-1H-indole-6-carboxylic acid (2-hydroxy-1-hydroxymethyl-ethyl)-amide as a light brown solid, m.p. 247–249° C. MS: 365(MH⁺).

(s) 1-methyl-3-(5H-pyrrolo[2,3-b]pyrazin-6-yl)-1H-indole-5-carboxylic acid (2-hydroxy-1,1-dimethyl-ethyl)-amide, A1-B1-C31, the product of the combination of group A1 in Table 1 and B1 in Table 2 and C31 in Table 3:

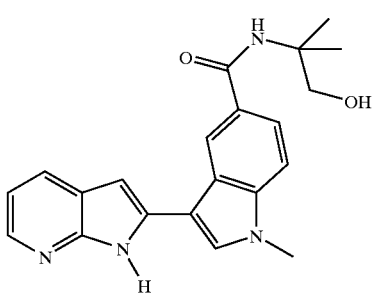

By proceeding in a similar manner to Example 14(a) but using 1-methyl-3-(5H-pyrrolo[2,3-b]pyrazin-6-yl)-1H-indole-5-carboxylic acid [Example 15(i)] and 2-amino-2-methyl-1-propanol there was prepared 1-methyl-3-(5H-pyrrolo[2,3-b]pyrazin-6-yl)-1H-indole-5-carboxylic acid (2-hydroxy-1,1-dimethyl-ethyl)-amide as a yellow solid, m.p. 210–214° C. MS: 364(MH+).

(t) 3-A6-(4-tert-butylphenyl-5H-pyrrolo[2,3-b]pyrazin-7-yl]-N-methylpropionamide A33-B55, the product of the combination of group A33 in Table 1 and B55 in Table 2:

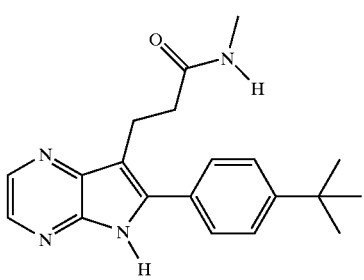

By proceeding in a manner similar to Example 14(a) above but using 3-[6-(4-tert-butylphenyl-5H-pyrrolo[2,3-b]pyrazin-7-yl]-propionic acid [Example 25(a)] and methylamine, there was prepared 3-[6-(4-tert-butylphenyl-5H-pyrrolo[2,3-b]pyrazin-7-yl]-N-methylpropionamide as an off-white solid, m.p. 222–228° C. MS: 337(MH+).

(u) 3-[16-(4-tert-butylphenyl-5H-pyrrolo[23-b]pyrazin-7-yl]-N,N-dimethylpropionamide, A34-B55, the product of the combination of group A33 in Table 1 and B55 in Table 2:

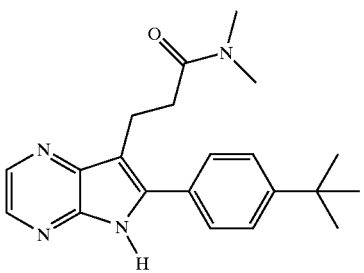

By proceeding in a manner similar to Example 14(a) above but using 3-[6-(4-tert-butylphenyl-5H-pyrrolo[2,3-b]pyrazin-7-yl]-propionic acid [Example 25(a)] and dimethylamine, there was prepared 3-[6-(4-tert-butylphenyl-5H-pyrrolo[2,3-b]pyrazin-7-yl]-N,N-dimethylpropionamide as an off-white solid, m.p. 203–204° C. MS: 351(MH+).

(v) 1-methyl-3-(5H-pyrrolo[2,3-b]pyrazin-6-yl)-1H-indole-5-carboxylic acid 2-methoxyethylamide, A1-B1-C25, the product of the combination of group A1 in Table 1 and B1 in Table 2 and C25 in Table 3:

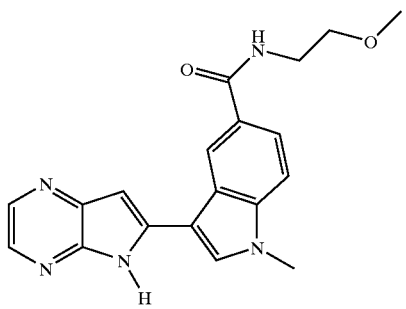

By proceeding in a manner similar to Example 14(a) above but using 1-methyl-3-(5H-pyrrolo[2,3-b]pyrazin-6-yl)-1H-indole-5-carboxylic acid [Example 15(i)] and 2-methoxyethylamine, there was prepared 1-methyl-3-(5H-pyrrolo[2,3-b]pyrazin-6-yl)-1H-indole-5-carboxylic acid 2-methoxyethylamide as an orange solid. MS: 350(MH+). HPLC (Method C): $R_T$=1.27 minutes.

(w) 1-methyl-3-(5H-pyrrolo[2,3-b]pyrazin-6-yl)-1H-indole-5-carboxylic acid 2-thien-2-ylethylamide, A1-B1-C27, the product of the combination of group A1 in Table 1 and B1 in Table 2 and C27 in Table 3:

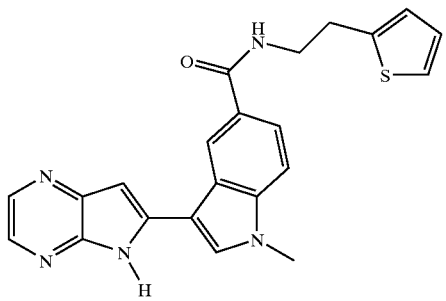

By proceeding in a manner similar to Example 14(a) above but using 1-methyl-3-(5H-pyrrolo[2,3-b]pyrazin-6-yl)-1H-indole-5-carboxylic acid [Example 15(i)] and 2-thien-2-ylethylamine, there was prepared 1-methyl-3-(5H-pyrrolo[2,3-b]pyrazin-6-yl)-1H-indole-5-carboxylic acid 2-thien-2-ylethylamide as a yellow solid. MS: 402(MH+). HPLC (Method C): $R_T$=1.45 minutes.

(x) 1-methyl-3-(5H-pyrrolo[2,3-b]pyrazin-6-yl)-1H-indole-5-carboxylic acid 2-fluoroethylamide, A1-B1-C53, the product of the combination of group A1 in Table 1 and B1 in Table 2 and C53 in Table 3:

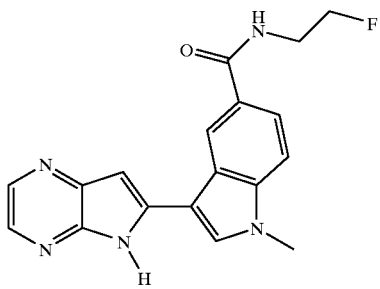

By proceeding in a manner similar to Example 14(a) above but using 1-methyl-3-(5H-pyrrolo[2,3-b]pyrazin-6-yl)-1H-indole-5-carboxylic acid [15(i)] and 2-fluoroethylamine, there was prepared 1-methyl-3-(5H-pyrrolo[2,3-b]pyrazin-6-yl)-1H-indole-5-carboxylic acid 2-fluoroethylamide as an orange solid. MS: 338(MH$^+$). HPLC (Method C): R$_T$=1.30 minutes.

(y) 1-methyl-3-(5H-pyrrolo[2,3-b]pyrazin-6-yl)-1H-indole-5-carboxylic acid 2-carboethoxyethylamide, A1-B1-C54, the product of the combination of group A2 in Table 1 and B1 in Table 2 and C54 in Table 3:

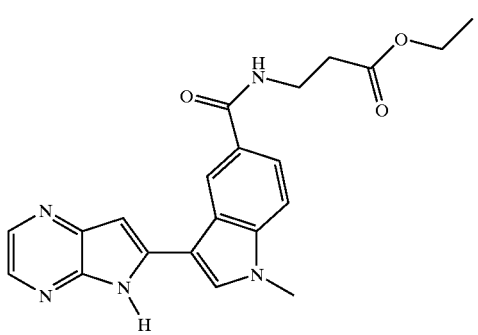

By proceeding in a manner similar to Example 14(a) above but using 1-methyl-3-(5H-pyrrolo[2,3-b]pyrazin-6-yl)-1H-indole-5-carboxylic acid [Example 15(i)] and β-alanine ethyl ester hydrochloride, there was prepared 1-methyl-3-(5H-pyrrolo[2,3-b]pyrazin-6-yl)-1H-indole-5-carboxylic acid 2-carboethoxyethylamide as an orange solid. MS: 392(MH$^+$). HPLC (Method C): RT=1.38 minutes.

(z) 1-methyl-3-(5H-pyrrolo[2,3-b]pyrazin-6-yl)-1H-indole-5-carboxylic acid (hydroxymethyl)-carbomethoxy-methylamide, A1-B1-C52, the product of the combination of group A1 in Table 1 and B1 in Table 2 and C52 in Table 3:

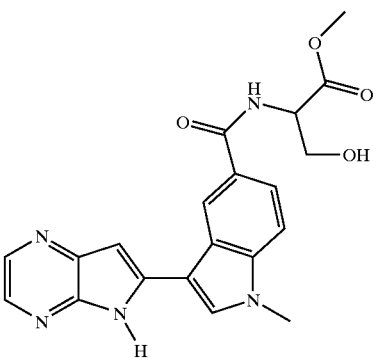

By proceeding in a manner similar to Example 14(a) above but using 1-methyl-3-(5H-pyrrolo[2,3-b]pyrazin-6-yl)-1H-indole-5-carboxylic acid [Example 15(i)] and serine methyl ester hydrochloride, there was prepared 1-methyl-3-(5H-pyrrolo[2,3-b]pyrazin-6-yl)-1H-indole-5-carboxylic acid (hydroxymethyl)-carbomethoxy-methylamide as an orange solid. MS: 394(MH$^+$). HPLC (Method C): R$_T$=1.24 minutes.

(aa) 1-methyl-3-(5H-pyrrolo[2,3-b]pyrazin-6-yl)-1H-indole-5-carboxylic acid 2-hydroxyethylamide, A1-B1-C34, the product of the combination of group A1 in Table 1 and B1 in Table 2 and C34 in Table 3:

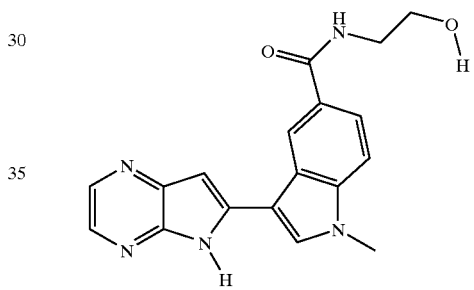

By proceeding in a manner similar to Example 14(a) above but using 1-methyl-3-(5H-pyrrolo[2,3-b]pyrazin-6-yl)-1H-indole-5-carboxylic acid [Example 15(i)] and ethanolamine, there was prepared 1-methyl-3-(5H-pyrrolo[2,3-b]pyrazin-6-yl)-1H-indole-5-carboxylic acid 2-hydroxyethylamide as a yellow solid, m.p. 171–173° C. (with decomposition). MS: 336(MH$^+$).

(ab) 1-methyl-3-(5H-pyrrolo[2,3-b]pyrazin-6-yl)-1H-indole-5-carboxylic acid methylamide, A1-B1-C23, the product of the combination of group A1 in Table 1 and B1 in Table 2 and C23 in Table 3:

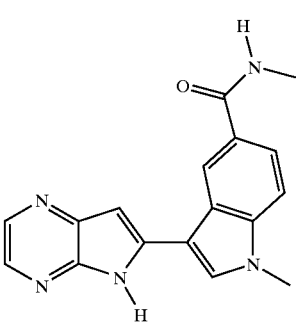

By proceeding in a manner similar to Example 14(a) above but using 1-methyl-3-(5H-pyrrolo[2,3-b]pyrazin-6-yl)-1H-indole-5-carboxylic acid [Example 15(i)] and methylamine, there was prepared 1-methyl-3-(5H-pyrrolo[2,3-b]pyrazin-6-yl)-1H-indole-5-carboxylic acid methylamide as a beige solid, MS: 304(MH⁺). ¹H-NMR [(CD₃)₂SO]: δ 8.64 (1H, broad s); 8.59 (d, 1H, J=1.0 Hz); 8.27(d, 1H, J=2.4 Hz); 8.17 (s, 1H); 8.15 (d, 1H, J=2.4 Hz); 7.82(dd, 1H, J=1.0 Hz, 7.9 Hz); 7.62 (d, 1H, J=7.9 Hz); 7.21 (s, 1H); 3.96 (s, 3H); 2.82 (s, 3H).

(ac) 1-methyl-3-(5H-pyrrolo[2,3-b]pyrazin-6-yl)-1H-indole-5-carboxylic acid dimethylamide, A1-B1-C55, the product of the combination of group A1 in Table 1 and B1 in Table 2 and C55 in Table 3:

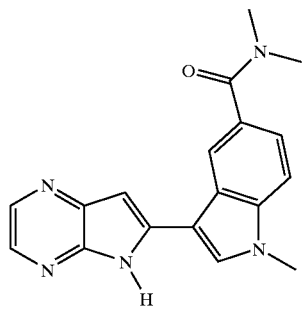

By proceeding in a manner similar to Example 14(a) above but 1-methyl-3-(5H-pyrrolo[2,3-b]pyrazin-6-yl)-1H-indole-5-carboxylic acid [Example 15(i)] and dimethylamine, there was prepared 1-methyl-3-(5H-pyrrolo[2,3-b]pyrazin-6-yl)-1H-indole-5-carboxylic acid dimethylamide as a yellow solid. MS: 320(MH⁺). ¹H NMR [(CD₃)₂SO]: δ 8.26 (d, 1H, J=2.1 Hz); 8.18 (s, 1H); 8.15 (d, 1H, J=2.1 Hz); 7.62(d, 1H, J=8.1 Hz); 7.372 (dd, 1H, J=1.0 Hz, 8.1 Hz); 6.98 (s, 1H); 3.94 (s, 3H); 3.05 (s, 6H).

(ad) [1-methyl-3-(5H-pyrrolo[2,3-b]pyrazin-6-yl)-1H-indol-5-yl]morpholin-4-yl ketone, A1-B1-C56, the product of the combination of group A1 in Table 1 and B1 in Table 2 and C56 in Table 3:

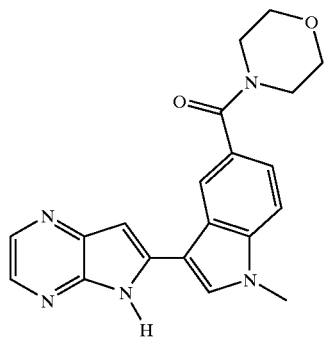

By proceeding in a manner similar to Example 14(a) above but using 1-methyl-3-(5H-pyrrolo[2,3-b]pyrazin-6-yl)-1H-indole-5-carboxylic acid [Example 15(i)] and morpholine, there was prepared [1-methyl-3-(5H-pyrrolo[2,3-b]pyrazin-6-yl)-1H-indol-5-yl]morpholin-4-yl ketone as a yellow solid, MS: 362(MH⁺).

(ae) 4-hydroxy-[1-[1-methyl-3-(5H-pyrrolo[2,3-b]pyrazin-6-yl)-1H-indol-5-yl]carbonyl-piperidine, A1-B1-C57, the product of the combination of group A1 in Table 1 and B1 in Table 2 and C57 in Table 3:

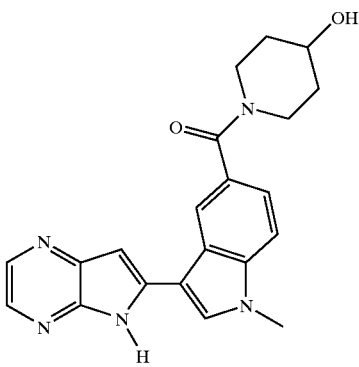

By proceeding in a manner similar to Example 14(a) above but using 1-methyl-3-(5H-pyrrolo[2,3-b]pyrazin-6-yl)-1H-indole-5-carboxylic acid [Example 15(i)] and 4-hydroxypiperidine, there was prepared 4-hydroxy-[1-[1-methyl-3-(5H-pyrrolo[2,3-b]pyrazin-6-yl)-1H-indol-5-yl]carbonylpiperidine as a yellow solid, MS: 376(MH⁺), 398 (MNa⁺).

(af) 3-[1-methyl-3-(5H-pyrrolo[2,3-b]pyrazin-6-yl)-1H-indol-5-yl]carbonylaminopropionic acid methylamide, A1-B1-C26, the product of the combination of group A1 in Table 1 and B1 in Table 2 and C26 in Table 3:

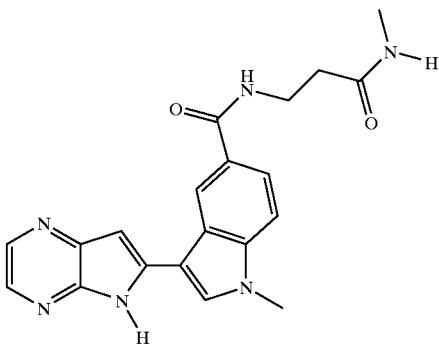

By proceeding in a manner similar to Example 14(a) above but using 3-[1-methyl-3-(5H-pyrrolo[2,3-b]pyrazin-6-yl)-1H-indol-5-yl]carbonylaminopropionic acid [Example 15(1)] and methylamine, there was prepared 3-[1-methyl-3-(5H-pyrrolo[2,3-b]pyrazin-6-yl)-1H-indol-5-yl]carbonylaminopropionic acid methylamide as a yellow solid. MS: 377(MH⁺). HPLC (Method C): R_T=1.20 minutes.

(ag) 1-methyl-3-(5H-pyrrolo[2,3-b]pyrazin-6-yl)-1H-indole-5-carboxylic acid 3-hydroxypropylamide, A1-B1-C34, the product of the combination of group A1 in Table 1 and B1 in Table 2 and C34 in Table 3:

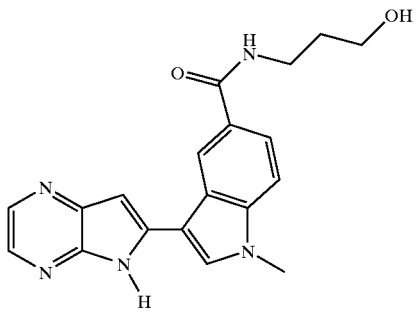

By proceeding in a manner similar to Example 14(a) above but using 1-methyl-3-(5H-pyrrolo[2,3-b]pyrazin-6-yl)-1H-indole-5-carboxylic acid [Example 15(i)] and 3-hydroxypropylamine, there was prepared 1-methyl-3-(5H-pyrrolo[2,3-b]pyrazin-6-yl)-1H-indole-5-carboxylic acid 3-hydroxypropylamide as a yellow solid. MS: 350(MH$^+$). HPLC (Method C): R$_T$=1.22 minutes.

(ah) 3-{6-[4-(1-methyl)ethoxyphenyl]-5H-pyrrolo[2,3-b]pyrazin-7-yl}-N-methyl propionamide, A33-B63, the product of the combination of group A33 in Table 1 and B63 in Table 2:

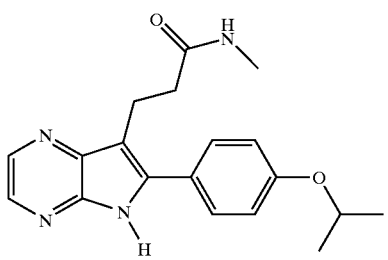

By proceeding in a manner similar to Example 14(a) above but using 3-{6-[4-(1-methyl)ethoxyphenyl]-5H-pyrrolo[2,3-b]pyrazin-7-yl}propionic acid [Example 25(b)] and methylamine, there was prepared 3-{6-[4-(1-methyl)ethoxyphenyl]-5H-pyrrolo[2,3-b]pyrazin-7-yl}-N-methyl propionamide as a yellow solid, MS: 339(MH$^+$). HPLC (Method C): R$_T$=1.49 minutes.

(ai) 3-[6-(4-methoxyphenyl)-5H-pyrrolo[2,3-b]pyrazin-7-yl]-N-methyl propionamide, A33-B77, the product of the combination of group A33 in Table 1 and B77 in Table 2:

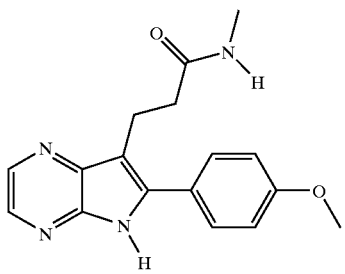

By proceeding in a manner similar to Example 14(a) above but using 3-[6-(4-methoxyphenyl)-5H-pyrrolo[2,3-b]pyrazin-7-yl]propionic acid [Example 25(d)] and methylamine, there was prepared 3-[6-(4-methoxyphenyl)-5H-pyrrolo[2,3-b]pyrazin-7-yl]propionic acid methylamide as an off-white solid. $^1$H NMR [(CD$_3$)$_2$SO]: δ 12.0 (s, 1H) 8.3 (d, 1H), 8.2 (d, 1H), 7.7 (d, 2H), 7.1 (d, 2H), 3.8(s, 3H), 3.05 (t, 2H), 2.6 (t, 2H) 2.5 (s, 3H). MS: 310(MH$^+$).

(aj) 3-{6-[4-(1-methyl)ethoxyphenyl]-5H-pyrrolo[2,3-b]pyrazin-7-yl}propionamide, A32-B63, the product of the combination of group A32 in Table 1 and B63 in Table 2:

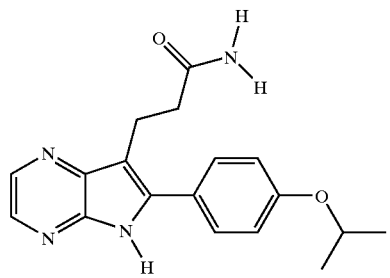

By proceeding in a manner similar to Example 14(a) above but using 3-{6-[4-(1-methyl)ethoxyphenyl]-5H-pyrrolo[2,3-b]pyrazin-7-yl}propionic acid [Example 25(b)] and ammonium chloride, there was prepared 3-{6-[4-(1-methyl)ethoxyphenyl]-5H-pyrrolo[2,3-b]pyrazin-7-yl}propionamide as a white solid. MS: 325(MH$^+$). HPLC (Method C): R$_T$=1.44 minutes.

(ak) 3-{6-(4-hydroxyphenyl)-5H-pyrrolo[2,3-b]pyrazin-7-yl}propionamide, A32-B78, the product of the combination of group A32 in Table 1 and B78 in Table 2:

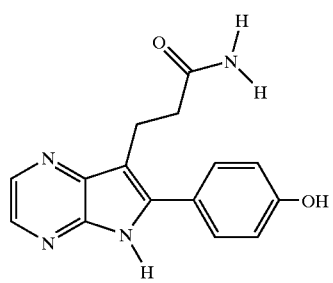

By proceeding in a manner similar to Example 14(a) above but using 3-{6-(4-hydroxyphenyl)-5H-pyrrolo[2,3-b]pyrazin-7-yl}propionic acid [Example 30] and ammonium chloride, there was prepared 3-{6-(4-hydroxyphenyl)-5H-pyrrolo[2,3-b]pyrazin-7-yl propionamide as a white solid. MS: 283(MH$^+$). HPLC (Method C): R$_T$=2.18 minutes.

(al) 3-[6-(4-fluorophenyl)-5H-pyrrolo[2,3-b]pyrazin-7-yl]-N-methyl propionamide, A33-B89, the product of the combination of group A33 in Table 1 and B89 in Table 2:

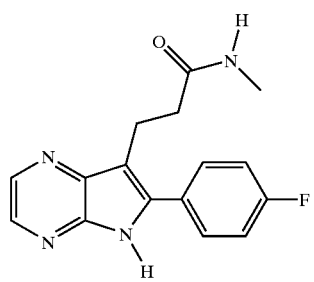

By proceeding in a manner similar to Example 14(a) above but using 3-[6-(4-fluorophenyl)-5H-pyrrolo[2,3-b]

pyrazin-7-yl]propionic acid [Example 25(c)] and methylamine, there was prepared 3-[6-(4-fluorophenyl)-5H-pyrrolo[2,3-b]pyrazin-7-yl]-N-methyl propionamide as an off-white solid. $^1$H NMR [(CD$_3$)$_2$SO]: δ 12.5 (s, 11H) 8.4 (d, 1H), 8.2 (d, 1H), 7.8 (d, 2H), 7.4 (d, 2H), 3.1 (t, 2H), 2.6 (t, 2H), 2.5 (s, 3H). MS: 298(MH$^+$).

(am) 3-[4-(3,5-dimethyl-isoxazolyl-4-yl)-1H-pyrrolo[2,3-b]pyridin-2-yl]-1-methyl-1H-indole-5-carboxylic acid (2-methoxy-ethyl)-amide, A83-B1-C25, the product of the combination of group A83 in Table 1 and B1 in Table 2 and C25 in Table 3:

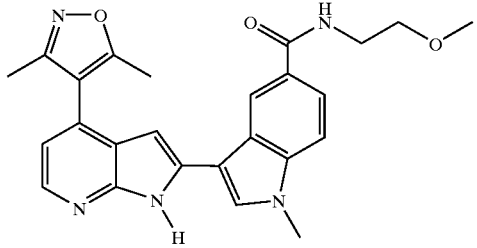

By proceeding in a manner similar to Example 14(a) above but using 3-[4-(3,5-dimethyl-isoxazole-4-yl)-1H-pyrrolo[2,3-b]pyridine-2-yl]-1-methyl-1H-indole-5-carboxylic acid [Example 15(m)] and 2-methoxyethylamine, there was prepared 3-[4-(3,5-dimethyl-isoxazolyl-4-yl)-1H-pyrrolo[2,3-b]pyridin-2-yl]-1-methyl-1H-indole-5-carboxylic acid (2-methoxy-ethyl)-amide as a solid, m.p. 249-250° C. MS: 443(M$^+$).

(an) 3-[4-(3,5-dimethyl-isoxazolyl-4-yl)-1H-pyrrolo[2,3-b]pyridin-2-yl]-1H-indole-5-carboxylic acid (2-methoxy-ethyl)-amide, A83-B2-C25, the product of the combination of group A83 in Table 1 and B2 in Table 2 and C25 in Table 3:

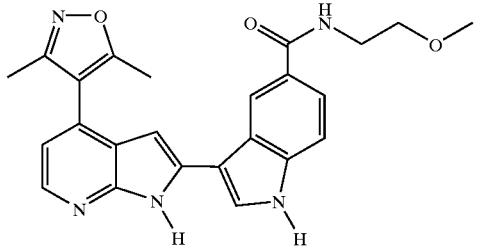

By proceeding in a manner similar to Example 14(a) above but using 3-[4-(3,5-dimethyl-isoxazole-4-yl)-1H-pyrrolo[2,3-b]pyridine-2-yl]-1H-indole-5-carboxylic acid [Example 15(n)] and 2-methoxyethylamine, there was prepared 3-[4-(3,5-dimethyl-isoxazolyl-4-yl)-1H-pyrrolo[2,3-b]pyridin-2-yl]-1H-indole-5-carboxylic acid (2-methoxy-ethyl)-amide as a white solid, m.p. 274–275° C. MS: 430 (MH$^+$).

(ao) 3-(4-cyano-1H-pyrrolo[2,3-b]pyridin-2-yl)-1-methyl-1H-indole-5-carboxylic acid (2-hydroxy-1,1-dimethyl-ethyl)-amide, A3-B1-C31, the product of the combination of group A3 in Table 1 and B1 in Table 2 and C31 in Table 3:

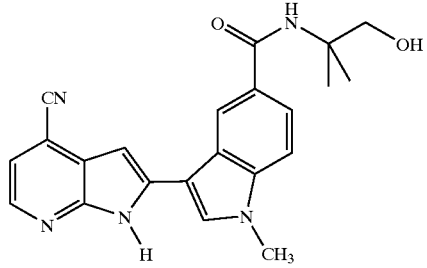

By proceeding in a manner similar to Example 14(a) above but using 3-(4-cyano-1H-pyrrolo[2,3-b]pyridine-2-yl]-1-methyl-1H-indole-5-carboxylic acid [Example 15(r)] and 2-amino-2-methylpropanol, there was prepared 3-(4-cyano-1H-pyrrolo[2,3-b]pyridin-2-yl]-1-methyl-1H-indole-5-carboxylic acid (2-hydroxy-1,1-dimethyl-ethyl)-amide as a solid. MS: 388(MH$^+$). HPLC(Method C): R$_T$=2.81 minutes.

(ap) 3-(4-cyano-1H-pyrrolo[2,3-b]pyridin-2-yl]-1-methyl-1H-indole-5-carboxylic acid (2-hydroxy-2-methyl-propyl)-amide, A3-B1-C97, the product of the combination of group A3 in Table 1 and B1 in Table 2 and C97 in Table 3:

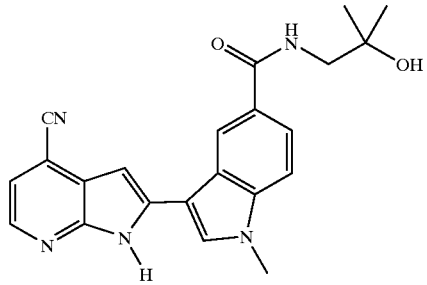

By proceeding in a manner similar to Example 14(a) above but using 3-(4-cyano-1H-pyrrolo[2,3-b]pyridine-2-yl]-1-methyl-1H-indole-5-carboxylic acid [Example 15(r)] and 3-amino-2-methyl-2-propanol (prepared according to the literature procedure of Cabella et. al. Tetrahedron, 1995, 51 (6), 18-17-1826), there was prepared 3-(4-cyano-1H-pyrrolo[2,3-b]pyridin-2-yl]-1-methyl-1H-indole-5-carboxylic acid (2-hydroxy-2-methyl-propyl)-amide as a yellow solid. LC-MS: METHOD D: R$_T$=2.69 minutes, 388 (MH$^+$).

(aq) 2-[5,6-dimethoxy-3-(1H-pyrrolo[2,3-b]pyridin-2-yl)-indol-1-yl]-1-morpholin-4-yl-ethanone, A2-B118-C$_1$, the product of the combination of group A2 in Table 1 and B118 in Table 2 and C1 in Table 3:

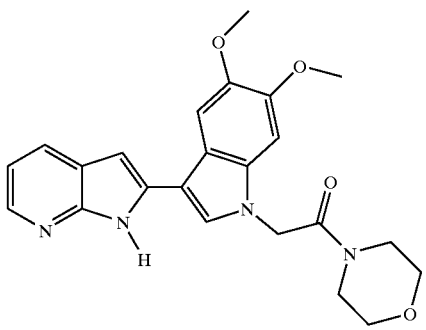

By proceeding in a manner similar to Example 14(a) but using [5,6-dimethoxy-3-(1H-pyrrolo[2,3-b]pyridin-2-yl)-indol-1-yl]-acetic acid [Example 13(g)] there was prepared 2-[5,6-dimethoxy-3-(1H-pyrrolo[2,3-b]pyridin-2-yl)-indol-1-yl]-1-morpholin-4-yl-ethanone as a pale yellow solid, m.p. 260° C. (with decomposition). TLC: $R_F$=0.37 (dichloromethane/methanol, 9/1). MS: ESI; n/z=421 MH$^+$.

EXAMPLE 15

(a) [1-Methyl-3-(1H-pyrrolo[2,3-b]pyridin-2-yl)-1H-indol-5-yloxy]-acetic acid, A2-B1-C6, the product of the combination of group A2 in Table 1 and B1 in Table 2 and C6 in Table 3:

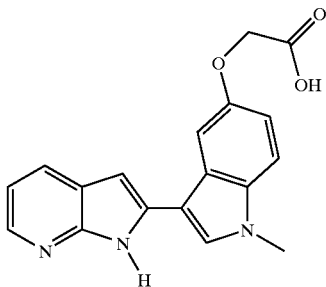

A solution of {1-methyl-3-[1-(toluene-4-sulfonyl)-1H-pyrrolo[2,3-b]pyridin-2-yl]-1H-indol-5-yloxy}-acetic acid ethyl ester [500 mg, Reference Example 15(b)] in methanol (25 mL) was treated with potassium hydroxide (5N, 3 mL) and then heated at reflux for 16 hours. The solvent was removed under reduced pressure and the residue was treated with water (10 mL). The pH of this mixture was adjusted to 7 by addition of acetic acid and the resulting colourless solid was collected by filtration then dried to give the title compound (170 mg) as a colourless solid, m.p.>300° C. MS: 322(MH$^+$).

(b) 2-[1-methyl-3-(1H-pyrrolo[2,3-b]pyridin-2-yl)-1H-indol-5-yloxy]-propionic acid, A2-B1-C2, the product of the combination of group A2 in Table 1 and B1 in Table2 and C2 in Table 3:

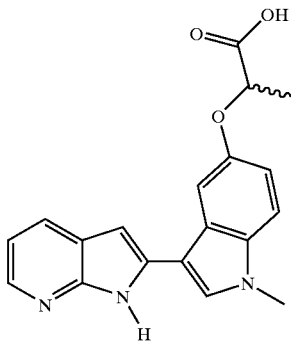

By proceeding in a manner similar to Example 15(a) above but using 2-{1-methyl-3-[1-(toluene-4-sulfonyl)-1H-pyrrolo[2,3-b]pyridin-2-yl]-1H-indol-5-yloxy}-propionic acid ethyl ester [Reference Example 15(c)], there was prepared 2-[1-methyl-3-(1H-pyrrolo[2,3-b]pyridin-2-yl)-1H-indol-5-yloxy]-propionic acid as a colourless solid, m.p. 177–178° C. MS: 336(MH$^+$).

(c) 1-[1-methyl-3-(1H-pyrrolo[2,3-b]pyridin-2-yl)-1H-indol-5-yloxy]-cyclobutane-1-carboxylic acid, A2-B1-C11, the product of the combination of group A2 in Table 1 and B1 in Table 2 and C11 in Table 3:

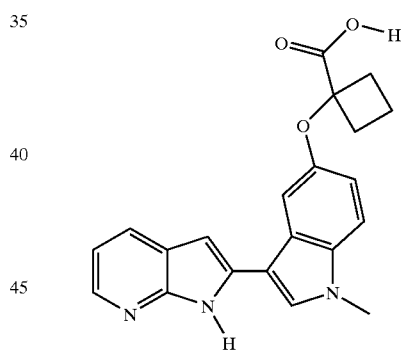

By proceeding in a manner similar to Example 15(a) above but using 1-{1-methyl-3-[1-(toluene-4-sulfonyl)-1H-pyrrolo[2,3-b]pyridin-2-yl]-1H-indol-5-yloxy}-cyclobutanecarboxylic acid ethyl ester [Reference Example 15(d)], there was prepared 1-[1-methyl-3-(1H-pyrrolo[2,3-b]pyridin-2-yl)-1H-indol-5-yloxy]-cyclobutane-1-carboxylic acid as a colourless solid, m.p. 168–169° C. MS: 362(MH$^+$).

(d) 1-methyl-3-(1H-pyrrolo[2,3-b]pyridin-2-yl)-1H-indole-5-carboxylic acid, A2-B1-C28, the product of the combination of group A2 in Table 1 and B1 in Table 2 and C28 in Table 3:

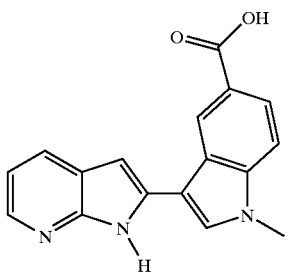

By proceeding in a manner similar to Example 15(a) above but using 1-methyl-3-[1-(toluene-4-sulfonyl)-1H-pyrrolo[2,3-b]pyridin-2-yl]-1H-indole-5-carboxylic acid, methyl ester [Reference Example 19(a)], there was prepared 1-methyl-3-(1H-pyrrolo[2,3-b]pyridin-2-yl)-1H-indole-5-carboxylic acid as a yellow solid, m.p.>300° C. MS: 291 (MH$^+$).

(e) 1-methyl-3-(1H-pyrrolo[2,3-b]pyridin-2-yl)-1H-indol-5-ol, A2-B1-C10, the product of the combination of group A2 in Table 1 and B1 in Table 2 and C10 in Table 3:

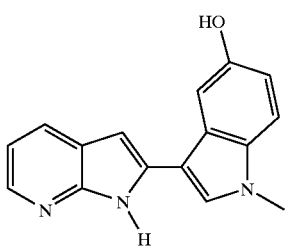

By proceeding in a manner similar to Example 15(a) above but using 1-methyl-3-[1-(toluene-4-sulfonyl)-1H-pyrrolo[2,3-b]pyridin-2-yl]-1H-indol-5-ol [Reference Example 14(a)], there was prepared 1-methyl-3-(1H-pyrrolo[2,3-b]pyridin-2-yl)-1H-indol-5-ol as a yellow solid, m.p. 199–200° C. MS: 264(MH$^+$).

(f) 1-{1-(cyclobutanecarboxylic acid)-3-[1H-pyrrolo[2,3-b]pyridin-2-yl]-1H-indol-5-yloxy}-cyclobutanecarboxylic acid, A2-B12-C11, the product of the combination of group A2 in Table 1 and B12 in Table 2 and C11 in Table 3:

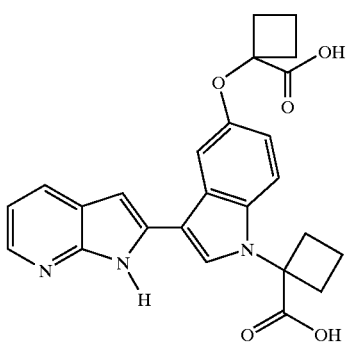

By proceeding in a manner similar to Example 15(a) above but using 1-{1-(cyclobutanecarboxylic acid ethyl ester)-3-[1-(toluene-4-sulfonyl)-1H-pyrrolo[2,3-b]pyridin-2-yl]-1H-indol-5-yloxy}-cyclobutanecarboxylic acid ethyl ester [Reference Example 23(d)], there was prepared 1-{1-(cyclobutanecarboxylic acid)-3-[1H-pyrrolo[2,3-b]pyridin-2-yl]-1H-indol-5-yloxy}-cyclobutanecarboxylic acid as a yellow solid, m.p. 240° C. (with decomposition). MS: 444(MH$^-$).

(g) 1-methyl-3-(1H-pyrrolo[2,3-b]pyridin-2-yl)-1H-indole-6-carboxylic acid, A2-B18-C28, the product of the combination of group A2 in Table 1 and B18 in Table 2 and C28 in Table 3:

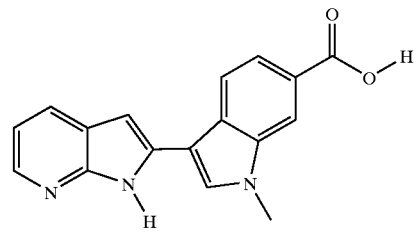

By proceeding in a manner similar to Example 15(a) above but using 1-methyl-3-[1-(toluene-4-sulfonyl)-1H-pyrrolo[2,3-b]pyridin-2-yl]-1H-indole-6-carboxylic acid, methyl ester [Reference Example 13(g)], there was prepared 1-methyl-3-(1H-pyrrolo[2,3-b]pyridin-2-yl)-1H-indole-6-carboxylic acid as a yellow solid, m.p. 359–361° C. MS 292(MH$^+$).

(h) 3-[1-methyl-3-(1H-pyrrolo[2,3-b]pyridin-2-yl)-1H-indol-5-yl]-propionic acid, A2-B1-C21, the product of the combination of group A2 in Table 1 and B1 in Table 2 and C21 in Table 3:

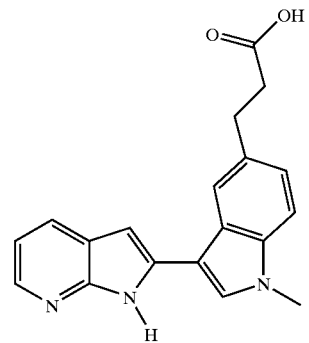

By proceeding in a manner similar to Example 15(a) above but using 3-{1-methyl-3-[1-(toluene-4-sulfonyl)-1H-pyrrolo[2,3-b]pyridin-2-yl]-1H-indol-5-yl}-propionic acid ethyl ester [Reference Example 38(a)], there was prepared 3-[1-methyl-3-(1H-pyrrolo[2,3-b]pyridin-2-yl)-1H-indol-5-yl]-propionic acid as a yellow solid, m.p. 268–270° C. MS 320 (MH$^+$).

(i) 1-methyl-3-(5H-pyrrolo[2,3-b]pyrazin-6-yl)-1H-indole-5-carboxylic acid, A1-B1-C28, the product of the combination of group A1 in Table 1 and B1 in Table 2 and C28 in Table 3:

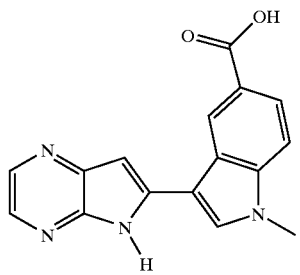

By proceeding in a similar manner to Example 15(a) but using 1-methyl-3-(5H-pyrrolo[2,3-b]pyrazin-6-yl)-1H-indole-5-carboxylic acid, methyl ester [Reference Example 19(b)] there was prepared 1-methyl-3-(5H-pyrrolo[2,3-b]pyrazin-6-yl)-1H-indole-5-carboxylic acid as a brown solid, m.p. 350° C. HPLC (METHOD A): RT=5.85 minutes.

(j) [2-methoxy-5-(5H-pyrrolo[2,3-b]pyrazin-6-yl)-phenoxy]acetic acid, A1-B67, the product of the combination of group A1 in Table 1 and B67 in Table 2:

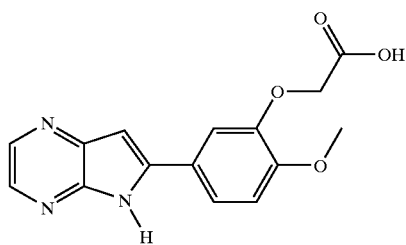

By proceeding in a manner similar to Example 15(a) above but using [2-methoxy-5-(5H-pyrrolo[2,3-b]pyrazin-6-yl)-phenoxy]-acetic acid ethyl ester [Example 27], there was prepared [2-methoxy-5-(5H-pyrrolo[2,3-b]pyrazin-6-yl)-phenoxy]acetic acid as a white solid, m.p. 330–332° C. MS: 300(MH$^+$).

(k) 3-[2-dimethylamino-5-(5H-pyrrolo[2,3-b]pyrazin-6-yl)-phenyl]propionic acid, A32-B74, the product of the combination of group A32 in Table 1 and B74 in Table 2:

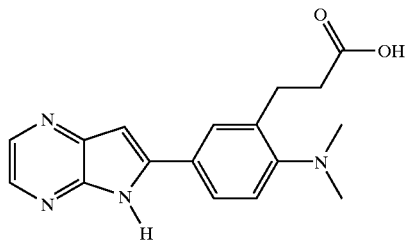

By proceeding in a manner similar to Example 15(a) above but using ethyl 3-[2-dimethylamino-5-(5H-pyrrolo[2,3-b]pyrazin-6-yl)phenyl]propionate [Reference Example 38(b)], there was prepared 3-[2-dimethylamino-5-(5H-pyrrolo[2,3-b]pyrazin-6-yl)-phenyl]propionic acid as an orange solid, m.p. 269–271° C. MS: 311(MH$^+$).

(l) 3-[1-methyl-3-(5H-pyrrolo[2,3-b]pyrazin-6-yl)-1H-indol-5-yl]carbonylaminopropionic acid, A1-B1-C58, the product of the combination of group A1 in Table 1 and B1 in Table 2 and C58 in Table 3:

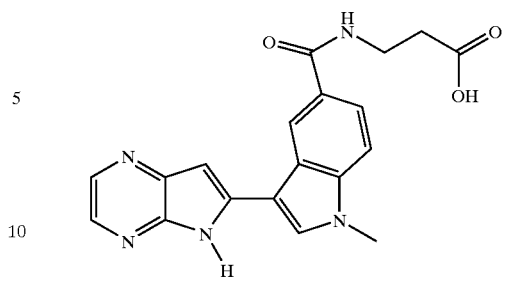

By proceeding in a manner similar to Example 15(a) above but using 1-methyl-3-(5H-pyrrolo[2,3-b]pyrazin-6-yl)-1H-indole-5-carboxylic acid 2-carboethoxyethylamide [Example 14(y)] and sodium hydroxide, there was prepared 3-[1-methyl-3-(5H-pyrrolo[2,3-b]pyrazin-6-yl)-1H-indol-5-yl]carbonylaminopropionic acid as an orange solid (35 mg). MS: 364(MH$^+$). HPLC (Method C): R$_T$=1.24 minutes.

(m) 3-[4-(3,5-dimethyl-isoxazole-4-yl)-1H-pyrrolo[2,3-b]pyridine-2-yl]-1-methyl-1H-indole-5-carboxylic acid, A83-B1-C28, the product of the combination of group A83 in Table 1 and B1 in Table 2 and C28 in Table 3:

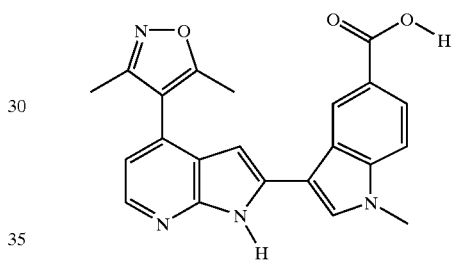

By proceeding in a manner similar to Example 15(a) above but using 3-[4-(3,5-dimethyl-isoxazole-4-yl)-1-(toluene-4-sulfonyl)-1H-pyrrolo[2,3-b]pyridine-2-yl]-1-methyl-1H-indole-5-carboxylic acid, methyl ester [Reference Example 13(m)], there was prepared 3-[4-(3,5-dimethyl-isoxazole-4-yl)-1H-pyrrolo[2,3-b]pyridine-2-yl]-1-methyl-1H-indole-5-carboxylic acid as a yellow solid, m.p.>305° C. LC-MS (METHOD D): R$_T$=2.57 minutes.

(n) 3-[4-(3,5-methyl-isoxazole-4-yl)-1H-pyrrolo[2,3-b]pyridine-2-yl]-H-indole-5-carboxylic acid, A83-B2-C28, the product of the combination of group A83 in Table 1 and B2 in Table 2 and C28 in Table 3:

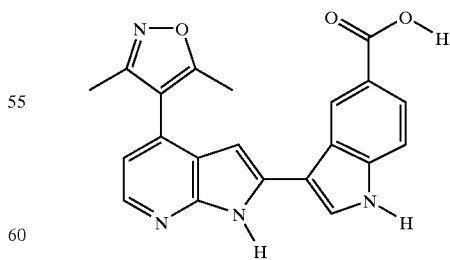

By proceeding in a manner similar to Example 15(a) above but using 3-[4-(3,5-dimethyl-isoxazole-4-yl)-1-(toluene-4-sulfonyl)-1H-pyrrolo[2,3-b]pyridine-2-yl]-1H-indole-5-carboxylic acid, methyl ester [Reference Example 12(1)], there was prepared 3-[4-(3,5-dimethyl-isoxazole-4- yl)-1H-pyrrolo[2,3-b]pyridine-2-yl]-1H-indole-5-carboxylic acid as a yellow solid, m.p.>300° C. MS: 373 (MH⁺).

(o) 4-(3,5-dimethyl-isoxazole-4-yl)-2-(5-methoxy-1-methyl-1H-indol-3-yl)-1H-pyrrolo[2,3-b]pyridine, A83-B1-C1, the product of the combination of group A83 in Table 1 and B1 in Table 2 and C1 in Table 3:

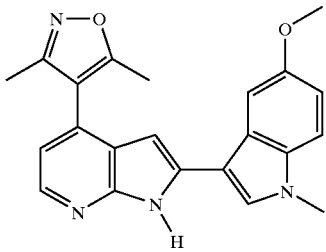

By proceeding in a manner similar to Example 15(a) above but using 4-(3,5-dimethyl-isoazol-4-yl)-2-(5-methoxy-1-methyl-1H-indol-3-yl)-1-(toluene-4-sulfonyl)-1H-pyrrolo[2,3-b]pyridine [Reference Example 13(m)], there was prepared 4-(3,5-dimethyl-isoxazole-4-yl)-2-(5-methoxy-1-methyl-1H-indol-3-yl)-1H-pyrrolo[2,3-b]pyridine as a yellow solid, m.p. 254–255° C. MS: 373 (MH⁺).

(p) 4-(3,5-dimethyl-isoxazole-4-yl)-2-(5-methoxy-1H-indol-3-yl)-1H-pyrrolo[2,3-b]pyridine, A83-B2-C1, the product of the combination of group A83 in Table 1 and B2 in Table 2 and C1 in Table 3:

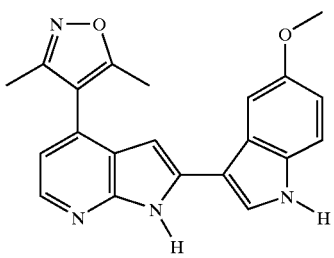

By proceeding in a manner similar to Example 15(a) above but using 4-(3,5-dimethyl-isoazol-4-yl)-2-(5-methoxy-1H-indol-3-yl)-1-(toluene-4-sulfonyl)-1H-pyrrolo[2,3-b]pyridine [Reference Example 12(m)], there was prepared 4-(3,5-dimethyl-isoxazole-4-yl)-2-(5-methoxy-1H-indol-3-yl)-1H-pyrrolo[2,3-b]pyridine as a yellow solid, m.p. 270–271° C. TLC: $R_F$=0.29 (ethyl acetate/heptane, 4:1).

(q) 3-(4-methoxy-1H-pyrrolo[2,3-b]pyridine-2-yl)-1-methyl-1H-indole-5-carboxylic acid, A5-B1-C28, the product of the combination of group A5 in Table 1 and B1 in Table 2 and C28 in Table 3:

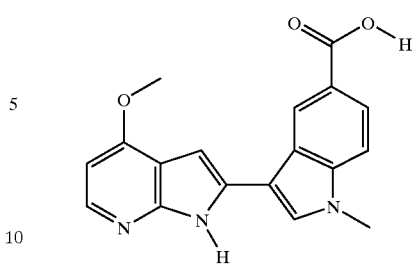

By proceeding in a manner similar to Example 15(a) above but using 3-[4-(methoxy-1-(toluene-4-sulfonyl)-1H-pyrrolo[2,3-b]pyridine-2-yl]-1-methyl-1H-indole-5-carboxylic acid, methyl ester [Reference Example 2(q)], there was prepared 3-(4-methoxy-1H-pyrrolo[2,3-b]pyridine-2-yl)-1-methyl-1H-indole-5-carboxylic acid as a pink solid. LC-MS: METHOD D: $R_T$=2.39 minutes, 322 (MH⁺).

(r) 3-(4-cyano-1H-pyrrolo[2,3-b]pyridine-2-yl)-1-methyl-1H-indole-5-carboxylic acid, A3-B1-C28, the product of the combination of group A3 in Table 1 and B1 in Table 2 and C28 in Table 3:

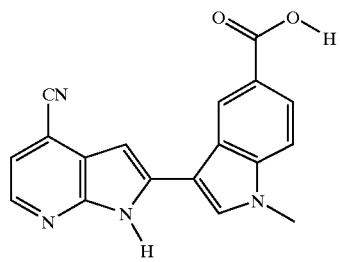

By proceeding in a manner similar to Example 15(a) above but using 3-(4-cyano-1H-pyrrolo[2,3-b]pyridine-2-yl)-1-methyl-1H-indole-5-carboxylic acid, methyl ester [Reference Example 81], there was prepared 3-(4-cyano-1H-pyrrolo[2,3-b]pyridine-2-yl)-1-methyl-1H-indole-5-carboxylic acid as a pink solid. HPLC (Method C): $R_T$=2.89 minutes. MS: 317(MH⁺).

(s) 3-(1H-pyrrolo[2,3-b]pyridine-2-yl)-1H-indole-5-carboxylic acid, A2-B2-C28, the product of the combination of group A2 in Table 1 and B2 in Table 2 and C28 in Table 3:

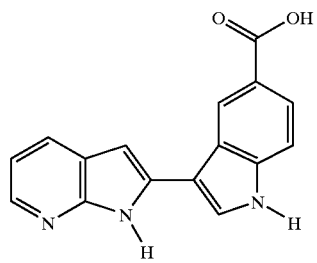

By proceeding in a manner similar to Example 15(a) above but using 1-(toluene-4-sulfonyl)-3-[1-(toluene-4-sulfonyl)-1H-pyrrolo[2,3-b]pyridine-2-yl)-1H-indole-5-carboxylic acid, methyl ester [Reference Example 12 (p)], there was prepared 3-(1H-pyrrolo[2,3-b]pyridine-2-yl)-1H-indole-5-carboxylic acid as a yellow solid, m.p.>300° C. ¹H NMR [(CD$_3$)$_2$SO]: δ 12.85–12.95 (1H, s); 12.10–12.00 (1H, s); 8.65 (1H, s); 8.31 (1H, dd); 8.28 (1H, d); 8.25 (1H, dd); 7.85 (1H, dd); 7.55 (1H, d); 7.30 (1H, m); 6.97 (1H, d).

(t) 2-(5-methoxyl-1H-indol-3-yl)-1H-pyrrolo[2,3-b]pyridine-4-carboxylic acid, A67-B2-C1, the product of the combination of group A67 in Table 1 and B2 in Table 2 and C1 in Table 3:

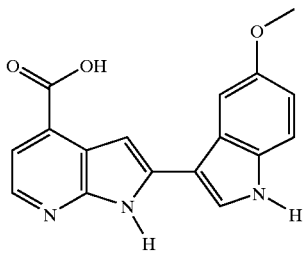

By proceeding in a manner similar to Example 15(a) above but using 2-(5-methoxy-1H-indol-3-yl)-1-(toluene-4-sulfonyl)-1H-pyrrolo[2,3-b]pyridine-4-carboxylic acid tert-butyl ester [Reference Example 67(b)], there was prepared 2-(5-methoxyl-1H-indol-3-yl)-1H-pyrrolo[2,3-b]pyridine-4-carboxylic acid as a dark solid. MS: 308(MH$^+$), TLC: R$_F$=0.04 (ethyl acetate/heptane, 3:1).

(u) Potassium 2-(5-methoxyl-1H-indol-3-yl)-1H-pyrrolo[2,3-b]pyridine-4-carboxylate, potassium salt of A2-B2-C28, the product of the combination of group A2 in Table 1 and B2 in Table 2 and C28 in Table 3:

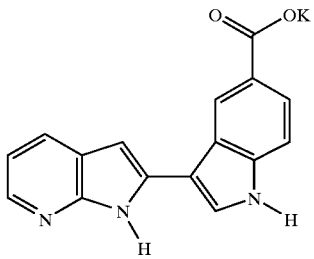

By proceeding in a manner similar to Example 15(a) above but using 1-methyl-3-[1-(toluene-4-sulfonyl)-1H-pyrrolo[2,3-b]pyridin-2-yl]1H-indole-5-carboxylic acid, methyl ester [Reference Example 19(a)] and evaporation of the reaction mixture followed by suspension in a minimal volume of water, collection of the solid and drying at 60° C. under vacuum, there was prepared potassium 2-(5-methoxyl-1H-indol-3-yl)-1-H-pyrrolo[2,3-b]pyridine-4-carboxylate. TLC: R$_F$=0.000 (ethyl acetate/pentane, 2:3). $^1$H NMR [(CD$_3$)$_2$SO]: δ 8.57 (1H, s); 8.10 (1H, dd); 7.90 (3H, m); 7.33 (1H, d); 7.00 (1H, dd); 6.75 (1H, d).

EXAMPLE 16

(a) 2-[1-Methoxy-3-(1H-pyrrolo[2,3-b]pyridin-2-yl)-1H-indol-5-yloxy]-ethanol, A2-B1-C3, the product of the combination of group A2 in Table 1 and B1 in Table 2 and C3 in Table 3:

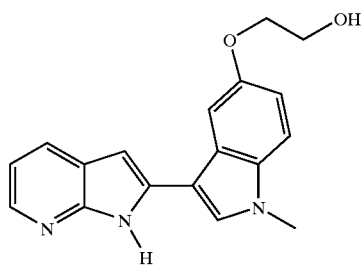

A solution of {1-methyl-3-[1-(toluene-4-sulfonyl)-1H-pyrrolo[2,3-b]pyridin-2-yl]-1H-indol-5-yloxy}-acetic acid ethyl ester [120 mg, Reference Example 15(b)] in dry tetrahydrofuran (5 mL) was treated with lithium aluminium hydride (1.0M solution in tetrahydrofuran, 50 μl) at 0° C. under a nitrogen atmosphere. The mixture was allowed to warn to ambient temperature, then stirred for 3 hours and then carefully poured into water (75 ). The mixture was extracted three times with ethyl acetate (25 mL). The combined organic extracts were washed with brine (75 mL), then dried over sodium sulfate and then evaporated to give the title compound (45 mg) as a colourless solid, m.p. 209–210° C. MS: 308(MH$^+$).

(b) 2-[1-methyl-3-(1H-pyrrolo[2,3-b]pyridin-2-yl)-1H-indol-5-yloxy]-propan-1-ol, A2-B1-C7, the product of the combination of group A2 in Table 1 and B1 in Table 2 and C7 in Table 3:

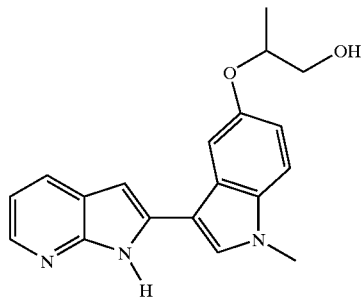

By proceeding in a manner similar to Example 16(a) above but using 2-{1-methyl-3-[1-(toluene-4-sulfonyl)-1H-pyrrolo[2,3-b]pyridin-2-yl]-1H-indol-5-yloxy}-propionic acid ethyl ester [Reference Example 15(c)], there was prepared 2-[1-methyl-3-(1H-pyrrolo[2,3-b]pyridin-2-yl)-1H-indol-5-yloxy]-propan-1-ol as a colourless solid, m.p. 164–165° C. MS: 320(MH$^+$).

(c) {1-[1-methyl-3-(1H-pyrrolo[2,3-b]pyridin-2-yl)-1H-indol-5-yloxy]-cyclobutyl}-methanol, A2-B1-C12, the product of the combination of group A2 in Table 1 and B1 in Table 2 and C12 in Table 3:

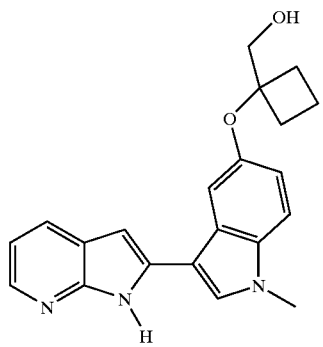

By proceeding in a manner similar to Example 16(a) above but using 1-{1-methyl-3-[1-(toluene-4-sulfonyl)-1H- pyrrolo[2,3-b]pyridin-2-yl]-1H-indol-5-yloxy}-cyclobutanecarboxylic acid ethyl ester [Reference Example 15(d)], there was prepared 1-[1-methyl-3-(1H-pyrrolo[2,3-b]pyridin-2-yl)-1H-indol-5-yloxy]-cyclobutyl}-methanol as a colourless solid, m.p. 144–146° C. MS: 348(MH⁺). HPLC (METHOD A): $R_T$=6.37 minutes.

(d) 2-(6-phenyl-5H-pyrrolo[2,3-b]pyrazin-7-yl)-ethanol, A44-B100, the product of the combination of group A44 in Table 1 and B100 in Table 2:

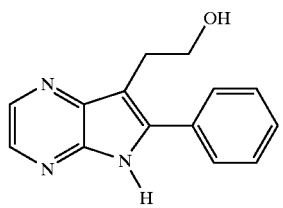

By proceeding in a manner similar to Example 16(a) above but using (6-phenyl-5H-pyrrolo[2,3-b]pyrazin-7-yl)-acetic acid [Reference Example 35], there was prepared 2-(6-phenyl-5H-pyrrolo[2,3-b]pyrazin-7-yl)-ethanol as a colourless solid, m.p. 201–202° C. MS: 348(MH⁺). HPLC (METHOD A): $R_T$=6.37 minutes. [Elemental analysis:—C, 70.68; H, 5.77; N,17.44%. Calculated for $C_{13}H_{11}N_3O$:—C, 70.28; H, 5.48; N, 17.56%].

(e) 2-[2-methoxy-5-(5H-pyrrolo[2,3-b]pyrazin-6-yl)-phenoxy]-ethanol, A1-B66, the product of the combination of group A1 in Table 1 and B66 in Table 2:

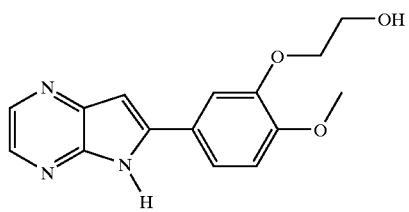

By proceeding in a manner similar to Example 16(a) above but using [2-methoxy-5-(5H-pyrrolo[2,3-b]pyrazin-6-yl)-phenoxy]-acetic acid ethyl ester [Example 27], there was prepared 2-[2-methoxy-5-(5H-pyrrolo[2,3-b]pyrazin-6-yl)-phenoxy]-ethanol as a yellow solid, m.p. 203–205° C. MS: 286(MH⁺).

(f) 3-[2-dimethylamino-5-(5H-pyrrolo[2,3-b]pyrazin-6-yl)-phenyl]-propan-1-ol, A1-B73, the product of the combination of group A1 in Table 1 and B73 in Table 2:

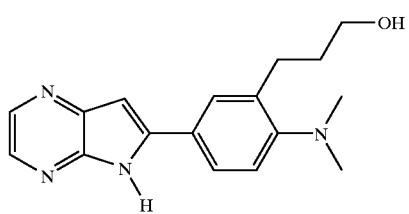

By proceeding in a manner similar to Example 16(a) above but using ethyl 3-[2-dimethylamino-5-(5H-pyrrolo[2,3-b]pyrazin-6-yl)phenyl]propionate [Reference Example 38(b)], there was prepared 3-[2-dimethylamino-5-(5H-pyrrolo[2,3-b]pyrazin-6-yl)-phenyl]-propan-1-ol as a yellow solid, m.p. 203–204° C. MS: 297(MH⁺).

(g) 3-{6-[4-(1-methyl)ethoxyphenyl]-5H-pyrrolo[2,3-b]pyrazin-7-yl}propanol, A30-B63, the product of the combination of group A30 in Table 1 and B63 in Table 2:

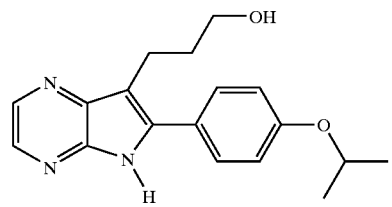

By proceeding in a manner similar to Example 16(a) above but using 3-{6-[4-(1-methyl)ethoxyphenyl]-5H-pyrrolo[2,3-b]pyrazin-7-yl}propionic acid [Example 25(b)] there was prepared 3-{6-[4-(1-methyl)ethoxyphenyl]-5H-pyrrolo[2,3-b]pyrazin-7-yl}propanol as a yellow solid (7 mg). MS: 312(MH⁺). HPLC (Method C): $R_T$=2.9 minutes.

EXAMPLE 17

(a) 2-(5-Methoxy-1-methyl-1H-indol-3-yl)-1H-pyrrolo[2,3-b]pyridine, A2-B1-C1, the product of the combination of group A2 in Table 1 and B1 in Table 2 and C1 in Table 3:

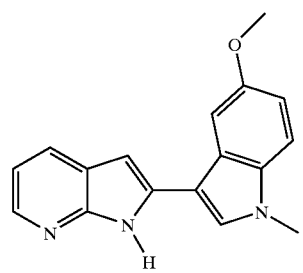

A solution of 2-(5-methoxy-1-methyl-1H-indol-3-yl)-1-(toluene-4-sulfonyl)-1H-pyrrolo[2,3-b]pyridine [1.45 g, Reference Example 13(b)] in methanol (100 mL) was treated with potassium hydroxide (5N, 15 mL) then heated at reflux for 2 hours. The reaction mixture was cooled then evaporated. The residue was treated with water (150 mL) and the resulting solid was filtered then dried to give the title compound (0.75 g) as a tan solid, m.p. 226–227° C. MS: 278(MH⁺).

(b) 3-[1-methyl-3-(1H-pyrrolo[2,3-b]pyridin-2-yl)-1H-indol-5-yloxy]-propane-1,2-diol, A2-B1-C9, the product of the combination of group A2 in Table 1 and B1 in Table 2 and C9 in Table 3:

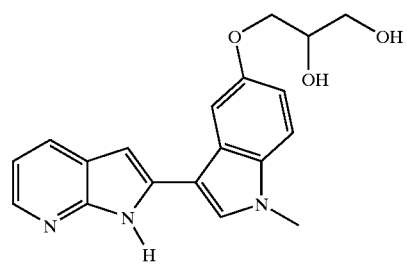

By proceeding in a manner similar to Example 17(a) above but using 3-{1-methyl-3-[1-(toluene-4-sulfonyl)-1H-pyrrolo[2,3-b]pyridin-2-yl]-1H-indol-5-yloxy}-propane-1,2-diol [Reference Example 16], there was prepared 3-[1- methyl-3-(1H-pyrrolo[2,3-b]pyridin-2-yl)-1H-indol-5-yloxy]-propane-1,2-diol as a colourless solid, m.p. 202–203° C. MS: 338(MH⁺).

(c) 3-[1-methyl-3-(H1-pyrrolo[2,3-b]pyridin-2-yl)-1H-indol-5-yloxy]-propan-1-ol, A2-B1-C4, the product of the combination of group A2 in Table 1 and B1 in Table 2 and C4 in Table 3:

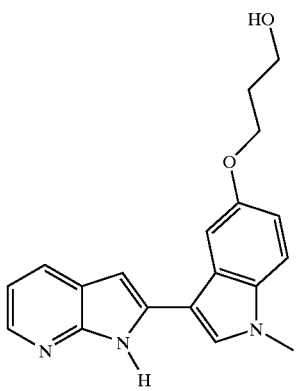

By proceeding in a manner similar to Example 17(a) above but using 3-{1-methyl-3-[1-(toluene-4-sulfonyl)-1H-pyrrolo[2,3-b]pyridin-2-yl]-1H-indol-5-yloxy}-propan-1-ol [Reference Example 17], there was prepared 3-[1-methyl-3-(1H-pyrrolo[2,3-b]pyridin-2-yl)-1H-indol-5-yloxy]-propan-1-ol as a yellow solid, m.p. 192–193° C. MS: 322(MH⁺).

(d) 3-[1-methyl-3-(1H-pyrrolo[2,3-b]pyridin-2-yl)-1H-indol-5-yloxy]-propan-2-ol, A2-B1-C5, the product of the combination of group A2 in Table 1 and B1 in Table 2 and C5 in Table 3:

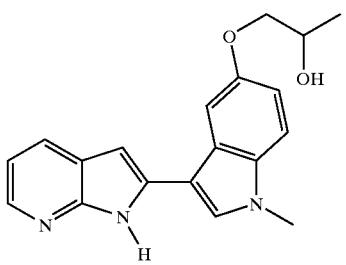

By proceeding in a manner similar to Example 17(a) above but using 3-{1-methyl-3-[1-(toluene-4-sulfonyl)-1H-pyrrolo[2,3-b]pyridin-2-yl]-1H-indol-5-yloxy}-propan-2-ol [Reference Example 17], there was prepared 3-[1-methyl-3-(1H-pyrrolo[2,3-b]pyridin-2-yl)-1H-indol-5-yloxy]-propan-2-ol as a yellow solid, m.p. 201–202° C. MS: 32(MH⁺).

(e) 2-[1-methyl-5-(2H-tetrazol-5-yl)-1H-indol-3-yl]-1H-pyrrolo[2,3-b]pyridine, A2-B1-C36, the product of the combination of group A2 in Table 1 and B1 in Table 2 and C36 in Table 3:

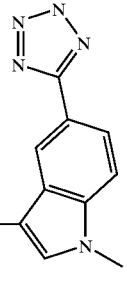

By proceeding in a manner similar to Example 17(a) above but using 2-[1-methyl-5-(1-trimethylstannanyl-1H-tetrazol-5-yl)-1H-indol-3-yl]-1-(toluene-4-sulfonyl)-1H-pyrrolo[2,3-b]pyridine [Reference Example 20], there was prepared 2-[1-methyl-5-(2H-tetrazol-5-yl)-1H-indol-3-yl]-1H-pyrrolo[2,3-b]pyridine as a yellow solid, m.p. 303° C. MS: 316(MH⁺).

(f) 2-[1-methyl-5-(2-methyl-2H-tetrazol-5-yl)-1H-indol-3-yl]-1H-pyrrolo[2,3-b]pyridine, A2-B1-C35, the product of the combination of group A2 in Table 1 and B1 in Table 2 and C35 in Table 3:

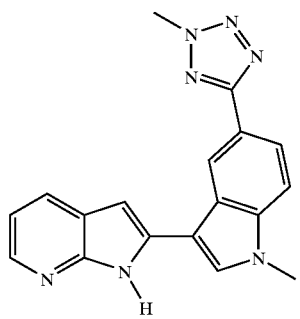

By proceeding in a manner similar to Example 17(a) above but using 2-[1-methyl-5-(2-methyl-2H-tetrazol-5-yl)-1H-indol-3-yl]-1-(toluene-4-sulfonyl)-1H-pyrrolo[2,3-b]pyridine [Reference Example 21], there was prepared 2-[1-methyl-5-(2-methyl-2H-tetrazol-5-yl)-1H-indol-3-yl]-1H-pyrrolo[2,3-b]pyridine as a beige solid, m.p. 299–300° C. (with decomposition). MS: 330(MH⁺).

(g) 2-[1-methyl-5-(1-methyl-1H-tetrazol-5-yl)-1H-indol-3-yl]-1H-pyrrolo[2,3-b]pyridine

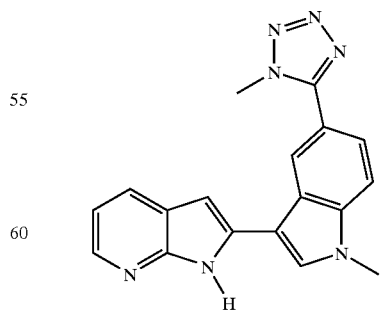

By proceeding in a manner similar to Example 17(a) above but using 2-[1-methyl-5-(1-methyl-1H-tetrazol-5-yl)-1H-indol-3-yl]-1-(toluene-4-sulfonyl)-1H-pyrrolo[2,3-b]

pyridine [Reference Example 21], there was prepared 2-[1-methyl-5-(1-methyl-1H-tetrazol-5-yl)-1H-indol-3-yl]-1H-pyrrolo[2,3-b]pyridine as a beige solid, m.p. 286–289° C. (with decomposition). MS: 330(MH⁺).

(h) 1-[1-methyl-3-(1H-pyrrolo[2,3-b]pyridin-2-yl)-1H-indol-5-yl]-ethanone, A2-B1-C20, the product of the combination of group A2 in Table 1 and B1 in Table 2 and C20 in Table 3:

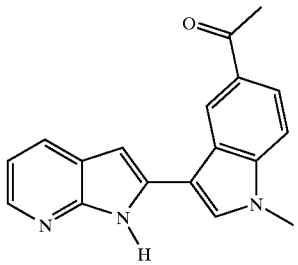

By proceeding in a manner similar to Example 17(a) above but using 1-[1-methyl-3-{(1-(toluene-4-sulfonyl)-1H-pyrrolo[2,3-b]pyridin-2-yl}-1H-indol-5-yl]-ethanone [Reference Example 22], there was prepared 1-[1-methyl-3-(1H-pyrrolo[2,3-b]pyridin-2-yl)-1H-indol-5-yl]-ethanone as a beige solid, m.p. 210° C. (with decomposition). MS: 290(MH⁺).

(i) 2-(5,6-dimethoxy-1-methyl-1H-indol-3-yl)-1H-pyrrolo[2,3-b]pyridine, A2-B17-C1, the product of the combination of group A2 in Table 1 and B17 in Table 2 and C1 in Table 3:

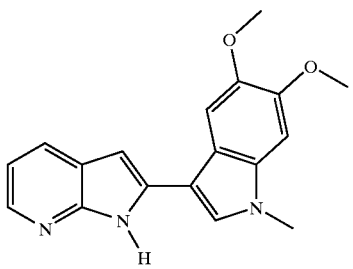

By proceeding in a manner similar to Example 17(a) above but using 2-(5,6-dimethoxy-1-methyl-1H-indol-3-yl)-1-(toluene-4-sulfonyl)-1H-pyrrolo[2,3-b]pyridine [Reference Example 13(d)], there was prepared 2-(5,6-dimethoxy-1-methyl-1H-indol-3-yl)-1H-pyrrolo[2,3-b] pyridine as a beige solid, m.p. 283–285° C. (with decomposition). MS: 308(MH⁺). ¹H NMR [(CD₃)₂SO]: δ☐☐ 11.75 (1H, s), 8.10 (1H, dd), 7.85 (1H, dd), 7.77 (1H, s), 7.41 (1H, s), 7.13 (1H, s), 7.00 (1H, dd), 6.75 (1H, s), 3.85 (3H, s), 3.84 (3H, s), 3.80 (3H, s).

(j) (R)-3-[1-methyl-3-(1H-pyrrolo[2,3-b]pyridin-2-yl)-1H-indol-5-yloxy]-propane-1,2-diol, A2-B1-C80, the product of the combination of group A2 in Table 1 and B1 in Table 2 and C80 in Table 3:

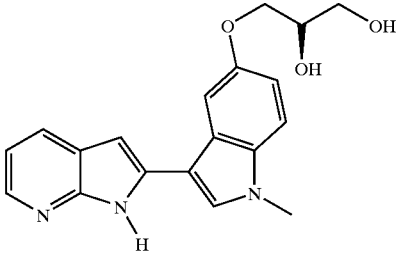

By proceeding in a manner similar to Example 17(a) above but using (R)-3-{1-methyl-3-[i-(toluene-4-sulfonyl)-1H-pyrrolo[2,3-b]pyridin-2-yl]-1H-indol-5-yloxy}-propane-1,2-diol [Reference Example 24(a)], there was prepared (R)-3-[1-methyl-3-(1H-pyrrolo[2,3-b]pyridin-2-yl)-1H-indol-5-yloxy]-propane-1,2-diol as a colourless solid, m.p. 182–185° C. MS: 338(MH⁺).

(k) (S)-3-[1-methyl-3-(1H-pyrrolo[2,3-b]pyridin-2-yl)-1H-indol-5-yloxy]-propane-1,2-diol, A2-B1-C79, the product of the combination of group A2 in Table 1 and B1 in Table 2 and C79 in Table 3:

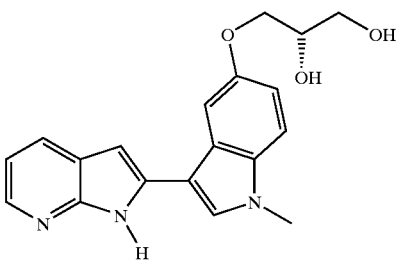

By proceeding in a manner similar to Example 17(a) above but using (S)-3-{1-methyl-3-[1-(toluene-4-sulfonyl)-1H-pyrrolo[2,3-b]pyridin-2-yl]-1H-indol-5-yloxy}-propane-1,2-diol [Reference Example 24(b)], there was prepared (S)-3-[1-methyl-3-(1H-pyrrolo[2,3-b]pyridin-2-yl)-1H-indol-5-yloxy]-propane-1,2-diol as a colourless solid, m.p. 153–156° C. MS: 338(MH⁺).

(l) 2-[5-(2-methoxy-1-methyl-ethoxy)-1-methyl-1H-indol-3-yl]-1H-pyrrolo[2,3-b]pyridine, A2-B1-C17, the product of the combination of group A2 in Table 1 and B1 in Table 2 and C17 in Table 3:

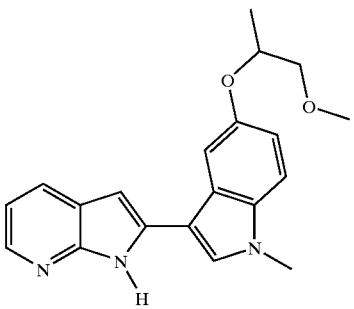

By proceeding in a manner similar to Example 17(a) above but using 2-[5-(2-methoxy-1-methyl-ethoxy)-1-methyl-1H-indol-3-yl]-1-(toluene-4-sulfonyl)-1H-pyrrolo[2,3-b]pyridine [Reference Example 25], there was prepared 2-[5-(2-methoxy-1-methyl-ethoxy)-1-methyl-1H-indol-3- yl]-1H-pyrrolo[2,3-b]pyridine as a yellow solid, m.p. 150–151° C. MS: 336(MH⁺).

(m) 2-[1-methyl-5-(5-methyl-[1,2,4]oxadiazol-3-yl)-1H-indol-3-yl]-1H-pyrrolo[2,3-b]pyridine, A2-B1-C68, the product of the combination of group A2 in Table 1 and B1 in Table 2 and C68 in Table 3:

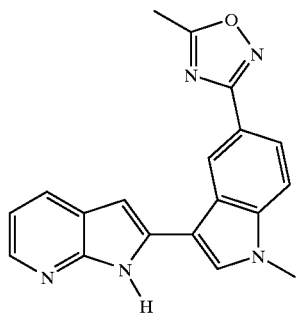

By proceeding in a manner similar to Example 17(a) above but using 2-[1-methyl-5-(5-methyl-[1,2,4]oxadiazol-3-yl)-1H-indol-3-yl]-1-(toluene-4-sulfonyl)-1H-pyrrolo[2,3-b]pyridine [Reference example 27], there was prepared 2-[1-methyl-5-(5-methyl-[1,2,4]oxadiazol-3-yl)-1H-indol-3-yl]-1H-pyrrolo[2,3-b]pyridine as a cream solid, m.p. 290–294° C. MS: 330(MH⁺).

(n) (R)-3-[6-methoxy-1-methyl-3-(1H-pyrrolo[2,3-b]pyridin-2-yl)-1H-indol-5-yloxy]-propane-1,2-diol, A2-B17-C80, the product of the combination of group A2 in Table 1 and B17 in Table 2 and C80 in Table 3:

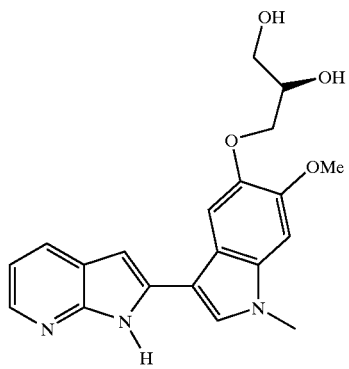

By proceeding in a manner similar to Example 17(a) above but using (R)-3-{6-methoxy-1-methyl-3-[1-(toluene-4-sulfonyl)-1H-pyrrolo[2,3-b] pyridin-2-yl]-1H-indol-5-yloxy}-propane-1,2-diol [Reference Example 24(c)], there was prepared (R)-3-[6-methoxy-1-methyl-3-(1H-pyrrolo[2,3-b]pyridin-2-yl)-1H-indol-5-yloxy]-propane-1,2-diol as a cream solid. MS: 368(MH⁺). HPLC (METHOD A): $R_T$=5.81 minutes.

(o) 6-methoxy-1-methyl-3-(1H-pyrrolo[2,3-b]pyridin-2-yl)-1H-indol-5-ol, A2-B17-C10, the product of the combination of group A2 in Table 1 and B17 in Table 2 and C10 in Table 3:

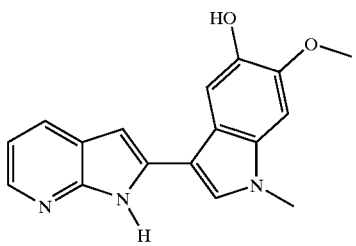

By proceeding in a manner similar to Example 17(a) above but using 2-(5-hydroxy-6-methoxy-1-methyl-1H-indol-3-yl)-1-(toluene-4-sulfonyl)-1H-pyrrolo[2,3-b] pyridine [Reference Example 28], there was prepared 6-methoxy-1-methyl-3-(1H-pyrrolo[2,3-b]pyridin-2-yl)-1H-indol-5-ol as a brown solid. MS: 294(MH⁺). HPLC (METHOD A): $R_T$=6.37 minutes.

(p) 2-(5-methoxy-1-methyl-1H-indol-3-yl)-4-phenyl-1H-pyrrolo[2,3-b]pyridine, A13-B1-C1, the product of the combination of group A13 in Table 1 and B1 in Table 2 and C1 in Table 3:

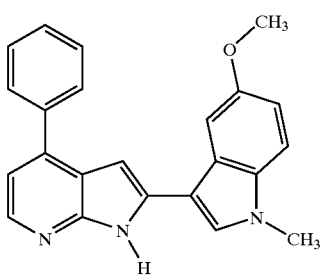

By proceeding in a similar manner to Example 17(a) but using 2-(5-methoxy-1-methyl-1H-indol-3-yl)-4-phenyl-1-(toluene-4-sulfonyl)-1H-pyrrolo[2,3-b]pyridine [Reference Example 2(m)] there was prepared 2-(5-methoxy-1-methyl-1H-indol-3-yl)-4-phenyl-1H-pyrrolo[2,3-b]pyridine as a yellow solid. ¹H NMR [(CD₃)₂SO]; δ 11.98 (1H, s); 8.21 (1H, d, J=3.5 Hz); 7.94 (1H, s); 7.86 (2H, d, J=8.8 Hz); 7.59 (2H, t, J=8.8 Hz); 7.47 (2H, m); 7.39 (1H, d, J=1.9 Hz); 7.17(1H, d, J=3.5 Hz); 6.93 (1H, dd, J=8.8, 1.9 Hz); 6.82 (1H, s); 3.84 (3H, s); 3.82 (3H, s).

(q) 2-[1-methyl-5-(pyridin-4-yl)-1H-indol-3-yl]-4-1H-pyrrolo[2,3-b]pyridine, A2-B1-C37, the product of the combination of group A2 in Table 1 and B1 in Table 2 and C37 in Table 3:

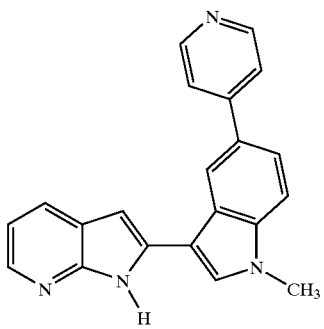

By proceeding in a similar manner to Example 17(a) but using 2-[5-(pyridin-4-yl)-1-methyl-1H-indol-3-yl]-1-

(toluene-4-sulfonyl)-1H-pyrrolo[2,3-b]pyridine (Reference Example 60) there was prepared 2-[1-methyl-5-(pyridin-4-yl)-1H-indol-3-yl]-4-1H-pyrrolo[2,3-b]pyridine as a yellow solid, m.p. 325–330° C. ¹H NMR [(CD₃)₂SO]; δ 8.65 (2H, d, J=7.2 Hz); 8.20 (1H, s); 8.15 (1H, m); 8.04 (1H, s); 7.88 (3H, m); 7.72 (2H, m); 7.03 (1H, t, J=7.2 Hz); 6.96 (1H, s); 3.93 (3H, s).

(r) 2-(5-methoxy-1-methyl-1H-indol-3-yl)-1H-pyrrolo[2,3-b]pyridine-4-carbonitrile, A3-B1-C1, the product of the combination of group A31 in Table 1 and B1 in Table 2 and C1 in Table 3:

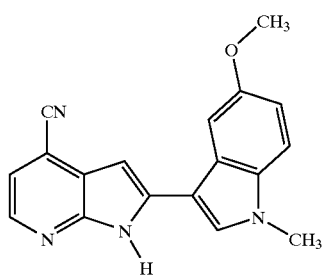

By proceeding in a similar manner to Example 17(a) above but using 2-(5-methoxy-1-methyl-1H-indol-3-yl)-1-(toluene-4-sulfonyl)-1H-pyrrolo[2,3-b]pyridine-4-carbonitrile [Reference Example 13(h)] there was prepared 2-(5-methoxy-1-methyl-1H-indol-3-yl)-1H-pyrrolo[2,3-b]pyridine-4-carbonitrile as an orange solid, m.p. 304–305° C. ¹H NMR [(CD₃)₂SO]: δ 12.60 (1H, s); 8.24 (1H, s); 8.07 (1H, s); 7.50 (3H, m); 6.96 (1H, d, J=8.6 Hz); 6.88 (1H, s); 3.91 (3H, s); 3.86 (3H, s).

(s) 4-chloro-2-(5-methoxy-1-methyl-1H-indol-3-yl)-1H-pyrrolo[2,3-b]pyridine, A28-B1-C1, the product of the combination of group A28 in Table 1 and B1 in Table 2 and C1 in Table 3:

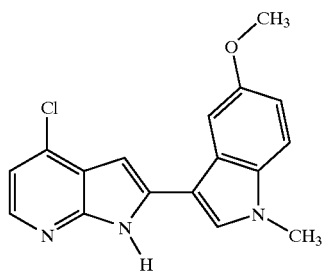

By proceeding in a similar manner to Example 17(a) above but using 4-chloro-2-(5-methoxy-1-methyl-1H-indol-3-yl)-1-(toluene-4-sulfonyl)-1H-pyrrolo[2,3-b]pyridine [Reference Example 13(i)] there was prepared 4-chloro-2-(5-methoxy-1-methyl-1H-indol-3-yl)-1H-pyrrolo[2,3-b]pyridine as a tan solid, m.p. 250–252° C. MS: 312(MH⁺).

(t) 2-(5-methoxy-1-methyl-1H-indol-3-yl)-4-(pyridin-3-yl)-1H-pyrrolo[2,3-b]pyridine, A15-B1-C1, the product of the combination of group A15 in Table 1 and B1 in Table 2 and C1 in Table 3:

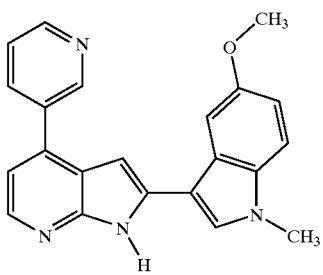

By proceeding in a similar manner to Example 17(a) above but using 2-(5-methoxy-1-methyl-1H-indol-3-yl)₄-(pyridin-3-yl)-1-(toluene-4-sulfonyl)-1H-pyrrolo[2,3-b]pyridine [Reference Example 2(o)] there was prepared 2-(5-methoxy-1-methyl-1H-indol-3-yl)₄-(pyridin-3-yl)-1H-pyrrolo[2,3-b]pyridine as a yellow solid, m.p. 248–249° C. MS: 355(MH⁺).

(u) 2-(5-methoxy-1-methyl-1H-indol-2-yl)-1H-pyrrolo[2,3-b]pyridine, A2-B20-C₁, the product of the combination of group A2 in Table 1 and B20 in Table 2 and C1 in Table 3:

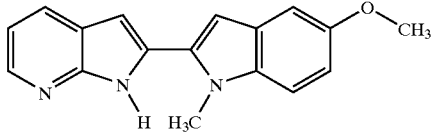

By proceeding in a similar manner to Example 17(a) above but using 2-(5-methoxy-1-methyl-1H-indol-2-yl)-1-(toluene-4-sulfonyl)-1H-pyrrolo[2,3-b]pyridine [Reference Example 2(p)], and recrystallising the reaction product from ethyl acetate then washing with diethyl ether, there was prepared 2-(5-methoxy-1-methyl-1H-indol-2-yl)-1H-pyrrolo[2,3-b]pyridine as a yellow crystalline solid, m.p. 234–235° C. ¹H-NMR {(CD₃)₂SO}: δ 12.15–12.10 (s, 1H); 8.275–8.225 (dd, 1H); 8.00–7.975 (dd, 1H); 7.475–7.45 (d, 1H); 7.125–7.075 (m, 2H); 6.925–6.90 (s, 1H); 6.875–6.825 (m, 2H); 3.95–3.90 (s, 3H); 3.80–3.775 (s, 3H).

(v) 2-(5-methoxy-1-methyl-1H-indol-3-yl)-3-methyl-1H-pyrrolo[2,3-b]pyridine, A84-B1-C₁, the product of the combination of group A84 in table 1 and B1 in table 2 and C1 in table 3:

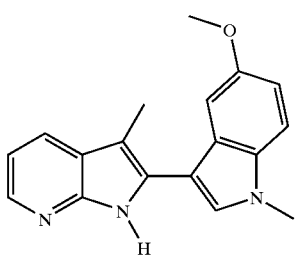

By proceeding in a manner similar to Example 17(a) above but using 2-(5-methoxy-1-methyl-1H-indol-3-yl)-3-methyl-1-(toluene-4-sulfonyl)-1H-pyrrolo[2,3-b]pyridine [Reference Example 13(k)], there was prepared 2-(5-methoxy-1-methyl-1H-indol-3-yl)-3-methyl-1H-pyrrolo[2,3-b]pyridine as a beige solid, m.p. 237° C. [Elemental analysis: C, 74.15; H, 6.10; N, 14.54%. Calculated for C₁₈H₁₇N₃O:—C, 74.21; H, 5.88; N, 14.42%].

(w) 2-(1H-pyrrol-2-yl)-1H-pyrrolo[2,3-b]pyridine, A2-B115, the product of the combination of group A2 in table 1 and B115 in table 2:

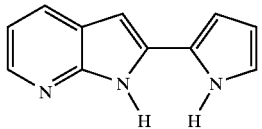

By proceeding in a manner similar to Example 17(a) above but using 2-(1H-pyrrol-2-yl)-1-(toluene-4-sulfonyl)-1H-pyrrolo[2,3-b]pyridine [Reference Example 67(g)], there was prepared 2-(1H-pyrrol-2-yl)-1H-pyrrolo[2,3-b]pyridine as a yellow solid, m.p. 240° C. (with decomposition). [Elemental analysis:—C, 72.11; H, 4.95; N, 22.94%. Calculated for $C_{11}H_9N_3$—C, 72.33; H, 4.97; N, 21.85%]. MS: EI (70 eV); m/z =183 M+·(100%); 155 (30%).

(x) 2-(1-methyl-1H-pyrrol-2-yl)-1H-pyrrolo[2,3-b]pyridine, A2-B53, the product of the combination of group A2 in table 1 and B53 in table 2:

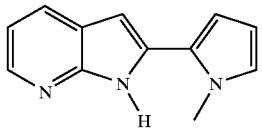

By proceeding in a manner similar to Example 17(a) but using 2-(1-methyl-1H-pyrrol-2-yl)-1-(toluene-4-sulfonyl)-1H-pyrrolo[2,3-b]pyridine [Reference Example 13(1)], there was prepared 2-(1-methyl-1H-pyrrol-2-yl)-1H-pyrrolo[2,3-b]pyridine as a white solid, m.p. 183° C. MS: EI (70 eV); m/z=197 M+·(100%).

(y) 4-chloro-2-(5-methoxy-1H-indol-3-yl)-1H-pyrrolo[2,3-b]pyridine A28-B2-C1, the product of in Table 1 and B2 in Table 2 and C1 in Table 3:

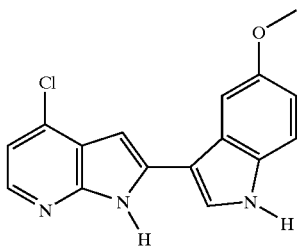

By proceeding in a manner similar to Example 17(a) above but using 4-chloro-2-(5-methoxy-1H-indol-3-yl)-1-(toluene-4-sulfonyl)-1H-pyrrolo{2,3-b]pyridine [Reference Example 12(h)], there was prepared 4-chloro-2-(5-methoxy-1H-indol-3-yl)-1H-pyrrolo[2,3-b]pyridine as a solid. LC-MS: METHOD D: $R_T$=2.76 minutes, 298(MH+).

(z) 5-methoxy-1-methyl-3-(1H-pyrrolo[2,3-b]pyridin-2-yl)-1H-indol-6-ol, A2-B119-$C_1$, the product of the combination of group A2 in Table 1 and B119 in Table 2 and C1 in Table 3:

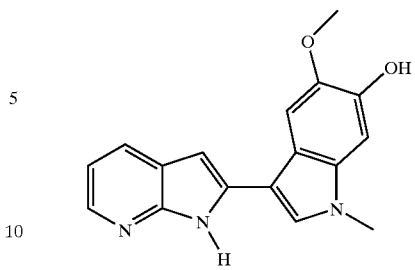

By proceeding in a manner similar to Example 17(a) above but using 2-(6-hydroxy-5-methoxy-1-methyl-1H-indol-3-yl)-1-(toluene-4-sulfonyl)-1H-pyrrolo[2,3-b]pyridine [Reference Example 83], there was prepared 5-methoxy-1-methyl-3-(1H-pyrrolo[2,3-b]pyridin-2-yl)-1H-indol-6-ol as an off-white solid, m.p. 250° C. MS: EI (70 eV); m/z=293 M+·(100%).

(aa) 2-(6-isopropoxy-5-methoxy-1-methyl-1H-indol-3-yl)-1H-pyrrolo[2,3-b]pyridine, A2-B120-C1 the product of the combination of group A2 in Table 1 and B120 in Table 2 and C1 in Table 3:

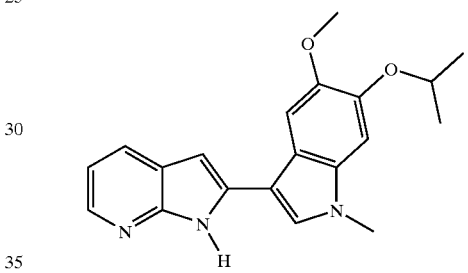

By proceeding in a manner similar to Example 17(a) above but using 2-(6-isopropoxy-5-methoxy-1-methyl-1H-indol-3-yl)-1-(toluene-4-sulfonyl)-1H-pyrrolo[2,3-b]pyridine [Reference Example 84], there was prepared 2-(6-isopropoxy-5-methoxy-1-methyl-1H-indol-3-yl)-1H-pyrrolo[2,3-b]pyridine as an off-white solid, m.p. 216° C. MS: EI (70 eV); m/z=335 M+(100%); 293 (90%); 278 (35%).

(ab) 2-[5,6-dimethoxy-1-(2-morpholin-4-yl-ethyl)-1H-indol-3-yl]-1H-pyrrolo[2,3-b]pyridine, A2-B122-C1, the product of the combination of group A2 in Table 1 and B122 in Table 2 and C1 in Table 3:

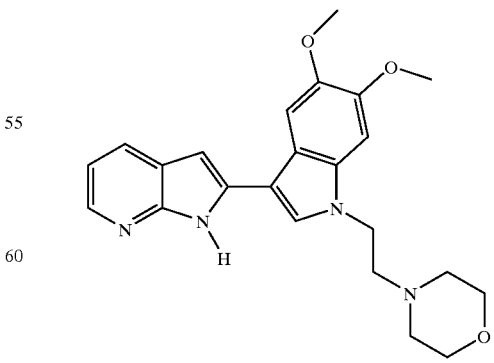

By proceeding in a manner similar to Example 17(a) above but using 2-[5,6-dimethoxy-1-(2-morpholin-4-ylethyl)-1H-indol-3-yl]-1-(toluene-4-sulfonyl)-1H-pyrrolo[2,3-b]pyridine [Reference Example 13(r)], there was prepared 2-[5,6-dimethoxy-1-(2-morpholin-4-yl-ethyl)-1H-indol-3-yl]-1H-pyrrolo[2,3-b]pyridine as pale pink solid, m.p. 218° C. MS: ESI; m/z=407 MH+.

EXAMPLE 18

1-Methyl-3-(1H-pyrrolo[2,3-b]pyridin-2-yl)-1H-indol-5-ylamine, A2-B1-C63, the product of the combination of group A2 in Table 1 and B1 in Table 2 and C63 in Table 3:

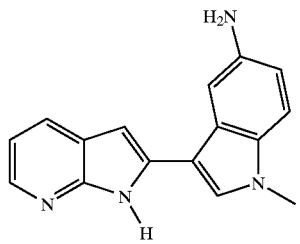

A stirred solution of [1-methyl-3-(1H-pyrrolo[2,3-b]pyridin-2-yl)-1H-indol-5-yl]-carbamic acid, tert-butyl ester [0.2 g, Reference Example 30] in dichloromethane was treated with trifluoroacetic acid (2 mL). After stirring at ambient temperature for 16 hours the reaction mixture was evaporated. The residue was suspended in saturated sodium bicarbonate solution (10 mL) and the resulting solid was filtered then dried to give the title compound as a yellow solid, m.p. 247–248° C. MS: 263(MH+).

EXAMPLE 19

(a) N-[1-Methyl-3-(1H-pyrrolo[2,3-b]pyridin-2-yl)-1H-indol-5-yl]-methanesulfonamide, A2-B1-C62, the product of the combination of group A2 in Table 1 and B1 in Table 2 and C62 in Table 3:

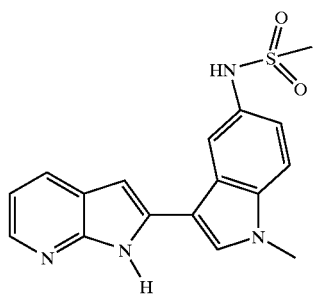

A solution of 1-methyl-3-(1H-pyrrolo[2,3-b]pyridin-2-yl)-1H-indol-5-ylamine [52.4 mg, Example 18] in dichloromethane (5 mL) was treated with triethylamine (30 μl) followed by methane sulfonyl chloride (17 μl). After stirring at ambient temperature for 16 hours the reaction mixture was diluted with dichloromethane (10 mL), then washed with water (10 mL), then washed with brine (10 mL), then dried over magnesium sulfate and then evaporated. The residual solid was triturated with diethyl ether to give the title compound as a yellow solid, m.p. 223–224° C. MS: 341(MH+).

(b) N-[1-methyl-3-(1H-pyrrolo[2,3-b]pyridin-2-yl)-1H-indol-5-yl]-acetamide, A2-B1-C45, the product of the combination of group A2 in Table 1 and B1 in Table 2 and C45 in Table 3:

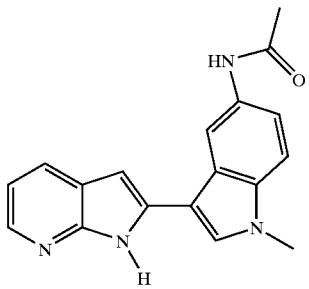

By proceeding in a manner similar to Example 19(a) above but using acetyl chloride, there was prepared N-[1-methyl-3-(1H-pyrrolo[2,3-b]pyridin-2-yl)-1H-indol-5-yl]-acetamide as a yellow solid, m.p. 220–221° C. MS: 305 (MH+).

(c) N-{1-methyl-3-(1H-pyrrolo[2,3-b]pyridin-2-yl)-1H-indol-5-yl]methyl}thien-2-yl-sulfonamide, A2-B1-C69, the product of the combination of group A2 in Table 1 and B1 in Table 2 and C69 in Table 3:

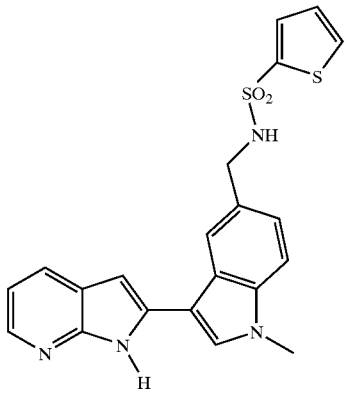

By proceeding in a manner similar to Example 19(a) above but using [3-(1H-pyrrolo[2,3-b]pyridin-2-yl)-1-methyl-1H-indol-5-yl]-methylamine [Example 52] and 2-thienyl sulfonyl chloride there was prepared N-{1-methyl-3-(1H-pyrrolo[2,3-b]pyridin-2-yl)-1H-indol-5-yl]methyl}thien-2-ylsulfonamide as a pale orange solid, m.p. 226–227° C.

EXAMPLE 20

(a) {1-[5-(1-Hydroxymethyl-cyclobutoxy)-3-(1H-pyrrolo[2,3-b]pyridin-2-yl)-indol—yl]-cyclobutyl}-methanol, A2-B13-C12, the product of the combination of group A2 in Table 1 and B13 in Table 2 and C12 in Table 3:

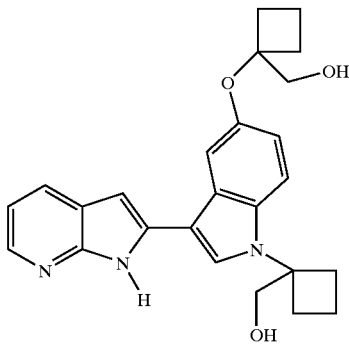

A stirred solution of 1-{1-(cyclobutanecarboxylic acid ethyl ester)-3-[1-(toluene-4-sulfonyl)-1H-pyrrolo[2,3-b]

pyridin-2-yl]-1H-indol-5-yloxy}-cyclobutanecarboxylic acid ethyl ester [0.54 g, Reference Example 23(d)] in tetrahydrofuran (50 mL) at 0° C. under nitrogen was treated dropwise with a solution of lithium tetrahydridoaluminate in tetrahydrofuran (4.9 mL, 1.0M). After stirring for 2 hours at 0° C. the reaction mixture was stood at ambient temperature for a further 18 hours then treated dropwise with water (20 mL) and then filtered through Hyflo Super Cel®, diatomaceous earth. The filter pad was washed with ethyl acetate (20 mL), the two-phase filtrate was separated and the aqueous layer was extracted twice with ethyl acetate (25 mL). The combined organic phases were washed with brine (25 mL), then dried over magnesium sulfate and then evaporated. The residue was triturated with diethyl ether and the insoluble material was subjected to flash column chromatography on silica eluting with a mixture of dichloromethane and methanol (19:1, v/v) to give the title compound (0.19 g) as a cream solid, m.p. 165–166° C. MS: 418(MH⁺).

(b) {1-[1-methyl-3-(5H-pyrrolo[2,3-b]pyrazin-6-yl)-1H-indol-5-yloxy]-cyclobutyl}-methanol, A1-B1-C13, the product of the combination of group A1 in Table 1 and B1 in Table 2 and C13 in Table 3:

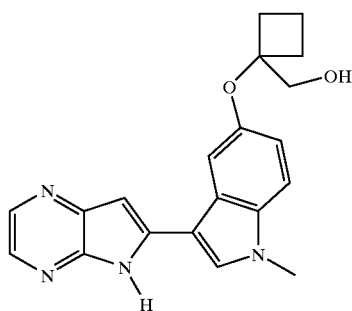

By proceeding in a similar manner to Example 20(a) above but using {1-[1-methyl-3-(5H-pyrrolo[2,3-b]pyrazin-6-yl)-1H-indol-5-yloxy]-cyclobutylcarboxylic acid ethyl ester [Reference Example 15(e)] there was prepared {1-[1-methyl-3-(5H-pyrrolo[2,3-b]pyrazin-6-yl)-1H-indol-5-yloxy]-cyclobutyl}-methanol as a brown solid, m.p. 267–271° C. MS: 349(MH⁺).

EXAMPLE 21

(a) 2-(5-Methoxy-1-methyl-1H-indol-3-yl)-1H-pyrrolo[2,3-b]pyridine methanesulfonate

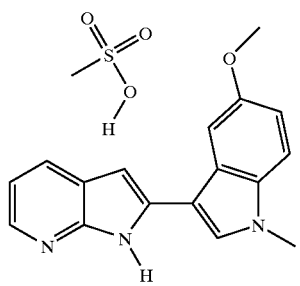

Methane sulfonic acid (70 µl) was added to a solution of 2-(5-methoxy-1-methyl-1H-indol-3-yl)-1H-pyrrolo[2,3-b]pyridine [300 mg, Example 17(a)] in tetrahydrofuran (20 mL) at ambient temperature. The mixture was stirred for 45 minutes and the resultant precipitate isolated by filtration to give the title compound (390 mg), as a yellow solid, m.p. 256–257° C. [Elemental analysis: C, 57.60; H, 4.77; N, 10.90%. Calculated for $C_{13}H_{11}N_3O$: C, 57.90; H, 5.13; N, 11.25%].

(b) 6-(5-methoxy-1-methyl-1H-indol-3-yl)-5H-pyrrolo[2,3-b]pyrazine methanesulfonate

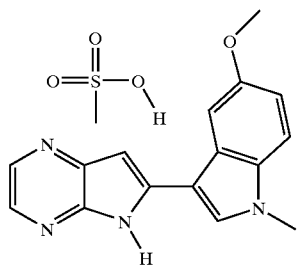

By proceeding in a manner similar to Example 21(a) above but using 6-(5-methoxy-1-methyl-1H-indol-3-yl)-5H-pyrrolo[2,3-b]pyrazine [Example 1(a)], there was prepared 6-(5-methoxy-1-methyl-1H-indol-3-yl)-5H-pyrrolo[2,3-b]pyrazine methanesulfonate as a yellow solid, m.p. 245–250° C. MS: 279(MH⁺).

(c) 2-[5-methoxy-3-(1H-pyrrolo[2,3-b]pyridin-2-yl)-indol-1-yl]-1-morpholin-4-yl-ethanone methanesulfonate

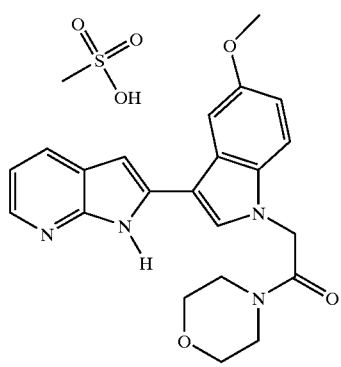

By proceeding in a manner similar to Example 21(a) above but using 2-[5-methoxy-3-(1H-pyrrolo[2,3-b]pyridin-2-yl)-indol-1-yl]-1-morpholin-4-yl-ethanone [Example 14(a)], there was prepared 2-[5-methoxy-3-(1H-pyrrolo[2,3-b]pyridin-2-yl)-indol-1-yl]-1-morpholin-4-yl-ethanone methanesulfonate as a yellow solid, m.p. 214–215° C. MS: 391(MH⁺).

(d) 1-methyl-3-(1H-pyrrolo[2,3-b]pyridin-2-yl)-1H-indole-5-carboxylic acid (2-hydroxy-1,1-dimethyl-ethyl)-amide Methanesulfonate

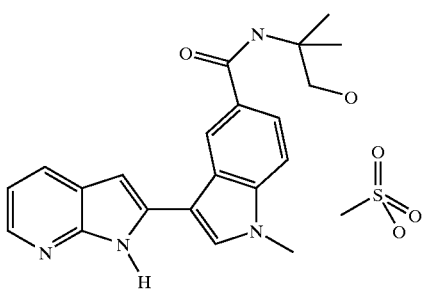

By proceeding in a manner similar to Example 21(a) above but using 1-methyl-3-(1H-pyrrolo[2,3-b]pyridin-2-yl)-1H-indole-5-carboxylic acid (2-hydroxy-1,1-dimethyl-ethyl)-amide [Example 14(m)], there was prepared 1-methyl-3-(1H-pyrrolo[2,3-b]pyridin-2-yl)-1H-indole-5-carboxylic acid (2-hydroxy-1,1-dimethyl-ethyl)-amide methanesulfonate as a yellow solid, m.p. 190–192° C. MS: 363(MH⁺).

(e) 6-[5-(2-hydroxy-1,1-dimethylethylcarbamoyl)-1-methyl-1H-indol-3-yl]-5H-pyrrolo[2,3-b]pyrazine Methanesulfonate

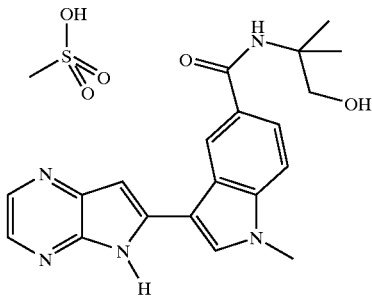

By proceeding in a similar manner to Example 21(a) but using 1-methyl-3-(5H-pyrrolo[2,3-b]pyrazin-6-yl)-1H-indole-5-carboxylic acid (2-hydroxy-1,1-dimethyl-ethyl)-amide [Example 14(s)] there was prepared 6-[5-(2-hydroxy-1,1-dimethylethylcarbamoyl)-1-methyl-1H-indol-3-yl]-5H-pyrrolo[2,3-b]pyrazine methanesulfonate as a brown solid, m.p. 240° C. (with decomposition). ¹H NMR [(CD₃)₂SO]: δ 8.50 (1H, s); 8.37 (1H, d, J=3.0 Hz); 8.32 (1H, d, J=3.0 Hz); 8.29 (1H, s); 7.82 (1H, d, J=8.2 Hz); 7.77 (1H, s); 7.64 (1H, d, J=8.2 Hz); 7.20 (1H, s); 3.95 (3H, s); 3.59 (2H, s); 2.37 (3H, s); 1.38 (6H, s).

(f) 2-[5-methoxy-3-(5H-pyrrolo[2,3-b]pyrazin-6-yl)-indol-1-yl]-1-morpholin-4-yl-ethanone Methanesulfonate

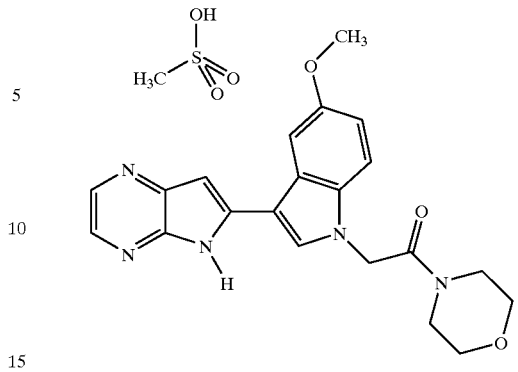

By proceeding in a similar manner to Example 21(a) but using 2-[5-methoxy-3-(5H-pyrrolo[2,3-b]pyrazin-6-yl)-indol-1-yl]-1-morpholin-4-yl-ethanone (Example 12) there was prepared 2-[5-methoxy-3-(5H-pyrrolo[2,3-b]pyrazin-6-yl)-indol-1-yl]-1-morpholin-4-yl-ethanone methanesulfonate, m.p. 250° C. ¹HNMR [(CD₃)₂SO]: δ 8.32 (1H, s); 8.22 (1H, s); 8.11 91H, s); 7.50 (1H, s); 7.44 (1H, d, J=8.8 Hz); 7.04 (1H, s); 6.93 91H, d, J=8.8 Hz); 5.36 (2H, s); 3.90 (3H, s); 3.61 (8H, m); 2.31 (3H, s).

(g) 2-(5,6-dimethoxy-1-methyl-1H-indol-3-yl)-1H-pyrrolo[2,3-b]pyridine Methanesulfonate

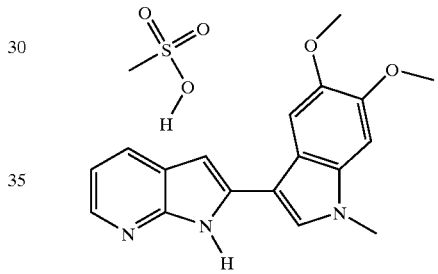

By proceeding in a similar manner to Example 21(a) but using 2-(5,6-dimethoxy-1-methyl-1H-indol-3-yl)-1H-pyrrolo[2,3-b]pyridine [Example 17(i)] there was prepared 2-(5,6-dimethoxy-1-methyl-1H-indol-3-yl)-1H-pyrrolo[2,3-b]pyridine methanesulfonate. ¹H NMR [(CD₃)₂SO]: δ 8.25 (2H, m), 7.90 (1H, s), 7.42 (1H, s), 7.33 (1H, dd), 7.16 (1H, s), 7.04 (1H, s), 3.90 (3H, s), 3.85 (3H, s), 3.84 (3H, s), 2.36 (3H, s).

EXAMPLE 22

5-[6-(4-tert-Butylphenyl-5H-pyrrolo[2,3-b]pyrazin-7-yl]ethyl-2H-tetrazole, A35-B55, the product of the combination of group A35 in Table 1 and B55 in Table 2:

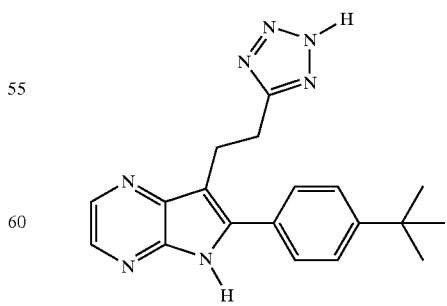

To a stirred solution of 3-[6-(4-tert-butylphenyl-5H-pyrrolo[2,3-b]pyrazin-7-yl]-propionitrile [0.2 g, Example 23] in toluene (25 mL), at room temperature under nitrogen, was added azidotributyltin (0.61 mL). The reaction mixture was heated at 117° C. After 24 hours, an additional aliquot of azidotributyltin (0.21 mL) was added and the reaction mixture was heated for a further 24 hours. The reaction mixture was quenched with glacial acetic acid (44 mL) and stirred for 15 minutes before partitioning between water and ethyl acetate. The two layers were separated and the organic fraction was washed with water, dried over magnesium sulfate and then evaporated. The residue was subjected to flash column chromatography on silica eluting with ethyl acetate to give the title compound (0.06 g) as an off-white solid. MS: 348(MH+). HPLC (Method B): $R_T$=1.64 minutes.

EXAMPLE 23

3-[6-(4-tert-Butylphenyl-5H-pyrrolo[2,3-b]pyrazin-7-yl]-2H-propionitrile, A45-B55, the product of the combination of group A45 in Table 1 and B55 in Table 2:

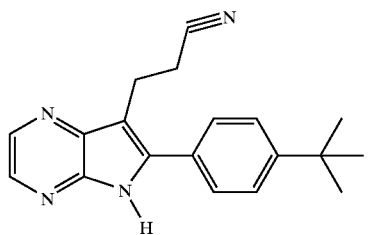

To a solution of 3-[6-(4-tert-butylphenyl-5H-pyrrolo[2,3-b]pyrazin-7-yl]-propionamide [0.1 g, Example 24] in tetrahydrofuran (15 mL) at room temperature was added triethylamine (1 mL) and phosphorus oxychloride (1 mL). The reaction mixture was heated at reflux for 30 minutes then poured into a 10% solution of sodium hydrogen carbonate. The mixture was extracted with ethyl acetate and the combined organic extracts were washed with water, dried over magnesium sulfate and evaporated. The residue was subjected to flash column chromatography on silica eluting with first a mixture of ethyl acetate and pentane (1:1, v/v) then with ethyl acetate to give the title compound as a white solid. m.p. 215–216° C. MS: 305(MH+).

EXAMPLE 24

3-[6-(4-tert-Butylphenyl-5H-pyrrolo[2,3-b]pyrazin-7-yl]-propionamide, A32-B55, the product of the combination of group A32 in Table 1 and B55 in Table 2:

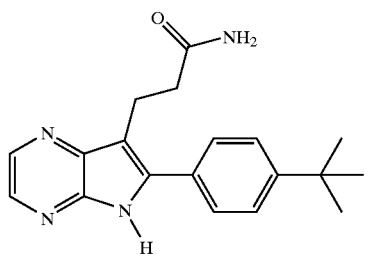

To a solution of 3-[6-(4-tert-butylphenyl-5H-pyrrolo[2,3-b]pyrazin-7-yl]-propionic acid [0.51 g, Example 25(a)] in dimethylformamide (15 mL) at room temperature under nitrogen was added O-benzotriazol-1-yl-N,N,N',N',-tetramethyluronium tetrafluoroborate (0.54 g) and triethylamine (0.22 mL). Ammonia gas was bubbled through the solution for 5 minutes and the stoppered reaction mixture was allowed to stand at room temperature overnight. The solution was then poured into water and extracted with ethyl acetate. The organic extracts were washed with water and dried over sodium sulfate to afford the title compound as a white solid without further purification. MS: 323(MH+). HPLC (Method B): $R_T$=4.49 minutes.

EXAMPLE 25

(a) 3-[6-(4-tert-Butylphenyl-5H-pyrrolo[2,3-b]pyrazin-7-yl]-propionic acid, A31-B55, the product of the combination of group A31 in Table 1 and B55 in Table 2:

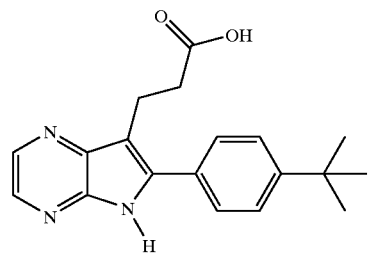

To a solution of dimethyl 3-[6-(4-tert-butylphenyl-5H-pyrrolo[2,3-b]pyrazin-7-yl]-propionic-1,1-diacid 1,1-dicarboxylate [0.4 g, Reference Example 44(a)] in methanol (20 mL) was added 1N sodium hydroxide solution (4 mL). The reaction mixture was heated at 50° C. for 6 hours then allowed to stand at room temperature overnight. The solvent was removed by evaporation, 6N sulfuric acid solution (50 mL) was added and the reaction mixture refluxed for 2 hours. After cooling, the solution was basified to pH 4 with 1N sodium hydroxide solution and the resultant precipitate isolated by filtration and dried under vacuum to afford the title compound (0.26 g) as an off-white solid without further purification, m.p. 274–275° C. MS: 324(MH+).

(b) 3-{6-[4-(1-methyl)ethoxyphenyl]-5H-pyrrolo[2,3-b]pyrazin-7-yl}propionic acid, A31-B63, the product of the combination of group A31 in Table 1 and B63 in Table 2:

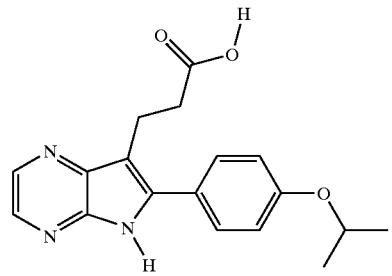

By proceeding in a manner similar to Example 25(a) but using dimethyl 3-[6-(4-(1-methyl)ethoxyphenyl)-5H-pyrrolo[2,3-b]pyrazin-7-yl]-propionic 1,1-diacid 1,1-dicarboxylate [Reference Example 44(b)], there was prepared 3-{6-[4-(1-methyl)ethoxyphenyl]-5H-pyrrolo[2,3-b]pyrazin-7-yl}propionic acid as a yellow solid. MS: 326 (MH+). HPLC (Method C): $R_T$=1.56 minutes.

(c) 3-[6-(4-fluorophenyl)-5H-pyrrolo[2,3-b]pyrazin-7-yl]propionic acid, A31-B89, the product of the combination of group A31 in Table 1 and B89 in Table 2:

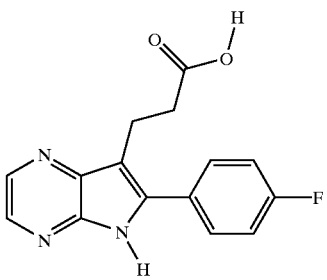

By proceeding in a manner similar to Example 25(a) but using dimethyl 3-[6-(4-fluorophenyl)-5H-pyrrolo[2,3-b]pyrazin-7-yl]-propionic 1,1-diacid 1,1-dicarboxylate [Reference Example 44(c)], there was prepared 3-[6-(4-fluorophenyl)-5H-pyrrolo[2,3-b]pyrazin-7-yl]propionic acid as an off-white solid. $^1$H NMR [(CD$_3$)$_2$SO]: δ 12.3 (s, 1H) 8.4 (d, 1H), 8.2 (d, 1H), 7.8 (d, 2H), 7.4 (d, 2H), 3.1 (t, 2H), 2.7 (t, 2H). MS: 285(MH$^+$).

(d) 3-[6-(4-methoxyphenyl)-5H-pyrrolo[2,3-b]pyrazin-7-yl]propionic acid, A31-B77, the product of the combination of group A31 in Table 1 and B77 in Table 2:

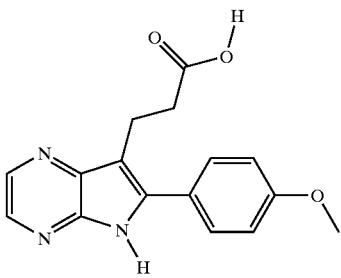

By proceeding in a manner similar to Example 25(a) above but using dimethyl 3-[6-(4-methoxyphenyl)-5H-pyrrolo[2,3-b]pyrazin-7-yl]-propionic 1,1-diacid 1,1-dicarboxylate [Reference Example 44(d)], there was prepared 3-[6-(4-methoxyphenyl)-5H-pyrrolo[2,3-b]pyrazin-7-yl]propionic acid as an off-white solid. $^1$H NMR [(CD$_3$)$_2$SO]: δ 12.0 (s, 1H) 8.3 (d, 1H), 8.2 (d, 1H), 7.7 (d, 2H), 7.1 (d, 2H), 3.8 (s, 3H), 3.05 (t, 2H), 2.6 (t, 2H). MS: 297(MH$^+$).

EXAMPLE 26
3-[6-(4-tert-Butyl-phenyl)-5H-pyrrolo[2,3-b]pyrazin-7-yl]-propan-1-ol, A30-B55, the product of the combination of group A301 in Table 1 and B55 in Table 2:

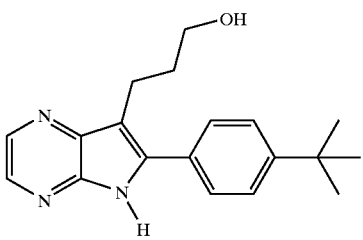

To a mixture of 4N hydrochloric acid in dioxane and methanol (5 mL 1:1, v/v) was added 3-[6-(4-tert-butylphenyl-5H-pyrrolo[2,3-b]pyrazin-7-yl]-propionic acid [0.02 g, Example 25(a)] and the reaction mixture was allowed to stir at room temperature overnight. After evaporation, the residue was suspended between sodium hydrogen carbonate solution (10%) and ethyl acetate. The phases were separated and the organic fraction was washed with water and dried over sodium sulfate. After evaporation, the residue was suspended in diethyl ether (50 mL). Lithium aluminium hydride (0.12 mL of 1M solution in diethyl ether) was added and the suspension heated to reflux for 2 hour. An additional aliquot of lithium aluminium hydride (0.12 mL of 1M solution in diethyl ether) was added and the reaction mixture was heated for a further 1 hour. The reaction was quenched with a cold aqueous (10%) solution of potassium hydrogen sulfate added dropwise until hydrogen evolution ceased, diluted with water and extracted with ether. The combined organic fractions were washed with water, dried over sodium sulfate and subjected to flash column chromatography on silica eluting with ethyl acetate to give the title compound (0.035 g) as an off-white solid, m.p. 187–189° C. MS: 310(MH$^+$).

EXAMPLE 27
[2-Methoxy-5-(5H-pyrrolo[2,3-b]pyrazin-6-yl)-phenoxy]acetic Acid Ethyl Ester, A1-B68, the product of the Combination of Group A1 in Table 1 and B68 in Table 2:

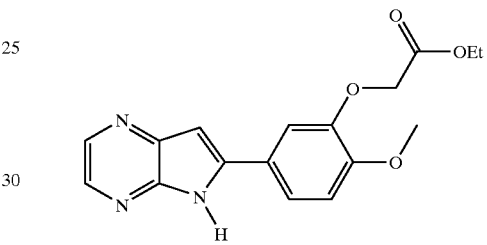

To a solution of 2-methoxy-5-(5H-pyrrolo[2,3-b]pyrazin-6-yl)-phenol [0.5 g, Example 28] in dimethylformamide (10 mL) and cesium carbonate (0.67 g) was added ethyl chloroacetate (0.025 g). The reaction mixture was heated at 50° C. overnight. After cooling, the dimethylformamide was removed in vacuo and the residue partitioned between ethyl acetate and water. The organic fraction was dried over sodium sulfate, evaporated and subjected to flash column chromatography on silica eluting with 2.5% methanol in dichloromethane. This product was further triturated with a mixture of ethyl acetate and pentane to give the title compound as a white solid, m.p. 183–184° C. MS: 328(MH$^+$).

EXAMPLE 28
2-Methoxy-5-(5H-pyrrolo[2,3-b]pyrazin-6-yl)phenol, A1-B70, the product of the combination of group A1 in Table 1 and B70 in Table 2:

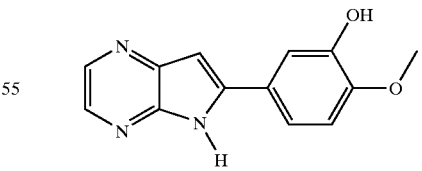

To a solution of 6-(3-tert-butyldimethylsilyloxy-4-methoxy)phenyl-5H-pyrrolo[2,3-b]pyrazine [1.0 g, Reference example 491 in tetrahydrofuran (50 mL) was added tetrabutylammonium fluoride (5.63 mL of a 1M solution in tetrahydrofuran). The reaction mixture was stirred at room temperature for 3 hours. The tetrahydrofuran was removed under reduced pressure and the residue was suspended in water. The resultant solid was collected by filtration and

EXAMPLE 29

3-Fluoro-2-(5-methoxy-1-methyl-1H-indol-3-yl)-1H-pyrrolo[2,3-b]pyridine, A62-B1-C1, the product of the combination of group A62 in Table 1 and B1 in Table 2 and C1 in Table 3:

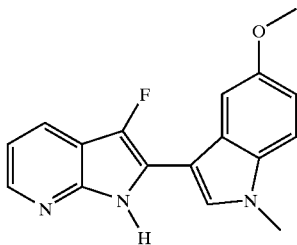

A solution of 2-(5-methoxy-1-methyl-1H-indol-3-yl)-1H-pyrrolo[2,3-b]pyridine [0.1 g, Example 17(a)] in dry tetrahydrofuran (4 mL), at 0° C., was treated with methyl magnesium bromide (0.042 mL) and after stirring for a further 20 minutes at 0° C. this mixture was treated with 1-chloromethyl-4-fluoro-1,4-diazoniabicyclo[2,2,2]octane bis(tetrafluoroborate) (0.13 g). The reaction mixture was stirred at room temperature for 4 hours, then stood at room temperature overnight, then heated at 40° C. for 4 hours, then heated at 80° C. for 2 hours, then cooled to room temperature and then partitioned between ethyl acetate and water. The aqueous layer was extracted three times with ethyl acetate (25 mL). The combined extracts and ethyl acetate layer from the partitioning were washed with brine, then dried over magnesium sulfate and then evaporated. The residue was triturated with ethyl acetate to give the title compound (0.057 g) as a white solid, m.p. 248–250° C. $^1$H NMR [(CD$_3$)$_2$SO]: δ 12.20 (1H, s); 8.24 (1H, m); 7.81 (1H, s); 7.79 (1H, d, J=9.6 Hz); 7.46 (1H, d, J=9.6 Hz); 7.27 (1H, s); 7.18 (1H, dd, J=13.1, 6.0 Hz); 6.90 (1H, d, J=9.6 Hz); 3.88 (3H, s); 3.80 (3H, s).

EXAMPLE 30

3-{6-(4-Hydroxyphenyl)-5H-pyrrolo[2,3-b]pyrazin-7-yl}propionic acid, A31-B78, the product of the combination of group A31 in Table 1 and B78 in Table 2:

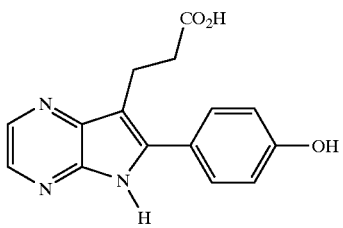

To a solution of dimethyl 3-[6-(4-(1-methyl)ethoxyphenyl)-5H-pyrrolo[2,3-b]pyrazin-7-yl]-propionic 1,1-diacid 1,1-dicarboxylate [0.77 g, Reference Example 44(b)] in methanol (45 mL) was added 1N sodium hydroxide solution (7.7 mL). The reaction mixture was heated at 50° C. for 6 hours then allowed to stand at room temperature overnight. The solvent was removed by evaporation, 6N sulfuric acid solution (20 mL) was added and the reaction mixture refluxed for 12 hours. After cooling, the solution was basified to pH 4 with 4N sodium hydroxide solution and the resultant precipitate filtered and dried under vacuum to afford the title compound (0.42 g) as a yellow solid which was used without further purification. MS: 284(MH$^+$). HPLC (Method C): R$_T$=2.3 minutes.

EXAMPLE 31

Ethyl 3-{6-(4-hydroxyphenyl)-5H-pyrrolo[2,3-b]pyrazin-7-yl}propionate, A57-B78, the product of the combination of group A57 in Table 1 and B78 in Table 2:

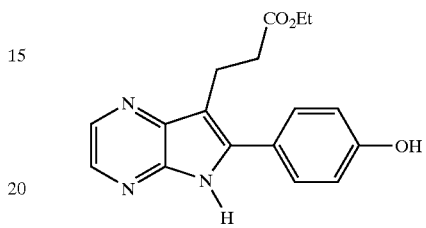

A solution of 3-[{6-(4-hydroxyphenyl)-5H-pyrrolo[2,3-b]pyrazin-7-yl}propionic acid (0.02 g) [Example 30] in ethanol (2 mL) was treated with a catalytic amount of para-toluenesulfonic acid. The mixture was refluxed for 4 hours, the solvent removed by evaporation and the precipitate filtered. The solid was then taken in ethyl acetate, the organic layer washed with water, brine, dried over magnesium sulfate and evaporated to give a yellow solid which was subjected to flash chromatography on silica, eluting with ethyl acetate) to give the title compound. MS: 298 (MH$^+$). HPLC (Method C): R$_T$=2.58 minutes.

EXAMPLE 32 AND REFERENCE EXAMPLE 100

2-(5-Methoxy-1H-indol-3-yl)-1H-pyrrolo[2,3-b]pyridine-4-carbonitrile, A3-B2-C1, the product of the combination of group A3 in Table 1 and B2 in Table 2 and C1 in Table 3:

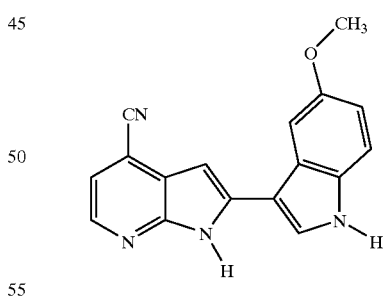

By proceeding in a similar manner to Reference Example 12(a) but using 2-iodo-1-(toluene-4-sulfonyl)-1H-pyrrolo[2,3-b]pyridine-4-carbonitrile [Reference Example 62(a)] there was prepared the 2-(5-methoxy-1H-indol-3-yl)-1H-pyrrolo[2,3-b]pyridine-4-carbonitrile as a yellow solid, m.p. 303–304° C., TLC R$_F$=0.07 (ethyl acetate/heptane 1:1) and 2-(5-methoxy-1H-indol-3-yl)-1-(toluene-4-sulfonyl)-1H-pyrrolo[2,3-b]pyridine-4-carbonitrile [Reference Example 100] as a brown oil. MS: 443(MH$^+$). TLC: R$_F$=0.38 (ethyl acetate/heptane 1:1).

EXAMPLE 33

6-(4-Methylsulfinylphenyl)-5H-pyrrolo[2,3-b]pyrazine, A1-B93, the product of the combination of group A1 in Table 1 and B93 in Table 2:

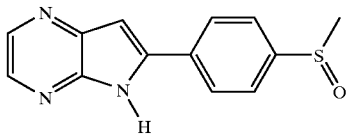

A stirred suspension of 6-(4-methylthiophenyl)-5H-pyrrolo[2,3-b]pyrazine [0.236$^2$ g, Example 1(ah)] in dichloromethane (20 mL) was treated with TBA oxone (2.545 g). After 2 hours the resulting orange solution was evaporated. The residue was subjected to flash chromatography eluting with a mixture of methanol and dichloromethane (1:1, v/v) to give the title compound as a white solid. MS: 258(MH$^+$). $^1$H NMR [(CD$_3$)$_2$SO]: δ 12.66 (1H, s); 8.41 (1H, s); 8.24 (3H, m); 7.82 (2H, d, J=8.7 Hz); 7.33 (1H, s); 2.81 (3H, s).

EXAMPLE 34

6-(4-Methylsulfonylphenyl)-5H-pyrrolo[2,3-b]pyrazine, A1-B94, the product of the combination of group A1 in Table 1 and B94 in Table 2:

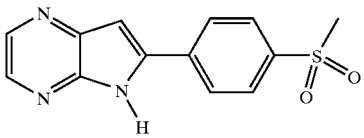

A stirred suspension of 6-(4-methylthiophenyl)-5H-pyrrolo[2,3-b]pyrazine [0.125 g, Example 1(ah)] in dichloromethane (15 mL) was treated with TBA oxone (1.35 g). After 4 hours the reaction mixture was evaporated. The residue was subjected to flash chromatography eluting with a mixture of methanol and dichloromethane (1:1, v/v) to give the title compound as a white solid. MS: 274(MH$^+$). $^1$H NMR [(CD$_3$)$_2$SO]: δ 12.78 (1H, s); 8.44 (1H, s); 8.28 (3H, m); 8.04 (2H, d, J=8.8 Hz); 7.40 (1H, s); 3.27 (3H, s).

EXAMPLE 35

3-(6-(4-tert-Butylphenyl)-5H-pyrrolo[2,3-b]pyrazin-7-yl)propylamine, A46-B55, the product of the combination of group A46 in Table 1 and B55 in Table 2:

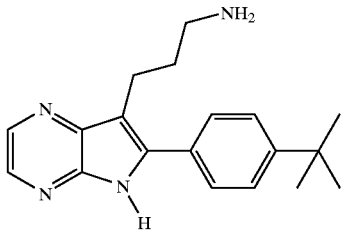

A solution of the 3-[6-(4-tert-butylphenyl-5H-pyrrolo[2,3-b]pyrazin-7-yl]-propionamide [0.2 g, Example 24] in dry tetrahydrofuran (20 mL) was treated with a solution of lithium aluminium hydride in diethyl ether (5 mL, 1M). The solution was stirred at room temperature for 24 hours then treated with water (20 mL). This mixture was filtered through celite and the celite was washed twice with ethyl acetate (20 mL). The combined filtrate and washings were washed with water, then with brine, then dried over magnesium sulfate and then evaporated to give the title compound as a yellow solid (0.12 g). MS: 309(MH$^+$). HPLC (Method C): R$_T$=2.54 minutes.

EXAMPLE 36

(a) N-{3-(6-(4-tert-Butylphenyl)-5H-pyrrolo[2,3-b]pyrazin-7-yl)propyl}acetamide, A39-B55, the product of the combination of group A39 in Table 1 and B55 in Table 2:

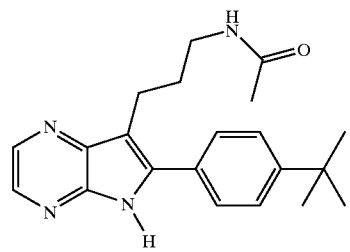

A solution of 3-(6-(4-tert-butylphenyl)-5H-pyrrolo[2,3-b]pyrazin-7-yl)propylamine (0.0324 mmol) [Example 35] in tetrahydrofuran (1.5 mL) was treated with acetyl chloride (0.0324 mmol) and triethylamine (0.0788 mmol). The solution was stirred at room temperature for 12 hours and then treated with water and ethyl acetate. The organic phase was dried over magnesium sulfate and then evaporated. The residue was subjected to column chromatography on silica eluting with ethyl acetate followed by a mixture of ethyl acetate and methanol (9:1, v/v) to give the title compound as a yellow solid. MS: 351(MH$^+$). HPLC (Method C): R$_T$=3.05 minutes.

(b) N-{3-(6-(4-tert-butylphenyl)-5H-pyrrolo[2,3-b]pyrazin-7-yl)propyl}cyclopropylcarboxylic acid amide, A47-B55, the product of the combination of group A47 in Table 1 and B55 in Table 2:

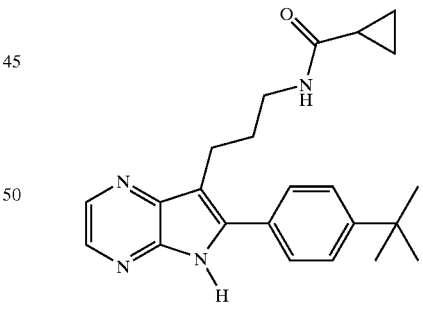

By proceeding in a manner similar to Example 36(a) above but using cyclopropylcarbonyl chloride, there was prepared N-{3-(6-(4-tert-butylphenyl)-5H-pyrrolo[2,3-b]pyrazin-7-yl)propyl}cyclopropylcarboxylic acid amide as a yellow gummy solid. MS: 377(MH$^+$). HPLC (Method C): R$_T$=3.25 minutes.

(c) N-{3-(6-(4-tert-butylphenyl)-5H-pyrrolo[2,3-b]pyrazin-7-yl)propyl}butyramide, A48-B55, the product of the combination of group A48 in Table 1 and B55 in Table 2:

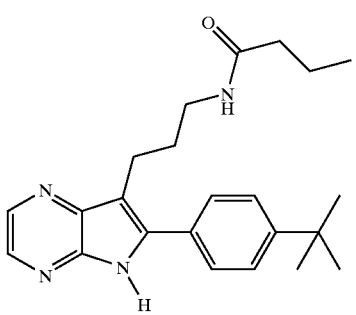

By proceeding in a manner similar to Example 36(a) above but using n-butyroyl chloride, there was prepared N-[3-(6-(4-tert-butylphenyl)-5H-pyrrolo[2,3-b]pyrazin-7-yl)propyl]butyramide as a yellow gummy solid. MS: 379 (MH$^+$). HPLC (Method C): R$_T$=3.28 minutes.

(d) N-{3-(6-(4-tert-butylphenyl)-5H-pyrrolo[2,3-b]pyrazin-7-yl)propyl}methoxyacetamide, A49-B55, the product of the combination of group A49 in Table 1 and B55 in Table 2:

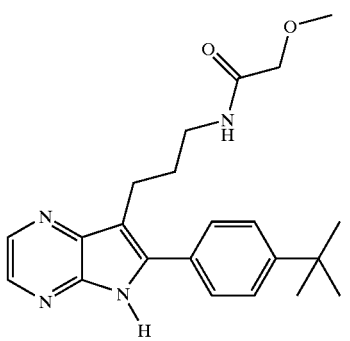

By proceeding in a manner similar to Example 36(a) above but using methoxyacetyl chloride, there was prepared N-{3-(6-(4-tert-butylphenyl)-5H-pyrrolo[2,3-b]pyrazin-7-yl)propyl}methoxyacetamide as a white solid. MS: 381 (MH$^+$). HPLC (Method C): R$_T$=3.15 minutes.

(e) N-{3-(6-(4-tert-butylphenyl)-5H-pyrrolo[2,3-b]pyrazin-7-yl)propyl}thien-2-ylcarboxylic acid amide, A50-B55, the product of the combination of group A50 in Table 1 and B55 in Table 2:

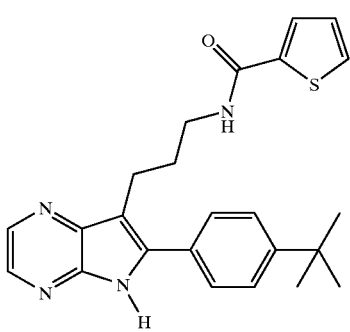

By proceeding in a manner similar to Example 36(a) above but using thien-2-ylcarbonyl chloride, there was prepared N-{3-(6-(4-tert-butylphenyl)-5H-pyrrolo[2,3-b]pyrazin-7-yl)propyl}thien-2-ylcarboxylic acid amide as a yellow solid. MS: 419(MH$^+$). HPLC (Method C): R$_T$=3.28 minutes.

EXAMPLE 37

(a) N-{3-(6-(4-tert-Butylphenyl)-5H-pyrrolo[2,3-b]pyrazin-7-yl)propyl}-N'n-propyl urea, A51-B55, the product of the combination of group A51 in Table 1 and B55 in Table 2:

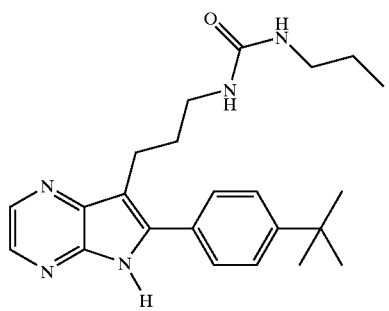

A solution of 3-(6-(4-tert-butylphenyl)-5H-pyrrolo[2,3-b]pyrazin-7-yl)propylamine (0.0324 mmol) [Example 35] in tetrahydrofuran (2 mL) was treated with n-propyl-isocyanate (0.0324 mmol). The solution was stirred at room temperature for 12 hours and then treated with water (3 mL). The resulting precipitate was filtered, then washed with water and then dried under vacuum at 50° C. to give the title compound as a beige solid. MS: 394(MH$^+$). HPLC (Method C): R$_T$=3.25 minutes.

b) N-{3-(6-(4-tert-butylphenyl)-5H-pyrrolo[2,3-b]pyrazin-7-yl)propyl}-N'-carboethoxymethyl urea, A52-B55, the product of the combination of group A52 in Table 1 and B55 in Table 2:

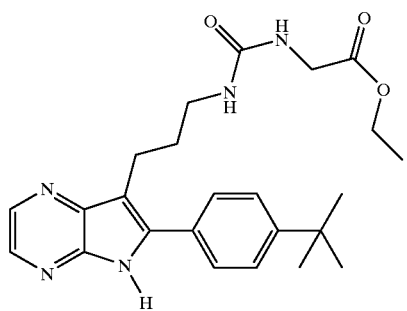

By proceeding in a manner similar to Example 37(a) above but using ethyl-isocyanatoacetate, there was prepared N-{3-(6-(4-tert-butylphenyl)-5H-pyrrolo[2,3-b]pyrazin-7-yl)propyl}-N'-carboethoxymethyl urea as a yellow solid. MS: 437(MH$^+$). HPLC (Method C): R$_T$=3.18 minutes.

c) N-{1-methyl-3-(1H-pyrrolo[2,3-b]pyridin-2-yl)-1H-indol-5-yl]methyl}-N'-tetrahydropyran-2-ylurea, A2-B1-C74, the product of the combination of group A2 in Table 1 and B1 in Table 2 and C74 in Table 3:

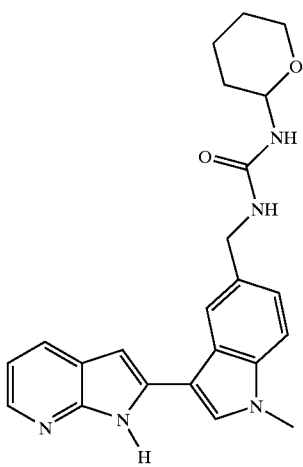

By proceeding in a manner similar to Example 37(a) above but using [3-(1H-pyrrolo[2,3-b]pyridin-2-yl)-1-methyl-1H-indol-5-yl]-methylamine [Example 52] and tetrahydropyran-2-yl isocyanate there was prepared N-{1-methyl-3-(1H-pyrrolo[2,3-b]pyridin-2-yl)-1H-indol-5-yl]methyl}-N'-tetrahydropyran-2-ylurea as a solid, m.p. 229–231° C.

EXAMPLE 38

N-{3-(6-(4-tert-Butylphenyl)-5H-pyrrolo[2,3-b]pyrazin-7-yl)propyl}-N',N'-diethyl urea, A53-B55, the product of the combination of group A53 in Table 1 and B55 in Table 2:

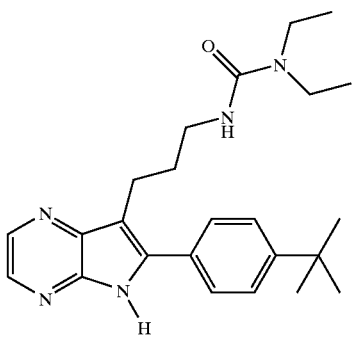

A solution of 3-(6-(4-tert-butylphenyl)-5H-pyrrolo[2,3-b]pyrazin-7-yl)propylamine [0.0324 mmol, Example 35] in tetrahydrofuran (1.5 mL) was treated with diethylcarbamyl chloride (0.0324 mmol) and triethylamine (0.0788 mmol). The solution was stirred at room temperature for 12 hours and water and ethyl acetate were added. The layers were separated and the organic solution was dried over magnesium sulfate. The drying agent was filtered and the solvent was evaporated. The residue was purified by column chromatography (silica gel, ethyl acetate followed by 10% methanol in ethyl acetate) to give the title compound as a yellow solid. MS: 408(MH$^+$). HPLC (Method C): R$_T$=3.43 minutes.

EXAMPLE 39

(a) N-{3-(6-(4-tert-Butylphenyl)-5H-pyrrolo[2,3-b]pyrazin-7-yl)propy}methanesulfonamide, A38-B55, the product of the combination of group A38 in Table 1 and B55 in Table 2:

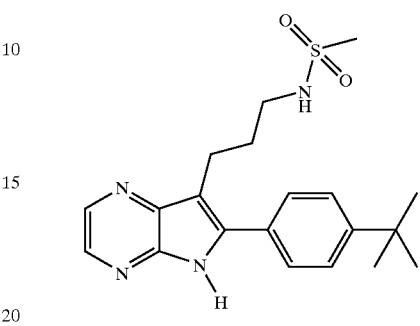

A solution of 3-(6-(4-tert-butylphenyl)-5H-pyrrolo[2,3-b]pyrazin-7-yl)propylamine [0.0324 mmol, Example 35] in tetrahydrofuran (1.5 mL) was treated with methanesulfonyl chloride (0.0324 mmol) and triethylamine (0.0788 mmol). The solution was stirred at room temperature for 12 hours and water and ethyl acetate were added. The layers were separated and the organic solution was dried over magnesium sulfate. The drying agent was filtered and the solvent was evaporated. The residue was purified by column chromatography (silica gel, ethyl acetate followed by 10% methanol in ethyl acetate) to give the title compound as a yellow solid. MS: 387(MH$^+$). HPLC (Method C): R$_T$=3.23 minutes.

(b) N-{3-(6-(4-tert-Butylphenyl)-5H-pyrrolo[2,3-b]pyrazin-7-yl)propyl}thien-2-ylsulfonamide, A50-B55, the product of the combination of group A50 in Table 1 and B55 in Table 2:

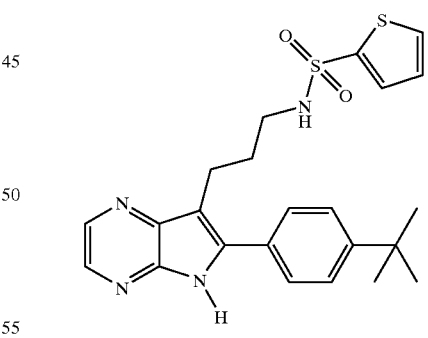

By proceeding in a manner similar to Example 39(a) above but using thien-2-ylsulfonyl chloride, there was prepared N-{3-(6-(4-tert-Butylphenyl)-5H-pyrrolo[2,3-b]pyrazin-7-yl)propyl}thien-2-ylsulfonamide as a yellow solid. MS: 455(MH$^+$). HPLC (Method C): R$_T$=3.56 minutes.

(c) N-{3-(6-(4-tert-butylphenyl)-5H-pyrrolo[2,3-b]pyrazin-7-yl)propyl}dimethylisoxazol-4-ylsulfonamide, A54-B55, the product of the combination of group A54 in Table 1 and B55 in Table 2:

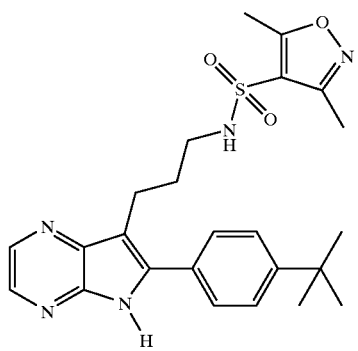

By proceeding in a manner similar to Example 39(a) above but using 3,5-dimethylisoxazol-4-ylsulfonyl chloride, there was prepared N-{3-(6-(4-tert-butylphenyl)-5H-pyrrolo[2,3-b]pyrazin-7-yl)propyl}dimethylisoxazol-4-ylsulfonamide as a gummy white solid. MS: 468(MH+). HPLC (Method C): $R_T$=3.55 minutes.

(d) N-{3-(6-(4-tert-butylphenyl)-5H-pyrrolo[2,3-b]pyrazin-7-yl)propyl}1-methylimidazol-4-ylsulfonamide, A56-B55, the product of the combination of group A56 in Table 1 and B55 in Table 2:

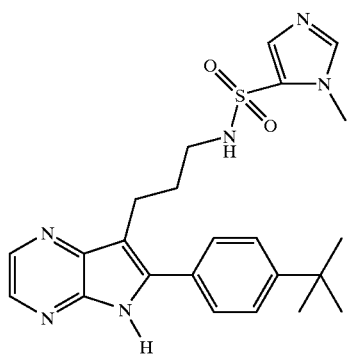

By proceeding in a manner similar to Example 39(a) above but using 1-methylimidazol-4-ylsulfonyl chloride, there was prepared N-{3-(6-(4-tert-butylphenyl)-5H-pyrrolo[2,3-b]pyrazin-7-yl)propyl}1-methylimidazol-4-ylsulfonamide as a gummy white solid. MS: 453(MH+). HPLC (Method C): $R_T$=3.13 minutes.

EXAMPLE 40

(a) 2-(5-Methoxy-1-methyl-1H-indol-3-yl)-1H-pyrrolo[2,3-b]pyridine-4 carboxylic acid (2-hydroxy-1,1-dimethyl-ethyl)-amide, A68-B1-C1, the product of the combination of group A68 in Table 1 and B1 in Table 2 and C1 in Table 3:

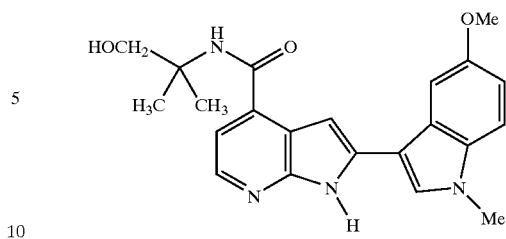

A solution of 2-(5-methoxy-1-methyl-1H-indol-3-yl)-1H-pyrrolo[2,3-b]pyridine-4 carboxylic acid [32 mg, Example 41(a)] in dry dimethylformamide (10 mL), under nitrogen, was treated with diisopropylethylamine (35 µL) followed by O-(7-azabenzotriazol-1-yl)-1,1,3,3-tetramethyluronium hexafluorophosphate (38 mg). After stirring at room temperature for 1 hour this mixture was treated with a solution of 2-amino-2-methyl-1-propanol (10.5 µL) in dry dimethylformamide (1 mL) and stirring was then continued for a further 2 hours. The reaction mixture was evaporated and the residue was treated with saturated aqueous sodium bicarbonate solution (115 mL). This mixture was stirred for 1 hour and the resulting yellow solid was filtered, then washed well with water and then dried at 100° C. under vacuum to give the title compound (34 mg) as a yellow solid, m.p. 210–212° C.

(b) 3-(4-chloro-1H-pyrrolo[2,3-b]pyridin-2-yl)-1-methyl-1H-indole-5-carboxylic acid (2-hydroxy-1,1-dimethyl-ethyl)-amide, A28-B1-C31, the product of the combination of group A28 in Table 1 and B1 in Table 2 and C31 in Table 3:

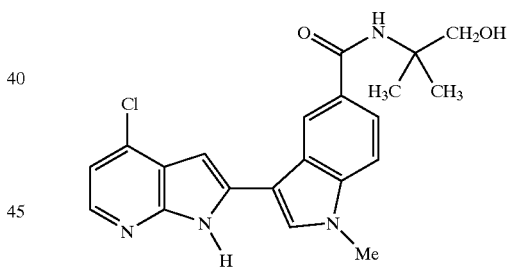

By proceeding in a manner similar to Example 40(a) above but using a mixture of 3-(4-chloro-1H-pyrrolo[2,3-b]pyridin-2-yl)-1-methyl-1H-indole-5-carboxylic acid and 3-(4-chloro-1H-pyrrolo[2,3-b]pyridin-2-yl)-1-methyl-1H-indole-5-carboxylic acid, methyl ester [Example 41(b)] and subjecting the crude reaction product to chromatography on silica, eluting initially with a mixture of ethyl acetate and heptane (85:15, v/v) then ramping up to ethyl acetate, there was prepared 3-(4-chloro-1H-pyrrolo[2,3-b]pyridin-2-yl)-1-methyl-1H-indole-5-carboxylic acid (2-hydroxy-1,1-dimethyl-ethyl)-amide as a reddish grey solid. MS: 397, 399(M+). $R_T$=4.038 minutes.

(c) [2-(5-methoxy-1-methyl-1H-indol-3-yl)-1H-pyrrolo[2,3-b]pyridin-4-yl]-morpholin-4-yl-methanone, A12-B1-$C_1$, the product of the combination of group A12 in Table 1 and B1 in Table 2 and C1 in Table 3:

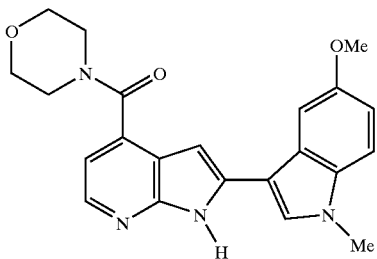

By proceeding in a manner similar to Example 40(a) above but using morpholine to replace the 2-amino-2-methyl-1-propanol there was prepared [2-(5-methoxy-1-methyl-1H-indol-3-yl)-1H-pyrrolo[2,3-b]pyridin-4-yl]-morpholin-4-yl-methanone as a solid, m.p. 259–260° C. MS: 391(MH$^+$).

(d) 3-[6-(4-hydroxyphenyl)-5H-pyrrolo[2,3-b]pyrazin-7-yl]-N-methylpropionamide, A33-B78, the product of the combination of group A33 in Table 1 and B78 in Table 2:

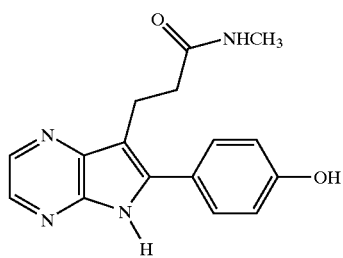

By proceeding in a manner similar to Example 40(a) above but using 3-[6-(4-hydroxyphenyl)-5H-pyrrolo[2,3-b]pyrazin-7-yl]-propionic acid (Example 30) and N-methylamine there was prepared 3-[6-(4-hydroxyphenyl)-5H-pyrrolo[2,3-b]pyrazin-7-yl]-N-methylpropionamide as a solid. MS: 297(MH$^+$).

(e) 2-(1-ethyl-5-methoxy-1H-indol-3-yl)-1H-pyrrolo[2,3,-b]pyridine-4-carboxylic acid (2-hydroxy-1,1-dimethyl-ethyl)-amide, A68-B3-C1, the product of the combination of group A68 in Table 1 and B3 in Table 2 and C1 in Table 3:

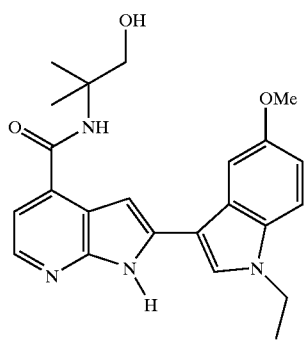

By proceeding in a manner similar to Example 40(a) above but using 2-(1-ethyl-5-methoxy-1H-indol-3-yl)-1H-pyrrolo[2,3,-b]pyridine-4-carboxylic acid [Example 41(c)], there was prepared 2-(1-ethyl-5-methoxy-1H-indol-3-yl)-1H-pyrrolo[2,3,-b]pyridine-4-carboxylic acid (2-hydroxy-1,1-dimethyl-ethyl)-amide as a green solid, m.p. 244–245° C. MS: 407(MH$^+$).

(f) 2-(5-methoxy-1-methyl-1H-indol-3-yl)-1H-pyrrolo[2,3,-b]pyridine-4-carboxylic acid (2-methoxy-ethyl) amide, A69-B1-C$_1$, the product of the combination of group A69 in Table 1 and B1 in Table 2 and C1 in Table 3:

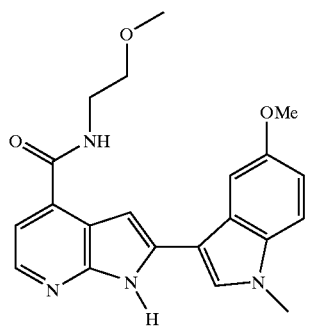

By proceeding in a manner similar to Example 40(a) above but using 2-(5-methoxy-1-methyl-1H-indol-3-yl)-1H-pyrrolo[2,3,-b]pyridine-4-carboxylic acid [Example 41(a)], and 2-methoxy-ethylamine there was prepared 2-(5-methoxy-1-methyl-1H-indol-3-yl)-1H-pyrrolo[2,3,-b]pyridine-4-carboxylic acid (2-methoxy-ethyl) amide as a yellow solid, m.p. 248–249° C. MS: 379(MH$^+$).

(g) 2-(5-methoxy-1-methyl-1H-indol-3-yl)-1H-pyrrolo[2,3,-b]pyridine-4-carboxylic acid (2-hydroxy-2-methyl-propyl) amide, A70-B1-C1, the product of the combination of group A70 in Table 1 and B1 in Table 2 and C1 in Table 3:

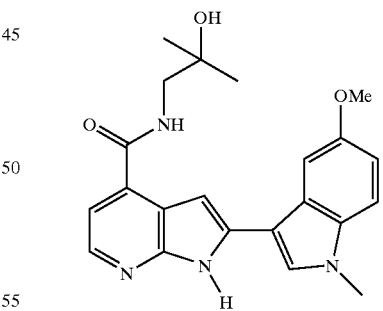

By proceeding in a manner similar to Example 40(a) above but using 2-(5-methoxy-1-methyl-1H-indol-3Y$^1$)-1H-pyrrolo[2,3,-b]pyridine-4-carboxylic acid [Example 41(a)], and 1-amino-2-methyl-propan-2-ol (prepared according to the literature procedure of Cabella et. al. Tetrahedron, 1995, 51 (6), 18-17-1826), there was prepared 2-(5-methoxy-1-methyl-1H-indol-3-yl)-1H-pyrrolo[2,3,-b]pyridine-4-carboxylic acid (2-hydroxy-2-methyl-propyl) amide as a solid. LC-MS: METHOD D: R$_T$=2.54 minutes, 393.3 (MH$^+$).

(h) 2-(5-methoxy-1-methyl-1H-indol-3-yl)-1H-pyrrolo[2,3,-b]pyridine-4-carboxylic acid (2-hydroxy-propyl) amide A85-B1-C₁, the product of the combination of group A85 in Table 1 and B1 in Table 2 and C1 in Table 3:

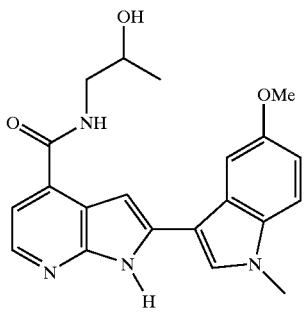

By proceeding in a manner similar to Example 40(a) above but using 2-(5-methoxy-1-methyl-1H-indol-3-yl)-1H-pyrrolo[2,3,-b]pyridine-4-carboxylic acid [Example 41(a)], and 1-amino-propan-2-ol there was prepared 2-(5-methoxy-1-methyl-1H-indol-3-yl)-1H-pyrrolo[2,3,-b]pyridine-4-carboxylic acid (2-hydroxy-propyl) amide as a solid. LC-MS: METHOD D: $R_T$=2.74 minutes, 379(MH⁺).

(i) 2-(5-methoxy-1-methyl-1H-indol-3-yl)-1H-pyrrolo[2,3,-b]pyridine-4-carboxylic acid (2-hydroxy-ethyl) amide A86-B1-C₁, the product of the combination of group A86 in Table 1 and B1 in Table 2 and C1 in Table 3:

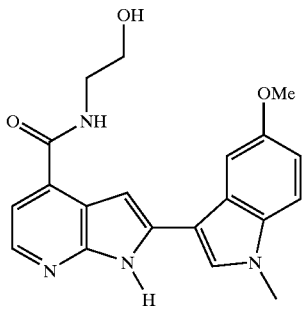

By proceeding in a manner similar to Example 40(a) above but using 2-(5-methoxy-1-methyl-1H-indol-3-yl)-1H-pyrrolo[2,3,-b]pyridine-4-carboxylic acid [Example 41(a)], and 2-amino-ethanol there was prepared 2-(5-methoxy-1-methyl-1H-indol-3-yl)-1H-pyrrolo[2,3,-b]pyridine-4-carboxylic acid (2-hydroxy-ethyl) amide as a solid. LC-MS: METHOD D: $R_T$=2.22 minutes, 365(MH⁺).

(j) 2-(5-methoxy-1H-indol-3-yl)-1H-pyrrolo[2,3,-b]pyridine-4-carboxylic acid (2-methoxy-ethyl) amide A69-B2-C1, the product of the combination of group A69 in Table 1 and B2 in Table 2 and C1 in Table 3:

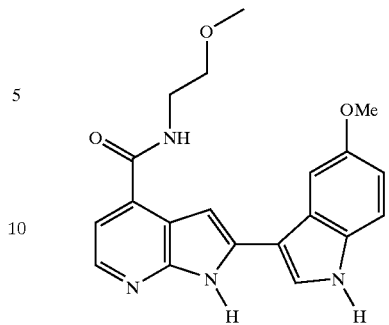

By proceeding in a manner similar to Example 40(a) above but using 2-(5-methoxy-1H-indol-3-yl)-1H-pyrrolo[2,3,-b]pyridine-4-carboxylic acid [Example 15(t)], and 2-methoxy-ethylamine there was prepared 2-(5-methoxy-1H-indol-3-yl)-1H-pyrrolo[2,3,-b]pyridine-4-carboxylic acid (2-methoxy-ethyl) amide as a solid. LC-MS (METHOD D): $R_T$=3.65 minutes, 365(MH⁺).

EXAMPLE 41

(a) 2-(5-Methoxy-1-methyl-1H-indol-3-yl)-1H-pyrrolo[2,3-b]pyridine-4 carboxylic acid, A67-B1-C₁, the product of the combination of group A67 in Table 1 and B1 in Table 2 and C1 in Table 3:

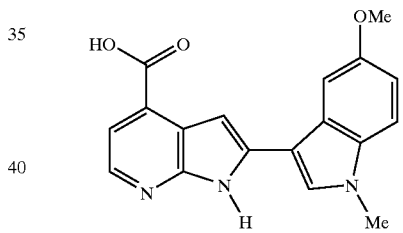

A solution of 2-(5-methoxy-1-methyl-1H-indol-3-yl)-1-(toluene-4-sulfonyl)-1H-pyrrolo[2,3-b]pyridine-4 carboxylic acid, tert-butyl ester [106 mg, Reference Example 2(n)] in methanol (10 mL) was treated with potassium hydroxide solution (1 mL, 5N) then heated at reflux temperature for 1 hour and then evaporated. The residue was treated with water (15 mL) and the mixture washed with ethyl acetate (10 mL). The pH of the aqueous solution was then adjusted to 4 by addition of hydrochloric acid and cooled in ice. The resulting yellow solid was filtered washed well with water and then dried at 80° C. under vacuum to give the title compound (33 mg) as a yellow solid, m.p.>300° C. MS: 322(MH⁺).

(b) 3-(4-chloro-1H-pyrrolo[2,3-b]pyridin-2-yl)-1-methyl-1H-indole-5-carboxylic acid, A28-B1-C28, the product of the combination of group A28 in Table 1 and B1 in Table 2 and C28 in Table 3; and 3-(4-chloro-1H-pyrrolo[2,3-b]pyridin-2-yl)-1-methyl-1H-indole-5-carboxylic acid, methyl ester:

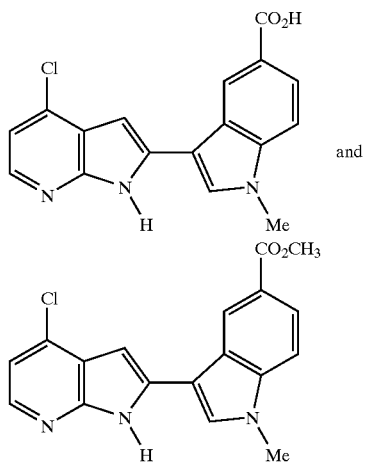

By proceeding in a manner similar to Example 41(a) above but using 3-(4-chloro-1-(toluene-4-sulfonyl)-1-methyl-1H-pyrrolo[2,3-b]pyridin-2-yl)-1H-indole-5-carboxylic acid, methyl ester [Reference Example 19(d)] there was prepared a 60:40 mixture of 3-(4-chloro-1H-pyrrolo[2,3-b]pyridin-2-yl)-1-methyl-1H-indole-5-carboxylic acid and 3-(4-chloro-1H-pyrrolo[2,3-b]pyridin-2-yl)-1-methyl-1H-indole-5-carboxylic acid, methyl ester as an off-white solid. MS: 326 and 340(M+).

(c) 2-(1-ethyl-5-methoxy-1H-indol-3-yl)-1H-pyrrolo[2,3,-b]pyridine-4-carboxylic acid, A67-B3-C1, the product of the combination of group A67 in Table 1 and B3 in Table 2 and C1 in Table 3:

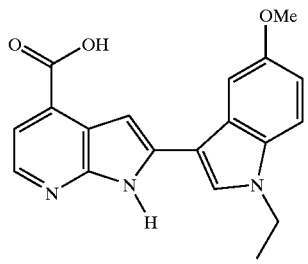

By proceeding in a manner similar to Example 41(a) above but using 2-(1-ethyl-5-methoxy-1H-indol-3-yl)-1-(toluene-4-sulfonyl)-1H-pyrrolo[2,3,-b]pyridine-4-carboxylic acid tert-butyl ester [Reference Example 13(o)], there was prepared 2-(1-ethyl-5-methoxy-1H-indol-3-yl)-1H-pyrrolo[2,3,-b]pyridine-4-carboxylic acid as a tan solid. MS: 336(MH+). TLC: $R_F$=0.24 (ethyl acetate/heptane, 1:1).

EXAMPLE 42

2-(5-Methoxy-1H-indol-3-yl)-1H-pyrrolo[2,3-b]pyridine-4 carboxamide, A10-B2-C1, the product of the combination of group A10 in Table 1 and B2 in Table 2 and C1 in Table 3:

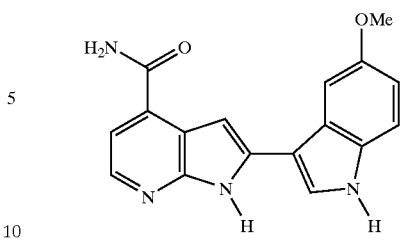

A suspension of 2-(5-methoxy-1H-indol-3-yl)-1-(toluene-4-sulfonyl)-1H-pyrrolo[2,3-b]pyridine-4 carbonitrile [0.25 g, Reference Example 67(e)] in methanol (25 mL) was treated with sodium hydroxide solution (1.5 g in 4 mL water). The mixture was cooled in an ice-bath and then treated dropwise with hydrogen peroxide (0.35 mL, 30%). After stirring at room temperature for 1 hour a further aliquot of hydrogen peroxide (0.3 mL) was added to the reaction mixture and stirring was continued for a further 3 hours then the reaction was quenched by addition of sodium metabisulfite to remove excess hydrogen peroxide. The reaction mixture was then diluted with water (75 mL) and extracted twice with ethyl acetate (50 mL). The combined extracts were washed twice with brine (30 mL), then dried over sodium sulfate and then evaporated. The residual yellow solid was subjected to chromatography on silica eluting with a mixture of ethyl acetate and dichloromethane (1:1, v/v) to give, after trituration with methanol and washing with diethyl ether, the title compound (50 mg) as a yellow solid, m.p.>320° C. MS: 307(MH+).

EXAMPLE 43

3-[6-(4-Morpholin-4-yl phenyl)-5H-pyrrolo[2,3-b]pyrazin-7-yl]-N-methylpropionamide, A33-B59, the product of the combination of group A33 in Table 1 and B59 in Table 2:

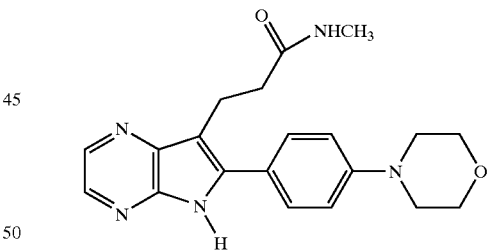

A mixture of 3-[6-(4-trifluoromethanesulfonyloxyphenyl)-5H-pyrrolo[2,3-b]pyrazin-7-yl]-N-methylpropionamide [30 mg, Reference Example 18(d)], acetonitrile (2 mL) and morpholine (0.5 mL) was heated at 200° C. in a microwave oven for 4 hours. The reaction mixture was then evaporated and the residue was triturated with ethyl acetate to give the title compound as a solid. MS: 429.1(MH+).

EXAMPLE 44

6-(4-Pyrrolidin-1-yl phenyl)-5H-pyrrolo[2,3-b]pyrazine, A1-B82, the product of the combination of group A1 in Table 1 and B82 in Table 2:

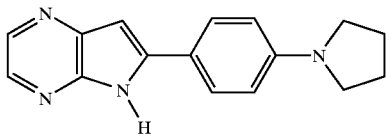

A mixture of 6-(4-trifluoromethanesulfonyloxyphenyl)-5H-pyrrolo[2,3-b]pyrazine [20 mg, Reference Example 18(e)], dioxane (3 mL) and pyrrolidine (0.2 mL) was heated at 200° C. in a microwave oven for 1 hour. The reaction mixture was then evaporated and the residue was subjected to chromatography on silica eluting with a mixture of ethyl acetate and heptane (1:1, v/v) to give, after trituration with a mixture of ethyl acetate and methanol, the title compound (11 mg) as a yellow solid. MS: 265.1(MH$^+$). R$_T$=2.92 minutes.

EXAMPLE 45

(a) 6-(4-(Furan-2-yl)phenyl)-5H-pyrrolo[2,3-b]pyrazine, A1-B100, the product of the combination of group A1 in Table 1 and B100 in Table 2:

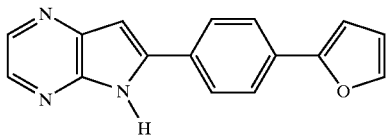

A mixture of 6-(4-trifluoromethanesulfonyloxyphenyl)-5H-pyrrolo[2,3-b]pyrazine [20 mg, Reference Example 18(e)], dioxane (2.5 mL), furan-2-boronic acid (9.8 mg), sodium carbonate solution (0.06 mL, 2N), and tetrakis(triphenylphosphine)palladium[0] (4 mg) was heated at 180° C. in a microwave oven for 40 minutes. The reaction mixture was then evaporated and the residue was subjected to chromatography on silica eluting with a mixture of ethyl acetate and pentane (1:1, v/v) to give, after trituration with a mixture of ethyl acetate and methanol, the title compound (7 mg) as a yellow solid. MS: 262.1(MH$^+$). R$_T$=3.05 minutes.

(b) 6-(4-(3,5-dimethylisoxazol-4-yl)phenyl)-5H-pyrrolo[2,3-b]pyrazine, A1-B99, the product of the combination of group A1 in Table 1 and B99 in Table 2:—

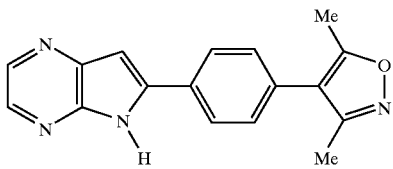

By proceeding in a manner similar to Example 45(a) above but using 3,5-dimethylisoxazole-4-boronic acid, and subjecting the reaction product to chromatography on silica eluting with ethyl acetate, there was prepared 6-(4-(3,5-dimethylisoxazol-4-yl)phenyl)-5H-pyrrolo[2,3-b]pyrazine as beige solid. MS: 279(MH$^+$). R$_T$=3.19 minutes.

EXAMPLE 46

2-[4-(5H-Pyrrolo[2,3,-b]pyrazin-6-yl)phenyl]-propan-2-ol, A1-B56, the product of the combination of group A1 in Table 1 and B56 in Table 2:

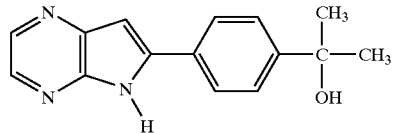

A suspension of magnesium (2 mg) in tetrahydrofuran (2 mL) was treated with methyl iodide (0.06 mL) and when the all magnesium had reacted this solution was treated with a solution of 1-[4-(5H-pyrrolo[2,3-b]pyrazin-6-yl)phenyl]ethanone (10 mg, Example 47) in tetrahydrofuran. After stirring at room temperature overnight the mixture was treated with methyl magnesium chloride (0.04 ml of 2N solution in tetrahydrofuran) and after stirring for a further 2 hours TLC (ethyl acetate) indicated complete reaction. The reaction mixture was then poured into saturated ammonium chloride solution and this mixture was then extracted with ethyl acetate. The extract was evaporated and the residual solid (14 mg) was subjected to thin layer chromatography on alumina eluting with a mixture of ethyl acetate and methanol (95:5, v/v) to give the title compound as a beige solid. MS: 254(MH$^+$). R$_T$=2.5 minutes.

EXAMPLE 47

1-[4-(5H-Pyrrolo[2,3-b]pyrazin-6-yl)phenyl]ethanone, A1-B99, the product of the combination of group A1 in Table 1 and B99 in Table 2:

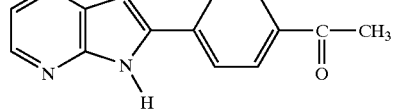

6-(4-trifluoromethanesulfonyloxyphenyl)-5H-pyrrolo[2,3-b]pyrazine [100 mg, Reference Example 18(e)] was added to dry, degassed dimethylformamide (3 mL), under nitrogen, followed by triethylamine (0.081 mL), n-butylvinyl ether (0.49 mL) 1,3-bis(diphenylphosphino)butane (34 mg) and palladium acetate (17 mg). The mixture was heated at 80° C. for 12 hours, then cooled to room temperature, then treated with hydrochloric acid (7 mL, 1N), then stirred at room temperature for 1 hour, and then subjected to chromatography on silica eluting with a mixture of ethyl acetate and heptane (1:1, v/v) to give the title compound (26 mg) as a pale yellow solid. MS: 328.1(MH$^+$). R$_T$=2.59 minutes.

EXAMPLE 48

6-[4-(4-[2-Morpholin-4-ylethyl]-piperazin-1-yl)phenyl]-5H-pyrrolo[2,3-b]pyrazine, A1-B84, the product of the combination of group A1 in Table 1 and B84 in Table 2:

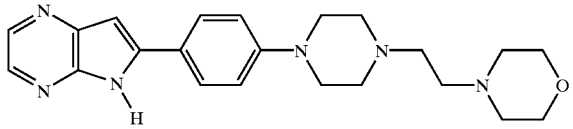

A mixture of 6-(4-piperazin-1-ylphenyl)-5H-pyrrolo[2,3-b]pyrazine (Example 49) and water (5 mL) was treated with potassium hydroxide (71 mg) and after complete solution this mixture was then treated with morpholinoethyl chloride (59 mg) and the resulting slurry was stirred at room temperature overnight. The reaction mixture was treated with water (100 mL), and then extracted three times with ethyl acetate (100 mL). The combined extracts were washed with brine and then evaporated. The residual orange solid was treated with ethyl acetate and methanol and this solution was then acidified by addition of hydrochloric acid (2N) in methanol and then concentrated on a steam bath to give after treatment with ethyl acetate and dichloromethane the title compound (55 mg) as an orange solid. LC-MS: Method A:R$_T$=2.09 minutes, 393(MH$^+$).

EXAMPLE 49

6-(4-Piperazin-1-ylphenyl)-5H-pyrrolo[2,3-b]pyrazine, A1-B83, the product of the combination of group A1 in Table 1 and B83 in Table 2:

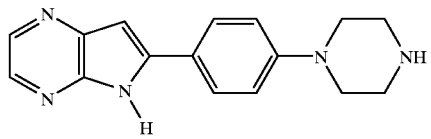

A solution of 4-[4-(5H-pyrrolo[2,3,-b]pyrazin-6-yl) phenyl]piperazine-1-carboxylic acid, tert-butyl ester [100 mg, Reference Example 3(e)] in anhydrous methanolic hydrogen chloride (15 mL, 2N) was heated at 60° C. for 18 hours then evaporated. The residue was suspended in dichloromethane (20 mL) then treated with Argonaut Technologies MP carbonate resin, then stirred at room temperature for 4 hours. After 1 hour the mixture was treated with methanol (2 mL) to aid in solution of the hydrochloride salt. The solid was washed twice with a mixture of dichloromethane and methanol (22 mL, 10:1, v/v). The filtrate was evaporated and the residue was subjected to chromatography on silica gel eluting with a mixture of chloroform, methanol and ammonium hydroxide (9:1:0.1, v/v/v) to give the title compound (25 mg) as an off-white solid. LC-MS: Method A: R$_T$=2.11 minutes, 280.1(MH$^+$).

EXAMPLE 50

2-Methyl-4-[6-(4-tert-Butyl-phenyl)-5H-pyrrolo[2,3-b]pyrazin-7-yl]-butan-2-ol, A59-B55, the product of the combination of group A59 in Table 1 and B55 in Table 2:

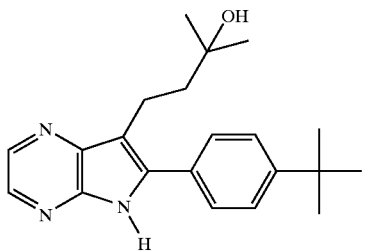

A solution of 4-[6-(4-tert-butyl-phenyl)-5H-pyrrolo[2,3-b]pyrazin-7-yl]-butan-2-one (10 g, Example 51) in tetrahydrofuran (2.3 mL), then diluted with ether (25 mL), then cooled to 0° C. and then treated with a solution of methyl magnesium bromide in diethyl ether (10 mL, 3M). The mixture was allowed to warm to room temperature, then after 3 hours cooled to 0° C., then treated with a further aliquot of a solution of methyl magnesium bromide in diethyl ether (0.3 mL, 3M), then allowed to warm to room temperature and then kept at room temperature overnight. The reaction mixture was then poured into hydrochloric acid (1N) and this mixture was made basic by addition of sodium hydroxide solution (10N) and then extracted with ethyl acetate. The combined extracts were washed with water, then dried over sodium sulfate and then evaporated. The residue was subjected to chromatography on silica eluting with ethyl acetate to give the title compound (0.5 g) as an off white solid. MS: 338(MH$^+$).

EXAMPLE 51

4-[6-(4-tert-Butyl-phenyl)-5H-pyrrolo[2,3-b]pyrazin-7-yl]-butan-2-one, A58-B55, the product of the combination of group A58 in Table 1 and B55 in Table 2:

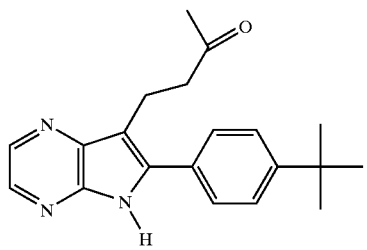

A solution of methyl acetoacetate (1.35 mL) in N-methylpyrrolidone (15 mL), cooled to 0° C., was treated portionwise with sodium hydride (0.33 g, 60% dispersion in mineral oil) and after stirring at 0° C. for 30 minutes this mixture was then treated with a solution of [6-(4-tert-butylphenyl-5H-pyrrolo[2,3-b]pyrazin-7-yl] methyltrimethylammonium iodide [2 g, Reference Example 45(a)] in N-methylpyrrolidone (100 mL). After stirring at room temperature overnight the reaction mixture was subjected to chromatography on silica eluting with a mixture of heptane and ethyl acetate. The resulting 2-acetyl-[6-(4-tert-butyl-phenyl)-5H-pyrrolo[2,3-b]pyrazin-7-yl]propionic acid, methyl ester (1.2 g) was dissolved in a mixture of sodium hydroxide (250 mL, 2N), methanol (25 mL) and tetrahydrofuran. This solution was then heated at 50° C. for 1 hour, then evaporated, then acidified by addition of hydrochloric acid (25 mL, 2N) and then extracted with ethyl acetate. The organic extract was dried over sodium sulfate and then evaporated to give the title compound (1 g). MS: 322(MH$^+$).

EXAMPLE 52

[3-(1H-Pyrrolo[2,3-b]pyridin-2-yl)-1-methyl-1H-indol-5-yl]-methylamine, A2-B1-C71, the product of the combination of group A2 in Table 1 and B1 in Table 2 and C71 in Table 3:

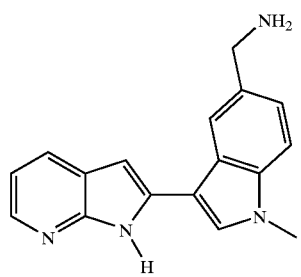

A solution of lithium aluminium hydride in tetrahydrofuran (14.04 mL, 1M) was treated with a solution of 3-[1-(toluene-4-sulfonyl)-1H-pyrrolo[2,3-b]pyridin-2-yl]-1-methyl-1H-indole-5-carbonitrile [2 g, Reference Example 13(c)] in dry tetrahydrofuran (20 mL). The resulting suspension was stirred at room temperature for 5 hours then treated a further aliquot of lithium aluminium hydride in tetrahydrofuran (4.64 mL, 1M) and stirring was continued for a further hour. The reaction mixture was cooled to 0° C., then treated with water (1.63 mL), and then filtered. The insoluble material was washed with ethyl acetate and the combined filtrate and washings were evaporated to give the title compound as an orange solid (1.1 g). MS: 277(MH$^+$).

EXAMPLE 53
2-{[5-Methoxy-3-(1H-pyrrolo[2,3-b]pyridin-2-yl)-indol-1-yl]-1-(1-methylpiperazin-4yl}-ethanone, A2-B30-C1, the product of the combination of group A2 in Table 1 and B30 in Table 2 and C1 in Table 3:

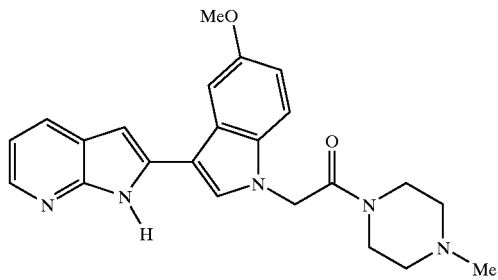

A solution of [5-methoxy-3-(1H-pyrrolo[2,3-b]pyridin-2-yl)-indol-1-yl]-acetic acid [9.6 mg, Example 13(a)] in dry dimethylformamide (0.31 mL) was combined with 2-(1H-benzotriazole-1-yl)1,1,3,3-tetramethyluronium hexafluorophosphate (11.2 mg) in dry dimethylformamide (0.1 mL), then mixed for 1 hour at room temperature and then treated with a solution of N-methylpiperazine (6 mg) and diisopropylethylamine 5.24 μl in dry dimethylformamide (0.116 mL). The reaction mixture was agitated for 20 hours at room temperature. The crude mixture was then subjected to LC-MS triggered purification affording the title compound. LC-MS: METHOD C: $R_T$=2.99 minutes, 404[M+H]$^+$.

By proceeding in a similar manner to Example 53, but replacing N-methylpiperazine with an appropriately substituted amine of formula HNY$^1$Y$^2$, there was prepared EXAMPLE 53(a) to EXAMPLE 53(cg) in Table 4.

TABLE 4
| STRUCTURE and Example number | HNY¹Y² | Formula | LC-MS: Molecular [M + H]⁺ | R_T (minutes) | METHOD C Nomenclature |
|---|---|---|---|---|---|
| 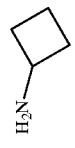 EXAMPLE 53 (a) | 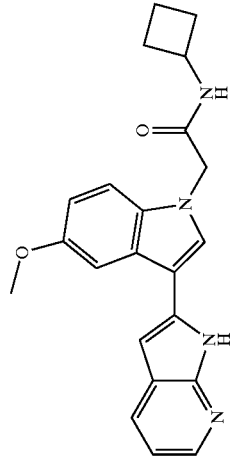 | C22H22N4O2 | 375 | 3.37 | N-Cyclobutyl-2-[5-methoxy-3-(1H-pyrrolo[2,3-b]pyridin-2-yl)-indol-1-yl]-acetamide |
|  EXAMPLE 53 (b) | | C24H24N6O2 | 429 | 2.94 | N-(3-Imidazol-1-yl-propyl)-2-[5-methoxy-3-(1H-pyrrolo[2,3-b]pyridin-2-yl)-indol-1-yl]-acetamide |
|  EXAMPLE 53 (c) | | C22H20N4O2 | 373 | 3.30 | 1-(2,5-Dihydro-pyrrol-1-yl)-2-[5-methoxy-3-(1H-pyrrolo[2,3-b]pyridin-2-yl)-indol-1-yl]-ethanone |

TABLE 4-continued
| STRUCTURE and Example number | HNY¹Y² | Formula | LC-MS: Molecular [M + H]⁺ | R_T (minutes) | METHOD C Nomenclature |
|---|---|---|---|---|---|
| EXAMPLE 53 (d) 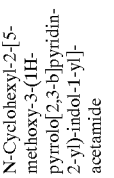 | 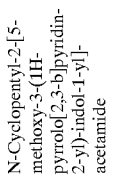 | C24H26N4O2 | 403 | 3.55 | N-Cyclohexyl-2-[5-methoxy-3-(1H-pyrrolo[2,3-b]pyridin-2-yl)-indol-1-yl]-acetamide |
| EXAMPLE 53 (e) 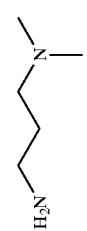 | | C23H24N4O2 | 389 | 3.46 | N-Cyclopentyl-2-[5-methoxy-3-(1H-pyrrolo[2,3-b]pyridin-2-yl)-indol-1-yl]-acetamide |
| EXAMPLE 53 (f) 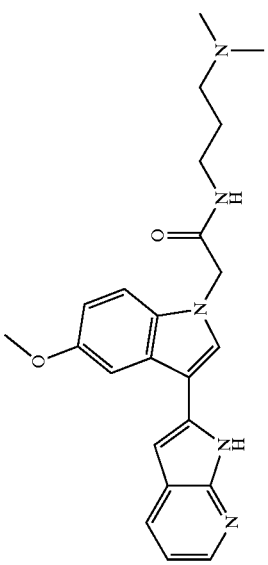 | | C23H27N5O2 | 406 | 3.93 | N-(3-Dimethyl-amino-propyl)-2-[5-methoxy-3-(1H-pyrrolo[2,3-b]pyridin-2-yl)-indol-1-yl]-acetamide |

TABLE 4-continued

| STRUCTURE and Example number | HNY¹Y² | Formula | LC-MS: Molecular [M + H]⁺ | R_T (minutes) | METHOD C Nomenclature |
|---|---|---|---|---|---|
| EXAMPLE 53 (g) | 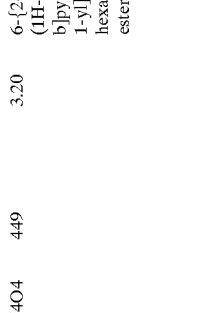 | C25H28N4O4 | 449 | 3.20 | 6-{2-[5-Methoxy-3-(1H-pyrrolo[2,3-b]pyridin-2-yl)-indol-1-yl]-acetylamino}-hexanoic acid methyl ester |
| EXAMPLE 53 (h) | 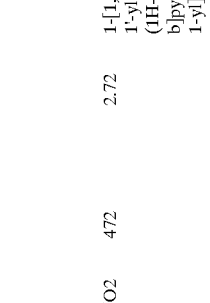 | C28H33N5O2 | 472 | 2.72 | 1-[1,4']Bipiperidinyl-1'-yl-2-[5-methoxy-3-(1H-pyrrolo[2,3-b]pyridin-2-yl)-indol-1-yl]-ethanone |
| EXAMPLE 53 (i) |  | C24H28N4O2 | 405 | 3.52 | N-(3,3-Dimethyl-butyl)-2-[5-methoxy-3-(1H-pyrrolo[2,3-b]pyridin-2-yl)-indol-1-yl]-acetamide |

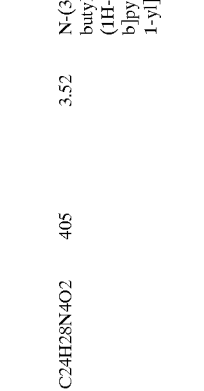

TABLE 4-continued

| STRUCTURE and Example number | HNY¹Y² | Formula | LC-MS: Molecular [M + H]⁺ | R_T (minutes) | METHOD C Nomenclature |
|---|---|---|---|---|---|
|  EXAMPLE 53 (j) | 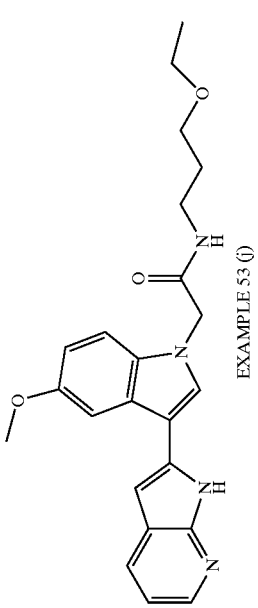 | C23H26N4O3 | 407 | 3.07 | N-(3-Ethoxy-propyl)-2-[5-methoxy-3-(1H-pyrrolo[2,3-b]pyridin-2-yl)-indol-1-yl]-acetamide |
| 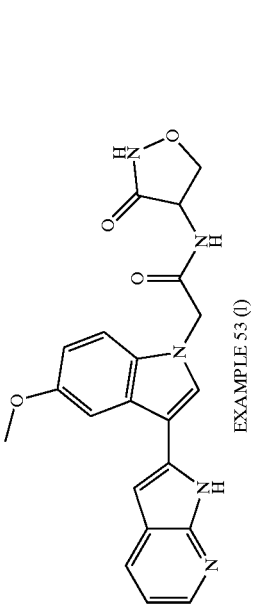 EXAMPLE 53 (k) | 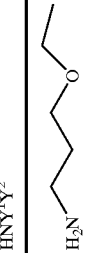 | C25H28N4O2 | 417 | 3.52 | 1-(3,3-Dimethyl-piperidin-1-yl)-2-[5-methoxy-3-(1H-pyrrolo[2,3-b]pyridin-2-yl)-indol-1-yl]-ethanone |
| 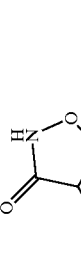 EXAMPLE 53 (l) | 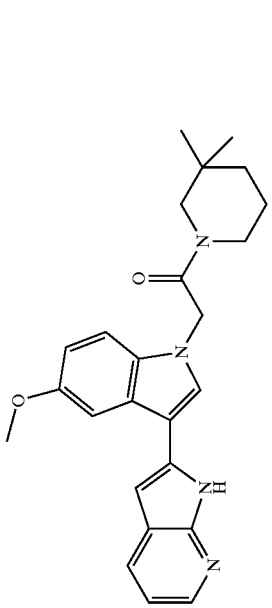 | C21H19N5O4 | 406 | 2.81 | 2-[5-Methoxy-3-(1H-pyrrolo[2,3-b]pyridin-2-yl)-indol-1-yl]-N-(3-oxo-isoxazolidin-4-yl)-acetamide |

TABLE 4-continued

| STRUCTURE and Example number | HNY¹Y² | Formula | LC-MS: Molecular [M + H]⁺ | METHOD C R_T (minutes) | Nomenclature |
|---|---|---|---|---|---|
| EXAMPLE 53 (m) | (4-chlorophenyl)piperazine | C28H26ClN5O2 | 500 | 3.71 | 1-[4-(4-Chlorophenyl)-piperazin-1-yl]-2-[5-methoxy-3-(1H-pyrrolo[2,3-b]pyridin-2-yl)-indol-1-yl]-ethanone |
| EXAMPLE 53 (n) | 4-hydroxypiperidine | C23H24N4O3 | 405 | 2.83 | 1-(4-Hydroxy-piperidin-1-yl)-2-[5-methoxy-3-(1H-pyrrolo[2,3-b]pyridin-2-yl)-indol-1-yl]-ethanone |
| EXAMPLE 53 (o) | thiazolidine | C21H20N4O2S | 393 | 3.13 | 2-[5-Methoxy-3-(1H-pyrrolo[2,3-b]pyridin-2-yl)-indol-1-yl]-1-thiazolidin-3-yl-ethanone |

TABLE 4-continued

| STRUCTURE and Example number | HNY¹Y² | Formula | LC-MS: Molecular [M + H]⁺ | R_T (minutes) | METHOD C Nomenclature |
|---|---|---|---|---|---|
| EXAMPLE 53 (p) | | C31H31N5O2 | 506 | 3.06 | 2-[5-Methoxy-3-(1H-pyrrolo[2,3-b]pyridin-2-yl)-indol-1-yl]-1-[4-(3-phenyl-allyl)-piperazin-1-yl]-ethanone |
| EXAMPLE 53 (q) | | C23H20N4O3 | 401 | 3.18 | N-Furan-2-ylmethyl-2-[5-methoxy-3-(1H-pyrrolo[2,3-b]pyridin-2-yl)-indol-1-yl]-acetamide |
| EXAMPLE 53 (r) | | C25H23N5O2 | 426 | 2.6 | 2-[5-Methoxy-3-(1H-pyrrolo[2,3-b]pyridin-2-yl)-indol-1-yl]-N-(2-pyridin-4-yl-ethyl)-acetamide |

TABLE 4-continued

| STRUCTURE and Example number | HNY¹Y² | Formula | LC-MS: Molecular [M + H]⁺ | R_T (minutes) | METHOD C Nomenclature |
|---|---|---|---|---|---|
| 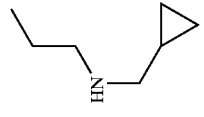 EXAMPLE 53 (s) | 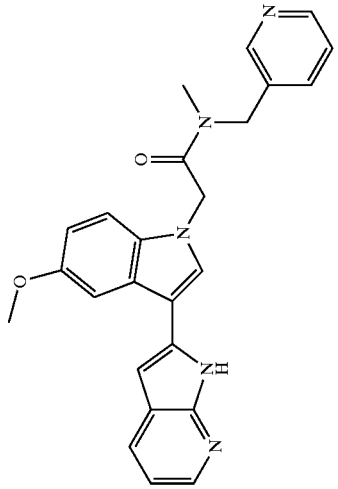 | C25H28N4O2 | 417 | 3.57 | N-Cyclopropylmethyl-2-[5-methoxy-3-(1H-pyrrolo[2,3-b]pyridin-2-yl)-indol-1-yl]-N-propyl-acetamide |
| 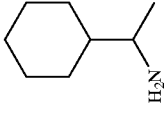 EXAMPLE 53 (t) | 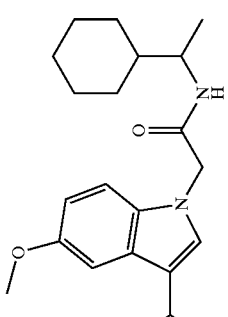 | C26H30N4O2 | 431 | 3.64 | N-(1-Cyclohexyl-ethyl)-2-[5-methoxy-3-(1H-pyrrolo[2,3-b]pyridin-2-yl)-indol-1-yl]-acetamide |
| 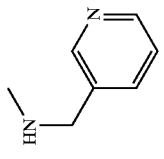 EXAMPLE 53 (u) | 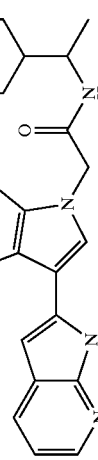 | C25H23N5O2 | 426 | 2.47 | 2-[5-Methoxy-3-(1H-pyrrolo[2,3-b]pyridin-2-yl)-indol-1-yl]-N-methyl-N-pyridin-3-ylmethyl-acetamide |

TABLE 4-continued

| STRUCTURE and Example number | HNY¹Y² | Formula | LC-MS: Molecular [M + H]⁺ | R_T (minutes) | METHOD C Nomenclature |
|---|---|---|---|---|---|
| 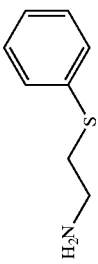<br>EXAMPLE 53 (v) | (3-methylphenyl piperazine structure) | C29H29N5O2 | 480 | 3.29 | 2-[5-Methoxy-3-(1H-pyrrolo[2,3-b]pyridin-2-yl)-indol-1-yl]-1-(4-m-tolyl-piperazin-1-yl)-ethanone |
| 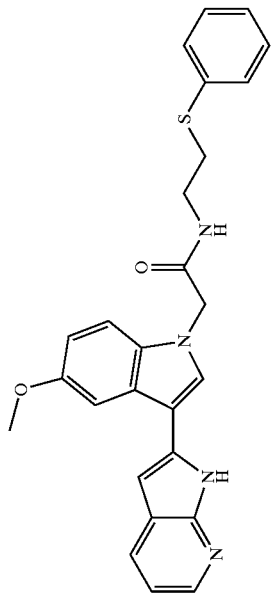<br>EXAMPLE 53 (w) | (2-phenylsulfanyl-ethylamine structure) | C26H24N4O2S | 457 | 3.30 | 2-[5-Methoxy-3-(1H-pyrrolo[2,3-b]pyridin-2-yl)-indol-1-yl]-N-(2-phenylsulfanyl-ethyl)-acetamide |

TABLE 4-continued

| STRUCTURE and Example number | HNY¹Y² | Formula | LC-MS: Molecular [M + H]⁺ | R_T (minutes) | METHOD C Nomenclature |
|---|---|---|---|---|---|
| EXAMPLE 53 (x) | 4-morpholinoaniline | C28H27N5O3 | 482.2 | 2.67 | 2-[5-Methoxy-3-(1H-pyrrolo[2,3-b]pyridin-2-yl)-indol-1-yl]-N-(4-morpholin-4-yl-phenyl)-acetamide |
| EXAMPLE 53 (y) | cyclopropylamine | C21H20N4O2 | 361 & 721 [2M + H]⁺ | 2.76 | N-Cyclopropyl-2-[5-methoxy-3-(1H-pyrrolo[2,3-b]pyridin-2-yl)-indol-1-yl]-acetamide |
| EXAMPLE 53 (z) | 2-methylpiperazine | C23H25N5O2 | 404 | 2.42 | 2-[5-Methoxy-3-(1H-pyrrolo[2,3-b]pyridin-2-yl)-indol-1-yl]-1-(3-methyl-piperazin-1-yl)-ethanone |

TABLE 4-continued

| STRUCTURE and Example number | HNY¹Y² | Formula | LC-MS: Molecular [M + H]⁺ | R_T (minutes) | METHOD C Nomenclature |
|---|---|---|---|---|---|
| 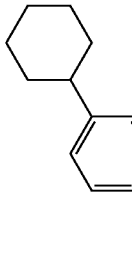<br>EXAMPLE 53 (aa) | 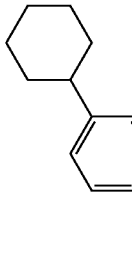 | C30H30N4O2 | 479.3 | 3.88 | N-(4-Cyclohexyl-phenyl)-2-[5-methoxy-3-(1H-pyrrolo[2,3-b]pyridin-2-yl)-indol-1-yl]-acetamide |
| 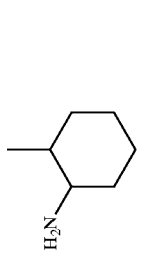<br>EXAMPLE 53 (ab) | 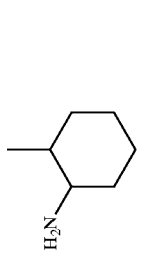 | C25H28N4O2 | 417.3 | 3.30 | 2-[5-Methoxy-3-(1H-pyrrolo[2,3-b]pyridin-2-yl)-indol-1-yl]-N-(2-methyl-cyclohexyl)-acetamide |
| 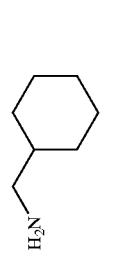<br>EXAMPLE 53 (ac) | 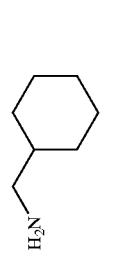 | C25H28N4O2 | 417 | 3.26 | N-Cyclohexylmethyl-2-[5-methoxy-3-(1H-pyrrolo[2,3-b]pyridin-2-yl)-indol-1-yl]-acetamide |

TABLE 4-continued

| STRUCTURE and Example number | HNY¹Y² | Formula | LC-MS: Molecular [M + H]⁺ | R_T (minutes) | METHOD C Nomenclature |
|---|---|---|---|---|---|
| EXAMPLE 53 (ad) | 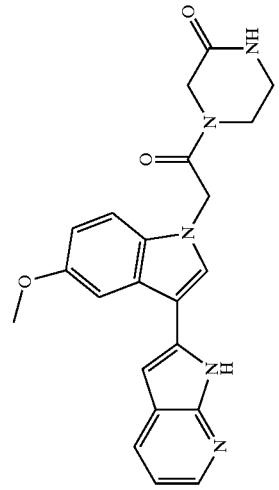 | C22H22N4O2 | 429 | 2.41 | 2-[5-Methoxy-3-(1H-pyrrolo[2,3-b]pyridin-2-yl)-indol-1-yl]-1-pyrrolidin-1-yl ethanone |
| EXAMPLE 53 (ae) | 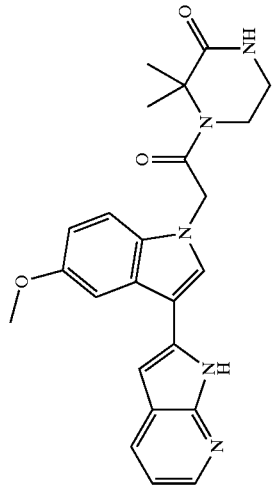 | C22H21N5O3 | 432 | 2.65 | 4-{2-[5-Methoxy-3-(1H-pyrrolo[2,3-b]pyridin-2-yl)-indol-1-yl]-acetyl}-piperazin-2-one |
| EXAMPLE 53 (af) | | C24H25N5O3 | 432 & 863 [2M + H]⁺ | 2.83 | 4-{2-[5-Methoxy-3-(1H-pyrrolo[2,3-b]pyridin-2-yl)-indol-1-yl]-acetyl}-3,3-dimethyl-piperazin-2-one |

TABLE 4-continued

| STRUCTURE and Example number | HNY¹Y² | Formula | LC-MS: Molecular [M + H]⁺ | $R_T$ (minutes) | METHOD C Nomenclature |
|---|---|---|---|---|---|
| 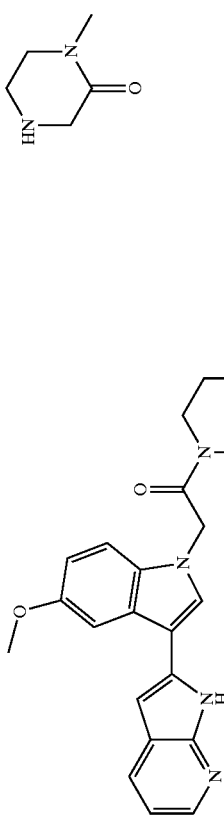 EXAMPLE 53 (ag) | 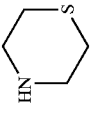 | C23H23N5O3 | 418 | 2.79 | 4-{2-[5-Methoxy-3-(1H-pyrrolo[2,3-b]pyridin-2-yl)-indol-1-yl]-acetyl}-1-methyl-piperazin-2-one |
|  EXAMPLE 53 (ah) | 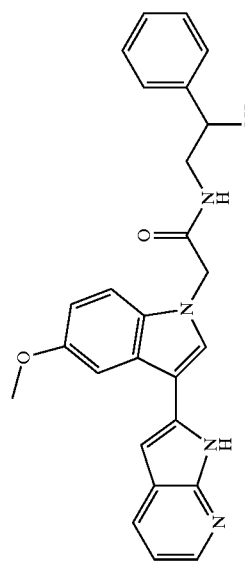 | C22H22N4O2S | 407 | 3.22 | 2-[5-Methoxy-3-(1H-pyrrolo[2,3-b]pyridin-2-yl)-indol-1-yl]-1-thiomorpholin-4-yl-ethanone |
| 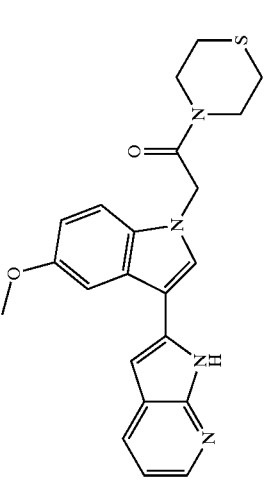 EXAMPLE 53 (ai) | 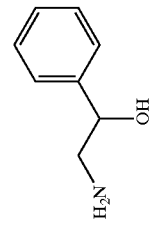 | C26H24N4O3 | 441 | 3.13 | N-(2-Hydroxy-2-phenyl-ethyl)-2-[5-methoxy-3-(1H-pyrrolo[2,3-b]pyridin-2-yl)-indol-1-yl]-acetamide |

TABLE 4-continued

| STRUCTURE and Example number | HNY¹Y² | Formula | LC-MS: Molecular [M + H]⁺ | R_T (minutes) | METHOD C Nomenclature |
|---|---|---|---|---|---|
| EXAMPLE 53 (aj) | (2,6-dimethylmorpholine) | C24H26N4O3 | 419 | 3.19 | 1-(2,6-Dimethyl-morpholin-4-yl)-2-[5-methoxy-3-(1H-pyrrolo[2,3-b]-pyridin-2-yl)-indol-1-yl]-ethanone |
| EXAMPLE 53 (ak) | (4-diethylaminomethyl aniline) | C29H31N5O2 | 482 | 2.88 | N-(4-Diethyl-aminomethyl-phenyl)-2-[5-methoxy-3-(1H-pyrrolo[2,3-b]pyridin-2-yl)-indol-1-yl]-acetamide |
| EXAMPLE 53 (al) | (tyramine) | C26H24N4O3 | 441 | 3.08 | N-[2-(4-Hydroxy-phenyl)-ethyl]-2-[5-methoxy-3-(1H-pyrrolo[2,3-b]pyridin-2-yl)-indol-1-yl]-acetamide |

TABLE 4-continued

| STRUCTURE and Example number | HNY¹Y² | Formula | LC-MS: Molecular [M + H]⁺ | R_T (minutes) | METHOD C Nomenclature |
|---|---|---|---|---|---|
| EXAMPLE 53 (am) | tetrahydrofurfurylamine (H₂N-CH₂-tetrahydrofuran-2-yl) | C23H24N4O3 | 405 | 3.01 | 2-[5-Methoxy-3-(1H-pyrrolo[2,3-b]pyridin-2-yl)-indol-1-yl]-N-(tetrahydro-furan-2-ylmethyl)-acetamide |
| EXAMPLE 53 (an) | 2-(aminomethyl)pyridine | C24H21N5O2 | 412 | 2.68 | 2-[5-Methoxy-3-(1H-pyrrolo[2,3-b]pyridin-2-yl)-indol-1-yl]-N-pyridin-2-ylmethyl-acetamide |
| EXAMPLE 53 (ao) | 1,2-dimethylpropylamine | C23H26N4O2 | 391 | 3.36 | N-(1,2-Dimethyl-propyl)-2-[5-methoxy-3-(1H-pyrrolo[2,3-b]pyridin-2-yl)-indol-1-yl]-acetamide |

TABLE 4-continued

| STRUCTURE and Example number | HNY¹Y² | Formula | LC-MS: Molecular [M + H]⁺ | R_T (minutes) | METHOD C Nomenclature |
|---|---|---|---|---|---|
| EXAMPLE 53 (ap) | | C30H25N5O3 | 504 | 3.25 | N-(3-Benzyloxy-pyridin-2-yl)-2-[5-methoxy-3-(1H-pyrrolo[2,3-b]pyridin-2-yl)-indol-1-yl]-acetamide |
| EXAMPLE 53 (aq) | | C27H21N5O2 | 448 | 3.05 | 2-[5-Methoxy-3-(1H-pyrrolo[2,3-b]pyridin-2-yl)-indol-1-yl]-N-quinolin-3-yl-acetamide |
| EXAMPLE 53 (ar) | | C27H21N5O2 | 448 | 3.49 | 2-[5-Methoxy-3-(1H-pyrrolo[2,3-b]pyridin-2-yl)-indol-1-yl]-N-quinolin-8-yl-acetamide |

TABLE 4-continued
| STRUCTURE and Example number | HNY¹Y² | Formula | LC-MS: Molecular [M + H]⁺ | R_T (minutes) | METHOD C Nomenclature |
|---|---|---|---|---|---|
| EXAMPLE 53 (as) | 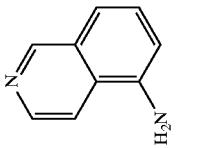 | C27H21N5O2 | 448 | 2.76 | N-Isoquinolin-5-yl-2-[5-methoxy-3-(1H-pyrrolo[2,3-b]pyridin-2-yl)-indol-1-yl]-acetamide |
| EXAMPLE 53 (at) | 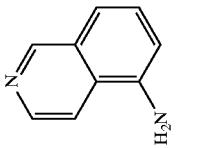 | C23H26N4O2 | 391 | 3.42 | 2-[5-Methoxy-3-(1H-pyrrolo[2,3-b]pyridin-2-yl)-indol-1-yl]-N-(3-methyl-butyl)-acetamide |
| EXAMPLE 53 (au) | 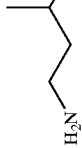 | C27H21N5O2 | 448 | 2.97 | N-Isoquinolin-1-yl-2-[5-methoxy-3-(1H-pyrrolo[2,3-b]pyridin-2-yl)-indol-1-yl]-acetamide |

TABLE 4-continued

| STRUCTURE and Example number | HNY¹Y² | Formula | LC-MS: Molecular [M + H]⁺ | $R_T$ (minutes) | METHOD C Nomenclature |
|---|---|---|---|---|---|
| 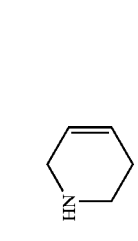<br>EXAMPLE 53 (av) | 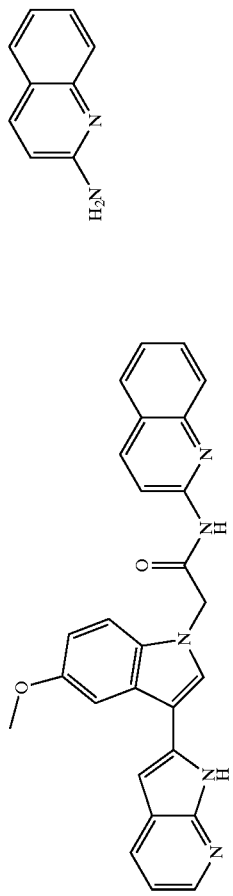 | C27H21N5O2 | 448 | 3.29 | 2-[5-Methoxy-3-(1H-pyrrolo[2,3-b]pyridin-2-yl)-indol-1-yl]-N-quinolin-2-yl-acetamide |
| 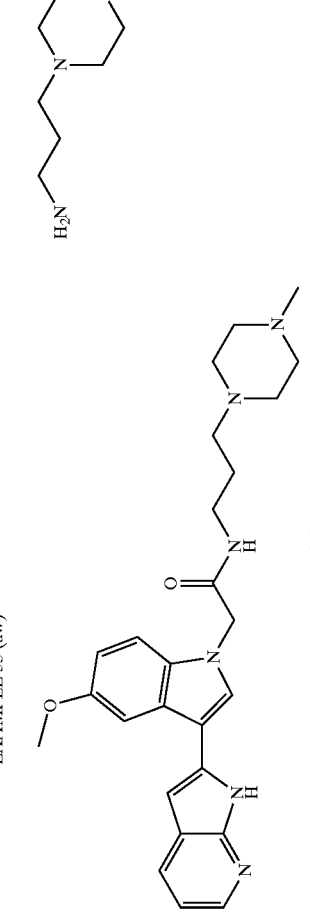<br>EXAMPLE 53 (aw) | 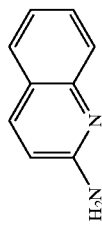 | C23H22N4O2 | 387 & 773, [2M + H]⁺ | 3.28 | 1-(3,6-Dihydro-2H-pyridin-1-yl)-2-[5-methoxy-3-(1H-pyrrolo[2,3-b]pyridin-2-yl)-indol-1-yl]-ethanone |
| 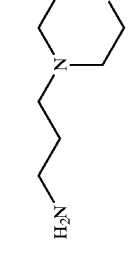<br>EXAMPLE 53 (ax) | 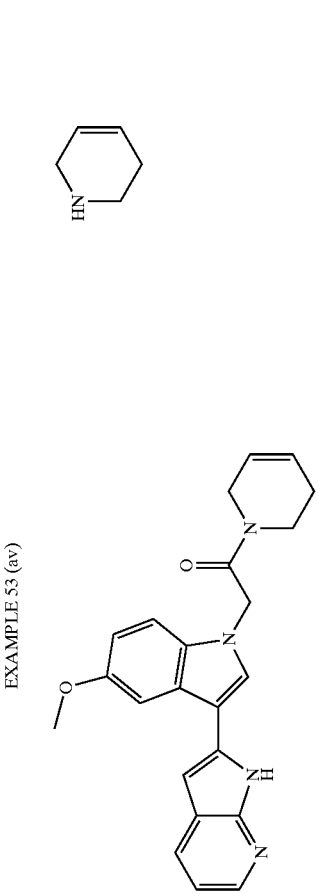 | C26H32N6O2 | 461 | 2.55 | 2-[5-Methoxy-3-(1H-pyrrolo[2,3-b]pyridin-2-yl)-indol-1-yl]-N-[3-(4-methyl-piperazin-1-yl)-propyl]-acetamide |

TABLE 4-continued

| STRUCTURE and Example number | HNY¹Y² | Formula | LC-MS: Molecular [M + H]⁺ | R_T (minutes) | METHOD C Nomenclature |
|---|---|---|---|---|---|
|  EXAMPLE 53 (ay) | 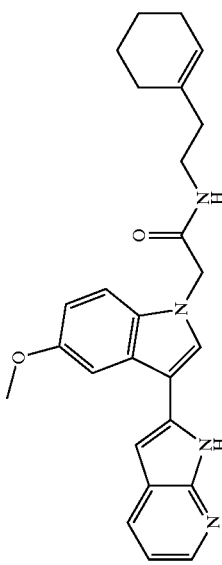 | C26H28N4O2 | 429 | 3.62 | N-(2-Cyclohex-1-enyl-ethyl)-2-[5-methoxy-3-(1H-pyrrolo[2,3-b]pyridin-2-yl)-indol-1-yl]-acetamide |
| 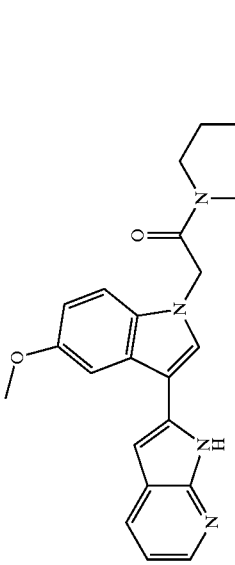 EXAMPLE 53 (az) | 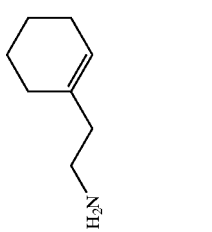 | C28H25N5O2 | 464 | 3.41 | N-[2-(1H-Indol-3-yl)-ethyl]-2-[5-methoxy-3-(1H-pyrrolo[2,3-b]pyridin-2-yl)-indol-1-yl]-acetamide |
| 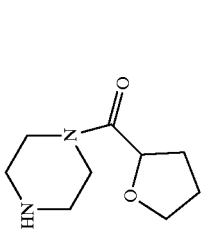 EXAMPLE 53 (ba) | 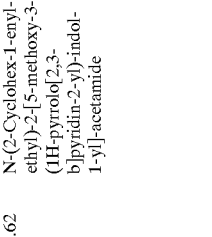 | C27H29N5O4 | 488 | 2.94 | 2-[5-Methoxy-3-(1H-pyrrolo[2,3-b]pyridin-2-yl)-indol-1-yl]-1-[4-(tetrahydro-furan-2-carbonyl)-piperazin-1-yl]-ethanone |

TABLE 4-continued

| STRUCTURE and Example number | HNY¹Y² | Formula | LC-MS: Molecular [M + H]⁺ | R_T (minutes) | METHOD C Nomenclature |
|---|---|---|---|---|---|
| EXAMPLE 53 (bb) | (1-aminoadamantane structure) | C28H30N4O2 | 455 | 3.84 | N-Adamantan-1-yl-2-[5-methoxy-3-(1H-pyrrolo[2,3-b]pyridin-2-yl)-indol-1-yl]-acetamide |
| EXAMPLE 53 (bc) | (N,N-dimethyl-N'-methylethylenediamine structure) | C23H27N5O2 | 406 | 2.72 | N-(2-Dimethylamino-ethyl)-2-[5-methoxy-3-(1H-pyrrolo[2,3-b]pyridin-2-yl)-indol-1-yl]-N-methyl-acetamide |

TABLE 4-continued
| STRUCTURE and Example number | HNY¹Y² | Formula | LC-MS: Molecular [M + H]⁺ | R_T (minutes) | METHOD C Nomenclature |
|---|---|---|---|---|---|
| EXAMPLE 53 (bd) 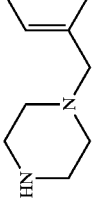 | 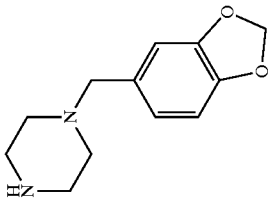 | C30H29N5O4 | 524 | 2.92 | 1-(4-Benzo[1,3]dioxol-5-ylmethyl-piperazin-1-yl)-2-[5-methoxy-3-(1H-pyrrolo[2,3-b]pyridin-2-yl)-indol-1-yl]-ethanone |
| EXAMPLE 53 (be)  | 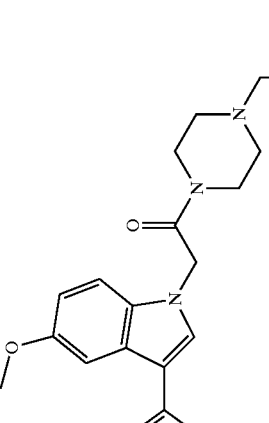 | C29H28ClN5O2 | 514 | 3.03 | 1-[4-(4-Chloro-benzyl)-piperazin-1-yl]-2-[5-methoxy-3-(1H-pyrrolo[2,3-b]pyridin-2-yl)-indol-1-yl]-ethanone |

TABLE 4-continued

| STRUCTURE and Example number | HNY¹Y² | Formula | LC-MS: Molecular [M + H]⁺ | R$_T$ (minutes) | METHOD C Nomenclature |
|---|---|---|---|---|---|
| EXAMPLE 53 (bf) | | C30H31N5O2 | 494 | 2.94 | 2-[5-Methoxy-3-(1H-pyrrolo[2,3-b]pyridin-2-yl)-indol-1-yl]-1-[4-(1-phenyl-ethyl)-piperazin-1-yl]-ethanone |
| EXAMPLE 53 (bg) | | C28H34N6O3 | 503 | 2.61 | 2-[5-Methoxy-3-(1H-pyrrolo[2,3-b]pyridin-2-yl)-indol-1-yl]-1-[4-(2-morpholin-4-yl-ethyl)-piperazin-1-yl]-ethanone |

TABLE 4-continued
| STRUCTURE and Example number | HNY¹Y² | Formula | LC-MS: Molecular [M + H]⁺ | R_T (minutes) | METHOD C Nomenclature |
|---|---|---|---|---|---|
| EXAMPLE 53 (bh) 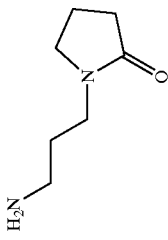 | | C29H29N5O3 | 496 | 3.16 | 1-[4-(4-Methoxy-phenyl)-piperazin-1-yl]-2-[5-methoxy-3-(1H-pyrrolo[2,3-b]pyridin-2-yl)-indol-1-yl]-ethanone |
| EXAMPLE 53 (bi) 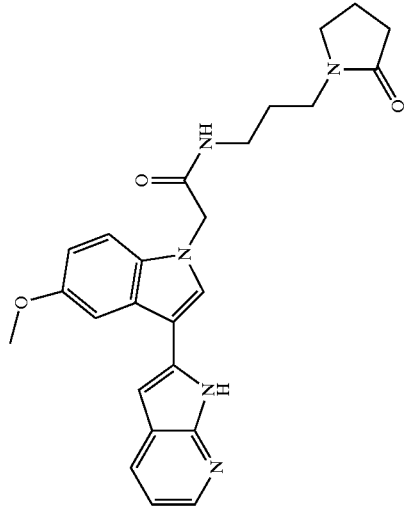 | | C25H27N5O3 | 446 | 3.26 | 2-[5-Methoxy-3-(1H-pyrrolo[2,3-b]pyridin-2-yl)-indol-1-yl]-N-[3-(2-oxo-pyrrolidin-1-yl)-propyl]-acetamide |

TABLE 4-continued

| STRUCTURE and Example number | HNY¹Y² | Formula | LC-MS: Molecular [M + H]⁺ | R_T (minutes) | METHOD C Nomenclature |
|---|---|---|---|---|---|
| EXAMPLE 53 (bj) | 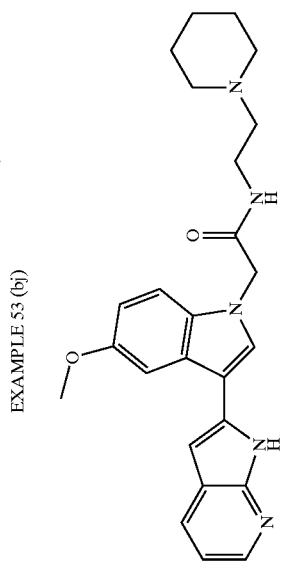 | C23H24N4O2 | 389 | 3.26 | 2-[5-Methoxy-3-(1H-pyrrolo[2,3-b]pyridin-2-yl)-indol-1-yl]-1-piperidin-1-yl-ethanone |
| EXAMPLE 53 (bk) | 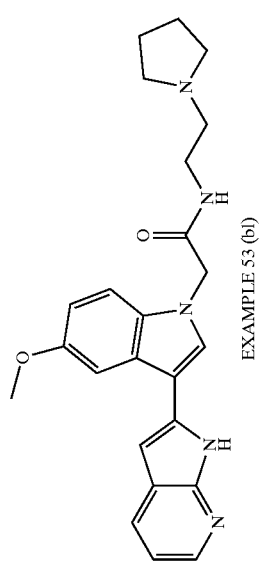 | C25H29N5O2 | 432 | 2.71 | 2-[5-Methoxy-3-(1H-pyrrolo[2,3-b]pyridin-2-yl)-indol-1-yl]-N-(2-piperidin-1-yl-ethyl)-acetamide |
| EXAMPLE 53 (bl) | | C24H27N5O2 | 418 | 2.66 | 2-[5-Methoxy-3-(1H-pyrrolo[2,3-b]pyridin-2-yl)-indol-1-yl]-N-(2-pyrrolidin-1-yl-ethyl)-acetamide |

TABLE 4-continued

| STRUCTURE and Example number | HNY¹Y² | Formula | LC-MS: Molecular [M + H]⁺ | R_T (minutes) | METHOD C Nomenclature |
|---|---|---|---|---|---|
| EXAMPLE 53 (bm) 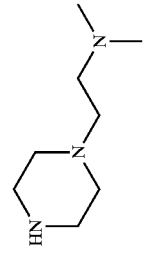 | 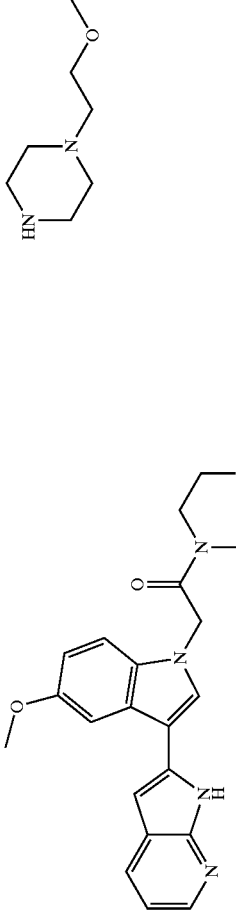 | C25H29N5O3 | 448 | 2.68 | 1-[4-(2-Methoxy-ethyl)-piperazin-1-yl]-2-[5-methoxy-3-(1H-pyrrolo[2,3-b]pyridin-2-yl)-indol-1-yl]-ethanone |
| EXAMPLE 53 (bn) 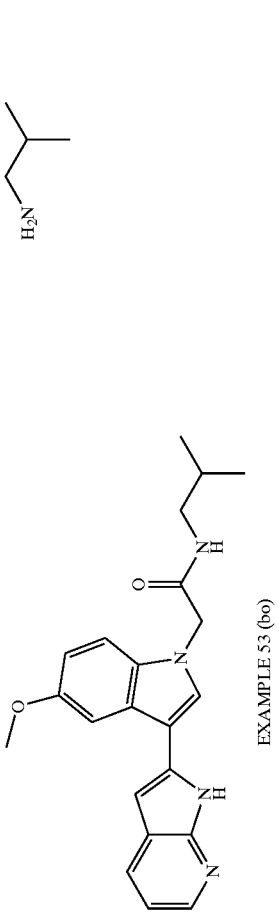 | 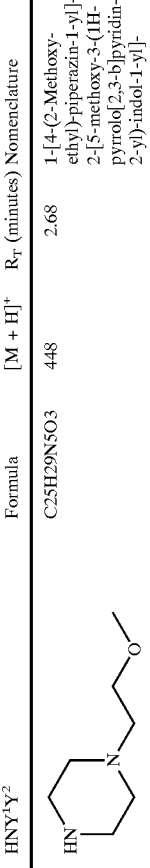 | C26H32N6O2 | 461 | 2.59 | 1-[4-(2-Dimethyl-amino-ethyl)-piperazin-1-yl]-2-[5-methoxy-3-(1H-pyrrolo[2,3-b]pyridin-2-yl)-indol-1-yl]-ethanone |
| EXAMPLE 53 (bo) 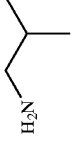 | 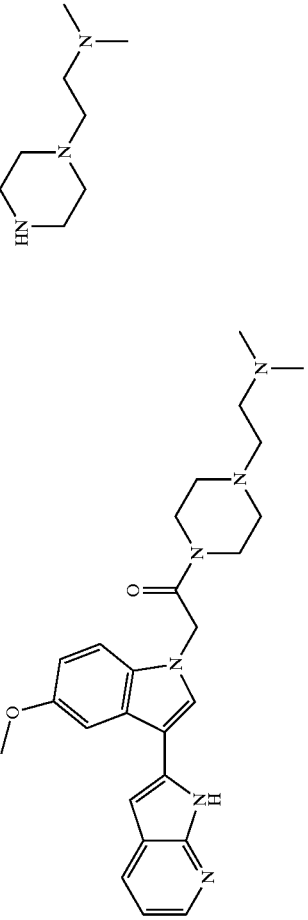 | C22H24N4O2 | 377 | 3.27 | N-Isobutyl-2-[5-methoxy-3-(1H-pyrrolo[2,3-b]pyridin-2-yl)-indol-1-yl]-acetamide |

TABLE 4-continued
| STRUCTURE and | | | LC-MS: Molecular | | METHOD C |
|---|---|---|---|---|---|
| Example number | HNY¹Y² | Formula | [M + H]⁺ | R_T (minutes) | Nomenclature |
| EXAMPLE 53 (bp) 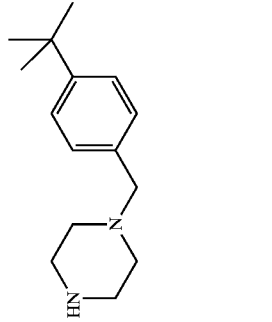 | 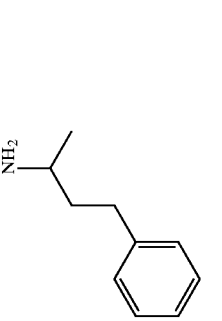 | C33H37N5O2 | 536 | 3.20 | 1-[4-(4-tert-Butyl-benzyl)-piperazin-1-yl]-2-[5-methoxy-3-(1H-pyrrolo[2,3-b]pyridin-2-yl)-indol-1-yl]-ethanone |
| EXAMPLE 53 (bq) | | C28H28N4O2 | 453 | 3.63 | 2-[5-Methoxy-3-(1H-pyrrolo[2,3-b]pyridin-2-yl)-indol-1-yl]-N-(1-methyl-3-phenyl-propyl)-acetamide |

TABLE 4-continued
| STRUCTURE and Example number | HNY¹Y² | Formula | LC-MS: Molecular [M + H]⁺ | R_T (minutes) | METHOD C Nomenclature |
|---|---|---|---|---|---|
| 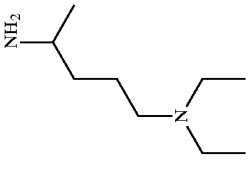<br>EXAMPLE 53 (br) | 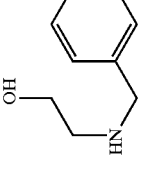 | C27H35N5O2 | 462 | 2.74 | N-(4-Diethylamino-1-methyl-butyl)-2-[5-methoxy-3-(1H-pyrrolo[2,3-b]pyridin-2-yl)-indol-1-yl]-acetamide |
| 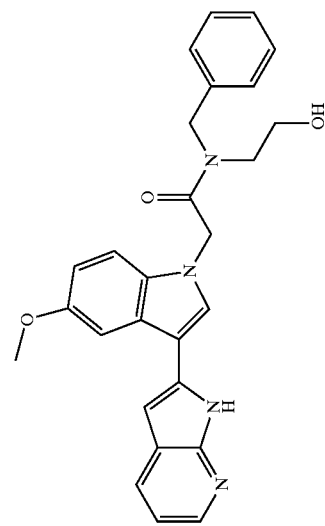<br>EXAMPLE 53 (bs) | | C27H26N4O3 | 455 | 3.33 | N-Benzyl-N-(2-hydroxy-ethyl)-2-[5-methoxy-3-(1H-pyrrolo[2,3-b]pyridin-2-yl)-indol-1-yl]-acetamide |

TABLE 4-continued

| STRUCTURE and Example number | HNY¹Y² | Formula | LC-MS: Molecular [M + H]⁺ | R_T (minutes) | METHOD C Nomenclature |
|---|---|---|---|---|---|
| EXAMPLE 53 (bt) | [piperazine with ethoxyethanol chain] | C26H31N5O4 | 478 | 2.65 | 1-{4-[2-(2-Hydroxy-ethoxy)-ethyl]-piperazin-1-yl}-2-[5-methoxy-3-(1H-pyrrolo[2,3-b]pyridin-2-yl)-indol-1-yl]-ethanone |
| EXAMPLE 53 (bu) | [2-amino-3-methylpentan-1-ol] | C24H28N4O3 | 421 | 3.19 | N-(1-Hydroxymethyl-2-methyl-butyl)-2-[5-methoxy-3-(1H-pyrrolo[2,3-b]pyridin-2-yl)-indol-1-yl]-acetamide |
| EXAMPLE 53 (bv) | [N-methylbenzylamine] | C26H24N4O2 | 425 | 3.52 | N-Benzyl-2-[5-methoxy-3-(1H-pyrrolo[2,3-b]pyridin-2-yl)-indol-1-yl]-N-methyl-acetamide |

TABLE 4-continued

| STRUCTURE and Example number | HNY¹Y² | Formula | LC-MS: Molecular [M + H]⁺ | R_T (minutes) | METHOD C Nomenclature |
|---|---|---|---|---|---|
| EXAMPLE 53 (bw) | H₂N-CH(CH₃)-CH₂-OCH₃ | C22H24N4O3 | 393 | 3.05 | N-(2-Methoxy-1-methyl-ethyl)-2-[5-methoxy-3-(1H-pyrrolo[2,3-b]pyridin-2-yl)-indol-1-yl]-acetamide |
| EXAMPLE 53 (bx) | H₂N-(CH₂)₃-OH | C21H22N4O3 | 379, & 757, [2M + H]⁺ | 2.79 | N-(3-Hydroxy-propyl)-2-[5-methoxy-3-(1H-pyrrolo[2,3-b]pyridin-2-yl)-indol-1-yl]-acetamide |
| EXAMPLE 53 (by) | 3-methoxyaniline | C25H22N4O3 | 427 | 3.45 | N-(3-Methoxy-phenyl)-2-[5-methoxy-3-(1H-pyrrolo[2,3-b]pyridin-2-yl)-indol-1-yl]-acetamide |

TABLE 4-continued

| STRUCTURE and Example number | HNY¹Y² | Formula | LC-MS: Molecular [M + H]⁺ | R_T (minutes) | METHOD C Nomenclature |
|---|---|---|---|---|---|
| EXAMPLE 53 (bz) | | C35H33N5O2 | 556 | 3.25 | 1-(4-Benzhydryl-piperazin-1-yl)-2-[5-methoxy-3-(1H-pyrrolo[2,3-b]pyridin-2-yl)-indol-1-yl]-ethanone |
| EXAMPLE 53 (ca) | | C29H29N5O2 | 480 | 2.9 | 1-(4-Benzyl-piperazin-1-yl)-2-[5-methoxy-3-(1H-pyrrolo[2,3-b]pyridin-2-yl)-indol-1-yl]-ethanone |

TABLE 4-continued

| STRUCTURE and Example number | HNY¹Y² | Formula | LC-MS: Molecular [M + H]⁺ | R_T (minutes) | METHOD C Nomenclature |
|---|---|---|---|---|---|
| EXAMPLE 53 (cb) | | C25H29N5O2 | 432 | 2.67 | 2-[5-Methoxy-3-(1H-pyrrolo[2,3-b]pyridin-2-yl)-indol-1-yl]-N-(3-pyrrolidin-1-yl-propyl)-acetamide |
| EXAMPLE 53 (cc) | | C30H31N5O2 | 494 | 2.89 | N-(1-Benzyl-piperidin-4-yl)-2-[5-methoxy-3-(1H-pyrrolo[2,3-b]pyridin-2-yl)-indol-1-yl]-acetamide |

TABLE 4-continued

| STRUCTURE and Example number | HNY¹Y² | Formula | LC-MS: Molecular [M + H]⁺ | $R_T$ (minutes) | METHOD C Nomenclature |
|---|---|---|---|---|---|
| EXAMPLE 53 (cd) | | C29H27ClN4O3 | 515 | 3.50 | 1-[4-(4-Chloro-phenyl)-4-hydroxy-piperidin-1-yl]-2-[5-methoxy-3-(1H-pyrrolo[2,3-b]pyridin-2-yl)-indol-1-yl]-ethanone |
| EXAMPLE 53 (ce) | | C25H28N4O4 | 449 | 3.44 | 2-[2-[5-Methoxy-3-(1H-pyrrolo[2,3-b]pyridin-2-yl)-indol-1-yl]-acetylamino}-3-methyl-pentanoic acid methyl ester |

TABLE 4-continued
| STRUCTURE and | | LC-MS: Molecular | | METHOD C |
|---|---|---|---|---|
| Example number | HNY¹Y² | Formula | [M + H]⁺ | R_T (minutes) | Nomenclature |
| | 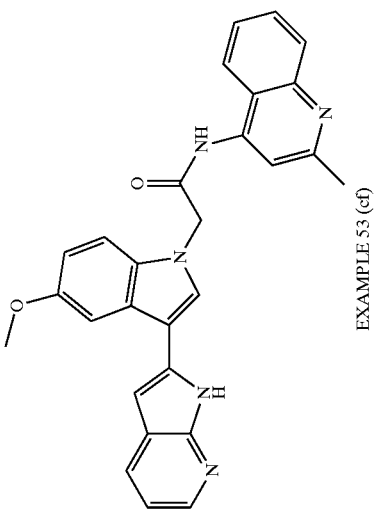 | C28H23N5O2 | 462 | 2.89 | 2-[5-Methoxy-3-(1H-pyrrolo[2,3-b]pyridin-2-yl)-indol-1-yl]-N-(2-methyl-quinolin-4-yl)-acetamide |
| 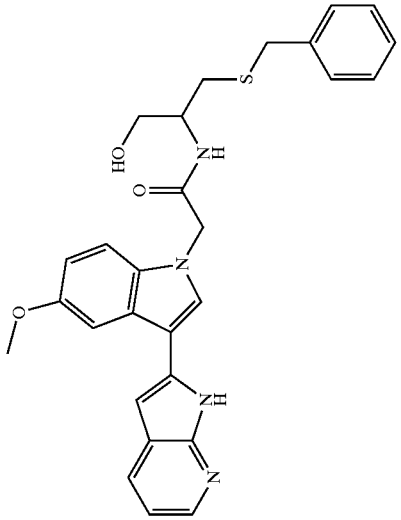
EXAMPLE 53 (cf) | | | | | |
| | 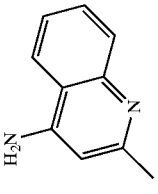 | C28H28N4O3S | 501 | 3.40 | N-(2-Benzylsulfanyl-1-hydroxymethyl-ethyl)-2-[5-methoxy-3-(1H-pyrrolo[2,3-b]pyridin-2-yl)-indol-1-yl]-acetamide |
| 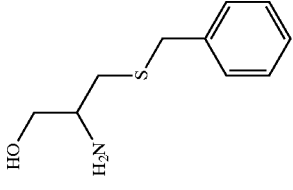
EXAMPLE 53 (cg) | | | | | |

EXAMPLE 54

[2-(1H-Pyrrolo[2,3-b]pyridin-2-yl)-pyrrol-1-yl]-acetic acid, A2-B116, the product of the combination of group A2 in Table 1 and B116 in Table 2:

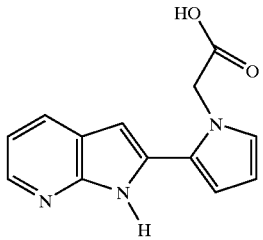

A suspension of [2-(1-(toluene-4-sulfonyl)-1H-pyrrolo[2,3-b]pyridin-2-yl)-pyrrol-1-yl]-acetic acid, tert-butyl ester [400 mg, Reference Example 76] in methanolic potassium hydroxide solution (15.4 mL, 100 mg/mL) was agitated for 19 hours at room temperature then treated with dichloromethane (15 mL). This mixture was titrated with aqueous hydrochloric acid (1N) to adjsut the pH to 2, then decanted. The organic phase was separated and the aqueous phase was extracted with dichloromethane (10 mL). The combined organic phases were washed with water (15 mL) and then evaporated yielding the title compound (137 mg). LC-MS: METHOD C: $R_T$=2.20 minutes, 242.1[M+H$^+$ and 198.1 (decarboxylated fragment).

EXAMPLE 55

2-{[2-(1H-Pyrrolo[2,3-b]pyridin-2-yl)-pyrrol-1-yl]-1-cyclopropylamino}-ethanone.

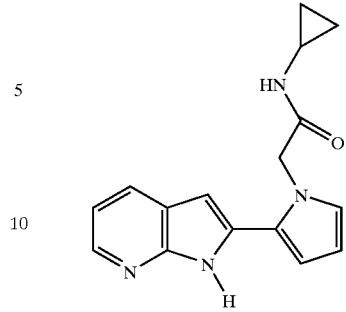

A mixture of [2-(1H-pyrrolo[2,3-b]pyridin-2-yl)-pyrrol-1-yl]-acetic acid [10 mg, Example 54] and 2-(1H-benzotriazole-1-yl)1,1,3,3-tetramethyluronium hexafluorophosphate (15.7 mg) in dry dimethylformamide (0.2 mL) was agitated for 1 hour then treated with cyclopropylamine (5.68 μL) and diisopropylethylamine (7.16 μL) in dry dimethylformamide (0.226 mL). After agitating for a further 15 hours the crude mixture was subjected to LC-MS triggered purification affording the title compound. LC-MS: METHOD C: $R_T$=2.44 minutes, 281[M+H]$^+$ and 224 (fragment corresponding to the breaking of the amide bond).

By proceeding in a similar manner to Example CCR4, but replacing cyclopropylamine with an appropriately substituted amine of formula HNY$^1$Y$^2$, there was prepared EXAMPLE 55(a) to EXAMPLE 55(q) in Table 5. In the LC-MS of EXAMPLE 55(a) to EXAMPLE 55(q) the major ion was 224(fragment corresponding to the breaking of the amide bond).

TABLE 5

| STRUCTURE and Example number | HNY¹Y² | Formula | LC-MS: Molecular [M + H]⁺ | R_T (minutes) | METHOD C Nomenclature |
|---|---|---|---|---|---|
| EXAMPLE 55 (a) | H₂N-propyl-O-ethyl | C18H22N4O2 | 327 | 2.44 | N-(3-Ethoxy-propyl)-2-[2-(1H-pyrrolo[2,3-b]pyridin-2-yl)-pyrrol-1-yl]-acetamide |
| EXAMPLE 55 (b) | pyrrolidine | C17H18N4O | 295 | 2.40 | 1-Pyrrolidin-1-yl-2-[2-(1H-pyrrolo[2,3-b]pyridin-2-yl)-pyrrol-1-yl]-ethanone |
| EXAMPLE 55 (c) | 1,2,3,6-tetrahydropyridine | C18H18N4O | 307 | 2.56 | 1-(3,6-Dihydro-2H-pyridin-1-yl)-2-[2-(1H-pyrrolo[2,3-b]pyridin-2-yl)-pyrrol-1-yl]-ethanone |

TABLE 5-continued
| STRUCTURE and Example number | HNY¹Y² | Formula | LC-MS: Molecular [M + H]⁺ | R_T (minutes) | METHOD C Nomenclature |
|---|---|---|---|---|---|
| 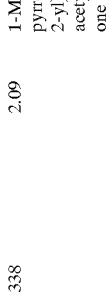 EXAMPLE 55 (d) |  | C18H19N5O2 | 338 | 2.09 | 1-Methyl-4-{2-[2-(1H-pyrrolo[2,3-b]pyridin-2-yl)-pyrrol-1-yl]-acetyl]-piperazin-2-one |
|  EXAMPLE 55(e) |  | C18H20N4O2 | 325 | 2.33 | 2-[2-(1H-Pyrrolo[2,3-b]pyridin-2-yl)-pyrrol-1-yl]-N-(tetrahydro-furan-2-ylmethyl)-acetamide |
|  EXAMPLE 55(f) |  | C19H22N4O2 | 339 | 2.51 | 1-(2,6-Dimethyl-morpholin-4-yl)-2-[2-(1H-pyrrolo[2,3-b]pyridin-2-yl)-pyrrol-1-yl]-ethanone |

TABLE 5-continued
| STRUCTURE and Example number | HNY$^1$Y$^2$ | Formula | LC-MS: Molecular [M + H]$^+$ | R$_T$ (minutes) | METHOD C Nomenclature |
|---|---|---|---|---|---|
| 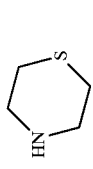 EXAMPLE 55(g) | 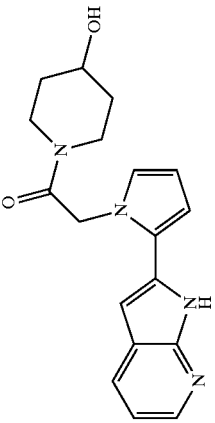 | C17H18N4OS | 327 | 2.52 | 2-[2-(1H-Pyrrolo[2,3-b]pyridin-2-yl)-pyrrolo-1-yl]-1-thiomorpholin-4-yl-ethanone |
| 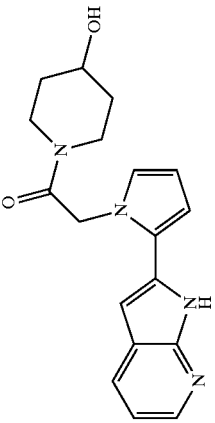 EXAMPLE 55(h) | 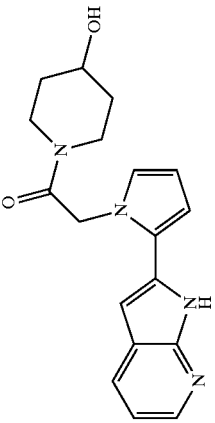 | C18H20N4O2 | 325 | 2.10 | 1-(4-Hydroxy-piperidin-1-yl)-2-[2-(1H-pyrrolo[2,3-b]pyridin-2-yl)-pyrrol-1-yl]-ethanone |
| 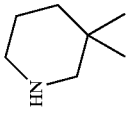 EXAMPLE 55(i) | 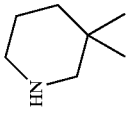 | C20H24N4O | 337 | 2.94 | 1-(3,3-Dimethyl-piperidin-1-yl)-2-[2-(1H-pyrrolo[2,3-b]pyridin-2-yl)-pyrrol-1-yl]-ethanone |

TABLE 5-continued

| STRUCTURE and Example number | HNY¹Y² | Formula | LC-MS: Molecular [M + H]⁺ | R_T (minutes) | METHOD C Nomenclature |
|---|---|---|---|---|---|
| EXAMPLE 55(j) | | C17H17N5O2 | 324 | 2.02 | 4-{2-[2-(1H-Pyrrolo[2,3-b]pyridin-2-yl)-pyrrol-1-yl]-acetyl}-piperazin-2-one |
| EXAMPLE 55(k) | | C18H22N4O | 311 | 3.00 | N-(1-Methyl-butyl)-2-[2-(1H-pyrrolo[2,3-b]pyridin-2-yl)-pyrrol-1-yl]-acetamide |
| EXAMPLE 55(l) | | C20H22N4O | 335 | 3.11 | N-Bicyclo[2.2.1]hept-2-yl-2-[2-(1H-pyrrolo[2,3-b]pyridin-2-yl)-pyrrol-1-yl]-acetamide |

TABLE 5-continued

| STRUCTURE and Example number | HNY¹Y² | Formula | LC-MS: Molecular [M + H]⁺ | R_T (minutes) | METHOD C Nomenclature |
|---|---|---|---|---|---|
| EXAMPLE 55 (m) | H₂N-(CH₂)₃-piperazine-N-Me | C21H28N6O | 381 | 2.18 | N-[3-(4-Methyl-piperazin-1-yl)-propyl]-2-[2-(1H-pyrrolo[2,3-b]pyridin-2-yl)-pyrrol-1-yl]-acetamide |
| EXAMPLE 55 (n) | (CH₃)₂N-(CH₂)₃-piperazine | C22H30N6O | 395 | 2.12 | 1-[4-(3-Dimethylamino-propyl)-piperazin-1-yl]-2-[2-(1H-pyrrolo[2,3-b]pyridin-2-yl)-pyrrol-1-yl]-ethanone |
| EXAMPLE 55 (o) | N-methylpiperazine | C18H21N5O | 324 | 2.15 | 1-(4-Methyl-piperazin-1-yl)-2-[2-(1H-pyrrolo[2,3-b]pyridin-2-yl)-pyrrol-1-yl]-ethanone |

TABLE 5-continued
| STRUCTURE and | | | LC-MS: Molecular | | METHOD C |
|---|---|---|---|---|---|
| Example number | HNY¹Y² | Formula | [M + H]⁺ | R$_T$ (minutes) | Nomenclature |
| 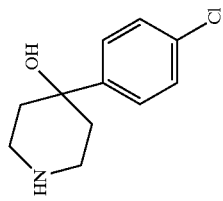 EXAMPLE 55 (p) | | C24H23ClN4O2 | 435 | 3.19 | 1-[4-(4-Chlorophenyl)-4-hydroxy-piperidin-1-yl]-2-[2-(1H-pyrrolo[2,3-b]pyridin-2-yl)-pyrrol-1-yl]-ethanone |
| 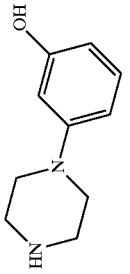 EXAMPLE 55 (q) | | C23H23N5O2 | 402 | 2.74 | 1-[4-(3-Hydroxy-phenyl)-piperazin-1-yl]-2-[2-(1H-pyrrolo[2,3-b]pyridin-2-yl)-pyrrol-1-yl]-ethanone |

EXAMPLE 56

3-[5-Methoxy-2-(1H-pyrrolo[2,3-b]pyridin-2-yl)-1-(toluene-4-sulfonyl)-indol-1-yl]-propionic acid.

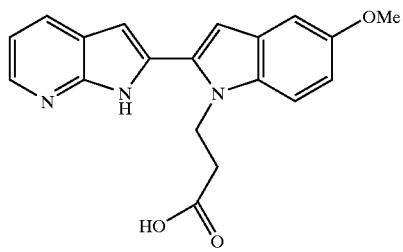

A mixture of 3-[5-methoxy-2-(1H-pyrrolo[2,3-b]pyridin-2-yl)-1-(toluene-4-sulfonyl)-indol-1-yl]-propionic acid, methyl ester [100 mg, Reference example 77] and potassium hydroxide [352 mg] in methanol (3.5 mL) was agitated at room temperature for 21.5 hours. The reaction mixture was then evaporated and the residue was resuspended in dichloromethane (10 mL) to which water (5 mL) was added. This mixture was titrated until pH=2 with 1N aqueous hydrochloric acid. The resulting precipitate was filtered yielding the title compound (46 mg) as a cream solid. LC-MS: METHOD C: $R_T$=2.76 minutes, 336.14 [M+H]+ and 224 (fragment of major intensity corresponding to the breaking of the amide bond.

EXAMPLE 57

3-[5-Methoxy-2-(1H-pyrrolo[2,3-b]pyridin-2-yl)-indol-1-yl]-1-morpholin-4-yl-propan-1-one

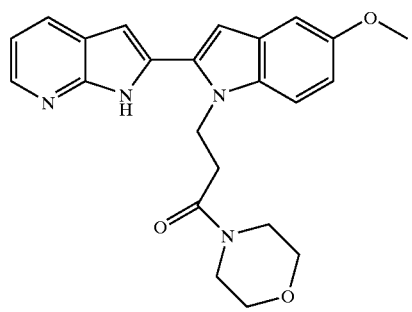

A mixture of 3-[5-methoxy-2-(1H-pyrrolo[2,3-b]pyridin-2-yl)-1-(toluene-4-sulfonyl)-indol-1-yl]-propionic acid [10 mg, Example 56] and 2-(1H-benzotriazole-1-yl)1,1,3,3-tetramethyluronium hexafluorophosphate (11.2 mg) in dry dimethylformamide (0.41 mL) was agitated for 45 minutes then treated with a solution of morpholine (5.23 μL) and diisopropylethylamine (5.24 μL) in dry dimethylformamide (0.126 mL). The reaction mixture was agitated for a further 15 hours then subjected to LC-MS triggered purification affording the title compound. LC-MS: METHOD C: $R_T$=2.78 minutes, 405.2[M+H]+.

By proceeding in a similar manner to Example 57, but replacing morpholine with an appropriately substituted amine of formula $HNY^1Y^2$, there was prepared EXAMPLE 57(a) to EXAMPLE 57(f) in Table 6.

TABLE 6

| STRUCTURE and Example number | $HNY^1Y^2$ | Molecular Formula | LC-MS: METHOD C [M + H]+ | $R_T$ (minutes) | Nomenclature |
|---|---|---|---|---|---|
| EXAMPLE 57 (a) | | C25H22N4O2 | 411.2 | 3.18 | 3-[5-Methoxy-2-(1H-pyrrolo[2,3-b]pyridin-2-yl)-indol-1-yl]-N-phenyl-propionamide |
| EXAMPLE 57 (b) | | C23H24N4O2S | 421.2 | 3.07 | 3-[5-Methoxy-2-(1H-pyrrolo[2,3-b]pyridin-2-yl)-indol-1-yl]-1-thiomorpholin-4-yl-propan-1-one |

TABLE 6-continued

| STRUCTURE and Example number | HNY¹Y² | Molecular Formula | LC-MS: METHOD C [M + H]⁺ | R_T (minutes) | Nomenclature |
|---|---|---|---|---|---|
| 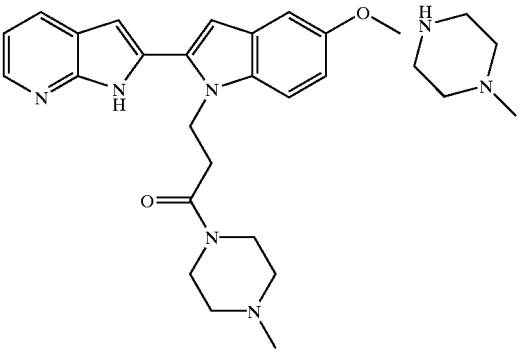 EXAMPLE 57 (c) | | C24H27N5O2 | 418.2 | 2.42 | 3-[5-Methoxy-2-(1H-pyrrolo[2,3-b]pyridin-2-yl)-indol-1-yl]-1-(4-methyl-piperazin-1-yl)-propan-1-one |
| 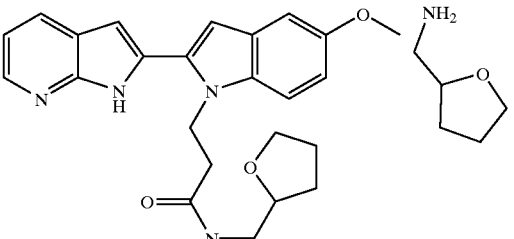 EXAMPLE 57 (d) | | C24H26N4O3 | 419 | 3.13 | 3-[5-Methoxy-2-(1H-pyrrolo[2,3-b]pyridin-2-yl)-indol-1-yl]-N-(tetrahydro-furan-2-ylmethyl)-propionamide |
| 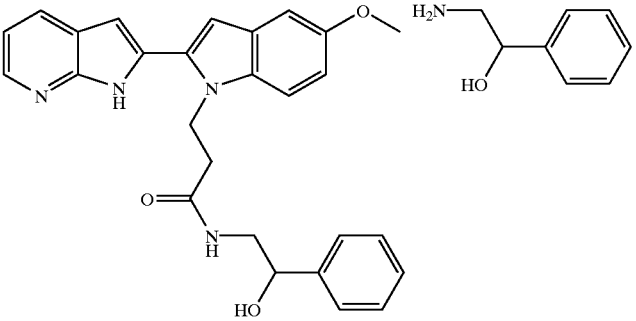 EXAMPLE 57 (e) | | C27H26N4O3 | 455 | 3.13 | N-(2-Hydroxy-2-phenyl-ethyl)-3-[5-methoxy-2-(1H-pyrrolo[2,3-b]pyridin-2-yl)-indol-1-yl]-propionamide |
| 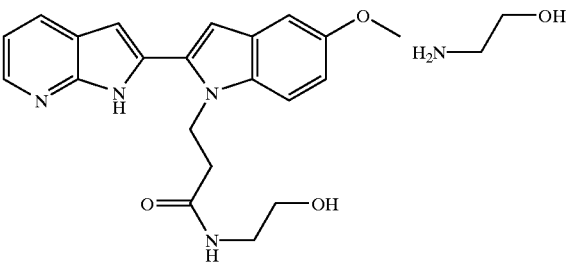 EXAMPLE 57 (f) | | C21H22N4O3 | 379 & 757 [2M + H]⁺ | 2.67 | N-(2-Hydroxy-ethyl)-3-[5-methoxy-2-(1H-pyrrolo[2,3-b]pyridin-2-yl)-indol-1-yl]-propionamide |

EXAMPLE 58
1-[4-(4-Chloro-phenyl)-4-hydroxy-piperidin-1-yl]-2-[5-methoxy-2-(1H-pyrrolo[2,3-b]pyridin-2-yl)-indol-1-yl]-ethanone

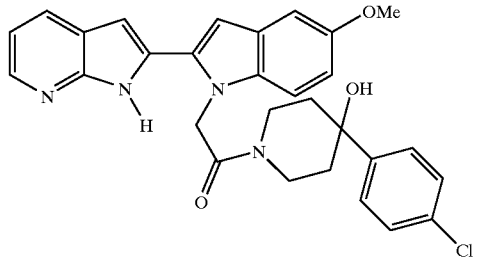

A solution of 3-[5-methoxy-2-(1H-pyrrolo[2,3-b]pyridin-2-yl)-1-(toluene-4-sulfonyl)-indol-1-yl acid, tert-butyl ester [22.6 mg, Reference Example 78] in methanolic potassium hydroxide solution (742 µL, 100 mg/mL) was agitated for 15 hours at room temperature and then evaporated. The residue was suspended in dichloromethane (1 mL) and treated with water followed by aqueous hydrochloric acid (1N) until the pH of the solution was 1. The organic phase was decanted, then dried over magnesium sulfate and then evaporated. The residue was suspended in dry dimethylformamide (1.27 mL) and this mixture was treated with 2-(1H-benzotriazole-1-yl) 1,1,3,3-tetramethyluronium hexafluorophosphate (32 mg). After agitating for 1 hour the mixture was treated with 4-(4-chorophenyl)-4-hydroxypiperidine (35.6 mg) and diisopropylethylamine (14.7 µL), then agitated for a further 15 hours and then evaporated using a centrifuge evaporator. The residue was suspended in dimethylsulfoxide (3 mL) and subjected to LC-MS triggered purification in 6 injections affording the title compound (1.5 mg). LC-MS: METHOD C: $R_T$=3.28 minutes, 515.1[M+H]$^+$ and 304.1(fragment of major intensity corresponding to the breaking of the amide bond).

EXAMPLE 59
2-(5-Methoxy-1-methyl-1H-indol-3-yl)-4-morpholin-4-yl-1H-pyrrolo[2,3-b]pyridine, A20-B1-C1, the product of the combination of group A20 in Table 1 and B1 in Table 2 and C1 in Table 3:

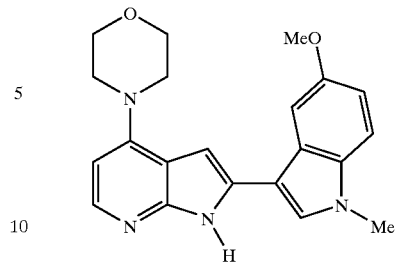

Into a tube containing cesium carbonate (153 mg) was added (i) a solution of 4-chloro-2-(5-methoxy-1-methyl-1H-indol-3-yl)-1-(toluene-4-sulfonyl)-1H-pyrrolo[2,3-b]pyridine [50 mg, Reference Example 13(i)] in 1,2-dimethoxyethane (1 mL), (ii) tris-(dibenzylideneacetone)-dipalladium(0) (15 mg) in 1,2-dimethoxyethane (0.5 mL), (iii) 2-dicyclohexylphosphino-2'-(N,N-dimethylamino)-biphenyl (42 mg) in 1,2-dimethoxyethane (0.5 mL) and (iv) morpholine (30 mg). This mixture was heated under agitation at 80° C. for 15 hours and then filtered on a silica plug that was then washed with dichloromethane and methanol (1 mL each). The combined filtrate plus washings were evaporated using a centrifuge evaporator. The residue was dissolved in dimethylsulfoxyde (1 mL) and then subjected to LC-MS triggered purification (injections corresponding to 20 mg crude compound) affording 4-(morpholine-4-yl)-2-(5-methoxy-1-methyl-1H-indol-3-yl)-1-(toluene-4-sulfonyl)-1H-pyrrolo[2,3-b]pyridine which was resuspended in methanol (2 mL) and magnesium turnings (89 mg, 15 equivalents from the mass measured after evaporation of the chromatographic solvent) were added. The suspension was then agitated for 15 hours at room temperature and then filtered on Celite. The filtrate was evaporated and the residue was solubilized in dimethylsulfoxide and subjected to LC-MS triggered purification according affording the title compound. LC-MS: METHOD C: $R_T$=3.27 minutes, 363.3 [M+H]$^+$.

By proceeding in a similar manner to Example 59, but replacing morpholine with an appropriately substituted amine of formula HNY$^1$Y$^2$, there was prepared EXAMPLE 59(a) to EXAMPLE 59(p) in Table 7.

TABLE 7

| STRUCTURE and Example number | HNY$^1$Y$^2$ | Molecular Formula | LC-MS: METHOD C [M + H]$^+$ | $R_T$ (minutes) | Nomenclature |
|---|---|---|---|---|---|
| EXAMPLE 59 (a) | | C22H24N4O | 361 | 3.72 | 2-(5-Methoxy-1-methyl-1H-indol-3-yl)-4-piperidin-1-yl-1H-pyrrolo[2,3-b]pyridine |

TABLE 7-continued

| STRUCTURE and Example number | HNY¹Y² | Molecular Formula | LC-MS: METHOD C | | Nomenclature |
|---|---|---|---|---|---|
| | | | [M + H]⁺ | R_T (minutes) | |
| EXAMPLE 59 (b) | 2-methoxyaniline | C24H22N4O2 | 399.3 | 3.59 | [2-(5-Methoxy-1-methyl-1H-indol-3-yl)-1H-pyrrolo[2,3-b]pyridin-4-yl]-(2-methoxy-phenyl)-amine |
| EXAMPLE 59 (c) | 2-methylaniline | C24H22N4O | 383.3 | 3.68 | [2-(5-Methoxy-1-methyl-1H-indol-3-yl)-1H-pyrrolo[2,3-b]pyridin-4-yl]-o-tolyl-amine |
| EXAMPLE 59 (d) | 3-methoxyaniline | C24H22N4O2 | 399.3 | 3.64 | [2-(5-Methoxy-1-methyl-1H-indol-3-yl)-1H-pyrrolo[2,3-b]pyridin-4-yl]-(3-methoxy-phenyl)-amine |
| EXAMPLE 59 (e) | 3-methylaniline | C24H22N4O | 383.2 | 3.74 | [2-(5-Methoxy-1-methyl-1H-indol-3-yl)-1H-pyrrolo[2,3-b]pyridin-4-yl]-m-tolyl-amine |
| EXAMPLE 59 (f) | 4-fluoroaniline | C23H19FN4O | 387.2 | 3.62 | (4-Fluoro-phenyl)-[2-(5-methoxy-1-methyl-1H-indol-3-yl)-1H-pyrrolo[2,3-b]pyridin-4-yl]-amine |

TABLE 7-continued

| STRUCTURE and Example number | HNY¹Y² | Molecular Formula | LC-MS: METHOD C | | Nomenclature |
|---|---|---|---|---|---|
| | | | [M + H]⁺ | R_T (minutes) | |
| EXAMPLE 59 (g) | 4-methoxyaniline | C24H22N4O2 | 399.3 | 3.60 | [2-(5-Methoxy-1-methyl-1H-indol-3-yl)-1H-pyrrolo[2,3-b]pyridin-4-yl]-(4-methoxy-phenyl)-amine |
| EXAMPLE 59 (h) | p-toluidine | C24H22N4O | 383.3 | 3.75 | [2-(5-Methoxy-1-methyl-1H-indol-3-yl)-1H-pyrrolo[2,3-b]pyridin-4-yl]-p-tolyl-amine |
| EXAMPLE 59 (i) | benzylamine | C24H22N4O | 383.3 | 3.63 | Benzyl-[2-(5-methoxy-1-methyl-1H-indol-3-yl)-1H-pyrrolo[2,3-b]pyridin-4-yl]-amine |
| EXAMPLE 59 (j) | 4-fluorobenzylamine | C24H21FN4O | 401.3 | 3.68 | (4-Fluoro-benzyl)-[2-(5-methoxy-1-methyl-1H-indol-3-yl)-1H-pyrrolo[2,3-b]pyridin-4-yl]-amine |
| EXAMPLE 59 (k) | 4-methoxybenzylamine | C25H24N4O2 | 413.3 | 3.65 | (4-Methoxy-benzyl)-[2-(5-methoxy-1-methyl-1H-indol-3-yl)-1H-pyrrolo[2,3-b]pyridin-4-yl]-amine |

TABLE 7-continued

| STRUCTURE and Example number | HNY¹Y² | Molecular Formula | LC-MS: METHOD C | | Nomenclature |
|---|---|---|---|---|---|
| | | | [M + H]⁺ | R_T (minutes) | |
| EXAMPLE 59 (l) | H₂N-CH₂CH₂-OCH₃ | C20H22N4O2 | 351.3 | 3.23 | (2-Methoxy-ethyl)-[2-(5-methoxy-1-methyl-1H-indol-3-yl)-1H-pyrrolo[2,3-b]pyridin-4-yl]-amine |
| EXAMPLE 59 (m) | 3-aminobenzoic acid methyl ester | C25H22N4O3 | 427.3 | 3.59 | 3-[2-(5-Methoxy-1-methyl-1H-indol-3-yl)-1H-pyrrolo[2,3-b]pyridin-4-ylamino]-benzoic acid methyl ester |
| EXAMPLE 59 (n) | cyclopropylmethylamine | C21H22N4O | 347 | 3.55 | Cyclopropylmethyl-[2-(5-methoxy-1-methyl-1H-indol-3-yl)-1H-pyrrolo[2,3-b]pyridin-4-yl]-amine |
| EXAMPLE 59 (o) | aniline | C23H20N4O | 369.2 | 3.38 | [2-(5-Methoxy-1-methyl-1H-indol-3-yl)-1H-pyrrolo[2,3-b]pyridin-4-yl]-phenyl-amine |

TABLE 7-continued

| STRUCTURE and Example number | HNY¹Y² | Molecular Formula | LC-MS: METHOD C [M + H]⁺ | R_T (minutes) | Nomenclature |
|---|---|---|---|---|---|
| 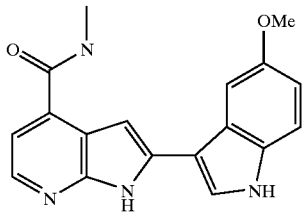 EXAMPLE 59 (p) | H₂N~~~ | C21H24N4O | 349.2 | 3.43 | Butyl-[2-(5-methoxy-1-methyl-1H-indol-3-yl)-1H-pyrrolo[2,3-b]pyridin-4-yl]-amine |

EXAMPLE 60

2-(5-Methoxy-1H-indol-3-yl)-1H-pyrrolo[2,3,-b]pyridine-4-carboxylic acid methylamide, A9-B2-C1, the product of the combination of group A9 in Table 1 and B2 in Table 2 and C1 in Table 3:

A solution of 2-(5-methoxy-1H-indol-3-yl)-1H-pyrrolo[2,3-b]pyridine-4-carboxylic acid [0.11 g, Example 15(t)] in dimethyl formamide (5 mL) at room temperature was treated with triethylamine (0.048 mL), methylamine (0.19 mL) and 2-(1H-benzotriazole-1-yl)-1,1,3,3-tetramethyluronium tetrafluoroborate. The reaction mixture was allowed to stir at room temperature overnight, then poured into water (20 mL) and then extracted twice with ethyl acetate (20 mL). The combine extracts were washed with water (5 mL), then dried over sodium sulfate and then evaporated. The residue was subjected to flash column chromatography on silica gel eluting with a mixture of methanol and ethyl acetate (49:1, v/v) to afford the title compound as a yellow solid. MS: 321(MH⁺). ¹H NMR[CD₃)₂SO]: d 12.0 1H, s); 11.4 (1H, s); 8.4 (1H, d); 8.2 (1H, d); 8.0 (1H, s); 7.54 (1H, d); 7.40 (1H, s); 7.35 (1H, d); 7.10 (1H, s); 6.85 (1H, d); 3.80 (3H, s); 2.90 (3H, d).

EXAMPLE 61 AND REFERENCE EXAMPLE 101

2-(5-Methoxy-1H-indol-3-yl)-1H-pyrrolo[2,3,-b]pyridine-4-carboxylic acid, tert-butyl ester and 2-(5-methoxy-1H-indol-3-yl)-1-1(toluene-4-sulfonyl)-1H-pyrrolo[2,3,-b]pyridine-4-carboxylic acid tert-butyl ester

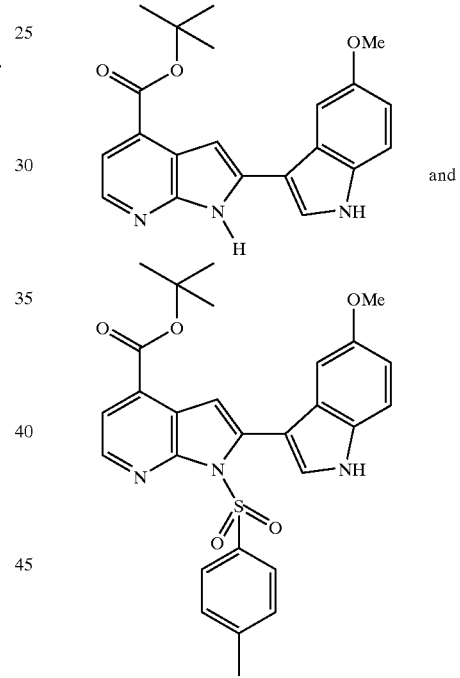

By proceeding in a similar manner to Reference Example 67(a) but using 1-tert-butyloxycarbonyl-5-methoxy-1H-indole-3-boronic acid [Reference Example 74(b)] and 2-iodo-1-(toluene-4-sulfonyl)-1H-pyrrolo[2,3-b]pyridine-4 carboxylic acid, tert-butyl ester[Reference Example 62(e)] and subjecting the crude mixture to chromatography on silica gel eluting with a mixture of ethyl acetate and heptane (3:7 v:v) there was prepared 2-(5-methoxy-1H-indol-3-yl)-1H-pyrrolo[2,3,-b]pyridine-4-carboxylic acid tert-butyl ester as a tan solid MS: 364(MH⁺) and 2-(5-methoxy-1H-indol-3-yl)-1-1(toluene-4-sulfonyl)-1H-pyrrolo[2,3,-b] pyridine-4-carboxylic acid tert-butyl ester (Reference Example 101) as a yellow/green oil. MS: 518(MH⁺).

EXAMPLE 62 TO EXAMPLE 126

The following compounds of Formula I in Table 8 are provided by the methods described in this Application:

TABLE 8
| STRUCTURE and Example number | MP (° C.) | Molecular Formula | $R_F$ | LC-MS: METHOD D | | Micro-anaylsis % Found |
| --- | --- | --- | --- | --- | --- | --- |
| | | | | $[M + H]^+$ | $R_T$ (minutes) | |
| 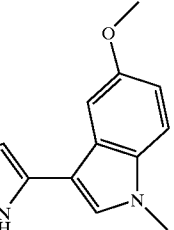 EXAMPLE 62 | | C17H15N3O2 | | 294 | 2.35 | |
| 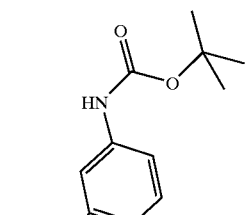 EXAMPLE 63 | | C21H22N4O3 | | 379 | 2.55 | |
| 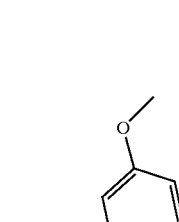 EXAMPLE 64 | | C21H20N4O2 | | 361 | 3.63 | |
| 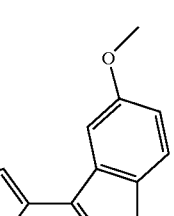 EXAMPLE 65 | | C18H17N3O | | 292 | 3.75 | |

TABLE 8-continued
| STRUCTURE and Example number | MP (° C.) | Molecular Formula | $R_F$ | LC-MS: METHOD D [M + H]⁺ | $R_T$ (minutes) | Micro-analysis % Found |
|---|---|---|---|---|---|---|
| 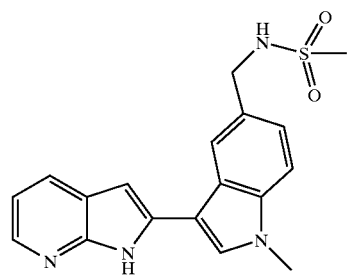EXAMPLE 66 | 168–170 | C18H18N4O2S | | 355 | | |
| 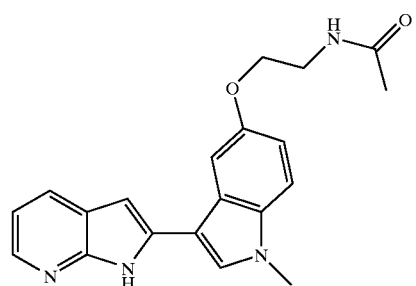EXAMPLE 67 | | C20H20N4O2 | 0.15ᵃ | | | |
| 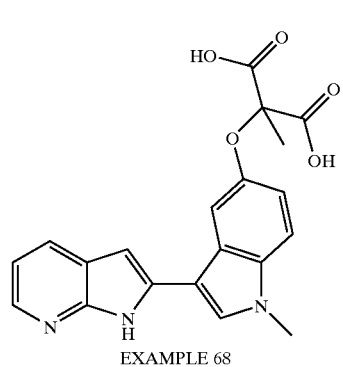EXAMPLE 68 | 225–226 | C20H17N3O5 | | | 5.86 HPLC Method A | |
| 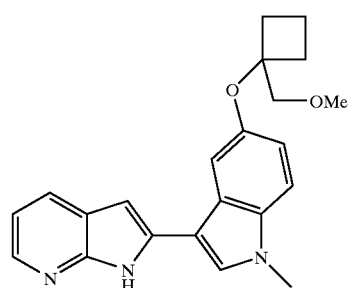EXAMPLE 69 | 98–99 | C22H23N3O2 | | | 8.15 HPLC Method A | |

TABLE 8-continued
| STRUCTURE and Example number | MP (° C.) | Molecular Formula | $R_F$ | LC-MS: METHOD D [M + H]⁺   $R_T$ (minutes) | Micro-anaylsis % Found |
|---|---|---|---|---|---|
| 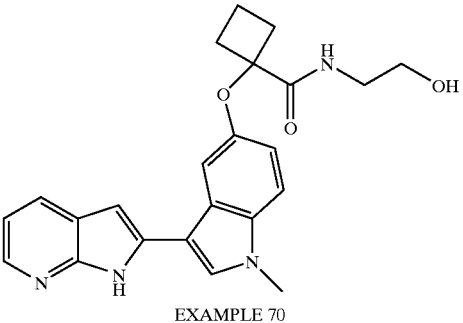 EXAMPLE 70 | 244–245 | C23H24N4O3 | 0.56[b] | | |
| 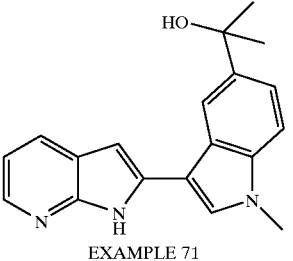 EXAMPLE 71 | | C19H18N3 | | 306 | |
| 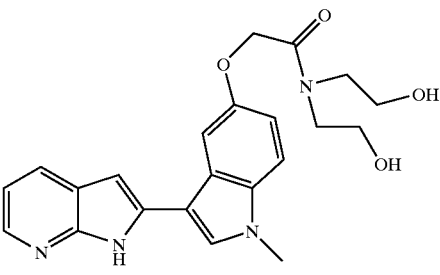 EXAMPLE 72 | 175–176 | C22H24N4O4 | | | C: 61.63 H: 5.80 N: 13.30 |
| 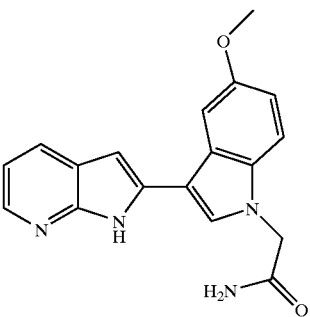 EXAMPLE 73 | >299 dec. | C18H16N4O2 | | 321 | |

TABLE 8-continued
| STRUCTURE and Example number | MP (° C.) | Molecular Formula | $R_F$ | LC-MS: METHOD D [M + H]+ | $R_T$ (minutes) | Microanaylsis % Found |
|---|---|---|---|---|---|---|
| 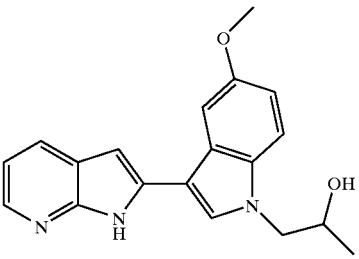EXAMPLE 74 | | C19H19N3O2 | 0.15a | | 6.44 HPLC Method A | |
| 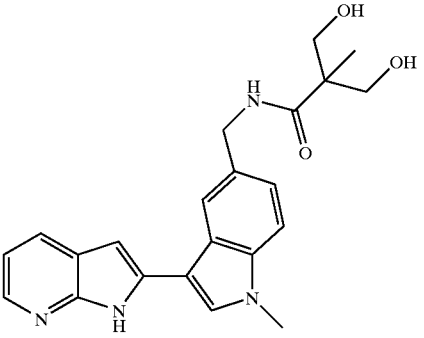EXAMPLE 75 | | C22H24N4O3 | | 393 | | |
| 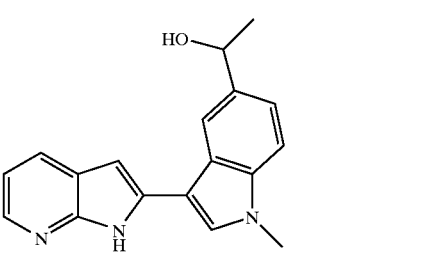EXAMPLE 76 | 225–227 | C18H17N3O | | 292 | | |
| 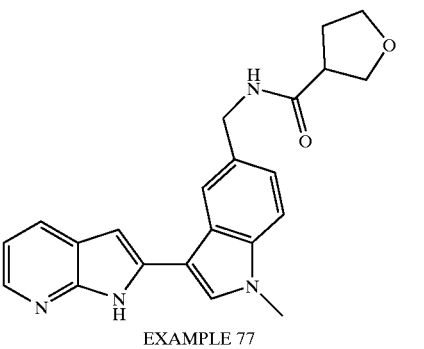EXAMPLE 77 | | C22H22N4O2 | | 375 | | |

TABLE 8-continued

| STRUCTURE and Example number | MP (° C.) | Molecular Formula | R_F | LC-MS: METHOD D [M + H]+ | R_T (minutes) | Micro-anaylsis % Found |
|---|---|---|---|---|---|---|
| EXAMPLE 78 | | C20H20N4O3 | | | | C: 61.30 H: 5.09 N: 14.04 |
| EXAMPLE 79 | | C22H24N4O2 | | 377 | 4.34 | |
| EXAMPLE 80 | 231–232 | C20H20N4O3 | 0.61c | | | |
| EXAMPLE 81 | >297 dec. | C20H21N5O | | | | |

TABLE 8-continued
| STRUCTURE and Example number | MP (° C.) | Molecular Formula | $R_F$ | LC-MS: METHOD D [M + H]$^+$  $R_T$ (minutes) | Micro-anaylsis % Found |
|---|---|---|---|---|---|
| 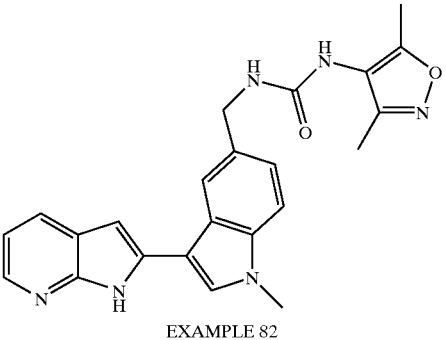 EXAMPLE 82 | 239–240 | C23H22N6O2 | | | |
| 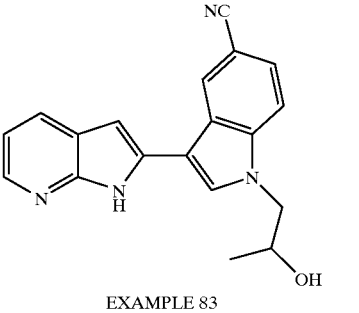 EXAMPLE 83 | 266–267 | C19H16N4O | | 317 | |
| 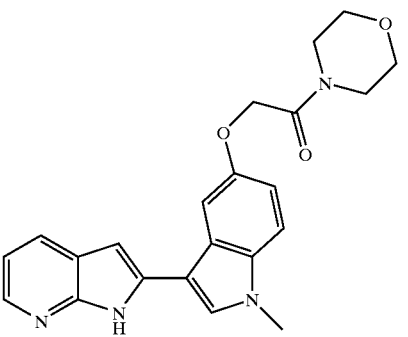 EXAMPLE 84 | | C22H22N4O3 | | | |
$^1$H NMR [(CD$_3$)$_2$SO]:
δ 11.80(1H, s); 8.11(1H, dd, J=4.8, 1.4 Hz);
7.92(1H, s); 7.82(1H, dd, J=8.0, 1.4 Hz);
7.45(2H, m); 7.01(1H, dd, J=8.0, 4.8 Hz),
6.94(1H, dd, J=8.8, 2.4 Hz);
6.75(1H, d, J=2.0 Hz); 4.91(2H, s);
3.83(3H, s); 3.65–3.47(8H, m).

TABLE 8-continued
| STRUCTURE and Example number | MP (° C.) | Molecular Formula | $R_F$ | LC-MS: METHOD D [M + H]+ | $R_T$ (minutes) | Micro-anaylsis % Found |
|---|---|---|---|---|---|---|
| 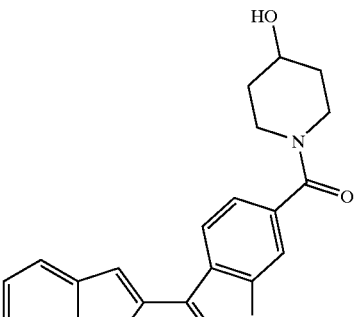 EXAMPLE 85 | 217–200 | C22H22N4O2 | | 375 | | |
| 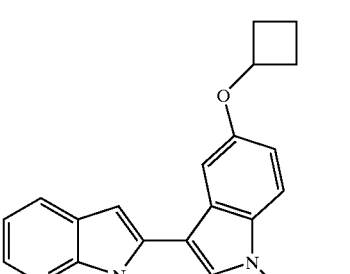 EXAMPLE 86 | 205–206 | C20H19N3O | | | | |
| 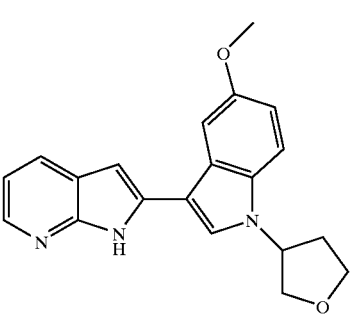 EXAMPLE 87 | 199–200 | C20H19N3O2 | 0.12[d] | | | |
| 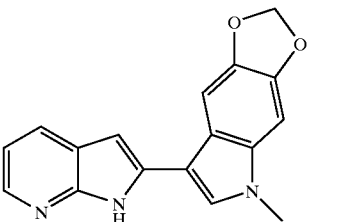 EXAMPLE 88 | | C17H13N3O2 | | | | C: 68.87 H: 4.10 N: 13.82 |

TABLE 8-continued

| STRUCTURE and Example number | MP (° C.) | Molecular Formula | R_F | LC-MS: METHOD D [M + H]+ | R_T (minutes) | Microanaylsis % Found |
|---|---|---|---|---|---|---|
| EXAMPLE 89 | | C19H18N4O | | 319 | | |
| EXAMPLE 90 | | C24H26N4O3 | | 419 | 3.29 | |
| EXAMPLE 91 | 189–190 | C19H17N3O | 0.09[a] | | | |
| EXAMPLE 92 | 247–253 | C19H12F3N5O | | 384 | | |

TABLE 8-continued
| STRUCTURE and Example number | MP (° C.) | Molecular Formula | $R_F$ | LC-MS: METHOD D [M + H]$^+$ | $R_T$ (minutes) | Microanaylsis % Found |
|---|---|---|---|---|---|---|
| 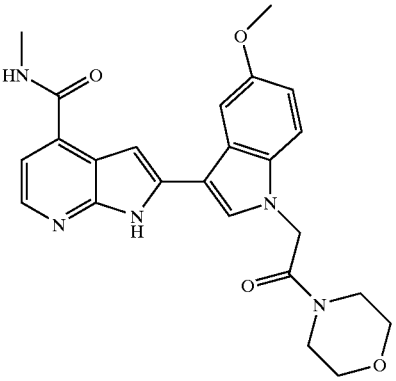 EXAMPLE 93 | | C24H25N5O4 | | 448 | 2.27 | |
| 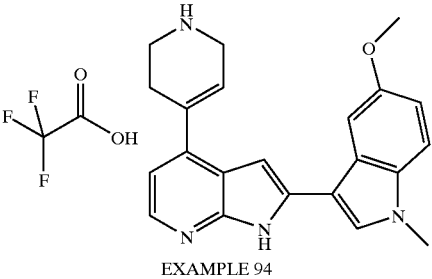 EXAMPLE 94 | | C22H22N4O. C2HF3O2 | | 359 | 2.05 | |
| 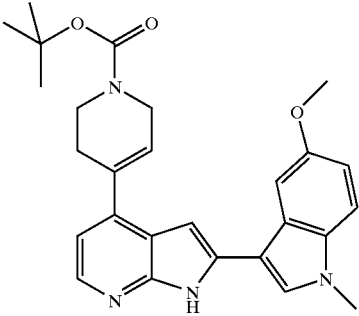 EXAMPLE 95 | | C26H28N4O3 | | 459 | | |
| 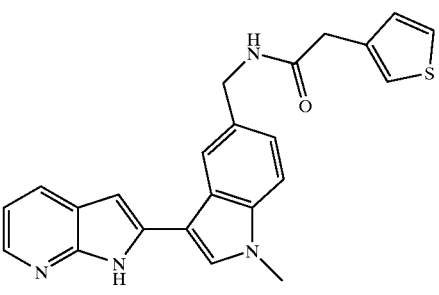 EXAMPLE 96 | 214–215 | C23H20N4OS | | | | |

TABLE 8-continued
| STRUCTURE and Example number | MP (° C.) | Molecular Formula | $R_F$ | LC-MS: METHOD D [M + H]$^+$ | $R_T$ (minutes) | Micro-anaylsis % Found |
|---|---|---|---|---|---|---|
| 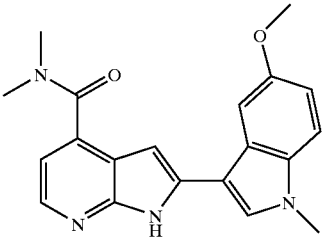<br>EXAMPLE 97 | | C20H20N4O2 | | | 2.57 | |
| 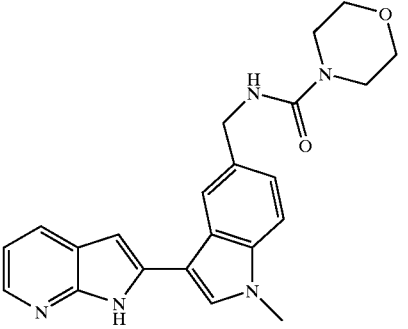<br>EXAMPLE 98 | | C22H23N5O2 | | 390 | | |
| 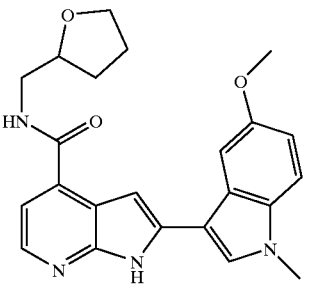<br>EXAMPLE 99 | | C23H24N4O3 | | 405 | 2.72 | |
| 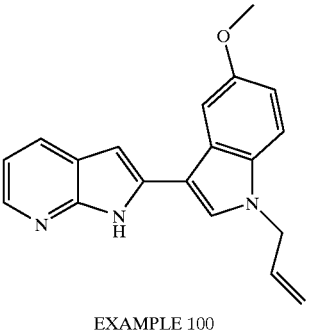<br>EXAMPLE 100 | 180–181 | C19H17N3O | | | | |

TABLE 8-continued
| STRUCTURE and Example number | MP (° C.) | Molecular Formula | $R_F$ | LC-MS: METHOD D [M + H]$^+$ | $R_T$ (minutes) | Micro-analysis % Found |
|---|---|---|---|---|---|---|
| 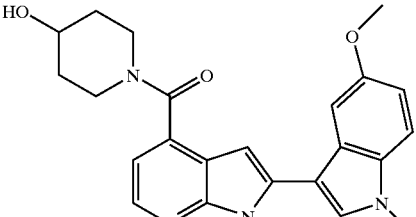 EXAMPLE 101 | | C23H24N4O3 | | 405 | 2.37 | |
| 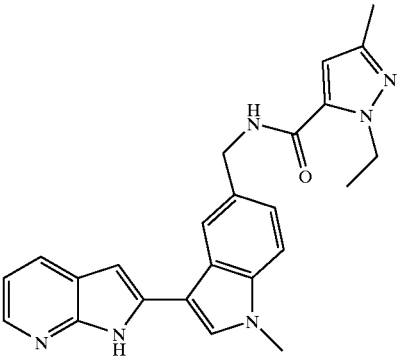 EXAMPLE 102 | 249–250 | C24H24N6O | | 413 | | |
| 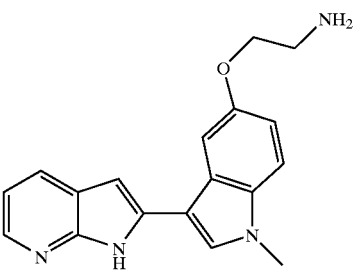 EXAMPLE 103 | 100 decomp. | C18H18N4O | 0.05$^e$ | | | |
| 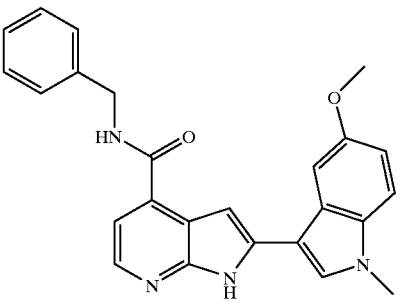 EXAMPLE 104 | | C25H22N4O2 | | 411 | 4.72 | |

TABLE 8-continued

| STRUCTURE and Example number | MP (° C.) | Molecular Formula | $R_F$ | LC-MS: METHOD D [M + H]⁺ | $R_T$ (minutes) | Micro-anaylsis % Found |
|---|---|---|---|---|---|---|
| EXAMPLE 105 | 298–300 | C25H23N5O3S | | 474 | | |
| EXAMPLE 106 | | C22H22N4O2 | | 375 | 2.89 | |
| EXAMPLE 107 | | C20H19N3O | | | | |

¹H NMR [(CD₃)₂SO]:
δ 11.75(1H, s); 8.25(1H, s);
8.11(1H, dd, J=4.8, 1.4 Hz);
7.85(1H, dd, J=7.8, 1.4 Hz);
7.46(1H, d, J=8.8 Hz); 7.42(1H, d, J=2.4 Hz);
7.01(1H, dd, J=7.8, 4.8 Hz);
6.87(1H, dd, J=8.8, 2.4 Hz),
6.78(1H, d, J=2.4 Hz);
4.99(1H, quint, J=8.0 Hz);
3.86(3H, s); 2.58–2.53(2H, m),
1.93–1.88(2H, m).

| | | | | | | |
|---|---|---|---|---|---|---|
| EXAMPLE 108 | 259–260 | C22H22N4O3 | | 391 | | |

TABLE 8-continued
| STRUCTURE and Example number | MP (° C.) | Molecular Formula | R_F | LC-MS: METHOD D [M + H]+ | R_T (minutes) | Micro-analysis % Found |
|---|---|---|---|---|---|---|
| 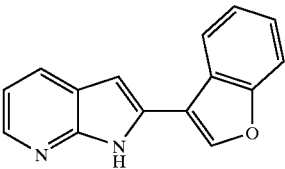 EXAMPLE 109 | 208–209 | C15H10N2O | | 235 | | |
| 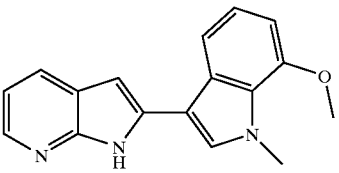 EXAMPLE 110 | | C17H15N3O | | | | |
| 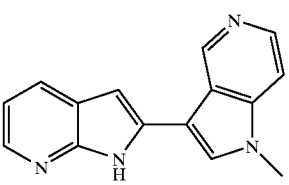 EXAMPLE 111 | 290–291 | C15H12N4 | | | | C: 62.33 H: 5.36 N: 19.27 |
| 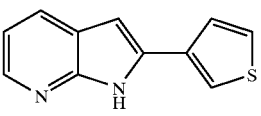 EXAMPLE 112 | 224–226 | C11H8N2S | | 201 | | |
| 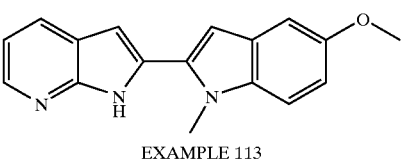 EXAMPLE 113 | 234–235 | C17H15N3O | | | | C: 73.17 H: 5.42 N: 15.22 |
| 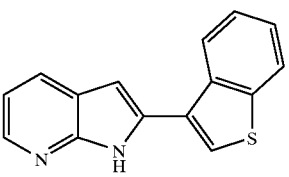 EXAMPLE 114 | | C15H10N2S | | | | |
¹H NMR [(CD₃)₂SO]:
δ 8.13(1H, dd); 7.85(1H, dd); 7.83(1H, s); 7.57(1H, dd); 7.08(1H, t); 7.00(1H, dd); 6.78(1H, d); 6.73(1H, d); 4.08(3H, s); 3.93(3H, s).

TABLE 8-continued
| STRUCTURE and Example number | MP (° C.) | Molecular Formula | $R_F$ | LC-MS: METHOD D [M + H]$^+$ | $R_T$ (minutes) | Micro-anaylsis % Found |
|---|---|---|---|---|---|---|
| 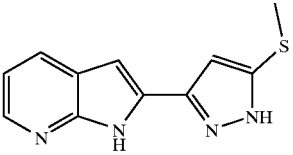 EXAMPLE 115 | 248–250 | C11H10N4S | | | | C: 57.71<br>H: 4.27<br>N: 23.16<br>S: 13.22 |
| 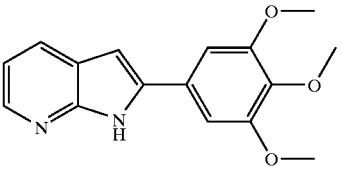 EXAMPLE 116 | 179–182 | C16H16N2O3 | | | | |
| 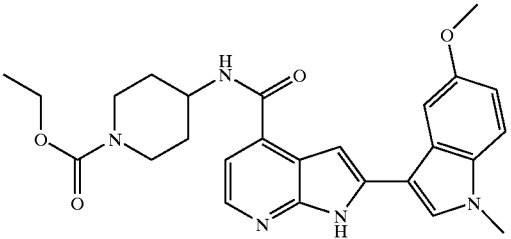 EXAMPLE 117 | | C26H29N5O4 | | 476 | 2.84 | |
| 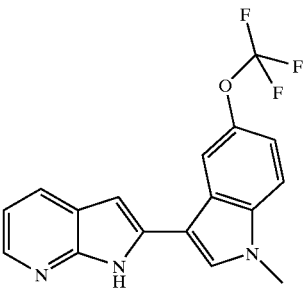 EXAMPLE 118 | 234–235 | C17H12F3N3O | | | | C: 61.77<br>H: 3.63<br>N: 12.23<br>F: 16.81 |
| 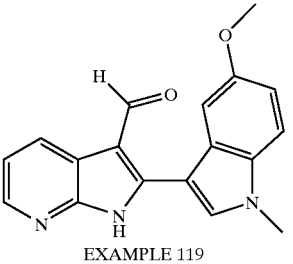 EXAMPLE 119 | | C18H15N3O2 | | | | C: 69.12<br>H: 4.64<br>N: 13.29 |

TABLE 8-continued
| STRUCTURE and Example number | MP (° C.) | Molecular Formula | $R_F$ | LC-MS: METHOD D [M + H]⁺ | $R_T$ (minutes) | Micro-anaylsis % Found |
|---|---|---|---|---|---|---|
| 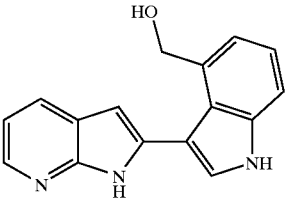 EXAMPLE 120 | 288–289 | C16H13N3O | | | | C: 72.20 H: 4.81 N: 15.73 |
| 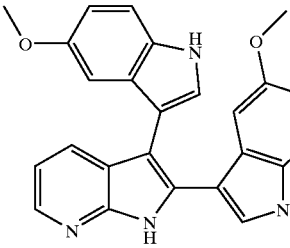 EXAMPLE 121 | | C25H20N4O2 | | 409 | 2.67 | |
| 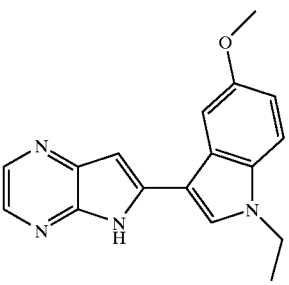 EXAMPLE 122 | | C17H16N4O | | 293 | 1.39 | |
| 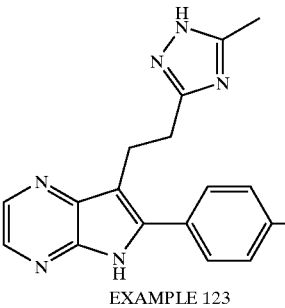 EXAMPLE 123 | | C21H24N6 | | 348 | 2.47 | |
| 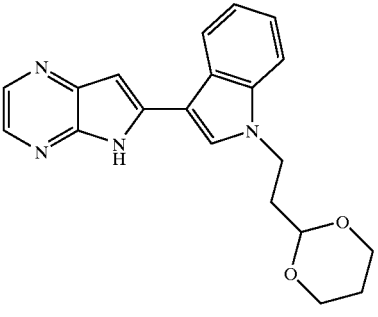 EXAMPLE 124 | | C20H20N4O2 | 0.1ᶠ | | | C: 65.72 H: 5.51 N 15.67 |

TABLE 8-continued

| STRUCTURE and Example number | MP (° C.) | Molecular Formula | $R_F$ | LC-MS: METHOD D [M + H]⁺ | $R_T$ (minutes) | Micro-analysis % Found |
|---|---|---|---|---|---|---|
| 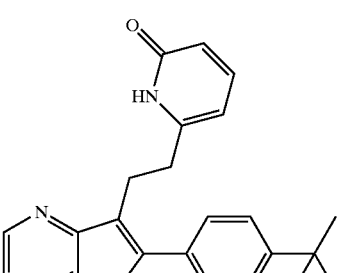<br>EXAMPLE 125 | | C23H24N4O | | 373.5 | 5.96 HPLC Method A | |
| 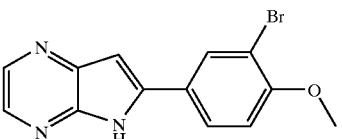<br>EXAMPLE 126 | | C13H10BrN3O | | 303.9 | 2.37 | |

<sup>a</sup>ethyl acetate
<sup>b</sup>methanol/dichloromethane 1:9 v:v
<sup>c</sup>methanol/ethyl acetate 1:9 v:v
<sup>d</sup>penane/ethyl acetate 1:2 v:v
<sup>e</sup>methanol/ethyl acetate 1:4 v:v
<sup>f</sup>pentane/ethyl acetate 1:1 v:v

EXAMPLE 127

The following compounds of Formula I in Table 9 may be prepared by the methods described in this Application:

TABLE 9

| Structure | Nomenclature |
|---|---|
| 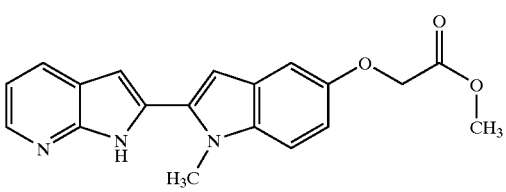 | [1-Methyl-2-(1H-pyrrolo[2,3-b]pyridin-2-yl)-1H-indol-5-yloxy]-acetic acid methyl ester |
| 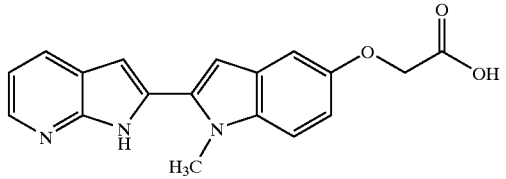 | [1-Methyl-2-(1H-pyrrolo[2,3-b]pyridin-2-yl)-1H-indol-5-yloxy]-acetic acid |
| 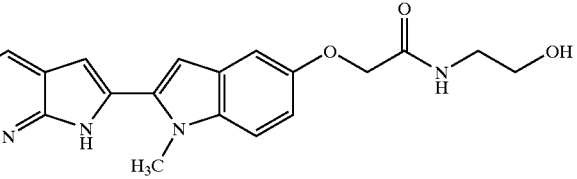 | N-(2-Hydroxy-ethyl)-2-[1-methyl-2-(1H-pyrrolo[2,3-b]pyridin-2-yl)-1H-indol-5-yloxy]-acetamide |

TABLE 9-continued

| Structure | Nomenclature |
|---|---|
| 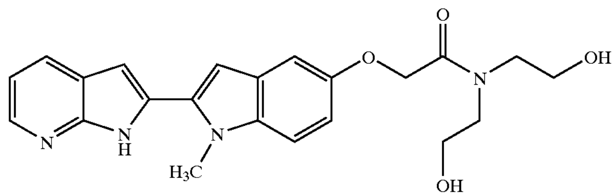 | N,N-Bis-(2-hydroxy-ethyl)-2-[1-methyl-2-(1H-pyrrolo[2,3-b]pyridin-2-yl)-1H-indol-5-yloxy]-acetamide |
| 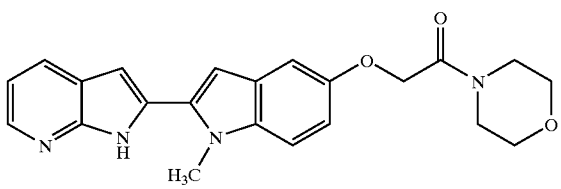 | 2-[1-Methyl-2-(1H-pyrrolo[2,3-b]pyridin-2-yl)-1H-indol-5-yloxy]-1-morpholin-4-yl-ethanone |
| 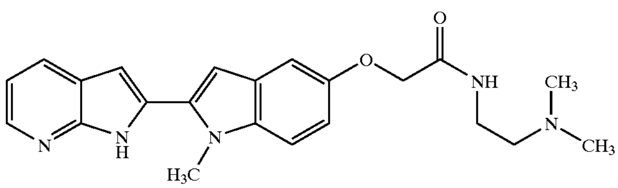 | N-(2-Dimethylamino-ethyl)-2-[1-methyl-2-(1H-pyrrolo[2,3-b]pyridin-2-yl)-1H-indol-5-yloxy]-acetamide |
| 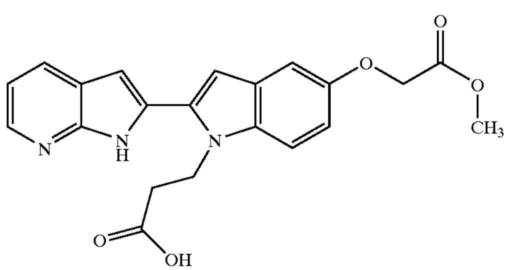 | 3-[5-Methoxycarbonylmethoxy-2-(1H-pyrrolo[2,3-b]pyridin-2-yl)-indol-1-yl]-propionic acid |
| 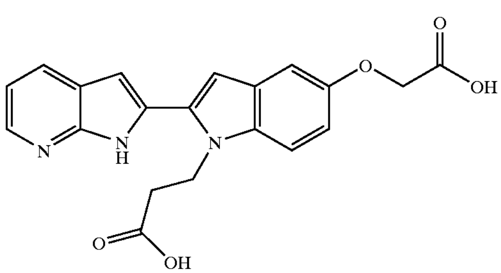 | 3-[5-Carboxymethoxy-2-(1H-pyrrolo[2,3-b]pyridin-2-yl)-indol-1-yl]-propionic acid |
| 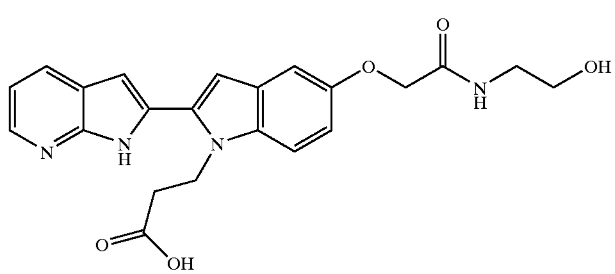 | 3-[5-[(2-Hydroxy-ethylcarbamoyl)-methoxy]-2-(1H-pyrrolo[2,3-b]pyridin-2-yl)-indol-1-yl]-propionic acid |

TABLE 9-continued

| Structure | Nomenclature |
|---|---|
| 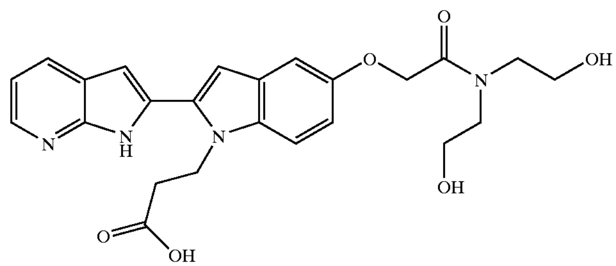 | 3-[5-{[Bis-(2-hydroxy-ethyl)-carbamoyl]-methoxy}-2-(1H-pyrrolo[2,3-b]pyridin-2-yl)-indol-1-yl]-propionic acid |
| 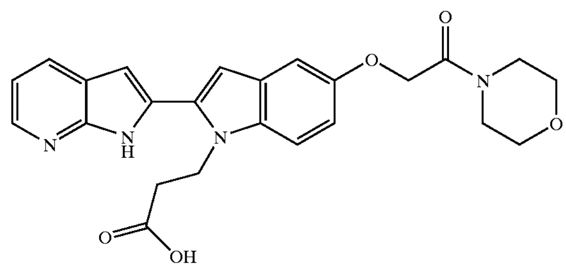 | 3-[5-(2-Morpholin-4-yl-2-oxo-ethoxy)-2-(1H-pyrrolo[2,3-b]pyridin-2-yl)-indol-1-yl]-propionic acid |
| 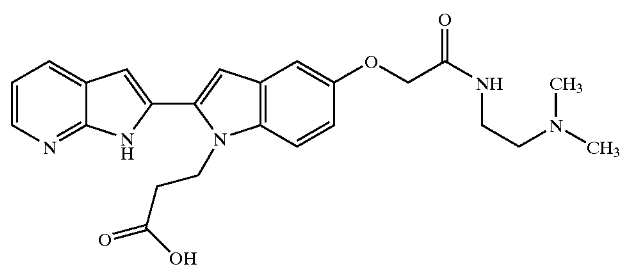 | 3-[5-[(2-Dimethylamino-ethylcarbamoyl)-methoxy]-2-(1H-pyrrolo[2,3-b]pyridin-2-yl)-indol-1-yl]-propionic acid |
| 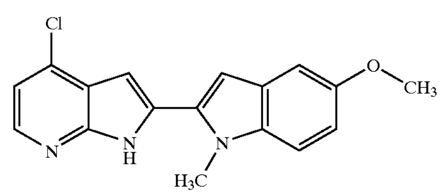 | 4-Chloro-2-(5-methoxy-1-methyl-1H-indol-2-yl)-1H-pyrrolo[2,3-b]pyridine |
| 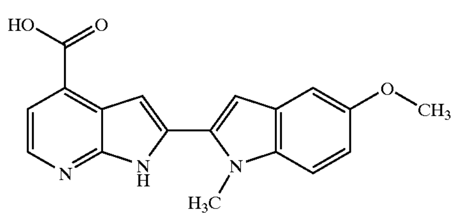 | 2-(5-Methoxy-1-methyl-1H-indol-2-yl)-1H-pyrrolo[2,3-b]pyridine-4-carboxylic acid |
| 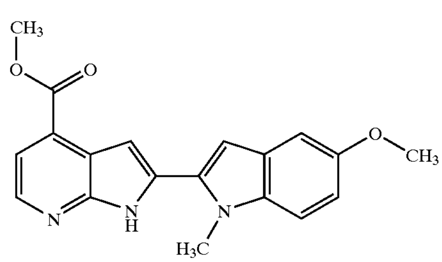 | 2-(5-Methoxy-1-methyl-1H-indol-2-yl)-1H-pyrrolo[2,3-b]pyridine-4-carboxylic acid methyl ester |

TABLE 9-continued

| Structure | Nomenclature |
|---|---|
| 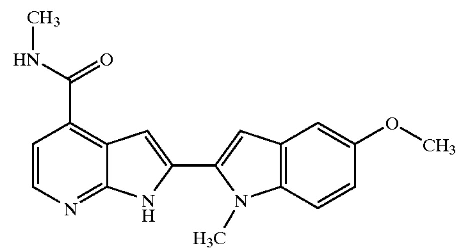 | 2-(5-Methoxy-1-methyl-1H-indol-2-yl)-1H-pyrrolo[2,3-b]pyridine-4-carboxylic acid methylamide |
| 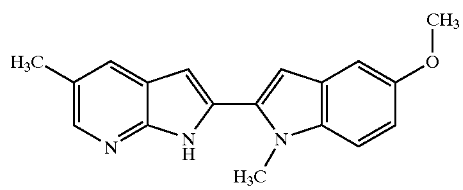 | 2-(5-Methoxy-1-methyl-1H-indol-2-yl)-5-methyl-1H-pyrrolo[2,3-b]pyridine |
| 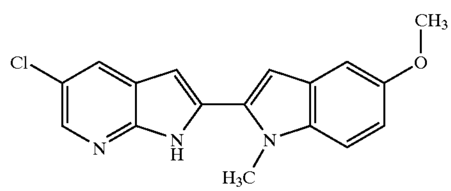 | 5-Chloro-2-(5-methoxy-1-methyl-1H-indol-2-yl)-1H-pyrrolo[2,3-b]pyridine |
| 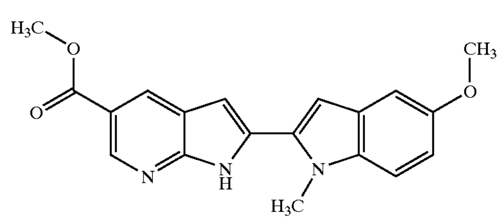 | 2-(5-Methoxy-1-methyl-1H-indol-2-yl)-1H-pyrrolo[2,3-b]pyridine-5-carboxylic acid methyl ester |
| 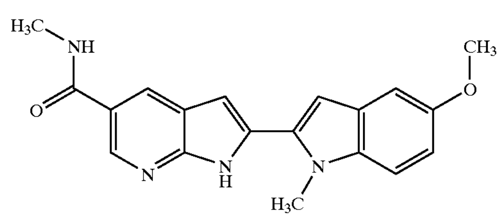 | 2-(5-Methoxy-1-methyl-1H-indol-2-yl)-1H-pyrrolo[2,3-b]pyridine-5-carboxylic acid methylamide |
| 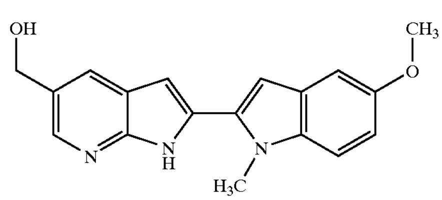 | [2-(5-Methoxy-1-methyl-1H-indol-2-yl)-1H-pyrrolo[2,3-b]pyridin-5-yl]-methanol |
| 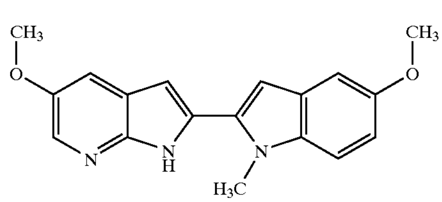 | 5-Methoxy-2-(5-methoxy-1-methyl-1H-indol-2-yl)-1H-pyrrolo[2,3-b]pyridine |

TABLE 9-continued

| Structure | Nomenclature |
|---|---|
| 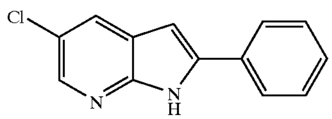 | 5-Chloro-2-phenyl-1H-pyrrolo[2,3-b]pyridine |
| 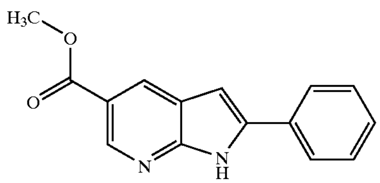 | 2-Phenyl-1H-pyrrolo[2,3-b]pyridine-5-carboxylic acid methyl ester |
| 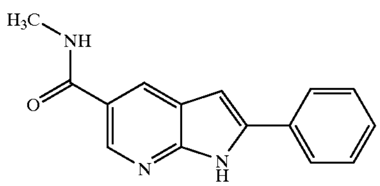 | 2-Phenyl-1H-pyrrolo[2,3-b]pyridine-5-carboxylic acid methylamide |
| 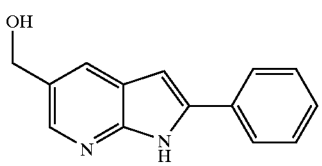 | (2-Phenyl-1H-pyrrolo[2,3-b]pyridin-5-yl)-methanol |
| 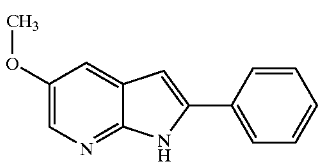 | 5-Methoxy-2-phenyl-1H-pyrrolo[2,3-b]pyridine |
| 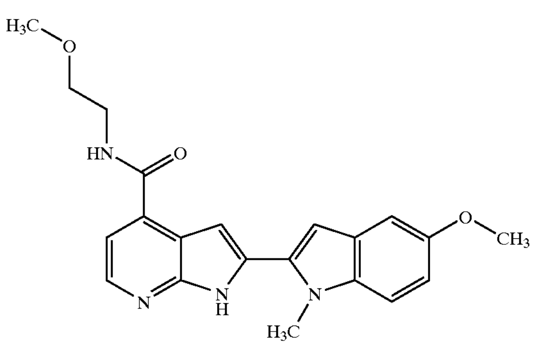 | 2-(5-Methoxy-1-methyl-1H-indol-2-yl)-1H-pyrrolo[2,3-b]pyridine-4-carboxylic acid(2-methoxy-ethyl)-amide |
| 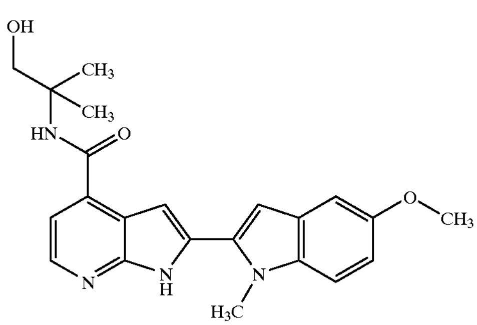 | 2-(5-Methoxy-1-methyl-1H-indol-2-yl)-1H-pyrrolo[2,3-b]pyridine-4-carboxylic acid(2-hydroxy-1,1-dimethyl-ethyl)-amide |

TABLE 9-continued

| Structure | Nomenclature |
|---|---|
| 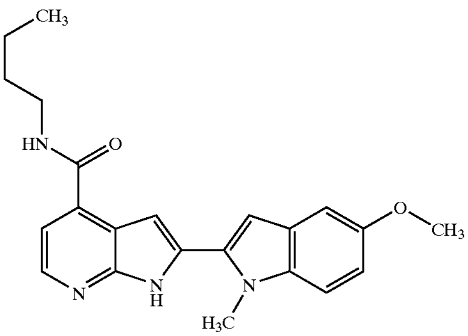 | 2-(5-Methoxy-1-methyl-1H-indol-2-yl)-1H-pyrrolo[2,3-b]pyridine-4-carboxylic acid butylamide |
| 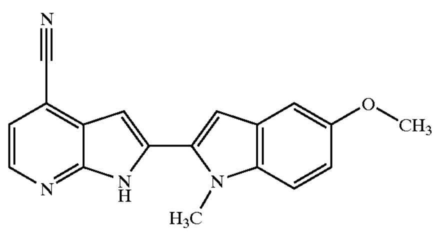 | 2-(5-Methoxy-1-methyl-1H-indol-2-yl)-1H-pyrrolo[2,3-b]pyridine-4-carbonitrile |
| 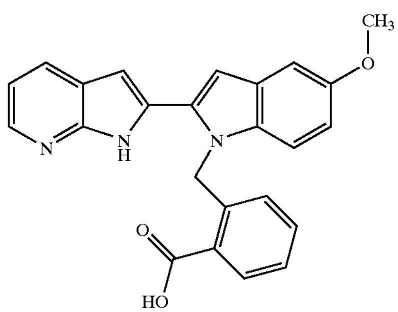 | 2-[5-Methoxy-2-(1H-pyrrolo[2,3-b]pyridin-2-yl)-indol-1-ylmethyl]-benzoic acid |
| 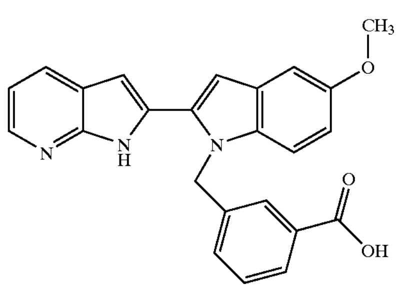 | 3-[5-Methoxy-2-(1H-pyrrolo[2,3-b]pyridin-2-yl)-indol-1-ylmethyl]-benzoic acid |
| 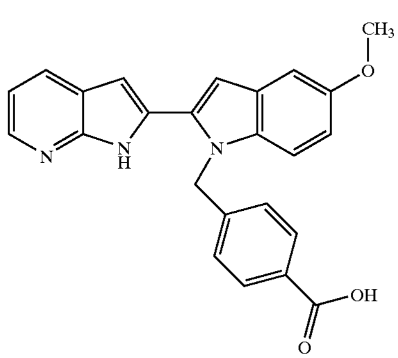 | 4-[5-Methoxy-2-(1H-pyrrolo[2,3-b]pyridin-2-yl)-indol-1-ylmethyl]-benzoic acid |

TABLE 9-continued

| Structure | Nomenclature |
|---|---|
| 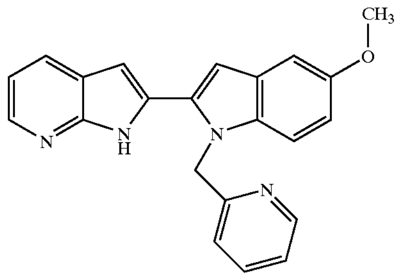 | 2-(5-Methoxy-1-pyridin-2-ylmethyl-1H-indol-2-yl)-1H-pyrrolo[2,3-b]pyridine |
| 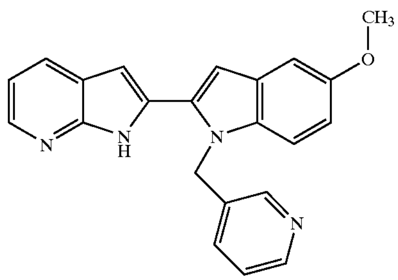 | 2-(5-Methoxy-1-pyridin-3-ylmethyl-1H-indol-2-yl)-1H-pyrrolo[2,3-b]pyridine |
| 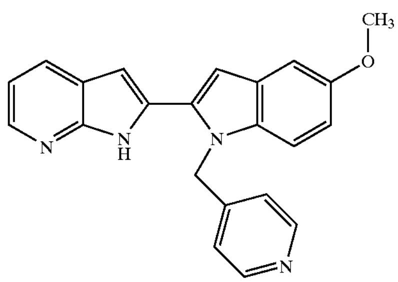 | 2-(5-Methoxy-1-pyridin-4-ylmethyl-1H-indol-2-yl)-1H-pyrrolo[2,3-b]pyridine |

REFERENCE EXAMPLE 1

(a) 5-Methoxy-1-methyl-1H-indole-3-carbonitrile

5-Methoxy-1-methyl-1H-indole-3-carboxaldehyde [76 g, Reference Example 2(a)] and hydroxylamine hydrochloride (55.9 g) were stirred together in dimethylformamide (900 mL) under reflux for 1 hour. The mixture was allowed to cool, then poured into water and then extracted with ethyl acetate. The combined extracts were washed with water then evaporated to give the title compound (53 g) as a pale brown solid, m.p. 100–104° C. $^1$H NMR [$(CD_3)_2SO$]: δ 8.17 (1H, s); 7.54 (1H, d, J=9.0 Hz); 7.09 (1H, d, J=2.4 Hz); 6.97 (1H, dd, J=9.0 and 2.4 Hz); 3.82 and 3.84 (6H, s).

(b) By proceeding in a manner similar to Reference Example 1(a) above but using 1-methyl-5-phenylpyrazole-3-carbaldehyde [Reference Example 53(b)] there was prepared 1-methyl-3-cyano-5-phenylpyrazole.

REFERENCE EXAMPLE 2

(a) 5-Methoxy-1-methyl-1H-indole-3-carboxaldehyde

A solution of 5-methoxyindole-3-carboxaldehyde (80 g) in dimethylformamide (1L) under nitrogen was treated portion-wise with sodium hydride (20.1 g, 60% dispersion in mineral oil) over 15 minutes. After stirring at ambient temperature for 30 minutes the mixture was treated dropwise with methyl iodide (31.3 mL) over 10 minutes and stirring was then continued for a further 2 hours. The reaction mixture was poured cautiously into water then extracted with ethyl acetate. The organic phase was washed with water, then dried over sodium sulfate and then evaporated. The residue was triturated with pentane to give the title compound (76 g) as a pale brown solid, m.p. 133–134° C. $^1$H NMR [$(CD_3)_2SO$]: δ 9.86 (1H, s); 8.20 (1H, s); 7.60 (1H, d, J=2.6 Hz); 7.50 (1H, d, J=8.9 Hz); 6.96 (1H, dd, J=8.9 and 2.6 Hz); 3.86 and 3.80 (6H, s).

(b) By proceeding in a manner similar to Reference Example 2(a) above but using indole-3-carbonitrile, there was prepared 1-methyl-1H-indole-3-carbonitrile, as a colourless crystalline solid, m.p. 61–63° C.

(c) By proceeding in a manner similar to Reference Example 2(a) above but using indole-5-carbonitrile, there was prepared 1-methyl-1H-indole-5-carbonitrile, as a colourless crystalline solid, m.p. 77–79° C.

(d) By proceeding in a manner similar to Reference Example 2(a) above but using indole-3-carbonitrile and (3-bromopropoxy)-tert-butyldimethylsilane, there was prepared 1-[3-(tert-butyl-dimethyl-silanyloxy)-propyl]-1H-indole-3-carbonitrile, as a clear colourless oil. TLC: $R_F$=0.6 (dichloromethane). $^1$H NMR ($CDCl_3$): δ 7.70 (1H, d, J=8 Hz); 7.56 (1H, s); 7.39 (1H, d, J=8 Hz); 7.27 (1H, t, J=8 Hz); 7.22 (1H, t, J=8 Hz); 4.25 (2H, t, J=6 Hz); 3.49 (2H, t, J=6 Hz); 1.95 (2H, quintet, J=6 Hz); 0.87 (9H, s); 0.00 (6H, s).

(e) By proceeding in a manner similar to Reference Example 2(a) above but using 5-methoxy-1H-indole-3-carbonitrile

[Reference Example 1(a)] and (3-bromopropoxy)-tert-butyldimethylsilane, there was prepared 1-[3-(tert-butyl-dimethyl-silanyloxy)-propyl]-5-methoxy-1H-indole-3-carbonitrile, as a clear colourless oil. $^1$H NMR [(CD$_3$)$_2$SO]: δ 8.18 (1H, s); 7.55 (1H, d, J=9 Hz); 7.09 (1H, d, J=2 Hz); 6.95 (1H, dd, J=9 and 2 Hz); 4.27 (2H, t, J=6 Hz); 3.82 (3H, s); 3.53 (2H, t, J=6 Hz); 1.95 (2H, quintet, J=6 Hz); 0.87 (9H, s); 0.00 (6H, s).

(f) By proceeding in a manner similar to Reference Example 2(a) above but using indole-3-carbonitrile and (2-bromoethoxy)-tert-butyldimethylsilane, there was prepared 1-[2-(tert-butyl-dimethyl-silanyloxy)-ethyl]-1H-indole-3-carbonitrile, as a clear colourless oil. TLC: R$_F$=0.65 (dichloromethane).

(g) By proceeding in a manner similar to Reference Example 2(a) above but using 5-methoxy-1H-indole-3-carbonitrile [Reference Example 1(a)] and benzyl bromide, there was prepared 1-benzyl-5-methoxy-1H-indole-3-carbonitrile, as a brown solid, MS: 263.22(MH$^+$). TLC: R$_F$=0.8 (dichloromethane/methanol: 19/1).

(h) By proceeding in a manner similar to Reference Example 2(a) above but using 5-methoxy-1H-indole-3-carbonitrile [Reference Example 1(a)] and 2-bromoethoxy-dimethyl-tertiarybutylsilane, there was prepared 1-[2-(tertiarybutyl-dimethyl-silanyloxy)-ethyl]-5-methoxy-1H-indole-3-carbonitrile, as a pale yellow solid, MS: 331.23(MH$^+$). TLC: R$_F$=0.6 (pentane/ethyl acetate: 8/2).

(i) By proceeding in a manner similar to Reference Example 2(a) above but using 1H-pyrrole-3-carbonitrile (prepared as described in Tetrahedron Letters, 1972, 52, 5337–5340), there was prepared 1-methyl-1H-pyrrole-3-carbonitrile, as a brown oil, MS: 107(MH$^+$). $^1$H NMR [CDCl$_3$]: δ 7.09 (1H, m); 6.60 (1H, m); 6.40 (1H, m); 3.68 (3H, s).

(j) By proceeding in a manner similar to Reference Example 2(a) above but using 1H-pyrrole-2-carbonitrile, there was prepared 1-methyl-1H-pyrrole-2-carbonitrile as a colourless liquid. MS: 106(MH$^+$). $^1$H NMR [CDCl$_3$]: δ 6.80 (1H, m); 6.67 (1H, m); 6.15 (1H, m); 3.79 (3H, s).

(k) By proceeding in a manner similar to Reference Example 2(a) above but using 2-phenyl-1H-pyrrole-4-carbonitrile (prepared as described in Synthetic Communications, 25, (1995) 6, 795–802), there was prepared 1-methyl-2-phenyl-1H-pyrrole-4-carbonitrile as a cream solid, m.p. 50–51° C. MS: 183(MH$^+$).

(l) By proceeding in a similar manner to Reference Example 2(a) but using 4-methoxy-2-(5-methoxy-1H-indol-3-yl)-1-(toluene-4-sulfonyl)-1H-pyrrolo[2,3-b]pyridine (Reference Example 39) there was prepared 4-methoxy-2-(5-methoxy-1-methyl-1H-indol-3-yl)-1-(toluene-4-sulfonyl)-1H-pyrrolo[2,3-b]pyridine as a dark oil. HPLC (METHOD A): R$_T$9.49 minutes. TLC: R$_F$=0.50 (pentane/ethyl acetate: 1/1).

(m) By proceeding in a similar manner to Reference Example 2(a) but using 2-(5-methoxy-1H-indol-3-yl)-4-phenyl-1-(toluene-4-sulfonyl)-1H-pyrrolo[2,3-b]pyridine (Reference Example 12(g)) there was prepared 2-(5-methoxy-1-methyl-1H-indol-3-yl)-4-phenyl-1-(toluene-4-sulfonyl)-1H-pyrrolo[2,3-b]pyridine as a tan solid. $^1$H NMR [(CD$_3$)$_2$SO]; δ 8.39 (1H, d, J=4.4 Hz); 7.71 (2H, d, J=7.2 Hz); 7.63 (3H, m); 7.52 (2H, t, J=8.5 Hz); 7.44 (3H, m); 7.29 (2H, d, J=7.2 Hz); 6.94 (1H, s); 6.86 (1H, d, J=8.5 Hz); 6.82 (1H, s); 3.86 (3H, s); 3.71 (3H, s); 2.29 (3H, s).

(n) By proceeding in a similar manner to Reference Example 2(a) but using 2-(5-methoxy-1H-indol-3-yl)-1-(toluene-4-sulfonyl)-1H-pyrrolo[2,3-b]pyridine-4 carboxylic acid, tert-butyl ester [Reference Example 67(b)] and methyl iodide there was prepared 2-(5-methoxy-1-methyl-1H-indol-3-yl)-1-(toluene-4-sulfonyl)-1H-pyrrolo[2,3-b]pyridine-4 carboxylic acid, tert-butyl ester as a dark oil which was used directly without further purification.

(o) By proceeding in a similar manner to Reference Example 2(a) but using 2-(5-methoxy-1H-indol-3-yl)-4-(pyridin-3-yl)-1-(toluene-4-sulfonyl)-1H-pyrrolo[2,3-b]pyridine [Reference Example 67(d)] and methyl iodide there was prepared 2-(5-methoxy-1-methyl-1H-indol-3-yl)-4-(pyridin-3-yl)-1-(toluene-4-sulfonyl)-1H-pyrrolo[2,3-b]pyridine as a tan coloured oil which was used directly without further purification.

(p) By proceeding in a similar manner to Reference Example 2(a) but using 2-(5-methoxy-1H-indol-2-yl)-1-(toluene-4-sulfonyl)-1H-pyrrolo[2,3-b]pyridine [Reference Example 70] and methyl iodide there was prepared 2-(5-methoxy-1-methyl-1H-indol-2-yl)-1-(toluene-4-sulfonyl)-1H-pyrrolo[2,3-b]pyridine.

(q) By proceeding in a manner similar to Reference Example 2(a) above but using 3-[4-methoxyl-1-(toluene-4-sulfonyl)-1H-pyrrolo[2,3-b]pyridine-2-yl]-1H-indole-5-carboxylic acid, methyl ester [Reference Example 12(n)], there was prepared 3-[4-methoxyl-1-(toluene-4-sulfonyl)-1H-pyrrolo[2,3-b]pyridine-2-yl]-1-methyl-1H-indole-5-carboxylic acid, methyl ester as an ivory solid. LC-MS: METHOD D: R$_T$=3.26 minutes, 490(MH$^+$).

(r) By proceeding in a manner similar to Reference Example 2(a) above but using 3-[4-chloro-1-(toluene-4-sulfonyl)-1H-pyrrolo[2,3-b]pyridine-2-yl]-1H-indole-5-carboxylic acid, methyl ester [Reference Example 12(o)], there was prepared 3-[4-chloro-1-(toluene-4-sulfonyl)-1H-pyrrolo[2,3-b]pyridine-2-yl]-1-methyl-1H-indole-5-carboxylic acid, methyl ester as a white solid. MS: 494(MH$^+$). HPLC(Method C): R$_T$=4.88 minutes.

(s) By proceeding in a manner similar to Reference Example 2(a) above but using indole-3-carbonitrile and (2-bromomethoxyl-ethyl)-trimethyl-silane there was prepared 1-(2-trimethylsilanyl-ethoxymethyl)-1H-indole-3-carbonitrile. $^1$H NMR [(CD$_3$)$_2$SO]: δ 8.45 (1H, s); 7.73 (1H, dd), 7.66 (1H, dd); 7.38 (1H, m); 7.30 (1H, m); 5.64 (2H, s); 3.47 (2H, t); 0.9–0.8 (4H, m); –0.10 (9H, s).

REFERENCE EXAMPLE 3

(a) 6-[1-[3-(tert-Butyl-dimethyl-silanyloxy)-propyl]-1H-indol-3-yl]-5H-pyrrolo[2,3-b]pyrazine By proceeding in a manner similar to Example 1(a) herein but using 1-[3-(tert-butyl-dimethyl-silanyloxy)-propyl]-1H-indole-3-carbonitrile [Reference Example 2(d)], there was prepared the title compound as a solid. $^1$H NMR [(CD$_3$)$_2$SO]: δ 12.1–12.2 (1H, broad s); 8.27 (1H, d, J=2.7 Hz); 8.14 (1H, s); 8.10, 7.59 (each 1H, d, J=7.8 Hz); 8.09 (1H, d, J=2.7 Hz); 7.29, 7.23 (each 1H, td, J=7.1 and 1.1 Hz); 6.96 (1H, s); 4.33 (2H, t, J=7.1 Hz); 3.62 (2H, t, J=6.0 Hz); 2.03 (2H, quintet, J=6.2 Hz); 0.89 (9H, s); 0.00 (6H, s). MS: 407 (MH$^+$).

(b) By proceeding in a manner similar to Example 1(a) herein but using 1-[3-(tert-butyl-dimethyl-silanyloxy)-propyl]-5-methoxy-1H-indole-3-carbonitrile [Reference Example 2(e)], there was prepared 6-{1-[3-(tert-butyl-dimethyl-silanyloxy)-propyl]-5-methoxy-1H-indol-3-yl}-5H-pyrrolo[2,3-b]pyrazine as a solid, TLC: R$_F$=0.4 (ethyl acetate/pentane: 1/1). $^1$H NMR [(CD$_3$)$_2$SO]: δ 8.27 (1H, d, 4 Hz); 8.08 (2H, m); 7.50 (2H, m); 6.96 (1H, s); 6.91 (1H, dd, 6, 2 Hz); 4.29 (2H, t, 6 Hz); 3.89 (3H, s); 3.61 (2H, t, 6 Hz); 2.00 (2H, m); 0.89 (9H, s); 0.03 (6H, s).

(c) By proceeding in a manner similar to Example 1(a) herein but using 1-[2-(tert-butyl-dimethyl-silanyloxy)-ethyl]-1H-indole-3-carbonitrile [Reference Example 2(f)], there was prepared 6-{1-[3-(tert-butyl-dimethyl-silanyloxy)-ethyl]-1H-indol-3-yl}-5H-pyrrolo[2,3-b]pyrazine as a solid, TLC: $R_F$=0.3 (ethyl acetate/pentane: 1/1). MS: 393(MH$^+$).

(d) By proceeding in a manner similar to Example 1(a) herein but using 1-[2-(tert-butyl-dimethyl-silanyloxy)-ethyl]-5-methoxy-1H-indole-3-carbonitrile [Reference Example 2(h)], there was prepared 6-{1-[2-(tert-butyl-dimethyl-silanyloxy)-ethyl]-5-methoxy-1H-indol-3-yl}-5H-pyrrolo[2,3-b]pyrazine as a brown solid, TLC: $R_F$=0.4 (dichloromethane/methanol: 19/1). MS: 423(MH$^+$).

(e) By proceeding in a manner similar to Example 1(a) herein but using 4-(4-cyanophenyl)piperazine-1-carboxylic acid, tert-butyl ester [Reference Example 75], and subjecting the reaction product to chromatography on silica using gradient elution conditions [from a mixture of ethyl acetate and heptane (1:1, v/v) to ethyl acetate], there was prepared 4-[4-(5H-pyrrolo[2,3,-b]pyrazin-6-yl)phenyl]piperazine-1-carboxylic acid, tert-butyl ester as a an off-white solid. LC-MS: Method A: $R_T$=3.42 minutes, 380(MH$^+$).

(f) By proceeding in a manner similar to Example 1(a) herein but using 1-(2-trimethylsilanyl-ethoxymethyl)-1H-indole-3-carbonitrile [Reference Example 2(s)], there was prepared 6-{1-(2-trimethylsianyl-ethoxymethyl)-1H-indol-3-yl]-5H-pyrrolo[2,3-b]pyrazine as a pale yellow solid. TLC $R_F$=0.20 (ethyl acetate/pentane, 1:1).

REFERENCE EXAMPLE 4
3-[3-(5H-Pyrrolo[2,3-b]pyrazin-6-yl)-indol-1-yl]-propylbromide To a solution of 3-[3-(5H-pyrrolo[2,3-b]pyrazin-6-yl)-indol-1-yl]-propan-1-ol [1 g, Example 2(a)] and carbon tetrabromide (1.59 g) in dichloromethane (40 mL) at ambient temperature was added a solution of triphenylphosphine (1.1 g) in dichloromethane (10 mL) over 2 minutes. The reaction mixture was stirred at ambient temperature for 3 hour, then stood for 18 hours and then evaporated to give the title compound which was used without further purification.

REFERENCE EXAMPLE 5
Indolizine-1-carbonitrile

A mixture of 2-pyridylacetontrile (5 g), and chloroacetaldehyde (4.42 g of 50% wt. solution in water) was heated at reflux in 1,4-dioxane (25 mL) for 5.5 hours. The reaction mixture was allowed to cool to ambient temperature then evaporated. The residue was partitioned between ethyl acetate (100 mL) and hydrochloric acid (100 mL, 1M). The aqueous layer was extracted twice with ethyl acetate (100 mL). The combined organic phases were washed with brine (50 mL), then dried over magnesium sulfate and then evaporated. The residue was subjected to flash column chromatography on silica eluting with dichloromethane to give the title compound (1.83 g) as a colourless solid, m.p. 53–54° C. MS: 143(MH$^+$).

REFERENCE EXAMPLE 6
3-Methyl-indolizine-1-carbonitrile

A solution of propionaldehyde (36 mL) in diethyl ether (200 mL) and 1,4-dioxane (1.7 mL) at 5° C. under nitrogen was treated dropwise with bromine (24.7 mL) over 2 hours whilst maintaining the temperature at 5° C. After the addition was complete, the reaction mixture was stirred for a further 30 minutes and then washed carefully with saturated sodium bicarbonate solution (100 mL). The organic phase was dried over sodium sulfate then concentrated in vacuo at 10° C. and then added immediately to a solution of 2-pyridylacetonitrile (8.36 mL) in acetone (50 mL). The resultant mixture was heated at reflux under nitrogen for 6 hours, then allowed to stand at ambient temperature overnight and then evaporated. The residue was partitioned between ethyl acetate (500 mL) and hydrochloric acid (100 mL, 1M). The organic layer was washed with brine (100 mL) and then evaporated. The residue was subjected to flash column chromatography on silica eluting with a mixture of ethyl acetate and pentane (1:4, v/v) and then triturated with diethyl ether to give the title compound (4.0 g) as a white solid, m.p. 98–100° C. MS: 157(MH$^+$).

REFERENCE EXAMPLE 7
Sodium-1-formyl-piperidine-2-carboxylate

To a solution of piperidine-2-carboxylic acid (30 g) in formic acid (230 mL) was added acetic anhydride (147 mL) dropwise. The resultant exotherm was controlled by cooling the reaction mixture in an ice/water bath. After stirring at ambient temperature for 24 hours the reaction mixture was diluted with water (20 mL) and then concentrated in vacuo. The resultant oil was dissolved in a mixture of methanol (50 mL) and acetonitrile (500 mL). Sodium hydroxide solution (10M, 23 mL) was added and the reaction mixture stirred for 8 hours. The resultant precipitate was filtered, washed with acetonitrile, and ethyl acetate and dried in a vacuum oven to afford the title compound as a white solid which was used immediately without further purification.

REFERENCE EXAMPLE 8
5,6,7,8-Tetrahydro-indolizine-1-carbonitrile

To a solution of sodium-1-formyl-piperidine-2-carboxylate (2.0 g) (Reference Example 7) in dichloromethane (50 mL) at ambient temperature under nitrogen was added para-toluenesulfonyl chloride (2.31 g). After stirring for 10 minutes the mixture was treated dropwise with acrylonitrile (0.88 mL) and triethylamine (1.5 mL) and stirring was continued for a further 1 hour when a second portion of triethylamine (1.0 mL) was added. The reaction mixture was stirred for 18 hours and the dichloromethane removed in vacuo. The residue was taken up in water (50 mL) and extracted with ethyl acetate (200 mL). The combined organic extracts were evaporated in vacuo and the residue was subjected to flash column chromatography on silica eluting with a mixture of ethyl acetate and pentane (1:4, v/v) to give the title compound (1.38 g) as an orange oil, MS: 147(MH$^+$). $^1$H NMR(CDCl$_3$): δ 6.48 (1H, d, J=3.1 Hz); 6.36 (1H, d, J=3.1 Hz); 3.91 (2H, t, J=6.0 Hz); 2.89 (2H, t, J=6.0 Hz); 1.98 (2H, m); 1.88 (2H, m).

REFERENCE EXAMPLE 9

(a) 1-(Toluene-4-sulfonyl)-1H-pyrrolo[2,3-b]pyridine

To a solution of 7-azaindole (25 g), para-toluenesulfonyl chloride (44.5 g) and a catalytic amount of tetrabutylammonium sulfate in dry toluene (300 mL) was added sodium hydroxide (160 g in 500 mL of water). The biphasic solution was stirred at ambient temperature for 3 hours then extracted twice with toluene (100 mL). The combined extracts were dried over magnesium sulfate then concentrated under vacuo. The resultant solid was triturated with diethyl ether then dried at 60° C. under vacuo to yield the title compound (39.74 g) as a pale yellow solid, m.p. 136–138° C.

(b) By proceeding in a similar manner to Reference Example 9(a) but using 4-nitro-1H-pyrrolo[2,3-b]pyridine (prepared according to the procedure described by A. Ippolito et al., J. Med. Chem. (1982), 25(10), 1258–61) there was prepared 4-nitro-1-(1-toluene-4-sulfonyl)-1H-pyrrolo[2,3-b]pyridine as an orange solid, m.p. 145–146° C. HPLC (METHOD A): $R_T$=10.80 minutes.

(c) By proceeding in a similar manner to Reference Example 9(a) but using 4-chloro-1H-pyrrolo[2,3-b]pyridine (Reference Example 64) there was prepared 4-chloro-1-(toluene-4-sulfonyl)-1H-pyrrolo[2,3-b]pyridine as a white solid. MS: 307(MH$^+$). $^1$H NMR (CDCl$_3$): δ 8.3 (d, 1H), 8.05 (d, 2H), 7.8 (d, 1H), 7.3 (d, 2H), 7.2 (d, 1H), 6.7 (d, 1H), 2.4 (s, 3H).

(d) By proceeding in a similar manner to Reference Example 9(a) but using 5-bromo-1H-pyrrolo[2,3-b]pyridine there was prepared 5-bromo-1-(toluene-4-sulfonyl)-1H-pyrrolo[2,3-b]pyridine as a white solid, m.p. 138–140° C.

(e) By proceeding in a similar manner to Reference Example 9(a) but using 6-phenyl-5H-pyrrolo[2,3-b]pyrazine (Reference Example 42) there was prepared 6-phenyl-5-(toluene-4-sulfonyl)-5H-pyrrolo[2,3-b]pyrazine as a white solid. $^1$H NMR [(CD$_3$)$_2$SO]: δ 8.44 (1H, d, J=4.5 Hz); 8.04 (2H, d, J=8.2 Hz); 7.98 (1H, d, J=4.5 Hz); 7.69 (2H, d, J=6.8 Hz); 7.57 (tt, J=6.2, 1.8 Hz); 7.51 (1H, tt, J=6.8, 1.8 Hz); 7.44 (2H, d, J=8.2 Hz); 7.42 (1H, d, J=4.5 Hz); 6.92 (1H, d, J=4.5 Hz) which was without further purification.

(f) By proceeding in a similar manner to Reference Example 9(a) but using 1H-pyrrolo[2,3-b]pyridine-4 carboxylic acid, tert-butyl ester [Reference Example 68] there was prepared 1-(toluene-4-sulfonyl)-1H-pyrrolo[2,3-b]pyridine-4 carboxylic acid, tert-butyl ester as a yellow solid. MS: 373(MH$^+$).

(g) By proceeding in a similar manner to Reference Example 9(a) but using 4-(pyridin-3-yl)-1H-pyrrolo[2,3-b]pyridine [Reference Example 67(c)] there was prepared 4-(pyridin-3-yl)-1-(toluene-4-sulfonyl)-1H-pyrrolo[2,3-b]pyridine as a white solid, m.p. 175–176° C. MS: 350 (MH$^+$).

(h) By proceeding in a manner similar to Reference Example 9(a) above but using 3-methyl-1H-pyrrolo[2,3-b]pyridine [prepared according to the procedure described by D. Hands et al, Synthesis (1996), (7), 877–882], there was prepared 3-methyl-1-(toluene-4-sulfonyl)-1H-pyrrolo[2,3-b]pyridine as an orange solid. MS: EI (70 eV); m/z=286 M$^+$.(40%); 221 (100%); 131 (45%); 104 (30%); 91 (60%).

(i) By proceeding in a manner similar to Reference Example 9(a) above but using 4-(3,5-dimethyl-isoxazole-4-yl)-1H-pyrrolo[2,3-b]pyridine [Reference Example 80], there was prepared 4-(3,5-dimethyl-isoxazole-4-yl)-1-(toluene-4-sulfonyl)-1H-pyrrolo[2,3-b]pyridine as a white solid. TLC: $R_F$=0.60 (ethyl acetate/heptane, 1:1). MS: 368 (MH$^+$).

(j) By proceeding in a manner similar to Reference Example 9(a) above but using 1H-Indole-5-carboxylic acid methyl ester, there was prepared 1-(toluene-4-sulfonyl)-1H-indole-5-carboxylic acid methyl ester as a yellow solid. m.p. 139–140° C.

REFERENCE EXAMPLE 10

2-Iodo-1-(toluene-4-sulfonyl)-1H-pyrrolo[2,3-b]pyridine

A solution of 1-(toluene-4-sulfonyl)-1H-pyrrolo[2,3-b]pyridine [54.4 g, Reference Example 9(a)] tetrahydrofuran (1200 mL) cooled to −78° C., was treated with a solution of butyllithium in hexanes (2.5M, 92 mL) over a 20 minute period. The solution was maintained at −78° C. for 30 minutes, then a solution of iodine (101 g) in tetrahydrofuran (600 mL) was added until the iodine colour persisted (ca.300 mL). The mixture was allowed to warm slowly to ambient temperature and the solvent removed under vacuo. The residue was partitioned between ethyl acetate (1000 mL) and water (500 mL) and the aqueous layer was extracted twice with ethyl acetate (500 mL). The combined organics were combined, dried over sodium sulfate and removed under reduced pressure to give a yellow solid which was triturated with diethyl ether to give the title compound (79.6 g) as a pale yellow solid, m.p. 105–107° C. MS: 399(MH$^+$).

REFERENCE EXAMPLE 11

(a) 3-Bromo-5-methoxy-indole-1-carboxylic Acid, Tert-Butyl Ester

A solution of 5-methoxyindole (10 g) in dry dimethylformamide (150 mL) at ambient temperature was treated with bromine (4 mL) dropwise ensuring the temperature did not rise above 30° C. The mixture was treated immediately with triethylamine (28 mL) and 4-dimethylaminopyridine (0.5 g) followed by a solution of di-tert-butyldicarbonate (18 g) in dry dimethylformamide (80 mL) and stirring was continued for a further 4 hours. The reaction mixture was evaporated and the residue was partitioned between ethyl acetate (250 mL) and water (200 mL). The aqueous layer was extracted with ethyl acetate (100 mL). The combined organic phases were washed with water (100 mL), then with brine (100 mL), then dried over magnesium sulfate and then evaporated. The residue was subjected to flash column chromatography on silica eluting with a mixture of pentane and ethyl acetate (19/1, v/v) to give the title compound (23.4 g) as a colourless solid, m.p. 111–112° C.

(b) By proceeding in a manner similar to Reference Example 11(a) above but using 5-cyano-indole, there was prepared 3-bromo-5-cyano-indole-1-carboxylic acid, tert-butyl ester as a grey solid, m.p. 172–174° C. MS: 322(MH$^+$).

(c) By proceeding in a manner similar to Reference Example 11(a) above but using 5,6-dimethoxy-indole, there was prepared 3-bromo-5,6-dimethoxy-indole-1-carboxylic acid, tert-butyl ester as a lilac solid. TLC: $R_F$=0.6 (pentane/ethyl acetate: 19/1).

(d) By proceeding in a manner similar to Reference Example 11(a) above but using 5-benzyloxy-6-methoxy-indole [prepared according to the method described by Benigni, J. D. and Minnis, R. L., J. Heterocycl. Chem., 387, 2, 1965] there was prepared 5-benzyloxy-3-bromo-6-methoxy-indole-1-carboxylic acid, tert-butyl ester as a colourless solid. MS: 433(MH$^+$). HPLC (METHOD A): $R_T$=13.99 minutes.

(e) By proceeding in a manner similar to Reference Example 11(a) above but using 5-amino-indole and an excess of di-tert-butyldicarbonate there was prepared 3-bromo-5-tert-butoxycarbonylamino-indole-1-carboxylic acid, tert-butyl ester as an orange oil. MS: 412(MH$^+$). TLC: $R_F$=0.8 (pentane/ethyl acetate: 9/1).

(f) By proceeding in a manner similar to Reference Example 11(a) above but using 1H-indole-6-carboxylic acid, methyl ester [Reference Example 31] there was prepared 3-bromo-indole-1,6-dicarboxylic acid, 1-tert-butyl ester 6-methyl ester as a pale violet solid, m.p. 117–119° C. MS: 355(MH$^+$).

(g) By proceeding in a manner similar to Reference Example 11(a) above but using 1H-indole-5-carboxylic acid methyl ester, there was prepared 3-bromo-indole-1,5-dicarboxylic acid, 1-tert-butyl ester 5-methyl ester as a solid. MS: 320 (MH$^+$), HPLC (Method C): $R_T$=4.54 minutes

REFERENCE EXAMPLE 12

(a) 2-(5-Methoxy-1H-indol-3-yl)-1-(toluene-4-sulfonyl)-1H-pyrrolo[2,3-b]pyridine A stirred solution of 3-bromo-5-methoxy-indole-1-carboxylic acid, tert-butyl ester [50 g, Reference Example 11(a)] in tetrahydrofuran (800 mL), under nitrogen, was treated with tributylborate (49.5 mL) then cooled to −100° C. and then treated with a solution of n-butyllithium in hexanes (94 mL, 2.5M) whilst keeping the temperature below −90° C. Once the addition was complete the mixture was allowed to warm slowly to room temperature over 1 hour and quenched by the addition of ice (10 g). The organics were removed under reduced pressure and the residue was partitioned between ethyl acetate (500 mL) and water (400 mL). The organic layer was dried over magnesium sulfate and then evaporated. The resulting boronic acid, a cream coloured solid (28 g), was dissolved in dimethylformamide (600 mL) and the solution was treated with 2-iodo-1-(toluene-4-sulfonyl)-1H-pyrrolo[2,3-b]pyridine [38.3 g, Reference Example 10], then with saturated aqueous sodium bicarbonate (200 mL) and then with tetrakis(triphenylphosphine)palladium[0] (3 g). The mixture was heated at reflux for 4 hours then allowed to cool to ambient temperature then concentrated to remove the dimethylformamide. The residue was partitioned between water (400 mL) and ethyl acetate (500 mL) and the aqueous was extracted twice with ethyl acetate (300 mL). The combined organics were dried over sodium sulfate then evaporated. The residual brown gum was triturated with ethyl acetate to give the title compound (27 g) as a pale green solid. MS: 418.43(MH$^+$).

(b) By proceeding in a manner similar to Reference Example 12(a) above but using 3-bromo-5-cyano-indole-1-carboxylic acid, tert-butyl ester [Reference Example 11(b)], there was prepared 3-[1-(toluene-4-sulfonyl)-1H-pyrrolo[2,3-b]pyridin-2-yl]-1H-indole-5-carbonitrile as a colourless solid, m.p. 209–214° C. MS: 413(MH$^+$).

(c) By proceeding in a manner similar to Reference Example 12(a) above but using 3-bromo-5,6-dimethoxy-indole-1-carboxylic acid, tert-butyl ester [Reference Example 11(c)], there was prepared 2-(5,6-dimethoxy-1H-indol-3-yl)-1-(toluene-4-sulfonyl)-1H-pyrrolo[2,3-b]pyridine as a brown solid, MS: 446(M−H$^+$).

(d) By proceeding in a manner similar to Reference Example 12(a) above but using 5-benzyloxy-3-bromo-6-methoxy-indole-1-carboxylic acid, tert-butyl ester [Reference Example 11(d)], there was prepared 2-(5-benzyloxy-6-methoxy-1H-indol-3-yl)-1-(toluene-4-sulfonyl)-1H-pyrrolo[2,3-b]pyridine as a colourless solid. MS: 524 (MH$^+$). HPLC (METHOD A):$R_T$=10.09 minutes.

(e) By proceeding in a manner similar to Reference Example 12(a) above but using 3-bromo-5-tert-butoxycarbonylamino-indole-1-carboxylic acid, tert-butyl ester [Reference Example 11(e)], there was prepared {3-[1-(toluene-4-sulfonyl)-1H-pyrrolo[2,3-b]pyridin-2-yl]-1H-indol-5-yl}-carbamic acid, tert-butyl ester as a tan solid. MS: 503(MH$^+$). TLC: $R_F$=0.62 (pentane/ethyl acetate: 1/1).

(f) By proceeding in a manner similar to Reference Example 12(a) above but using 3-bromo-indole-1,6-dicarboxylic acid, 1-tert-butyl ester 6-methyl ester [Reference Example 11(f)], there was prepared 3-[1-(toluene-4-sulfonyl)-1H-pyrrolo[2,3-b]pyridin-2-yl]-1H-indole-6-carboxylic acid, methyl ester as a pale yellow solid, m.p. 214–216° C. MS: 446(MH$^+$).

(g) By proceeding in a similar manner to Reference Example 12(a) but using 2-iodo-4-phenyl-1-(toluene-4-sulfonyl)-1H-pyrrolo[2,3-b]pyridine [Reference Example 62(d)] there was prepared 2-(5-methoxy-1H-indol-3-yl)-4-phenyl-1-(toluene-4-sulfonyl)-1H-pyrrolo[2,3-b]pyridine as a white solid. HPLC (METHOD A): $R_T$=11.63 minutes. MS: 494(MH$^+$).

(h) By proceeding in a similar manner to Reference Example 12(a) but using 4-chloro-2-iodo-1-(toluene-4-sulfonyl)-1H-pyrrolo[2,3-b]pyridine [Reference Example 62(b)] there was prepared 4-chloro-2-(5-methoxy-1H-indol-3-yl)-1-(toluene-4-sulfonyl)-1H-pyrrolo[2,3-b]pyridine as a white solid. MS: 452 (MH$^+$). $^1$H NMR (CDCl$_3$): δ 8.4 (d, 1H), 7.6 (d, 2H), 7.5 (s, 1H), 7.35 (d, 1H), 7.2 (d, 2H), 6.9 (m, 2H), 6.7 (s, 1H), 3.8 (s, 3H), 2.3 (s, 3H).

(i) By proceeding in a similar manner to Reference Example 12(a) but using 2-iodo-5-phenyl-1-(toluene-4-sulfonyl)-1H-pyrrolo[2,3-b]pyridine [Reference Example 62(c)] there was prepared 2-(5-methoxy-1H-indol-3-yl)-1-(toluene-4-sulfonyl)-5-phenyl-1H-pyrrolo[2,3-b]pyridine. MS:494(MH$^+$).

(j) By proceeding in a similar manner to Reference Example 12(a) but using 4-chloro-2-iodo-1-(para-toluenesulfonyl)-1H-pyrrolo[2,3-b]pyridine [Reference Example 62(b)] and 4-tertbutylphenyl boronic acid there was prepared 4-chloro-2-(4-tert-butylphenyl)-1-(para-toluenesulfonyl)-1H-pyrrolo[2,3-b]pyridine as a white solid. MS: 439 (MH$^+$). TLC: $R_F$=0.78 (ethyl acetate/heptane, 1:1).

(k) By proceeding in a manner similar to Reference Example 12(a) above but using 2-iodo-3-methyl-1-(toluene-4-sulfonyl)-1H-pyrrolo[2,3-b]pyridine [Reference Example 62(g)], there was prepared 2-(5-methoxy-1H-indol-3-yl)-3-methyl-1-(toluene-4-sulfonyl)-1H-pyrrolo[2,3-b]pyridine as a yellow solid. TLC: $R_F$=0.51 (ethyl acetate/cyclohexane 1:1). MS: EI (70 eV); m/z=431 M$^+$. (45%); 276 (100%); 244 (30%).

(l) By proceeding in a manner similar to Reference Example 12(a) above but using 4-(3,5-dimethyl-isoxazol-4-yl)-2-iodo-1-(toluene-4-sulfonyl)-1H-pyrrolo[2,3-b]pyridine [Reference Example 62(h)] and 3-bromo-indole-1,5-dicarboxylic acid, 1-tert-butyl ester 5-methyl ester [Reference Example 11(g)], there was prepared 3-[4-(3,5-dimethyl-isoxazole-4-yl)-1-(toluene-4-sulfonyl)-1H-pyrrolo[2,3-b]pyridine-2-yl]-1H-indole-5-carboxylic acid, methyl ester as a yellow solid, m.p. 155–156° C. TLC: $R_F$=0.32 (ethyl acetate/heptane, 1:1).

(m) By proceeding in a manner similar to Reference Example 12(a) above but using 4-(3,5-dimethyl-isoxazol-4-yl)-2-iodo-1-(toluene-4-sulfonyl)-1H-pyrrolo[2,3-b]pyridine [Reference Example 62(h)] and 3-bromo-5-methoxy-indole-1-carboxylic acid, tert-butyl ester [Reference Example 11(a)], there was prepared 4-(3,5-dimethyl-isoxazole-4-yl)-2-(5-methoxy-1H-indol-3-yl)-1-(toluene-4-sulfonyl)-1H-pyrrolo[2,3-b]pyridine as a yellow solid. TLC: $R_F$=0.26 (ethyl acetate/heptane 1:1). MS: 513 (MH$^+$).

(n) By proceeding in a manner similar to Reference Example 12(a) above but using 4-(methoxy)-2-iodo-1-(toluene-4-sulfonyl)-1H-pyrrolo[2,3-b]pyridine [Reference Example 62(i)] and 3-bromo-indole-1,5-dicarboxylic acid, 1-tert-butyl ester 5-methyl ester [Reference Example 11(g)], there was prepared 3-[4-methoxy-1-(toluene-4-sulfonyl)-1H-pyrrolo[2,3-b]pyridine-2-yl]-1H-indole-5-carboxylic acid, methyl ester as a white solid, MS: 476(MH$^+$). HPLC (Method C): $R_T$=4.72 minutes.

(o) By proceeding in a manner similar to Reference Example 12(a) above but using 4-(chloro)-2-iodo-1-(toluene-4-sulfonyl)-1H-pyrrolo[2,3-b]pyridine [Reference Example 62(b)] and 3-bromo-indole-1,5-dicarboxylic acid, 1-tertbutyl ester 5-methyl ester [Reference Example 11(g)], there was prepared 3-[4-chloro-1-(toluene-4-sulfonyl)-1H-pyrrolo[2,3-b]pyridine-2-yl]-1H-indole-5-carboxylic acid, methyl ester as an off-white solid. MS: 480(MH$^+$). HPLC(Method C): R$_T$=4.77 minutes.

(p) By proceeding in a manner similar to Reference Example 12(a) above but using trifluoro-methanesulfonic acid-1-(toluene-4-sulfonyl)-1H-indol-2-yl ester [Reference Example 71] and 1-(toluene-4-sulfonyl)-1H-indole-5-carboxylic acid, methyl ester, 3-boronic acid [Reference Example 85], starting from the addition of the boronic acid there was prepared 1-(toluene-4-sulfonyl)3-[(1-(toluene-4-sulfonyl)-1H-pyrrolo[2,3-b]pyridine-2-yl]-1H-indole-5-carboxylic acid, methyl ester as a colourless oil. TLC: R$_F$=0.27 (ethyl acetate/pentane, 1:1).

(q) By proceeding in a manner similar to Reference Example 12(a) but using 6-benzyloxy-3-iodo-5-methoxy-indole-1-carboxylic acid tert-butyl ester [Reference Example 82], there was prepared 2-o(6-benzyloxy-5-methoxy-1H-indol-3-yl)-1-(toluene-4-sulfonyl)-1H-pyrrolo[2,3-b]pyridine as a pale yellow solid, m.p. 222° C. TLC: R$_F$=0.33 (cyclohexane/ethyl acetate, 1/1).

REFERENCE EXAMPLE 13

(a) {5-Methoxy-3-[1-(toluene-4-sulfonyl)-1H-pyrrolo[2,3-b]pyridin-2-yl]-indol-1-ethyl ester A solution of 2-(5-methoxy-1H-indol-3-yl)-1-(toluene-4-sulfonyl)-1H-pyrrolo[2,3-b]pyridine [6.6 g, Reference Example 12(a)] in dimethylformamide (100 mL), under a nitrogen atmosphere, was treated with sodium hydride (700 mg, 60% dispersion in oil). After stirring at ambient temperature for 30 minutes the mixture was treated dropwise with ethyl chloroacetate (2.0 mL, 23.75 mmol) and stirring was continued for an additional 4 hours. The reaction mixture was evaporated and the residue was partitioned between ethyl acetate and water. The organic phase was washed with brine, then dried over sodium sulfate and then evaporated to give the title compound (5.77 g) as a yellow solid, MS: 504(MH$^+$). HPLC (METHOD A): R$_T$=11.88 minutes.

(b) By proceeding in a manner similar to Reference Example 13(a) above but using methyl iodide, there was prepared 2-(5-methoxy-1-methyl-1H-indol-3-yl)-1-(toluene-4-sulfonyl)-1H-pyrrolo[2,3-b]pyridine, as a yellow solid, m.p. 103–105° C. MS: 432(MH$^+$).

(c) By proceeding in a manner similar to Reference Example 13(a) above but using 3-[1-(toluene-4-sulfonyl)-1H-pyrrolo[2,3-b]pyridin-2-yl]-1H-indole-5-carbonitrile [Reference Example 12(b)] and methyl iodide, there was prepared 3-[1-(toluene-4-sulfonyl)-1H-pyrrolo[2,3-b]pyridin-2-yl]-1-methyl-1H-indole-5-carbonitrile, as a colourless solid, m.p. 189–191° C. MS: 427(MH$^+$).

(d) By proceeding in a manner similar to Reference Example 13(a) above but using 2-(5,6-dimethoxy-1H-indol-3-yl)-1-(toluene-4-sulfonyl)-1H-pyrrolo[2,3-b]pyridine [Reference Example 12(c)] and methyl iodide, there was prepared 2-(5,6-dimethoxy-1-methyl-1H-indol-3-yl)-1-(toluene-4-sulfonyl)-1H-pyrrolo[2,3-b]pyridine, as a brown solid, MS: 462(MH$^+$). $^1$H NMR [(CD$_3$)$_2$SO]: δ 11.22 (1H, s), 8.32 (1H, dd), 7.92 (1H, dd), 7.55 (2H, d), 7.45 (1H, s), 7.28 (1H, dd), 7.22 (2H, d), 7.00 (1H, s), 6.92 (1H, s), 6.75 (1H, s), 3.82 (3H, s), 3.72 (3H, s), 2.25 (3H, s).

(e) By proceeding in a manner similar to Reference Example 13(a) above but using 2-(5-benzyloxy-6-methoxy-1H-indol-3-yl)-1-(toluene-4-sulfonyl)-1H-pyrrolo[2,3-b]pyridine [Reference Example 12(d)] and methyl iodide, there was prepared 2-(5-benzyloxy-6-methoxy-1-methyl-1H-indol-3-yl)-1-(toluene-4-sulfonyl)-1H-pyrrolo[2,3-b]pyridine as a colourless solid. MS: 538(MH$^+$). HPLC (METHOD A): R$_T$=11.57 minutes.

(f) By proceeding in a manner similar to Reference Example 13(a) above but using {3-[1-(toluene-4-sulfonyl)-1H-pyrrolo[2,3-b]pyridin-2-yl]-1H-indol-5-yl}-carbamic acid, tert-butyl ester [Reference Example 12(e)] and methyl iodide, there was prepared {3-[1-(toluene-4-sulfonyl)-1H-pyrrolo[2,3-b]pyridin-2-yl]-1-methyl-1H-indol-5-yl}-carbamic acid, tert-butyl ester as a tan solid. MS: 517(MH$^+$). TLC: R$_F$=0.7 (pentane/ethyl acetate: 1/1).

(g) By proceeding in a manner similar to Reference Example 13(a) above but using 3-[1-(toluene-4-sulfonyl)-1H-pyrrolo[2,3-b]pyridin-2-yl]-1H-indole-6-carboxylic acid, methyl ester [Reference Example 12(f)] and methyl iodide, there was prepared 3-[1-(toluene-4-sulfonyl)-1H-pyrrolo[2,3-b]pyridin-2-yl]-1-methyl-1H-indole-6-carboxylic acid, methyl ester as a tan solid. MS: 460 (MH$^+$). TLC: R$_F$=0.6 (pentane/ethyl acetate: 1/1).

(h) By proceeding in a similar manner to Reference Example 13(a) above but using 2-(5-methoxy-1H-indol-3-yl)-1-(toluene-4-sulfonyl)-1H-pyrrolo[2,3-b]pyridine-4-carbonitrile (Reference Example 100) there was prepared 2-(5-methoxy-1-methyl-1H-indol-3-yl)-1-(toluene-4-sulfonyl)-1H-pyrrolo[2,3-b]pyridine-4-carbonitrile as a yellow oil. TLC: R$_F$=0.40 (ethyl acetate:heptane, 1:1). MS: 457(MH$^+$).

(i) By proceeding in a similar manner to Reference Example 13(a) above but using 4-chloro-2-(5-methoxy-1H-indol-3-yl)-1-(toluene-4-sulfonyl)-1H-pyrrolo[2,3-b] pyridine [Reference Example 12(h)] and methyl iodide, there was prepared 4-chloro-2-(5-methoxy-1-methyl-1H-indol-3-yl)-1-(toluene-4-sulfonyl)-1H-pyrrolo[2,3-b]pyridine as a off-white solid. MS: 466(MH$^+$). $^1$H NMR (CDCl$_3$): δ 8.35 (d, 1H); 7.56 (d, 2H), 7.39 (s, 1H); 7.16–7.3 (m, 2H), 7.05 (d, 2H), 6.95–7.0 (m, 2H) 6.6 (s, 1H) 3.9 (s, 3H) 3.8 (s, 3H) 2.3 (s, 3H).

(j) By proceeding in a similar manner to Reference Example 13(a) above but using 2-(5-methoxy-1H-indol-3-yl)-5-phenyl-1-(toluene-4-sulfonyl)-1H-pyrrolo[2,3-b] pyridine [Reference Example 12(i)] and methyl iodide, there was prepared 2-(5-methoxy-1-methyl-1H-indol-3-yl)-5-phenyl-1-(toluene-4-sulfonyl)-1H-pyrrolo[2,3-b]pyridine as a yellow solid, m.p. 181–183° C. MS: 508(MH$^+$).

(k) By proceeding in a manner similar to Reference Example 13(a) above but using 2-(5-methoxy-1H-indol-3-yl)-3-methyl-1-(toluene-4-sulfonyl)-1H-pyrrolo[2,3-b]pyridine [Reference Example 12(k)] and methyl iodide, there was prepared 2-(5-methoxy-1-methyl-1H-indol-3-yl)-3-methyl-1-(toluene-4-sulfonyl)-1H-pyrrolo[2,3-b]pyridine as a yellow solid. TLC: R$_F$=0.31 (ethyl acetate/cyclohexane, 4:6). MS: EI (70 eV); m/z=445 M$^+$. (45%); 290 (100%); 258 (25%).

(l) By proceeding in a manner similar to Reference Example 13(a) above but using 2-(1H-pyrrol-2-yl)-1-(toluene-4-sulfonyl)-1H-pyrrolo[2,3-b]pyridine [Reference Example 67(g)] and methyl iodide, there was prepared 2-(1-methyl-1H-pyrrol-2-yl)-1-(toluene-4-sulfonyl)-1H-pyrrolo[2,3-b]pyridine as a rust solid. TLC: R$_F$=0.28 (dichloromethane). MS: EI (70 eV); m/z=351 M$^+$. (45%); 196 (100%).

(m) By proceeding in a manner similar to Reference Example 13(a) above but using 3-[4-(3,5-dimethyl-isoxazole-4-yl)-1-(toluene-4-sulfonyl)-1H-pyrrolo[2,3-b]

pyridine-2-yl]-1H-indole-5-carboxylic acid, methyl ester [Reference Example [12(j)] and methyl iodide, there was prepared 3-[4-(3,5-dimethyl-isoxazole-4-yl)-1-(toluene-4-sulfonyl)-1H-pyrrolo[2,3-b]pyridine-2-yl]-1-methyl-1H-indole-5-carboxylic acid, methyl ester which was used directly in the preparation of Example 15(m).

(n) By proceeding in a manner similar to Reference Example 13(a) above but using 4-(3,5-dimethyl-isoxazole-4-yl)-2-(5-methoxy-1H-indol-3-yl)-1-(toluene-4-sulfonyl)-1H-pyrrolo[2,3-b]pyridine [Reference Example 12(k)] and methyl iodide, there was prepared 4-(3,5-dimethyl-isoxazol-4-yl)-2-(5-methoxy-1-methyl-1H-indol-3-yl)-1-(toluene-4-sufonyl)-1H-pyrrolo[2,3-b]pyridine as a yellow oil which was used immediately without further purification. MS: 527(MH$^+$), TLC R$_F$=0.35 (ethyl acetate/heptane 1:1).

(o) By proceeding in a manner similar to Reference Example 13(a) above but using 2-(5-methoxy-1H-indol-3-yl)-1-(toluene-4-sulfonyl)-1H-pyrrolo[2,3,-b]pyridine-4-carboxylic acid, tert-butyl ester [Reference Example 101] and ethyl iodide, there was prepared 2-(1-ethyl-5-methoxy-1H-indol-3-yl)-1-(toluene-4-sulfonyl)-1H-pyrrolo[2,3,-b]pyridine-4-carboxylic acid tert-butyl ester as a brown oil which was used directly in the preparation of Example 41(c). TLC: R$_F$=0.60 (ethyl acetate/heptane, 1:1).

(p) By proceeding in a manner similar to Reference Example 13(a) but using 2-(6-benzyloxy-5-methoxy-1H-indol-3-yl)-1-(toluene-4-sulfonyl)-1H-pyrrolo[2,3-b]pyridine [Reference Example 12(q)] and methyl iodide, there was prepared 2-(6-benzyloxy-5-methoxy-1-methyl-1H-indol-3-yl)-1-(toluene-4-sulfonyl)-1H-pyrrolo[2,3-b]pyridine as an off-white solid. TLC: R$_F$=0.41 (dichloromethane/ethyl acetate, 37/3). MS: EI (70 eV); m/z=537 M$^+$.(35%); 446 (100%); 291 (25%).

(q) By proceeding in a manner similar to Reference Example 13(a) but using 2-(5,6-dimethoxy-1H-indol-3-yl)-1-(toluene-4-sulfonyl)-1H-pyrrolo[2,3-b]pyridine (Reference Example 12(c)] and tert-butyl bromoacetate, there was prepared {5,6-dimethoxy-3-[1-(toluene-4-sulfonyl)-1H-pyrrolo[2,3-b]pyridin-2-yl]-indol-1-yl}-acetic acid tert-butyl ester as a pale green solid. TLC: R$_F$=0.62 (dichloromethane/methanol, 19/1). MS: CI (NH$_3$); m/z=562 MH$^+$.

(r) By proceeding in a manner similar to Reference Example 13(a) but using 2-(5,6-dimethoxy-1H-indol-3-yl)-1-(toluene-4-sulfonyl)-1H-pyrrolo[2,3-b]pyridine [Reference Example 12(c)], 4-(2-chloroethyl)morpholine hydrochloride and an excess of sodium hydride, there was prepared 2-[5,6-dimethoxy-1-(2-morpholin-4-yl-ethyl)-1H-indol-3-yl]-1-(toluene-4-sulfonyl)-1H-pyrrolo[2,3-b]pyridine as a purple foam. TLC: R$_F$=0.62 (dichloromethane/methanol, 9/1). MS: EI (70 eV); m/z=560 M$^+$.(50%); 292 (55%); 100 (100%).

REFERENCE EXAMPLE 14

(a) 3-1 1-(Toluene-4-sulfonyl)-1H-pyrrolo[2,3-b]pyridin-2-yl]-1-methyl-1H-indol-5-ol To a solution of 2-(5-methoxy-1-methyl-1H-indol-3-yl)-1-(toluene-4-sulfonyl)-1H-pyrrolo[2,3-b]pyridine [24.5 g, Reference Example 13(b)] in dichloromethane (500 mL), at 0° C. under an atmosphere of nitrogen, was added a solution of boron tribromide in dichloromethane (60 mL, 1.0M) and the mixture was stirred at 0° C. for 1 hour. The reaction mixture was allowed to warm slowly to ambient temperature and stirring continued for 12 hours. A solution of sodium carbonate (1M, 250 mL) was added to the mixture and stirring was continued vigorously for 3 hours. The precipitated solid was collected by filtration, washed with dichloromethane (100 mL) and dried to give the title compound (18.75 g) as a colourless solid, m.p. 256–257° C. MS: 418(MH$^+$).

(b) By proceeding in a manner similar to Reference Example 14(a) above but using 2-(5-methoxy-1H-indol-3-yl)-1-(toluene-4-sulfonyl)-1H-pyrrolo[2,3-b]pyridine [Reference example 12(a)], there was prepared 3-[1-(toluene-4-sulfonyl)-1H-pyrrolo[2,3-b]pyridin-2-yl]-1H-indol-5-ol as a beige solid, m.p. 188–191° C. MS: 403 (MH$^+$).

(c) By proceeding in a manner similar to Reference Example 14(a) above but using 4-chloro-2-(5-methoxy-1-methyl-1H-indol-3-yl)-1-(toluene-4-sulfonyl)-1H-pyrrolo[2,3-b]pyridine [Reference Example 13(i)], and subjecting the reaction product to chromatography on silica eluting with a mixture of dichloromethane and methanol (91:2, v/v) there was prepared 3-[4-chloro-1-(toluene-4-sulfonyl)-1H-pyrrolo[2,3-b]pyridin-2-yl]-1-methyl-1H-indol-5-ol as an off white solid LC-MS: Method A: R$_T$=3.01 minutes, 452.1(M$^+$).

REFERENCE EXAMPLE 15

(a) 2-(5-Allyloxy-1-methyl-1H-indol-3-yl)-1-(toluene-4-sulfonyl)-1H-pyrrolo[2,3-b]pyridine A solution of 1-methyl-3-[1-(toluene-4-sulfonyl)-1H-pyrrolo[2,3-b]pyridin-2-yl]-1H-indol-5-ol [2.1 g, Reference Example 14(a)] in dry dimethylformamide (50 mL) was treated with potassium tert-butoxide (620 mg) at 0° C. under nitrogen. After stirring for 10 minutes the mixture was treated with allyl bromide (480 µl) and then allowed to warm slowly to ambient temperature. Stirring was continued for a further 6 hours after which time the mixture was poured carefully into water and the aqueous phase extracted exhaustively with ethyl acetate. The combined organic extracts were washed twice with brine (100 mL), then dried over sodium sulfate and then evaporated. The residue was subjected to flash column chromatography on silica eluting with a mixture of ethyl acetate and pentane (1:1, v/v) to give the title compound (1.2 g) as a yellow foam, m.p. 257–259° C. MS: 458(MH$^+$).

(b) By proceeding in a manner similar to Reference Example 15(a) above but using ethyl-2-chloroacetate there was prepared {1-methyl-3-[1-(toluene-4-sulfonyl)-1H-pyrrolo[2,3-b]pyridin-2-yl]-1H-indol-5-yloxy}-acetic acid ethyl ester as a yellow solid. TLC: R$_F$=0.45 (ethyl acetate/pentane: 1/1). MS: 504(MH$^+$).

(c) By proceeding in a manner similar to Reference Example 15(a) above but using ethyl 2-bromoproprionate there was prepared 2-{1-methyl-3-[1-(toluene-4-sulfonyl)-1H-pyrrolo[2,3-b]pyridin-2-yl]-1H-indol-5-yloxy}-propionic acid ethyl ester as a yellow solid. TLC: R$_F$=0.47 (ethyl acetate/pentane: 1/1). MS: 519(MH$^+$).

(d) By proceeding in a manner similar to Reference Example 15(a) above but using ethyl-1-bromocyclobutanecarboxylate there was prepared 1-{1-methyl-3-[1-(toluene-4-sulfonyl)-1H-pyrrolo[2,3-b]pyridin-2-yl]-1H-indol-5-yloxy}-cyclobutanecarboxylic acid ethyl ester as a colourless solid, m.p. 189–190° C. MS: 544(MH$^+$).

(e) By proceeding in a similar manner to Reference Example 15(a) above but using 1-methyl-3-(5H-pyrrolo[2,3-b]

pyrazin-6-yl)-1H-indol-5-ol (Example 7) and ethyl 1-bromocyclobutane carboxylate there was prepared {1-[1-methyl-3-(5H-pyrrolo[2,3-b]pyrazin-6-yl)-1H-indol-5-yloxy]-cyclobutylcarboxylic acid ethyl ester as a tan solid. TLC: $R_F$=0.23 (dichloromethane/methanol, 19:1). HPLC (METHOD A): $R_T$=7.71 minutes.

REFERENCE EXAMPLE 16

3-{1-Methyl-3-[1-(toluene-4-sulfonyl)-1H-pyrrolo[2,3-b]pyridin-2-yl]-1H-indol-5-yloxy}-propane-1,2-diol A solution of 2-(5-allyloxy-1-methyl-1H-indol-3-yl)-1-(toluene-4-sulfonyl)-1H-pyrrolo[2,3-b]pyridine [45.7 mg, Reference Example 15(a)] in acetone (10 mL) was treated with a solution of 4-methylmorpholine-N-oxide (6 mg) in water (1 mL). This mixture was then treated with osmium tetroxide (2.5%/wt in tert-butanol, 6 drops) and the mixture stirred at room temperature for 12 hours. The reaction mixture was diluted with water (75 mL), and extracted exhaustively with ethyl acetate. The combined organics were washed twice with brine (75 mL), then dried over magnesium sulfate and then evaporated. The residue was subjected to flash column chromatography on silica eluting with ethyl acetate to give the title compound (33 mg) as a colourless solid. TLC: $R_F$=0.25 (ethyl acetate). MS: 492 (MH$^+$).

REFERENCE EXAMPLE 17

3-{1-Methyl-3-[1-(toluene-4-sulfonyl)-1H-pyrrolo[2,3-b]pyridin-2-yl]-1H-indol-5-yloxy}-propan-1-ol and 3-{1-Methyl-3-[1-(toluene-4-sulfonyl)-1H-pyrrolo[2,3-b]pyridin-2-yl]-1H-indol-5-yloxy}-propan-2-ol A solution of 2-(5-allyloxy-1-methyl-1H-indol-3-yl)-1-(toluene-4-sulfonyl)-1H-pyrrolo[2,3-b]pyridine [91 mg, Reference Example 15(a)] in dry tetrahydrofuran (5 mL) was treated with a solution of borane-tetrahydrofuran complex in tetrahydrofuran(1200 μl, 1.0M). After stirring at ambient temperature for 7 hours the reaction mixture was treated with ethanol (9 drops), 5N potassium hydroxide (4 drops) and hydrogen peroxide (6 drops) and stirring was continued for 12 hours during which time a white solid was precipitated. The reaction mixture was diluted with water (50 mL) and the pH of this mixture was adjusted to 10 by addition of potassium hydroxide solution (1M) before exhaustively extracting with ethyl acetate. The combined organic extracts were dried over sodium sulfate then evaporated. The residue was subjected to flash column chromatography on silica eluting with a mixture of ethyl acetate and pentane (2:1, v/v) to give 3-{1-methyl-3-[1-(toluene-4-sulfonyl)-1H-pyrrolo[2,3-b]pyridin-2-yl]-1H-indol-5-yloxy}-propan-1-ol (50 mg) as a colourless solid [TLC: $R_F$=0.15 (ethyl acetate). MS: 476(MH$^+$)] and 3-{1-methyl-3-[1-(toluene-4-sulfonyl)-1H-pyrrolo[2,3-b]pyridin-2-yl]-1H-indol-5-yloxy}-propan-2-ol (8 mg) as a colourless solid. [TLC: $R_F$=0.3 (ethyl acetate); MS: 476(MH$^+$)].

REFERENCE EXAMPLE 18

(a) Trifluoro-methanesulfonic acid 1-methyl-3-[1-(toluene-4-sulfonyl)-1H-pyrrolo[2,3-b]pyridin-2-yl]-1H-indol-5-yl ester A suspension of 1-methyl-3-[1-(toluene-4-sulfonyl)-1H-pyrrolo[2,3-b]pyridin-2-yl]-1H-indol-5-ol [398 mg, Reference Example 14(a)] in dichloromethane (10 mL), cooled to −78° C. under a nitrogen atmosphere, was treated with triethylamine (0.15 mL) followed by N-phenyltrifluoromethanesulfonimide (1.7 g). The resultant mixture was allowed to warm slowly to ambient temperature, stirring was continued for a further 12 hours then saturated sodium bicarbonate (20 mL) was added. The organic phase was separated and the aqueous phase was extracted twice with dichloromethane (20 mL). The combined organics were dried over sodium sulfate then evaporated. The residue was subjected to flash column chromatography on silica eluting with a mixture of ethyl acetate and pentane (2:3, v/v) to give the title compound (380 mg) as a colourless solid. MS: 492(MH$^+$). HPLC (METHOD A): $R_T$=2.02 minutes.

(b) By proceeding in a similar manner to Reference Example 18(a) but using 1-methyl-3-(5H-pyrrolo[2,3-b]pyrazin-6-yl)-1H-indol-5-ol (Example 7) there was prepared trifluoro-methanesulfonic acid 1-methyl-3-[5H-pyrrolo[2,3-b]pyrazin-6-yl]-1H-indol-5-yl ester as a purple solid. HPLC (METHOD A): $R_T$=8.12 minutes. $^1$H NMR [(CD$_3$)$_2$ SO]: δ 12.30 (1H, s); 8.32 (1H, s); 8.27 (1H, d, J=3.5 Hz); 8.23 (1H, s); 7.97 (1H, s); 7.76 (1H, d, J=8.6 Hz); 7.08 (1H, s); 3.96 (3H, s).

(c) By proceeding in a similar manner to Reference Example 18(a) but using 4-hydroxy-1H-pyrrolo[2,3-b]pyridine there was prepared trifluoro-methanesulfonic acid 1H-pyrrolo[2,3-b]pyridin-4-yl ester as a white solid. MS: 267(MH$^+$).

(d) By proceeding in a similar manner to Reference Example 18(a) but using 3-[6-(4-hydroxyphenyl)-5H-pyrrolo[2,3-b]pyrazin-7-yl]-N-methylpropionamide [Example 40(d)] there was prepared 3-[6-(4-trifluoromethanesulfonyloxyphenyl)-5H-pyrrolo[2,3-b]pyrazin-7-yl]-N-methylpropionamide as a white solid. MS: 429.1(MH$^+$).

(e) By proceeding in a similar manner to Reference Example 18(a) but using 6-(4-hydroxyphenyl)-5H-pyrrolo[2,3-b]pyrazine [Example 1(ao)] there was prepared 6-(4-trifluoromethanesulfonyloxyphenyl)-5H-pyrrolo[2,3-b]pyrazine as a cream solid. MS: 344(MH$^+$).

(f) By proceeding in a similar manner to Reference Example 18(a) but using 3-[4-chloro-1-(toluene-4-sulfonyl)-1H-pyrrolo[2,3-b]pyridin-2-yl]-1-methyl-1H-indol-5-ol [Reference Example 14(c)] there was prepared trifluoro-methanesulfonic acid 3-[4-chloro-1-(toluene-4-sulfonyl)-1H-pyrrolo[2,3-b]pyridin-2-yl]-1-methyl-1H-indol-5-yl ester as a white foam. LC-MS: Method A: RT=4.20 minutes, 584.1(M$^+$).

(g) By proceeding in a similar manner to Reference Example 18(a) but using 1H-pyrrolo[2,3-b]pyridine-4-ol [Reference Example 86] with a mixture of dichloromethane and dimethylformamide (10:4, v/v) as solvent and subjecting the crude product to flash column chromatography eluting with a mixture of ethyl acetate and heptane (1:2, v:v) there was prepared trifluoromethanesulfonic acid-1H-pyrrolo[2,3-b]pyridin-4-yl ester as a white solid. MS: 267(MH$^+$), TLC: $R_F$=0.46 (ethyl acetate/heptane, 1:1).

REFERENCE EXAMPLE 19

(a) 1-Methyl-3-[1-(toluene-4-sulfonyl)-1H-pyrrolo[2,3-b]pyridin-2-yl]-1H-indole-5-carboxylic acid, methyl ester A solution of trifluoro-methanesulfonic acid 1-methyl-3-[1-(toluene-4-sulfonyl)-1H-pyrrolo[2,3-b]pyridin-2-yl]-1H-indol-5-yl ester [300 mg, Reference Example 18(a)] in a mixture of dry dimethylformamide (10 mL), methanol (6 mL) and triethylamine (2 mL) was treated with palladium acetate (24 mg) and 1,3 bis(diphenylphosphino)propane and the mixture stirred at ambient temperature for 30 minutes. Carbon monoxide was introduced via a septum to the reaction vessel at a steady rate and the mixture heated at 90° C. until no starting material was present as indicated by TLC (ethyl acetate/pentane: 2/3). The mixture was then concentrated in vacuo and the residue partitioned between dichloromethane and water. The organic phase was washed with a saturated solution of lithium chloride, then dried over sodium sulfate and then evaporated. The residue was subjected to flash column chromatography on silica eluting with a mixture of ethyl acetate and pentane (2:3, v/v) to give the title compound (200 mg) as a colourless solid. MS: 460 (MH$^+$). HPLC (METHOD A): R$_T$=10.23 minutes.

(b) By proceeding in a similar manner to Reference Example 19(a) but using trifluoro-methanesulfonic acid 1-methyl-3-[5H-pyrrolo[2,3-b]pyrazin-6-yl]-1H-indol-5-yl ester [Reference Example 18(b)] there was prepared 1-methyl-3-(5H-pyrrolo[2,3-b]pyrazin-6-yl)-1H-indole-5-carboxylic acid, methyl ester as a brown solid. MS: 307(MH$^+$). HPLC (METHOD A): R$_T$=6.64 minutes.

(c) By proceeding in a similar manner to Reference Example 19(a) but using trifluoro-methanesulfonic acid 1H-pyrrolo[2,3-b]pyridin-4-yl ester [Reference Example 18(c)] there was prepared 1H-pyrrolo[2,3-b]pyridine-4 carboxylic acid, methyl ester as a yellow solid. MS: 177(MH$^+$). TLC: R$_F$=0.4 (ethyl acetate: heptane, 1:1, v/v).

(d) By proceeding in a similar manner to Reference Example 19(a) but using trifluoro-methanesulfonic acid 3-[4-chloro-1-(toluene-4-sulfonyl)-1H-pyrrolo[2,3-b]pyridin-2-yl]-1-methyl-1H-indol-5-yl ester [Reference Example 18(f)] there was prepared 3-(4-chloro-1-(toluene-4-sulfonyl)-1H-pyrrolo[2,3-b]pyridin-2-yl)-1-methyl-1H-indole-5-carboxylic acid, methyl ester as a white foam. LC-MS: Method A: R$_T$=3.95 minutes, 494(MH$^+$).

REFERENCE EXAMPLE 20
2-[1-Methyl-5-(1-trimethylstannany-1H-tetrazol-5-yl)-1H-indol-3-yl]-1-(toluene-4-sulfonyl)-1H-pyrrolo[2,3-b]pyridine A solution of 1-methyl-3-[1-(toluene-4-sulfonyl)-1H-pyrrolo[2,3-b]pyridin-2-yl]-1H-indole-5-carbonitrile [100 mg, Reference Example 13(c)] in toluene (10 mL) was treated with trimethyltin azide (56 mg, 0.28 mmol) then heated under reflux for 14 hours. The white precipitate was collected by filtration washed with toluene (10 mL) and then dried to give the title compound (125 mg) as a colourless solid, m.p. 240–243° C. (with decomposition). MS: 633 (MH$^+$).

REFERENCE EXAMPLE 21
2-[1-Methyl-5-(1-methyl-1H-tetrazol-5-yl)-1H-indol-3-yl]-1-(toluene-4-sulfonyl)-1H-pyrrolo[2,3-b]pyridine and 2-[1-Methyl-5-(2-methyl-2H-tetrazol-5-yl)-1H-indol-3-yl]-1-(toluene-4-sulfonyl)-1H-pyrrolo[2,3-b]pyridine Methyl iodide (2.5 mL) was added to a solution of 2-[1-methyl-5-(1-trimethylstannanyl-1H-tetrazol-5-yl)-1H-indol-3-yl]-1-(toluene-4-sulfonyl)-1H-pyrrolo[2,3-b]pyridine [620 mg, Reference Example 20] at ambient temperature. The mixture was then allowed to stir at ambient temperature for 4 hours then was poured into water and then extracted with ethyl acetate. The combined extract was washed with brine, then dried over magnesium sulfate and then evaporated. The residue was subjected to flash chromatography on silica eluting with a mixture of ethyl acetate and petroleum ether (1:1, v/v) to give 2-[1-methyl-5-(1-methyl-1H-tetrazol-5-yl)-1H-indol-3-yl]-1-(toluene-4-sulfonyl)-1H-pyrrolo[2,3-b]pyridine (191 mg) as a colourless solid, [MS: 506(MNa$^+$). $^1$H NMR [(CD$_3$)$_2$SO]: δ 8.39 (dd, 1H, J=4.8 and 1.6 Hz); 7.97 (m, 1H); 7.96 (d, 1H, J=4.0 Hz); 7.90 (s, 1H); 7.80 (dd, 1H, J=8.7 and 0.6 Hz); 7.70 (dd, 1H, J=8.7 and 1.8 Hz); 7.56 (m, 2H); 7.30 (dd, 1H, J=7.7 and 4.8 Hz); 7.22 (m, 2H); 6.82 (s, 1H); 4.19 (s, 3H); 4.0 (s, 3H); 2.23 (s, 3H)] and 2-[1-Methyl-5-(2-methyl-2H-tetrazol-5-yl)-1H-indol-3-yl]-1-(toluene-4-sulfonyl)-1H-pyrrolo[2,3-b]pyridine (77 mg) as a colourless solid, m.p. 215–218° C. [MS: 506(MNa$^+$)].

REFERENCE EXAMPLE 22
1-{1-Methyl-3-[1-(toluene-4-sulfonyl)-1H-pyrrolo[2,3-b]pyridin-2-yl]-1H-indol-5-yl}-ethanone To dry, degassed dimethylformamide (110 mL) under nitrogen at ambient temperature, was added trifluoro-methanesulfonic acid 1-methyl-3-[1-(toluene-4-sulfonyl)-1H-pyrrolo[2,3-b]pyridin-2-yl]-1H-indol-5-yl ester [2.2 g, Reference Example 18], triethylamine (1.15 mL), n-butylvinylether (2.87 mL), 1,3-bis (diphenylphosphinopropane) (413 mg) and palladium acetate (232 mg) sequentially. The mixture was heated at reflux for 2 hours then cooled to ambient temperature and then added to hydrochloric acid (90 mL, 1M). This mixture was extracted with dichloromethane (200 mL). The organic extract was washed with saturated aqueous sodium bicarbonate, then with brine, then dried over magnesium sulfate and then evaporated. The residue was subjected to flash chromatography on silica eluting with a mixture of ethyl acetate and pentane (2:3, v/v) to give the title compound (1.1 g) as a yellow solid, m.p. 177–178° C. MS: 444(MH$^+$).

REFERENCE EXAMPLE 23

(a) 2-[5-({S}-(+)-2,2-Dimethyl-[1,3]dioxolan-4-ylmethoxy)-1-methyl-1H-indol-3-yl]-1-(toluene-4-sulfonyl)-1H-pyrrolo[2,3-b]pyridine A solution of 1-methyl-3-[1-(toluene-4-sulfonyl)-1H-pyrrolo[2,3-b]pyridin-2-yl]-1H-indol-5-ol [1.17 g, Reference Example 14(a)] in dry dimethylformamide (50 mL) was treated with caesium carbonate (1.1 g) and tetrabutylammonium hydrogen sulfate (40 mg). After stirring at ambient temperature for 30 minutes the mixture was treated with (R)-(+)-2,2-dimethyl-1,3-dioxolane-4-ylmethyl-paratoluenesulfonate (0.96 g) then heated at 120° C. overnight. The reaction mixture was concentrated in vacuo and the residue partitioned twice between dichloromethane (100 mL) and water (50 mL) and the aqueous layers were extracted with dichloromethane (100 mL). The combined organic phases were washed twice with brine (150 mL), then dried over magnesium sulfate and then evaporated. The residue was subjected to flash chromatography on silica eluting with a mixture of dichloromethane and methanol (199:1, v/v) to give the title compound (1.04 g) as a yellow oil, MS: 532(MH$^+$). $^1$H NMR [(CD$_3$)$_2$SO]: δ 1.30 (3H, s); 1.37 (3H, s); 2.29 (3H, s); 3.76 (1H, dd, J=8.3 and 6.5 Hz); 3.90 (3H, s); 3.94–3.98 (2H, m); 4.10 (1H, dd, J=8.20 and 6.5 Hz); 4.41 (1H, m); 6.74 (1H, s); 6.91 (1H, dd, J=8.8 and 2.3 Hz); 6.98 (1H, d, J=2.4 Hz); 7.25 (2H, d, J=7.9 Hz); 7.29 (1H, dd, J=7.8 and 4.9 Hz); 7.44 (1H, d, J=8.8 Hz); 7.56 (1H, d, J=8.3 Hz); 7.63 (1H, s); 7.81 (2H, d, J=8.0 Hz); 7.92 (1H, dd, J=7.7 and 1.6 Hz); 8.33. (1H, dd, J=4.9 and 1.7 Hz).

(b) By proceeding in a manner similar to Reference Example 23(a) above but using (S)-(−)-2,2-dimethyl-1,3-dioxolane-4-ylmethyl-paratoluenesulfonate there was prepared 2-[5-({R}-(−)-2,2-dimethyl-[1,3-dioxolan-4-ylmethoxy)-1-methyl-1H-indol-3-yl]-1-(toluene-4-sulfonyl)-1H-pyrrolo[2,3-b]pyridine as a yellow oil, MS: 532(MH$^+$). $^1$H NMR [(CD$_3$)$_2$SO]: δ 1.33 (3H, s); 1.37 (3H, s); 2.29 (3H, s); 3.77 (1H, dd, J=8.3 and 6.5 Hz); 3.88 (3H, s); 3.97–3.99 (2H, m); 4.11 (1H, dd, J=8.3 and 6.6 Hz); 4.41 (1H, m); 6.74 (1H, s); 6.94 (1H, dd, J=8.8 and 2.3 Hz); 6.97 (1H, d, J=2.3 Hz); 7.25 (2H, d, J=8.1 Hz); 7.29 (1H, dd, J=7.8 and 4.9 Hz); 7.44 (1H, d. J=8.8 Hz); 7.57 (2H, d, J=8.4 Hz); 7.63 (1H, s); 7.95 (1H, dd, J=7.81 and 1.7 Hz); 8.33 (1H, dd, J=4.88 and 1.7 Hz).

(c) By proceeding in a manner similar to Reference Example 23(a) above but using 2-(5-hydroxy-6-methoxy-1-methyl-1H-indol-3-yl)-1-(toluene-4-sulfonyl)-1H-pyrrolo[2,3-b]pyridine [Reference Example 28(a)], there was prepared 2-[5-({S}-(+)-2,2-dimethyl-[1,3]dioxolan-4-ylmethoxy)-6-methoxy-1-methyl-1H-indol-3-yl]-1-(toluene-4-sulfonyl)-1H-pyrrolo[2,3-b]pyridine as a cream solid. MS: 548(MH$^+$). HPLC (METHOD A): $R_T$=11.60 minutes.

(d) By proceeding in a manner similar to Reference Example 23(a) above but using 3-[1-(toluene-4-sulfonyl)-1H-pyrrolo[2,3-b]pyridin-2-yl]-1H-indol-5-ol [Reference Example 14(b)] and ethyl 1-bromocyclobutane carboxylate, there was prepared 1-{1-(cyclobutanecarboxylic acid ethyl ester)-3-[1-(toluene-4-sulfonyl)-1H-pyrrolo[2,3-b]pyridin-2-yl]-1H-indol-5-yloxy}-cyclobutanecarboxylic acid ethyl ester as a cream solid. MS: 657(MH$^+$). $^1$H NMR [(CD$_3$)$_2$SO]: δ 8.35 (1H, dd, J=4.8 and 1.6 Hz); 7.9 (2H, m); 7.48 (3H, m); 7.28 (1H, dd, J=7.7 and 4.8 Hz); 7.24 (2H, d, J=8.4 Hz); 6.71 (1H, dd, J=8.9 and 2.4 Hz); 6.68 (1H, s); 6.64 (1H, d, J=2.4 Hz); 5.12 (1H, dd, J=8.8 and 8.8 Hz); 4.13–4.03 (4H, m); 3.66 (1H, dd, J=9.4 and 9.4 Hz); 2.64–1.82 (13H, m); 1.15 (3H, t, J=7.1 Hz); 0.94 (3H, t, J=7.1 Hz).

(e) 1-{1-methyl-3-[1-(toluene-4-sulfonyl)-1H-pyrrolo[2,3-b]pyridin-2-yl]-1-propan-2-one By proceeding in a manner similar to Reference Example 23(a) above but using 1-methyl-3-[1-(toluene-4-sulfonyl)-1H-pyrrolo[2,3-b]pyridin-2-yl]-1H-indol-5-ol [Reference Example 14(a)] and chloroacetone, there was prepared 1-{1-methyl-3-[1-(toluene-4-sulfonyl)-1H-pyrrolo[2,3-b]pyridin-2-yl]-1H-indol-5-yloxy}-propan-2-one as a pale yellow foam. $^1$H NMR [(CD$_3$)$_2$SO]: δ 8.35 (1H, dd); 7.93 (1H, dd); 7.62 (1H, s); 7.55 (2H, d); 7.48 (1H, d); 7.28 (3H, m); 6.92 (2H, m); 6.72 (1H, s); 4.70 (2H, s); 3.90 (3H, s); 2.28 (3H, s); 2.15 (3H, s).

REFERENCE EXAMPLE 24

(a) (R)-3-{1-Methyl-3-[1-(toluene-4-sulfonyl)-1H-pyrrolo[2,3-b]pyridin-2-yl]-H-indol-5-yloxyl-propane-1,2-diol A solution of 2-[5-({R}-(−)-2,2-dimethyl-[1,3]dioxolan-4-ylmethoxy)-1-methyl-1H-indol-3-yl]-1-(toluene-4-sulfonyl)-1H-pyrrolo[2,3-b]pyridine [1.04 g, Reference Example 23(b)] in methanol (20 mL) was treated with hydrochloric acid (20 mL, 1M) then heated under reflux for 3 hours. The reaction mixture was concentrated in vacuo and the residue subjected to flash chromatography on silica eluting with a mixture of ethyl acetate and pentane (2:1, v/v) to give the title compound (380 mg) as a clear oil. TLC: $R_F$=0.2 (pentane/ethyl acetate: 1/2). MS: 492(MH$^+$).

(b) By proceeding in a manner similar to Example 24(a) but using 2-[5-({S}-(+)-2,2-dimethyl-[1,3]dioxolan-4-ylmethoxy)-1-methyl-1H-indol-3-yl]-1-(toluene-4-sulfonyl)-1H-pyrrolo[2,3-b]pyridine [Reference Example 23(a)] there was prepared (S)-3-t 1-methyl-3-[1-(toluene-4-sulfonyl)-1-H-pyrrolo[2,3-b]pyridin-2-yl]-1H-indol-5-yloxy}-propane-1,2-diol as a clear oil.

MS: 492(MH$^+$). $^1$H NMR [(CD$_3$)$_2$SO]: δ 8.33 (1H, dd, 4.9, J=1.7 Hz); 7.92 (1H, dd, J=7.8 and 1.7 Hz); 7.62 (1H, s); 7.56 (2H, d, J=8.8 Hz); 7.45 (1H, d, J=8.8 Hz); 7.29 (1H, dd, J=7.8 and 4.8 Hz); 7.25 (2H, d, J=8.1 Hz); 6.96 (1H, d, J=2.3 Hz); 6.92 (1H, dd, J=8.8 and 2.3 Hz); 6.75 (1H, s); 4.93 (1H, s); 4.66 (1H, s); 5.13 (1H, d, J=5.13 Hz); 3.88 (3H, s); 3.80 (2H, d, J=5.9 Hz); 3.46 (2H, s); 2.23 (3H, s).

(c) By proceeding in a manner similar to Example 24(a) above but using 2-[5-({S}-(+)-2,2-dimethyl-[1,3]dioxolan-4-ylmethoxy)-6-methoxy-1-methyl-1H-indol-3-yl]-1-(toluene-4-sulfonyl)-1H-pyrrolo[2,3-b]pyridine [Reference Example 23(c)] there was prepared (S)-3-{6-methoxy-1-methyl-3-[1-(toluene-4-sulfonyl)-1H-pyrrolo[2,3-b]pyridin-2-yl]-1H-indol-5-yloxy}-propane-1,2-diol as a cream solid. MS: 522(MH$^+$). HPLC (METHOD A): $R_T$=8.15 minutes.

REFERENCE EXAMPLE 25

2-[5-(2-Methoxy-1-methyl-ethoxy)-1-methyl-1H-indol-3-yl]-1-(toluene-4-sulfonyl)-1H-pyrrolo[2,3-b]pyridine A solution of triphenylphosphine (470 mg) and diisopropyldiazodicarboxylate (350 μl) in dry toluene (15 mL) was treated with 1-methyl-3-[1-(toluene-4-sulfonyl)-1H-pyrrolo[2,3-b]pyridin-2-yl]-1H-indol-5-ol [150 mg, Reference Example 14(a)] followed by 1-methoxy-2-propanol (150 μl). The resulting mixture was heated under reflux for 5 hours then cooled and then evaporated. The residue was subjected to flash chromatography on silica eluting with a mixture of ethyl acetate and pentane (1:1, v/v) to give the title compound (50 mg) as a clear oil. TLC: $R_F$=0.65 (pentane/ethyl acetate: 1/1). MS: 480(MH$^+$).

REFERENCE EXAMPLE 26

N-Hydroxy-1-methyl-3-[1-(toluene-4-sulfonyl)-1H-pyrrolo[2,3-b]pyridin-2-yl]-1H-indol-5-carboxamidine A solution of 1-methyl-3-[1-(toluene-4-sulfonyl)-1H-pyrrolo[2,3-b]pyridin-2-yl]-1H-indole-5-carbonitrile [2.11 g, Reference Example 13(c)] in ethanol (150 mL) at ambient temperature was treated with hydroxylamine hydrochloride (1.7$^2$ g) and potassium carbonate (3.43 g). The reaction mixture was heated at reflux under nitrogen for 15 hours then filtered. The filtrate was evaporated to give the title compound (2.8 g) as a dark green solid. MS: 460(MH$^+$). HPLC (METHOD A): $R_T$=6.19 minutes.

REFERENCE EXAMPLE 27

2-[1-Methyl-5-(5-methyl-[1,2,4]oxadiazol-3-yl)-1H-indol-3-yl]-1-(toluene-4-sulfonyl)-1H-pyrrolo[2,3-b]pyridine To a suspension of N-hydroxy-1-methyl-3-[1-(toluene-4-sulfonyl)-1H-pyrrolo[2,3-b]pyridin-2-yl]-1H-indole-5carboxamidine [0.7 g, Reference Example 26] in toluene (30 mL) at ambient temperature under nitrogen was added acetic anhydride (0.467 g). The reaction mixture was heated at reflux for 4.5 hours then filtered. The filtrate was evaporated to give the title compound (0.32 g) as a dark red oil which was used immediately without further purification.

REFERENCE EXAMPLE 28

2-(5-Hydroxy-6-methoxy-1-methyl-1H-indol-3-yl)-1-(toluene-4-sulfonyl)-1H-pyrrolo[2,3-b]pyridine A solution of 2-(5-benzyloxy-6-methoxy-1-methyl-1H-indol-3-yl)-1-(toluene-4-sulfonyl)-1H-pyrrolo[2,3-b]pyridine [6.26 g, Reference Example 13(e)] in acetonitrile (500 mL) was treated with sodium iodide (4.38 g) followed by trimethylsilyl chloride (3.17 mL). The mixture stirred at 40° C. for 3 hours then treated with further portions of sodium iodide (4.38 g) and trimethylsilyl chloride (3.17 mL). After stirring at 40° C. for a further 12 hours the reaction mixture was evaporated. The residue was treated with water (200 mL) and the mixture was extracted three times with ethyl acetate (200 mL). The combined extracts were dried over magnesium sulfate then evaporated. The residual brown foam was triturated with ethyl acetate and diisopropyl ether to give the title compound (3.04 g) as a light brown solid, m.p. 211–214° C. HPLC (METHOD A): $R_T$=9.30 minutes.

REFERENCE EXAMPLE 29

1-{6-Methoxy-1-methyl-3-[1-(toluene-4-sulfonyl)-1H-pyrrolo[2,3-b]pyridin-2-yl]-1H-indol-5-yloxy}-Cyclobutanecarboxylic acid ethyl ester Sodium hydride (43 mg, 60% dispersion in mineral oil) was added to a stirred solution of 2-(5-hydroxy-6-methoxy-1-methyl-1H-indol-3-yl)-1-(toluene-4-sulfonyl)-1H-pyrrolo[2,3-b]pyridine [400 mg, Reference Example 28(a)] in dry dimethylformamide (20 mL) under a nitrogen atmosphere at ambient temperature. The mixture was allowed to stir for 1 hour then treated with ethyl-1-bromocyclobutanecarboxylate (216 µl) and stirring was continued overnight. Additional portions of sodium hydride (43 mg, 60% dispersion in mineral oil) and ethyl 1-bromocyclobutanecarboxylate (216 µl) were then added, then the mixture was heated at 50° C. for 5 hours. The cooled reaction mixture was evaporated and the residue was partitioned between ethyl acetate and water. The organic phase was washed with water, then with brine, then dried over magnesium sulfate and then evaporated. The yellow residue was subjected to flash chromatography on silica eluting with a mixture of ethyl acetate and pentane (2:3, v/v) to give the title compound (266 mg) as a yellow oil. MS: 576(MH$^+$). HPLC (METHOD A): $R_T$=11.07 minutes.

REFERENCE EXAMPLE 30

[1-Methyl-3-(1H-pyrrolo[2,3-b]pyridin-2-yl)-1H-indol-5-yl]-carbamic acid, tert-butyl ester A solution of {1-methyl-3-[1-(toluene-4-sulfonyl)-1H-pyrrolo[2,3-b]pyridin-2-yl]-1H-indol-5-yl}-carbamic acid, tert-butyl ester [0.3 g, Reference Example 13(f)] in methanol (15 mL) was treated with potassium hydroxide solution (5N, 2 mL) then heated at reflux for 4 hours. The reaction mixture was evaporated and the residue triturated with water to give the title compound (0.2 g) as a tan solid. MS: 263(MH$^+$). TLC: $R_F$=0.3 (ethyl acetate).

REFERENCE EXAMPLE 31

1H-Indole-6-carboxylic acid methyl ester

A solution of 1H-indole-6-carboxylic acid (10 g) in methanol (300 mL) was treated with concentrated sulfuric acid (0.5 mL) then heated on a steam bath for 10 hours. The solvent was removed under reduced pressure and the residue partitioned between saturated sodium bicarbonate solution (150 mL) and dichloromethane (150 mL). The aqueous layer was further extracted twice with dichloromethane (150 mL). The combined organics were dried over sodium sulfate then evaporated. The residue was subjected to flash chromatography on silica eluting with a mixture of ethyl acetate and pentane (7:3, v/v) to give the title compound (7.4 g) as a white solid, m.p. 79–81° C. MS: 176(MH$^+$).

REFERENCE EXAMPLE 32

Dimethyl-(6-phenyl-5H-pyrrolo[2,3-b]pyrazin-7-ylmethyl)-amine

A solution of dimethylamine in tetrahydrofuran (0.5 mL, 2.0M) at 0° C. was treated with glacial acetic acid (15 µl) then with formaldehyde (75 µl, 40% solution). After stirring at 0° C. for 10 minutes this mixture was treated with 6-phenyl-5H-pyrrolo[2,3-b]pyrazine [0.195 g, Example 2(c)] and then with tetrahydrofuran (3 mL) to ensure complete dissolution. The reaction mixture was allowed to warm to ambient temperature, then stirred overnight, then diluted with ethyl acetate (5 mL) and then extracted three times with hydrochloric acid (5 mL, 1N). The combined acid extracts were adjusted to pH 6–7 by addition of potassium hydroxide solution (5N). The resulting pale yellow solid was filtered, then washed with water and then dried to give the title compound (0.16 g) as a pale yellow solid, m.p. 191–192°C.

REFERENCE EXAMPLE 33

Trimethyl-(6-phenyl-5H-pyrrolo[2,3-b]pyrazin-7-ylmethyl)-ammonium iodide

A solution of dimethyl-(6-phenyl-5H-pyrrolo[2,3-b]pyrazin-7-ylmethyl)-amine [5.1 g, Reference Example 32] in ethyl acetate (100 mL) at 0° C. was treated with a solution of iodomethane (40 mL) in ethanol (150 mL). The resulting mixture was stirred at 0° C. for 2 hours. The precipitated solid was filtered then washed with ethyl acetate (10 mL) and then with diethyl ether (20 mL) to give the title compound as a yellow solid (4.5 g), m.p. 224–225° C.

REFERENCE EXAMPLE 34

(6-Phenyl-5H-pyrrolo[2,3-b]pyrazin-7-yl)-acetonitrile

A solution of potassium cyanide (0.84 g) in water (20 mL) was added rapidly to a stirred solution of trimethyl-(6-phenyl-5H-pyrrolo[2,3-b]pyrazin-7-ylmethyl)-ammonium iodide [1.1 g, Reference Example 33] in dimethylformamide (20 mL) and the mixture heated at 75° C. for 6 hours. The cooled solution was diluted with water (100 mL) and the precipitated solid filtered to give the title compound as a yellow solid, m.p. 247–248° C.

REFERENCE EXAMPLE 35

(6-Phenyl-5H-pyrrolo[2,3-b]pyrazin-7-yl)-acetic acid

A solution of (6-phenyl-5H-pyrrolo[2,3-b]pyrazin-7-yl)-acetonitrile [70 mg, Reference Example 34] in potassium hydroxide (10M, 5 mL) was heated at 100° C. for 1.5 hours. The reaction mixture was allowed to cooled, then diluted with water (25 mL) and then acidified to pH 1 by addition of concentrated hydrochloric acid. The resulting pale yellow solid was filtered, then washed with water and then dried to give the title compound (40 mg) as a yellow solid, m.p. 276–277° C.

REFERENCE EXAMPLE 36

1-Methyl-3-[1-(toluene-4-sulfonyl)-1H-pyrrolo[2,3-b]pyridin-2-yl]-1H-indole-5-carbaldehyde To a solution of 1-methyl-3-[1-(toluene-4-sulfonyl)-1H-pyrrolo[2,3-b]pyridin-2-yl]-1H-indole-5-carbonitrile [500 mg, Reference Example 13(c)] in tetrahydrofuran (20 mL) at 0° C. was added diisobutylaluminium hydride (12 mL, 1M in tetrahydrofuran) under an atmosphere of nitrogen. The resultant solution was then allowed to warm to ambient temperature and stirred at this temperature for 2 hours. The reaction mixture was then poured into a solution of cold 1N aqueous hydrochloric acid (20 mL). After 1 hour, the mixture was made alkaline with saturated aqueous sodium hydroxide and extracted with ethyl acetate (40 mL). The organic layer was separated and the aqueous further extracted with ethyl acetate (2×20 mL). The organic extracts were combined, dried over magnesium sulfate and concentrated in vacuo to give the title compound (221 mg) as a white solid, m.p. 188–189° C. MS: 430(MH$^+$).

REFERENCE EXAMPLE 37

3-{1-Methyl-3-[1-(toluene-4-sulfonyl)-1H-pyrrolo[2,3-b]pyridin-2-yl]-1H-indol-5-yl}-acrylic acid ethyl ester Triethylphosphonoacetate (60 mL) was added at 0° C. to a suspension of sodium hydride (22.4 mg, 60% dispersion in mineral oil) in dimethoxyethane (3 mL). The resultant suspension was stirred at ambient temperature for 1 hour. 1-Methyl-3-[1-(toluene-4-sulfonyl)-1H-pyrrolo[2,3-b] pyridin-2-yl]-1H-indole-5-carbaldehyde [120 mg, Reference Example 36] in dimethoxyethane (2 mL) was added and stirring was continued for 3 hours. The reaction mixture was then poured into water and extracted twice with ethyl acetate (30 mL). The combined organics were then washed with brine before drying over magnesium sulfate and then concentrated in vacuo to give the title compound (126 mg) as a yellow solid, m.p. 159–162° C. MS: 500(MH$^+$).

REFERENCE EXAMPLE 38

(a) 3-{1-Methyl-3-[1-(toluene-4-sulfonyl)-1H-pyrrolo[2,3-b]pyridin-2-yl]-1H-indol-5-yl}-propionic acid ethyl ester Palladium (15.7 mg, 10% on activated carbon) was added to a suspension of 3-{1-methyl-3-[1-(toluene-4-sulfonyl)-1H-pyrrolo[2,3-b]pyridin-2-yl]-1H-indol-5-yl}-acrylic acid ethyl ester [100 mg, Reference Example 37] in industrial methylated spirit (25 mL). The resultant suspension was then stirred under an atmosphere of hydrogen for 16 hours. The reaction mixture was then filtered through a pad of celite and the filtrate evaporated in vacuo. The resultant solid was triturated with water, filtered and dried to give the title compound (92 mg) as a white solid, m.p. 280–282° C. MS: 502(MH$^+$).

(b) By proceeding in a manner similar to Example 38(a) above but using ethyl 3-[2-dimethylamino-5-(5H-pyrrolo [2,3-b]pyrazin-6-yl)phenyl]prop-2-enonate (Reference Example 47), there was prepared ethyl 3-[2-dimethylamino-5-(5H-pyrrolo[2,3-b]pyrazin-6-yl) phenyl]propionate as an orange gum which was used directly in the next reaction. $^1$H NMR [(CD3)$_2$SO]; δ 8.33 (1H, s); 8.17 (1H, s); 7.94 (1H, s); 7.82 (1H, d, J=8.4 Hz); 7.20 (1H, d, J=8.4 Hz); 7.03 (1H, s); 4.07 (2H, q, J=7.6 Hz); 3.38 (2H, t, J=7.1 Hz); 3.00 (2H, t, J=7.1 Hz); 2.70 (6H, s); 1.19 (3H, t, J=7.1 Hz).

REFERENCE EXAMPLE 39

4-Methoxy-2-(5-methoxy-1H-indol-3-yl)-1-(toluene-4-sulfonyl)-1H-pyrrolo[2,3-b]pyridine By proceeding in a similar manner to Example 18 but using 2-(1-N-tert-butyloxycarbonyl-5-methoxy-1H-indol-3-yl)-4-methoxy-1-(toluene-4-sulfonyl)-1H-pyrrolo[2,3-b] pyridine (Reference Example 40) there was prepared the title compound as a tan solid. HPLC (METHOD A): R$_T$=8.49 minutes. MS: 448(MH$^+$).

REFERENCE EXAMPLE 40

2-(1-tert-Butyloxycarbonyl-5-methoxy-1H-indol-3-yl)-4-methoxy-1-(toluene-4-sulfonyl)-1H-pyrrolo[2,3-b]pyridine A stirred solution of diisopropylamine (0.21 mL) in tetrahydrofuran (5 mL), at −70° C. and under nitrogen, was treated with a solution of n-butyllithium in hexanes (0.6 mL, 2.5M) over 5 minutes, whilst maintaining the temperature below −65° C. After stirring for 1 hour the mixture was added, at −30° C., to a solution of 4-methoxy-1-(toluene-4-sulfonyl)-1H-pyrrolo[2,3-b]pyridine (Reference Example 41, 280 mg) in tetrahydrofuran (10 mL), whilst maintaining the temperature below −25° C. After allowing to warm to −15° C. over 1 hour a solution of zinc chloride in tetrahydrofuran (2.8 mL, 0.5M) was added, maintaining the temperature below −10° C. After 30 minutes the reaction mixture was treated with tetrakis(triphenylphosphine) palladium [0] (54 mg) and 3-bromo-5-methoxy-indole-1-carboxylic acid tert-butyl ester (Reference Example 11(a), 152 mg) and stirred at 60° C. for 16 hours, then treated with water (30 mL). The mixture was extracted with ethyl acetate (3×25 mL). The combined organics were washed with brine (2×15 mL), dried over magnesium sulfate and then evaporated. The residue was subjected to flash chromatography on silica eluting with a mixture of ethyl acetate and pentane (1:1, v/v) to give the title compound (45 mg) as a white foam. TLC R$_F$=0.34 (ethyl acetate/pentane: 1/1). HPLC (METHOD A): R$_T$=9.72 minutes.

REFERENCE EXAMPLE 41

4-Methoxy-1-(1-toluene-4-sulfonyl)-1H-pyrrolo[2,3-b] pyridine

Method A: A mixture of 4-nitro-1-(1-toluene-4-sulfonyl)-1H-pyrrolo[2,3-b]pyridine [Reference Example 9(b), 0.77 g] and dry dimethylformamide (25 mL) was treated with sodium methoxide (0.17 g) and stirred at 50° C. for 16 hours. A further portion of sodium methoxide (0.085 g) was then added and stirring continued for 8 hours, then the dimethylformamide was removed in vacuo. The residue was dissolved in ethyl acetate (100 mL) and washed with a water/ brine mixture (1/1, 60 mL). The organics were dried over magnesium sulfate and then evaporated. The residue was subjected to flash chromatography on silica eluting with ethyl acetate to give the title compound as a cream solid. HPLC: R$_T$=9.73 minutes. $^1$H NMR [(CD$_3$)$_2$SO]: δ 8.22 (1H, d, J=8.2 Hz); 7.96 (2H, d, J=9.4 Hz); 7.71 (1H, d, J=3.5 Hz); 7.39 (2H, d, J=9.4 Hz); 6.89 (1H, d, J=8.2 Hz); 6.72 (1H, d, J=3.5 Hz); 3.93 (3H, s); 2.30 (3H, s).

Method B: To 4-chloro-1H-pyrrolo[2,3-b]pyridine [2,3 g, Reference Example 64] in a stainless steel pressure vessel was added sodium hydroxide (2 g), and methanol (40 mL). The pressure vessel was sealed and heated at 170° C. for 4 hours. After cooling, water (100 mL) was added and the mixture was neutralised by addition of excess solid carbon dioxide pellets (30 g). After concentration to a slurry and filtration, the residue was washed twice with water (5 mL) to afford 4-methoxy-1H-pyrrolo[2,3-b]pyridine as a solid. To a mixture of 4-methoxy-1H-pyrrolo[2,3-b]pyridine (5.85 g) in toluene (150 mL) and water (150 mL) was added potassium hydroxide pellets (2.5 g), 4-methylbenzene sulfonyl chloride (7.53 g) and tetra-n-butyl ammonium hydrogen sulfate (0.02 g). This mixture was stirred at room temperature for 20 hours then extracted four times with ethyl acetate (100 mL). The combined organic extracts were concentrated and then subjected to flash column chromatography on silica eluting with a mixture of ethyl acetate and heptane (35:65, v/v) to afford the title compound as a white solid.

REFERENCE EXAMPLE 42

4-Phenyl-1H-pyrrolo[2,3-b]pyridine

A suspension of 1-(2,6-dimethyl-1,4-dihydropyridin-4-one)-1H-pyrrolo[2,3-b]pyridinium tetrafluoroborate (Reference Example 43, 1.0 g) in tetrahydrofuran (100 mL) was treated with a solution of phenylmagnesium bromide in tetrahydrofuran (9.6 mL, 1M) and stirred at room temperature for 72 hours before adding water ((100 mL) and the tetrahydrofuran removed in vacuo. The residue was extracted with chloroform (3×100 mL), and the combined organics dried over sodium sulfate and evaporated. The residue was subjected to flash chromatography on silica eluting with a mixture of dichloromethane and methanol (99:1 v/v) to give the title compound (83 mg) as a white solid. MS: 195(MH$^+$). $^1$H NMR [(CD$_3$)$_2$SO]: δ 8.27 (1H, d, J=4.1 Hz); 7.78 (2H, d, J=8.2 Hz); 7.57 (3H, m); 7.48 (1H, t, J=8.2 Hz); 7.19 (1H, d, J=3.5 Hz); 6.60 (1H, s).

REFERENCE EXAMPLE 43
1-(2,6-Dimethyl-1,4-dihydropyridin-4-one)-1H-pyrrolo[2,3-b]pyridinium tetrafluoroborate A mixture of ethyl O-2,4,6-trimethylsulfonylacetohydroxamate (28.5 g) in perchloric acid (160 mL, 70%) was stirred at room temperature for 2 hours, then dichloromethane (30 mL) was added. The mixture was poured onto ice/water (1 liter) and rapidly extracted three times with dichloromethane (100 mL). The combined organics were washed twice with brine (100 mL) and dried over sodium sulfate. The organics were then added slowly to a solution of 1H-pyrrolo[2,3-b]pyridine (11.8 g) in dichloromethane (100 mL). Filtration gave 1-amino-1H-pyrrolo[2,3-b]pyridinium 2,4,6-trimethylphenylsulfonate, which was used directly in the next step.

A mixture of 1-amino-1H-pyrrolo[2,3-b]pyridinium 2,4,6-trimethylphenylsulfonate (16.6 g) and 3-acetyl-6-methyl-2H-pyran-2,4(3H)-dione (8.8 g) in concentrated hydrochloric acid (40 mL) was stirred at reflux for 4 hours, then cooled and concentrated in vacuo. The residue was dissolved in ethanol (30 mL) and diluted with a solution of tetrafluoroboric acid in diethyl ether (54% v/v, 30 mL) and stirred for 1 hour at room temperature. Filtration gave the title compound (15.0 g) as a white solid, m.p. 247–248° C. $^1$H NMR [(CD$_3$)$_2$SO]: δ 9.24 (1H, d, J=7.5 Hz); 9.13 (1H, d, J=7.5 Hz); 8.08 (1H, d, J=4.2 Hz); 7.93 (1H, t, J=7.5 Hz); 7.22 (1H, d, J=4.2 Hz); 6.83 (2H, s); 1.96 (6H, s).

REFERENCE EXAMPLE 44
(a) Dimethyl 3-[6-(4-tert-butylphenyl-5H-pyrrolo[2,3-b]pyrazin-7-yl]-propionic 1,1-diacid-dicarboxylate To a solution of dimethyl malonate (1.3 g) dissolved in N-methylpyrrolidinone (30 mL) at 0° C. under nitrogen was added sodium hydride (0.39 g). After 10 minutes, a solution of [6-(4-tert-butylphenyl-5H-pyrrolo[2,3-b]pyrazin-7-yl]methyltrimethylammonium iodide [1.12 g, Reference Example 45(a)] was added and the reaction mixture was warmed to room temperature and allowed to stir for 3 hours. The reaction mixture was poured into water (200 mL) and extracted three times with ethyl acetate (100 mL). The combined organic fractions were dried over magnesium sulfate and then evaporated. The residue was subjected to flash column chromatography on silica eluting with a mixture of ethyl acetate and pentane (1:1, v/v) to give the title compound (0.5 g) as a white solid. $^1$H NMR(CDCl$_3$): δ 9.48 (1H, s); 8.42 (1H, s); 8.16 (1H, s); 7.64 (2H, d, J=9.0 Hz); 7.58 (2H, d, J=9.0 Hz); 4.45 (1H, t, J=8.2 Hz); 3.63 (2H, d, J=8.2 Hz); 3.58 (6H, s); 1.40 (9H, s).

(b) By proceeding in a manner similar to Reference Example 44(a) above but using [6-(4-(1-methyl)ethoxy)phenyl-5H-pyrrolo[2,3-b]pyrazin-7-yl]methyltrimethyl ammonium iodide [Reference Example 45(b)], there was prepared dimethyl 3-[6-(4-(1-methyl)ethoxyphenyl)-5H-pyrrolo[2,3-b]pyrazin-7-yl]-propionic 1,1-diacid 1,1-dicarboxylate as a beige solid. MS: 398(MH$^+$). $^1$H NMR [CDCl$_3$]: δ 10.1(broad s, 1H); 8.41(d, 1H, J=2.3 Hz); 8.16(d, 1H, J=2.3 Hz); 7.62(d, 2H, J=8.21 Hz); 7.03(d, 2H, J=8.20 Hz); 4.64(m, 1H); 4.45(t, 1H); 3.78(d, 1H); 3.60(s, 6H); 1.41(d, 6H, J=4.41 Hz).

(c) By proceeding in a manner similar to Reference Example 44(a) above but using [6-(4-fluorophenyl)-5H-pyrrolo[2,3-b]pyrazin-7-yl]methyltrimethylammonium iodide [Reference Example 45(c)], there was prepared dimethyl 3-[6-(4-fluorophenyl)-5H-pyrrolo[2,3-b]pyrazin-7-yl]-propionic 1,1-diacid 1,1-dicarboxylate as an off-white solid. NMR DMSO 12.2 (s, 1H), 8.4 (d, 1H), 8.2 (d, 1H), 7.8 (d, 2H), 7.4 (d, 2H), 4.4 (t, 1H) 3.7 (s, 6H), 3.6 (d, 2H). MS: 357(MH$^+$).

(d) By proceeding in a manner similar to Reference 44(a) above but using [6-(4-methoxyphenyl)-5H-pyrrolo[2,3-b]pyrazin-7-yl]methyltrimethylammonium iodide [Reference Example 45(d)], there was prepared dimethyl 3-[6-(4-methoxyphenyl)-5H-pyrrolo[2,3-b]pyrazin-7-yl]-propionic 1,1-diacid 1,1-dicarboxylate as an off-white solid. MS: 369(MH$^+$).

REFERENCE EXAMPLE 45
(a) [6-(4-tert-Butylphenyl-5H-pyrrolo[2,3-b]pyrazin-7-yl]methyltrimethelammonium iodide To a solution of [6-(4-tert-butylphenyl-5H-pyrrolo[2,3-b]pyrazin-7-yl]methyldimethylamine [0.8 g. Reference Example 46(a)] in tetrahydrofuran (50 mL) under nitrogen at 40° C. was added methyl iodide (4.5 mL). The reaction mixture was stirred for 4 hours and the solvent was evaporated. The residue was chased with toluene (30 mL) and dried under vacuum to afford the title compound as a yellow solid which was used immediately without further purification in the next reaction.

(b) By proceeding in a manner similar to Reference Example 45(a) above but using 6-(4-(1-methyl)ethoxy)phenyl-5H-pyrrolo[2,3-b]pyrazin-7-yl]methyldimethylamine [Reference Example 46(b)], there was prepared [6-(4-(1-methyl)ethoxy)phenyl-5H-pyrrolo[2,3-b]pyrazin-7-yl]methyltrimethylammonium iodide as a beige solid, which was used immediately without further purification.

(c) By proceeding in a manner similar to Reference Example 45(a) above but using [6-(4-fluorophenyl-5H-pyrrolo[2,3-b]pyrazin-7-yl]methyldimethylamine [Reference Example 46(c)], there was prepared 6-(4-fluorophenyl)-5H-pyrrolo[2,3-b]pyrazin-7-yl]methyltrimethylammonium iodide as a yellow solid. $^1$H NMR [(CD$_3$)$_2$SO]: δ 13.0 (s, 1H), 8.5 (d, 1H), 8.4 (d, 1H), 7.7 (d, 2H), 7.6 (d, 2H), 3.1 (d, 2H), 2.9 (s, 9H). MS: 285 (MH$^+$).

(d) By proceeding in a manner similar to Reference Example 45(a) above but using [6-(4-methoxyphenyl-5H-pyrrolo[2,3-b]pyrazin-7-yl]methyldimethylamine [Reference Example 46(d)], there was prepared 6-(4-methoxyphenyl)-5H-pyrrolo[2,3-b]pyrazin-7-yl]methyltrimethylammonium iodide as an off-white solid. MS: 297(MH$^+$).

REFERENCE EXAMPLE 46
(a) [6-(4-tert-Butylphenyl-5H-pyrrolo[2,3-b]pyrazin-7-yl]methyldimethylamine To a solution of dimethylamine (15 mL of a 2M solution in tetrahydrofuran) and acetic acid (0.45 mL) at 0° C. was added formaldehyde (2.25 mL of a 40% aqueous solution). The reaction mixture was stirred for 10 minutes. A solution of 6-(4-tert-butylphenyl)-5H-pyrrolo[2,3-b]pyrazine [6.9 g, Example 1(w)] in tetrahydrofuran (400 mL) was added and the reaction mixture allowed to stir at room temperature overnight. The reaction mixture was washed with 1N sodium hydroxide solution, brine, dried over magnesium sulfate and evaporated in vacuo. The residue was subjected to flash column chromatography on silica eluting with a mixture of tetrahydrofuran and methanol (1:1, v/v) to give the title compound (0.8 g) as a yellow solid. MS: 309(MH$^+$). HPLC (Method A): R$_T$=1.93 minutes.

(b) By proceeding in a manner similar to Reference Example 46(a) above but using 6-[4-(1-methyl)ethoxyphenyl]-5H-pyrrolo[2,3-b]pyrazine [Example 1(aa)], there was prepared 6-(4-(1-methyl)ethoxy)phenyl-5H-pyrrolo[2,3-b]pyrazin-7-yl]methyl-dimethylamine as a beige solid.

(c) By proceeding in a manner similar to Reference Example 46(a) above but using 6-(4-fluorophenyl)-5H-pyrrolo[2,3-b]pyrazine [Example 1(ae)], there was prepared [6-(4-fluorophenyl-5H-pyrrolo[2,3-b]pyrazin-7-yl]methyldimethylamine as an off-white solid. $^1$H NMR [(CD$_3$)$_2$SO]: δ 12.0 (s, 1H), 8.5 (d, 1H), 8.2 (d, 1H), 7.7 (d, 2H), 7.6 (d, 2H), 3.9 (d, 2H), 2.9 (s, 6H). MS: 270(MH$^+$).

(d) By proceeding in a manner similar to Reference Example 46(a) above but using 6-(4-methoxyphenyl)-5H-pyrrolo[2,3-b]pyrazine [Example 1(af)], there was prepared [6-(4-methoxyphenyl-5H-pyrrolo[2,3-b]pyrazin-7-yl]methyldimethylamine as a off-white solid. MS: 282 (MH$^+$).

REFERENCE EXAMPLE 47

Ethyl 3-[2-dimethylamino-5-(5H-pyrrolo[2,3-b]pyrazin-6-yl)phenyl]prop-2-enonate

To a solution of 6-(3-bromo-4-dimethylamino)phenyl-5H-pyrrolo[2,3-b]pyrazine [0.1 g, Reference Example 48] in dry dimethylformamide (10 mL) in a schlenk tube was added ethyl acrylate (0.25 mL), palladium (II) acetate (0.05 g), tri-(2-methylphenyl)phosphine (0.07 g) and tributylamine (0.8 g). The tube was sealed and heated at 95° C. for 24 hours then allowed to stand at room temperature for a further 24 hours. The reaction mixture was quenched with water (150 mL) and extracted into ethyl acetate (100 mL), washed with brine and dried over magnesium sulfate. After concentration in vacuo the resultant orange gum was triturated with toluene to afford the title compound as an orange solid (0.04 g). TLC: R$_F$=0.46 (ethyl acetate). $^1$H NMR [(CD$_3$)$_2$SO]: δ 12.40 (1H, s); 8.38 (1H, s); 8.34 (1H, s); 8.02 (1H, d, J=8.6 Hz); 7.89 (1H, d, J=16.5 Hz); 7.22 (1H, d, J=8.6 Hz); 7.19 (1H, s); 6.81 91H, d, J=16.5 Hz); 4.23 (2H, q, J=7.1 Hz); 2.78 (6H, s); 1.30 (3H, t, J=7.1 Hz).

REFERENCE EXAMPLE 48

6-(3-Bromo-4-dimethylamino)phenyl-5H-pyrrolo[2,3-b]pyrazine

To a stirred solution of 4-(dimethylamino)benzonitrile (2.19 g) in chloroform (15 mL) was added pyridine (1.2 mL) and a solution of bromine (0.75 mL) in chloroform (15 mL) dropwise over 45 minutes. Upon complete addition, the mixture was stirred for a further 30 minutes. The reaction mixture was diluted with dichloromethane and washed with water, brine and evaporated to afford a yellow oil of 3-bromo-4-dimethylaminobenzonitrile which was dissolved in tetrahydrofuran (25 mL). Meanwhile, a stirred solution of diisopropylamine (2.7 mL) in tetrahydrofuran (50 mL), at −15° C. and under nitrogen, was treated with a solution of n-butyllithium in hexanes (7.70 mL, 2.5M) over 30 minutes, whilst maintaining the temperature below −10° C. After stirring for 30 minutes the mixture was treated with methylpyrazine (1.21 g) over 15 minutes, then stirred for 1 hour. The solution of 3-bromo-4-(dimethylamino)benzonitrile was added over 1 hour, keeping the temperature below −10° C. The reaction mixture was allowed to warm to room temperature over 2 hours, then stood overnight, then treated with water (10 mL). The tetrahydrofuran was removed in vacuo and the resultant mixture was treated with a mixture of water and ethyl acetate (1:1 v/v) and the mixture stirred for 15 minutes. The resultant precipitate was collected by filtration and washed thoroughly with water/ethyl acetate (1:1 v/v) to afford the title compound as a yellow solid (1.0 g). TLC: R$_F$=0.41 (ethyl acetate).

REFERENCE EXAMPLE 49

6-(3-tert-Butyldimethylsilyloxy-4-methoxy)phenyl-5H-pyrrolo[2,3-b]pyrazine

A stirred solution of diisopropylamine (3.6 mL) in tetrahydrofuran (133 mL), at −15° C. and under nitrogen, was treated with a solution of n-butyllithium in hexanes (11.21 mL, 2.5M) over 30 minutes, whilst maintaining the temperature below −10° C. After stirring for 30 minutes the mixture was treated with methylpyrazine (2.04 g) over 15 minutes, then stirred for 1 hour and then treated with a solution of 3-tert-butyldimethylsilyloxy-4-methoxybenzonitrile (5.7 g, Reference Example 50) in tetrahydrofuran (20 mL) over 1 hour, keeping the temperature below −10° C. The reaction mixture was allowed to warm to room temperature over 2 hours, then stood overnight, then treated with water (10 mL). The tetrahydrofuran was removed in vacuo and the resultant mixture was partitioned between ethyl acetate and water. The two layers were separated, and the aqueous layer was extracted with ethyl acetate. The combined organics were dried over sodium sulfate and evaporated. The residue was subjected to flash chromatography on silica eluting with a mixture of dichloromethane and methanol (32:1, v/v) to give the title compound (1.62 g) as a tan solid, which was used directly in the next step. $^1$H NMR [(CD$_3$)$_2$SO]: δ 8.12 (1H, s); 7.96 (1H, s); 7.44 (1H, d, J=8.2 Hz); 7.33 (1H, s); 6.93 (1H, d, J=8.2 Hz); 6.84 (1H, s); 3.63 (3H, s); 0.82 (9H, s); 0.01 (6H, s).

REFERENCE EXAMPLE 50

3-tert-Butyldimethylsilyloxy-4-methoxybenzonitrile

A solution of iso-vanillin (10.0 g) in dimethylformamide (100 mL) was treated with hydroxylamine hydrochloride (9.14 g) and heated under reflux for 1 hour. The dimethylformamide was removed under reduced pressure and the residue partitioned between ethyl acetate and water. The aqueous fraction was exhaustively extracted with ethyl acetate and the combined organic fractions were dried over sodium sulfate and concentrated in vacuo to afford a brown solid, which was dissolved in tetrahydrofuran (200 mL). After treatment with sodium hydride (2.8 g), the reaction mixture was stirred at room temperature for 1 hour. A solution of tert-butyldimethylsilyl chloride (10.9 g) in tetrahydrofuran (50 mL) was added and the mixture stirred under nitrogen overnight. The mixture was partitioned between water and diethyl ether. The organic extract was dried over sodium sulfate, concentrated in vacuo and subjected to flash column chromatography on silica eluting with a mixture of pentane and dichloromethane (1:3, v/v) to give the title compound (14.7 g) as a colourless oil which was used immediately in the next reaction. $^1$H NMR [(CD$_3$)$_2$SO]: δ 7.30 (1H, d, J=8.0 Hz); 7.11 (1H, s); 7.01 (1H, s); 3.70 (3H, s); 0.81 (9H, s); 0.01 (6H, s).

REFERENCE EXAMPLE 51

4-(1-Methyl)ethoxybenzonitrile

A solution of 4-cyanobenzene (1 g) in hexamethylenetetramine (10 mL) was stirred at ambient temperature until dissolution. 25% aqueous sodium hydroxide (2.7 mL) was then added and the resulting solution stirred at ambient temperature for 30 minutes. 1-Methylethyl iodide (5.71 g) was added dropwise and the resulting solution stirred at ambient temperature for 5 hours then poured into water (30 mL). The mixture was extracted three times with ethyl acetate (30 mL) and the combined organic extracts were washed with water, then with brine, then dried over magnesium sulfate and then evaporated. The residue was subjected to flash chromatography on silica eluting with a mixture of ethyl acetate and heptane (1:1, v/v) to give the title compound (1.2 g) as a white solid. MS: 162(MH+). ¹H NMR(CD₃)₂SO: δ:7.58(d, 2H, J=8.12 Hz); 6.84(d, 2H, J=8.12 Hz); 4.62(m, 1H); 1.38(d, 6H, J=5.4 Hz).

REFERENCE EXAMPLE 52
1H-5-Cyano-1 methyl-2-(methylthio)imidazole

A solution of 1H-1-methyl-2-(methylthio)imidazole-5-carboxaldehyde (0.76 g) [Reference Example 53(a)] in dimethylformamide (15 mL) was treated with hydroxylamine hydrochloride (0.68 g). The mixture was refluxed for 4 hours, cooled to ambient temperature and poured into water. Ethyl acetate was added and the organic layer washed with water, brine, dried over magnesium sulfate and evaporated to give the title compound (0.47 g) as a beige solid which was used without further purification, m.p. 115° C. MS: 154(MH+).

REFERENCE EXAMPLE 53

(a) 1H-1-Methyl-2-(methylthio) imidazole-5-carboxaldehyde

A stirred solution of 1H-1-methyl-2-(methylthio)imidazol-5ylmethanol (8.1 g) [Reference Example 54] and manganese dioxide (28.97 g) in dichloromethane (160 mL) was refluxed for 7 hours. The reaction mixture was cooled to ambient temperature and filtered through a pad of celite. The dichloromethane was evaporated to give the title compound (6.61 g) as a yellow solid, which was used immediately in the next reaction.
(b) By proceeding in a manner similar to Reference Example 53(a) above but using 1-methyl-5-phenylpyrazol-3-ylmethanol [Reference Example 66], there was prepared 1-methyl-5-phenylpyrazole-3-carbaldehyde, m.p. 106–108° C.

REFERENCE EXAMPLE 54
1H-1-Methyl-2-(methylthio)imidazol-5ylmethanol

To a stirring suspension of 1H-1-methyl-2-(thio)imidazol-5ylmethanol (5 g) [Reference example 55] in methanol (500 mL) is added dropwise 1N sodium hydroxide solution (36 mL) at room temperature. The suspension was stirred at ambient temperature for 10 minutes. Iodomethane was added dropwise and stirring was continued for 12 hours. After evaporation of the methanol, the residue was dissolved in dichloromethane and water was added. The organic layer was washed with water, brine, dried over magnesium sulfate and evaporated. The residue was crystallized from ether to give the title compound (4.3 g) as a white solid, m.p. 51° C.

REFERENCE EXAMPLE 55
1H-1-Methyl-2-(thio)imidazol-5ylmethanol

A mixture of 12.8 g of dihydroxyacetone dimer, 20.7 g of potassium thiocyanate and 12.4 g of methylamine was added to a solution of 16 mL of acetic acid and 100 mL of butanol. The resulting white mixture was stirred for 70 h after which it was suspended in 50 mL of water and filtered. The solid was washed with water (60 mL), then diethyl ether (60 mL) and dried in vacuo to give the title compound (16 g) as a white solid, m.p 204° C.

REFERENCE EXAMPLE 56

(a) 3-Cyano-1-methyl-1H-indazole

Sodium hydride (0.37 g, 60% dispersion in mineral oil) was added to a solution of 3-cyano-1H-indazole (1.20 g, Reference Example 57) in dry dimethylformamide (30 mL) under a nitrogen atmosphere at ambient temperature. The mixture was allowed to stir for 1 hour then treated with methyl iodide (0.85 mL) and stirring was continued for 1 hour. The reaction mixture was then poured into ice-water (15 mL). The precipitated solid was filtered then washed with water and then dried to give the title compound (0.80 g) as a beige solid, m.p.73° C. ¹H NMR [(CD₃)₂SO]: δ 7.91 (m, 2H); 7.60 (t, 1H); 7.42 (t, 1H); 4.21 (s, 3H).

(b) By proceeding in a manner similar to Reference Example 56(a) above but using 3-cyano-4-phenyl-1H-pyrrole [Reference Example 58], there was prepared 3-cyano-1-methyl-4-phenyl-1H-pyrrole.
(c) By proceeding in a manner similar to Reference Example 56(a) above but using 2-phenyl-1H-pyrrole-3-carbonitrile [prepared according to the procedure described by I. A. Benages et al., J. Org. Chem. (1978), 43(22), 4273–6], there was prepared 1-methyl-2-phenyl-1H-pyrrole-3-carbonitrile as a pink oil. TLC: $R_F$=0.86 (ethyl acetate/dichloromethane, 1:1).
(d) By proceeding in a manner similar to Reference Example 56(a) above but using 5-methyl-1H-pyrrole-3-carbonitrile [prepared according to the procedure described by A. Padwa et al., J. Am. Chem. Soc. (1986), 108(21), 6739–46], there was prepared 1,5-dimethyl-1H-pyrrole-3-carbonitrile as a yellow solid, m.p.54° C. TLC: $R_F$=0.50 (ethyl acetate/cyclohexane, 1:1).
(e) By proceeding in a manner similar to Reference Example 56(a) but using 4-methyl-1H-pyrrole-3-carbonitrile [prepared according to the procedure described by A. R. Katritzky et al, Heterocycles (1997), 44, 67–70], there was prepared 1,4-dimethyl-1H-pyrrole-3-carbonitrile as a yellow oil. TLC: $R_F$=0.64 (ethyl acetate/cyclohexane, 1:1).

REFERENCE EXAMPLE 57
3-Cyano-1H-Indazole

A solution of o-aminobenzyl cyanide (0.5 g) in aqueous hydrochloric acid 1N (9.6 mL), was treated with a solution of aqueous sodium nitrite 1N (3.85 mL). After stirring at room temperature for 15 minutes, the reaction mixture was filtered. The solid was recrystallised from ethanol to give the title compound (0.4 g) as a yellow solid, m.p. 138–140° C. ¹H NMR [(CD₃)₂SO]: δ 7.89 (d, 1H, J=7.7 Hz); 7.76 (d, 1H, J=7.9 Hz); 7.48 (t, 1H); 7.41 (t, 1H).

REFERENCE EXAMPLE 58
3-Cyano-4-phenyl-1H-pyrrole

A solution of cinnamonitrile (16.53 g) and (para-toluenesulfonyl)methylisocyanide (25 g) in a mixture of ether and dimethyl sulfoxide (450 mL, 2:1) was added dropwise to a stirred suspension of sodium hydride (6.14 g, 60% dispersion in mineral oil) in ether (50 mL). An exothermic reaction took place. The reaction mixture was then stirred at room temperature for 2 hours, then diluted with water (500 mL) and this mixture was extracted three times with ether (250 mL). The combined extracts were washed with brine, then dried over magnesium sulfate and then evaporated. The residue was subjected to filter chromatography on a pad of silica eluting with a mixture of ethyl acetate and pentane (1 L, 1:4, v/v) and then with a mixture of ethyl acetate and pentane (2 L, 2:3, v/v). Fractions containing the required material were evaporated and the residue was suspended in pentane (500 mL) with stirring, then filtered to give the title compound as a solid, m.p. 120–122° C. MS: 167(MH⁻).

REFERENCE EXAMPLE 59
4-Pyrazinyl-1-butene

A solution of lithium diisopropylamine[prepared from a solution of butyl lithium in hexanes (100 mL, 2.5M) and diisopropylamine (25.3 g) at −35° C.] was treated with a solution of 2-methylpyrazine (23.5 g) in dry tetrahydrofuran (300 mL) at −20° C. The mixture was stirred at −20° C. for 1 hour then cooled to −78° C. and treated with a solution of allyl bromide (30.8 g) in dry tetrahydrofuran (300 mL). This mixture was warmed to room temperature and stirred at this temperature for 2 hours then left overnight and then treated with saturated ammonium chloride solution (50 mL) followed by water (200 mL). The mixture was then extracted twice with ether (200 mL). The combined extracts were dried over magnesium sulfate then evaporated. The residue was distilled to give the title compound (22 g) as a colourless oil, b.p. 70° C./1 mm Hg.

REFERENCE EXAMPLE 60
2-[5-(pyridin-4-yl)-1-methyl-1H-indol-3-yl]-1-(toluene-4-sulfonyl)-1H-pyrrolo[2,3-b]pyridine A mixture of 2-[5-(1-benzyloxycarbonyl-1,2,5,6-tetrahydropyridin-4-yl)-1-methyl-1H-indol-3-yl]-1-(toluene-4-sulfonyl)-1H-pyrrolo[2,3-b]pyridine (1.7 g, Reference Example 61) ethanol (53 mL) and palladium on carbon (0.35 g) was stirred in the presence of hydrogen for 4 hours, then left standing at room temperature overnight. After a further day a further quantity of palladium on carbon (0.18 g, 10%) was added and stirring was continued in the presence of hydrogen for a further 8 hours. After standing at room temperature for 4 days the reaction mixture was filtered through Hyflo and the filter pad was washed well with ethanol. The combined filtrate and washings was treated with palladium on carbon (0.35 g) and the mixture was stirred in the presence of hydrogen. The mixture was filtered through Hyflo and the filter pad was washed well with ethanol. The combined filtrate and washings was evaporated and the residue was subjected to flash chromatography on silica eluting with a mixture of ethyl acetate and pentane (4:1, v/v) to give the title compound as a light brown solid, m.p. 82–85° C.

REFERENCE EXAMPLE 61
2-[5-(1-benzyloxycarbonyl-1,2,5,6-tetrahydropyridin-4-yl)-1-methyl-1H-indol-3-yl]-1-(toluene-4-sulfonyl)-1H-pyrrolo[2,3-b]pyridine A mixture of benzyl 1-[3,6-dihydro-4-(4,4,5,5-tetramethyl-1,3,2-dioxaborolan-2-yl](2H)pyridinecarboxylate (2 g, prepared according to the procedure described by P. Eastwood, Tetrahedron Letters, 2000, 41, pages 3705–3708), dichloro[1,1'-bis(diphenylphosphino)-ferrocene]palladium[II] (0.25 g,) and potassium carbonate (2.42 g), under nitrogen, was treated with a solution of trifluoro-methanesulfonic acid 1-methyl-3-[1-(toluene-4-sulfonyl)-1H-pyrrolo[2,3-b]pyridin-2-yl]-1H-indol-5-yl ester [1.6 g, Reference Example 18(a)] in dimethylformamide(76 mL). The mixture was heated at 80° C. for 4 hours (TLC indicated that starting material was still present), then treated with a further quantity of trifluoro-methanesulfonic acid 1-methyl-3-[1-(toluene-4-sulfonyl)-1H-pyrrolo[2,3-b]pyridin-2-yl]-1H-indol-5-yl ester (0.15 g), then heated at reflux temperature for 4 hours and then left at room temperature overnight. A further quantity of trifluoro-methanesulfonic acid 1-methyl-3-[1-(toluene-4-sulfonyl)-1H-pyrrolo[2,3-b]pyridin-2-yl]-1H-indol -5-yl ester [0.15 g, Reference Example 18(a)] was added and the mixture was heated at reflux temperature for a further 4 hours then evaporated. The residue was partitioned between ethyl acetate and water, and the aqueous layer was extracted three times with ethyl acetate (50 mL). The combined organic phases were washed with brine, then dried overmagnesium sulfate and then evaporated. The residue was subjected to flash chromatography on silica eluting with a mixture of ethyl acetate and pentane (1:1, v/v) to give the title compound as a light brown viscous liquid which was used without further purification.

REFERENCE EXAMPLE 62
(a) 2-Iodo-1-(toluene-4-sulfonyl)-1H-pyrrolo[2,3-b]pyridine-4-carbonitrile A stirred solution of diisopropylamine (0.38 mL) in tetrahydrofuran (7 mL), at −70° C. and under nitrogen, was treated with a solution of n-butyllithium in hexanes (1.06 mL, 2.5M) over 5 minutes, whilst maintaining the temperature below −65° C. After stirring for 20 minutes the mixture was added, at −70° C., to a solution of 1-(toluene-4-sulfonyl)-1H-pyrrolo[2,3-b]pyridine-4-carbonitrile (0.65 g, Reference Example 63) in tetrahydrofuran (15 mL) and stirred at −70° C. for 45 minutes. A solution of iodine (0.9 g) in tetrahydrofuran (10 mL) was then added at −70° C. The reaction mixture was allowed to warm up to room temperature over 1 hour, and stirred for 18 hours, then treated with water (10 mL). The reaction mixture was evaporated in vacuo and the residue partitioned between ethyl acetate (75 mL) and water (50 mL). The insoluble material was filtered, washed with ether and dried in vacuo to give the title compound (0.45 g) as a white solid. The filtrate was separated and the organics washed sequentially with saturated sodium thiosulfate solution (2×30 mL), water (30 mL) and brine (30 mL), dried over sodium sulfate and evaporated. The residue was triturated with diethyl ether to give a further quantity of the title compound (0.25 g) as a cream solid. TLC $R_F$=0.43 (ethyl acetate/heptane 1:1). MS: 424 (MH$^+$).

(b) By proceeding in a similar manner to Reference Example 62(a) but using 4-chloro-1-(toluene-4-sulfonyl)-1H-pyrrolo[2,3-b]pyridine [Reference Example 9(c)], there was prepared 4-chloro-2-iodo-1-(toluene-4-sulfonyl)-1H-pyrrolo[2,3-b]pyridine as an off white foam. MS: 432(MH$^+$). $^1$H NMR (CDCl$_3$): δ 8.25 (d, 1H), 8.05 (d, 2H), 7.3 (d, 2H), 7.15 (d, 1H), 7.1 (s, 1H), 2.4 (s, 3H)

(c) By proceeding in a similar manner to Reference Example 62(a) but using 5-phenyl-1-(toluene-4-sulfonyl)-1H-pyrrolo[2,3-b]pyridine [Reference Example 67], there was prepared 2-iodo-5-phenyl-1-(toluene-4-sulfonyl)-1H-pyrrolo[2,3-b]pyridine as a light brown solid.

(d) By proceeding in a similar manner to Reference Example 62(a) but using 4-phenyl-1-(toluene-4-sulfonyl)-1H-pyrrolo[2,3-b]pyridine [Reference Example 9(e)], there was prepared the 2-iodo-4-phenyl-1-(toluene-4-sulfonyl)-1H-pyrrolo[2,3-b]pyridine as a white solid. $^1$H NMR [(CD$_3$)$_2$SO]; δ 8.43 (1H, d, J=4.5 Hz); 8.04 (2H, d, J=8.2 Hz); 7.98 (1H, d, J=4.5 Hz); 7.69 (2H, dd, J=7.2, 1.9 Hz); 7.56 (2H, tt, J=7.2, 1.9 Hz); 7.44 (2H, d, J=8.2 Hz); 7.42 (1H, d, J=5.0 Hz), 6.92 (1H, d, J=4.0 Hz), which was used without further purification.

(e) By proceeding in a similar manner to Reference Example 62(a) but using 1-(toluene-4-sulfonyl)-1H-pyrrolo[2,3-b]pyridine-4 carboxylic acid, tert-butyl ester [Reference Example 9(f)] and subjecting the crude reaction product to chromatography on silica eluting with a mixture of ethyl acetate and heptane (1:4, v/v) there was prepared 2-iodo-1-(toluene-4-sulfonyl)-1H-pyrrolo[2,3-b]pyridine-4 carboxylic acid, tert-butyl ester as a dark oil. MS: 499(MH$^+$).

(f) By proceeding in a similar manner to Reference Example 62(a) but using 4-(pyridin-3-yl)-1-(toluene-4-sulfonyl)-1H-pyrrolo[2,3-b]pyridine [Reference Example 9(g)] there was prepared 2-iodo-4-(pyridin-3-yl)-1-(toluene-4-sulfonyl)-1H-pyrrolo[2,3-b]pyridine as a tan solid which was used without further purification.

(g) By proceeding in a manner similar to Reference Example 62(a) above but using 3-methyl-1-(toluene-4-sulfonyl)-1H-pyrrolo[2,3-b]pyridine [Reference Example 9(h)], there was prepared 2-iodo-3-methyl-1-(toluene-4-sulfonyl)-1H-pyrrolo[2,3-b]pyridine as a beige solid, m.p. 175° C. TLC: $R_F$=0.69 (ethyl acetate/cyclohexane, 1:1).

(h) By proceeding in a manner similar to Reference Example 62(a) above but using 4-(3,5-dimethyl-isoxazole-4-yl)-1-(toluene-4-sulfonyl)-1H-pyrrolo[2,3-b]pyridine [Reference Example 9(i)], there was prepared 4-(3,5-dimethyl-isoxazole-4-yl)-2-iodo-1-(toluene-4-sulfonyl)-1H-pyrrolo[2,3-b]pyridine as a white solid, m.p. 166–167° C. MS: 494(MH$^+$).

(i) By proceeding in a manner similar to Reference Example 62(a) above but using 4-methoxy-1-(toluene-4-sulfonyl)-1H-pyrrolo[2,3-b]pyridine [Reference Example 41], there was prepared 2-iodo-4-methoxy-1-(toluene-4-sulfonyl)-1H-pyrrolo[2,3-b]pyridine as a white solid. MS: 429(MH$^+$).HPLC (Method C) $R_T$=4.74 minutes.

REFERENCE EXAMPLE 63

1-(Toluene-4-sulfonyl)-1H-pyrrolo[2,3-b]pyridine-4-carbonitrile

A mixture of 1-(2,6-dimethyl-1,4-dihydropyridin-4-one)-1H-pyrrolo[2,3-b] pyridinium tetrafluoroborate (Reference Example 43, 5.0 g) and water (80 mL) was treated with a saturated aqueous solution of potassium cyanide (25 mL) and stirred at room temperature for 48 hours. A solution of toluene-4-sulfonyl chloride (2.9 g) in toluene (100 mL), a solution of sodium hydroxide (4.0 g) in water (10 mL) and tetrabutylammonium hydrogen sulfate (0.05 g) were added and stirred at room temperature 72 hours. The mixture was filtered through Celite and partitioned. The aqueous was extracted three times with ethyl acetate (50 mL) and the combined organics were washed with water (50 mL), brine (50 mL), dried over magnesium sulfate and evaporated in vacuo. The residue was subjected to flash chromatography on silica eluting with a mixture of ethyl acetate and heptane (3/7, v/v) to give the title compound (1.1 g) as a white solid, TLC: RF=0.60 (ethyl acetate/heptane, 3:7); $^1$H NMR [(CD$_3$)$_2$SO]: δ 8.54 (1H, d, J=4.7 Hz); 8.08 (2H, d, J=8.2 Hz); 7.95 (1H, d, J=3.6 Hz); 7.44 (1H, d, J=4.3 Hz); 7.31 (2H, d, J=8.2 Hz); 6.82 (1H, d, J=3.3 Hz); 2.39 (3H, s); and 1H-pyrrolo[2,3-b]pyridine-4-carbonitrile (0.13 g) as a white solid, TLC RF=0.24 (ethyl acetate/heptane 3:7); $^1$H NMR [(CD$_3$)$_2$SO]: δ 10.19 (1H, s); 8.44 (1H, d, J=4.6 Hz); 7.59 (1H, m); 7.40 (1H, d, J=4.6 Hz), 6.78 (1H, m).

REFERENCE EXAMPLE 64

4-Chloro-1H-pyrrolo[2,3-b]pyridine

1H-Pyrrolo[2,3-b]pyridine-N-oxide (10.0 g, Reference Example 65) in phosphorous oxychloride (75 mL) was heated at reflux for 8 hours. The excess phosphorous oxychloride was evaporated and the residue was taken up in water and the solution was brought to a pH=8–9, the resultant precipitate was filtered and air-dried to give the title compound as an off-white solid (10.2 g). MS: 152(MH$^+$). $^1$H NMR (CDCl$_3$): δ 8.2 (d, 1H), 7.5 (d, 1H), 7.2 (d, 2H), 6.6 (d, 2H).

REFERENCE EXAMPLE 65

1H-Pyrrolo[2,3-b]pyridine-N-oxide

A solution of 3-chloroperbenzoic acid (224.3 g) in dichloromethane (1500 mL) was cooled to 0° C. To this a solution of 1H-pyrrolo[2,3-b]pyridine (59.1 g) in dichloromethane (500 mL) was added dropwise over 30 minutes. The reaction mixture was stirred at room temperature for 1 hour. The solution was concentrated, diluted with methanol (1500 mL) and treated with 10% potassium carbonate in water (300 mL). The slurry was filtered and the filtrate was evaporated to dryness. The residue was chromatographed on neutral alumina with 20% methanol in dichloromethane to give the title compound as a tan solid (47.0 g). MS: 135(MH$^+$). $^1$HNMR (CDCl$_3$): δ 13.1 (s, 1H), 8.2 (d, 1H), 7.65 (d, 1H), 7.4 (d, 1H), 7.0 (m, 1H), 6.55 (d, 1H).

REFERENCE EXAMPLE 66

1-Methyl-5-phenylpyrazol-3-ylmethanol

A stirred suspension of sodium borohydride (1.28 g) in dry tetrahydrofuran (80 mL) was treated with calcium chloride (1.88 g). The mixture was stirred for 1 hour then treated with a solution of ethyl 1-methyl-5-phenylpyrazol-3-ylcarboxylate (5.2 g, prepared according to the procedure described by Martins et al., J. Heterocycl. Chem. (1999), 36(1), 217–220) in dry tetrahydrofuran (40 mL). After stirring at room temperature for 3 days and at reflux temperature for 8 hours the mixture was treated with sodium hydroxide solution (50 mL, 1N). This mixture was stirred at room temperature for 1 hour, then evaporated to remove the organic solvents and then extracted three times with dichloromethane (140 mL). The combined extracts were washed with water, then dried over magnesium sulfate and then evaporated to give the title compound as a white solid, m.p. 95–99° C.

REFERENCE EXAMPLE 67

(a) 5-Phenyl-1-(toluene-4-sulfonyl)-1H-pyrrolo[2,3-b]pyridine

A mixture of phenyl boronic acid (1.74 g), 5-bromo-1-(toluene-4-sulfonyl)-1H-pyrrolo[2,3-b]pyridine [5 g, Reference Example 9(d)], (tetrakis)triphenylphosphine palladium [0] (0.49 g) and saturated aqueous sodium bicarbonate solution (133 mL) and dimethylformamide (266 mL), under nitrogen, was heated at reflux temperature overnight. The reaction mixture was filtered through Hyflo and then evaporated. The residue was partitioned between ethyl acetate (50 mL) and water (25 mL) and the aqueous layer was extracted with ethyl acetate (25 mL). The combined organic phases were washed with water (25 mL), then with brine (20 mL), then dried over magnesium sulfate and then evaporated. The residue subjected to chromatography on silica eluting with a mixture of pentane and ether (1;1, v/v) to give the title compound as a white solid, mp. 151–152° C. MS: 335 (MH$^+$).

(b) By proceeding in a similar manner to Reference Example 67(a) but using 1-tert-butyloxycarbonyl-5-methoxy-1H-indole-3-boronic acid [Reference Example 74(b)] and 2-iodo-1-(toluene-4-sulfonyl)-1H-pyrrolo[2,3-b]pyridine-4 carboxylic acid, tert-butyl ester [Reference Example 62(e)] and subjecting the crude product to chromatography on silica eluting with a mixture of ethyl acetate and heptane (3:7, v/v) there was prepared 2-(5-methoxy-1H-indol-3-yl)-1-(toluene-4-sulfonyl) -1H-pyrrolo[2,3-b]pyridine-4 carboxylic acid, tert-butyl ester as a yellow oil. MS: 518(MH$^+$).

(c) By proceeding in a similar manner to Reference Example 67(a) but using pyridine-3-boronic acid and trifluoromethanesulfonic acid 1H-pyrrolo[2,3-b]pyridin-4-yl ester [Reference Example 18(c)] there was prepared 4-(pyridin-3-yl)-1H-pyrrolo[2,3-b]pyridine as a yellow solid, m.p. 162–163° C. MS: 196(MH$^+$).

(d) By proceeding in a similar manner to Reference Example 67(a) but using 1-tert-butyloxycarbonyl-5-methoxy-1H-indole-3-boronic acid [Reference Example 74(b)] and 2-iodo-4-(pyridin-3-yl)-1-(toluene-4-sulfonyl)-1H-pyrrolo[2,3-b]pyridine [Reference Example 62(f)] and subjecting the crude product to chromatography on silica eluting with ethyl acetate there was prepared 2-(5-methoxy-1H-indol-3-yl)-4-(pyridin-3-yl)-1-(toluene-4-sulfonyl)-1H-pyrrolo[2,3-b]pyridine as a yellow oil. MS: 495(MH$^+$).

(e) By proceeding in a similar manner to Reference Example 67(a) but using 1-tert-butyloxycarbonyl-5-methoxy-1H-indole-3-boronic acid [Reference Example 74(b)] and 2-iodo-1-(toluene-4-sulfonyl)-1H-pyrrolo[2,3-b]pyridine-4-carbonitrile [Reference Example 62(a)] and subjecting the crude product to chromatography on silica eluting with ethyl acetate there was prepared 2-(5-methoxy-1H-indol-3-yl)-1-(toluene-4-sulfonyl)-1H-pyrrolo[2,3-b]pyridine-4 carbonitrile as a green-brown solid. MS: 443(MH$^+$).

(f) By proceeding in a similar manner to Reference Example 67(a) but using a mixture of 1-tert-butyloxycarbonyl-5-methoxy-1H-indole-3-boronic acid and 1-tert-butyloxycarbonyl-5-methoxy-1H-indole-2-boronic acid [Reference Example 74(a)] and trifluoro-methanesulfonic acid 1-(toluene-4-sulfonyl)-1H-pyrrolo[2,3-b]pyridin-2-yl ester [Reference Example 71] there was prepared a mixture of 2-(1-N-tert-butyloxycarbonyl-5-methoxy-1H-indol-2-yl)-1-(toluene-4-sulfonyl)-1H-pyrrolo[2,3-b]pyridine and 2-(1-N-tert-butyloxycarbonyl-5-methoxy-1H-indol-3-yl)-1-(toluene-4-sulfonyl)-1H-pyrrolo[2,3-b]pyridine.

(g) By proceeding in a manner similar to Reference Example 67(a) but using 2-iodo-1-(toluene-4-sulfonyl)-1H-pyrrolo[2,3-b]pyridine [Reference Example 10(a)] and 1-tert-butyloxycarbonyl-1H-pyrrole-2-boronic acid, there was prepared 2-(1H-pyrrol-2-yl)-1-(toluene-4-sulfonyl)-1H-pyrrolo[2,3-b]pyridine as a brown solid. TLC: R$_F$=0.25 (dichloromethane). MS: EI (70 eV); m/z=337 M$^+$. (80%); 182 (100%); 155 (20%).

REFERENCE EXAMPLE 68

1H-pyrrolo[2,3-b]pyridine-4 carboxylic Acid, Tert-Butyl Ester

A stirred suspension of 1H-pyrrolo[2,3-b]pyridine-4 carboxylic acid (0.2 g, reference Example 69) in dry dimethylformamide (5 mL), under nitrogen, was treated with 1,1'-carbonyldiimidazole (0.2 g). After stirring at room temperature for 1 hour the resulting tan coloured solution was treated with tert-butanol (260 µL) and DBU (203 µL). This mixture was stirred at 40° C. overnight then evaporated. The residue was partitioned between water (30 mL) and ethyl acetate (30 mL) and the aqueous layer was then extracted twice with ethyl acetate (10 mL). The combined organics were washed twice with brine (10 mL), then dried over sodium sulfate and then evaporated to give the title compound (0.21 g) as a yellow solid.

REFERENCE EXAMPLE 69

1H-pyrrolo[2,3-b]pyridine-4 Carboxylic Acid

A solution of 1H-pyrrolo[2,3-b]pyridine-4 carboxylic acid, methyl ester [1.8 g, Reference Example 19(c)] in methanol (60 mL) was treated with sodium hydroxide solution (25 mL, 2N) and the mixture was stirred at room temperature for 2 hours then evaporated. The residue was treated with water (50 mL) and the pH of the mixture was adjusted to 34 by addition of hydrochloric acid. The resulting yellow solid was filtered, then washed well with water and then dried to give the title compound (1.1 g) as a yellow solid.

REFERENCE EXAMPLE 70

2-(5-methoxy-1H-indol-2-yl)-1-(toluene-4-sulfonyl)-1H-pyrrolo[2,3-b]pyridine

A stirred solution of 2-(1-N-tert-butyloxycarbonyl-5-methoxy-1H-indol-3-yl)-1-(toluene-4-sulfonyl)-1H-pyrrolo[2,3-b]pyridine [2.2 g, Reference Example 67(f)] in dichloromethane (150 mL) was treated with trifluoroacetic acid (20 mL). After stirring at room temperature for 3 hours the reaction mixture was poured into water (300 mL) and this mixture was neutralised by addition of sodium bicarbonate. The aqueous phase was separated and extracted with dichloromethane (100 mL). The combined organic phase and extract were washed with brine (100 mL), then dried over magnesium sulfate and then evaporated. The residue was triturated with pentane to give a tan solid (1.7 g) which was warmed with ethyl acetate (50 mL). The insoluble material was washed well with ethyl acetate to give the title compound (0.8 g), m.p. 226–227° C.

REFERENCE EXAMPLE 71

Trifluoro-methanesulfonic acid 1-(toluene-4-sulfonyl)-1H-pyrrolo[2,3-b]pyridin-2-yl Ester A solution of 2,3-dihydro-1-(toluene-4-sulfonyl)-1H-pyrrolo[2,3-b]pyridin-2-one (11.7 g, Reference Example 72) and diisopropylethylamine (8.5 mL) in dichloromethane (500 mL), cooled to 0° C. and under a nitrogen atmosphere, was treated dropwise with trifluoromethanesulfonic anhydride (6.4 mL). The resultant mixture was stirred at 0° C. for 2 hours then treated with water (300 mL). The aqueous phase was neutralised by addition of sodium bicarbonate then extracted twice with dichloromethane (200 mL). The combined extracts and organic phase from the reaction were dried over magnesium sulfate then evaporated. The residue was subjected to flash column chromatography on silica eluting with a mixture of ethyl acetate and pentane (1:4, v/v) to give after trituration with pentane and petroleum ether the title compound (9.08 g) as a white solid.

REFERENCE EXAMPLE 72

2,3-dihydro-1-(toluene-4-sulfonyl)-1H-pyrrolo[2,3-b]pyridin-2-one

A solution of 1-(toluene-4-sulfonyl)-1H-pyrrolo[2,3-b]pyridine-2-carbaldehyde (24.3 g, Reference Example 73) in dichloromethane (700 mL), under nitrogen and at 5° C., was treated with 3-chloroperbenzoic acid (26.7 g, 70%). After stirring at 5° C. for 16 hours a further aliquot of 3-chloroperbenzoic acid (15 g, 70%) was added and stirring was continued for a further 6 hours at 5° C. The reaction mixture was then treated with sodium sulfite solution (1L, 10%), the organic phase was separated and the aqueous phase was extracted twice with dichloromethane (200mL). The combined organic phase and extracts were washed with water (400 mL), dried over magnesium sulfate and then evaporated. The residue was subjected to flash column chromatography on silica eluting initially with a mixture of ethyl acetate and pentane (1:3, v/v) and then with a mixture of dichloromethane and methanol (95:5, v/v) to give the title compound (11.7 g) as an orange solid.

REFERENCE EXAMPLE 73

1-(toluene-4-sulfonyl)-1H-pyrrolo[2,3-b]pyridine-2-carbaldehyde

A solution of lithium diisopropylamine {prepared by treating a solution of diisopropylamine (33.6 mL) in tetrahydrofuran (250 mL) with butyl lithium in hexanes (70.4 mL, 2.5M) at −35° C., at −75° C., was treated dropwise with a solution of 1-(toluene-4-sulfonyl)-1H-pyrrolo[2,3-b]pyridine [40 g, Reference Example 9(a)] in dry tetrahydrofuran (250 mL) at −75° C. whilst maintaining the reaction temperature below −60° C. After stirring at −75° C. for 3 hours the reaction mixture was allowed to warm to 5° C. over 2 hours then recooled to −75° C. and then treated with dimethylformamide(62 mL). The reaction mixture was left to warm to room temperature over 1 hour then poured into hydrochloric acid (800 mL, 1%) and then evaporated to remove the tetrahydrofuran. The resulting suspension was filtered and the solid was washed with water, then dried and then was subjected to flash column chromatography on silica eluting with dichloromethane to give the title compound (24.37 g) as a white solid.

REFERENCE EXAMPLE 74

(a) 1-tert-butyloxycarbonyl-5-methoxy-1H-indole-3-boronic acid and 1-tert-butyloxycarbonyl-5-methoxy-1H-indole-2-boronic Acid A solution of 1-tert-butyloxycarbonyl-3-bromo-5-methoxy-1H-indole [6 g, Reference Example 11(a)] in dry tetrahydrofuran (100 mL), cooled to −80° C. and under nitrogen, was treated with a solution of tert-butyl lithium in pentane (22.6 mL, 1.5M). After stirring at −80° C. for 2 minutes this mixture was then treated with tributyl borate (5.9 mL) and stirring was continued at −80° C. for 20 minutes. The reaction mixture was then allowed to warm to 0° C., then carefully treated with hydrochloric acid (50 mL, 1N), then extracted twice with ethyl acetate (75 mL). The combined extracts were washed with brine (50 mL) then dried over magnesium sulfate and then evaporated to give the a mixture of 1-tert-butyloxycarbonyl-5-methoxy-1H-indole-3-boronic acid and 1-tert-butyloxycarbonyl-5-methoxy-1H-indole-2-boronic acid (6.2 g) as a brown oil. MS: 291(M$^+$). This material was used directly without further purification.

(b) By proceeding in a similar manner to Reference Example 74(a) but carrying out the reaction at −100° C. there was prepared 1-tert-butyloxycarbonyl-5-methoxy-1H-indole-3-boronic acid as a brown oil. MS: 291(M$^+$). This material was used directly without further purification.

REFERENCE EXAMPLE 75

4-(4-cyanophenyl)piperazine-1-carboxylic Acid, Tert-Butyl Ester

A mixture of 4-fluorobenzonitrile (3.6 g) and N-tert-butyloxycarbonylpiperazine (5.58 g) in acetonitrile (60 mL) was heated at 80° C. for 72 hours. The reaction mixture was then cooled to room temperature and then treated with a mixture of sodium bicarbonate solution and ethyl acetate (300 mL, 1:1, v/v). The organic phase was separated and then evaporated. The residue was subjected to chromatography on silica gel eluting with a mixtures of heptane and ethyl acetate (from 3:7 to 1:1, v/v) to give the title compound (2 g) as a white solid.

REFERENCE EXAMPLE 76

[2-(1-(Toluene-4-sulfonyl)-1H-pyrrolo[2,3-b]pyridin-2-yl)-pyrrol-1-yl]-acetic Acid Tertio Butyl Ester

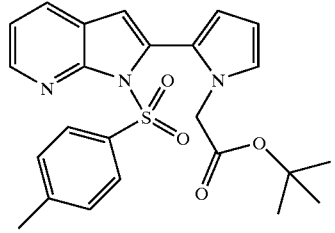

A solution of 2-(1H-pyrrol-2-yl)-1-(toluene-4-sulfonyl)-1H-pyrrolo[2,3-b]pyridine [1.15 g, Reference Example 67(g)] in dry tetrahydrofuran (40 mL), under an argon athmosphere and at room temperature, was treated with sodium hydride (163 mg, 60% dispersion in oil) then dropwise with a solution of tert-butyl bromoacetate (1.33 g) in dry tetrahydrofuran (4 mL). The mixture was agitated for 24 hours at room temperature then treated with saturated aqueous ammonium chloride solution (3 mL) and then extracted with ethyl acetate (10 mL). The organic phase was washed with water (15 mL), then dried over magnesium sulfate and then evaporated. The residue was triturated with ether and filtered yielding the title compound (1.19 g) as a beige solid. LC-MS; Method C: R$_T$=4.31 minutes, 452.18[M+H]$^+$.

REFERENCE EXAMPLE 77

3-[5-Methoxy-2-(1H-pyrrolo[2,3-b]pyridin-2-yl)-1-(toluene-4-sulfonyl)-indol-1-yl]-propionic Acid Methyl Ester.

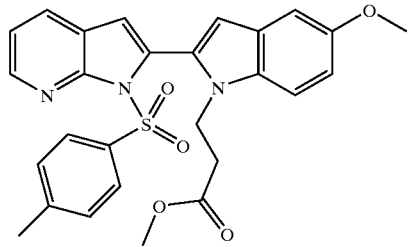

A solution of 2-(5-methoxy-1H-indol-2-yl)-1-(toluene-4-sulfonyl)-1H-pyrrolo[2,3-b]pyridine [582 mg, Reference Example 70] in dry dimethylformamide (40 mL) was treated with methyl-3-bromopropionate (610 μL) and potassium carbonate (387 mg). The reaction mixture was heated under agitation at 92° C. for 48 hours, then treated with further aliquots of methyl-3-bromopropionate (458 μL) and potassium carbonate (580 mg), then heated under agitation for an additional 24 hour period, then treated with further aliquots of methyl-3-bromopropionate (153 μL) and potassium carbonate (193 mg) and then heated under agitation for an additional 3.5 hour period. The reaction mixture was cooled to room temperature and then evaporated. The residue was partitioned between ethyl acetate and water. The organic phase was washed with aqueous hydrochloric acid (1N), the with aqueous sodium hydroxide (1N), then dried over magnesium sulfate and then evaporated yielding a brown oil (700 mg) which was subjected to LC-MS triggered purification (in 34 injections) yielding the title compound (433 mg) as a yellow solid. LC-MS:Method C: R$_T$=4.16 minutes, 504.07[M+H]$^+$.

REFERENCE EXAMPLE 78
3-[5-Methoxy-2-(1H-pyrrolo[2,3-b]pyridin-2-yl)-1-(toluene-4-sulfonyl)-indol-1-yl]-acetic Acid Tert-Butyl Ester.

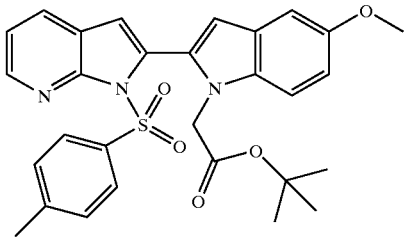

A solution of 2-(5-methoxy-1H-indol-2-yl)-1-(toluene-4-sulfonyl)-1H-pyrrolo[2,3-b]pyridine [20 mg, Reference Example 70] in dry tetrahydrofuran (1.5 mL), under argon, was treated with sodium hydride (3 mg, 60% dispersion in oil), then the mixture was agitated at room temperature for 15 minutes and then the mixture was treated with tert-butylbromoacetate (14 μL) and this mixture was agitated for 3 days at room temperature. The reaction mixture was treated with ethyl acetate (2 mL) and a few drops of a saturated aqueous ammonium chloride solution. The organic phase was then dried over magnesium sulfate and then evaporated yielding the title compound (22 mg) as a yellow solid. LC-MS: Method C: $R_T$=4.44 minutes, 532.1[M+H]$^+$.

REFERENCE EXAMPLE 79
1-{1-Methyl-3-[1-toluene-4-sulfonyl)-1H-pyrrolo[2,3-b]pyridin-2-yl]-1H-indol-5-yloxy}-propan-2-ol

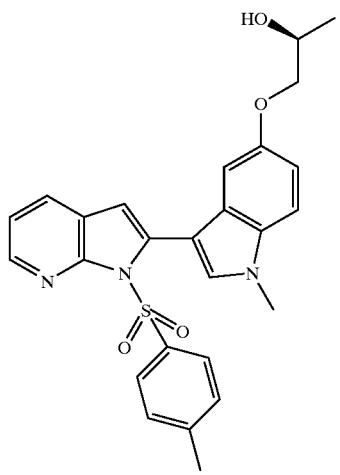

To a solution of 1-{1-methyl-3-[1-toluene-4-sulfonyl)-1H-pyrrolo[2,3-b]pyridin-2-yl]-1H-indol-5-yloxy}-propan-2-one [0.2 g, Reference Example 23(e)] in dry tetrahydrofuran (5 mL) under nitrogen at −78° C. was added (−)-diisopinocampheyl boron chloride (0.3 g). The reaction mixture was stirred for 30 minutes at −78° C. and then at −20° C. for a further 5 hours. The reaction mixture was poured into water (40 mL), treated with solid sodium bicarbonate (1.0 g) and stirred at room temperature for one hour before extraction with ethyl actetate (2×25 mL). The combined organic extracts were washed with water (30 mL), the with brine (25 mL), then dried over sodium sulfate and then evaporated. The residue was subjected to flash column chromatography on silica gel eluting with ethyl acetate and pentane (1:1, v:v) to afford the title compound as a yellow oil. TLC: $R_F$=0.22 (ethyl acetate/pentane 1:1).

REFERENCE EXAMPLE 80
4-(3,5-Dimethyl-isoxazole-4-yl)-1H-pyrrolo[2,3-b]pyridine

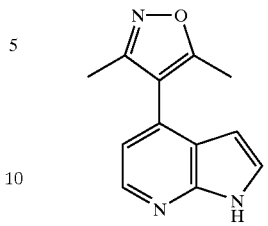

To a solution of trifluoro-methanesulfonic acid-1H-pyrrolo[2,3-b]pyridin-4-yl ester [4.05 g, Reference Example 18(g)] and 3,5-dimethylisoxazole-4-boronic acid (2.31 g) in dimethylformamide (100 mL) was added tetrakis (triphenylphosphine)palladium[0] (0.1 g) and saturated sodium bicarbonate solution (30 mL). The resulting mixture was stirred at 110° C. for 5 hours. The reaction mixture was cooled and filtered through celite. The filtrate was evaporated to dryness and the residue partitioned between ethyl acetate (100 mL) and water (50 mL). The aqueous phase was extracted with ethyl acetate and the combined organic fractions were washed twice with brine (30 mL), then dried over magnesium sulfate and then evaporated to afford the title compound as an orange oil which was used immediately without further purification for the preparation of Reference Example 9(i).

REFERENCE EXAMPLE 81
3-(4-cyano-1H-pyrrolo[2,3-b]pyridin-2-yl)-1-methyl-1H-indole-5-carboxylic Acid, Methyl Ester

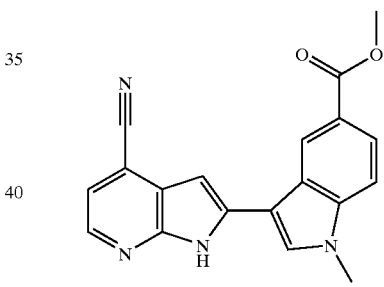

A mixture of 3-[4-chloro-1-(toluene-4-sulfonyl)-1H-pyrrolo[2,3-b]pyridine-2-yl]-1-methyl-1H-indole-5-carboxylic acid, methyl ester [0.4 g, Reference Example 2(r)], zinc powder (0.05 g), zinc cyanide (0.117 g), [1,1'-bis(diphenylphosphino)ferrocene] dichloropalladium (II) complex with dichlroromethane (catalytic) and N,N-dimethylacetamide (8 mL) was heated at 130–150° C. for 5 hours. The reaction mixture was cooled, filtered and the precipitated washed with dimethylformamide (2 mL). The filtrate was diluted with ethyl acetate (120 mL) and the solution extracted with water (2×20 mL). The combined organic layer was evaporated and the residue subjected to flash column chromatography on silica gel eluting with a mixture of heptane and ethyl acetate (7:3 v/v) moving to neat ethyl acetate to give the title compound (0.12 g) as a bright yellow solid. MS: 331(MH$^+$). HPLC(Method C): $R_T$=4.01 minutes.

REFERENCE EXAMPLE 82
6-Benzyloxy-3-iodo-5-methoxy-indole-1-carboxylic Acid Tert-Butyl Ester A solution of 6-benzyloxy-5-methoxyindole (1.90 g, prepared according to procedure described by Benigni, J. D.

and Minnis, R. L., J. Heterocycl. Chem. 1965, 2, 387 and Sinhababu, A. K. and Borchardt, R. T., J. Org. Chem. 1983, 48, 3347) in dry dimethylformamide (37.5 mL) was treated with ground potassium hydroxide (1.24 g) and a solution of iodine (1.96 g) in dry dimethylformamide (37.5 mL) dropwise at room temperature. The reaction mixture was stirred at room temperature for 2 hours, then treated with 4-dimethylaminopyridine (69 mg) followed by a solution of di-tert-butyldicarbonate (2.05 g) in dry dimethylformamide and stirring was continued for a further 1 hour. The reaction mixture was poured into aqueous sodium sulfite solution (0.2%). The aqueous phase was extracted three times with ethyl acetate (100 mL). The combined organic phases were washed with water (100 mL), then with brine (100 mL), then dried over magnesium sulfate and then evaporated. The residue was subjected to flash column chromatography on silica eluting with a mixture of cyclohexane and ethyl acetate (1:9, v/v) to give the title compound (3.35 g) as a white solid. TLC: $R_F$=0.58 (dichloromethane). MS: EI (70 eV); m/z=479 M$^+$ (45%); 423 (100%); 332 (75%).

REFERENCE EXAMPLE 83

2-(6-Hydroxy-5-methoxy-1-methyl-1H-indol-3-yl)-1-(toluene-4-sulfonyl)-1H-pyrrolo[2,3-b]pyridine A solution of 2-(6-benzyloxy-5-methoxy-1-methyl-1H-indol-3-yl)-1-(toluene-4-sulfonyl)-1H-pyrrolo[2,3-b]pyridine [1.24 g, Reference Example 13(p)] in acetonitrile (100 mL) was treated with iodotrimethylsilane (820 μl). The reaction mixture was stirred at 50° C. for 2 hours and then concentrated in vacuo. The residue was treated with water (40 mL) and the mixture was extracted three times with dichloromethane (100 mL). The combined organic phases were washed with brine (40 mL), then dried over magnesium sulfate and then evaporated. The residue was subjected to flash column chromatography on silica eluting with a mixture of cyclohexane and ethyl acetate (1:1, v/v) to give the title compound (686 mg) as a white foam. TLC: $R_F$=0.27 (cyclohexane/ethyl acetate: 1/1). MS: EI (70 eV); m/z=447 M$^+$.(45%); 292 (100%).

REFERENCE EXAMPLE 84

2-(6-Isopropoxy-5-methoxy-1-methyl-1H-indol-3-yl)-1-(toluene-4-sulfonyl)-1H-pyrrolo[2,3-b]pyridine Potassium carbonate (70 mg) was added to a solution of 2-(6-hydroxy-5-methoxy-1-methyl-1H-indol-3-yl)-1-(toluene-4-sulfonyl)-1H-pyrrolo[2,3-b]pyridine [112 mg, Reference Example 83] in dry dimethylformamide (5 mL) under an argon atmosphere at ambient temperature. The mixture was allowed to stir for 10 minutes then treated with 2-bromopropane (66 μl) and heated at 70° C. for 3 hours. Additional portions of potassium carbonate (70 mg) and 2-bromopropane (66 μl) were then added and the mixture was stirred and heated at 70° C. for 4 hours. The cooled reaction mixture was poured in water (20 mL) and extracted three times with ethyl acetate (40 mL). The combined organic phases were washed with brine (20 mL), then dried over magnesium sulfate and then evaporated. The brown residue was subjected to flash column chromatography on silica eluting with a mixture of cyclohexane and ethyl acetate (3:2, v/v) to give the title compound (56 mg) as an off-white foam. TLC: $R_F$=0.47 (cyclohexane/ethyl acetate, 1/1). MS: CI (NH$_3$); m/z=490 MH$^+$.

REFERENCE EXAMPLE 85

Methyl 1-(toluene-4-sulfonyl)-1H-indole-5-carboxylate 3-boronic Acid

To a solution of mercuric acetate (0.72 g) in glacial acetic acid (25 mL) at room temperature was added 1-(toluene-4-sulfonyl)-1H-indole-5-carboxylic acid methyl ester [0.75 g, Reference Example 90)] and the reaction mixture was stirred at room temperature for 6 hours and allowed to stand over night. The reaction mixture was diluted with water (50 mL) and stirred for a further three hours. The resultant white solid was collected by filtration, washed with water (2×10 mL) and dried to afford methyl-3-acetomercurio-1-(toluene-4-sulfonyl)-1H-indole-5-carboxylate (1.1 g). To a solution of the meruric acetate derivative (1.1 g) in dry tetrahydrofuran (25 mL) under a nitrogen atmosphere was added borane tetrahydrofuran complex (15 mL of a 1.0M solution in tetrahydrofuran). The mixture was stirred at room temperature for 2.5 hours before careful addition of water (5 mL) while cooling with a water bath. The reaction mixture was filtered and the filtrate concentrated to 25 mL before dilution in ethyl acetate (75 mL). The organic fraction was washed with water (30 mL) and brine (30 mL), dried over magnesium sulfate and evaporated to 10 mL. The product was precipitated by addition of a small amount of pentane. The resultant solid was isolate by filtration and washed with pentane to afford the title compound as a white solid (0.5 g). MP: 188–190° C.

REFERENCE EXAMPLE 86

1H-pyrrolo[2,3-b]pyridine-4-ol

4-Chloro-1H-pyrrolo-[2,3-b]pyridine [80 g, Reference Example 64] was treated with 10% aqueous sodium hydroxide solution (330 g) and heated to 180° C. for 8 hours in a parr bomb with magnetic stirring. The reaction mixture was cooled to room temperature and excess sodium hydroxide was neutralized with a large excess of solid carbon dioxide pellets. Undissolved starting material was removed by filtration and the filtrate was concentrated in vacuo. The residue was extracted with hot methanol (3×1000 mL). The combined methanol extracts were concentrated and the residue purified by flash column chromatography on silica gel eluting with a mixture of dichloromethane and methanol (9:1 v:v to 4:1 v:v) to afford the title compound as a solid (63 g). TLC: $R_F$=0.32 (dichloromethane/methanol 4/1).

In vitro Test Procedures

A. In vitro Test Procedures for Syk

1. Inhibitory Effects of Compounds on Syk Kinase

Inhibitory effects of compounds on Syk kinase were determined using a time-resolved fluorescent assay.

The catalytic domain of Syk kinase (residues A340-N635) was expressed as a fusion protein in yeast cells and purified to homogeneity. Kinase activity was determined in 50 mM Tris-HCl buffer pH 7.0 containing 50 mM NaCl, 5 mM MgCl$_2$, 5 mM MnCl$_2$, 1 μM adenosine triphosphate and 10 μM synthetic peptide Biotin-(β-Alanine)$_3$-DEEDYEIPP-NH$_2$. Enzyme reactions were terminated by the addition of buffer containing 0.4M KF, 133 mM EDTA, pH 7.0, containing a streptavidin-XL665 conjugate and a monoclonal phosphospecfic antibody conjugated to a europium cryptate (Eu-K). Features of the two fluorophores, XL-665 and Eu-K are given in G. Mathis et al., Anticancer Research, 1997, 17, pages 3011–3014. The specific long time signal of XL-665, produced only when the synthetic peptide is phosphorylated by Syk, was measured on a Packard Discovery Microplate analyzer or on an LJL Biosystems Analyst AD microplate reader. Inhibition of syk activity with compounds of the invention was expressed as percentage inhibition of control activity exhibited in the absence of test compounds. Particular compounds of the invention inhibit syk activity with IC$_{50}$s in the range 100 micromolar to 3 nanomolar. Preferred compounds of the invention inhibit syk activity with IC$_{50}$s in the range 100 nanomolar to 3 nanomolar. Especially preferred compounds of the invention inhibit syk activity with IC$_{50}$s in the range 10 nanomolar to 3 nanomolar.

2. Antigen-Induced Degranulation of Rat Bosophilic Leukemia (RBL) Cells as Measured by [3H] 5-hydoxytrEyptamine (Serotonin) Release 2.1 Cell Culture, Labelling of RBL-2H3 Cells and Performance of Assay.

Method A: For each 24-well culture plate to be set up, $6 \times 10^6$ cells RBL-2H3 cells were washed and resuspended in 15 mL DMEM-10 containing 25 µl of 1 µCi/mL [$^3$H]-serotonin (0.5 µCi/ml final concentration) and 1 µg/mL (15 mL) of anti-DNP IgE. 0.5 mL of cell suspension was added into each well of a 24-well plate. Cells were incubated for 2 days at 37° C., until they have reached confluence. The medium was gently aspirated from each well and the cells were then washed with assay buffer. A final volume of 200 mL of assay buffer (+ or − the test compounds at the appropriate concentrations) was then added to each of three replicate wells. 100 ng/mL of DNP (antigen) was then added to all wells (excluding negative control wells i.e. to measure spontaneous [$^3$H]-serotonin release in the absence of receptor cross-linking). The cells were incubated for 30 minutes at 37° C. and the reaction was stopped by transferring 100 µl of the supernatant from each sample into a liquid scintillation microtitre plate kept on ice. 200 µl of scintillant −40 was then added to each well of the microtitre plate and the plate was read on a Topcount Liquid Scintillation Counter.

Method B: RBL-2H3 cells are maintained in T75 flasks at 37° C. and 5%$CO_2$, and passaged every 3–4 days. To harvest cells, 5 ml trypsin-EDTA is used to rinse the flask once, then 5 ml trypsin is added to each flask, and incubated at room temperature for 2 minutes. Cells are transferred to a tube with 14 ml medium, spun down at 1100 rpm RT for 5 minutes and resuspended at $2 \times 10^5$/ml. Cells are sensitized by adding 1 µl of DNP-specific IgE to every 10 ml of cells. 200 µl of cells are added to each well of a flat-bottom 96 well plate (40,000 cells/well), and the plate incubated overnight at 37° C. and 5%$CO_2$. The next day compounds are prepared in 100% DMSO at 10 mM. Each compound is then diluted 1:100 in assay buffer and then diluted further in 1% DMSO-assay buffer to obtain final concentrations of 0.03–30 µM. 80 µl assay buffer is added to each well, followed by 10 µl of diluted compound. Incubation follows for 5 minutes. 10 µl of DNP-HSA (10 ng/ml) is added to each well and incubated at 37° C. (no $CO_2$) for 30 minutes. As one control, 1% DMSO alone (no compound) is added to a set of wells to determine total release. As another control, add buffer instead of DNP-HSA to another set of wells to determine the assay background. After the 30 minutes incubation, the supernatants are transferred to a new 96-well plate. Add 50 µl supernatant to each well of an assay plate. Add 100 µl of substrate solution to each well and incubate at 37° C. for 90 minutes. Add 50 µl of 0.4 M glycine solution to stop the reaction and the plate is read at 405 nm on a Molecular Devices SpectraMax 250 plate reader.

2.2 Calculation of Results

Method A (i) The mean±s.e.m. of each set of triplicate wells was calculated.
(ii) Maximum response was the positive control wells containing antigen (10 ng/mL) but no compound.
(iii) Minimum response was the control wells containing no antigen and no compound.
(iv) Using these values as the maximum (100%) and minimum (0%) values respectively, the data was normalised to give a percentage of the maximum response.
(v) A dose response curve was plotted and the $IC_{50}$ of the compound was calculated.

Method B (i) The mean±SD of each set of triplicate wells was calculated.
(ii) Maximum response was the positive control wells containing antigen (100 ng/mL) but no compound.
(iii) Minimum response was the control wells containing buffer (no antigen) and no compound.
(iv) Using these values as the maximum (100%) and minimum (0%) values respectively, the experimental data was calculated to yield a percentage of the maximum response (designated % control).
(v) A dose response curve was plotted and the $IC_{50}$ of the compound was calculated using Prism GraphPad software and nonlinear least squares regression analysis.

Compounds of the invention inhibit antigen-induced degranulation of Rat Bosophilic leukemia (RBL) cells with $EC_{50}$s in the range 100 micromolar to 0.01 micromolar.

B. In vitro Test Procedures for KDR

1. Inhibitory Effects of Compounds on KDR

Inhibitory effects of compounds on KDR-substrate phosphorylation assay—were determined using a flashplate (96-multiwell plates, New England Nuclear) assay.

The cytoplasmic domain of human enzyme has been cloned as glutathione S-transferase (GST) fusion into the pFastBac-GST tagged (reading frame) B baculovirus expression vector. The protein has been expressed in SF21 cells and purified to about 60% homogeneity.

Kinase activity was determined in 20 mM 4-morpholinepropanesulfonic acid sodium salt, 10 mM $MgCl_2$, 10 mM $MnCl_2$, 1 mM Dithiothreitol, 2.5 mM ethyleneglycol-bis (beta-aminoethylether)-N,N'-tetraacetic acid, 10 mM β-glycerophosphate, pH 7.2 containing 10 mM $MgCl_2$, 100 µM $Na_3VO_4$, 1 mM NaF. 10 µl of compound were added to 70 µl of kinase buffer containing 100 ng of Kinase Domain Receptor (KDR) enzyme at 4° C. Reaction was started by addition of 20 µl of solution containing 2 µg of substrate (SH2-SH3 fragment of PLCγ expressed as GST fusion protein), 2 µCi $\gamma^{33}$P[ATP] and 2 µM cold ATP. After 1 h incubation at 37° C., reaction was stopped by addition of 1 volume (100 µl) of 200 mM EDTA. The assay buffer was then discarded and the wells washed three fold with 300 µl of phosphate buffered saline. Radioactivity was measured in each well using a Packard Model Top Count NXT instrument.

Background signal was deduced from the measurement of radioactivity in quadruplate wells containing radioactive ATP and substrate alone in kinase buffer.

Control activity was deduced from the measurement of radioactivity of quadruplate wells containing the complete assay cocktail ($\gamma^{33}$P-[ATP], KDR and PLCg substrate) in the absence of test compound. Inhibition of KDR activity with compound of the invention was expressed as percentage inhibition of control activity exhibited in the absence of test compound.

SU5614 1 µM (Calbiochem) was included in each plate in quadruplate as a control of inhibition.

$IC_{50}$'s were calculated for compounds of the invention by plotting a dose-response curve. $IC_{50}$ corresponded to the concentration of compound of the invention that induced a 50% inhibition of kinase activity.

Particular compounds of the invention inhibit KDR activity with $IC_{50}$s in the range 100 micromolar to 0.3 micromolar.

2. Cellular Activity on Endothelial Cell

2.1 Inhibition of Vascular Endothelial Growth Factor (VEGF)-Dependent Human Dermal Microvascular Endothelial Cells (HDMEC) Proliferation.

The anti-KDR activity of the molecules of the invention was evaluated by [$^{14}$C]-thymidine uptake on HDMEC (Human Dermal Microvascular Endothelial Cell) in response to VEGF.

HDMEC (Promocell, passage 5 to 7) were seeded in 100 μl at 5,000 cells per well in Cytostar 96-multiwell plates (Amersham) precoated with Attachment factor (AF, Cascad Biologics) at 37° C., 5% $CO_2$, at day 1. On day 2, complete cell medium (Basal medium supplemented with 5% of Fetal calf serum (FCS) and cocktail of growth factors) was replaced by minimum medium (basal medium supplemented with 5% of FCS) and cells were incubated for another 24 h. On day 3, medium was replaced by 200 μl of fresh minimum medium supplemented or not with 100 ng/ml VEGF (R&D System) and containing or not compounds of the invention and 0.1 μCi [$^{14}$C]-thymidine. Cells were incubated at 37° C., 5% $CO_2$ for 4 days. [$^{14}$C]-thymidine uptake was then quantified by counting the radioactivity. Assays were performed in three replicate wells. The final concentration of DMSO in the assay is 0.1%. The % inhibition is calculated as $[cpm_{(+VEGF)} - cpm_{(+VEGF+cpd)} / cpm_{(+VEGF)} - cpm_{(BM5\%FCS)}] \times 100$.

2.2 Effect of Molecules on VEGF-Independent HDMEC Growth:

HDMEC (5,000 cells per well) are seeded in complete medium (CM) in Cytostar 96-multiwell plates (Amersham) precoated with Attachment factor (AF, Cascad Biologics) at 37° C., 5% $CO_2$, at day 1. Complete medium is then removed and cells are incubated in 200 μl of complete medium containing molecules of the invention and [$^{14}$C]-thymidine (0.1 μCi). The uptake of [$^{14}$C]-thymidine is quantified using Wallac betaplate after 3 days of incubation. The % inhibition is calculated as $[cpm_{(CM)} - cpm_{(CM+cpd)} / cpm_{(CM)}] \times 100$.

C. In vitro Test Procedures for Aurora2

1. Inhibitory Effects of Compounds on Aurora2 Kinase

Inhibitory effects of compounds on Aurora2 kinase were determined using a nichel-chelate flashplate radioactive assay.

N-terminally His-tagged full length recombinant aurora2 was expressed in E. coli and purified to near homogeneity.

N-terminally His-tagged NuMA (Nuclear protein that associates with the Mitotic Apparatus) C-terminal fragment (Q1687-H2101) was expressed in E. coli, purified by nichel chelate chromatography and used as substrate in Aurora2 kinase assay. For kinase activity determination NuMAsubstrate was freshly equilibrated in kinase buffer (50 mM Tris-HCl, pH 7.5, 50 mM NaCl, 10 mM $MgCl_2$) supplemented with 10% (v/v) glycerol and 0.05% (w/v) NP40 by chromatography on a Pharmacia PD10 column.

The kinase activity of Aurora2 was measured in a nichel chelate flashplate (New England Nuclear, model SMP107). Each well contained 100 μl of the following solution: 0.02 μM Aurora2; 0.5 μM NuMAsubstrate; 1 μM ATP supplemented with 0.5 μCi[γ-$^{33}$P]-ATP. The solutions were incubated for 30 minutes at 37° C. The assay buffer was then discarded and the wells rinsed twice with 300 μl of kinase buffer. Radioactivity was measured in each well using a Packard Model Top Count NXT instrument.

Background signal was deduced from the measurement of radioactivity in duplicate wells containing radioactive ATP alone in kinase buffer treated in the same manner as other samples.

Control activity was deduced from the measurement of radioactivity of duplicate wells containing the complete assay cocktail (ATP, Aurora2 and NuMA substrate) in the absence of test compound. Inhibition of Aurora2 activity with compound of the invention was expressed as percentage inhibition of control activity exhibited in the absence of test compound. Staurosporin was included in each plate as a control of inhibition.

$IC_{50}$'s were calculated for compounds of the invention by plotting a dose-response curve. $IC_{50}$ corresponded to the concentration of compound of the invention that induced a 50% inhibition of kinase activity.

Particular compounds of the invention inhibit Aurora2 activity with $IC_{50}$s in the range 100 micromolar to 0.1 micromolar. Preferred compounds of the invention inhibit Aurora2 activity with $IC_{50}$s in the range 100 nanomolar to 10 nanomolar.

D. In vitro Test Procedures for FAK

1. Inhibitory Effects of Compounds on FAK

Inhibitory effects of compounds on FAK kinase—autophosphorylation assay—were determined using a time-resolved fluorescent assay.

The full length cDNA of human enzyme has been cloned into the pFastBac HTc baculovirus expression vector. The protein has been expressed and purified to about 70% homogeneity.

Kinase activity was determined in 50 mM Hepes pH 7.2 containing 10 mM $MgCl_2$, 100 μM $Na_3VO_4$, 15 μM adenosine triphosphate. Enzyme reactions were terminated by the addition of Hepes buffer pH 7.0, containing 0.4 M KF, 133 mM EDTA, BSA 0.1% containing an anti-6His antibody labelled with XL665 (FAK is His-tagged) and a monoclonal tyrosine phosphospecfic antibody conjugated to a europium cryptate (Eu-K). Features of the two fluorophores, XL-665 and Eu-K are given in G. Mathis et al., Anticancer Research, 1997, 17, pages 3011–3014. The specific long time signal of XL-665, produced only when the FAK enzyme is autophosphorylated, was measured on a Packard Discovery Microplate analyzer. Inhibition of FAK activity with compounds of the invention was expressed as percentage inhibition of control activity exhibited in the absence of test compounds.

2. Proliferation/Viability of Human Melanoma SK-MeI-28 Cells as Measured by [$^{14}$C] Thymidine Uptake

2.1 Cell Culture, Labelling of SK-MeI-28 Cells and Performance of Assay.

SK-MeI-28 were seeded at 5,000 cells per well in Cytostar 96-multiwell plates (Amersham) at 37° C., 5% $CO_2$, at day 1. On day 2, cell medium was replaced by fresh Eagle's minimum essential medium (MEM) culture medium supplemented with 10% FCS, 1% non essential amino acids, 1% sodium pyruvate and containing 0.1 μCi of [$^{14}$C]-Thymidine plus increasing concentrations of compounds in a 200 μl final volume. Cells were incubated at 37° C., 5% $CO_2$ for 48 hours. [$^{14}$C]-Thymidine uptake was quantified by counting the radioactivity 48 hours after initiation of treatment. Assays were performed in three replicate wells.

2.2 Calculation of Results (i) The mean±s.e.m. of each set of triplicate wells was calculated.
(ii) Maximum response was the positive control wells containing cells but no compound.
(iii) Minimum response was the control wells containing no cell and no compound.
(iv) Using these values as the maximum (100%) and minimum (0%) values respectively, the data were normalized to give a percentage of the maximum response.

(v) A dose response curve was plotted and the $IC_{50}$ (the concentration of drug that induces a 50% decrease in [$^{14}C$]-thymidine uptake) of the compound was calculated.

3. Migration of Human Melanoma SK-MeI-28 Cells on Fibronectin Matrix 3.1 Cell Culture and Performance of Assay.

SK-MeI-28 (250,000 cells) were pretreated with increasing concentrations of compounds for 15 min at 37° C., 5% $CO_2$. They were then loaded in presence of the compound on the upper side of 12 μm 12-multiwell chemotaxis Boyden chambers (Becton Dickinson) and allowed to migrate to the lower chamber containing fibronectin (10 μg/ml) as chemoattractant in basal RPMI culture medium for 24 hours at 37° C., 5% $CO_2$. Cells were then fixed and stained in Diff-Quick (Diff-Quick Fix, I and II solutions, Dade Behring) and cells from the upper side of the chamber were removed. Stain was solubilized from lower side adherent cells and cell migration was quantified by optic density measurement. Assays were performed in two replicate wells.

3.2 Calculation of Results (i) The mean±s.e.m. of each set of duplicate wells was calculated.
(ii) Maximum response was positive control wells containing cells but no compound and allowed to migrate on fibronectin.
(iii) Minimum response was the control wells containing cells but no compound and allowed to migrate on basal culture medium w/o chemoattractant.
(iv) Using these values as the maximum (100%) and minimum (0%) values respectively, the data were normalized to give a percentage of the maximum response.
(v) A dose response curve was plotted and the $IC_{50}$ (the concentration of drug that induces a 50% decrease in cell migration) of the compound was calculated.

Particular compounds of the invention inhibit FAK activity with $IC_{50}$s in the range 100 micromolar to 0.3 micromolar.

E. In vitro Test Procedures for IGF1R

1. Inhibitory Effects of Compounds on IGF1R

Inhibitory effects of compounds on IGF1R—autophosphorylation activity—were determined using a time-resolved fluorescent assay.

The cytoplasmic domain of human IGF1R has been cloned as glutathione S-transferase (GST) fusion into the pFastBac-GST tagged baculovirus expression vector. The protein has been expressed in SF21 cells and purified to about 80% homogeneity.

Kinase activity was determined in 50 mM Hepes pH 7.5 containing 5 mM $MnCl_2$, 50 mM NaCl, 3% Glycerol, 0.025% Tween 20, 120 μM adenosine triphosphate. Enzyme reactions were terminated by the addition of 100 mM Hepes buffer pH 7.0, containing 0.4 M KF, 133 mM EDTA, BSA 0.1% containing an anti-GST antibody labelled with XL665 and an anti-phosphotyrosine antibody conjugated to a europium cryptate (Eu-K). Features of the two fluorophores, XL-665 and Eu-K are given in G. Mathis et al., Anticancer Research, 1997, 17, pages 3011–3014. The specific long time signal of XL-665, produced only when the IGF1R enzyme is autophosphorylated, was measured on a Victor analyser (Perkin-elmer). Inhibition of IGF1R kinase activity with compounds of the invention was expressed as percentage inhibition of control activity exhibited in the absence of test compounds.

2. Proliferation/Viability of Human Breast Carcinome MCF-7 Cells as Measured by [$^{14}C$] Thymidine Uptake 2.1 Cell Culture, Labelling of MCF-7 Cells and Performance of Assay.

The antiproliferative effect of the molecules on MCF-7 cells was evaluated by [$^{14}C$]-thymidine uptake 72 hours after IGF1-induced cell proliferation.

MCF-7 cells were seeded at 25,000 cells per well in Cytostar 96-multiwell plates (Amersham) at 37° C., 5% $CO_2$, at day 1, left overnight in EMEM medium supplemented with 10% of FCS to allowed cell attachment. At day 2, the medium culture was changed for EMEM/HamF12, 50/50 in order to deprivate the cells for 24 hours. On day 3, cell medium was replaced by fresh EMEM with 1% of sodium pyruvate, penicillin, streptamicin and 50 ng/ml final concentration of IGF1. Then, 0.1 μCi of [$^{14}C$]-Thymidine and 3 μl of compounds were added in 213 μl final volume. Cells were incubated at 37° C., 5% $CO_2$ for 72 hours. [$^{14}C$]-Thymidine uptake was quantified by counting the radioactivity 72 hours after IGF1-induced proliferation (Microbeta trilux counter, Perkin-elmer). $IC_{50}$ determinations were performed in duplicate with 10 increasing concentrations.

2.2 Calculation of Results (i) The mean±s.e.m. of each set of duplicate wells was calculated.
(ii) Maximum response signal value was calculated from the positive control wells containing cells stimulated by IGF1 but no compound.
(iii) Minimum response signal value was calculated from the control wells containing cells unstimulated by IGF1 and no compound.
(iv) Using these values as the maximum (100%) and minimum (0%) values respectively, the data were normalized to give a percentage of the maximum response.
(v) A dose response curve of 10 points was plotted and the $IC_{50}$ (the concentration of drug that induces a 50% decrease in specific signal) of the compound was calculated by non-linear regression analysis.

3. IGF1R autophosphorylation in MCF7 Cell Line After IGF1 Stimulation 3.1 Cell Culture and Performance of Assay.

IGF1-induced IGF1R autophosphorylation in cells was evaluated by ELISA technique.

MCF-7 cells were seeded at 600 000 cells per well in 6-multiwell plates, left over night in 10% serum and then serum-starved for 24 h. Compounds are added to medium 1 hour before IGF1 stimulation. After 10 minutes of IGF1 stimulation, cells are lysed with Hepes 50 mM pH 7.6, Triton X100 1%, Orthovanadate 2 mM, proteases inhibitors. Cell lysates are incubated on 96-multiwell plates pre-coated with anti-IGF1R antibody, followed by incubation with an anti-phosphotyrosine antibody coupled to peroxydase enzyme. Peroxidase activity level (measured by OD with a luminescent substrate) reflects receptor phosphorylation status.

3.2 Calculation of Results (i) The mean±s.e.m. of each set of duplicate wells was calculated.
(ii) Maximum response signal value was calculated from positive control wells containing lysates of cells stimulated by IGF1 but no compound.
(iii) Minimum response signal value was calculated from the control wells containing lysates of unstimulated cells and no compounds.
(iv) Using these values as the maximum (100%) and minimum (0%) values respectively, the data were normalized to give a percentage of the maximum response.

(v) A dose response curve was plotted and the IC$_{50}$ (the concentration of drug that induces a 50% decrease in OD measure) of the compound was calculated.

Particular compounds of the invention inhibit IGF1R activity with IC$_{50}$s in the range 100 micromolar to 60 nanomolar. Preferred compounds of the invention inhibit IGF1R activity with IC$_{50}$s in the range 100 nanomolar to 60 nanomolar.

In Vivo Test Procedures for SYK Inhibitors

1. Inhibition of Antigen Induced Airway Inflammation—Single-and Multiple-Day Oral Dosing Studies.

Compounds of the invention were assessed in the allergic Brown Norway rat. The models used in these in vivo studies mimic relevant pathological features of allergic airway disease. These studies demonstrated that compounds of the invention inhibit the accumulation of inflammatory cells in the airways allergic twenty-four hours after antigen inhalation. The endpoints measured included the appearance of inflammatory leukocytes in the bronchoalveolar lavage fluid (BALF), lung digest fluid, and in the tissue as quantified by histopathological analysis.

Protocol for Sensitization and Challenge

Brown Norway rats were sensitized on days 0, 12 and 21 with ovalbumin (100,ag, i.p) administered with aluminium hydroxide (100 mg, i.p). On day 30, the rats were exposed to a 1% aerosol of ovalbumin for a period of 30 minutes. The animals were then returned to housing.

Protocol for Dosing

Test drug was administered orally 1 hour before the initiation of the allergen inhalation challenge. Four hours after the end of the antigen inhalation challenge, a second dose of drug was given orally. Doses of compound were administered at half log divisions between 3 and 100 mg/kg.

In separate studies drug was administered two times daily for 4 days before the inhalation of antigen. The final dose of compound in these studies was also given at 4 hours after the antigen challenge.

Protocol for Bronchoalveolar Lavage (BAL) Recovery

Twenty-four hours after the antigen inhalation challenge, cells were recovered from the airway lumen by bronchoalveolar lavage by euthanizing the animals, and washing the lungs with three 5-ml aliquots of RPMI/FCS. The washes were allowed to remain in the lungs for 30 seconds each before gentile removal. The three samples were pooled and total and differential white blood cell counts were measured on BAL samples. An ARGOS system was used to assess total cells and differential cell counts were made using light microscopy of Wright-Giemsa stained cytocentrifuge preparations.

Protocol for Histopathology of Lungs

Immediately after BAL, the lungs were insufflated with 10% neutral buffered formalin (NBF), at 30 cm water pressure. The lungs were removed and placed in jars of 10% NBF. After fixation in 10% NBF for a minimum of 24 hours the lungs were processed through graded alcohol and into wax locks. The lungs were blocked longitudinally and one 2 μm longitudinal section for each animal was cut at the level of the main bronchi. Sections were then stained with haematoxylin and eosin. Pathological assessment of sections was performed and a grading for the bronchiolar epithelium and sub-mucosa was assigned Protocol for Lung Digest In some studies the lung itself was digested, to recover the inflammatory cells localized within the tissue. In these studies the cells were obtained by perfusing the left lung with RPMI/FCS in order to remove the blood pool of cells immediately after BAL. In the se studies the he right hand side of the lung was insufflated and fixed with buffered formalin for histopathological analysis. The lung to undergo digestion was standardized across animals by taking a 300 mg the section of the lung tissue and exposing it to collagenase digestion. This freed the cells within the lung tissue and allowed their recovery. Total and differential cell counts were performed on these recovered cells.

Results (i) Following antigen inhalation there was a significant increase in the numbers of eosinophils and neutrophils in the non-drug treated groups. His was evidenced by the significant increase in BAL and tissue digest eosinophil and neutrophils numbers as well as the lung histopathology score.

(ii) No changes in BAL macrophage/monocyte cell numbers were observed with antigen challenge or with any drug treatment.

(iii) The compound as able to inhibit significantly the infiltration of neutrophils and eosinophils 24 hours after antigenic challenge compared to the non-drug treated controls as assessed in all three methods noted above. The dose range for efficacy was between 3 and 100 mg/kg po.

(iv) In the multiple-day drug administration studies, there was quantitatively similar inhibition of the cellular influx as seen in the single day studies.

These results indicate that compounds of the invention demonstrate anti-inflammatory activity when given prophylacticlly in a rat model of antigen induced leukocyte infiltration 2. Inhibition of antigen Induced Airway Inflammation-Single-Day ip Dosing Studies Protocol for sensitization and challenge Brown Norway rats were sensitized on days 0, 12 and 21 with ovalbumin (100 μg, i.p) administered with aluminium hydroxide (100 mg, i.p). On day 30, the rats were exposed to a 1% aerosol of ovalbumin for a period of 30 minutes. The animals were then returned to housing.

Protocol for Dosing

Test drug was administered four times intraperitoneally rather than po. The dosing regimen was 30 min pre-challenge and 2, 4 and 8 hours after allergen inhalation challenge.

Protocol for Bronchoalveolar lavage (BAL) Recovery

Twenty-four hours after the antigen inhalation challenge, cells were recovered from the airway lumen by bronchoalveolar lavage by euthanizing the animals, and washing the lungs with three 5-ml aliquots of RPMI/FCS. The washes were allowed to remain in the lungs for 30 seconds each before gentile removal. The three samples were pooled and total and differential white blood cell counts were measured on BAL samples. An ARGOS system was used to assess total cells and differential cell counts were made using light microscopy of Wright-Giemsa stained cytocentrifuge preparations.

Protocol for Fistopathology of Lungs

Immediately after BAL, the lungs were insufflated with 10% neutral buffered formalin (NBF), at 30 cm water pressure. The lungs were removed and placed in jars of 10% NBF. After fixation in 10% NBF for a minimum of 24 hours the lungs were processed through graded alcohol and into wax locks. The lungs were blocked longitudinally and one 2 μm longitudinal section for each animal was cut at the level of the main bronchi. Sections were then stained with haematoxylin and eosin. Pathological assessment of sections was performed and a grading for the bronchiolar epithelium and sub-mucosa was assigned Protocol for Lung Digest In some studies the lung itself was digested, to recover the inflammatory cells localized within the tissue. In these studies the cells were obtained by perfusing the left lung with RPMI/FCS in order to remove the blood pool of cells immediately after BAL. In the se studies the he right hand side of the lung was insufflated and fixed with buffered formalin for histopathological analysis. The lung to undergo digestion was standardized across animals by taking a 300 mg the section of the lung tissue and exposing it to collagenase digestion. This freed the cells within the lung tissue and allowed their recovery. Total and differential cell counts were performed on these recovered cells.

Results (i) Following antigen inhalation there was a significant increase in the numbers of eosinophils and neutrophils in the non-drug treated groups. This was evidenced by the significant increase in BAL and tissue digest eosinophil and neutrophil numbers as well as the lung histopathology score.

(ii) Compounds of the invention were able to inhibit significantly the infiltration of neutrophils and eosinophils 24 hours after antigenic challenge compared to the non-drug treated controls as assessed in all three methods noted above. The dose range for efficacy was between 3 and 100 mg/kg po.

These results indicate that compounds of the invention demonstrate anti-inflammatory activity when given prophylacticlly in a rat model of antigen induced leukocyte infiltration either orally or intraperitoneally.

3. Inhibition of Acute Antigen Induced Bronchoconstriction in the Allergic Rat

Protocol for Sensitization and Challenge

Brown Norway rats were sensitized on days 0, 12 and 21 with ovalbumin (100 $\mu$g, i.p) administered with aluminium hydroxide (100 mg, i.p). On the day of study the rats were surgically prepared for the measurement of pulmonary mechanics and mechanically ventilated. After a five-minute equilibration period, the animals received a bolus of ovalbumin (1 mg per rat). The animals were then followed for 15 minutes and peak changes from base line resistance recorded as the response to antigen challenge.

Protocol for Dosing

Test drug was given either p.o. or i.p. 24 and 2 hours before the iv bolus injection of ovalbumin. The range of compound delivered in these studies was 10–100 mg/kg po.

Results

Following antigen challenge in the non-drug treated and budesonide control-treated animals there was a significant increase in the airway resistance over baseline. In contrast, compounds of the invention significantly inhibited the antigen-induced bronchoconstriction.

These results indicate that compounds of the invention inhibit antigen-induced bronchoconstriction.

4. Inhibition of Sephadex Induced Rat Lung Edema and Cytokine Gene Expression in the Allergic Rat Protocol for Sephadex Administration Male Sprague-Dawley rats (400 g), were dosed i.t. with vehicle (saline) or Sephadex (5 mg/kg) in a dose volume of 1 ml/kg under halothane anesthesia (4% in oxygen for 3 min).

Protocol for Dosing

Drug was administered p.o. 1 hour before and 5 hours after Sephadex i.t in a dose volume of 1 ml/kg.

Protocol for Assessing Edema as an Endpoint

Twenty-four hours after Sephadex administration the animals were sacrificed with Euthatal (1 ml/kg i.p.), the heart and lungs removed en bloc. An increase in wet weight was used as an index of edema. The wet weight determined and then corrected for 100 g initial body weight.

Protocol for RT-PCR (Measurement of Cytokine Gene Expression)

RNA was isolated from lung tissue by a guanidium thiocyanate-phenol-chloroform extraction technique. RNA was reverse transcribed to cDNA using AMV reverse transcriptase. cDNA for IL-5, IL4, eotaxin and GAPDH (control gene) were amplified by PCR using oligonucleotide sequences synthesized (Gibco) from published sequences.

The PCR reagents were overlaid with mineral oil and amplification was carried out through 25–35 cycles of denaturation at 95° C. for 1 minute, annealing at 55–65° C. for 1 minute and extending at 72° C. for 7 minutes. The PCR products, stained with ethidium bromide, were electrophoresed in 2% agarose gels to visualize cDNA bands.

Bands of each target fragment were visualized by ultraviolet transillumination and photographed. Photographs were scanned on a densitometer and integrated optical densities (OD×mm) of each band were calculated by image analysis software (Imagemaster, Pharmacia). For each animal, the amount of each cytokine PCR product was normalized to the amount of GAPDH PCR product.

Results (i) Sephadex instillation alone evoked a significant edema of 32%

(ii) Compounds of the invention inhibited the edema in a dose dependant manner by at doses of 10, 30 and 100 mg/kg (iii) Sephadex caused an increased expression of the Th-2 cytokines IL4 and IL-5 together with the CC chemokine eotaxin in the lung 24 hours after challenge. There was a trend toward an increase in the expression of IL-5 and eotaxin mRNA.

(iv) L-4 mRNA expression was dose dependently inhibited by compounds of the invention.

Compounds of the invention inhibit Sephadex induced lung edema in the rat, which is associated with a reduction in Sephadex induction of IL4.

5. Inhibition of Antigen-Induced Histamine Release in the Allergic Brown-Norway Rat Protocol for Sensitization and Challenge Brown Norway rats were sensitized on days 0, 12 and 21 with ovalbumin (100 $\mu$g, i.p) administered with aluminium hydroxide (100 mg, i.p). On the day of study, the rats were surgically prepared for the infusion of antigen. After a five-minute equilibration period, the animals received a bolus of ovalbumin (1 mg per rat). Blood samples were taken 2 minutes after ovalbumin challenge and plasma histamine levels were measured using a histamine ELISA.

Protocol for Dosing

Test drug was given i.p. 30 min before ovalbumin challenge. Only a single 30 mg/kg i.p. concentration was used in this study Results Following antigen challenge, preferred compounds of the invention for inhibition of syk activity significantly inhibited the antigen-induced histamine release in comparison to the vehicle treated group.

These results indicate that compounds of the invention inhibit antigen-induced histamine release.

6. Inhibition of ED-1+Alveolar Macrophages in Rat Lung Tissue
Protocol for Sensitization and Challenge
Brown Norway rats were sensitized on days 0, 12 and 21 with ovalbumin (100 μg, i.p) administered with aluminium hydroxide (100 mg, i.p). On day 30, the rats were exposed to a 1% aerosol of ovalbumin for a period of 30 minutes. The animals were then returned to housing.
Protocol for Dosing
Test drug was given either p.o. or i.p. 24 and 2 hours before the iv bolus injection of ovalbumin. The range of compound delivered in these studies was 10–100 mg/kg po.
Protocol for ED1 Quantification
Alveolar macrophages were quantified following immunostaining with ED-1 antibody in paraffin-embedded lung tissue sections.
Results (i) Ovalbumin challenge resulted in a 10-fold increase in the number of ED1+ macrophages in the alveolar bed.
(ii) Inhibition of Syk Kinase significantly reduced the ovalbumin-induced increase in ED1 alveolar macrophages in a dose-dependent manner.

Oral administration of compounds of the invention produced a dose-related reduction in ED-1+ alveolar macrophages following ovalbumin challenge.

7. Inhibition of Antigen-Induced Airway Neutrophilia in the Brown-Norway Rat
Protocol for Sensitization and Challenge
Brown Norway rats were sensitized on days 0, 12 and 21 with ovalbumin (100 μg, i.p) administered with aluminium hydroxide (100 mg, i.p). On day 30, the rats were exposed to a 1% aerosol of ovalbumin for a period of 30 minutes. The animals were then returned to housing.
Protocol for Drug Dosing
One hour before antigen challenge, rats were dosed orally. The range of compound delivered in these studies was 1–100 mg/kg po.
Protocol for Cell Analysis
Four hours after challenge, cells were recovered from the airway lumen by bronchoalveolar lavage (RPMI/FCS as previously described). Immediately after lavage, lungs were perfused with RPMI/FCS to remove the blood pool of cells. 300 mg of tissue was chopped and cells were recovered by enzymatic (collagenase) disaggregation. Differential cell counts were made by light microscopy of stained cytocentrifuge preparations stained with Wright-Giemsa stain.
Results (i) Four hours after antigen challenge a significant increase in neutrophils was observed in both the BAL and lung tissue.
(ii) The ovalbumin-induced increase in neutrophils in the BAL, but not the lung tissue, was significantly suppressed by compounds of the invention.

8. Inhibitory Effects on LPS-Induced TNFα Production/Release
Protocol
In vivo challenge of mice with bacterial lipopolysacchride (LPS) leads to production of pro-inflammatory cytokines, including TNFα and IL-1β. At numerous time following dosing with compounds of the invention, BALB/c mice (males, 25 gbw) were challenged with LPS (40 μg, i.p., E. coli serotype 0111:B4). Sera collected at 90 minutes following LPS challenge were analyzed by ELISA for levels of pro-inflammatory cytokines, including TNFα.

Results
Oral dosing of mice with compounds of the invention (3–60 mg/kg) produced a dose dependent inhibition of serum levels of TNFα without significantly affecting levels of IL-1β. Duration of action studies demonstrated that oral dosing with compounds of the invention could produce significant inhibition of serum TNFα levels when compounds were administered up to 4 hours prior to LPS-challenge. LPS-induced increases in serum TNFα levels in vehicle-treated mice were compared to compound-treated mice using a one way ANOVA and Dunnett's test for multiple comparisons. Significance was accepted at $p<0.05$ 9. Inhibitory Effects on Collagen-Induced Arthritis in Rats:
Protocol
Collagen-induced arthritis (CIA) can be elicited in susceptible strains of rats, mice and non-human primates. CIA was induced in female Lewis rats (140–150 gbw) by the intradermal injection of bovine cII (400 ug) suspended in incomplete Freund's adjuvant (IFA) on days 0 and 7. Oral dosing with compounds of the invention was initiated on day 6 and continued daily until study termination on day 21.
Results
Ankle joint swelling was measured 3×/week with the aid of calipers. Data are presented as decrease in joint swelling compared to vehicle-treated rats. A significant inhibition in joint inflammation was observed in rats orally dosed with compounds of the invention (30 mg/kg b.i.d). Significance ($p<0.05$) is determined by a one-way Anova and Dunnett's test for multiple comparisons.

10. Inhibitory Effects on MoAb-Induced Arthritis in Mice:
Protocol
Not only can CIA be induced by the injection of cII, but a passive form of disease can also be elicited by injection of mice with a cocktail of monoclonal antibodies (MoAb) raised against 4 cross-reacting/disease epitopes derived from chick cII. Induction of arthritis is dependent on the formation of immune complexes, complement activation and neutrophil/macrophage migration into the joints. Due to the role played by Fcγ receptors (FcγRI and FcγRIII) in the induction of arthritis, this model was also chosen to profile compounds of the invention. BALB/c mice (males, 6–8 weeks of age) were injected on day 0 with MoAb (2 mg, i.v.) and day 2 with LPS (25 μg, i.p.). Dosing with compounds of the invention was initiated on the day of MoAb injection and continuing until study termination on day 14. Mouse joints were macroscopically scored 3×/week for the development of arthritis (% incidence of disease) and disease severity (the number of mice having at least one affected paw divided by the total number of animals per group). Disease severity scores for each animal range from 0–4/paw (with a possible maximum score of 16/mouse) depending on clinical signs of disease which are assessed from 0=no visible signs of arthritis (negative) to 4=ankylosis or total loss of joint function.
Results
Significant dose-dependnet inhibition in joint swelling was observed in mice orally dosed with compounds of the invention (10, 30 mg/kg b.i.d). Additionally, significant dosed-dependent inhibition of histological parameters, pannus, inflammation, cartilage ad bone erosion was also observed in mice orally dosed with either 10 or 30 mg/kg b.i.d.

11. Inhibition of Arthus Reaction in the Mouse Ear
Protocol
Ear thickness was measured at baseline in Balb/c mice. This was followed by oral administration of compound 15 minutes before the intradermal injection of IgG to ovalbumin in the right ear and saline control vehicle in the left ear performed under anesthesia. Immediately after administration of IgG the animals were challenged with 100 μl of ovalbumin mixed with Evans blue into the tail vein. At time-points 15 minutes, 45 minutes, 2.15 hours, 4.5 hours, and 6 hours the thickness of the ears were re-measured and then removed for analysis of Evans blue content.

Results

At all time points, both Evans blue extravasation and increased ear thickness were increased in the control treated animals and significantly inhibited compared to the controls in the compound treated animals. The left ears in all animals were not significantly changed from baseline. Therefore, compounds of the invention significantly suppressed the Arthus reaction.

12. Passive Cutaneous Anaphylaxis in the Mouse Ear

BALB/c mice were sensitized, in both ears, with an intradermal injection of 25 ug of monoclonal IgE anti DNP. After 16 to 20 hours, compounds of the invention were delivered intradermally to the right ear, and the left ear of the same mouse was injected with. The thickness of the ears were measured 10 min after intradermal injections, and values were recorded as time zero. 15 min after the delivery of compound or the vehicle, the animal was injected iv (tail vein) with of 150 ug of DNP and ear swelling was recorded at 15, 30 and 60 min. The net increase in each ear was calculated by subtracting the values at time 0 from those at time 15, 30 and 60 min. The percent inhibition of ear swelling is 1-Rt/Lt.

Results

Compounds of the invention significantly inhibited ear swelling, at all time-points 13. Airway Reactivity and Eosinophilia in Allergic Antigen Challenged Mice Protocol Sensitization:

Mice are sensitized with an intraperitoneal (i.p.) injection of 0.2 ml saline containing 1 mg of $Al_2OH_3$ hydrogel suspension and 10 ug of ovalbumin (ova) on days 0 and 7.

Dosing and Challenge:

The sensitized mice were dosed orally with compounds of the invention twice daily at 30 mg/kg from the initiation of sensitization. The mice were challenged from day 14 for 4 days for 25 min exposure to an aerosolized solution of 6% ova. 18 hrs after the last ova challenge, the airway hyper-reactivity to aerosolized methacholine was measured wusing whole-body barometric plethysmography. The next day the animals were sacrificed and bronchoalveolar lavage collected and the eosinophils quantified.

Results

Treatment with compounds of the invention in the above protocol inhibited the induction of airway hyperreactivity that was measurable in control animals. The inhibition of the hyperreactivity was not statistically significant. In addition the eosinophilia found in the control treated animals was also not significantly inhibited though there was a small decrease in the magnitude of this response in the compound treated animals.

14. Skin Allergic Inflammation in Mice

Protocol

The mice were sensitized ip with OVA+Alum on day 0 and 7. On day 20 the animals were challenged subcutaneously with OVA. Compound was given orally 15 min before and 2 h after challenge with OVA.

Results

The compound of invention inhibited the resultant mast activation, Neutrophils influx, Th2 lymphocyte and Eosinophil infiltration.

What is claimed is:

1. A compound of formula (I):

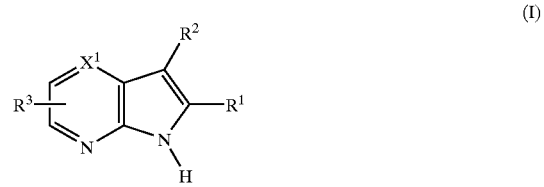

wherein:

$R^1$ represents aryl or heteroaryl, said aryl being a carbocyclic moiety which is monocyclic or multicyclic, is either unsaturated or partially saturated, and has 6 to 14 ring members each of which is a carbon atom and is either substituted or non-substituted; said hetroaryl being a monocyclic or multicyclic carbocyclic moiety which is non-saturated or partially saturated and has 5 to 10 ring members each of which is either substituted or non-substituted and at least one of which is a non-carbon atom;

$R^2$ represents hydrogen, acyl, cyano, halo, $C_{2-6}$ alkenyl, $-Z^2R^4$, $-SO_2NY^3Y^4$, $-NY^1Y^2$ or substituted or non-substituted $C_{1-6}$ alkyl;

$R^3$ represents hydrogen, aryl, cyano, halo, heteroaryl, $C_{1-6}$ alkyl, $-Z^2R^4$, $-C(=O)-OR^5$ or $-C(=O)-NY^3Y^4$;

$R^4$ represents alkyl, cycloalkyl, cycloalkyl-alkyl, heterocycloalkyl or heterocycloalkyl-alkyl each of which is substituted or non-substituted; said cycloalkyl being a saturated monocyclic or bicyclic ring system with 3 to 10 ring members that are substituted or non-substituted carbon atoms; said heterocycloalkyl being a ring moiety with 3 to 7 members that are substituted or non-substituted or said heterocycloalkyl being a ring moiety with 3 to 7 members that are substituted or not-substituted, which is further fused with one or more aryl or heroaryl to form a multicyclic structure; said alkyl has 1–12 carbon atoms and said aryl and heteroaryl are as defined above;

$R^5$ represents hydrogen, alkyl, alkenyl, aryl, aryl-alkyl, heteroaryl or heteroaryl-alkyl where alkyl and alkenyl each has 1 to 12 carbon atoms;

$R^6$ represents hydrogen or $C_{1-6}$ alkyl;

$R^7$ represents alkyl, aryl, aryl-alkyl, cycloalkyl, cycloalkyl-alkyl, heteroaryl, heteroaryl-alkyl, heterocyclo-alkyl or heterocycloalkyl-alkyl;where alkyl has 1 to 12 carbon atoms;

$R^8$ is same as $R^6$;

$X^1$ represents C-aryl, C-heteroaryl, C-heterocycloalkyl, C-heterocycloalkenyl, C-halo, C—CN, C—$R^4$, C—$NY^1Y^2$, C—OH, C—C(=O)—$OR^5$, C—C(=O)—$NY^1Y^2$, C—N($R^8$)—C(=O)—R, C—N($R^6$)—C(=C)—$OR^7$, C—N($R^6$)—C(=O)—$NY^3Y^4$, C—N($R^6$)—$SO_2$—$NY^3Y^4$, C—N($R^6$)—$SO_2$—R, C—$SO_2$—$NY^3Y^4$, C—$NO_2$, C-alkenyl or C-alkynyl; said C-alkenyl or C-alkynyl being optionally substituted by aryl, cyano, halo, hydroxy, heteroaryl, heterocycloalkyl, nitro, —C(=O)—$NY^1Y^2$, —C(=O)—$OR^5$, —$NY^1Y^2$, —N($R^6$)—C(=O)—$R^7$, —N($R^6$)—C(=O)—$NY^3Y^4$, —N($R^6$)—C(=O)—$OR^7$, —N($R^6$)—$SO_2$—$R^7$, —N($R^6$)—$SO_2$—$NY^3Y^4$, —$SO_2$—$NY^1Y^2$ or —$Z^2R^4$;

$Y^1$ and $Y^2$ are independently hydrogen, alkenyl, aryl, cycloalkyl, heteroaryl or alkyl optionally substituted by one ar more groups selected from the group consisting of aryl, halo, hetoroaryl, heterocycloalkyl, hydroxy, —C(=O)—NY³Y⁴, —C(=O)—OR⁵, —NY³Y⁴, —N(R⁶)—C(=O)—R⁷, —N(R⁶)—C(=O)—NY³Y⁴, —N(R⁶)—SO₂—R⁷, —N(R⁶)—SO₂—NY³Y⁴ and —OR⁷; or the group —NY¹Y² may form a cyclic amine;

$Y^3$ and $Y^4$ are independently hydrogen, alkenyl, alkyl, aryl, arylalkyl, cycloalkyl, heteroaryl or heteroarylalkyl; or the group —NY³Y⁴ may form a cyclic amine;

$Z^1$ represents O or S;

$Z^2$ represents O or $S(O)_n$;

n is 0, 1, or 2;

or an N-oxide, prodrug, acid bioisostere, pharmaceutically acceptable salt or solvate of said compound; or an N-oxide, prodrug, or acid bioisostere of said salt or solvate.

2. A compound according to claim 1, wherein R¹ is aryl or heteroaryl which is substituted by one or more groups selected from alkylenedioxy, alkenyl, alkenyloxy, alkynyl, aryl, cyano, halo, hydroxy, heteroaryl, heterocycloalkyl, nitro, R⁴, —C(=O)—R, —C(=O)—OR⁵, —C(=O)—NY¹Y², —NY¹Y², —N(R⁶)—C(=O)—R⁷, —N(R⁶)—C(=O)—NY³Y⁴, —N(R⁶)—C(=O)—OR⁷, —N(R⁶)—SO₂—R⁷, —N(R⁶)—SO₂—NY³Y⁴, —SO₂—NY¹Y² and —Z²R, where R is aryl, heteroaryl, alkenyl, alkyl, cycloalkyl, cycloalkylalkyl, heterocycloalkyl or heterocycloalkylalkyl each of which is non-substituted or substituted by a substituent selected from aryl, cycloalkyl, cyano, halo, heteroaryl, heterocycloalkyl, —CHO (or a 5-, 6- or 7-membered cyclic acetal derivative thereof), —C(=O)—NY¹Y², —C(=O)—OR⁵, —NY¹Y², —N(R⁶)—C(=O)—R⁷, —N(R⁶)—C(=O)—NY³Y⁴, —N(R⁶)—SO₂—R⁷, —N(R⁶)—SO₂—NY³Y⁴, —Z³R⁷ and one or more groups selected from hydroxy, alkoxy and carboxy.

3. A compound according to claim 1 wherein R¹ is optionally substituted azaheteroaryl.

4. A compound according to claim 3 wherein R¹ is optionally substituted indolyl, optionally substituted pyridyl, optionally substituted pyrrolyl, optionally substituted pyrazolyl, optionally substituted quinolinyl, optionally substituted isoquinolinyl, optionally substituted imidazolyl, optionally substituted indazolyl, optionally substituted indolizinyl optionally substituted tetrahydroindolizinyl or optionally substituted indazolinyl.

5. A compound according to claim 4 wherein R¹ is optionally substituted indolyl, optionally substituted indolizinyl or optionally substituted pyrrolyl.

6. A compound according to claim 5 wherein R¹ is optionally substituted indol-3-yl, indolizin-1-yl, optionally substituted pyrrol-3-yl, optionally substituted indol-2-yl or optionally substituted pyrrol-2-yl.

7. A compound according to claim 1 wherein R¹ is optionally substituted aryl.

8. A compound according to claim 7 wherein R¹ is optionally substituted phenyl.

9. A compound according to claim 1 wherein R² is hydrogen, acyl or halo.

10. A compound according to claim 1 wherein R² is lower alkyl optionally substituted by cyano, halo, hydroxy, heteroaryl, —C(=O)—NY¹Y², tetrazolyl, —C(=O)—R, —CO₂R⁸, —NY³Y⁴, —N(R⁶)—C(=O)—R, —N(R⁶)—C(=O)—NY¹Y², —N(R⁶)—SO₂—R⁷, or —N(R⁶)—SO₂—NY³Y⁴.

11. A compound according to claim 1 wherein R² is lower alkenyl.

12. A compound according to claim 1 wherein R³ is hydrogen.

13. A compound according to claim 1 wherein R³ is —C(=O)—OR⁵.

14. A compound according to claim 1 wherein R³ is lower alkyl.

15. A compound according to claim 1 wherein R³ is methyl.

16. A compound according to claim 1 wherein X¹ is C-halo, C—CN or C—OH.

17. A compound according to claim 1 wherein X¹ is C-aryl.

18. A compound according to claim 1 wherein X¹ is C-heteroaryl or C-azaheteroaryl.

19. A compound according to claim 1 wherein X¹ is C—Z²R.

20. A compound according to claim 1 wherein X¹ is C-lower alkoxy.

21. A compound according to claim 1 wherein X¹ is C—C(=O)—OR⁵ or C—C(=O)—NY¹Y².

22. A compound according to claim 1 wherein X¹ is C—C(=O)—NH₂, C—C(=O)—NH—CH₃, C—C(=O)—NH—CH₂—CH₂—CH₂—CH₃,

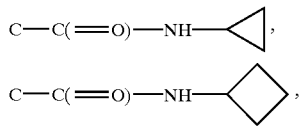

C—C(=O)—NH—CH₂—CH₂OH, C—C(=O)—NH—CH₂—CH(CH₃)OH, C—C(=O)—NH—CH₂—C(CH₃)₂—OH, C—C(=O)—NH—C(CH₃)₂—CH₂OH, C—C(=O)—NH—CH₂CH₂OCH₃,

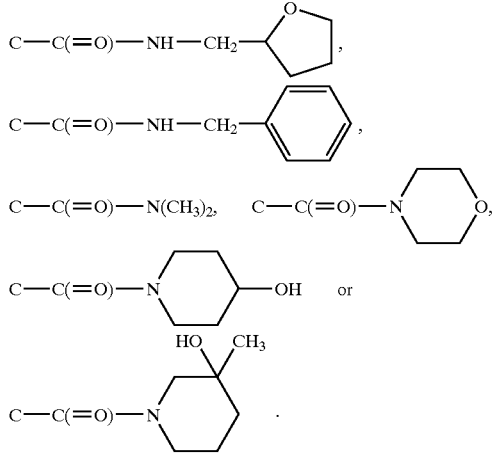

23. A compound according to claim 1 wherein X¹ is C—C(=O)—NH—C(CH₃)₂—CH₂OH.

24. A compound according to claim 1 wherein X¹ is C—NY¹Y².

25. A compound according to claim 1 wherein X¹ is

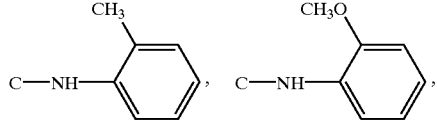

-continued

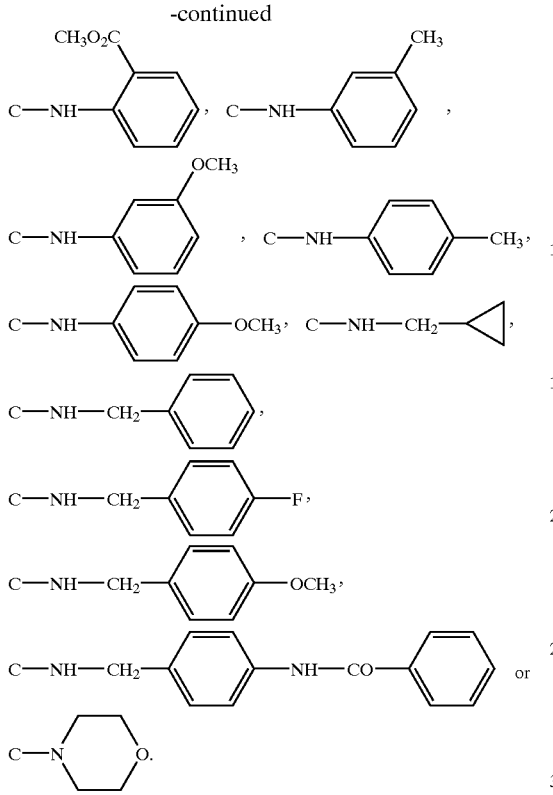

26. A compound according to claim 1 wherein $X^1$ is

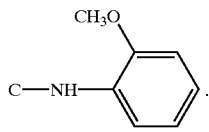

27. A compound according to claim 1 wherein $X^1$ is C-heterocycloalkenyl.

28. A compound according to claim 1 wherein $X^1$ is

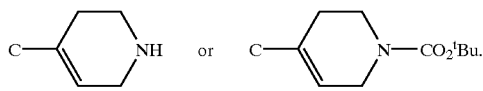

29. A compound according to claim 1, which is of formula (Ia):

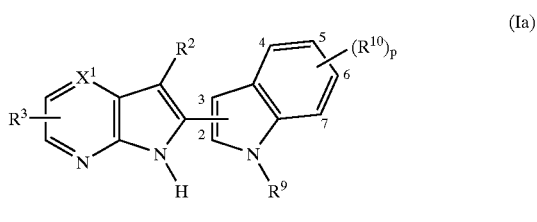

wherein:

$R^2$, $R^3$, $R^4$ and $X^1$ are defined in claim 1;

$R^9$ is hydrogen, alkenyl or $R^4$; $R^{10}$ is alkenyloxy, carboxy (or an acid bioisoitere), cyano, halo, hydroxy, heteroaryl, $R^4$, —C(=O)—R, —C(=O)—$NY^1Y^2$, —$OR^4$, —N($R^6$)—C(=O)—$R^7$, —N($R^6$)—$SO_2$—$R^7$, or —$NY^1Y^2$; p is zero, or an integer 1 or 2; and the residue

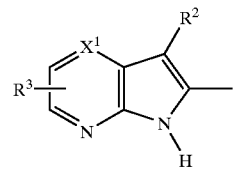

is attached to position 2 or 3 of the indole ring of formula Ia; or an N-oxide, prodrug, or pharmaceutically acceptable salt or solvate of said compound; or an N-oxide or prodrug of said salt or solvate.

30. A compound according to 29 wherein $R^2$ is hydrogen;

$R^3$ Is hydrogen;

$X^1$ is C-aryl, C-heteroaryl, C-halo, C—CN, C-lower alkoxy, C—C(=O)—$OR^5$, C(=O)—$NY^1Y^2$, or C—$NY^1Y^2$;

$R^9$ is hydrogen, $C_{1-4}$alkyl, $C_{1-4}$alkyl substituted by hydroxy, $C_{1-4}$alkyl substituted by —N($R^6$)C(=O)—$R^7$, $C_{1-4}$alkyl substituted by —C(=O)13 $NY^1Y^2$, or cycloalkylalkyl substituted by hydroxy;

$R^{10}$ is carboxy or an acid bioisostere; hydroxy; alkyl substituted by carboxy; alkyl substituted by —N($R^6$)—$SO_2$—$R^7$; akyl substituted by —N($R^6$)—CO—$NY^3Y^4$; heteroaryl; —$OR^4$ wherein $R^4$ is alkyl;

—$OR^4$ wherein $R^4$ is alkyl or cycloalkylalkyl substituted by one or more hydroxy groups; —$OR^4$ wherein $R^4$ is alkyl substituted by one or more alkoxy groups: —$OR^4$ wherein $R^4$ is alkyl or cycloalkyl substituted by one or more carboxy groups; —$OR^4$ wherein $R^4$ is cycloalkyl substituted by —C(=O)—$NY^1Y^2$; —C(=O)—R wherein R is alkyl; —C(=O)—$NY^1Y^2$; or —N($R^6$)—C(=O)—$R^7$; and wherein the $R^{10}$ group is attached to position 5, or position 6, of the indolyl ring when p is 1; and the $R^{10}$ groups are attached to positions 5 and 6 of the indolyl ring when p is 2; or an N-oxide, prodrug, or pharmaceutically acceptable salt or solvate of such compound; or an N-oxide or prodrug of such salt or solvate.

31. A compound according to claim 1, which is of formula (Ib)

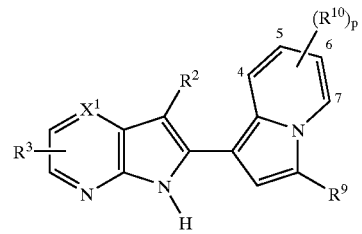

wherein $R^2$, $R^3$, $R^4$, and $X^1$ are defined in claim 1;

$R^9$ is hydrogen, alkenyl or $R^4$; $R^{10}$ is alkenyloxy, carboxy (or an acid bioisostere), cyano, halo, hydroxy, heteroaryl, $R^4$, —C(=O)—R, —C(=O)—$NY^1Y^2$, —OR⁴, —N(R⁶)—C(=O)—R⁷, —N(R⁶)—SO₂—R⁷ or —NY¹Y²; p is zero, or an integer 1 or 2; or an N-oxide, prodrug, or pharmaceutically acceptable salt or solvate of said compound; or an N-Oxide or prodrug of said salt or solvate.

32. A compound according to claim 31 wherein R⁹ is hydrogen.

33. A compound according to claim 31 wherein R⁹ is C₁₋₄alkyl.

34. A compound according to claim 31 wherein R⁹ is —CH₃.

35. A compound according to claim 31 wherein p is zero.

36. A compound according to claim 31 wherein:
R² is hydrogen;
R³ is hydrogen;
X¹ C-aryl, C-heteroaryl, C-halo, C—CN, C-lower alkoxy, C—C(=O)—OR⁵, C—C(=O)—NY¹Y²; C—NY¹Y²;
R⁹ is hydrogen or C₁₋₄alkyl;
p is zero; or
an N-oxide, prodrug or pharmaceutically acceptable salt or solvate of said compound; or an
N-oxide or prodrug of said salt or solvate.

37. A compound according to claim 1, which is of formula (Ic):

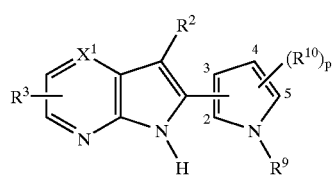

wherein:
R², R³, R⁴ and X¹ are defined in claim 1;
R⁹ is hydrogen, alkenyl or R⁴; R¹⁰ is alkenyloxy, carboxy (or an acid bioisostere), cyano, halo, hydroxy, heteroaryl, R⁴, —C(=O)—R, —C(=O)—NY¹Y², —OR⁴, —N(R⁶)—C(=O)—R⁷, —N(R⁶)—SO₂—R⁷ or —NY¹Y²; p is zero, or an integer 1 or 2; and the residue

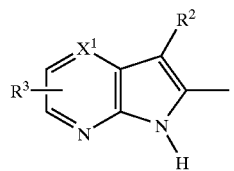

is attached to position 2 or 3 of the pyrrole ring of formula Ic and the group —(R¹⁰)ₚ is attached to position 4 or 5 of the pyrrole ring; or an N-oxide, prodrug, or pharmaceutically acceptable salt or solvate of said compound; or an
N-oxide or prodrug of said salt or solvate.

38. A compound according to claim 37 wherein:
R₂ is hydrogen;
R₃ is hydrogen;
X¹ is C-aryl, C-heteroaryl, C-halo, C—CN, C-lower alkoxy, C—C(=O)—OR⁵, C—C=O)—NY¹Y², or C—NY¹Y²;

R⁹ is C₁₋₄alkyl;
p is 1; and
R¹⁰ is aryl.

39. A compound according to claim 1 which is of formula (Id):

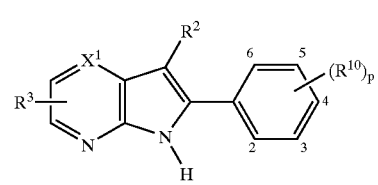

wherein
R², R³, R⁴ and X¹ are defined in claim 1; and
R¹⁰ is alkenyloxy, carboxy or an acid bioisostere, cyano, halo, hydroxy, heteroaryl, R⁴, —C(=O)—R, —C(=O)—NY¹Y², —OR⁴, —N(R⁶)—C(=O)—R⁷, —N(R⁶)—SO₂—R⁷ or —NY¹Y², or an N-oxide, prodrug, or pharmaceutically acceptable salt or solvate of said compound; or an N-oxide or prodrug of said salt or solvate.

40. A compound according to claim 39 wherein R² is hydrogen, lower alkyl, lower alkyl substituted by —CONY¹Y², lower alkyl substituted by carboxy, lower alkyl substituted by tetrazolyl; lower alkyl substituted by hydroxy, or lower alkyl substituted by —N(R⁶)—SO₂—R⁷, —N(R⁶)—C(=O)—R or —C(=O)—R.

41. A method of inhibiting the catalytic activity of Syk in a mammal comprising administering to said mammal a pharmaceutically affective amount of a compound according to claim 1.

42. A method of inhibiting the catalytic activity of FAK in a mammal comprising administering to said mammal a pharmaceutically effective amount of a compound according to claim 1.

43. A method of inhibiting the catalytic activity of KDR in a mammal comprising administering to said mammal a pharmaceutically effective amount of a compound according to claim 1.

44. A method of inhibiting the catalytic activity of IGFIR in a mammal comprising administering to said mammal a pharmaceutically effective amount of a compound according to claim 1.

45. A method according to claim 41 wherein said mammal are suffering a the inflammatory disease asthma.

46. A compound according to claim 1 wherein:
R¹ represents aryl or heteroaryl each optionally substituted by one or more groups selected from alkylenedioxy, alkenyl, alkenyloxy, alkynyl, aryl, hydroxy, heteroaryl, heterocycloalkyl, —C(=O)—R, —C(=O)—NY¹Y², —N(R⁶)—C(=O)—R⁷, —N(R⁶)—C(=O)—NY³Y⁴, —N(R⁶)—C(=O)—OR⁷, —N(R⁶)—SO₂—R⁷, —N(R⁶)—SO₂—NY³Y⁴, and —SO₂—NY¹Y²;

or an N-oxide, prodrug, acid bioisostere, pharmaceutically acceptable salt or solvate of said compound; or an N-oxide, prodrug, or acid bioisostere of said salt or solvate.

47. A compound of claim 1, which is
6-(5-methoxy-1-methyl-1H-indol-3-yl)-5H-pyrrolo[2,3-b]pyrazine;
6-(1-methyl-1H-indol-3-yl)-5H-pyrrolo[2,3-b]pyrazine;
6-(3-bromophenyl)-5H-pyrrolo[2,3-b]pyrazine;

7-iso-propyl-6-phenyl-5H-pyrrolo[2,3-b]pyrazine;
6-(4-bromophenyl)-5H-pyrrolo[2,3-b]pyrazine;
2-(4-bromophenyl)-1H-pyrrolo[2,3-b]pyrazine;
6-(4-[1,3]dioxan-2-yl-phenyl)-5H-pyrrolo[2,3-b]pyrazine;
6-(3-[1,3]dioxan-2-yl-phenyl)-5H-pyrrolo[2,3-b]pyrazine;
2-(5H-pyrrolo[2,3-b]pyrazin-6-yl)-quinoline;
3-(5H-pyrrolo[2,3-b]pyrazin-6-yl)-isoquinoline;
6-[1-methyl-1H-indol-5-yl]-5H-pyrrolo[2,3-b]pyrazine;
6-(5-methoxy-1-methyl-1H-indol-3-yl)-2methyl-5H-pyrrolo[2,3-b]pyrazine;
3-methyl-6-(1-methyl-1H-indol-3-yl)-5H-pyrrolo[2,3-b]pyrazine;
6-(1-benzyl-5-methoxy-1H-indol-3-yl)-5H-pyrrolo[2,3-b]pyrazine;
6-(1-methyl-1H-pyrrol-3-yl)-5H-pyrrolo[2,3-b]pyrazine;
6-(1-methyl-1H-pyrrol-2-yl)-5H-pyrrolo[2,3-b]pyrazine;
6-indolizin-1-yl-5H-pyrrolo[2,3-b]pyrazine;
6-(3-methyl-indolizin-1-yl)-5H-pyrrolo[2,3-b]pyrazine;
6-(1-methyl-2-phenyl-1H-pyrrol-4-yl)-5H-pyrrolo[2,3-b]pyrazine;
6-(5,6,7,8-tetrahydro-indolizin-1-yl)-5H-pyrrolo[2,3-b]pyrazine;
6-furan-3-yl-5H-pyrrolo[2,3-b]pyrazine;
dimethyl-[4-(5H-pyrrolo[2,3-b]pyrazin-6-yl)-phenyl]-amine;
6-(5-methoxy-1-methyl-1H-indol-3-yl)-7-methyl-5H-pyrrolo[2,3-b]pyrazine;
6-(4-tert-butylphenyl)-5H-pyrrolo[2,3-b]pyrazine;
6-(4-tert-butylphenyl)-7-methyl-5H-pyrrolo[2,3-b]pyrazine;
6-(3,4-dimethoxyphenyl)-5H-pyrrolo[2,3-b]pyrazine;
6-(4-aminophenyl)-7-methyl-5H-pyrrolo[2,3-b]pyrazine;
6-[4-(1-methyl)ethoxyphenyl]-5H-pyrrolo[2,3-b]pyrazine;
6-(1H-1-methyl-2-(methylthio)imidazol-5-yl)-5H-pyrrolo[2,3-b]pyrazine;
6-(1-methyl-1H-indazol-3-yl)-5H-pyrrolo[2,3-b]pyrazine;
6-(1-methyl-4-phenyl-1H-pyrrol-3-yl)-5H-pyrrolo[2,3-b]pyrazine;
6-(4-fluorophenyl)-5H-pyrrolo[2,3-b]pyrazine;
6-(4-methoxyphenyl)-5H-pyrrolo[2,3-b]pyrazine;
6-[4-tert-butyl)phenyl]-7-prop-1-enyl)-5H-pyrrolo[2,3-b]pyrazine;
6-(4-methylthiophenyl)-5H-pyrrolo[2,3-b]pyrazine;
6-(3-methoxyphenyl)-5H-pyrrolo[2,3-b]pyrazine;
6-(1-methyl-1H-pyrazol-4-yl)-5H-pyrrolo[2,3-b]pyrazine;
6-(1-methyl-5-phenyl-1H-pyrazol-3-yl)-5H-pyrrolo[2,3-b]pyrazine;
6-(pyridin-2-yl)-5H-pyrrolo[2,3-b]pyrazine;
6-(pyridin-4-yl)-5H-pyrrolo[2,3-b]pyrazine;
6-(3,4-dimethylphenyl)-5H-pyrrolo[2,3-b]pyrazine;
6-(4-hydroxyphenyl)-5H-pyrrolo[2,3-b]pyrazine;
6-(4-trifluoromethoxyphenyl)-5H-pyrrolo[2,3-b]pyrazine;
6-(4-aminophenyl)-5H-pyrrolo[2,3-b]pyrazine;
6-(1-methyl-2-phenyl-1H-pyrrol-3-yl)-5H-pyrrolo[2,3-b]pyrazine;
6-(1,5-dimethyl-1H-pyrrol-3-yl)-5H-pyrrolo[2,3-b]pyrazine;
6-(1,4-dimethyl-1H-pyrrol-3-yl)-5H-pyrrolo[2,3-b]pyrazine;
2-(1-methyl-4-phenyl-1H-pyrrol-3-yl)-1H-pyrrolo[2,3-b]pyridine;
3-[3-(5H-pyrrolo[2,3-b]pyrazin-6-yl)-indol-1-yl]-propan-1-ol;
3-[5-methoxy-3-(5H-pyrrolo[2,3-b]pyrazin-6-yl)-indol-1-yl]-propan-1-ol;
2-[3-(5H-pyrrolo[2,3-b]pyrazin-6-yl)-indol-1-yl]-ethanol;
6-(1H-indol-3-yl)-5H-pyrrolo[2,3-b]pyrazine;
2-[5-methoxy-3-(5H-pyrrolo[2,3-b]pyrazin-6-yl)-indol-1-yl]-ethanol;
3-[3-(5H-pyrrolo[2,3-b]pyrazin-6-yl)-indol-1-yl]-propylamine;
3-[5-methoxy-3-(5H-pyrrolo[2,3-b]pyrazin-6-yl)-indol-1-yl]-propylamine;
N-{3-[3-(5H-pyrrolo[2,3-b]pyrazin-6-yl)-indol-1-yl]-propyl}-acetamine;
N-[4-(5H-pyrrolo[2,3-b]pyrazin-6-yl)-phenyl]acetamine;
6-[1-(3-morpholin-4-yl-propyl)-1H-indol-3-yl]-5H-pyrrolo[2,3-b]pyrazine;
6-[1-(3-piperidin-1-yl-propyl)-1H-indol-3-yl]-5H-pyrrolo[2,3-b]pyrazine;
6-{1-[3-(pyridin-3-yloxy)-propyl]-1H-indol-3-yl}-5H-pyrrolo[2,3-b]pyrazine;
1-methyl-3-(5H-pyrrolo[2,3-b]pyrazin-6-yl)-1H-indol-5-ol;
6-(2-chloro-5-methoxy-1-methyl-1H-indol-3-yl)-5H-pyrrolo[2,3-b]pyrazine;
3-(5H-pyrrolo[2,3-b]pyrazin-6-yl)-benzaldehyde;
4-(5H-pyrrolo[2,3-b]pyrazin-6-yl)-benzaldehyde;
[3-(5H-pyrrolo[2,3-b]pyrazin-6-yl)-indol-1-yl]-methanol;
[3-(5H-pyrrolo[2,3-b]pyrazin-6-yl)phenyl]-methanol;
[4-(5H-pyrrolo[2,3-b]pyrazin-6-yl)phenyl]-methanol;
6-(5-methoxy-1H-indol-3-yl)-5H-pyrrolo[2,3-b]pyrazine;
2-[5-methoxy-3-(5H-pyrrolo[2,3-b]pyrazin-6-yl)-indol-1-yl]-1-morpholin-4-yl-ethanone;
2-[5-methoxy-1-(2-morpholin-4-yl-2-oxo-ethyl)-1H-indol-3-yl]-1H-pyrrolo-[2,3-b]pyridine-4-carbonitrile;
[5-methoxy-3-(1H-pyrrolo[2,3-b]pyridin-2-yl)-indol-1-yl]-acetic acid;
4-methoxy-2-(5-methoxy-1-methyl-1H-indol-3-yl)-1H-pyrrolo[2,3-b]pyridine;
4-methoxy-2-(5-methoxy-1H-indol-3-yl)-1H-pyrrolo[2,3-b]pyridine;
4-chloro-2-(4-tert-butylphenyl)-1H-pyrrolo[2,3-b]pyridine;
2-(5-methoxy-1-methyl-1H-indol-3-yl)-5-phenyl-1H-pyrrolo[2,3-b]pyridine;
1-[1-methyl-3-(1H-pyrrolo[2,3-b]pyridin-2-yl)-1H-indol-5-yloxy]-propan-2-ol;
5,6-dimethoxy-3-(1H-pyrrolo[2,3-b]pyridin-2-yl)-indol-1-yl]-acetic acid;
2-[5-methoxy-3-(1H-pyrrolo[2,3-b]pyridin-2-yl)-indol-1-yl]-1-morpholin-4-yl-ethanone;

1-[1-methyl-3-(1H-pyrrolo[2,3-b]pyridin-2-yl)-1H-indol-5-yloxy]-cyclobutanecarboxylic acid amide;
1-[1-methyl-3-(1H-pyrrolo[2,3-b]pyridin-2-yl)-1H-indol-5-yloxy]-cyclobutanecarboxylic acid methylamide;
1-methyl-3-(1H-pyrrolo[2,3-b]pyridin-2-yl)-1H-indole-5-carboxylic acid methylamide;
1-methyl-3-(1H-pyrrolo[2,3-b]pyridin-2-yl)-1H-indole-5-carboxylic acid (2-hydroxy-ethyl)-amide;
1-methyl-3-(1H-pyrrolo[2,3-b]pyridin-2-yl)-1H-indole-5-carboxylic acid (2-morpholin-4-yl-ethyl)-amide;
1-methyl-3-(1H-pyrrolo[2,3-b]pyridin-2-yl)-1H-indole-5-carboxylic acid (2-carbamoyl-ethyl)-amide;
1-methyl-3-(1H-pyrrolo[2,3-b]pyridin-2-yl)-1H-indole-5-carboxylic acid bis-(2-hydroxy-ethyl)-amide;
1-methyl-3-(1H-pyrrolo[2,3-b]pyridin-2-yl)-1H-indole-5-carboxylic acid amide;
1-methyl-3-(1H-pyrrolo[2,3-b]pyridin-2-yl)-1H-indole-5-carboxylic acid (2-hydroxy-1,1-bis-hydroxymethyl-ethyl)-amide;
1-methyl-3-(1H-pyrrolo[2,3-b]pyridin-2-yl)-1H-indole-5-carboxylic acid (2-hydroxy-1-hydroxymethyl-1-methyl-ethyl)-amide;
1-methyl-3-(1H-pyrrolo[2,3-b]pyridin-2-yl)-1H-indole-5-carboxylic acid (2,3-dihydroxy-propyl)-amide;
1-methyl-3-(1H-pyrrolo[2,3-b]pyridin-2-yl)-1H-indole-5-carboxylic acid (2-hydroxy-1,1-dimethyl-ethyl)-amide;
1-methyl-3-(1H-pyrrolo[2,3-b]pyridin-2-yl)-1H-indole-5-carboxylic acid (2-hydroxy-1-hydroxymethyl-ethyl)-amide;
1-methyl-3-(1H-pyrrolo[2,3-b]pyridin-2-yl)-1H-indole-6-carboxylic acid (2-carbamoyl-ethyl)-amide;
1-methyl-3-(1H-pyrrolo[2,3-b]pyridin-2-yl)-1H-indole-6-carboxylic acid (2-hydroxy-ethyl)-amide;
1-methyl-3-(1H-pyrrolo[2,3-b]pyridin-2-yl)-1H-indole-6-carboxylic acid (1H-[1,2,4]triazol-3-yl)-amide;
1-methyl-3-(1H-pyrrolo[2,3-b]pyridin-2-yl)-1H-indole-6-carboxylic acid (2-hydroxy-1-hydroxymethyl-ethyl)-amide;
1-methyl-3-(5H-pyrrolo[2,3-b]pyrazin-6-yl)-1H-indole-5-carboxylic acid (2-hydroxy-1,1-dimethyl-ethyl)-amide;
3-[6-(4-tert-butylphenyl)-5H-pyrrolo[2,3-b]pyrazin-7-yl]-N-methylpropionamide;
3-[6-(4-tert-butylphenyl)-5H-pyrrolo[2,3-b]pyrazin-7-yl]-N,N-dimethylpropionamide;
1-methyl-3-(5H-pyrrolo[2,3-b]pyrazin-6-yl)-1H-indole-5-carboxylic acid 2-methoxyethylamide;
1-methyl-3-(5H-pyrrolo[2,3-b]pyrazin-6-yl)-1H-indole-5-carboxylic acid 2-thien-2-ylethylamide;
1-methyl-3-(5H-pyrrolo[2,3-b]pyrazin-6-yl)-1H-indole-5-carboxylic acid 2-fluoroethylamide;
1-methyl-3-(5H-pyrrolo[2,3-b]pyrazin-6-yl)-1H-indole-5-carboxylic acid 2-carboethoxyethylamide;
1-methyl-3-(5H-pyrrolo[2,3-b]pyrazin-6-yl)-1H-indole-5-carboxylic acid (hydroxymethyl)-carbomethoxy-methylamide;
1-methyl-3-(5H-pyrrolo[2,3-b]pyrazin-6-yl)-1H-indole-5-carboxylic acid 2-hydroxyethylamide;
1-methyl-3-(5H-pyrrolo[2,3-b]pyrazin-6-yl)-1H-indole-5-carboxylic acid methylamide;
1-methyl-3-(5H-pyrrolo[2,3-b]pyrazin-6-yl)-1H-indole-5-carboxylic acid dimethylamide;
[1-methyl-3-(5H-pyrrolo[2,3-b]pyrazin-6-yl)-1H-indol-5-yl] morpholin-4-yl ketone;
4-hydroxy-[1-[1-methyl-3-(5H-pyrrolo[2,3-b]pyrazin-6-yl)-1H-indol-5-yl]carbonylpiperidine
3-[1-methyl-3-(5H-pyrrolo[2,3-b]pyrazin-6-yl)-1H-indol-5-yl]carbonylaminopropionic acid methylamide;
1-methyl-3-(5H-pyrrolo[2,3-b]pyrazin-6-yl)-1H-indole-5-carboxylic acid 3-hydroxypropylamide;
3-{6-[4-(1-methyl)ethoxyphenyl]-5H-pyrrolo[2,3-b]pyrazin-7-yl}propionic acid methylamide;
3-[6-(4-methoxyphenyl)-5H-pyrrolo[2,3-b]pyrazin-7-yl]propionic acid methylamide;
3-{6-[4-(1-methyl)ethoxyphenyl]-5H-pyrrolo[2,3-b]pyrazin-7-yl}propionamide;
3-{6-(4-hydroxyphenyl)-5H-pyrrolo[2,3-b]pyrazin-7-yl}propionamide;
3-[6-(4-fluorophenyl)-5H-pyrrolo[2,3-b]pyrazin-7-yl]propionic acid methylamide;
3-[4-(3,5-dimethyl-isoxazolyl-4-yl)-1H-pyrrolo[2,3-b]pyridin-2-yl]-1-methyl-1H-indole-5-carboxylic acid (2-methoxy-ethyl)-amide;
3-[4-(3,5-dimethyl-isoxazolyl-4-yl)-1H-pyrrolo[2,3-b]pyridin-2-yl]-1H-indole-5-carboxylic acid (2-methoxy-ethyl)-amide;
3-(4-cyano-1H-pyrrolo[2,3-b]pyridin-2-yl)-1-methyl-1H-indole-5-carboxylic acid (2-hydroxy-1,1-dimethyl-ethyl)-amide;
3-(4-cyano-1H-pyrrolo[2,3-b]pyridin-2-yl)-1-methyl-1H-indole-5-carboxylic acid (2-hydroxy-2-methyl-propyl)-amide;
2-[5,6-dimethoxy-3-(1H-pyrrolo[2,3-b]pyridin-2-yl)-indol-1-yl]-1-morpholin-4-yl-ethanone;
[1-methyl-3-(1H-pyrrolo[2,3-b]pyridin-2-yl)-1H-indol-5-yloxy]-acetic acid;
2-[1-methyl-3-(1H-pyrrolo[2,3-b]pyridin-2-yl)-1H-indol-5-yloxy]-propionic acid;
1-[]-methyl-3-(1H-pyrrolo[2,3-b]pyridin-2-yl)-1H-indol-5-yloxy]-cyclobutanecarboxylic acid;
1-methyl-3-(1H-pyrrolo[2,3-b]pyridin-2-yl)-1H-indole-5-carboxylic acid;
1-methyl-3-(1H-pyrrolo[2,3-b]pyridin-2-yl)-1H-indol-5-ol;
1-{1-(cyclobutanecarboxylic acid)-3-1H-pyrrolo[2,3-b]pyridin-2-yl]-1H-indol-5-yloxy}-cyclobutanecarboxylic acid;
1-methyl-3-(1H-pyrrolo[2,3-b]pyridin-2-yl)-1H-indole-6-carboxylic acid;
3-[1-methyl-3-(1H-pyrrolo[2,3-b]pyridin-2-yl)-1H-indol-5-yl]-propionic acid;
1-methyl-3-(5H-pyrrolo[2,3-b]pyrazin-6-yl)-1H-indole-5-carboxylic acid;
[2-methoxy-5-(5H-pyrrolo[2,3-b]pyrazin-6-yl)-phenoxy]acetic acid;
3-[2-dimethylamino-5-(5H-pyrrolo[2,3-b]pyrazin-6-yl)-phenyl]propionic acid;
3-[1-methyl-3-(5H-pyrrolo[2,3-b]pyrazin-6-yl)-1H-indol-5-yl]carbonylaminopropionic acid;
3-[4-(3,5-dimethyl-isoxazole-4-yl)-1H-pyrrolo[2,3-b]pyridine-2-yl]-1-methyl-1H-indole-5-carboxylic acid;
3-[4-(3,5-methyl-isoxazole-4-yl)-1H-pyrrolo[2,3-b]pyridine-2-yl]-1H-indole-5-carboxylic acid;
4-(3,5-dimethyl-isoxazole-4-yl)-2-(5-methoxy-1-methyl-1H-indol-3-yl)-1H-pyrrolo[2,3-b]pyridine;

4-(3,5-dimethyl-isoxazole-4-yl)-2-(5-methoxy-1H-indol-3-yl)-1H-pyrrolo[2,3-b]pyridine;

3-(4-methoxy-1H-pyrrolo[2,3-b]pyridine-2-yl)-1-methyl-1H-indole-5-carboxylic acid;

3-(4-cyano-1H-pyrrolo[2,3-b]pyridine-2-yl)-1-methyl-1H-indole-5-carboxylic acid;

3-(1H-pyrrolo[2,3-b]pyridine-2-yl)-1H-indole-5-carboxylic acid;

2-(5-methoxyl-1H-indol-3-yl)-1H-pyrrolo[2,3-b]pyridine-4-carboxylic acid;

potassium 2-(5-methoxyl-1H-indol-3-yl)-1H-pyrrolo[2,3-b]pyridine-4-carboxylate;

2-[1-methyl-3-(1H-pyrrolo[2,3-b]pyridin-2-yl)-1H-indol-5-yloxy]-ethanol;

2-[1-methyl-3-(1H-pyrrolo[2,3-b]pyridin-2-yl)-1H-indol-5-yloxy]-propan-1-ol;

{1-[1-methyl-3-(1H-pyrrolo[2,3-b]pyridin-2-yl)-1H-indol-5-yloxy]-cyclobutyl}-methanol;

2-(6-phenyl-5H-pyrrolo[2,3-b]pyrazin-7-yl)-ethanol;

3-[1-methyl-3-(5H-pyrrolo[2,3-b]pyrazin-6-yl)-1H-indol-5-yl]carbonylaminopropionic acid;

2-[2-methoxy-5-(5H-pyrrolo[2,3-b]pyrazin-6-yl)-phenoxy]-ethanol;

3-[2-dimethylamino-5-(5H-pyrrolo[2,3-b]pyrazin-6-yl)-phenyl]-propan-1-ol;

3-{6-[4-(1-methyl)ethoxyphenyl]-5H-pyrrolo[2,3-b]pyrazin-7-yl}propanol;

2-(5-methoxy-1-methyl-1H-indol-3-yl)-1H-pyrrolo[2,3-b]pyridine;

3-[1-methyl-3-(1H-pyrrolo[2,3-b]pyridin-2-yl)-1H-indol-5-yloxy]-propane-1,2-diol;

3-[1-methyl-3-(1H-pyrrolo[2,3-b]pyridin-2-yl)-1H-indol-5-yloxy]-propan-1-ol;

3-[1-methyl-3-(1H-pyrrolo[2,3-b]pyridin-2-yl)-1H-indol-5-yloxy]-propan-2-ol;

2-[1-methyl-5-(2H-tetrazol-5-yl)-1H-indol-3-yl]-1H-pyrrolo[2,3-b]pyridine;

2-[1-methyl-5-(2-methyl-2H-tetrazol-5-yl)-1H-indol-3-yl]-1H-pyrrolo[2,3-b]pyridine;

2-[1-methyl-5-(1-methyl-1H-tetrazol-5-yl)-1H-indol-3-yl]-1H-pyrrolo[2,3-b]pyridine;

1-[1-methyl-3-(1H-pyrrolo[2,3-b]pyridin-2-yl)-1H-indol-5-yl]-ethanone;

2-(5,6-dimethoxy-1-methyl-1H-indol-3-yl)-1H-pyrrolo[2,3-b]pyridine;

(S)-3-[1-methyl-3-(1H-pyrrolo[2,3-b]pyridin-2-yl)-1H-indol-5-yloxy]-propane-1,2-diol;

(R)-3-[1-methyl-3-(1H-pyrrolo[2,3-b]pyridin-2-yl)-1H-indol-5-yloxy]-propane-1,2-diol;

2-[5-(2-methoxy-1-methyl-ethoxy)-1-methyl-1H-indol-3-yl]-1H-pyrrolo[2,3-b]pyridine;

2-[1-methyl-5-(5-methyl-[1,2,4]oxadiazol-3-yl)-1H-indol-3-yl]-1H-pyrrolo[2,3-b]pyridine;

(R)-3-[6-methoxy-1-methyl-3-(1H-pyrrolo[2,3-b]pyridin-2-yl)-1H-indol-5-yloxy]-propane-1,2-diol;

6-methoxy-1-methyl-3-(1H-pyrrolo[2,3-b]pyridin-2-yl)-1H-indol-5-ol;

2-(5-methoxy-1-methyl-1H-indol-3-yl)-4-phenyl-1H-pyrrolo[2,3-b]pyridine;

2-[5-(pyridin-4-yl)-1-methyl-1H-indol-3-yl]-1H-pyrrolo[2,3-b]pyridine;

2-(5-methoxy-1-methyl-1H-indol-3-yl)-1H-pyrrolo[2,3-b]pyridine-4-carbonitrile;

4-chloro-2-(5-methoxy-1-methyl-1H-indol-3-yl)-1H-pyrrolo[2,3-b]pyridine;

2-(5-methoxy-1-methyl-1H-indol-3-yl)-4-(pyridin-3-yl)-1H-pyrrolo[2,3-b]pyridine;

2-(5-methoxy-1-methyl-1H-indol-2-yl)-1H-pyrrolo[2,3-b]pyridine;

2-(5-methoxy-1-methyl-1H-indol-3-yl)-3-methyl-1H-pyrrolo[2,3-b]pyridine;

2-(1H-pyrrol-2-yl)-1H-pyrrolo[2,3-b]pyridine;

2-(1-methyl-1H-pyrrol-2-yl)-1H-pyrrolo[2,3-b]pyridine;

4-chloro-2-(5-methoxy-1H-indol-3-yl)-1H-pyrrolo[2,3-b]pyridine;

5-methoxy-1-methyl-3-(1H-pyrrolo[2,3-b]pyridin-2-yl)-1H-indol-6-ol;

2-(6-isopropoxy-5-methoxy-1-methyl-1H-indol-3-yl)-1H-pyrrolo[2,3-b]pyridine;

2-[5,6-dimethoxy-1-(2-morpholin-4-yl-ethyl)-1H-indol-3-yl]-1H-pyrrolo[2,3-b]pyridine;

1-methyl-3-(1H-pyrrolo[2,3-b]pyridin-2-yl)-1H-indol-5-ylamine;

N-[1-methyl-3-(1H-pyrrolo[2,3-b]pyridin-2-yl)-1H-indol-5-yl]-methanesulfonamide;

N-[1-methyl-3-(1H-pyrrolo[2,3-b]pyridin-2-yl)-1H-indol-5-yl]-acetamide;

N-{1-methyl-3-(1H-pyrrolo[2,3-b]pyridin-2-yl)-1H-indol-5-yl]methyl}thien-2-yl-sulfonamide;

{1-[5-(1-hydroxymethyl-cyclobutoxy)-3-(1H-pyrrolo[2,3-b]pyridin-2-yl)-indol-1-yl]-cyclobutyl}-methanol;

{1-[1-methyl-3-(5H-pyrrolo[2,3-b]pyrazin-6-yl)-1H-indol-5-yloxy]-cyclobutyl}-methanol;

5-[6-(4-tert-butylphenyl)-5H-pyrrolo[2,3-b]pyrazin-7-yl]ethyl-2H-tetrazole;

3-[6-(4-tert-butylphenyl)-5H-pyrrolo[2,3-b]pyrazin-7-yl]-propionitrile;

3-[6-(4-tert-butylphenyl-5H-pyrrolo[2,3-b]pyrazin-7-yl]-propionamide;

3-[6-(4-tert-butylphenyl)-5H-pyrrolo[2,3-b]pyrazin-7-yl]-propionic acid;

3-{6-[4-(1-methyl)ethoxyphenyl]-5H-pyrrolo[2,3-b]pyrazin-7-yl}propionic acid;

3-[6-(4-fluorophenyl)-5H-pyrrolo[2,3-b]pyrazin-7-yl]propionic acid;

3-[6-(4-methoxyphenyl)-5H-pyrrolo[2,3-b]pyrazin-7-yl]propionic acid;

3-[6-(4-tert-butyl-phenyl)-5H-pyrrolo[2,3-b]pyrazin-7-yl]-propan-1-ol;

[2-methoxy-5-(5H-pyrrolo[2,3-b]pyrazin-6-yl)-phenoxy]acetic acid ethyl ester;

2-methoxy-5-(5H-pyrrolo[2,3-b]pyrazin-6-yl)phenol;

3-fluoro-2-(5-methoxy-1-methyl-1H-indol-3-yl)-1H-pyrrolo[2,3-b]pyridine;

3-{6-(4-hydroxyphenyl)-5H-pyrrolo[2,3-b]pyrazin-7-yl}propionic acid;

ethyl 3-{6-(4-hydroxyphenyl)-5H-pyrrolo[2,3-b]pyrazin-7-yl}propionate;

2-(5-methoxy-1H-indol-3-yl)-1H-pyrrolo[2,3-b]pyridine-4-carbonitrile;

6-(4-methylsulfinylphenyl)-5H-pyrrolo[2,3-b]pyrazine;

6-(4-methylsulfonylphenyl)-5H-pyrrolo[2,3-b]pyrazine;

3-(6-(4-tert-butylphenyl)-5H-pyrrolo[2,3-b]pyrazin-7-yl) propylamine;

N-{3-(6-(4-tert-butylphenyl)-5H-pyrrolo[2,3-b]pyrazin-7-yl)propyl}acetamide;

N-{3-(6-(4-tert-butylphenyl)-5H-pyrrolo[2,3-b]pyrazin-7-yl)propyl}cyclopropylcarboxylic acid amide;

N-{3-(6-(4-tert-butylphenyl)-5H-pyrrolo[2,3-b]pyrazin-7-yl)propyl}butyramide;

N-{3-(6-(4-tert-butylphenyl)-5H-pyrrolo[2,3-b]pyrazin-7-yl)propyl}methoxyacetamide;

N-{3-(6-(4-tert-butylphenyl)-5H-pyrrolo[2,3-b]pyrazin-7-yl)propyl}thien-2ylcarboxylic acid amide;

N-{3-(6-(4-tert-butylphenyl)-5H-pyrrolo[2,3-b]pyrazin-7-yl)propyl}-N'-propyl urea;

N-{3-(6-(4-tert-butylphenyl)-5H-pyrrolo[2,3-b]pyrazin-7-yl)propyl}-N'-carboethoxoymethyl urea;

N-{1-methyl-3-(1H-pyrrolo[2,3-b]pyridin-2-yl)-1H-indol-5-yl-]methyl}-N'-tetrahydropyran-2-ylurea;

N-{3-(6-(4-tert-butylphenyl)-5H-pyrrolo[2,3-b]pyrazin-7-yl)propyl}-N',N'-diethyl urea;

N-{3-(6-(4-tert-butylphenyl)-5H-pyrrolo[2,3-b]pyrazin-7-yl)propyl}methanesulfonamide;

N-{3-(6-(4-tert-butylphenyl)-5H-pyrrolo[2,3-b]pyrazin-7-yl)propyl}thien-2-ylsulfonamide;

N-{3-(6-(4-tert-butylphenyl)-5H-pyrrolo[2,3-b]pyrazin-7-yl)propyl}dimethylisoxazol-4-ylsulfonamide;

N-{3-(6-(4-tert-butylphenyl)-5H-pyrrolo[2,3-b]pyrazin-7-yl)propyl}1-methylimidazol-4-ylsulfonamide;

2-(5-methoxy-1-methyl-1H-indol-3-yl)-1H-pyrrolo[2,3-b]pyridine-4 carboxylic acid (2-hydroxy-1,1-dimethyl-ethyl)-amide;

3-(4-chloro-1H-pyrrolo[2,3-b]pyridin-2-yl)-1-methyl-1H-indole-5-carboxylic acid (2-hydroxy-1,1-dimethyl-ethyl)-amide;

[2-(5-methoxy-1-methyl-1H-indol-3-yl)-1H-pyrrolo[2,3-b]pyridine-4-yl]-morpholin-4-yl-methanone;

3-[6-(4-hydroxyphenyl)-5H-pyrrolo[2,3-b]pyrazin-7-yl]-N-methylpropionamide;

2-(1-ethyl-5-methoxy-1H-indol-3-yl)-1H-pyrrolo[2,3,-b]pyridine-4-carboxylic acid (2-hydroxy-1,1-dimethyl-ethyl)-amide;

2-(5-methoxy-1-methyl-1H-indol-3-yl)-1H-pyrrolo[2,3,-b]pyridine-4-carboxylic acid (2-methoxy-ethyl) amide;

2-(5-methoxy-1-methyl-1H-indol-3-yl)-1H-pyrrolo[2,3,-b]pyridine-4-carboxylic acid (2-hydroxy-2-methyl-propyl) amide;

2-(5-methoxy-1-methyl-1H-indol-3-yl)-1H-pyrrolo[2,3,-b]pyridine-4-carboxylic acid (2-hydroxy-propyl) amide;

2-(5-methoxy-1-methyl-1H-indol-3-yl)-1H-pyrrolo[2,3,-b]pyridine-4-carboxylic acid (2-hydroxy-ethyl) amide;

2-(5-methoxy-1H-indol-3-yl)-1H-pyrrolo[2,3,-b]pyridine-4-carboxylic acid (2-methoxy-ethyl) amide;

2-(5-methoxy-1-methyl-1H-indol-3-yl)-1H-pyrrolo[2,3,-b]pyridine-4-carboxylic acid;

3-(4-chloro-1H-pyrrolo[2,3-b]pyridin-2-yl)-1-methyl-1H-indole-5-carboxylic acid;

2-(1-ethyl-5-methoxy-1H-indol-3-yl)-1H-pyrrolo[2,3,-b]pyridine-4-carboxylic acid;

2-(5-methoxy-1H-indol-3-yl)-1H-pyrrolo[2,3-b]pyridine-4 carboxamide;

3-[6-(4-morpholin4-yl phenyl)-5H-pyrrolo[2,3-b]pyrazin-7-yl]-N-methylpropionamide;

6-(4-pyrrolidin-1-yl phenyl)-5H-pyrrolo[2,3-b]pyrazine;

6-(4-(furan-2-yl)phenyl)-5H-pyrrolo[2,3-b]pyrazine;

6-(4-(3,5-dimethylisoxazol-4-yl)phenyl)-5H-pyrrolo[2,3-b]pyrazine;

2-[4-(5H-pyrrolo[2,3-b]pyrazin-6-yl)phenyl]-propan-2-ol;

1-[4-(5H-pyrrolo[2,3-b]pyrazin-6-yl)phenyl]ethanone;

6-[4-(4-{2-morpholin-4-ylethyl}-piperazin-1-yl)phenyl]-5H-pyrrolo[2,3-b]pyrazine;

6-(4-piperazin-1-ylphenyl)-5H-pyrrolo[2,3-b]pyrazine;

2-methyl-4-[6-(4-tert-butyl-phenyl)-5H-pyrrolo[2,3-b]pyrazin-7yl]-butan-2-ol;

[3-(1H-pyrrolo[2,3-b]pyridin-2-yl)-1-methyl-1H-indol-5-yl]-methylamine;

2-{[5-methoxy-3-(1H-pyrrolo[2,3-b]pyridin-2-yl)-indol-1-yl]-1-(1-methylpiperazin)-4yl}-ethanone;

N-cyclobutyl-2-[5-methoxy-3-(1H-pyrrolo[2,3-b]pyridin-2-yl)-indol-1-yl]-acetamide;

N-(3-imidazol-1-yl-propyl)-2-[5-methoxy-3-(1H-pyrrolo[2,3-b]pyridin-2-yl)-indol-1-yl]-acetamide;

1-(2,5-dihydro-pyrrol-1-yl)-2-[5-methoxy-3-(1H-pyrrolo[2,3-b]pyridin-2-yl)-indol-1-yl]-ethanone;

N-cyclohexyl-2-[5-methoxy-3-(1H-pyrrolo[2,3-b]pyridin-2-yl)-indol-1-yl]-acetamide;

N-cyclopentyl-2-[5-methoxy-3-(1H-pyrrolo[2,3-b]pyridin-2-yl)-indol-1-yl]-acetamide;

N-(3-dimethyl-amino-propyl)-2-[5-methoxy-3-(1H-pyrrolo[2,3-b]pyridin-2-yl)-indol-1-yl]-acetamide;

6-{2-[5-methoxy-3-(1H-pyrrolo[2,3-b]pyridin-2-yl)-indol-1-yl]-acetylamino}-hexanoic acid methyl ester;

1-[1,4]bipiperidinyl-1'-yl-2-[5-methoxy-3-(1H-pyrrolo[2,3-b]pyridin-2-yl)-indol-1-yl]-ethanone;

N-(3,3-dimethyl-butyl)-2-[5-methoxy-3-(1H-pyrrolo[2,3-b]pyridin-2-yl)-indol-1-yl]-acetamide;

N-(3-ethoxy-propyl)-2-[5-methoxy-3-(1H-pyrrolo[2,3-b]pyridin-2-yl)-indol-1-yl]-acetamide;

1-(3,3-dimethyl-piperidin-1-yl)-2-[5-methoxy-3-(1H-pyrrolo[2,3-b]pyridin-2-yl)-indol-1-yl]-ethanone;

2-[5-methoxy-3-(1H-pyrrolo[2,3-b]pyridin-2-yl)-indol-1-yl]-N-(3-oxo-isoxazolidin-4-yl)-acetamide;

1-[4-(4-chloro-phenyl)-piperazin-1-yl]-2-[5-methoxy-3-(1H-pyrrolo[2,3-b]pyridin-2-yl)-indol-1-yl]-ethanone;

1-(4-hydroxy-piperidin-1-yl)-2-[5-methoxy-3-(1H-pyrrolo[2,3-b]pyridin-2-yl)-indol-1-yl]-ethanone;

2-[5-methoxy-3-(1H-pyrrolo[2,3-b]pyridin-2-yl)-indol-1-yl]-1-thiazolidin-3-yl-ethanone;

2-[5-methoxy-3-(1H-pyrrolo[2,3-b]pyridin-2-yl)-indol-1-yl]-1-[4-(3-phenyl-allyl)-piperazin-1-yl]-ethanone;

N-furan-2-ylmethyl-2-[5-methoxy-3-(1H-pyrrolo[2,3-b]pyridin-2-yl)-indol-1-yl]-acetamide;

2-[5-methoxy-3-(1H-pyrrolo[2,3-b]pyridin-2-yl)-indol-1-yl]-N-(2-pyridin-4-yl-ethyl)-acetamide;

N-cyclopropylmethyl-2-[5-methoxy-3-(1H-pyrrolo[2,3-b]pyridin-2-yl)-indol-1-yl]-N-propyl-acetamide;

N-(1-cyclohexyl-ethyl)-2-[5-methoxy-3-(1H-pyrrolo[2,3-b]pyridin-2-yl)-indol-1-yl]-1-acetamide;

2-[5-methoxy-3-(1H-pyrrolo[2,3-b]pyridin-2-yl)-indol-1-yl]-N-methyl-N-pyridin-3-ylmethyl-acetamide;

2-[5-methoxy-3-(1H-pyrrolo[2,3-b]pyridin-2-yl)-indol-1-yl]-1-(4-m-tolyl-piperazin-1yl)-ethanone;

2-[5-methoxy-3-(1H-pyrrolo[2,3-b]pyridin-2-yl)-indol-1-yl]-N-(2-phenylsulfanyl-ethyl)-acetamide;

2-[5-methoxy-3-(1H-pyrrolo[2,3-b]pyridin-2-yl)-indol-1-yl]-N-(4-morpholin-4-yl-phenyl)-acetamide;
N-cyclopropyl-2-[5-methoxy-3-(1H-pyrrolo[2,3-b]pyridin-2-yl)-indol-1-yl]-acetamide;
2-[5-methoxy-3-(1H-pyrrolo[2,3-b]pyridin-2-yl)-indol-1-yl]-1-(3-methyl-piperazin-1-yl)-ethanone;
N-(4-cyclohexyl-phenyl)-2-[5-methoxy-3-(1H-pyrrolo[2,3-b]pyridin-2-yl)-indol-1-yl]-acetamide;
2-[5-methoxy-3-(1H-pyrrolo[2,3-b]pyridin-2-yl)-indol-1-yl]-N-(2-methyl-cyclohexyl)-acetamide;
N-cyclohexylmethyl-2-[5-methoxy-3-(1H-pyrrolo[2,3-b]pyridin-2-yl)-indol-1-yl]-acetamide;
2-[5-methoxy-3-(1H-pyrrolo[2,3-b]pyridin-2-yl)-indol-1-yl]-1-pyrrolidin-1-yl-ethanone;
4-{2-[5-methoxy-3-(1H-pyrrolo[2,3-b]pyridin-2-yl)-indol-1-yl]-acetyl}-piperazin-2-one;
4-{2-[5-methoxy-3-(1H-pyrrolo[2,3-b]pyridin-2-yl)-indol-1-yl]-acetyl}-3,3-dimethyl-piperazin-2-one;
4-{2-[5-methoxy-3-(1H-pyrrolo[2,3-b]pyridin-2-yl)-indol-1-yl]-acetyl}-1-methyl-piperazin-2-one;
2-[5-methoxy-3-(1H-pyrrolo[2,3-b]pyridin-2-yl)-indol-1-yl]-1-thiomorpholin-4-yl-ethanone;
N-(2-hydroxy-2-phenyl-ethyl)-2-[5-methoxy-3-(1H-pyrrolo[2,3-b]pyridin-2-yl)-indol-1-yl]-acetamide;
1-(2,6-dimethyl-morpholin-4-yl)-2-[5-methoxy-3-(1H-pyrrolo[2,3-b]pyridin-2-yl)-indol-1-yl]-ethanone;
N-(4-diethylaminomethyl-phenyl)-2-[5-methoxy-3-(1H-pyrrolo[2,3-b]pyridin-2-yl)-indol-1-yl]-acetamide;
N-[2-(4-hydroxy-phenyl)-ethyl]-2-[5-methoxy-3-(1H-pyrrolo[2,3-b]pyridin-2-yl)-indol-1-yl]-acetamide;
2-[5-methoxy-3-(1H-pyrrolo[2,3-b]pyridin-2-yl)-indol-1-yl]-N-(tetrahydro-furan-2-ylmethyl)-acetamide;
2-[5-methoxy-3-(1H-pyrrolo[2,3-b]pyridin-2-yl)-indol-1-yl]-N-pyridin-2-ylmethyl-acetamide;
N-(1,2-dimethyl-propyl)-2-[5-methoxy-3-(1H-pyrrolo[2,3-b]pyridin-2-yl)-indol-1-yl]-acetamide;
N-(3-benzyloxy-pyridin-2-yl)-2-[5-methoxy-3-(1H-pyrrolo[2,3-b]pyridin-2-yl)-indol-1-yl]-acetamide;
2-[5-methoxy-3-(1H-pyrrolo[2,3-b]pyridin-2-yl)-indol-1-yl]-N-quinolin-3-yl-acetamide;
2-[5-methoxy-3-(1H-pyrrolo[2,3-b]pyridin-2-yl)-indol-1-yl]-N-quinolin-8-yl-acetamide;
N-isoquinolin-5-yl-2-[5-methoxy-3-(1H-pyrrolo[2,3-b]pyridin-2-yl)-indol-1-yl]-acetamide;
2-[5-methoxy-3-(1H-pyrrolo[2,3-b]pyridin-2-yl)-indol-1-yl]-N-(3-methyl-butyl)-acetamide;
N-isoquinolin-1-yl-2-[5-methoxy-3-(1H-pyrrolo[2,3-b]pyridin-2-yl)-indol-1-yl]-acetamide;
2-[5-methoxy-3-(1H-pyrrolo[2,3-b]pyridin-2-yl)-indol-1-yl]-N-quinolin-2-yl-acetamide;
1-(3,6-dihydro-2H-pyridin-1-yl)-2-[5-methoxy-3-(1H-pyrrolo[2,3-b]pyridin-2-yl)-indol-1-yl]-ethanone;
2-[5-methoxy-3-(1H-pyrrolo[2,3-b]pyridin-2-yl)-indol-1-yl]-N-[3-(4-methyl-piperazin-1-yl)-propyl]-acetamide;
N-(2-cyclohex-1-enyl-ethyl)-2-[5-methoxy-3-(1H-pyrrolo[2,3-b]pyridin-2-yl)-indol-1-yl]-acetamide;
N-[2-(1H-indol-3-yl)-ethyl]-2-[5-methoxy-3-(1H-pyrrolo[2,3-b]pyridin-2-yl)-indol-1-yl]-acetamide;
2-[5-methoxy-3-(1H-pyrrolo[2,3-b]pyridin-2-yl)-indol-1-yl]-1-[4-(tetrahydro-furan-2-carbonyl)-piperazin-1-yl]-ethanone;
N-adamantan-1-yl-2-[5-methoxy-3-(1H-pyrrolo[2,3-b]pyridin-2-yl)-indol-1-yl]-acetamide;
N-(2-dimethylamino-ethyl)-2-[5-methoxy-3-(1H-pyrrolo[2,3-b]pyridin-2-yl)-indol-1-yl]-N-methyl-acetamide;
1-(4-benzo[1,3]dioxol-5-ylmethyl-piperazin-1-yl)-2-[5-methoxy-3-(1H-pyrrolo[2,3-b]pyridin-2-yl)-indol-1-yl]-ethanone;
1-[4-(4-chloro-benzyl)-piperazin-1-yl]-2-[5-methoxy-3-(1H-pyrrolo[2,3-b]pyridin-2-yl)-indol-1-yl]-ethanone;
2-[5-methoxy-3-(1H-pyrrolo[2,3-b]pyridin-2-yl)-indol-1-yl]-1-[4-(1-phenyl-ethyl)-piperazin-1-yl]-ethanone;
2-[5-methoxy-3-(1H-pyrrolo[2,3-b]pyridin-2-yl)-indol-1-yl]-1-[4-(2-morpholin-4yl-ethyl)-piperazin-1-yl]-ethanone;
1-[4-(4-methoxy-phenyl)-piperazin-1-yl]-2-[5-methoxy-3-(1H-pyrrolo[2,3-b]pyridin-2-yl)-indol-1-yl]-ethanone;
2-[5-methoxy-3-(1H-pyrrolo[2,3-b]pyridin-2-yl)-indol-1-yl]-N-[3-oxo-pyrrolidin-1-yl)-propyl]-acetamide;
2-[5-methoxy-3-(1H-pyrrolo[2,3-b]pyridin-2-yl)-indol-1-yl]-1-piperidin-1-yl-ethanone;
2-[5-methoxy-3-(1H-pyrrolo[2,3-b]pyridin-2-yl)-indol-1-yl]-N-(2-piperidin-1-yl-ethyl)-acetamide;
2-[5-methoxy-3-(1H-pyrrolo[2,3-b]pyridin-2-yl)-indol-1-yl]-N-(2-pyrrolidin-1-yl-ethyl)-acetamide;
1-[4-(2-methoxy-ethyl)-piperazin-1-yl]-2-[5-methoxy-3-(1H-pyrrolo[2,3-b]pyridin-2-yl)-indol-1-yl]-ethanone;
1-[4-(2-dimethylamino-ethyl)-piperazin-1-yl]-2-[5-methoxy-3-(1H-pyrrolo[2,3-b]pyridin-2-yl)-indol-1-yl]-ethanone;
N-isobutyl-2-[5-methoxy-3-(1H-pyrrolo[2,3-b]pyridin-2-yl)-indol-1-yl]-acetamide;
1-[4-(4-tert-butyl-benzyl)-piperazin-1yl]-2-[5-methoxy-3-(1H-pyrrolo[2,3-b]pyridin-2-yl)-indol-1-yl]-ethanone;
2-[5-methoxy-3-(1H-pyrrolo[2,3-b]pyridin-2-yl)-indol-1-yl]-N-(1-methyl-3-phenyl-propyl)-acetamide;
N-(4-diethylamino-1methyl-butyl)-2-[5-methoxy-3-(1H-pyrrolo[2,3-b]pyridin-2-yl)-indol-1-yl]-acetamide;
N-benzyl-N-(2-hydroxy-ethyl)-2-[5-methoxy-3-(1H-pyrrolo[2,3-b]pyridin-2-yl)-indol-1-yl]-acetamide;
1-(4-[2-(2-hydroxy-ethoxy)-ethyl]-piperazin-1-yl)-2-[5-methoxy-3-(1H-pyrrolo[2,3-b]pyridin-2-yl)-indol-1-yl]-ethanone;
N-(1-hydroxymethyl-2-methyl-butyl)-2-[5-methoxy-3-(1H-pyrrolo[2,3-b]pyridin-2-yl)-indol-1-yl]-acetamide;
N-benzyl-2-[5-methoxy-3-(1H-pyrrolo[2,3-b]pyridin-2-yl)-indol-1-yl]-N-methyl-acetamide;
N-(2-methoxy-1-methyl-ethyl)-2-[5-methoxy-3-(1H-pyrrolo[2,3-b]pyridin-2-yl)-indol-1-yl]-acetamide;
N-(3-hydroxy-propyl)-2-[5-methoxy-3-(1H-pyrrolo[2,3-b]pyridin-2-yl)-indol-1-yl]-acetamide;
N-(3-methoxy-phenyl)-2-[5-methoxy-3-(1H-pyrrolo[2,3-b]pyridin-2-yl)-indol-1-yl]-acetamide;
1-(4-benzhydryl-piperazin-1-yl)-2-[5-methoxy-3-(1H-pyrrolo[2,3-b]pyridin-2-yl)-indol-1-yl]-ethanone;
1-(4-benzyl-piperazin-1-yl)-2-[5-methoxy-3-(1H-pyrrolo[2,3-b]pyridin-2-yl)-indol-1-yl]-ethanone;
2-[5-methoxy-3-(1H-pyrrolo[2,3-b]pyridin-2-yl)-indol-1-yl]-N-(3-pyrrolidin-1-yl-propyl)-acetamide;
N-(1-benzyl-piperidin-4-yl)-2-[5-methoxy-3-(1H-pyrrolo[2,3-b]pyridin-2-yl)-indol-1-yl]-acetamide;
1-[4-(4-chloro-phenyl)-4-hydroxy-piperidin-1-yl]-2-[5-methoxy-3-(1H-pyrrolo[2,3-b]pyridin-2-yl)-indol-1-yl]-ethanone;

2-[2-[5-methoxy-3-(1H-pyrrolo[2,3-b]pyridin-2-yl)-
indol-1-yl]-acetylamino)-3-methyl-pentanoic acid
methyl ester;
2-[5-methoxy-3-(1H-pyrrolo[2,3-b]pyridin-2-yl)-indol-1-
yl]-N-(2-methyl-quinolin-4-yl)-acetamide;
N-(2-benzylsulfanyl-1-hydroxymethyl-ethyl)-2-[5-
methoxy-3-(1H-pyrrolo[2,3-b]pyridin-2-yl)-indol-1-
yl]-acetamide;
[2-(1H-pyrrolo[2,3-b]pyridin-2-yl)-pyrrol-1-yl]-acetic
acid;
2-{[2-(1H-pyrrolo[2,3-b]pyridin-2-yl)-pyrrol-1-yl]-
1cyclopropylamino}-ethanone;
N-(3-ethoxy-propyl)-2-[2-(1H-pyrrolo[2,3-b]pyridin-2-
yl)-pyrrol-1-yl]-acetamide;
1-pyrrolidin-1-yl-2-[2-(1H-pyrrolo[2,3-b]pyridin-2-yl)-
pyrrol-1-yl]-ethanone;
1-(3,6-dihydro-2H-pyridin-1-yl)-2-[2-(1H-pyrrolo[2,3-b]
pyridin-2-yl)-pyrrol-1-yl]-ethanone;
1-methyl-4-{2-[2-(1H-pyrrolo[2,3-b]pyridin-2-yl)-
pyrrol-1-yl]-acetyl}-piperazin-2-one;
2-[2-(1H-pyrrolo[2,3-b]pyridin-2-yl)-pyrrol-1-yl]-N-
(tetrahydro-furan-2-ylmethyl)-acetamide;
1-(2,6-dimethyl-morpholin-4-yl)-2-[2-(1H-pyrrolo[2,3-b]
pyridin-2-yl)-pyrrol-1-yl]-ethanone;
2-[2-(1H-pyrrolo[2,3-b]pyridin-2-yl)-pyrrol-1-yl]-1-
thiomorpholin-4-yl-ethanone;
1-(4-hydroxy-piperidin-1-yl)-2-[2-(1H-pyrrolo[2,3-b]
pyridin-2-yl)-pyrrol-1-yl]-ethanone;
1-(3,3-dimethyl-piperidin-1-yl)-2-[2-(1H-pyrrolo[2,3-b]
pyridin-2-yl)-pyrrol-1-yl]-ethanone;
4-{2-[2-(1H-pyrrolo[2,3-b]pyridin-2-yl)-pyrrol-1-yl]-
acetyl}-piperazin-2-one;
N-(1-methyl-butyl)-2-[2-(1H-pyrrolo[2,3-b]pyridin-2-
yl)-pyrrol-1-yl]-acetamide;
N-bicyclo[2.2.1]hept-2-yl-2-[2-(1H-pyrrolo[2,3-b]
pyridin-2-yl)-pyrrol-1-yl]-acetamide;
N-[3-(4-methyl-piperazin-1-yl)-propyl]-2-[2-(1H-pyrrolo
[2,3-b]pyridin-2-yl)-pyrrol-1-yl]-acetamide;
1-[4-(3-dimethylamino-propyl)-piperazin-1-yl]-2-[2-
(1H-pyrrolo[2,3-b]pyridin-2-yl)-pyrrol-1-yl]-
ethanone;
1-(4-methyl-piperazin-1-yl)-2-[2-(1H-pyrrolo[2,3-b]
pyridin-2-yl)-pyrrol-1-yl]-ethanone;
1-[4-(4-chloro-phenyl)-4-hydroxy-piperidin-1-yl]-2-[2-
(1H-pyrrolo[2,3-b]pyridin-2-yl)-pyrrol-1]-ethanone;
1-[4-(3-hydroxy-phenyl)-piperazin-1-yl]-2-[2-(1H-
pyrrolo[2,3-b]pyridin-2-yl)-pyrrol-1-yl]-ethanone;
3-[5-methoxy-2-(1H-pyrrolo[2,3-b]pyridin-2-yl)-indol-1-
yl]-propionic acid;
3-[5-methoxy-2-(1H-pyrrolo[2,3-b]pyridin-2-yl)-indol-1-
yl]-1-morpholin-4-yl-propan-1-one;
3-[5-methoxy-2-(1H-pyrrolo[2,3-b]pyridin-2-yl)-indol-1-
yl]-N-phenyl-propionamide;
3-[5-methoxy-2-(1H-pyrrolo[2,3-b]pyridin-2-yl)-indol-1-
yl]-1-thiomorpholin-4-yl-propan-1-one;
3-[5-methoxy-2-(1H-pyrrolo[2,3-b]pyridin-2-yl)-indol-1-
yl]-1-(4-methyl-piperazin-1-yl)-propan-1-one;
3-[5-methoxy-2-(1H-pyrrolo[2,3-b]pyridin-2-yl)-indol-1-
yl]-N-(tetrahydro-furan-2-ylmethyl)-propionamide;
N-(2-hydroxy-2-phenyl-ethyl)-3-[5-methoxy-2-(1H-
pyrrolo[2,3-b]pyridin-2-yl)-indol-1-yl]-propionamide;
N-(2-hydroxy-ethyl)-3-[5-methoxy-2-(1H-pyrrolo[2,3-b]
pyridin-2-yl)-indol-1-yl]-propionamide;

1-[4-(4-chloro-phenyl)-4-hydroxy-piperidin-1-yl]-2-[5-
methoxy-2-(1H-pyrrolo[2,3-b]pyridin-2-yl)-indol-1-
yl]-ethanone;
2-(5-methoxy-1-methyl-1H-indol-3-yl)-4-morpholin-4-
yl-1H-pyrrolo[2,3-b]pyridine;
2-(5-methoxy-1-methyl-1H-indol-3-yl)-4-piperidin-1-yl-
1H-pyrrolo[2,3-b]pyridine;
[2-(5-methoxy-1-methyl-1H-indol-3-yl)-1H-pyrrolo[2,3-
b]pyridin-4-yl]-(2-methoxy-phenyl)-amine;
[2-(5-methoxy-1-methyl-1H-indol-3-yl)-1H-pyrrolo[2,3-
b]pyridin-4-yl]-o-tolyl-amine;
[2-(5-methoxy-1-methyl-1H-indol-3-yl)-1H-pyrrolo[2,3-
b]pyridin-4-yl]-(3-methoxy-phenyl)-amine;
[2-(5-methoxy-1-methyl-1H-indol-3-yl)-1H-pyrrolo[2,3-
b]pyridin-4-yl]-m-tolyl-amine;
(4-fluoro-phenyl)-[2-(5-methoxy-1-methyl-1H-indol-3-
yl)-1H-pyrrolo[2,3-b]pyridin-4-yl]-amine;
[2-(5-methoxy-1-methyl-1H-indol-3-yl)-1H-pyrrolo[2,3-
b]pyridin-4-yl]-(4-methoxy-phenyl)-amine;
[2-(5-methoxy-1-methyl-1H-indol-3-yl)-1H-pyrrolo[2,3-
b]pyridin-4-yl]-p-tolyl-amine;
benzyl-[2-(5-methoxy-1-methyl-1H-indol-3-yl)-1H-
pyrrolo[2,3-b]pyridin-4-yl]-amine;
(4-fluoro-benzyl)-[2-(5-methoxy-1-methyl-1H-indol-3-
yl)-1H-pyrrolo[2,3-b]pyridin-4-yl]amine;
(4-methoxy-benzyl)-[2-(5-methoxy-1-methyl-1H-indol-
3-yl)-1H-pyrrolo[2,3-b]pyridin-4-yl]-amine;
(2-methoxy-ethyl)-[2-(5-methoxy-1-methyl-1H-indol-3-
yl)-1H-pyrrolo[2,3-b]pyridin-4-yl]-amine;
3-[2-(5-methoxy-1-methyl-1H-indol-3-yl)-1H-pyrrolo[2,
3-b]pyridin-4-ylamino]-benzoic acid methyl ester;
cyclopropylmethyl-[2-(5-methoxy-1-methyl-1H-indol-3-
yl)-1H-pyrrolo[2,3-b]pyridin-4-yl]-amine;
[2-(5-methoxy-1-methyl-1H-indol-3-yl)-1H-pyrrolo[2,3-
b]pyridin-4-yl]-phenyl-amine;
butyl-[2-(5-methoxy-1-methyl-1H-indol-3-yl)-1H-
pyrrolo[2,3-b]pyridin-4-yl]-amine;
2-(5-methoxy-1H-indol-3-yl)-1H-pyrrolo[2,3,-b]
pyridine-4-carboxylic acid methylamide; or
2-(5-methoxy-1H-indol-3-yl)-1H-pyrrolo[2,3,-b]
pyridine-4-carboxylic acid, tert-butyl ester;
or an N-oxide, prodrug, acid bioisostere, pharmaceuti-
cally acceptable salt or solvate of said compound; or an
N-oxide, prodrug, or acid bioisostere of said salt or
solvate.
48. A compound of claim 1, which is
6-(5-methoxy-1-methyl-1H-indol-3-yl)-5H-pyrrolo[2,3-
b]pyrazine;
6-(1-methyl-1H-indol-3-yl)-5H-pyrrolo[2,3-b]pyrazine;
3-[3-(5H-pyrrolo[2,3-b]pyrazin-6-yl)-indol-1-yl]-propan-
1-ol;
3-[5-methoxy-3-(5H-pyrrolo[2,3-b]pyrazin-6-yl)-indol-
1-yl]-propan-1-ol;
2-[5-methoxy-3-(5H-pyrrolo[2,3-b]pyrazin-6-yl)-indol-
1-yl]-ethanol;
6-(1H-indol-3-yl)-5H-pyrrolo[2,3-b]pyrazine;
N-[3-[3-(5H-pyrrolo[2,3-b]pyrazin-6-yl)-indol-1-yl]-
propyl]-acetamide;
1-methyl-3-(5H-pyrrolo[2,3-b]pyrazin-6-yl)-1H-indol-5-
ol;
[3-(5H-pyrrolo[2,3-b]pyrazin-6-yl)-indol-1-yl]-
methanol;

6-(5-methoxy-1H-indol-3-yl)-5H-pyrrolo[2,3-b]pyrazine;

2-[5-methoxy-3-(5H-pyrrolo[2,3-b]pyrazin-6-yl)-indol-1-yl]-1-morpholin-4-yl-ethanone;

2-[5-methoxy-1-(2-morpholin-4-yl-2-oxo-ethyl)-1H-indol-3-yl]-1H-pyrrolo[2,3-b]pyridine-4-carbonitrile;

4-methoxy-2-(5-methoxy-1-methyl-1H-indol-3-yl)-1H-pyrrolo[2,3-b]pyridine;

4-methoxy-2-(5-methoxy-1H-indol-3-yl)-1H-pyrrolo[2,3-b]pyridine;

1-[1-methyl-3-(1H-pyrrolo[2,3-b]pyridin-2-yl)-1H-indol-5-yloxy]-propan-2-ol;

1-[1-methyl-3-(1H-pyrrolo[2,3-b]pyridin-2-yl)-1H-indol-5-yloxy]-cyclobutanecarboxylic acid amide;

1-[1-methyl-3-(1H-pyrrolo[2,3-b]pyridin-2-yl)-1H-indol-5-yloxy]-cyclobutanecarboxylic acid methylamide;

1-methyl-3-(1H-pyrrolo[2,3-b]pyridin-2-yl)-1H-indole-5-carboxylic acid (2-hydroxy-ethyl)-amide;

1-methyl-3-(1H-pyrrolo[2,3-b]pyridin-2-yl)-1H-indole-5-carboxylic acid (2-carbamoyl-ethyl)-amide;

1-methyl-3-(1H-pyrrolo[2,3-b]pyridin-2-yl)-1H-indole-5-carboxylic acid amide;

1-methyl-3-(1H-pyrrolo[2,3-b]pyridin-2-yl)-1H-indole-5-carboxylic acid (2-hydroxy-1,1-dimethyl-ethyl)-amide;

1-methyl-3-(1H-pyrrolo[2,3-b]pyridin-2-yl)-1H-indole-5-carboxylic acid (2-hydroxy-1-hydroxymethyl-ethyl)-amide;

1-methyl-3-(1H-pyrrolo[2,3-b]pyridin-2-yl)-1H-indole-6-carboxylic acid (2-carbamoyl-ethyl)-amide;

1-methyl-3-(1H-pyrrolo[2,3-b]pyridin-2-yl)-1H-indole-6-carboxylic acid (1H-[1,2,4]triazol-3-yl)-amide;

1-methyl-3-(5H-pyrrolo[2,3-b]pyrazin-6-yl)-1H-indole-5-carboxylic acid 2-methoxyethylamide;

1-methyl-3-(5H-pyrrolo[2,3-b]pyrazin-6-yl)-1H-indole-5-carboxylic acid 2-hydroxyethylamide;

1-methyl-3-(5H-pyrrolo[2,3-b]pyrazin-6-yl)-1H-indole-5-carboxylic acid methylamide;

3-[4-(3,5-dimethyl-isoxazolyl-4-yl)-1H-pyrrolo[2,3-b]pyridin-2-yl]-1-methyl-1H-indole-5-carboxylic acid (2-methoxy-ethyl)-amide;

3-[4-(3,5-dimethyl-isoxazolyl-4-yl)-1H-pyrrolo[2,3-b]pyridin-2-yl]-1H-indole-5-carboxylic acid (2-methoxy-ethyl)-amide;

3-(4-cyano-1H-pyrrolo[2,3-b]pyridin-2-yl)-1-methyl-1H-indole-5-carboxylic acid (2-hydroxy-1,1-dimethyl-ethyl)-amide;

3-(4-cyano-1H-pyrrolo[2,3-b]pyridin-2-yl)-1-methyl-1H-indole-5-carboxylic acid (2-hydroxy-2-methyl-propyl)-amide;

[1-methyl-3-(1H-pyrrolo[2,3-b]pyridin-2-yl)-1H-indol-5-yloxy]-acetic acid;

2-[1-methyl-3-(1H-pyrrolo[2,3-b]pyridin-2-yl)-1H-indol-5-yloxy]-propionic acid;

1-[1-methyl-3-(1H-pyrrolo[2,3-b]pyridin-2-yl)-1H-indol-5-yloxy]-cyclobutane-1-carboxylic acid;

1-methyl-3-(1H-pyrrolo[2,3-b]pyridin-2-yl)-1H-indol-5-ol;

1-methyl-3-(1H-pyrrolo[2,3-b]pyridin-2-yl)-1H-indole-6-carboxylic acid;

3-[1-methyl-3-(1H-pyrrolo[2,3-b]pyridin-2-yl)-1H-indol-5-yl]-propionic acid;

1-methyl-3-(5H-pyrrolo[2,3-b]pyrazin-6-yl)-1H-indole-5-carboxylic acid;

3-[4-(3,5-dimethyl-isoxazole-4-yl)-1H-pyrrolo[2,3-b]pyridine-2-yl]-1-methyl-1H-indole-5-carboxylic acid;

3-[4-(3,5-methyl-isoxazole-4-yl)-1H-pyrrolo[2,3-b]pyridine-2-yl]-1H-indole-5-carboxylic acid;

4-(3,5-dimethyl-isoxazole-4-yl)-2-(5-methoxy-1-methyl-1H-indol-3-yl)-1H-pyrrolo[2,3-b]pyridine;

4-(3,5-dimethyl-isoxazole-4-yl)-2-(5-methoxy-1H-indol-3-yl)-1H-pyrrolo[2,3-b]pyridine;

3-(4-methoxy-1H-pyrrolo[2,3-b]pyridine-2-yl)-1-methyl-1H-indole-5-carboxylic acid;

3-(1H-pyrrolo[2,3-b]pyridine-2-yl)-1H-indole-5-carboxylic acid;

2-[1-methyl-3-(1H-pyrrolo[2,3-b]pyridin-2-yl)-1H-indol-5-yloxy]-ethanol;

2-[1-methyl-3-(1H-pyrrolo[2,3-b]pyridin-2-yl)-1H-indol-5-yloxy]-propan-1-ol;

(1-[1-methyl-3-(1H-pyrrolo[2,3-b]pyridin-2-yl)-1H-indol-5-yloxy]-cyclobutyl)-methanol;

2-(5-methoxy-1-methyl-1H-indol-3-yl)-1H-pyrrolo[2,3-b]pyridine;

3-[1-methyl-3-(1H-pyrrolo[2,3-b]pyridin-2-yl)-1H-indol-5-yloxy]-propane-1,2-diol;

3-[1-methyl-3-(1H-pyrrolo[2,3-b]pyridin-2-yl)-1H-indol-5-yloxy]-propan-1-ol;

3-[1-methyl-3-(1H-pyrrolo[2,3-b]pyridin-2-yl)-1H-indol-5-yloxy]-propan-2-ol;

2-[1-methyl-5-(2H-tetrazol-5-yl)-1H-indol-3-yl]-1H-pyrrolo[2,3-b]pyridine;

2-[1-methyl-5-(2-methyl-2H-tetrazol-5-yl)-1H-indol-3-yl]-1H-pyrrolo[2,3-b]pyridine;

1-[1-methyl-3-(1H-pyrrolo[2,3-b]pyridin-2-yl)-1H-indol-5-yl]-ethanone;

2-(5,6-dimethoxy-1-methyl-1H-indol-3-yl)-1H-pyrrolo[2,3-b]pyridine;

(R)-3-[1-methyl-3-(1H-pyrrolo[2,3-b]pyridin-2-yl)-1H-indol-5-yloxy]-propane-1,2-diol;

(A)-3-[1-methyl-3-(1H-pyrrolo[2,3-b]pyridin-2-yl)-1H-indol-5-yloxy]-propane-1,2-diol;

2-[5-(2-methoxy-1-methyl-ethoxy)-1-methyl-1H-indol-3-yl]-1H-pyrrolo[2,3-b]pyridine;

2-[1-methyl-5-(5-methyl-[1,2,4]oxadiazol-3-yl)-1H-indol-3-yl]-1H-pyrrolo[2,3-b]pyridine;

(R)-3-[6-methoxy-1-methyl-3-(1H-pyrrolo[2,3-b]pyridin-2-yl)-1H-indol-5-yloxy]-propane-1,2-diol;

6-methoxy-1-methyl-3-(1H-pyrrolo[2,3-b]pyridin-2-yl)-1H-indol-5-ol;

2-(5-methoxy-1-methyl-1H-indol-3-yl)-4-phenyl-1H-pyrrolo[2,3-b]pyridine;

2-(5-methoxy-1-methyl-1H-indol-3-yl)-1H-pyrrolo[2,3-b]pyridine-4-carbonitrile;

4-chloro-2-(5-methoxy-1-methyl-1H-indol-3-yl)-1H-pyrrolo[2,3-b]pyridine;

2-(5-methoxy-1-methyl-1H-indol-3-yl)-4-(pyridin-3-yl)-1H-pyrrolo[2,3-b]pyridine;

4-chloro-2-(5-methoxy-1H-indol-3-yl)-1H-pyrrolo[2,3-b]pyridine;

N-[1-methyl-3-(1H-pyrrolo[2,3-b]pyridin-2-yl)-1H-indol-5-yl]-acetamide;

{1-[5-(1-hydroxymethyl-cyclobutoxy)-3-(1H-pyrrolo[2,3-b]pyridin-2-yl)-indol-1-yl]-cyclobutyl}-methanol;

{1-[1-methyl-3-(5H-pyrrolo[2,3-b]pyrazin-6-yl)-1H-indol-5-yloxy]-cyclobutyl}-methanol;

2-(5-methoxy-1H-indol-3-yl)-1H-pyrrolo[2,3-b]pyridine-4-carbonitrile;

2-(5-methoxy-1-methyl-1H-indol-3-yl)-1H-pyrrolo[2,3-b]pyridine-4-carboxylic acid (2-hydroxy-1,1-dimethyl-ethyl)-amide;

3-(4-chloro-1H-pyrrolo[2,3-b]pyridin-2-yl)-1-methyl-1H-indole-5-carboxylic acid (2-hydroxy-1,1-dimethyl-ethyl)-amide;

2-(1-ethyl-5-methoxy-1H-indol-3-yl)-1H-pyrrolo[2,3,-b]pyridine-4-carboxylic acid (2-hydroxy-1,1-dimethyl-ethyl)-amide;

2-(5-methoxy-1-methyl-1H-indol-3-yl)-1H-pyrrolo[2,3,-b]pyridine-4-carboxylic acid (2-hydroxy-2-methyl-propyl)-amide;

2-(5-methoxy-1-methyl-1H-indol-3-yl)-1H-pyrrolo[2,3,-b]pyridine-4-carboxylic acid (2-hydroxy-propyl)-amide;

2-(5-methoxy-1-methyl-1H-indol-3-yl)-1H-pyrrolo[2,3,-b]pyridine-4-carboxylic acid (2-hydroxy-ethyl)-amide;

2-(5-methoxy-1H-indol-3-yl)-1H-pyrrolo[2,3,-b]pyridine-4-carboxylic acid (2-methoxy-ethyl)-amide;

2-(5-methoxy-1H-indol-3-yl)-1H-pyrrolo[2,3,-b]pyridine-4-carboxylic acid methylamide; or 2-(5-methoxy-1H-indol-3-yl)-1H-pyrrolo[2,3,-b]pyridine-4-carboxylic acid, tert-butyl ester;

or an N-oxide, prodrug, acid bioisostere, pharmaceutically acceptable salt or solvate of said compound; or an N-oxide, prodrug, or acid bioisostere of said salt or solvate.

49. A compound of claim 1, which is 6-(5-methoxy-1-methyl-1H-indol-3-yl)-5H-pyrrolo[2,3-b]pyrazine;

1-[1-methyl-3-(1H-pyrrolo[2,3-b]pyridin-2-yl)-1H-indol-5-yloxy]-cyclobutanecarboxylic acid amide;

3-[4-(3,5-dimethyl-isoxazolyl-4-yl)-1H-pyrrolo[2,3-b]pyridin-2-yl]-1-methyl-1H-indole-5-carboxylic acid (2-methoxy-ethyl)-amide;

3-(4-cyano-1H-pyrrolo[2,3-b]pyridin-2-yl]-1-methyl-1H-indole-5-carboxylic acid (2-hydroxy-2-methyl-propyl)-amide;

3-[4-(3,5-dimethyl-isoxazole-4-yl)-1H-pyrrolo[2,3-b]pyridine-2-yl]-1-methyl-1H-indole-5-carboxylic acid;

3-[4-(3,5-imethyl-isoxazole-4-yl)-1H-pyrrolo[2,3-b]pyridine-2-yl]-1H-indole-5-carboxylic acid;

4-(3,5-dimethyl-isoxazole-4-yl)-2-(5-methoxy-1-methyl-1H-indol-3-yl)-1H-pyrrolo[2,3-b]pyridine;

2-[1-methyl-5-(2H-tetrazol-5-yl)-1H-indol-3-yl]-1H-pyrrolo[2,3-b]pyridine;

2-(5-methoxy-1-methyl-1H-indol-3-yl)-1H-pyrrolo[2,3-b]pyridine-4-carbonitrile;

{1-[1-methyl-3-(5H-pyrrolo[2,3-b]pyrazin-6-yl)-1H-indol-5-yloxy]-cyclobutyl}-methanol;

2-(5-methoxy-1-methyl-1H-indol-3-yl)-1H-pyrrolo[2,3-b]pyridine-4 carboxylic acid (2-hydroxy-1,1-dimethyl-ethyl)-amide; or 2-(1-ethyl-5-methoxy-1H-indol-3-yl)-1H-pyrrolo[2,3,-b]pyridine-4-carboxylic acid (2-hydroxy-1,1-dimethyl-ethyl)-amide;

or an N-oxide, prodrug, acid bioisostere, pharmaceutically acceptable salt or solvate of said compound; or an N-oxide, prodrug, or acid bioisostere of said salt or solvate.

50. A compound of claim 1 which is 1-methyl-3-(1H-pyrrolo[2,3-b]pyridin-2-yl)-1H-indole-6-carboxylic acid;

2-[1-methyl-5-(pyridin-4-yl)-1H-indol-3-yl]-4-1H-pyrrolo[2,3-b]pyridine;

N-{1-methyl-3-(1H-pyrrolo[2,3-b]pyridin-2-yl)-1H-indol-5-yl]methyl}thien-2-yl-sulfonamide;

N-{1-methyl-3-(1H-pyrrolo[2,3-b]pyridin-2-yl)-1H-indol-5-yl]methyl}-N'-tetrahydropyran-2-ylurea;

2-[5-methoxy-3-(1H-pyrrolo[2,3-b]pyridin-2-yl)-indol-1-yl]-N-(2-methyl-quinolin-4-yl)-acetamide; or

[2-(5-methoxy-1-methyl-1H-indol-3-yl)-1H-pyrrolo[2,3-b]pyridin-4-yl]-(2-methoxy-phenyl)-amine;

or an N-oxide, prodrug, acid bioisostere, pharmaceutically acceptable salt or solvate of said compound; or an N-oxide, prodrug, or acid bioisostere of said salt or solvate.

* * * * *